(12) United States Patent
Sapountzis et al.

(10) Patent No.: US 8,889,665 B2
(45) Date of Patent: *Nov. 18, 2014

(54) CHEMICAL COMPOUNDS

(75) Inventors: Ioannis Sapountzis, Vienna (AT); Peter Ettmayer, Vienna (AT); Christian Klein, Vienna (AT); Andreas Mantoulidis, Vienna (AT); Steffen Steurer, Vienna (AT); Irene Waizenegger, Vienna (AT)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 1073 days.

This patent is subject to a terminal disclaimer.

(21) Appl. No.: 12/665,769

(22) PCT Filed: Jul. 1, 2008

(86) PCT No.: PCT/EP2008/058433
§ 371 (c)(1),
(2), (4) Date: Sep. 23, 2010

(87) PCT Pub. No.: WO2009/003999
PCT Pub. Date: Jan. 8, 2009

(65) Prior Publication Data
US 2011/0183952 A1   Jul. 28, 2011

(30) Foreign Application Priority Data

Jul. 2, 2007 (EP) .................................. 07111566

(51) Int. Cl.
| | | |
|---|---|---|
| *A61K 31/55* | (2006.01) | |
| *A61K 31/535* | (2006.01) | |
| *A61K 31/497* | (2006.01) | |
| *A61K 31/44* | (2006.01) | |
| *A61K 31/415* | (2006.01) | |
| *C07D 403/04* | (2006.01) | |
| *C07D 401/14* | (2006.01) | |
| *C07D 403/14* | (2006.01) | |
| *C07D 417/04* | (2006.01) | |
| *C07D 487/08* | (2006.01) | |
| *C07D 417/14* | (2006.01) | |
| *C07D 401/04* | (2006.01) | |

(52) U.S. Cl.
CPC ............ *C07D 401/04* (2013.01); *C07D 403/04* (2013.01); *C07D 401/14* (2013.01); *C07D 403/14* (2013.01); *C07D 417/04* (2013.01); *C07D 487/08* (2013.01); *C07D 417/14* (2013.01)
USPC .................. 514/210.2; 514/217.04; 514/218; 514/237.2; 514/254.05; 514/340; 514/403

(58) Field of Classification Search
None
See application file for complete search history.

(56) References Cited

U.S. PATENT DOCUMENTS

| 4,218,457 A | 8/1980 | Atsumi et al. |
|---|---|---|
| 5,990,133 A | 11/1999 | Gaster et al. |
| 6,492,403 B1 | 12/2002 | Illig et al. |
| 7,166,628 B2 | 1/2007 | Cogan et al. |
| 7,214,802 B2 | 5/2007 | Cogan et al. |
| 7,485,657 B2 | 2/2009 | Cogan et al. |
| 7,511,042 B2 | 3/2009 | Cogan et al. |
| 7,514,458 B2 | 4/2009 | Cogan et al. |
| 7,531,560 B2 | 5/2009 | Cogan et al. |
| 7,569,568 B2 | 8/2009 | Cogan et al. |
| 7,858,804 B2 | 12/2010 | Frutos et al. |
| 8,198,308 B2 | 6/2012 | Steurer et al. |
| 2004/0102492 A1 | 5/2004 | Cogan et al. |
| 2005/0153972 A1 | 7/2005 | Cogan et al. |
| 2005/0256113 A1 | 11/2005 | Cogan et al. |
| 2006/0079519 A1 | 4/2006 | Cogan et al. |
| 2006/0100204 A1 | 5/2006 | Cogan et al. |
| 2007/0032492 A1 | 2/2007 | Cogan et al. |
| 2007/0142371 A1 | 6/2007 | Cogan et al. |
| 2007/0155746 A1 | 7/2007 | Lang et al. |
| 2008/0009497 A1 | 1/2008 | Wittman et al. |

(Continued)

FOREIGN PATENT DOCUMENTS

| EP | 1364949 A1 | 11/2003 |
|---|---|---|
| FR | 2401916 A1 | 3/1979 |

(Continued)

OTHER PUBLICATIONS

Williams et al (Foye's Princples of Medicinal Chemistry, 5th Edition, pp. 59-63, 2002).*

(Continued)

*Primary Examiner* — Craig Ricci
(74) *Attorney, Agent, or Firm* — Michael P. Morris; Anthony P. Bottino; Alan R. Stempel

(57) ABSTRACT

The present invention encompasses compounds of general formula (1), wherein the groups $R^1$ to $R^3$ and L are defined as in claim 1, which are suitable for the treatment of diseases characterised by excessive or abnormal cell proliferation, and their use for preparing a medicament having the above-mentioned properties.

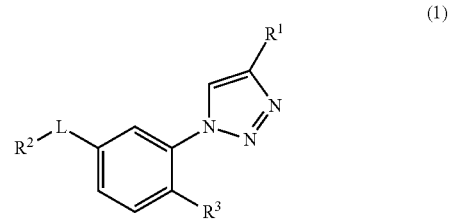

12 Claims, No Drawings

(56) References Cited

U.S. PATENT DOCUMENTS

| | | |
|---|---|---|
| 2008/0027070 A1 | 1/2008 | Noronha et al. |
| 2008/0045489 A1 | 2/2008 | Chao et al. |
| 2008/0132459 A1 | 6/2008 | Moradei et al. |
| 2008/0182837 A1 | 7/2008 | Steurer et al. |
| 2009/0127815 A1 | 5/2009 | Tani et al. |
| 2009/0239838 A1 | 9/2009 | Wittman et al. |
| 2010/0240657 A1 | 9/2010 | Sapountzis et al. |
| 2011/0059938 A1 | 3/2011 | Steurer et al. |
| 2011/0124623 A1 | 5/2011 | Wittman et al. |
| 2011/0183952 A1 | 7/2011 | Sapountzis et al. |
| 2011/0312939 A1 | 12/2011 | Steurer et al. |
| 2012/0046270 A1 | 2/2012 | Ettmayer et al. |
| 2012/0094975 A1 | 4/2012 | Mantoulidis et al. |
| 2013/0190286 A1 | 7/2013 | Steurer et al. |

FOREIGN PATENT DOCUMENTS

| | | | |
|---|---|---|---|
| JP | 03174153 A | 7/1991 | |
| WO | 9703967 A1 | 2/1997 | |
| WO | 0075120 A1 | 12/2000 | |
| WO | 0162737 | 8/2001 | |
| WO | 0162737 A2 | 8/2001 | |
| WO | 03037274 A2 | 5/2003 | |
| WO | 03051358 A1 | 6/2003 | |
| WO | 03059886 A1 | 7/2003 | |
| WO | 2004050642 A1 | 6/2004 | |
| WO | 2005023761 A2 | 3/2005 | |
| WO | 2005030705 A1 | 4/2005 | |
| WO | 2005040152 A1 | 5/2005 | |
| WO | 2005056535 A1 | 6/2005 | |
| WO | 2005090333 A1 | 9/2005 | |
| WO | WO 2005/090333 * | 9/2005 | ........... C07D 403/04 |
| WO | 2005115991 A1 | 12/2005 | |
| WO | 2006053227 A2 | 5/2006 | |
| WO | 2007056016 A2 | 5/2007 | |
| WO | 2007075896 A2 | 7/2007 | |
| WO | 2007076474 A1 | 7/2007 | |
| WO | 2007121390 A1 | 10/2007 | |
| WO | 2007132010 A1 | 11/2007 | |
| WO | 2008003770 A1 | 1/2008 | |
| WO | 2008021388 A1 | 2/2008 | |
| WO | 2008079909 A1 | 7/2008 | |
| WO | 2008089034 A2 | 7/2008 | |
| WO | 2008106692 A1 | 9/2008 | |
| WO | 2009003998 A2 | 1/2009 | |
| WO | 2009003999 A2 | 1/2009 | |
| WO | 2009012283 A1 | 1/2009 | |
| WO | 2010010154 A1 | 1/2010 | |
| WO | 2010026262 A1 | 3/2010 | |
| WO | 2010034838 A2 | 4/2010 | |
| WO | 2010094695 A1 | 8/2010 | |
| WO | 2011117381 A1 | 9/2011 | |
| WO | 2011117382 A1 | 9/2011 | |
| WO | 2012085127 A1 | 6/2012 | |
| WO | 2012101238 A1 | 8/2012 | |
| WO | 2012104388 A1 | 8/2012 | |

OTHER PUBLICATIONS

Patani et al (Chem Rev 96:3147-3176, 1996).*
Caplus: Chan, et al., 2002, CAS: 138:198127.
International Search Report for PCT/EP098/058433 mailed Jun. 4, 2009.
Subasinghe, N.L. et al., "Structure-based Design, Synthesis and SAR of a Novel Series of Thiopheneamidine Urokinase Plasminogen Activator Inhibitors", Bioorganice and Medicinal Chemistry Letters, 11, 2001, pp. 1379-1382.
Sparreboom, A. et al., "The Use of Oral Cytotoxic and Cytostatic Drugs in Cancer Treatment." European Journal of Cancer 38, 2002, pp. 18-22.

* cited by examiner

CHEMICAL COMPOUNDS

APPLICATION DATA

This application is a 371 National Stage filing of PCT/US2008/058433 filed on Jul. 1, 2008. This application also claims benefit to EP07111566.1 filed Jul. 2, 2007.

The present invention relates to new compounds of general formula (1)

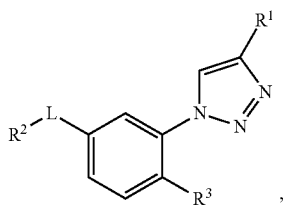

(1)

wherein the groups $R^1$ to $R^3$ and L have the meanings given in the claims and specification and the tautomers, racemates, enantiomers, diastereomers, mixtures, polymorphs and salts of all these forms and their use as medicaments.

BACKGROUND TO THE INVENTION

Phenyl-substituted, nitrogen-containing five-ring heteroaryls for inhibiting cytokine production and hence for treating inflammatory diseases are described in WO 2004/050642, WO 2005/056535, WO 2005/090333, WO 2005/115991 and US 2006/0100204.

The aim of the present invention is to discover new active substances which can be used for the prevention and/or treatment of diseases characterised by excessive or abnormal cell proliferation.

DETAILED DESCRIPTION OF THE INVENTION

It has now been found that, surprisingly, compounds of general formula (1) wherein the groups $R^1$ to $R^3$ and L have the meanings given hereinafter act as inhibitors of specific signal enzymes which are involved in controlling cell proliferation. Thus, the compounds according to the invention may be used for example for the treatment of diseases connected with the activity of these signal enzymes and characterised by excessive or abnormal cell proliferation.

The present invention therefore relates to compounds of general formula (1)

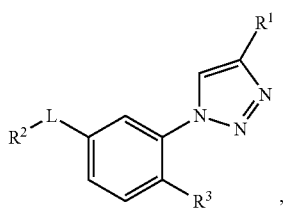

(1)

wherein $R^1$ denotes a 5-10-membered heteroaryl, optionally substituted by one or more identical or different group(s), each independently selected from among $R^a$ and $R^b$;

$R^2$ has the partial structure (i) or (ii)

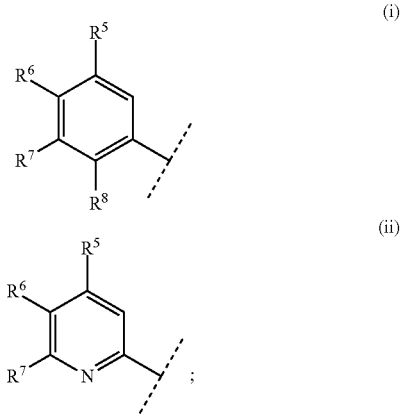

$R^3$ is selected from among hydrogen, halogen, —CN, —NO$_2$, —NR$^h$R$^h$, —OR$^h$, —C(O)R$^h$, —C(O)NR$^h$R$^h$, —SR$^h$, —S(O)R$^h$, —S(O)$_2$R$^h$, C$_{1-4}$alkyl, C$_{1-4}$haloalkyl, C$_{3-7}$cycloalkyl and 3-7 membered heterocycloalkyl;

$R^5$ is selected from among C$_{1-6}$alkyl, —OC$_{1-6}$alkyl, C$_{1-6}$haloalkyl, —OC$_{1-6}$haloalkyl, C$_{3-7}$cycloalkyl, 3-7 membered heterocycloalkyl, all the above-mentioned groups optionally being substituted by C$_{1-6}$alkyl, —CN or —OH;

a) where partial structure (i) is present one of the groups $R^6$, $R^7$ or $R^8$ and b) where partial structure (ii) is present one of the groups $R^6$ or $R^7$ has one of the partial structures (iii) to (vi)

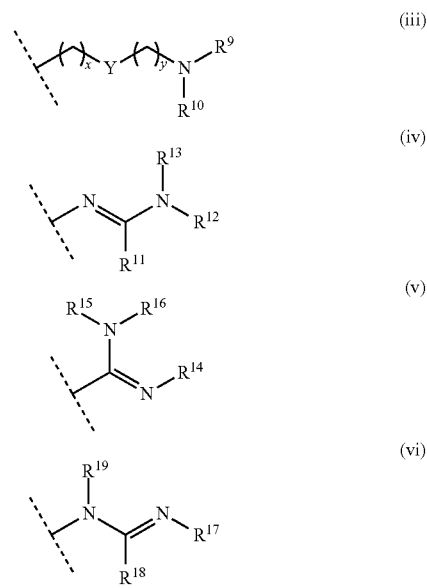

and in case a) the other two groups, each independently of one another, and in case b) the second group is/are selected from among hydrogen, C$_{1-6}$alkyl, —OC$_{1-6}$alkyl, —OH, —CN, —NHC$_{1-6}$alkyl, —N(C$_{1-6}$alkyl)$_2$ and halogen or c) where partial structure (i) is present $R^5$ denotes a C$_{1-6}$alkyl or C$_{3-4}$cycloalkyl substituted by a substituent —CN and $R^6$, $R^7$ and $R^8$ each denote hydrogen;

$R^9$ is selected from among hydrogen and $C_{1-6}$alkyl, $R^{10}$ is selected from among $R^a$ and —$OR^a$, or the group —$NR^9R^{10}$ in all denotes a nitrogen-containing, 3-14 membered heterocycloalkyl or 5-12 membered heteroaryl, optionally substituted by one or more identical or different group(s) selected from among $R^a$ and $R^b$;

$R^{11}$, $R^{12}$ and $R^{13}$ each independently of one another correspond to a group $R^a$, or $R^{11}$ corresponds to a group $R^a$ and the group —$NR^{12}R^{13}$ together denotes a nitrogen-containing 3-14-membered heterocycloalkyl, optionally substituted by one or more identical or different group(s) selected from among $R^a$ and $R^b$, or $R^{11}$ and $R^{12}$ together with the atoms to which they are bound form a nitrogen-containing, 4-14 membered heterocycloalkyl, optionally substituted by one or more identical or different group(s) selected from among $R^a$ and $R^b$, and $R^{13}$ corresponds to a group $R^a$;

$R^{14}$, $R^{15}$ and $R^{16}$ each independently of one another correspond to a group $R^a$, or $R^{14}$ corresponds to a group $R^a$ and the group $NR^{15}R^{16}$ together denotes a nitrogen-containing 3-14-membered heterocycloalkyl, optionally substituted by one or more identical or different group(s) selected from among $R^a$ and $R^b$, or $R^{14}$ and $R^{15}$ together with the atoms to which they are bound form a nitrogen-containing, 4-14 membered heterocycloalkyl, optionally substituted by one or more identical or different group(s) selected from among $R^a$ and $R^b$, and $R^{16}$ corresponds to a group $R^a$;

$R^{17}$, $R^{18}$ and $R^{19}$ each independently of one another correspond to a group $R^a$, or $R^{17}$ and $R^{18}$ together with the atoms to which they are bound form a nitrogen-containing, 3-14 membered heterocycloalkyl, optionally substituted by one or more identical or different group(s) selected from among $R^a$ and $R^b$, and $R^{19}$ corresponds to a group $R^a$, or $R^{17}$ and $R^{19}$ together with the atoms to which they are bound form a nitrogen-containing, 4-14 membered heterocycloalkyl, optionally substituted by one or more identical or different group(s) selected from among $R^a$ and $R^b$, and $R^{18}$ corresponds to a group $R^a$, or $R^{18}$ and $R^{19}$ together with the atoms to which they are bound form a nitrogen-containing, 4-14 membered heterocycloalkyl, optionally substituted by one or more identical or different group(s) selected from among $R^a$ and $R^b$, and $R^{17}$ corresponds to a group $R^a$;

L is selected from among —C(O)NH—, —NHC(O)—, —C(S)NH—, —NHC(S)—, —C(O)—, —C(S)—, —NH—, —S(O)—, —S(O)O—, —S(O)$_2$—, —S(O)$_2$O—, —S(O)NH—, —S(O)$_2$NH—, —OS(O)—, —OS(O)$_2$—, —OS(O)NH—, —OS(O)$_2$NH—, —C(O)O—, —C(O)S—, —C(NH)NH—, —OC(O)—, —OC(O)O—, —OC(O)NH—, —SC(O)—, —SC(O)O—, —SC(O)NH—, —NHC(NH)—, —NHS(O)—, —NHS(O)O—, —NHS(O)$_2$—, —NHS(O)$_2$O—, —NHS(O)$_2$NH—, —NHC(O)O—, —NHC(O)NH— and —NHC(S)NH— or denotes a bond;

Y is selected from among —O— and —S— or denotes a bond;

x and y each independently of one another have the value 0, 1, 2 or 3;

each $R^a$ independently of one another in each case denotes hydrogen or a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl;

each $R^b$ denotes a suitable substituent and is independently selected in each case from among —$OR^c$, —$SR^c$, —$NR^cR^c$, —$ONR^cR^c$, —$N(OR^c)R^c$, —$NR^gNR^cR^c$, halogen, —CN, —NC, —OCN, —SCN, —NO, —NO$_2$, —N$_3$, —C(O)$R^c$, —C(O)$OR^c$, —C(O)$NR^cR^c$, —C(O)$SR^c$, —C(O)$NR^g$ $NR^cR^c$, —C(O)$NR^gOR^c$, —[C(O)]$_2NR^cR^c$, —[C(O)$NR^g$]$_2R^c$, —C(S)$R^c$, —C(S)$OR^c$, —C(S)$NR^cR^c$, —C(S)$SR^c$, —C($NR^g$)$R^c$, —C($NR^g$)$R^c$, —N=$CR^cR^c$, —($NR^g$)$OR^c$, —C($NR^g$)$NR^cR^c$, —C($NR^g$)$SR^c$, —C($NR^g$) $NR^gNR^cR^c$, —C($NOR^g$)$R^c$, —C($NOR^g$)$NR^cR^c$, —C($NNR^gR^g$)$R^c$, —C[$NNR^gC(O)NR^gR^g$]$R^c$, —OS(O)$R^c$, —OS(O)$OR^c$, —OS(O)$NR^cR^c$, —OS(O)$_2R^c$, —OS(O)$_2OR^c$, —OS(O)$_2NR^cR^c$, —OC(O)$R^c$, —OC(O)$OR^c$, —OC(O)$SR^c$, —OC(O)$NR^cR^c$, —O[C(O)]$_2NR^cR^c$, —O[C(O)$NR^g$]$_2NR^cR^c$, —OC(S)$R^c$, —OC($NR^g$)$R^c$, —OC ($NR^g$)$NR^cR^c$, —ONR$^c$C(O)$R^c$, —S(O)$R^c$, —S(O)$OR^c$, —S(O)$NR^cR^c$, —S(O)$_2R^c$, —S(O)$_2OR^c$, —S(O)$_2$ $NR^cR^c$, —[S(O)$_2$]$_2NR^cR^c$, —SC(O)$R^c$, —SC(O)$OR^c$, —SC (O)$NR^cR^c$, —SC(S)$R^c$, —SC($NR^g$)$R^c$, —SC($NR^g$)$NR^cR^c$, —$NR^g$C(O)$R^c$, —$NR^g$C(O)$OR^c$, —$NR^g$C(O)$NR^cR^c$, 13 $NR^g$C(O)$SR^c$, —$NR^g$C(O)$NR^gNR^cR^c$, —$NR^g$C(S)$R^c$, —$NR^g$C(S)$NR^cR^c$, —$NR^g$C($NR^g$)$R^c$, —N=$CR^gNR^cR^c$, —$NR^g$C($NR^g$)$OR^c$, —$NR^g$C($NR^g$)$NR^cR^c$, —$NR^g$C($NR^g$) $SR^c$, —$NR^g$C($NOR^g$)$R^c$, —$NR^g$S(O)$R^c$, —$NR^g$S(O)$OR^c$, —$NR^g$S(O)$_2R^c$, —$NR^g$S(O)$_2OR^c$, —$NR^g$S(O)$_2NR^cR^c$, —$NR^gNR^g$C(O)$R^c$, —$NR^gNR^g$C(O)$NR^cR^c$, —$NR^gNR^g$C ($NR^g$)$R^c$, —$NR^g$[C(O)]$_2R^c$, —$NR^g$[C(O)]$_2OR^c$, —$NR^g$[C (O)]$_2NR^cR^c$, —[$NR^g$C(O)]$_2R^c$, —[$NR^g$C(O)]$_2OR^c$, —$NR^g$ [S(O)$_2$]$_2R^c$, —N($OR^g$)C(O)$R^c$, —N[C(O)$R^c$]$NR^cR^c$, —N[C (O)$R^c$]$_2$, —N[S(O)$_2R^c$]$_2$, —N{[C(O)]$_2R^c$}$_2$, —N{[C(O)]$_2OR^c$}$_2$ and —N{[C(O)]$_2NR^cR^c$}$_2$ as well as the bivalent substituents =O, =S, =$NR^g$, =$NOR^g$, =$NNR^gR^g$ and =$NNR^gC(O)NR^gR^g$, while these bivalent substituents may only be substituents in non-aromatic ring systems;

each $R^c$ independently of one another in each case denotes hydrogen or a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl;

each $R^d$ is a suitable substituent and is independently selected in each case from among —$OR^e$, —$SR^e$, —$NR^eR^e$, —$ONR^eR^e$, —$N(OR^e)R^e$, —$N(R^g)NR^eR^e$, halogen, —CN, —NC, —OCN, —SCN, —NO, —NO$_2$, —N$_3$, —C(O)$R^e$, —C(O)$OR^e$, —C(O)$NR^eR^e$, —C(O)$SR^e$, —C(O) $NR^gNR^eR^e$, —C(O)$NR^gOR^e$, —[C(O)]$_2NR^eR^e$, —[C(O) $NR^g$]$_2R^e$, —C(S)$R^e$, —C(S)$OR^e$, —C(S)$NR^eR^e$, —C(S)$SR^e$, —C($NR^g$)$R^e$, —N=$CR^eR^e$, —C($NR^g$)$OR^e$, —C($NR^g$)$NR^eR^e$, —C($NR^g$)$SR^e$, —C($NR^g$)$NR^gNR^eR^e$, —C($NOR^g$)$R^e$, —C($NOR^g$)$NR^eR^e$, —C($NNR^gR^g$)$R^e$, —C[$NNR^gC(O)NR^gR^g$]$R^e$, —OS(O)$R^e$, —OS(O)$OR^e$, —OS(O)$NR^eR^e$, —OS(O)$_2R^e$, —OS(O)$_2OR^e$, —OS(O)$_2NR^eR^e$, —OC(O)$R^e$, —OC(O)$OR^e$, —OC(O)$SR^e$, —OC(O)$NR^eR^e$, —O[C(O)]$_2NR^eR^e$, —O[C(O)$NR^g$]$_2$ $NR^eR^e$, —OC(S)$R^e$, —OC($NR^g$)$R^e$, —OC($NR^g$)$NR^eR^e$, —ONR$^g$C(O)$R^e$, —S(O)$R^e$, —S(O)$OR^e$, —S(O)$NR^eR^e$, —S(O)$_2R^e$, —S(O)$_2OR^e$, —S(O)$_2NR^eR^e$, —[S(O)$_2$]$_2$ NR$^e$R$^e$, —SC(O)R$^e$, —SC(O)OR$^e$, —SC(O)NR$^e$R$^e$, —SC(S)R$^e$, —SC(NR$^g$)R$^e$, —SC(NR$^g$)NR$^e$R$^e$, —NR$^g$C(O)R$^e$, —NR$^g$C(O)OR$^e$, —NR$^g$C(O)NR$^e$R$^e$, —NR$^g$C(O)SR$^e$, —NR$^g$C(O)NR$^g$NR$^e$R$^e$, —NR$^g$C(S)R$^e$, —NR$^g$C(S)NR$^e$R$^e$, —NR$^g$C(NR$^g$)R$^e$, —N=CR$^e$NR$^e$R$^e$, —NR$^g$C(NR$^g$)OR$^e$, —NR$^g$C(NR$^g$)NR$^e$R$^e$, —NR$^g$C(NR$^g$)SR$^e$, —NR$^g$C(NOR$^g$)R$^e$, —NR$^g$S(O)R$^e$, —NR$^g$S(O)OR$^e$, —NR$^g$S(O)$_2$R$^e$, —NR$^g$S(O)$_2$OR$^e$, —NR$^g$S(O)$_2$NR$^e$R$^e$, —NR$^g$NR$^g$C(O)R$^e$, —NR$^g$NR$^g$C(O)NR$^e$R$^e$, —NR$^g$NR$^g$C(NR$^g$)R$^e$, —NR$^g$[C(O)]$_2$R$^e$, —NR$^g$[C(O)]$_2$OR$^e$, —NR$^g$[C(O)]$_2$NR$^e$R$^e$, —[NR$^g$C(O)]$_2$R$^e$, —[NR$^g$C(O)]$_2$OR$^e$, —NR$^g$[S(O)$_2$]$_2$R$^e$, —N(OR$^g$)C(O)R$^e$, —N[C(O)R$^e$]NR$^e$R$^e$, —N[C(O)R$^e$]$_2$, —N[S(O)$_2$R$^e$]$_2$, —N{[C(O)]$_2$R$^e$}$_2$, —N{[C(O)]$_2$OR$^e$}$_2$ and —N{[C(O)]$_2$NR$^e$R$^e$}$_2$ as well as the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each R$^e$ independently of one another in each case denotes hydrogen or a group optionally substituted by one or more identical or different R$^f$ and/or R$^g$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl;

each R$^f$ is a suitable substituent and is independently selected in each case from among —OR$^g$, —SR$^g$, —NR$^g$R$^g$, —ONR$^g$R$^g$, —N(OR$^g$)R$^g$, —N(R$^h$)NR$^g$R$^g$, halogen, —CN, —NC, —OCN, —SCN, —NO, —NO$_2$, —N$_3$, —C(O)R$^g$, —C(O)OR$^g$, —C(O)NR$^g$R$^g$, —C(O)SR$^g$, —C(O)NR$^g$NR$^g$R$^g$, —C(O)NR$^h$OR$^g$, —[C(O)]$_2$NR$^g$R$^g$, —[C(O)NR$^h$]$_2$R$^g$, —C(S)R$^g$, —C(S)OR$^g$, —C(S)NR$^g$R$^g$, —C(S)SR$^g$, —C(NR$^h$)R$^g$, —N=CR$^g$R$^g$, —C(NR$^h$)OR$^g$, —C(NR$^h$)NR$^g$R$^g$, —C(NR$^h$)SR$^g$, —C(NR$^h$)NR$^h$NR$^g$R$^g$, —C(NOR$^h$)R$^g$, —C(NOR$^h$)NR$^g$R$^g$, —C(NNR$^h$R$^h$)R$^g$, —C[NNR$^h$C(O)NR$^h$R$^h$]R$^g$, —OS(O)R$^g$, —OS(O)OR$^g$, —OS(O)NR$^g$R$^g$, —OS(O)$_2$R$^g$, —OS(O)$_2$OR$^g$, —OS(O)$_2$NR$^g$R$^g$, —OC(O)R$^g$, —OC(O)OR$^g$, —OC(O)SR$^g$, —OC(O)NR$^g$R$^g$, —O[C(O)]$_2$NR$^g$R$^g$, —O[C(O)NR$^h$]$_2$NR$^g$R$^g$, —OC(S)R$^g$, —OC(NR$^h$)R$^g$, —OC(NR$^h$)NR$^g$R$^g$, —ONR$^h$C(O)R$^g$, —S(O)R$^g$, —S(O)OR$^g$, —S(O)NR$^g$R$^g$, —S(O)$_2$R$^g$, —S(O)$_2$OR$^g$, —S(O)$_2$NR$^g$R$^g$, —[S(O)$_2$]$_2$NR$^g$R$^g$, —SC(O)R$^g$, —SC(O)OR$^g$, —SC(O)NR$^g$R$^g$, —SC(S)R$^g$, —SC(NR$^h$)R$^g$, —SC(NR$^h$)NR$^g$R$^g$, —NR$^h$C(O)R$^g$, —NR$^h$C(O)OR$^g$, —NR$^h$C(O)NR$^g$R$^g$, —NR$^h$C(O)SR$^g$, —NR$^h$C(O)NR$^h$NR$^g$R$^g$, —NR$^h$C(S)R$^g$, —NR$^h$C(S)NR$^g$R$^g$, —NR$^h$C(NR$^h$)R$^g$, —N=CR$^g$NR$^g$R$^g$, —NR$^h$C(NR$^h$)OR$^g$, —NR$^h$C(NR$^h$)NR$^g$R$^g$, —NR$^h$C(NR$^h$)SR$^g$, —NR$^h$C(NOR$^h$)R$^g$, —NR$^h$S(O)R$^g$, —NR$^h$S(O)OR$^g$, —NR$^h$S(O)$_2$R$^g$, —NR$^h$S(O)$_2$OR$^g$, —NR$^h$S(O)$_2$NR$^g$R$^g$, —NR$^g$NR$^h$C(O)R$^g$, —NR$^h$NR$^h$C(O)NR$^g$R$^g$, —NR$^h$NR$^h$C(NR$^h$)R$^g$, —NR$^h$[C(O)]$_2$R$^g$, —NR$^h$[C(O)]$_2$OR$^g$, —NR$^h$[C(O)]$_2$NR$^g$R$^g$, —[NR$^h$C(O)]$_2$R$^g$, —[NR$^h$C(O)]$_2$OR$^g$, —NR$^h$[S(O)$_2$]$_2$R$^g$, —)OR$^h$)C(O)R$^g$, —N[C(O)R$^g$]NR$^g$R$^g$, —N[C(O)R$^g$]$_2$, —N[S(O)$_2$R$^g$]$_2$, —N{[C(O)]$_2$R$^g$}$_2$, —N{[C(O)]$_2$OR$^g$}$_2$ and —N{[C(O)]$_2$NR$^g$R$^g$}$_2$ as well as the bivalent substituents =O, =S, =NR$^h$, =NOR$^h$, =NNR$^h$R$^h$ and =NNR$^h$C(O)NR$^h$R$^h$, while these bivalent substituents may only be substituents in non-aromatic ring systems;

each R$^g$ in each case independently of one another denote hydrogen or a group optionally substituted by one or more identical or different R$^h$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl;

each R$^h$ is selected independently of one another in each case from among hydrogen, C$_{1-6}$alkyl, 2-6 membered heteroalkyl, C$_{1-6}$haloalkyl, C$_{3-10}$cycloalkyl, C$_{4-16}$cycloaklalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl;

while the compounds (1) may optionally also be present in the form of the tautomers, the racemates, the enantiomers, the diastereomers, the mixtures thereof, the polymorphs thereof or as pharmacologically acceptable salts of all the above-mentioned forms;

with the proviso that the compound

N-(5-tent-butyl-3-{[(2-dimethylamino-ethyl)-methyl-amino]-methyl}-2-methoxy-phenyl)-4-methyl-3-(4-pyridin-3-yl-[1.2.3]triazol-1-yl)-benzamide is excluded.

In one aspect (A1) the invention relates to compounds of general formula (1)

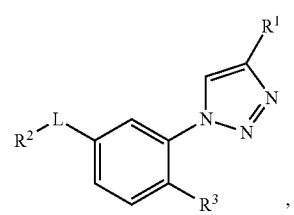

wherein

R$^1$ denotes a 5-10-membered heteroaryl, optionally substituted by one or more identical or different group(s), each independently selected from among R$^a$ and R$^b$;

R$^2$ has the partial structure (i) or (ii)

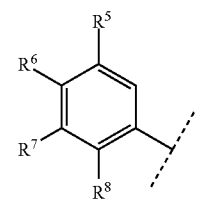

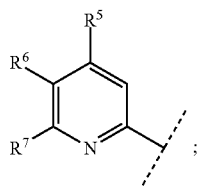

R$^3$ is selected from among hydrogen, halogen, —CN, —NO$_2$, —NR$^h$R$^h$, —OR$^h$, —C(O)R$^h$, —C(O)NR$^h$R$^h$, —SR$^h$, —S(O)R$^h$, —S(O)$_2$R$^h$, C$_{1-4}$alkyl, C$_{1-4}$haloalkyl, C$_{3-7}$cycloalkyl and 3-7 membered heterocycloalkyl;

R$^5$ is selected from among C$_{1-6}$alkyl, —OC$_{1-6}$alkyl, C$_{1-6}$haloalkyl, —OC$_{1-6}$haloalkyl, C$_{3-7}$cycloalkyl, 3-7 membered heterocycloalkyl, all the above-mentioned groups optionally being substituted by C$_{1-6}$alkyl, —CN or —OH;

a) where partial structure (i) is present one of the groups $R^6$, $R^7$ or $R^8$
and
b) where partial structure (ii) is present one of the groups $R^6$ or $R^7$ has one of the partial structures (iii) to (vi)

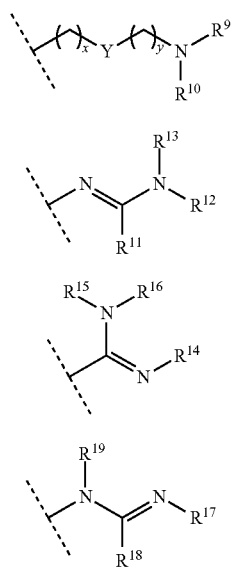

and in case a) the other two groups in each case independently of one another and in case b) the second group is/are selected from among hydrogen, $C_{1-6}$alkyl, —$OC_{1-6}$alkyl, —OH, —CN, —$NHC_{1-6}$alkyl, —$N(C_{1-6}$alkyl$)_2$ and halogen;
$R^9$ is selected from among hydrogen and $C_{1-6}$alkyl,
$R^{10}$ is selected from among $R^a$ and —$OR^a$,
or
the group —$NR^9R^{10}$ altogether denotes a nitrogen-containing, 3-14 membered heterocycloalkyl or 5-12 membered heteroaryl, optionally substituted by one or more identical or different group(s) selected from among $R^a$ and $R^b$;
$R^{11}$, $R^{12}$ and $R^{13}$ each independently of one another correspond to a group $R^a$,
or
$R^{11}$ corresponds to a group $R^a$ and the group —$NR^{12}R^{13}$ altogether denotes a nitrogen-containing 3-14-membered heterocycloalkyl, optionally substituted by one or more identical or different group(s) selected from among $R^a$ and $R^b$,
or
$R^{11}$ and $R^{12}$ together with the atoms to which they are bound form a nitrogen-containing, 4-14 membered heterocycloalkyl, optionally substituted by one or more identical or different group(s) selected from among $R^a$ and $R^b$, and $R^{13}$ corresponds to a group $R^a$;
$R^{14}$, $R^{15}$ and $R^{16}$ each independently of one another correspond to a group $R^a$,
or
$R^{14}$ corresponds to a group $R^a$ and the group $NR^{15}R^{16}$ altogether denotes a nitrogen-containing 3-14-membered heterocycloalkyl, optionally substituted by one or more identical or different group(s) selected from among $R^a$ and $R^b$,
or
$R^{14}$ and $R^{15}$ together with the atoms to which they are bound form a nitrogen-containing, 4-14 membered heterocycloalkyl, optionally substituted by one or more identical or different group(s) selected from among $R^a$ and $R^b$, and $R^{16}$ corresponds to a group $R^a$;

$R^{17}$, $R^{18}$ and $R^{19}$ each independently of one another correspond to a group $R^a$,
or
$R^{17}$ and $R^{18}$ together with the atoms to which they are bound form a nitrogen-containing, 3-14 membered heterocycloalkyl, optionally substituted by one or more identical or different group(s) selected from among $R^a$ and $R^b$, and $R^{19}$ corresponds to a group $R^a$,
or
$R^{17}$ and $R^{19}$ together with the atoms to which they are bound form a nitrogen-containing, 4-14 membered heterocycloalkyl, optionally substituted by one or more identical or different group(s) selected from among $R^a$ and $R^b$, and $R^{18}$ corresponds to a group $R^a$,
or
$R^{18}$ and $R^{19}$ together with the atoms to which they are bound form a nitrogen-containing, 4-14 membered heterocycloalkyl, optionally substituted by one or more identical or different group(s) selected from among $R^a$ and $R^b$, and $R^{17}$ corresponds to a group $R^a$;
L is selected from among —C(O)NH—, —NHC(O)—, —C(S)NH—, —NHC(S)—, —C(O)—, —C(S)—, —NH—, —S(O)—, —S(O)O—, —S(O)$_2$—, —S(O)$_2$O—, —S(O)NH—, —S(O)$_2$NH—, —OS(O)—, —OS(O)$_2$—, —OS(O)NH—, —OS(O)$_2$NH—, —C(O)O—, —C(O)S—, —C(NH)NH—, —OC(O)—, —OC(O)O—, —OC(O)NH—, —SC(O)—, —SC(O)O—, —SC(O)NH—, —NHC(NH)—, —NHS(O)—, —NHS(O)O—, —NHS(O)$_2$—, —NHS(O)$_2$O—, —NHS(O)$_2$NH—, —NHC(O)O—, —NHC(O)NH— and —NHC(S)NH— or denotes a bond;
Y is selected from among —O— and —S— or denotes a bond;
x and y each independently of one another have the value 0, 1, 2 or 3;
each $R^a$ denotes, independently of one another in each case, hydrogen or a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl;
each $R^b$ denotes a suitable substituent and is independently selected in each case from among —$OR^c$, —$SR^c$, —$NR^cR^c$, —$ONR^cR^c$, —$N(OR^c)R^c$, —$NR^gR^cR^c$, halogen, —CN, —NC, —OCN, —SCN, —NO, —NO$_2$, —N$_3$, —C(O)$R^c$, —C(O)$OR^c$, —C(O)$NR^cR^c$, —C(O)$SR^c$, —C(O)$NR^gNR^cR^c$, —C(O)$NR^gOR^c$, —[C(O)]$_2NR^cR^c$, —[C(O)$NR^g$]$_2R^c$, —C(S)$R^c$, —C(S)$OR^c$, —C(S)$NR^cR^c$, —C(S)$SR^c$, —C($NR^g$)$R^c$, —N=$CR^cR^c$, —C($NR^g$)$OR^c$, —C($NR^g$)$NR^cR^c$, —C($NR^g$)$SR^c$, —C($NR^g$)$NR^gNR^cR^c$, —C($NOR^g$)$R^c$, —C($NOR^g$)$NR^cR^c$, —C($NNR^gR^g$)$R^c$, —C[$NNR^gC(O)NR^gR^g$]$R^c$, —OS(O)$R^c$, —OS(O)$OR^c$, —OS(O)$NR^cR^c$, —OC(O)$_2R^c$, —OS(O)$_2OR^c$, —OS(O)$_2NR^cR^c$, —OC(O)$R^c$, —OC(O)$OR^c$, —OC(O)$SR^c$, —OC(O)$NR^cR^c$, —O[C(O)]$_2NR^cR^c$, —O[C(O)$NR^g$]$_2NR^cR^c$, —OC(S)$R^c$, —OC($NR^g$)$R^c$, —OC($NR^g$)$NR^cR^c$, —$ONR^gC(O)R^c$, —S(O)$R^c$, —S(O)$OR^c$, —S(O)$NR^cR^c$, —S(O)$_2R^c$, —S(O)$_2OR^c$, —S(O)$_2NR^cR^c$, —[S(O)$_2$]$_2NR^cR^c$, —SC(O)$R^c$, —SC(O)$OR^c$, —SC(O)$NR^cR^c$, —SC(S)$R^c$, —SC($NR^g$)$R^c$, —SC($NR^g$)$NR^cR^c$, —$NR^gC(O)R^c$, —$NR^gC(O)OR^c$, —$NR^gC(O)NR^cR^c$, —$NR^gC(O)SR^c$, —$NR^gC(O)NR^gNR^cR^c$, —$NR^gC(S)R^c$, —$NR^gC(S)NR^cR^c$, —$NR^gC(NR^g)R^c$, —N=$CR^cR^c$, —$NR^gC(NR^g)OR^c$, —$NR^gC(NR^g)NR^cR^c$, —$NR^gC(NR^g)SR^c$, —$NR^gC(NOR^g)R^c$, —$NR^gS(O)R^c$, —$NR^gS(O)OR^c$, —$NR^gS(O)_2R^c$, —$NR^gS(O)_2OR^c$, —$NR^gS(O)_2NR^cR^c$, —$NR^gNR^gC(O)R^c$, —NR$^g$NR$^g$C(O)NR$^c$R$^c$, —NR$^g$NR$^g$C(NR$^g$)R$^c$, —NR$^g$[C(O)]$_2$R$^c$, —NR$^g$[C(O)]$_2$OR$^c$, —NR$^g$[C(O)]$_2$NR$^c$R$^c$, —[NR$^g$C(O)]$_2$R$^c$, —[NR$^g$C(O)]$_2$OR$^c$, —NR$^g$[S(O)$_2$]$_2$R$^c$, —N(OR$^g$)C(O)R$^c$, —N[C(O)R$^c$]NR$^c$R$^c$, —N[C(O)R$^c$]$_2$, —N[S(O)$_2$R$^c$]$_2$, —N{[C(O)]$_2$R$^c$}$_2$, —N{[C(O)]$_2$OR$^c$}$_2$ and —N{[C(O)]$_2$NR$^c$R$^c$}$_2$ as well as the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each R$^c$ denotes, independently of one another in each case, hydrogen or a group optionally substituted by one or more identical or different R$^d$ and/or R$^e$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl;

each R$^d$ denotes a suitable substituent and is independently selected in each case from among —OR$^e$, —SR$^e$, —NR$^e$R$^e$, —ONR$^e$R$^e$, —N(OR$^e$)R$^e$, —N(R$^g$)NR$^e$R$^e$, halogen, —CN, —NC, —OCN, —SCN, —NO, —NO$_2$, —N$_3$, —C(O)R$^e$, —C(O)OR$^e$, —C(O)NR$^e$R$^e$, —C(O)SR$^e$, —C(O)NR$^g$NR$^e$R$^e$, —C(O)NR$^g$OR$^e$, —[C(O)]$_2$NR$^e$R$^e$, —[C(O)NR$^g$]$_2$R$^e$, —C(S)R$^e$, —C(S)OR$^e$, —C(S)NR$^e$R$^e$, —C(S)SR$^e$, —C(NR$^g$)R$^e$, —N=CR$^e$R$^e$, —C(NR$^g$)OR$^e$, —C(NR$^g$)NR$^e$R$^e$, —C(NR$^g$)SR$^e$, —C(NR$^g$)NR$^g$NR$^e$R$^e$, —C(NOR$^g$)R$^e$, —C(NOR$^g$)NR$^e$R$^e$, —C(NNR$^g$R$^g$)R$^e$, —C[NNR$^g$C(O)NR$^g$R$^g$]R$^e$, —OS(O)R$^e$, —OS(O)OR$^e$, —OS(O)NR$^e$R$^e$, —OS(O)$_2$R$^e$, —OS(O)$_2$OR$^e$, —OS(O)$_2$NR$^e$R$^e$, —OC(O)R$^e$, —OC(O)OR$^e$, —OC(O)SR$^e$, —OC(O)NR$^e$R$^e$, —O[C(O)]$_2$NR$^e$R$^e$, —O[C(O)NR$^g$]$_2$NR$^e$R$^e$, —OC(S)R$^e$, —OC(NR$^g$)R$^e$, —OC(NR$^g$)NR$^e$R$^e$, —ONR$^g$C(O)R$^e$, —S(O)R$^e$, —S(O)OR$^e$, —S(O)NR$^e$R$^e$, —S(O)$_2$R$^e$, —S(O)$_2$R$^e$, —S(O)$_2$OR$^e$, —S(O)$_2$NR$^e$R$^e$, [S(O)$_2$]$_2$NR$^e$R$^e$, —SC(O)R$^e$, —SC(O)OR$^e$, —SC(O)NR$^e$R$^e$, —SC(S)R$^e$, —SC(NR$^g$)R$^e$, —SC(NR$^g$)NR$^e$R$^e$, —NR$^g$C(O)R$^e$, —NR$^g$C(O)OR$^e$, —NR$^g$C(O)NR$^e$R$^e$, —NR$^g$C(O)SR$^e$, —NR$^g$C(O)NR$^g$NR$^e$R$^e$, —NR$^g$C(S)R$^e$, —NR$^g$C(S)NR$^e$R$^e$, —NR$^g$C(NR$^g$)R$^e$, —N=CR$^e$NR$^e$R$^e$, —NR$^g$C(NR$^g$)OR$^e$, —NR$^g$C(NR$^g$)NR$^e$R$^e$, —NR$^g$C(NR$^g$)SR$^e$, —NR$^g$C(NOR$^g$)R$^e$, —NR$^g$S(O)R$^e$, —NR$^g$S(O)OR$^e$, —NR$^g$S(O)$_2$R$^e$, —NR$^g$S(O)$_2$OR$^e$, —NR$^g$S(O)$_2$NR$^e$R$^e$, —NR$^g$NR$^g$C(O)R$^e$, —NR$^g$NR$^g$C(O)NR$^e$R$^e$, —NR$^g$NR$^g$C(NR$^g$)R$^e$, —NR$^g$[C(O)]$_2$R$^e$, —NR$^g$[C(O)]$_2$OR$^e$, —NR$^g$[C(O)]$_2$NR$^e$R$^e$, —[NR$^g$C(O)]$_2$R$^e$, —[NR$^g$C(O)]$_2$OR$^e$, —NR$^g$[S(O)$_2$]$_2$R$^e$, —N(OR$^g$)C(O)R$^e$, —N[C(O)R$^e$]NR$^e$R$^e$, —N[C(O)R$^e$]$_2$, —N[S(O)$_2$R$^e$]$_2$, —N{[C(O)]$_2$R$^e$}$_2$, —N{[C(O)]$_2$OR$^e$}$_2$ and —N{[C(O)]$_2$NR$^e$R$^e$}$_2$ as well as the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each R$^e$ denotes, independently of one another in each case, hydrogen or a group optionally substituted by one or more identical or different R$^f$ and/or R$^g$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl;

each R$^f$ denotes a suitable substituent and is independently selected in each case from among —OR$^g$, —SR$^g$, —NR$^g$R$^g$, —ONR$^g$R$^g$, —N(OR$^g$)R$^g$, —N(R$^h$)NR$^g$R$^g$, halogen, —CN, —NC, —OCN, —SCN, —NO, —NO$_2$, —N$_3$, —C(O)R$^g$, —C(O)OR$^g$, —C(O)NR$^g$R$^g$, —C(O)SR$^g$, —C(O)NR$^h$NR$^g$R$^g$, —C(O)NR$^h$OR$^g$, —[C(O)]$_2$NR$^g$R$^g$, —[C(O)NR$^h$]$_2$R$^g$, —C(S)R$^g$, —C(OS)OR$^g$, —C(S)NR$^g$R$^g$, —C(S)SR$^g$, —C(NR$^h$)R$^g$, —N=CR$^g$R$^g$, —C(NR$^h$)OR$^g$, —C(NR$^h$)NR$^g$R$^g$, —C(NR$^h$)SR$^g$, —C(NR$^h$)NR$^h$NR$^g$R$^g$, —C(NOR$^h$)R$^g$, —C(NOR$^h$)NR$^g$R$^g$, —C(NNR$^h$R$^h$)R$^g$, —C[NNR$^h$C(O)NR$^h$R$^h$]R$^g$, —OS(O)R$^g$, —OS(O)OR$^g$, —OS(O)NR$^g$R$^g$, —OS(O)$_2$R$^g$, —OS(O)$_2$OR$^g$, —OS(O)$_2$NR$^g$R$^g$, —OC(O)R$^g$, —OC(O)OR$^g$, —OC(O)SR$^g$, —OC(O)NR$^g$R$^g$, —O[C(O)]$_2$NR$^g$R$^g$, —O[C(O)NR$^h$]$_2$NR$^g$R$^g$, —OC(S)R$^g$, —OC(NR$^h$)R$^g$, —OC(NR$^h$)NR$^g$R$^g$, —ONR$^h$C(O)R$^g$, —S(O)R$^g$, —S(O)OR$^g$, —S(O)NR$^g$R$^g$, —S(O)$_2$R$^g$, —S(O)$_2$OR$^g$, —S(O)$_2$NR$^g$R$^g$, [S(O)$_2$]$_2$NR$^g$R$^g$, —SC(O)R$^g$, —SC(O)OR$^g$, —SC(O)NR$^g$R$^g$, —SC(S)R$^g$, —SC(NR$^h$)R$^g$, —SC(NR$^h$)NR$^g$R$^g$, —NR$^h$C(O)R$^g$, —NR$^h$C(O)OR$^g$, —NR$^h$C(O)NR$^g$R$^g$, —NR$^h$C(O)SR$^g$, —NR$^h$C(O)NR$^h$NR$^g$R$^g$, —NR$^h$C(S)R$^g$, —NR$^h$C(S)NR$^g$R$^g$, —NR$^h$C(NR$^h$)R$^g$, —N=CR$^g$NR$^g$R$^g$, —NR$^h$C(NR$^h$)OR$^g$, —NR$^h$C(NR$^h$)NR$^g$R$^g$, —NR$^h$C(NR$^h$)SR$^g$, —NR$^h$C(NOR$^h$)R$^g$, —NR$^h$S(O)R$^g$, —NR$^h$S(O)OR$^g$, —NR$^h$S(O)$_2$R$^g$, —NR$^h$S(O)$_2$OR$^g$, —NR$^h$S(O)$_2$NR$^g$R$^g$, —NR$^h$NR$^h$C(O)R$^g$, —NR$^h$NR$^h$C(O)NR$^g$R$^g$, —NR$^h$NR$^h$C(NR$^h$)R$^g$, —NR$^h$[C(O)]$_2$R$^g$, —NR$^h$[C(O)]$_2$OR$^g$, —NR$^h$[C(O)]$_2$NR$^g$R$^g$, —[NR$^h$C(O)]$_2$R$^g$, —[NR$^h$C(O)]$_2$OR$^g$, —NR$^h$[S(O)$_2$]$_2$R$^g$, —N(OR$^h$)C(O)R$^g$, —N[C(O)R$^g$]NR$^g$R$^g$, —N[C(O)R$^g$]$_2$, —N[S(O)$_2$R$^g$]$_2$, —N{[C(O)]$_2$R$^g$}$_2$, —N{[C(O)]$_2$OR$^g$}$_2$ and —N{[C(O)]$_2$NR$^g$R$^g$}$_2$ as well as the bivalent substituents =O, =S, =NR$^h$, =NOR$^h$, =NNR$^h$R$^h$ and =NNR$^h$C(O)NR$^h$R$^h$, while these bivalent substituents may only be substituents in non-aromatic ring systems;

each R$^g$ denotes, independently of one another in each case, hydrogen or a group optionally substituted by one or more identical or different R$^h$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl;

each R$^h$ is selected independently of one another in each case from among hydrogen, C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl;

while the compounds (1) may optionally also be in the form of the tautomers, the racemates, the enantiomers, the diastereomers, the mixtures thereof, the polymorphs thereof or as pharmacologically acceptable salts of all the above-mentioned forms;

with the proviso that the compound
N-(5-tert-butyl-3-{[(2-dimethylamino-ethyl)-methyl-amino]-methyl}-2-methoxy-phenyl)-4-methyl-3-(4-pyridin-3-yl-[1.2.3]triazol-1-yl)-benzamide
is excluded.

In another aspect (B1) the invention relates to compounds (1), wherein

R$^1$ denotes a heteroaryl selected from among pyridyl, pyrimidyl, thiazolyl, imidazolyl, pyrazolyl,

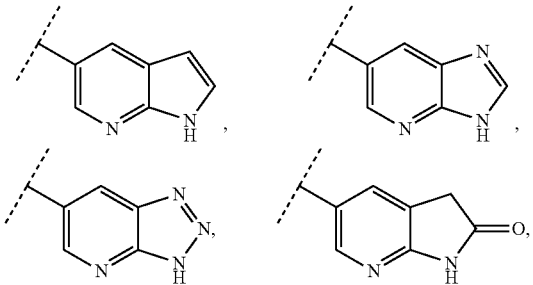

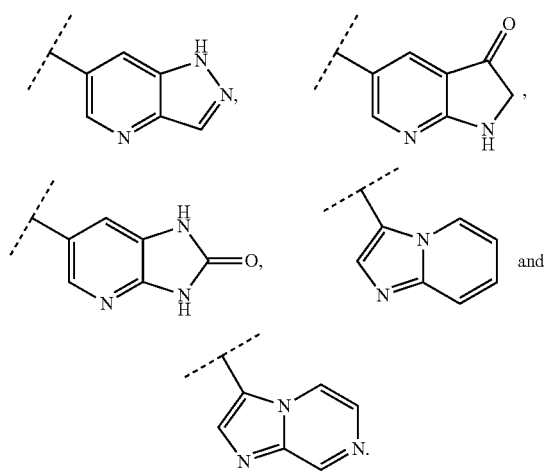

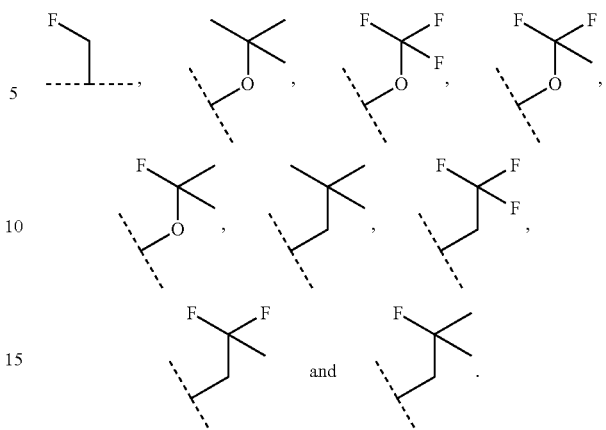

In another aspect (B2) the invention relates to compounds (1), wherein $R^1$ is mono- or polysubstituted by identical or different groups and the group(s) is/are each independently selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl, 4-14 membered heterocycloalkylalkyl, —OH, —OC$_{1-6}$alkyl, —NH$_2$, —NHC$_{1-6}$alkyl, —NHC$_{3-10}$cycloalkyl, —N(C$_{1-6}$alkyl)$_2$, —NHC(O)C$_{1-6}$alkyl, —NHC(O)OC$_{1-6}$alkyl, —NHC(O)NHC$_{1-6}$alkyl, halogen, —C(O)C$_{1-6}$alkyl, —C(O)C$_{3-10}$cycloalkyl, —SC$_{1-6}$alkyl, —C(O)OC$_{1-6}$alkyl, —C(O)NHC$_{1-6}$alkyl, —CN and —NHC(O)C$_{3-7}$cycloalkyl, all the above-mentioned groups optionally themselves being substituted by a substituent selected from among —OH, —OC$_{1-6}$alkyl, —OC$_{3-10}$cycloalkyl, —NH$_2$, —NHC$_{1-6}$alkyl, —NHC$_{1-6}$haloalkyl, —NHC$_{3-10}$cycloalkyl, —N(C$_{1-6}$alkyl)$_2$, halogen, —C(O)OC$_{1-6}$alkyl, C$_{1-6}$alkyl and 3-14 membered heterocycloalkyl.

In another aspect (C1) the invention relates to compounds (1), wherein $R^3$ is selected from among methyl, trifluoromethyl, ethyl, iso-propyl, 1-propyl, 1-butyl, 2-butyl, tent-butyl, fluorine, chlorine and bromine.

In another aspect (D1) the invention relates to compounds (1), wherein L is selected from among —C(O)NH— and —NHC(O)—.

In another aspect (A2) the invention relates to compounds (1), wherein $R^5$ is selected from among

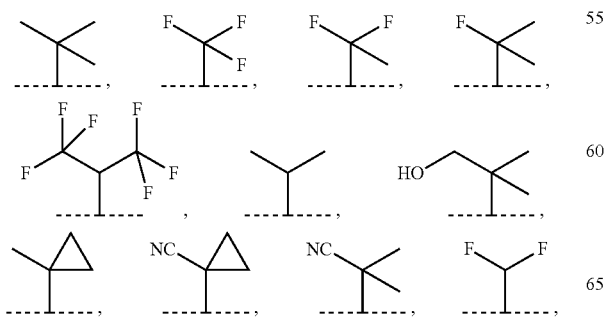

In another aspect (A3) the invention relates to compounds (1), wherein a) where partial structure (i) is present one of the groups $R^6$, $R^7$ or $R^8$ and b) where partial structure (ii) is present one of the groups $R^6$ or $R^7$ has one of the partial structures (iii-a) to (iii-h)

(iii-a)

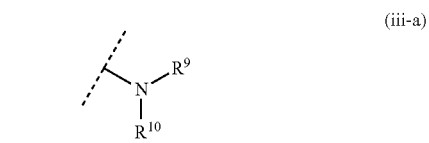

(iii-b)

(iii-c)

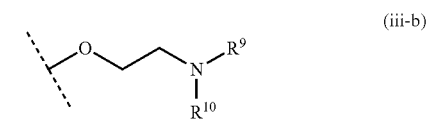

(iii-d)

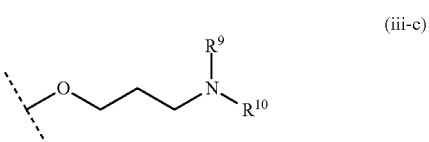

(iii-e)

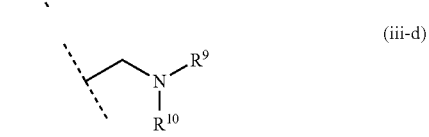

(iii-f)

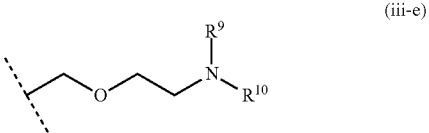

(iii-g)

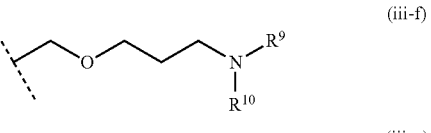

-continued (iii-h)

and $R^9$ and $R^{10}$ are as hereinbefore defined.

In another aspect (A4) the invention relates to compounds (1), wherein
a) where partial structure (i) is present
one of the groups $R^6$, $R^7$ or $R^8$ has the partial structure (iii-a), (iii-b) or (iii-c),
or
one of the groups $R^6$ or $R^7$ has the partial structure (iii-d),
or
$R^7$ has the partial structure (iii-e), (iii-f), (iii-g) or (iii-h);
and
b) where partial structure (ii) is present
$R^7$ has the partial structure (iii-a).

In another aspect (D2) the invention relates to compounds (1), wherein L denotes -NHC(O)—.

In another aspect (E1) the invention relates to compounds (1), wherein L denotes-C(O)NH—;
the partial structure (i) is present and
one of the groups $R^6$, $R^7$ or $R^8$ has the partial structure (iii-a)
or
$R^7$ has the partial structure (iii-d).

In another aspect (A5) the invention relates to compounds (1), wherein
a) where partial structure (i) is present
$R^7$ has the partial structure (iii-a), (iii-b), (iii-c), (iii-d), (iii-e), (iii-f), (iii-g) or (iii-h),
$R^6$ is selected from among hydrogen, $C_{1-6}$alkyl, —$OC_{1-6}$alkyl, chlorine and fluorine and
$R^8$ is selected from among hydrogen, $C_{1-6}$alkyl and —$OC_{1-6}$alkyl;
or
$R^6$ has the partial structure (iii-a), (iii-b), (iii-c), (iii-d), (iii-e), (iii-f), (iii-g) or (iii-h) and
$R^7$ and $R^8$ denote hydrogen;
or
$R^8$ has the partial structure (iii-a), (iii-b), (iii-c), (iii-d), (iii-e), (iii-f), (iii-g) or (iii-h) and
$R^6$ and $R^7$ denote hydrogen;
and
b) where partial structure (ii) is present
$R^7$ has the partial structure (iii-a), (iii-b), (iii-c), (iii-d), (iii-e), (iii-f), (iii-g) or (iii-h) and
$R^6$ denotes hydrogen.

In another aspect (A6) the invention relates to compounds (1), wherein
the partial structure (i) is present and
$R^7$ has the partial structure (iv).

In another aspect (D3) the invention relates to compounds (1), wherein L denotes—NHC(O)—.

In another aspect (A7) the invention relates to compounds (1), wherein $R^6$ and $R^8$ each denote hydrogen.

In another aspect (A8) the invention relates to compounds (1), wherein $R^{10}$ and $R^{13}$ are each independently of one another selected from among $R^{a1}$ and —$OC_{1-6}$alkyl;
$R^{a1}$ denotes hydrogen or a group optionally substituted by one or more identical or different $R^{b1}$ and/or $R^{c1}$, selected from among $C_{1-6}$alkyl, $C_{3-10}$cycloalkyl, 6-18 membered heteroarylalkyl, 3-14 membered heterocycloalkyl and 4-14 membered heterocycloalkylalkyl;

each $R^{b1}$ denotes a suitable substituent and is independently selected in each case from among —$OR^{c1}$, —$NR^{c1}R^{c1}$, —$C(O)R^{c1}$, —$C(O)NR^{c1}R^{c1}$, —$NHC(O)R^{c1}$ as well as the bivalent substituent =O, while the latter may only be a substituent in non-aromatic ring systems;

each $R^{c1}$ denotes, independently of one another in each case, hydrogen or a group optionally substituted by one or more identical or different $R^{d1}$ and/or $R^{e1}$, selected from among $C_{1-6}$alkyl, 5-12 membered heteroaryl and 3-14 membered heterocycloalkyl;

each $R^{d1}$ denotes the bivalent substituent =O, which may only be a substituent in non-aromatic ring systems; and each $R^{e1}$ is selected independently in each case from among hydrogen, $C_{1-6}$alkyl and 3-14 membered heterocycloalkyl;
or
the groups —$NR^9R^{10}$ and —$NR^{12}R^{13}$ altogether and independently of one another represent in each case a nitrogen-containing, 3-14 membered heterocycloalkyl or 5-12 membered heteroaryl, in each case optionally substituted by one or more identical or different group(s) selected from among $R^{a2}$ and $R^{b2}$;

each $R^{a2}$ denotes a group optionally substituted by one or more identical or different $R^{b2}$ and/or $R^{c2}$, selected from among $C_{1-6}$alkyl, $C_{3-10}$cycloalkyl, $C_{4-16}$cycloalkylalkyl, $C_{6-10}$aryl, 5-12 membered heteroaryl, 6-18 membered heteroarylalkyl and 3-14 membered heterocycloalkyl;

each $R^{b2}$ denotes a suitable substituent and is independently selected in each case from among —$OR^{c2}$, —$NR^{c2}R^{c2}$, halogen as well as the bivalent substituent =O, while the latter may only be a substituent in non-aromatic ring systems;

each $R^{c2}$ is selected independently in each case from among hydrogen, $C_{1-6}$alkyl, $C_{3-10}$cycloalkyl and 5-12 membered heteroaryl.

In another aspect (A9) the invention relates to compounds (1), wherein
$R^{10}$ and $R^{13}$ are selected independently in each case from among methyl; ethyl; allyl; 2-propyl; 2-hydroxyethyl; 2-aminoethyl; 2-methoxyethyl; 2,2-dimethoxyethyl; 2,3-dihydroxypropyl; 2-methylpropyl; cyclopropyl; cyclobutyl; cyclopentyl; 1,1-dimethylethyl; methoxy; 2,2-dimethylpropyl;

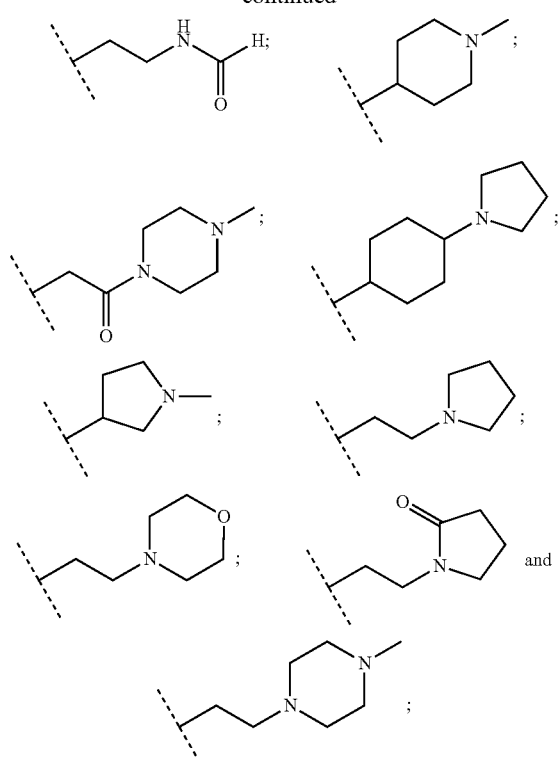
or
the groups —NR⁹R¹⁰ and —NR¹²R¹³ altogether and independently of one another denote
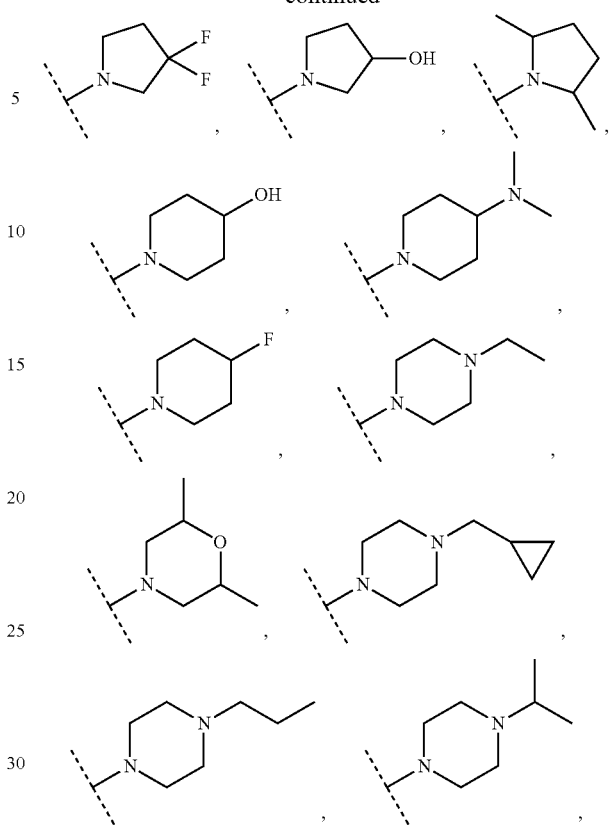
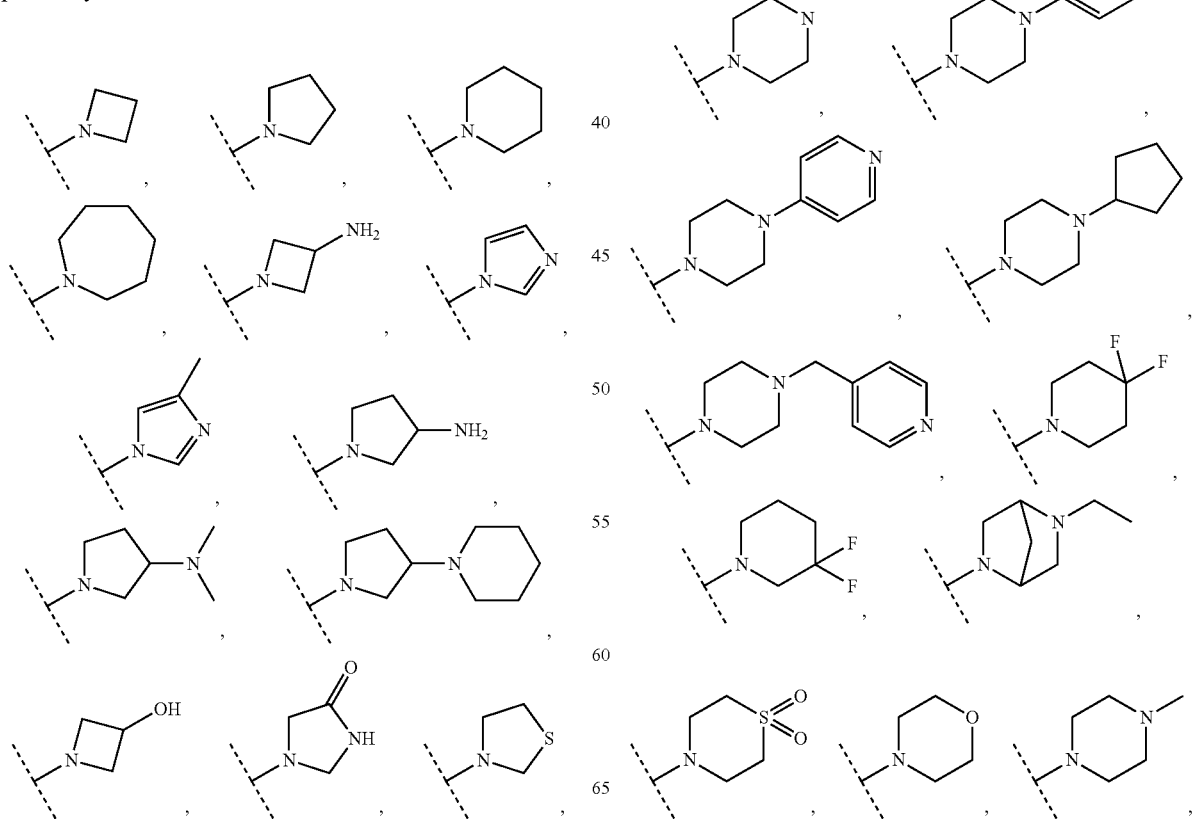

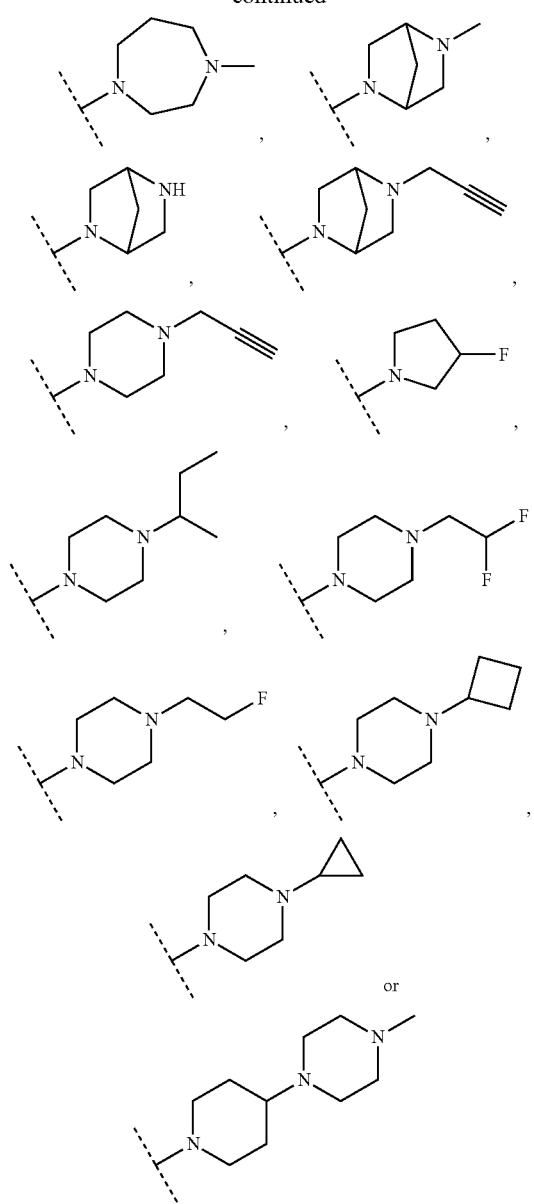
or
R[13] denotes C[1-6]alkyl and
R[11] and R[12] together with the atoms to which they are bound form a heterocycloalkyl, selected from among
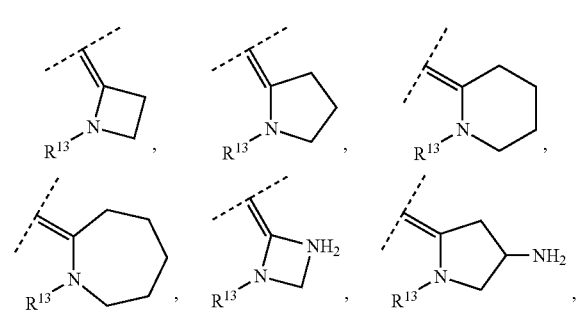
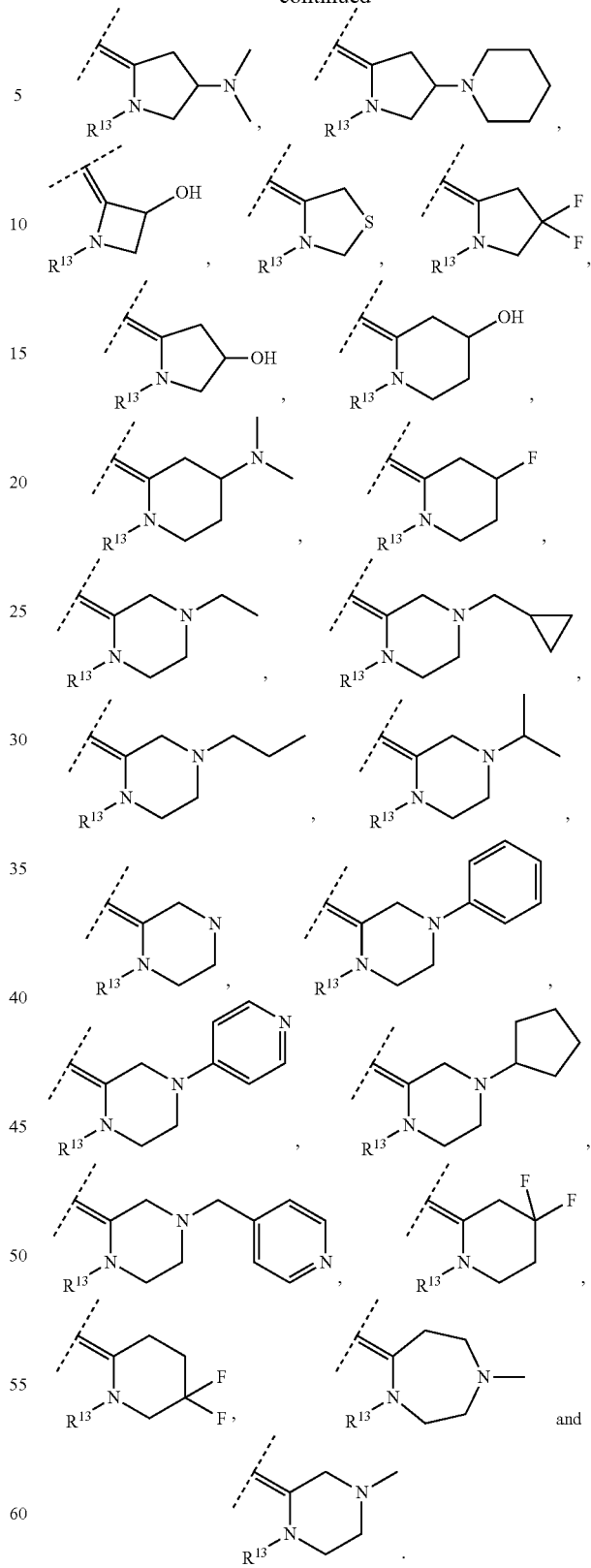
All the structural aspects mentioned hereinbefore relating to different molecular parts of the compounds according to the invention (1) maybe combined with one another in any desired manner, to produce preferred compounds (1). The invention expressly includes all the combinations of the aspects A1-A9, B1 and B2, C1, D1-D3 and E1 with one another.

In another aspect the invention relates to compounds—or the pharmacologically acceptable salts—of general formula (1) as medicaments.

In another aspect the invention relates to pharmaceutical preparations, containing as active substance one or more compounds of general formula (1) or the pharmacologically acceptable salts thereof, optionally in combination with conventional excipients and/or carriers.

In another aspect the invention relates to the use of compounds of general formula (1) for preparing a pharmaceutical composition for the treatment and/or prevention of cancer, infections, inflammations and autoimmune diseases.

In another aspect the invention relates to a pharmaceutical preparation comprising a compound of general formula (1), while the compounds (1) are optionally also in the form of the tautomers, the racemates, the enantiomers, the diastereomers, the mixtures thereof, the polymorphs thereof or as pharmacologically acceptable salts of all the above-mentioned forms, and at least one other cytostatic or cytotoxic active substance different from formula (1).

Definitions

As used herein, the following definitions apply, unless stated otherwise:

The use of the prefix $C_{x-y}$, where x and y in each case denote a natural number (x<y), indicates that the chain or ring structure or the combination of chain and ring structure mentioned and specified in direct connection may consist of a maximum of y and a minimum of x carbon atoms altogether.

The indication of number of members in groups that contain one or more heteroatom(s) (heteroalkyl, heteroaryl, heteroarylalkyl, heterocycloalkyl, heterocycloalkylalkyl) refers to the total number of atoms in all the ring members or chain members or the total of all the ring members and chain members.

Alkyl is made up of the sub-groups saturated hydrocarbon chains and unsaturated hydrocarbon chains, while the latter may be further subdivided into hydrocarbon chains with a double bond (alkenyl) and hydrocarbon chains with a triple bond (alkynyl). Alkenyl contains at least one double bond, alkynyl at least one triple bond. If a hydrocarbon chain should have both at least one double bond and at least one triple bond, by definition it belongs to the alkynyl sub-group. All the above-mentioned sub-groups may be further subdivided into straight-chain (unbranched) and branched. If an alkyl is substituted, it may be mono- or polysubstituted independently of one another at all the hydrogen-carrying carbon atoms.

Examples of individual sub-groups are listed below.

Straight-chain (Unbranched) or Branched, Saturated Hydrocarbon Chains:

methyl; ethyl; n-propyl; isopropyl (1-methylethyl); n-butyl; 1-methylpropyl; isobutyl (2-methylpropyl); sec.-butyl (1-methylpropyl); tent.-butyl (1.1-dimethylethyl); n-pentyl; 1-methylbutyl; 1-ethylpropyl; isopentyl (3-methylbutyl); neopentyl (2,2-dimethyl-propyl); n-hexyl; 2,3-dimethylbutyl; 2,2-dimethylbutyl; 3,3-dimethylbutyl; 2-methyl-pentyl; 3-methylpentyl; n-heptyl; 2-methylhexyl; 3-methylhexyl; 2,2-dimethylpentyl; 2,3-dimethylpentyl; 2,4-dimethylpentyl; 3,3-dimethylpentyl; 2,2,3-trimethylbutyl; 3-ethylpentyl; n-octyl; n-nonyl; n-decyl etc.

Straight-chained (Unbranched) or Branched Alkenyl:

vinyl (ethenyl); prop-1-enyl; allyl (prop-2-enyl); isopropenyl; but-1-enyl; but-2-enyl; but-3-enyl; 2-methyl-prop-2-enyl; 2-methyl-prop-1-enyl; 1-methyl-prop-2-enyl; 1-methyl-prop-1-enyl; 1-methylidenepropyl; pent-1-enyl; pent-2-enyl; pent-3-enyl; pent-4-enyl; 3-methyl-but-3-enyl; 3-methyl-but-2-enyl; 3-methyl-but-1-enyl; hex-1-enyl; hex-2-enyl; hex-3-enyl; hex-4-enyl; hex-5-enyl; 2,3-dimethyl-but-3-enyl; 2,3-dimethyl-but-2-enyl; 2-methylidene-3-methylbutyl; 2,3-dimethyl-but-1-enyl; hexa-1,3-dienyl; hexa-1,4-dienyl; penta-1,4-dienyl; penta-1,3-dienyl; buta-1,3-dienyl; 2,3-dimethylbuta-1,3-diene etc.

Straight-chain (Unbranched) or Branched Alkenyl:

ethynyl; prop-1-ynyl; prop-2-ynyl; but-1-ynyl; but-2-ynyl; but-3-ynyl; 1-methyl-prop-2-ynyl etc.

By the terms propyl, butyl, pentyl, hexyl, heptyl, octyl, nonyl, decyl etc. unless otherwise stated are meant saturated hydrocarbon groups with the corresponding number of carbon atoms, including all the isomeric forms.

By the terms propenyl, butenyl, pentenyl, hexenyl, heptenyl, octenyl, nonenyl, decenyl etc. unless otherwise stated are meant unsaturated hydrocarbon groups with the corresponding number of carbon atoms and a double bond, including all the isomeric forms, also (Z)/(E)-isomers, where applicable.

By the terms butadienyl, pentadienyl, hexadienyl, heptadienyl, octadienyl, nonadienyl, decadienyl etc. unless otherwise stated are meant unsaturated hydrocarbon groups with the corresponding number of carbon atoms and two double bonds, including all the isomeric forms, also (Z)/(E)-isomers, where applicable.

By the terms propynyl, butynyl, pentynyl, hexynyl, heptynyl, octynyl, nonynyl, decynyl etc. unless otherwise stated are meant unsaturated hydrocarbon groups with the corresponding number of carbon atoms and a triple bond, including all the isomeric forms.

By the term heteroalkyl are meant groups which are derived from the alkyl as herein-before defined in its widest sense by replacing, in the hydrocarbon chains, one or more of the groups —$CH_3$ independently of one another by the groups —OH, —SH or —$NH_2$, one or more of the groups —$CH_2$— independently of one another by the groups —O—, —S— or —NH—, one or more of the groups

by the group

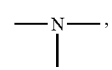

one or more of the groups =CH— by the group =N—, one or more of the groups =$CH_2$ by the group =NH or one or more of the groups ≡CH by the group ≡N, while a total of not more than three heteroatoms may be present in one heteroalkyl, there must be at least one carbon atom between two oxygen atoms and between two sulphur atoms or between one oxygen and one sulphur atom and the group as a whole must have chemical stability.

A direct result of the indirect definition/derivation from alkyl is that heteroalkyl is made up of the sub-groups saturated hydrocarbon chains with heteroatom(s), heteroalkenyl and heteroalkynyl, and it may be further subdivided into straight-chain (unbranched) and branched. If a heteroalkyl is substituted, it may be mono- or polysubstituted independently of one another at all the hydrogen-carrying oxygen, sulphur, nitrogen and/or carbon atoms. Heteroalkyl itself as a substituent may be attached to the molecule both through a carbon atom and through a heteroatom.

The following are listed by way of example:
dimethylaminomethyl; dimethylaminoethyl (1-dimethylaminoethyl; 2-dimethyl-aminoethyl); dimethylaminopropyl (1-dimethylaminopropyl, 2-dimethylaminopropyl, 3-dimethylaminopropyl); diethylaminomethyl; diethylaminoethyl (1-diethylaminoethyl, 2-diethylaminoethyl); diethylaminopropyl (1-diethylaminopropyl, 2-diethylamino-propyl, 3-diethylaminopropyl); diisopropylaminoethyl (1-diisopropylaminoethyl, 2-di-isopropylaminoethyl); bis-2-methoxyethylamino; [2-(dimethylamino-ethyl)-ethyl-amino]-methyl; 3-[2-(dimethylamino-ethyl)-ethyl-amino]-propyl; hydroxymethyl; 2-hydroxy-ethyl; 3-hydroxypropyl; methoxy; ethoxy; propoxy; methoxymethyl; 2-methoxyethyl etc.

Haloalkyl is derived from alkyl as hereinbefore defined in its broadest sense, by replacing one or more hydrogen atoms of the hydrocarbon chain independently of one another by halogen atoms, which may be identical or different. A direct result of the indirect definition/derivation from alkyl is that haloalkyl is made up of the sub-groups saturated hydrohalogen chains, haloalkenyl and haloalkynyl, and it may be further subdivided into straight-chain (unbranched) and branched. If a haloalkyl is substituted, it may be mono- or polysubstituted independently of one another at all the hydrogen-carrying carbon atoms.

Typical examples are listed below:
—$CF_3$; —$CHF_2$; —$CH_2F$; —$CF_2CF_3$; —$CHFCF_3$; —$CH_2CF_3$; —$CF_2CH_3$; —$CHFCH_3$; —$CF_2CF_2CF_3$; —$CF_2CH_2CH_3$; —$CF{=}CF_2$; —$CCl{=}CH_2$; —$CBr{=}CH_2$; —$Cl{=}CH_2$; —$C{\equiv}C{-}CF_3$; —$CHFCH_2CH_3$; —$CHFCH_2CF_3$, etc.

Halogen encompasses fluorine, chlorine, bromine and/or iodine atoms.

Cycloalkyl is made up of the sub-groups monocyclic hydrocarbon rings, bicyclic hydrocarbon rings and spirohydrocarbon rings, while each sub-group may be further subdivided into saturated and unsaturated (cycloalkenyl). By unsaturated is meant that there is at least one double bond in the ring system, but no aromatic system is formed. In bicyclic hydrocarbon rings two rings are linked such that they share at least two carbon atoms. In spirohydrocarbon rings one carbon atom (spiroatom) is shared by two rings. If a cycloalkyl is substituted, it may be mono-or polysubstituted independently of one another at all the hydrogen-carrying carbon atoms. Cycloalkyl itself as a substituent may be attached to the molecule through any suitable position of the ring system. The following individual sub-groups are listed by way of example:
Monocyclic Hydrocarbon Rings, Saturated:
cyclopropyl; cyclobutyl; cyclopentyl; cyclohexyl; cycloheptyl etc.
Monocyclic Hydrocarbon Rings, Unsaturated:
cycloprop-1-enyl; cycloprop-2-enyl; cyclobut-1-enyl; cyclobut-2-enyl; cyclopent-1-enyl; cyclopent-2-enyl; cyclopent-3-enyl; cyclohex-1-enyl; cyclohex-2-enyl; cyclohex-3-enyl; cyclohept-1-enyl; cyclohept-2-enyl; cyclohept-3-enyl; cyclohept-4-enyl; cyclobuta-1,3-dienyl; cyclopenta-1,4-dienyl; cyclopenta-1,3-dienyl; cyclopenta-2,4-dienyl; cyclohexa-1,3-dienyl; cyclohexa-1,5-dienyl; cyclohexa-2,4-dienyl; cyclohexa-1,4-dienyl; cyclohexa-2,5-dienyl etc.
Bicyclic Hydrocarbon Rings (Saturated and Unsaturated):
bicyclo[2.2.0]hexyl; bicyclo[3.2.0]heptyl; bicyclo[3.2.1]octyl; bicyclo[2.2.2]octyl; bicyclo[4.3.0]nonyl (octahydroindenyl); bicyclo[4.4.0]decyl (decahydronaphthalene); bicyclo[2.2.1]heptyl (norbornyl); (bicyclo[2.2.1]hepta-2,5-dienyl (norborna-2,5-dienyl); bicyclo[2.2.1]hept-2-enyl (norbornenyl); bicyclo[4.1.0]heptyl (norcaranyl); bicyclo-[3.1.1]heptyl (pinanyl) etc.
Spirohydrocarbon Rings (Saturated and Unsaturated):
spiro[2.5]octyl, spiro[3.3]heptyl, spiro[4.5]dec-2-ene, etc.

Cycloalkylalkyl denotes the combination of the alkyl and cycloalkyl groups defined hereinbefore, in each case in their broadest sense. The alkyl group as substituent is directly linked to the molecule and is in turn substituted by a cycloalkyl group. The linking of alkyl and cycloalkyl in both groups may be effected by means of any suitable carbon atoms. The sub-groups of alkyl and cycloalkyl are also included in the combination of the two groups.

Aryl denotes mono-, bi-or tricyclic carbon rings with at least one aromatic ring. If an aryl is substituted, the substitution may be mono-or polysubstitution in each case, at all the hydrogen-carrying carbon atoms, independently of one another. Aryl itself may be linked to the molecule as substituent via any suitable position of the ring system.

Typical examples are listed below:
phenyl, naphthyl, indanyl (2,3-dihydroindenyl), 1,2,3,4-tetrahydronaphthyl; fluorenyl, etc.

Arylalkyl denotes the combination of the groups alkyl and aryl as hereinbefore defined, in each case in their broadest sense. The alkyl group as substituent is directly linked to the molecule and is in turn substituted by an aryl group. The alkyl and aryl may be linked in both groups via any carbon atoms suitable for this purpose. The respective sub-groups of alkyl and aryl are also included in the combination of the two groups.

Typical examples are listed below:
benzyl; 1-phenylethyl; 2-phenylethyl; phenylvinyl; phenylallyl etc.

Heteroaryl denotes monocyclic aromatic rings or polycyclic rings with at least one aromatic ring, which, compared with corresponding aryl or cycloalkyl, contain instead of one or more carbon atoms one or more identical or different heteroatoms, selected independently of one another from among nitrogen, sulphur and oxygen, while the resulting group must be chemically stable. If a heteroaryl is substituted, the substitution may be mono-or polysubstitution in each case, at all the hydrogen-carrying carbon and/or nitrogen atoms, independently of one another. Heteroaryl itself as substituent may be linked to the molecule via any suitable position of the ring system, both carbon and nitrogen.

Typical examples are listed below.
Monocyclic Heteroaryls:
furyl; thienyl; pyrrolyl; oxazolyl; thiazolyl; isoxazolyl; isothiazolyl; pyrazolyl; imidazolyl; triazolyl; tetrazolyl; oxadiazolyl; thiadiazolyl; pyridyl; pyrimidyl; pyridazinyl; pyrazinyl; triazinyl; pyridyl-N-oxide; pyrrolyl-N-oxide; pyrimidinyl-N-oxide; pyridazinyl-N-oxide; pyrazinyl-N-oxide; imidazolyl-N-oxide; isoxazolyl-N-oxide; oxazolyl-N-oxide; thiazolyl-N-oxide; oxadiazolyl-N-oxide; thiadiazolyl-N-oxide; triazolyl-N-oxide; tetrazolyl-N-oxide etc.
Polycyclic Heteroaryls:
indolyl; isoindolyl; benzofuryl; benzothienyl; benzoxazolyl; benzothiazolyl; benzisoxazolyl; benzisothiazolyl; benzimidazolyl; indazolyl; isoquinolinyl; quinolinyl; quinoxalinyl; cinnolinyl; phthalazinyl; quinazolinyl; benzotriazinyl; indolizinyl; oxazolopyridyl; imidazopyridyl; naphthyridinyl; indolinyl; isochromanyl; chromanyl; tetrahydroisoquinolinyl; isoindolinyl; isobenzotetrahydrofuryl; isobenzotetrahydrothienyl; isobenzothienyl; benzoxazolyl; pyridopyridyl; benzotetrahydrofuryl; benzotetrahydro-thienyl; purinyl; benzodioxolyl; phenoxazinyl; phenothiazinyl; pteridinyl; benzothiazolyl; imidazopyridyl;

imidazothiazolyl; dihydrobenzisoxazinyl; benzisoxazinyl; benzoxazinyl; dihydrobenzisothiazinyl; benzopyranyl; benzothiopyranyl; cumarinyl; isocumarinyl; chromonyl; chromanonyl; tetrahydroquinolinyl; dihydroquinolinyl; dihydroquinolinonyl; dihydroisoquinolinonyl; dihydrocumarinyl; dihydroisocumarinyl; isoindolinonyl; benzodioxanyl; benzoxazolinonyl; quinolinyl-N-oxide; indolyl-N-oxide; indolinyl-N-oxide; isoquinolyl-N-oxide; quinazolinyl-N-oxide; quinoxalinyl-N-oxide; phthalazinyl-N-oxide; indolizinyl-N-oxide; indazolyl-N-oxide; benzothiazolyl-N-oxide; benzimidazolyl-N-oxide; benzo-thiopyranyl-S-oxide and benzothiopyranyl-S,S-dioxide etc.

Heteroarylalkyl denotes the combination of the alkyl and heteroaryl groups defined hereinbefore, in each case in their broadest sense. The alkyl group as substituent is directly linked to the molecule and is in turn substituted by a heteroaryl group. The linking of the alkyl and heteroaryl may be achieved on the alkyl side via any carbon atoms suitable for this purpose and on the heteroaryl side by any carbon or nitrogen atoms suitable for this purpose. The respective sub-groups of alkyl and heteroaryl are also included in the combination of the two groups.

By the term heterocycloalkyl are meant groups which are derived from the cycloalkyl as hereinbefore defined if in the hydrocarbon rings one or more of the groups —$CH_2$— are replaced independently of one another by the groups —O—, —S— or —NH— or one or more of the groups =CH— are replaced by the group =N—, while not more than five heteroatoms may be present in total, there must be at least one carbon atom between two oxygen atoms and between two sulphur atoms or between one oxygen and one sulphur atom and the group as a whole must be chemically stable. Heteroatoms may simultaneously be present in all the possible oxidation stages (sulphur→sulphoxide —SO—, sulphone —$SO_2$—; nitrogen→N-oxide). It is immediately apparent from the indirect definition/derivation from cycloalkyl that heterocycloalkyl is made up of the sub-groups monocyclic hetero-rings, bicyclic hetero-rings and spirohetero-rings, while each sub-group can also be further subdivided into saturated and unsaturated (heterocycloalkenyl). The term unsaturated means that in the ring system in question there is at least one double bond, but no aromatic system is formed. In bicyclic hetero-rings two rings are linked such that they have at least two atoms in common. In spirohetero-rings one carbon atom (spiroatom) is shared by two rings. If a heterocycloalkyl is substituted, the substitution may be mono-or poly-substitution in each case, at all the hydrogen-carrying carbon and/or nitrogen atoms, independently of one another. Heterocycloalkyl itself as substituent may be linked to the molecule via any suitable position of the ring system.

Typical examples of individual sub-groups are listed below.

Monocyclic Heterorings (Saturated and Unsaturated):
tetrahydrofuryl; pyrrolidinyl; pyrrolinyl; imidazolidinyl; thiazolidinyl; imidazolinyl; pyrazolidinyl; pyrazolinyl; piperidinyl; piperazinyl; oxiranyl; aziridinyl; azetidinyl; 1,4-dioxanyl; azepanyl; diazepanyl; morpholinyl; thiomorpholinyl; homomorpholinyl; homopiperidinyl; homopiperazinyl; homothiomorpholinyl; thiomorpholinyl-S-oxide; thiomorpholinyl-S,S-dioxide; 1,3-dioxolanyl; tetrahydropyranyl; tetrahydrothiopyranyl; [1,4]-oxazepanyl; tetrahydrothienyl; homothiomorpholinyl-S,S-dioxide; oxazolidinonyl; dihydropyrazolyl; dihydropyrrolyl; dihydropyrazinyl; dihydropyridyl; dihydro-pyrimidinyl; dihydrofuryl; dihydropyranyl; tetrahydrothienyl-S-oxide; tetrahydrothienyl-S,S-dioxide; homothiomorpholinyl-S-oxide; 2,3-dihydroazet; 2H-pyrrolyl; 4H-pyranyl; 1,4-dihydropyridinyl etc.

Bicyclic Heterorings (Saturated and Unsaturated):
8-azabicyclo[3.2.1] octyl; 8-azabicyclo[5.1.0] octyl; 2-oxa-5-azabicyclo[2.2.1]heptyl; 8-oxa-3-aza-bicyclo[3.2.1] octyl; 3,8-diaza-bicyclo [3.2.1]octyl; 2,5-diaza-bicyclo-[2.2.1]heptyl; 1-aza-bicyclo[2.2.2]octyl; 3,8-diaza-bicyclo [3.2.1]octyl; 3,9-diaza-bicyclo[4.2.1]nonyl; 2,6-diaza-bicyclo[3.2.2]nonyl etc.

Spiro-heterorings (Saturated and Unsaturated):
1,4-dioxa-spiro[4.5]decyl; 1-oxa-3.8-diaza-spiro[4.5]decyl; and 2,6-diaza-spiro[3.3]heptyl; 2,7-diaza-spiro[4.4] nonyl; 2,6-diaza-spiro[3.4]octyl; 3,9-diaza-spiro[5.5]undecyl; 2,8-diaza-spiro[4.5]decyl etc.

Heterocycloalkylalkyl denotes the combination of the alkyl and heterocycloalkyl groups defined hereinbefore, in each case in their broadest sense. The alkyl group as substituent is directly linked to the molecule and is in turn substituted by a heterocycloalkyl group. The linking of the alkyl and heterocycloalkyl may be achieved on the alkyl side via any carbon atoms suitable for this purpose and on the heterocycloalkyl side by any carbon or nitrogen atoms suitable for this purpose. The respective sub-groups of alkyl and heterocycloalkyl are also included in the combination of the two groups.

By the term "substituted" is meant that a hydrogen atom that is bound directly to the atom under consideration is replaced by another atom or another group of atoms. Alternatively substitution may take place at an atom if there are free electrons available at this atom. Depending on the starting conditions (number of hydrogen atoms, number of free electrons) mono-or polysubstitution may take place at an atom. Thus, for example, a free electron pair may be substituted by two monovalent substituents.

Bivalent substituents such as for example =S, =NR, =NOR, =NNRR, =NN(R)C(O)NRR, =$N_2$ or the like may only be substituents at carbon atoms, while the bivalent substituent =O may also be a substituent at heteroatoms. Generally speaking, substitution by a bivalent substituent may only take place at non-aromatic ring systems and requires exchange for two geminal hydrogen atoms, i.e. hydrogen atoms that are bound to the same carbon atom saturated before the substitution or for a free electron pair. Substitution by a bivalent substituent is therefore only possible at the group —$CH_2$— or heteroatoms of a non-aromatic ring system.

In addition to this, the term "suitable substituent" denotes a substituent which is suitable, on the one hand, on account of its valency and on the other hand leads to a system with chemical stability.

Groups or substituents are frequently selected from among alternative groups/substituents with a corresponding group designation (e.g. $R^a$, $R^b$ etc). If a group of thus kind used repeatedly to define a compound according to the invention in different parts of the molecule, it should always be borne in mind that the respective uses are to be regarded as being totally independent of one another.

List of Abbreviations

| | |
|---|---|
| abs. | absolute, anhydrous |
| Ac | acetyl |
| BINAP | 2,2'-bis(diphenylphosphino)-1,1'-binaphthyl |
| Bn | benzyl |
| Boc | tert.-butyloxycarbonyl |
| Bu | butyl |
| c | concentration |
| chex | cyclohexane |
| d | day(s) |
| DBAD | di-tert.-butyl-azodicarboxylate |

-continued

| | |
|---|---|
| TLC | thin layer chromatography |
| DCM | dichloromethane |
| DEA | diethylamine |
| DIPEA | N-ethyl-N,N-diisopropylamine (Hünig base) |
| DMAP | 4-N,N-dimethylaminopyridine |
| DME | 1,2-dimethoxyethane |
| DMF | N,N-dimethylformamide |
| DMSO | dimethylsulphoxide |
| EE | ethyl acetate |
| eq | equivalent(s) |
| ESI | electron spray ionization |
| Et | ethyl |
| EtOH | ethanol |
| h | hour |
| HATU | O-(7-azabenzotriazol-1-yl)-N,N,N',N'-tetramethyl-uronium tetrafluorophosphate |
| hex | hexyl |
| HPLC | high performance liquid chromatography |
| Hünig-base | N-ethyl-N,N-diisopropylamine |
| i | iso |
| IR | infrared spectroscopy |
| cat. | catalyst, catalytic |
| conc. | concentrated |
| b.p. | boiling point |
| LC | liquid chromatography |
| LHMDS | lithium-hexamethyldisilazane |
| sln. | solution |
| Me | methyl |
| MeOH | methanol |
| min | minutes |
| MPLC | medium pressure liquid chromatography |
| MS | mass spectrometry |
| NMP | N-methylpyrrolidone |
| NP | normal phase |
| n.a. | not available |
| Ph | phenyl |
| Pr | propyl |
| PS | polystyrene |
| Py | pyridine |
| rac | racemic |
| $R_f$ (Rf) | retention factor |
| RP | reversed phase |
| RT | room temperature |
| TBAF | tetrabutylammonium fluoride |
| TBTU | O-(benzotriazol-1-yl)-N,N,N',N'-tetramethyl-uronium tetrafluoroborate |
| temp. | temperature |
| tert. | tertiary |
| Tf | triflate |
| TFA | trifluoroacetic acid |
| THF | tetrahydrofuran |
| TMS | trimethylsilyl |
| $t_{Ret.}$ | retention time (HPLC) |
| TsOH | para-toluenesulphonic acid |
| UV | ultraviolet |

Features and advantages of the present invention will become apparent from the following detailed Examples, which illustrate the fundamentals of the invention by way of example, without restricting its scope:
Preparation of the Compounds According to the Invention
General Unless stated otherwise, all the reactions are carried out in commercially obtainable apparatus using methods that are commonly used in chemical laboratories.

Starting materials that are sensitive to air and/or moisture are stored under protective gas and corresponding reactions and manipulations therewith are carried out under protective gas (nitrogen or argon).

Microwave reactions are carried out in an initiator made by Biotage or in an Explorer made by CEM in sealed containers (preferably 2, 5 or 20 mL), preferably with stirring.
Chromatography For the preparative medium pressure chromatography (MPLC, normal phase) silica gel made by Millipore (name: Granula Silica Si-60A 35-70 µm) or C-18 RP-silica gel (RP-phase) made by Macherey Nagel (name: Polygoprep 100-50 C18) is used.

The thin layer chromatography is carried out on ready-made TLC silica gel 60 plates on glass (with fluorescence indicator F-254) made by Merck.

The preparative high pressure chromatography (HPLC) is carried out using columns made by Waters (named: XTerra Prep. MS C18, 5 µm, 30×100 mm or XTerra Prep. MS C18, 5 µm, 50×100 mm OBD or Symmetrie C18, 5 µm, 19×100 mm or Sunfire C18 OBD, 19×100 mm, 5 µm or Sunfire Prep C 10 µm OBD 50×150 mm or X-Bridge Prep C18 5 µm OBD 19×50 mm), Agilent (named: Zorbax SB-C8 5 µm PrepHT 21.2×50 mm) and Phenomenex (named: Gemini C18 5 µm AXIA 21.2×50 mm or Gemini C18 10 µm 50×150 mm), the analytical HPLC (reaction control) is carried out using columns made by Agilent (named: Zorbax SB-C8, 5 µm, 21.2×50 mm or Zorbax SB-C8 3.5 µm 2.1×50 mm) and Phenomenex (named: Gemini C18 3 µm 2×30 mm).
HPLC Mass Spectroscopy/UV Spectrometry The retention times/MS-ESI$^+$ for characterising the examples are obtained using an HPLC-MS apparatus (high performance liquid chromatography with mass detector) made by Agilent. Compounds that elute at the injection peak have the retention time $t_{Ret.}$=0.00.

The specifications for the apparatus are as follows:
Column: Waters, Xterra MS C18, 2.5 µm, 2.1×30 mm, Part.No. 186000592
Eluant: A: H$_2$O with 0.1% HCOOH; B: acetonitrile (HPLC grade)
Detection: MS: Positive and negative mode
Mass range: 120-900 m/z
Fragmentor: 120
Gain EMV: 1; Threshold: 150; Stepsize: 0.25; UV: 254 nm; Bandwide: 1
Injection: Inj. Vol. 5 µL
Separation: Flow 1.10 mL/min
Column temp.: 40° C.
Gradient: 0.00 min: 5% solvent B
  0.00-2.50 min: 5%→95% solvent B
  2.50-2.80 min: 95% solventB
  2.81-3.10 min: 95%→5% solvent B In addition, the following apparatus specification is used in some cases:
Column: Waters, Xterra MS C18, 2.5 µm, 2.1×50 mm, Part. No. 186000594
Eluant: A: deion. water with 0.1% HCOOH; B: acetonitrile with 0.1% HCOOH
Detection: MS: Positive and negative mode
Mass range: 100-1200 m/z
Fragmentor: 70
Gain EMV: Threshold: 1 mAU; Stepsize: 2 nm; UV: 254 nm as well as 230 nm;
Bandwide: 8
Injection: Standard 1 µL
Flow: 0.6 mL/min
Column temp.: 35° C.
Gradient: 0.00 min: 5% solvent B
  0.00-2.50 min: 5%→95% solvent B
  2.50-4.00 min: 95% solvent B
  4.00-4.50 min: 95%→5% solvent B
  4.50-6.00 min: 95% solvent A The compounds according to the invention are prepared by the methods of synthesis described hereinafter, in which substituents of the general formulae have the meanings given hereinbefore. These methods are intended as an illustration of the invention, without restricting its subject matter and the scope of the compounds claimed to these examples. Where the preparation of starting compounds is not described, they are commercially obtainable or may be prepared analogously to known compounds or methods described herein. Substances described in the literature are prepared according to the published methods of synthesis. Compounds depicted in reaction schemes A to O can also be isolated in form of their salts and used as such. Such salts [e.g. halides, sulfonates (e.g. tosylates), ammonium salts etc.] are obtained whenever the free base or the free acid form is reacted with an appropriate acid or base, respectively.

Reaction scheme A

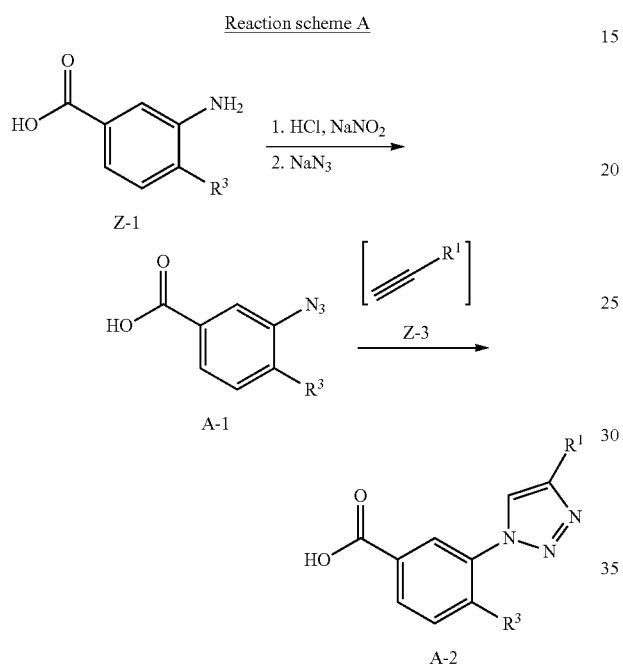

The benzoic acids A-2 are obtained by methods known in the literature by diazotising 3-aminobenzoic acids Z-1 in hydrochloric $NaNO_2$ solution and reacting with sodium azide to form the aromatic azides A-1. The cycloaddition (for inserting the group $R^1$) of the azides A-1 is carried out using methods known from the literature using a corresponding alkyne Z-3, $CuSO_4$ and sodium ascorbate and A-2 is obtained.

The alkynes Z-3 used to introduce the groups $R^1$ are either commercially obtainable or are prepared from aldehydes Z-2 that are commercially obtainable or synthesised using methods known from the literature, e.g. by means of the Bestmann-Ohira reagent. Moreover, the alkynes used may also be prepared from aryl bromides and iodides and trimethylsilylacetylene which are commercially obtainable or synthesised by methods known from the literature by means of a palladium-catalysed cross-coupling (Sonogashira) and subsequent cleaving of the silyl protecting group. Experimental procedures for the synthesis of compounds in which $R^1$ is a substituted imidazole utilizing halo imidazoles as intermediates are incorporated in here by reference to WO 2007/121390 and references cited therein. Other heteroaryls for $R^1$ can be introduced analogously. Sonogashira couplings with halo pyridyls, halo imidazolyls, halo pyrazolyls, halo thiazolyls, halo pyrimidyls result in intermediates e.g. 2-cyclopropyl-1-methyl-5-trimethylsilanylethynyl-1H-imidazole, 2-cyclopropyl-1-methyl-4-trimethylsilanylethynyl-1H-imidazole, 2-trimethylsilanylethynyl-pyridine, 5-trimethylsilanylethynyl-pyrimidine, 1,5-dimethyl-4-trimethylsilanylethynyl-1H-pyrazole or 5-trimethylsilanylethynyl-thiazole.

The benzoic acids A-2 that may be obtained directly by these reaction methods may be further modified in $R^1$ in a manner known from the literature or analogous to the literature to obtain other benzoic acids A-2. Thus, for example, the groups $R^1$ of directly accessible benzoic acids A-2, which consist of a halogen- or amino-substituted heteroaryl, may be converted by reactions of substitution (at the heteroaryl itself), alkylation, acylation or addition (at the amino group of the heteroaryl). In particular, transition metal-catalysed cross-coupling reactions (Ullmann, Buchwald-Hartwig, Sonogashira etc.) may be carried out on heteroarylbromides in $R^1$ in order to introduce various substituents.

Procedure for Synthesising A-1a:

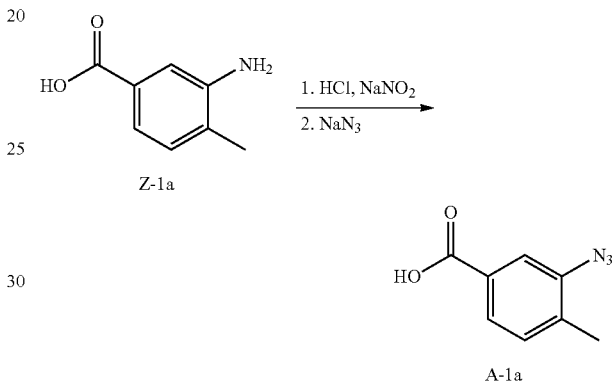

3-amino-4-methylbenzoic acid Z-1a (10 g, 65.5 mmol) is taken up in 2N HCl (300 mL), cooled to 0° C., mixed with a solution of sodium nitrite (5.42 g, 69 mmol) in 30 mL water and stirred for 30 min. Then a solution of sodium azide (4.73 g, 72 mmol) in 30 mL water is added dropwise, stirred for another 30 min after the addition has finished and then heated to RT. The precipitate of A-1a formed is filtered off, washed repeatedly with water and then freeze-dried (HPLC-MS: $t_{Ret.}$=1.61 min; MS (M+H)$^+$=178).

Analogously to this procedure further azides A-1 are obtained from the corresponding 3-aminobenzoic acid derivatives Z-1.

Alternatively, azides A-1 can be obtained from 3-iodobenzoic acids by reaction with sodium azide $NaN_3$, L-proline, an appropriate base (such as $Na_2CO_3$) in the presence of a Cu(I) source (such as CuI or $CuSO_4$) and a reducing agent (such as sodium ascorbate) in DMSO. In this way, 3-iodo-4-methyl-benzoic acid yields compound A-1a.

Procedure for Synthesising A-2a:

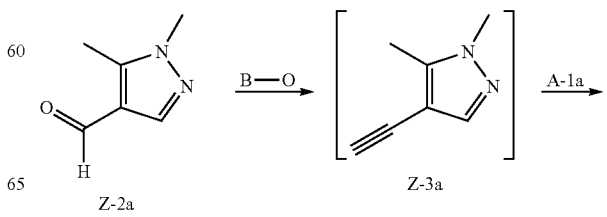

-continued

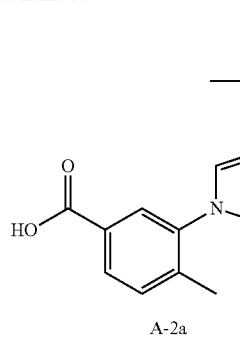

A-2a 1,5-dimethyl-1H-pyrazole-4-carbaldehyde Z-2a (2.803 g, 22.58 mmol) and the Bestmann-Ohira reagent (S. Müller et al. *Synlett* 1996, 521-522) (B-O, 5.964 g, 31.05 mmol) are placed in MeOH (75 mL) and combined with potassium carbonate (6.241 g, 45.16 mmol). After 3 d stirring at RT the azide A-1a (2.5 g, 14.11 mmol) is added and stirred. Then sodium ascorbate (3.075 g, 15.52 mmol) dissolved in 12.5 mL water and 28.2 mL of a 0.1 M CuSO$_4$-sln. (2.82 mmol) are added and the mixture is stirred for 3 d at RT. For working up the mixture is evaporated down under reduced pressure, mixed with water and adjusted to an acid pH (pH<5) by the addition of 1 N hydrochloric acid solution. The precipitate formed is filtered off, washed with a little acetonitrile and dried in the vacuum dryer. A-2a may be used again directly or purified by RP-HPLC separation (HPLC-MS: $t_{Ret.}$=1.59 min; MS (M+H)$^+$=298).

Procedure for Synthesising A-2b:

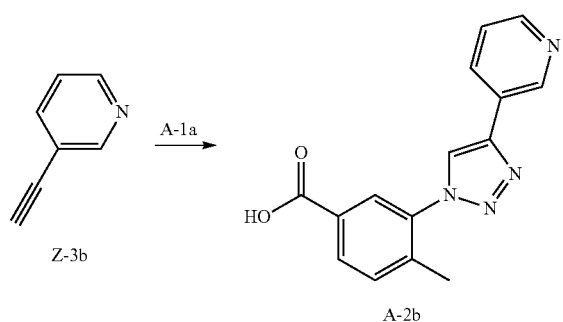

A-2b 3-ethynylpyridine Z-3b (956 mg, 9.27 mmol) and azide A-1a (1.64 g, 9.27 mmol) are taken up in 35 mL EtOH and 20 mL acetonitrile. Then 11.12 mL of sodium ascorbate solution (1.0 M, 11.12 mmol) and 18.53 mL CuSO$_4$-sln. (0.1 M, 1.85 mmol) are added and the mixture is stirred for 3 d at RT. For working up the mixture is evaporated down under reduced pressure, mixed with water and adjusted to an acid pH (pH<5) by the addition of 1 N hydrochloric acid solution. The precipitate formed is filtered off, washed with a little acetonitrile and dried in the vacuum dryer.

A-2b may be further used directly or purified by RP-HPLC separation (HPLC-MS: $t_{Ret.}$=1.33 min; MS (M+H)$^+$=281).

Procedure for Synthesising A2-c

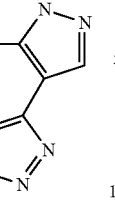

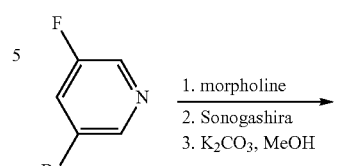

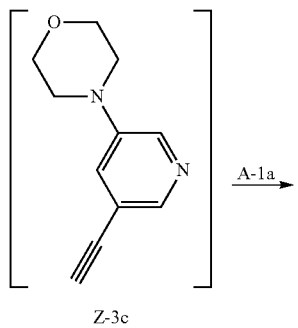

Z-3c

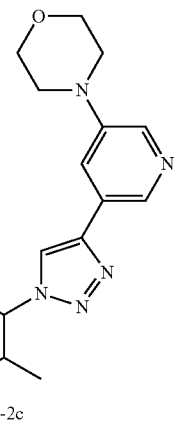

A-2c 3-bromo-5-fluoropyridine (6.29 g, 34.7 mmol) is placed in morpholine and heated for 5 d at 110° C. After cooling to RT, DCM is added and the organic phase is extracted 3x with 2 N hydrochloric acid. The aqueous phase is adjusted to pH 4 with sodium hydroxide solution, again extracted 3× with DCM, the combined organic phases are dried on MgSO$_4$, filtered and evaporated down. The crude product (8.30 g, 23.9 mmol) is suspended in diisopropylamine, combined with CuI (471 mg, 2.47 mmol), bis(triphenyl-phosphino)palladium(II)-chloride (838 mg, 1.19 mmol) and trimethylsilyl-acetylene (6.74 mL, 47.7 mmol) and stirred at 100° C. for 30 min under protective gas. Then 1 N hydrochloric acid is added and the aqueous phase is extracted 3× with DCM. The combined organic phases are dried on MgSO$_4$, filtered, evaporated down and purified by normal phase chromatography (cyclohexane/EtOAc). After elimination of the solvents an intermediate product is obtained, which is the still TMS-protected alkyne Z-3c (HPLC-MS: $t_{Ret.}$=2.14 min; MS (M+H)$^+$=261).

TMS-protected alkyne Z-3c (1.98 g, 7.62 mmol) is taken up in MeOH (110 mL), combined with K$_2$CO$_3$ (1.75 g, 12.6 mmol) and stirred for 2 h at RT. Azide A-1a (953 mg, 5.38 mmol), sodium ascorbate solution (1.0 M, 6.0 mL) and CuSO$_4$ solution (0.1 M, 5.1 mL) are added successively and the mixture is stirred for 5 d at RT. The reaction mixture is evaporated down, diluted with water and the pH is adjusted with 1 N hydrochloric acid to pH 5. The precipitate pf A-2c (HPLC-MS: $t_{Ret.}$=1.18 min; MS (M+H)$^+$=366) is extracted for 30 min, filtered off and dried.

Analogously to these procedures, further benzoic acids A-2 are obtained from the corresponding A-1 or Z-1 and Z-3 intermediates/educts.

The benzoic acids A-2 described are used in all the following reaction sequences (Schemes B to J) as synthesis components and in each case are coupled with anilines. These amide couplings are carried out using methods known from the literature with the aid of common coupling reagents, such as HATU or TBTU, for example, or the benzoic acids A-2 are activated using thionyl chloride, oxalyl chloride or Ghosez reagent using methods known from the literature to obtain the corresponding acid chloride and are then reacted with the respective anilines ($R^2$—$NH_2$). Reaction procedures by way of example are described therein.

Alternatively the 3-azidobenzoic acids A-1 may also be coupled to the respective aniline (insertion of $R^2$) and only then is the cycloaddition carried out (and optionally modification in $R^1$) as shown in Scheme A.

hydroxylamine $R^9R^{10}NH$ (type Ia→benzylamine) or aminoalcohol $R^9R^{10}N(CH_2)_yOH$ (or alkoxide, type Ib→benzylether) or by reductive amination of a corresponding aldehyde with an amine $R^9R^{10}$ NH (type Ia→benzylamine). In the former case the benzyl alcohols B-3 are reacted for this purpose by means of thionyl chloride using methods known from the literature to obtain the to corresponding benzyl chloride. In the latter case the benzylalcohols B-3 may be oxidised e.g. with $MnO_2$, Dess-Martin-Periodinane or other common oxidising agents to form the corresponding aldehydes and then reacted in acetic acid medium with $Na(OAc)_3BH$ or $Na(CN)BH_3$ and an amine $R^9R^{10}NH$ using methods known from the literature to obtain compounds of type Ia. The amines/hydroxylamines/aminoalcohols used are commercially obtainable or are synthesised using methods known from the literature.

The benzylalcohols B-3 are synthesised by an amide coupling reaction of the anilines B-2 (in order to introduce the

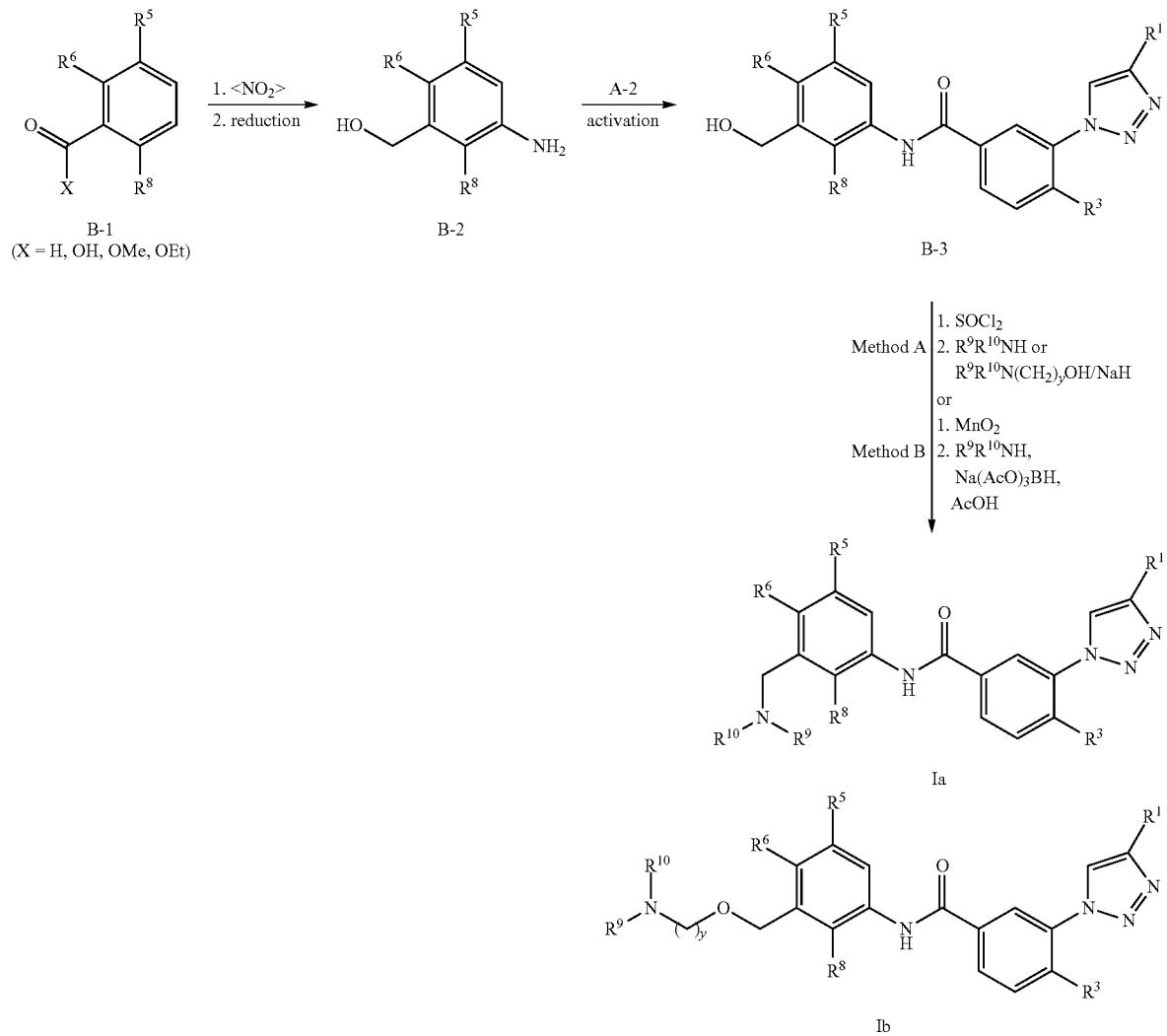

Reaction scheme B-I

Example compounds of type I (benzylethers or benzylamines in the m-position relative to the amide link→$R^7$) are prepared from benzylalcohols B-3 either by substitution of the corresponding benzyl chloride by means of an amine/ group $R^2$) and the corresponding benzoic acids A-2 described above. The anilines B-2 used are commercially obtainable or are synthesised using methods known from the literature from the corresponding carbonyl compounds B-1 by nitrogenation, e.g. with nitronium tetrafluoroborate, conc. nitric acid, fuming nitric acid or nitrating acid and subsequent reductions with e.g. Pd/C and hydrogen in THF, methanol or ethanol or Fe and ammonium chloride in ethanol via various intermediate products Z. In some cases, already nitrogenated educts Z-4 are available from commercial sources. Other intermediate steps may also be integrated into the reaction sequence for synthesising the amines B-2, such as the modification of another functional group in the substituents $R^6$ and/or $R^8$. (Cf. synthesis of B-2a→modification of $R^8$)

a) Procedure for Synthesising B-2a:

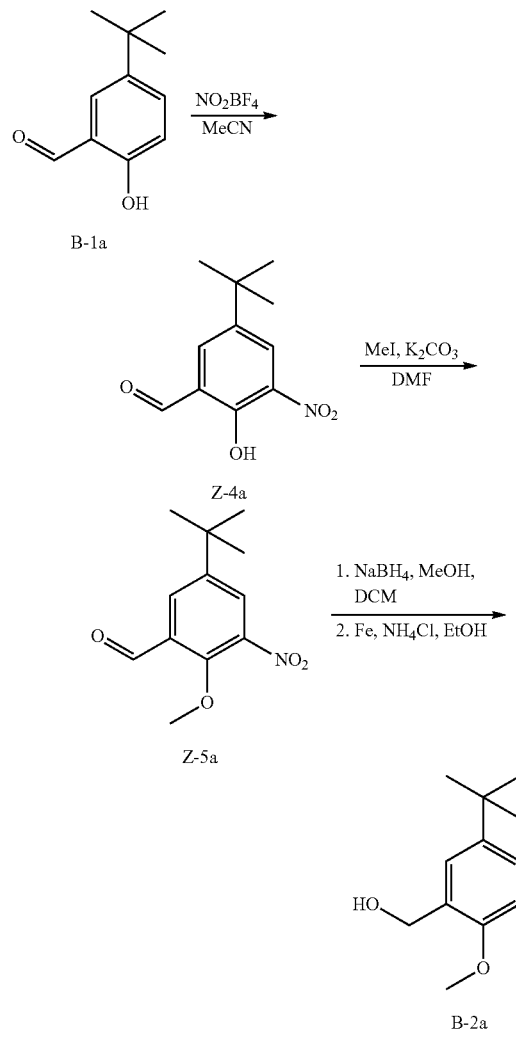

2-hydroxy-5-tert-butylbenzaldehyde B-1a (9.0 g, 50.5 mmol) is taken up in acetonitrile (400 mL), cooled to −30° C., mixed batchwise with $NO_2BF_4$ and stirred for 30 min. Then the reaction mixture is allowed to warm up to −15° C. within 1 h and stirred for a further 30 min at this temperature. The reaction mixture is diluted with EtOAc and the organic phase is washed with sat. $NaHCO_3$ solution and sat. NaCl solution. The organic phase is dried on $Na_2SO_4$, filtered, evaporated down using the rotary evaporator and the intermediate product Z-4a (HPLC-MS: $t_{Ret.}$=1.61 min; MS $(M+H)^+$=224) is further reacted directly.

Nitro compound Z-4a (2.3 g, 10.1 mmol) is taken up in DMF (20 mL), combined with $K_2CO_3$ (2.4 g, 17.0 mmol) and stirred for 15 min. Then the suspension is combined with methyl iodide (0.94 mL, 15 mmol) and stirred overnight at RT. The reaction mixture is diluted with EtOAc and the organic phase is washed twice with water and once with sat. NaCl solution. The organic phase is dried on $Na_2SO_4$, filtered, evaporated down using the rotary evaporator and the intermediate product Z-5a (HPLC-MS: $t_{Ret.}$=3.78 min; MS $(M+H)^+$=238) is further reacted directly.

Crude product Z-5a (1.05 g, 4.0 mmol) is taken up in a mixture of DCM and MeOH (1:1, 10 mL), combined with $NaBH_4$ (193 mg, 5.1 mmol) and stirred for 30 min at RT. The reaction mixture is combined with 2 N NaOH solution, extracted twice with DCM and the organic phase is washed with sat. NaCl solution. The organic phase is dried on $Na_2SO_4$, filtered, evaporated down using the rotary evaporator and the intermediate product Z-6a obtained (HPLC-MS: $t_{Ret.}$=3.49 min; MS $(M+H)^+$=240) is further reacted directly.

Crude product Z-6a (910 mg, 3.8 mmol) is taken up in EtOH (5 mL), combined with $NH_4Cl$ (110 mg, 1.9 mmol) and water (5 mL) and heated to 75° C. Then iron powder (2.1 g, 38 mmol) is added batchwise, the reaction mixture is stirred for 1 h and filtered to remove the excess iron powder. The solvent is eliminated by distillation using the rotary evaporator, the residue obtained is taken up in EtOAc and the organic phase is washed twice with sat. NaCl solution. The organic phase is dried on $MgSO_4$, filtered and evaporated down using the rotary evaporator and yields product B-2a (HPLC-MS: $t_{Ret.}$=1.50 min; MS $(M+H)^+$=210).

Analogously to these procedures, further anilines B-2 are obtained from the corresponding B-1 intermediates/educts or the corresponding commercially obtainable educt.

b) Procedure for Synthesising B-3a:

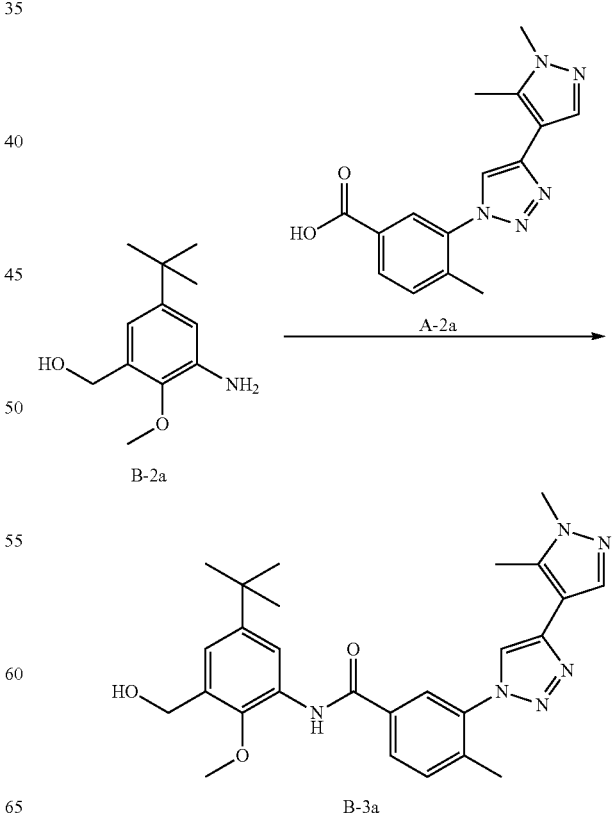

Benzoic acid A-2a (524 mg, 1.8 mmol) is taken up in 4 mL DCM and 4 mL THF, combined with oxalyl chloride (0.3 mL, 3.5 mmol) and one drop of DMF, stirred for 1 h at RT and then evaporated down using the rotary evaporator. The residue is taken up in 8 mL DCM and combined with the aniline B-2a (405 mg, 1.9 mmol) and DIPEA (0.7 mL, 4.0 mmol). The reaction mixture is stirred overnight at RT, evaporated down using the rotary evaporator, the residue is taken up in DMF and purified by preparative HPLC. The product-containing fractions of B-3a (HPLC-MS: $t_{Ret.}$=1.99 min; MS (M+H)$^+$=489) are freeze-dried.

Analogously to this procedure, further benzylalcohols B-3 are obtained from the corresponding B-2-and A-2 intermediates.

c) Procedure for Synthesising Ia-1 (Benzyl Chloride Route, Method A):

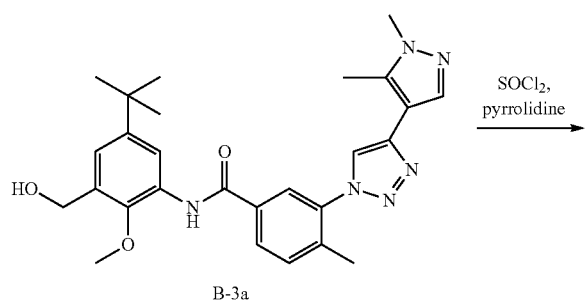

B-3a

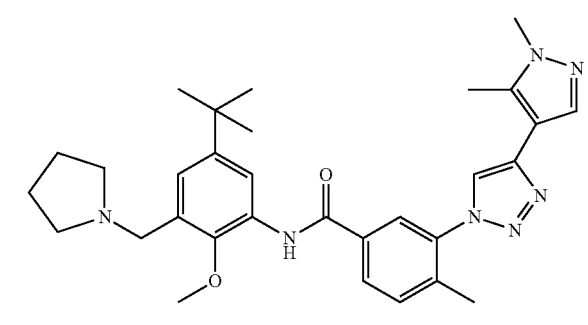

Ia-1

Benzylalcohol B-3a (30 mg, 0.06 mmol) is taken up in 2 mL DCM and combined with thionyl chloride (45 µL, 0.6 mmol) with stirring at RT. The reaction mixture is stirred for 3 h at RT, evaporated down, the residue is taken up in DMF (300 µL), combined with pyrrolidine (100 µL, 1.2 mmol) and stirred for 2 h at RT. The volatile constituents are eliminated using the rotary evaporator and the residue is purified by preparative HPLC. The product-containing fractions of Ia-1 (HPLC-MS: $t_{Ret.}$=1.62 min; MS (M+H)$^+$=542) are freeze-dried.

Analogously to this procedure further example compounds of type Ia are obtained from the corresponding B-3 intermediates.

d) Procedure for Synthesising Ia-1 (Oxidation-reductive Amination, Method B):

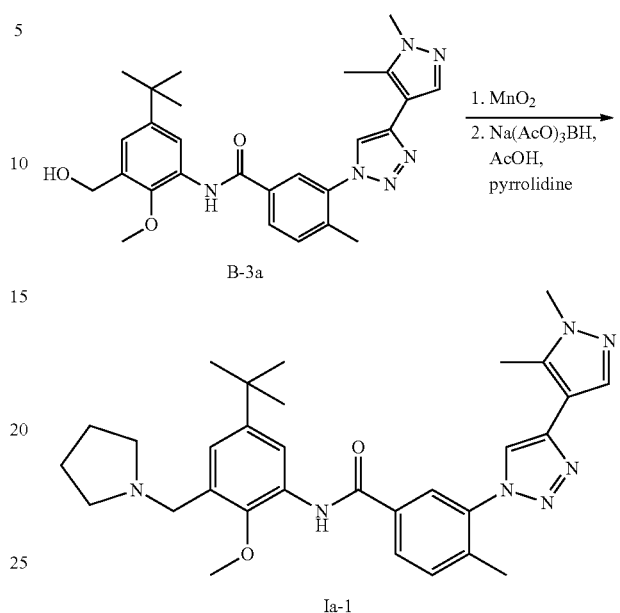

B-3a

Ia-1

Benzylalcohol B-3a (85 mg, 0.17 mmol) and MnO$_2$ (168 mg, 1.7 mmol) are taken up in 2 mL chlorobenzene and heated to 60° C. for 3 h. Then the mixture is left to cool to RT, filtered through Celite and the filtrate is evaporated down using the rotary evaporator. The residue is taken up in 3 mL DCM, combined with pyrrolidine (48 µL, 0.59 mmol) and stirred for 15 min. Then glacial acetic acid (34 µL, 0.59 mmol) is added and Na(AcO)$_3$BH (124.1 mg, 0.586 mmol) is added batchwise. The reaction mixture is stirred overnight at RT, evaporated down using the rotary evaporator, the residue is taken up in a little DMF and purified by preparative HPLC. The product-containing fractions of Ia-1 (HPLC-MS: $t_{Ret.}$=1.62 min; MS (M+H)$^+$=542) are freeze-dried.

Analogously to this procedure further example compounds of type Ia are obtained from the corresponding B-3 intermediates.

Reaction scheme B-II

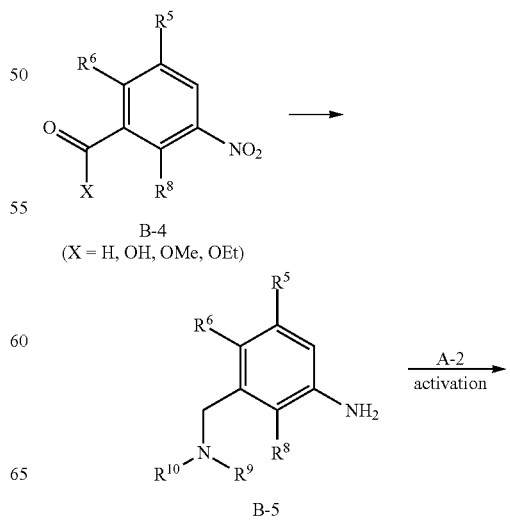

B-4
(X = H, OH, OMe, OEt)

B-5

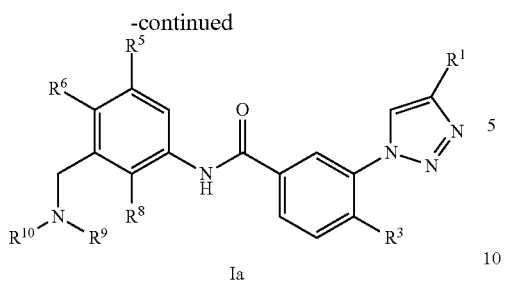

Ia

Example compounds of type Ia (benzylamine in the m-position to the amide link→R⁷) can also be prepared by a different sequence of the reaction steps shown in reaction scheme B-I (→reaction scheme B-II), by first synthesising the anilinic benzylamines B-5 using methods known from the literature from the nitro compounds B-4 by reducing the two functional groups, protecting the amino function (e.g. by means of the Boc protective group), activating the benzyl alcohol (for example to obtain the chloride or mesylate) and reacting the benzyl alcohol thus activated with secondary amines and then reacting with the components A-2 by standard amide linking methods to form the end compounds Ia.

e) Procedure for Synthesising Ia-198

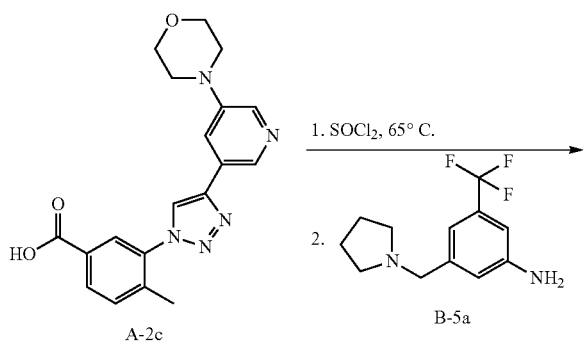

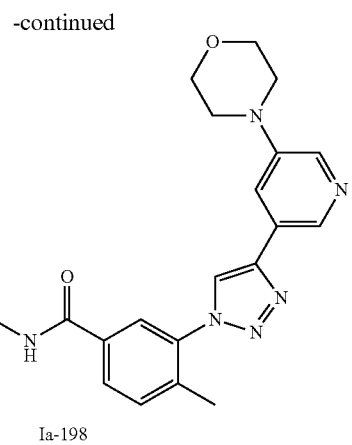

Ia-198

The benzoic acid A-2c (166 mg, 0.43 mmol) is heated in thionyl chloride (2 mL) for 3 h at 65° C. Then the thionyl chloride is eliminated using the rotary evaporator. The residue is taken up in DCM (3.5 mL) and combined with the aniline B-5a (150 mg, 0.62 mmol) in DCM (3.5 mL). The reaction mixture is stirred overnight at RT, evaporated down using the rotary evaporator, the residue is taken up in a little DMF and purified by preparative HPLC. The product-containing fractions of Ia-198 (HPLC-MS: $t_{Ret.}$=2.26 min; MS (M+H)⁺=592) are freeze-dried.

Analogously to this procedure further example compounds of type Ia are obtained from the corresponding A-2 and B-5 intermediates.

Analogously to the reaction methods a) to e) described above for synthesising Examples Ia-1 and Ia-198 the following Examples Ia-2 to Ia-266 (Table 1) or comparable further Examples may be obtained from the corresponding precursors, which are either commercially obtainable or are prepared using methods known from the literature.

TABLE 1

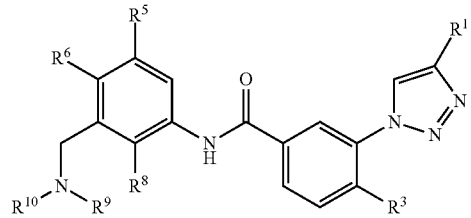

Examples Ia-1 to Ia-266

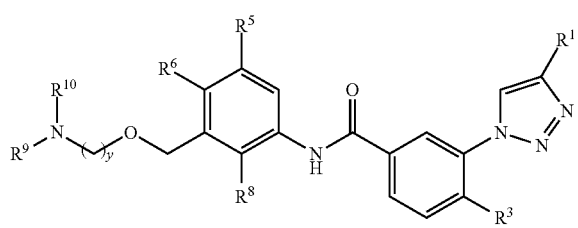

Example type Ib $t_{Ret.}$

TABLE 1-continued

| # | Structure | (HPLC) [min] | MS (M + H)+ |
|---|---|---|---|
| Ia-1 | 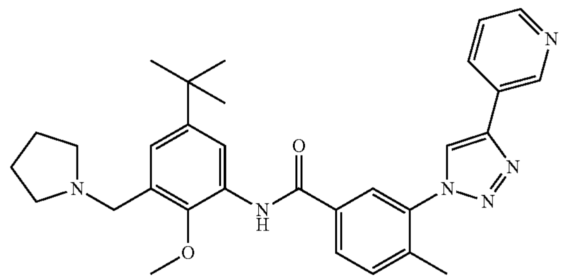 [SMILES: COc1c(CN2CCCC2)cc(C(C)(C)C)cc1NC(=O)c1ccc(C)c(-n2cc(-c3cccnc3)nn2)c1] | 1.52 | 525 |
| Ia-2 | 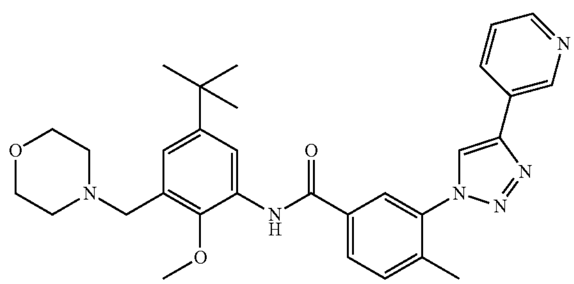 [SMILES: COc1c(CN2CCOCC2)cc(C(C)(C)C)cc1NC(=O)c1ccc(C)c(-n2cc(-c3cccnc3)nn2)c1] | 1.48 | 541 |
| Ia-3 | 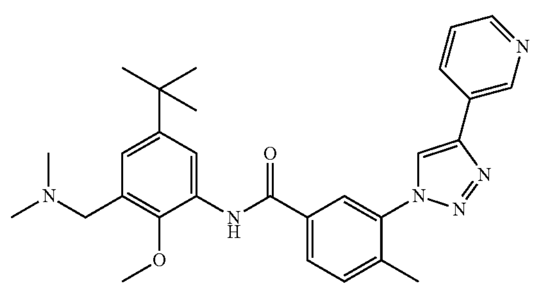 [SMILES: COc1c(CN(C)C)cc(C(C)(C)C)cc1NC(=O)c1ccc(C)c(-n2cc(-c3cccnc3)nn2)c1] | 1.46 | 499 |
| Ia-4 | 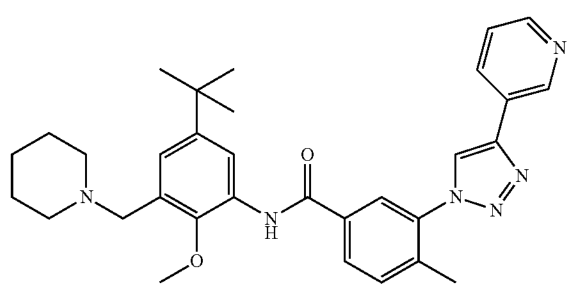 [SMILES: COc1c(CN2CCCCC2)cc(C(C)(C)C)cc1NC(=O)c1ccc(C)c(-n2cc(-c3cccnc3)nn2)c1] | 1.52 | 539 |
| Ia-5 | 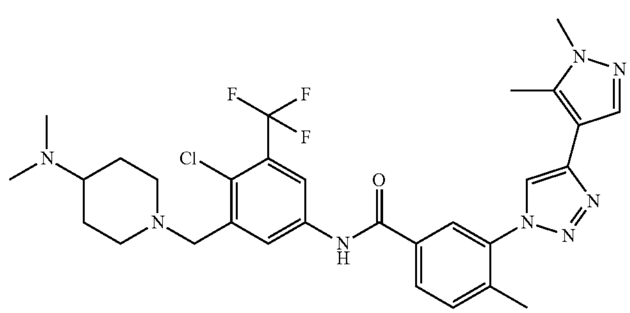 [SMILES: Cc1ccc(C(=O)Nc2cc(CN3CCC(N(C)C)CC3)c(Cl)c(C(F)(F)F)c2)cc1-n1cc(-c2cnn(C)c2C)nn1] | 1.45 | 615 |

TABLE 1-continued

| | | | |
|---|---|---|---|
| Ia-6 | (structure) | 2.27 | 546 |
| Ia-7 | (structure) | 1.59 | 532 |
| Ia-8 | (structure) | 1.61 | 546 |
| Ia-9 | (structure) | 1.62 | 558 |
| Ia-10 | (structure) | 1.50 | 575 |

TABLE 1-continued

| | | | |
|---|---|---|---|
| Ia-11 | (structure) | 1.56 | 548 |
| Ia-12 | (structure) | 1.65 | 572 |
| Ia-13 | (structure) | 1.69 | 574 |
| Ia-14 | (structure) | 1.63 | 544 |
| Ia-15 | (structure) | 1.56 | 518 |

TABLE 1-continued

| | | | |
|---|---|---|---|
| Ia-16 | (structure) | 1.69 | 587 |
| Ia-17 | (structure) | 1.60 | 560 |
| Ia-18 | (structure) | 1.49 | 559 |
| Ia-19 | (structure) | 1.42 | 547 |
| Ia-20 | (structure) | 1.45 | 561 |

TABLE 1-continued

| ID | Structure | Val1 | Val2 |
|---|---|---|---|
| Ia-21 | 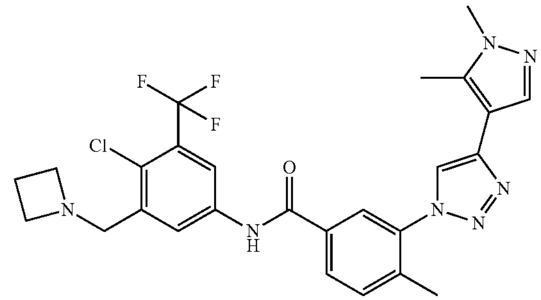 [SMILES: Cc1ccc(C(=O)Nc2cc(CN3CCC3)c(Cl)c(C(F)(F)F)c2)cc1-n1cc(-c2cnn(C)c2C)nn1] | 1.61 | 544 |
| Ia-22 | 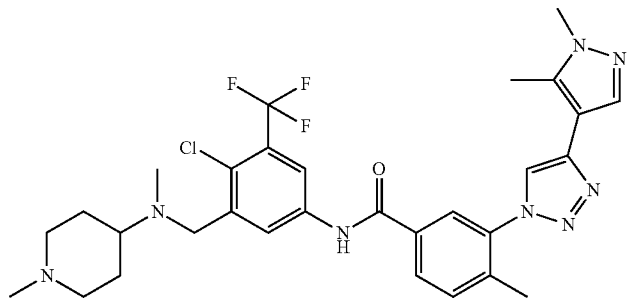 [SMILES: Cc1ccc(C(=O)Nc2cc(CN(C)C3CCN(C)CC3)c(Cl)c(C(F)(F)F)c2)cc1-n1cc(-c2cnn(C)c2C)nn1] | 1.44 | 615 |
| Ia-23 | 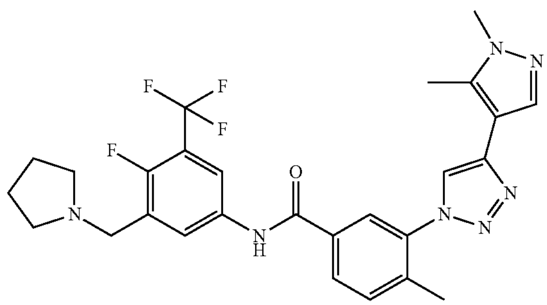 [SMILES: Cc1ccc(C(=O)Nc2cc(CN3CCCC3)c(F)c(C(F)(F)F)c2)cc1-n1cc(-c2cnn(C)c2C)nn1] | 2.27 | 542 |
| Ia-24 | 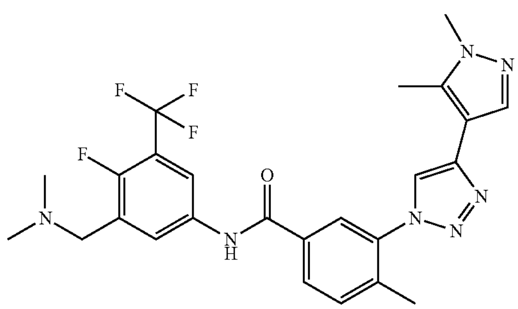 [SMILES: Cc1ccc(C(=O)Nc2cc(CN(C)C)c(F)c(C(F)(F)F)c2)cc1-n1cc(-c2cnn(C)c2C)nn1] | 2.14 | 516 |
| Ia-25 | 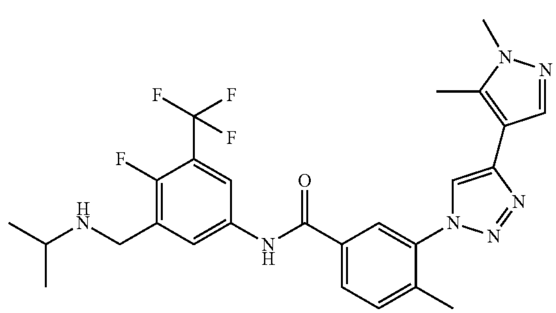 [SMILES: Cc1ccc(C(=O)Nc2cc(CNC(C)C)c(F)c(C(F)(F)F)c2)cc1-n1cc(-c2cnn(C)c2C)nn1] | 2.18 | 530 |

TABLE 1-continued

| ID | Structure | A | B |
|---|---|---|---|
| Ia-26 | 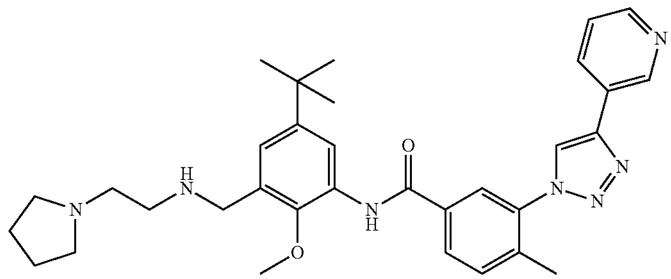 [SMILES: COc1c(CNCCN2CCCC2)cc(C(C)(C)C)cc1NC(=O)c1ccc(C)c(-n2cc(-c3cccnc3)nn2)c1] | 1.32 | 568 |
| Ia-27 | 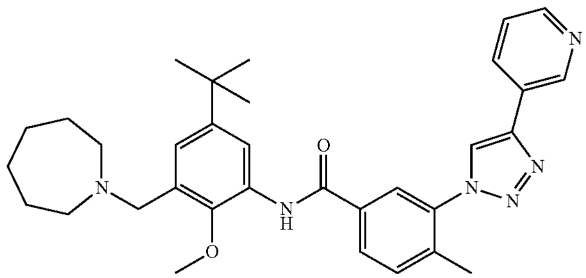 [SMILES: COc1c(CN2CCCCCC2)cc(C(C)(C)C)cc1NC(=O)c1ccc(C)c(-n2cc(-c3cccnc3)nn2)c1] | 1.59 | 553 |
| Ia-28 | 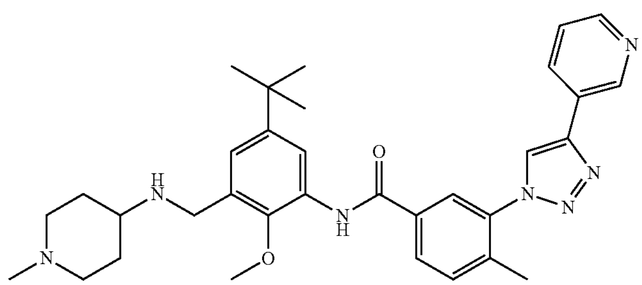 [SMILES: COc1c(CNC2CCN(C)CC2)cc(C(C)(C)C)cc1NC(=O)c1ccc(C)c(-n2cc(-c3cccnc3)nn2)c1] | 0.0 | 568 |
| Ia-29 | 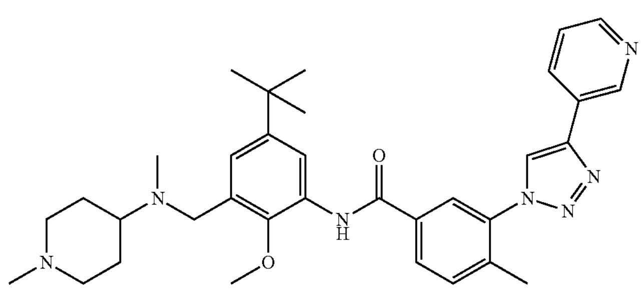 [SMILES: COc1c(CN(C)C2CCN(C)CC2)cc(C(C)(C)C)cc1NC(=O)c1ccc(C)c(-n2cc(-c3cccnc3)nn2)c1] | 1.30 | 582 |
| Ia-30 | 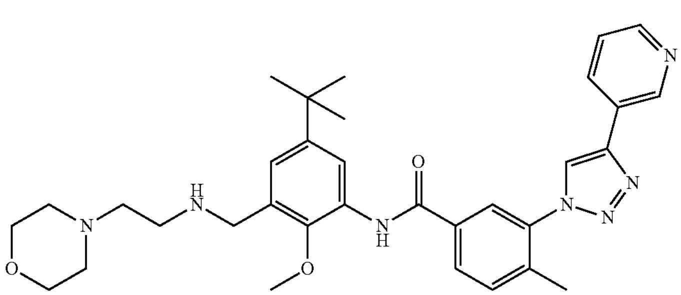 [SMILES: COc1c(CNCCN2CCOCC2)cc(C(C)(C)C)cc1NC(=O)c1ccc(C)c(-n2cc(-c3cccnc3)nn2)c1] | 1.40 | 584 |

TABLE 1-continued

| ID | Structure | A | B |
|---|---|---|---|
| Ia-31 | 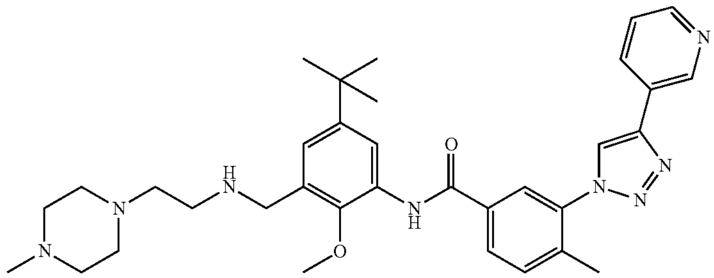 [SMILES: COc1c(CNCCN2CCN(C)CC2)cc(C(C)(C)C)cc1NC(=O)c1ccc(C)c(-n2cc(-c3cccnc3)nn2)c1] | 1.30 | 597 |
| Ia-32 | 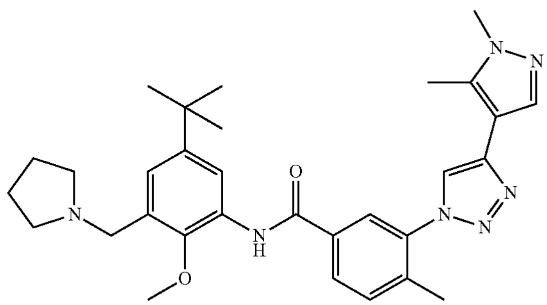 [SMILES: COc1c(CN2CCCC2)cc(C(C)(C)C)cc1NC(=O)c1ccc(C)c(-n2cc(-c3cnn(C)c3C)nn2)c1] | 1.62 | 542 |
| Ia-33 | 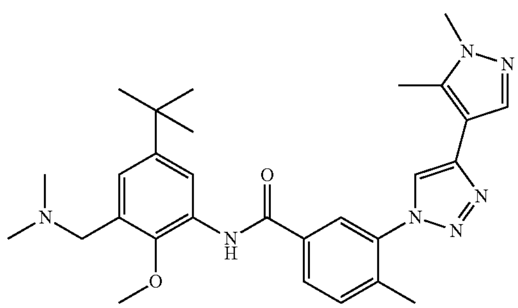 [SMILES: COc1c(CN(C)C)cc(C(C)(C)C)cc1NC(=O)c1ccc(C)c(-n2cc(-c3cnn(C)c3C)nn2)c1] | 1.58 | 516 |
| Ia-34 | 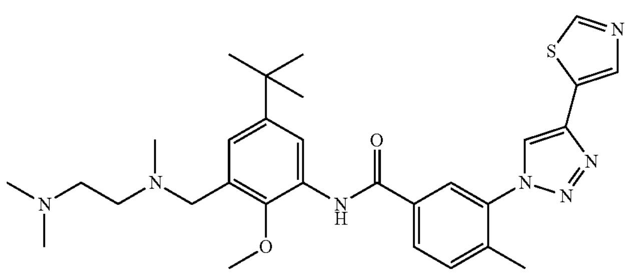 [SMILES: COc1c(CN(C)CCN(C)C)cc(C(C)(C)C)cc1NC(=O)c1ccc(C)c(-n2cc(-c3cncs3)nn2)c1] | 1.42 | 562 |
| Ia-35 | 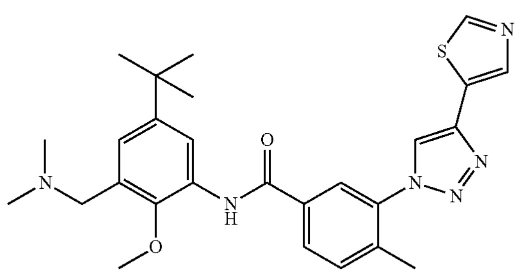 [SMILES: COc1c(CN(C)C)cc(C(C)(C)C)cc1NC(=O)c1ccc(C)c(-n2cc(-c3cncs3)nn2)c1] | 1.59 | 505 |

TABLE 1-continued

| | | | |
|---|---|---|---|
| Ia-36 | | 1.61 | 531 |
| Ia-37 | | 1.29 | 547 |
| Ia-38 | | 1.63 | 545 |
| Ia-39 | | 0.0 | 573 |
| Ia-40 | | 1.57 | 558 |

TABLE 1-continued
| | | | | |
|---|---|---|---|---|
| Ia-41 | 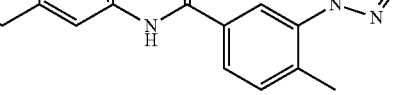 | | 1.55 | 487 |
| Ia-42 | 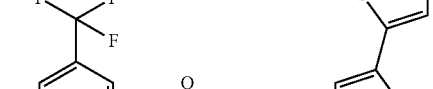 | | 1.52 | 473 |
| Ia-43 | 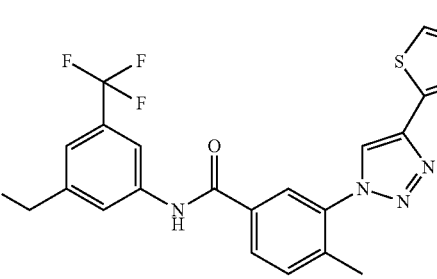 | | 1.56 | 513 |
| Ia-44 | 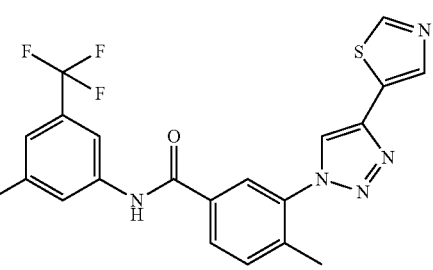 | | 1.57 | 499 |
| Ia-45 | 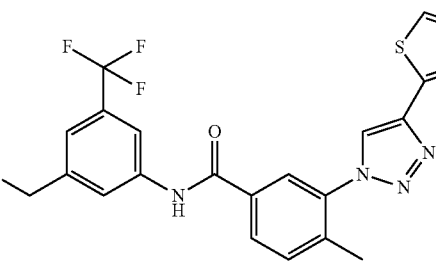 | | 1.54 | 529 |
| Ia-46 | 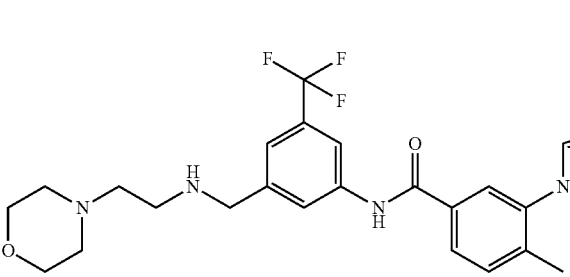 | | 1.46 | 572 |

TABLE 1-continued

| | | | |
|---|---|---|---|
| Ia-47 | [structure] | 1.55 | 524 |
| Ia-48 | [structure] | 1.50 | 484 |
| Ia-49 | [structure] | 1.56 | 510 |
| Ia-50 | [structure] | 1.72 | 574 |
| Ia-51 | [structure] | 2.00 | 560 |

TABLE 1-continued

| ID | Structure | Val1 | Val2 |
|---|---|---|---|
| Ia-52 | (structure) | 1.53 | 498 |
| Ia-53 | (structure) | 2.02 | 574 |
| Ia-54 | (structure) | 1.58 | 556 |
| Ia-55 | (structure) | 0.0 | 541 |
| Ia-56 | (structure) | 1.38 | 621 |

TABLE 1-continued

| ID | Structure | t | m/z |
|---|---|---|---|
| Ia-57 | (structure) | 1.41 | 527 |
| Ia-58 | (structure) | 1.42 | 527 |
| Ia-59 | (structure) | 1.50 | 555 |
| Ia-60 | (structure) | 1.58 | 554 |
| Ia-61 | (structure) | 1.56 | 542 |

TABLE 1-continued

| ID | Structure | | |
|---|---|---|---|
| Ia-62 | (structure) | 1.69 | 604 |
| Ia-63 | (structure) | 1.59 | 586 |
| Ia-64 | (structure) | 1.47 | 585 |
| Ia-65 | (structure) | 1.58 | 540 |
| Ia-66 | (structure) | 1.53 | 528 |

TABLE 1-continued

| | | | |
|---|---|---|---|
| Ia-67 | [structure] | 0.0 | 571 |
| Ia-68 | [structure] | 1.37 | 557 |
| Ia-69 | [structure] | 1.52 | 514/528 |
| Ia-70 | [structure] | 1.44 | 525 |
| Ia-71 | [structure] | 0.0 | 568 |

TABLE 1-continued

| | | | |
|---|---|---|---|
| Ia-72 | (structure) | 0.0 | 523 |
| Ia-73 | (structure) | 0.0 | 511 |
| Ia-74 | (structure) | 0.0 | 554 |
| Ia-75 | (structure) | 1.39 | 537 |
| Ia-76 | (structure) | 1.51 | 528 |

TABLE 1-continued

| | | | |
|---|---|---|---|
| Ia-77 | (structure) | 1.54 | 542 |
| Ia-78 | (structure) | 1.58 | 554 |
| Ia-79 | (structure) | 1.61 | 568 |
| Ia-80 | (structure) | 1.59 | 512 |
| Ia-81 | (structure) | 1.60 | 524 |

TABLE 1-continued
| Ia-82 | 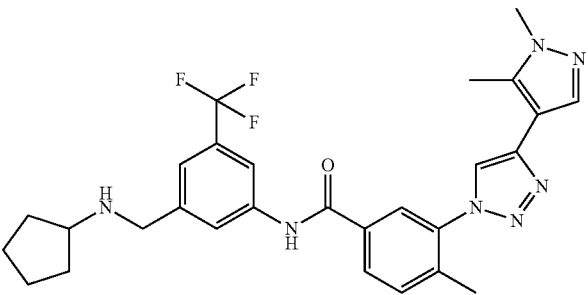 [SMILES: Cc1ccc(C(=O)Nc2cc(CNC3CCCC3)cc(C(F)(F)F)c2)cc1-n1cc(-c2cnn(C)c2C)nn1] | 1.64 | 538 |
| Ia-83 | 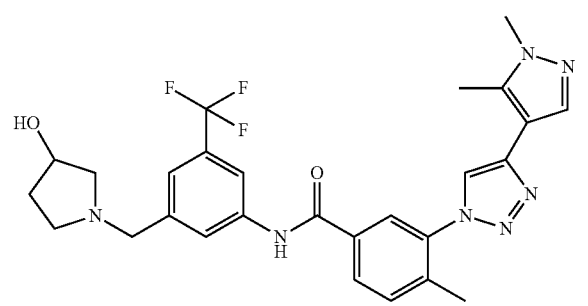 [SMILES: Cc1ccc(C(=O)Nc2cc(CN3CCC(O)C3)cc(C(F)(F)F)c2)cc1-n1cc(-c2cnn(C)c2C)nn1] | 1.52 | 540 |
| Ia-84 | 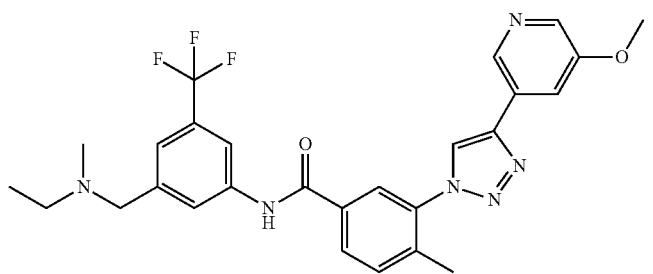 [SMILES: CCN(C)Cc1cc(NC(=O)c2ccc(C)c(-n3cc(-c4cncc(OC)c4)nn3)c2)cc(C(F)(F)F)c1] | 1.58 | 525 |
| Ia-85 | 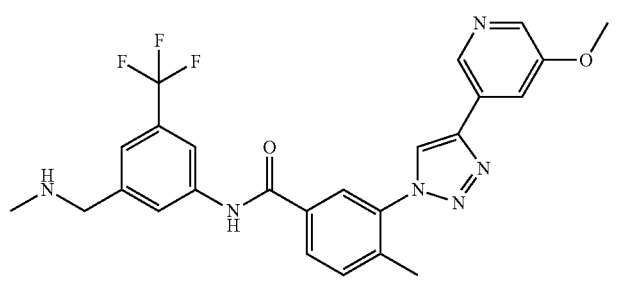 | 1.53 | 497 |
| Ia-86 | 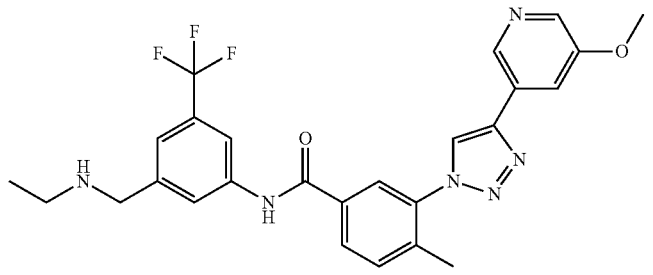 [SMILES: CCNCc1cc(NC(=O)c2ccc(C)c(-n3cc(-c4cncc(OC)c4)nn3)c2)cc(C(F)(F)F)c1] | 1.55 | 511 |

TABLE 1-continued
| Ia-87 | 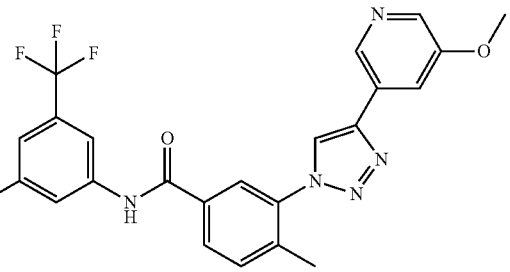 | 1.56 | 525 |
| Ia-88 | 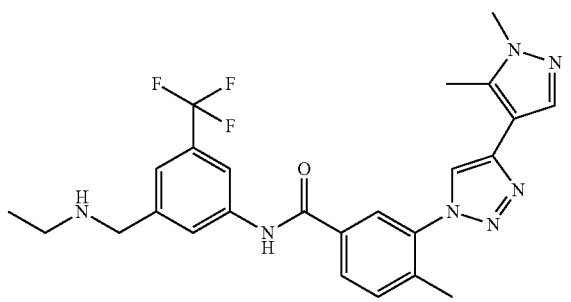 [SMILES: CCNCc1cc(NC(=O)c2ccc(C)c(-n3cc(-c4cnn(C)c4C)nn3)c2)cc(C(F)(F)F)c1] | 1.56 | 498 |
| Ia-89 | 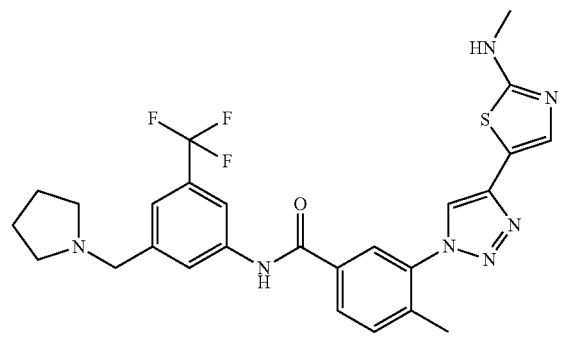 [SMILES: CNc1ncc(-c2cn(-c3cc(C(=O)Nc4cc(CN5CCCC5)cc(C(F)(F)F)c4)ccc3C)nn2)s1] | 2.26 | |
| Ia-90 | 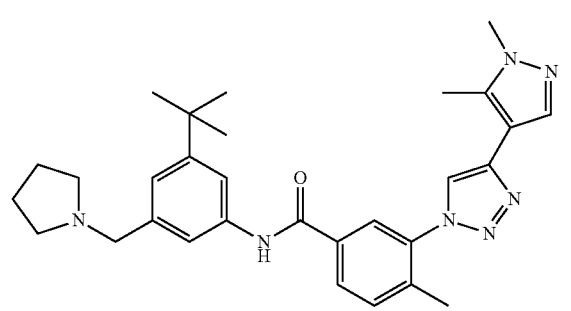 [SMILES: Cc1ccc(C(=O)Nc2cc(CN3CCCC3)cc(C(C)(C)C)c2)cc1-n1cc(-c2cnn(C)c2C)nn1] | 2.25 | 512 |
| Ia-91 | 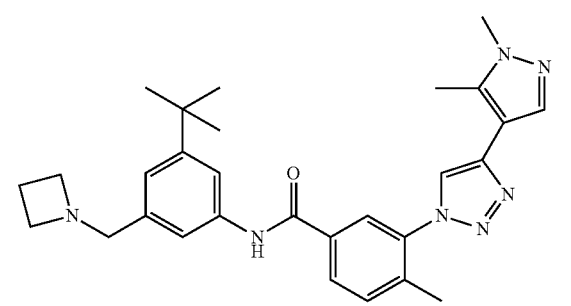 [SMILES: Cc1ccc(C(=O)Nc2cc(CN3CCC3)cc(C(C)(C)C)c2)cc1-n1cc(-c2cnn(C)c2C)nn1] | 2.20 | 498 |

TABLE 1-continued
| Ia-92 | 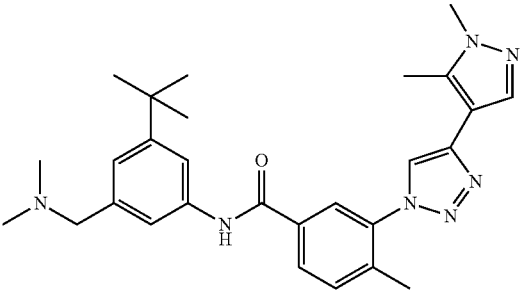 [SMILES: Cc1ccc(C(=O)Nc2cc(CN(C)C)cc(C(C)(C)C)c2)cc1-n1cc(-c2cnn(C)c2C)nn1] | 2.15 | 486 |
| Ia-93 | 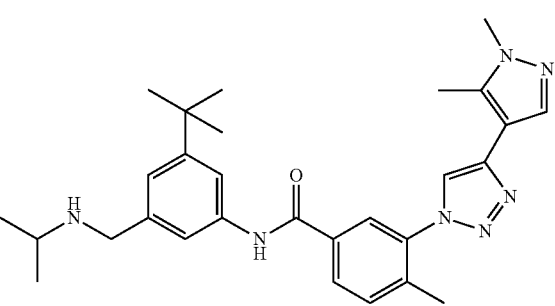 [SMILES: Cc1ccc(C(=O)Nc2cc(CNC(C)C)cc(C(C)(C)C)c2)cc1-n1cc(-c2cnn(C)c2C)nn1] | 2.21 | 500 |
| Ia-94 | 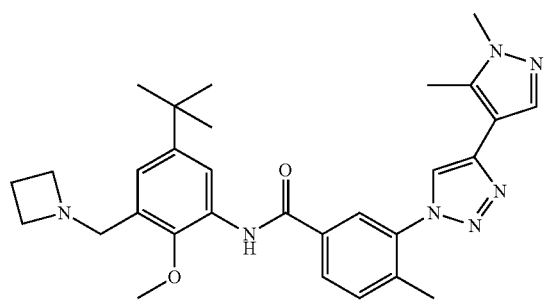 [SMILES: COc1c(CN2CCC2)cc(C(C)(C)C)cc1NC(=O)c1ccc(C)c(-n2cc(-c3cnn(C)c3C)nn2)c1] | 2.13 | 528 |
| Ia-95 | 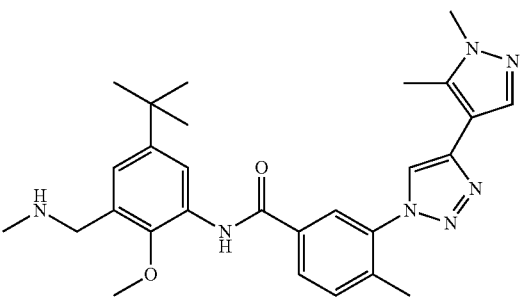 [SMILES: CNCc1cc(C(C)(C)C)cc(NC(=O)c2ccc(C)c(-n3cc(-c4cnn(C)c4C)nn3)c2)c1OC] | 2.06 | 502 |
| Ia-96 | 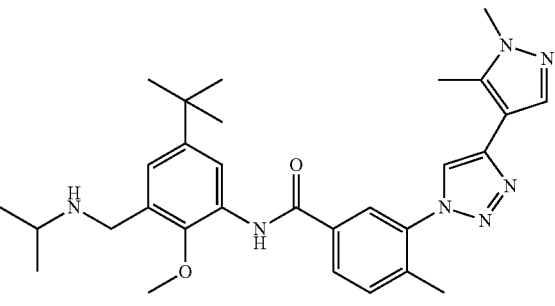 [SMILES: COc1c(CNC(C)C)cc(C(C)(C)C)cc1NC(=O)c1ccc(C)c(-n2cc(-c3cnn(C)c3C)nn2)c1] | 2.15 | 530 |

TABLE 1-continued
| | | | |
|---|---|---|---|
| Ia-97 | 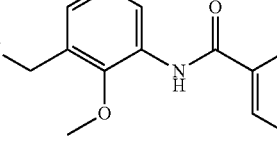 | 2.32 | 570 |
| Ia-98 | 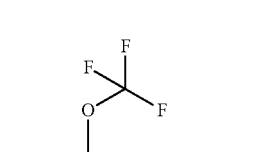 | 2.19 | 558 |
| Ia-99 | 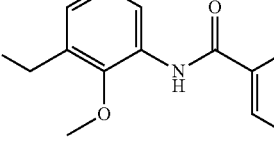 | 2.01 | 601 |
| Ia-100 | 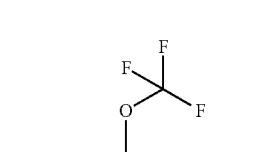 | 2.33 | 572 |
| Ia-101 | 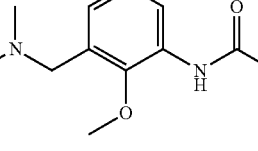 | 2.19 | 508 |

TABLE 1-continued

| | | | |
|---|---|---|---|
| Ia-102 | | 2.29 | 540 |
| Ia-103 | | 2.18 | 528 |
| Ia-104 | | 2.28 | 542 |
| Ia-105 | | 2.27 | 554 |
| Ia-106 | | 2.16 | 542 |

TABLE 1-continued

| ID | Structure | A | B |
|---|---|---|---|
| Ia-107 | 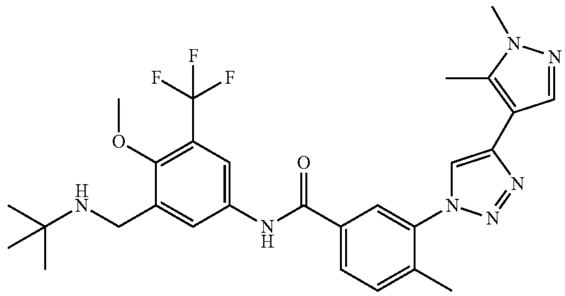 [SMILES: COc1c(CNC(C)(C)C)cc(NC(=O)c2ccc(C)c(-n3cc(-c4cnn(C)c4C)nn3)c2)cc1C(F)(F)F] | 2.26 | 556 |
| Ia-108 | 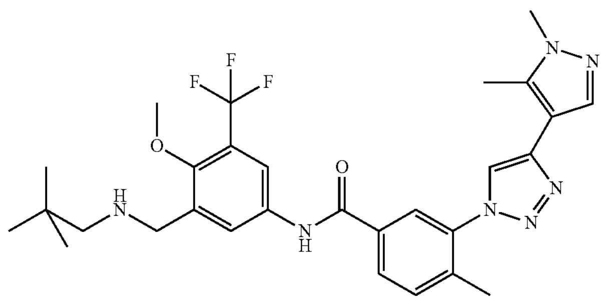 [SMILES: COc1c(CNCC(C)(C)C)cc(NC(=O)c2ccc(C)c(-n3cc(-c4cnn(C)c4C)nn3)c2)cc1C(F)(F)F] | 2.42 | 570 |
| Ia-109 | 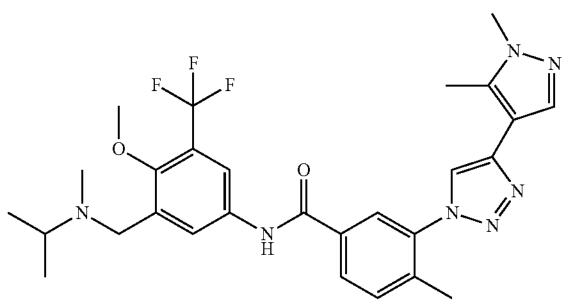 [SMILES: COc1c(CN(C)C(C)C)cc(NC(=O)c2ccc(C)c(-n3cc(-c4cnn(C)c4C)nn3)c2)cc1C(F)(F)F] | 2.38 | 556 |
| Ia-110 | 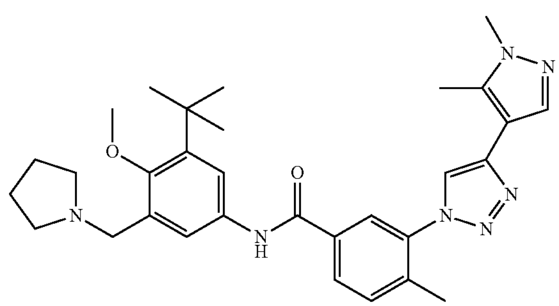 [SMILES: COc1c(CN2CCCC2)cc(NC(=O)c2ccc(C)c(-n3cc(-c4cnn(C)c4C)nn3)c2)cc1C(C)(C)C] | 2.36 | 542 |
| Ia-111 | 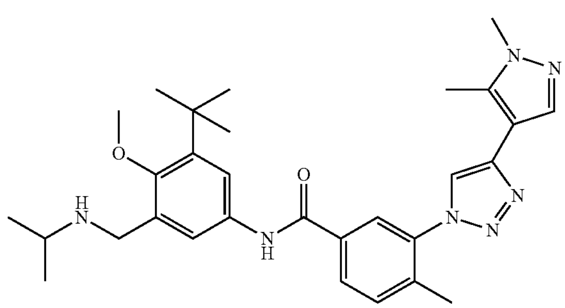 [SMILES: COc1c(CNC(C)C)cc(NC(=O)c2ccc(C)c(-n3cc(-c4cnn(C)c4C)nn3)c2)cc1C(C)(C)C] | 2.25 | 530 |

TABLE 1-continued

| | | | |
|---|---|---|---|
| Ia-112 | | 1.99 | 544 |
| Ia-113 | | 2.35 | 544 |
| Ia-114 | | 2.67 | 558 |
| Ia-115 | | 2.51 | 558 |
| Ia-116 | | 1.56 | 555 |

TABLE 1-continued

| Compound | Structure | Col A | Col B |
|---|---|---|---|
| Ia-117 | (structure) | 1.45 | 527 |
| Ia-118 | (structure) | 1.57 | 553 |
| Ia-119 | (structure) | 1.50 | 541 |
| Ia-120 | (structure) | 1.53 | 567 |
| Ia-121 | (structure) | 1.53 | 541 |
| Ia-122 | (structure) | 2.25 | 555 |

TABLE 1-continued
| Ia-123 | 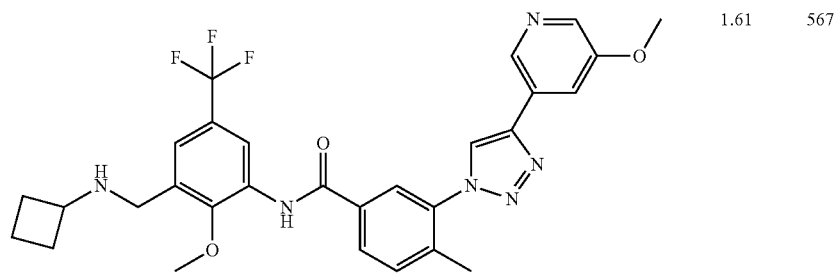 | 1.61 | 567 |
| Ia-124 | 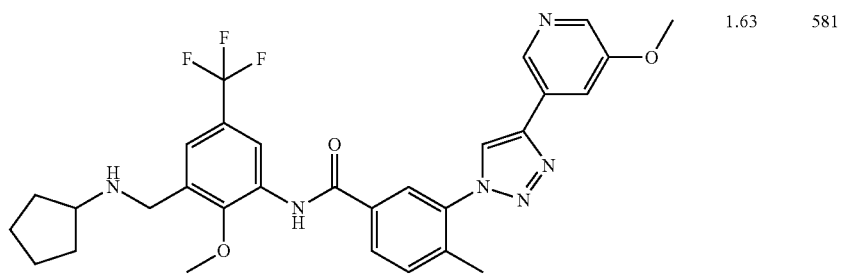 | 1.63 | 581 |
| Ia-125 | 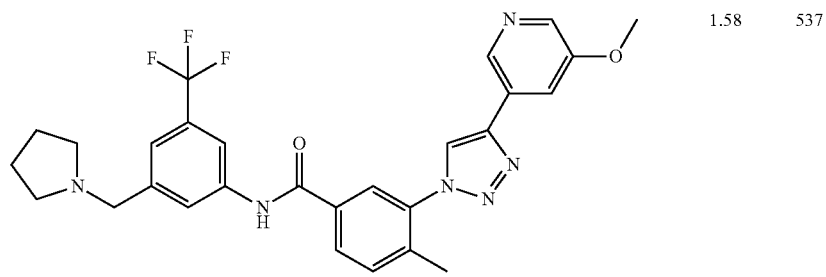 | 1.58 | 537 |
| Ia-126 | 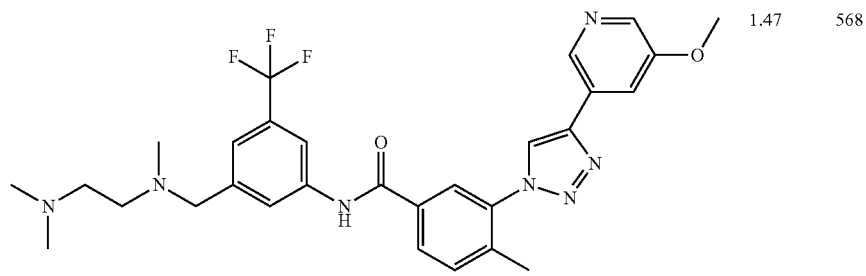 | 1.47 | 568 |
| Ia-127 | 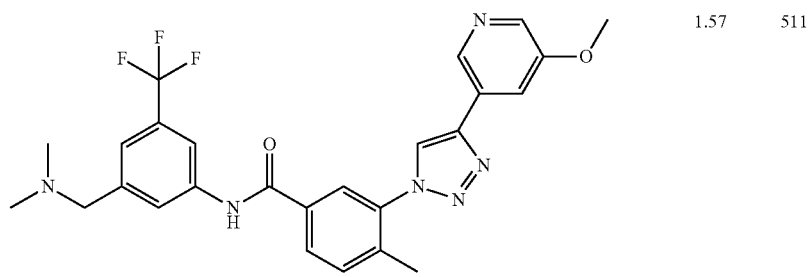 | 1.57 | 511 |

TABLE 1-continued

| | | | |
|---|---|---|---|
| Ia-128 | [structure] | 1.57 | 523 |
| Ia-129 | [structure] | 1.55 | 605 |
| Ia-130 | [structure] | 1.53 | 578 |
| Ia-131 | [structure] | 2.18 | 560 |
| Ia-132 | [structure] | 2.17 | 562 |

TABLE 1-continued

| | | | |
|---|---|---|---|
| Ia-133 | (structure) | 2.14 | 617 |
| Ia-134 | (structure) | 2.14 | 605 |
| Ia-135 | (structure) | 2.57 | 602 |
| Ia-136 | (structure) | 2.08 | 603 |
| Ia-137 | (structure) | 1.99 | 548 |

TABLE 1-continued

| Ia-138 | (structure) | 2.17 | 530 |
| Ia-139 | (structure) | 2.17 | 532 |
| Ia-140 | (structure) | 2.13 | 587 |
| Ia-141 | (structure) | 2.05 | 573 |
| Ia-142 | (structure) | 2.03 | 585 |

TABLE 1-continued

| | | | |
|---|---|---|---|
| Ia-143 | | 2.28 | 544 |
| Ia-144 | | 2.15 | 530 |
| Ia-145 | | 2.03 | 574 |
| Ia-146 | | 2.15 | 518 |
| Ia-147 | | 2.28 | 532 |

TABLE 1-continued

| | | | |
|---|---|---|---|
| Ia-148 | | 2.02 | 504 |
| Ia-149 | | 1.91 | 546 |
| Ia-150 | | 2.12 | 615 |
| Ia-151 | | 2.30 | 574 |
| Ia-152 | | 2.18 | 560 |

TABLE 1-continued

| | | | |
|---|---|---|---|
| Ia-153 | | 2.01 | 604 |
| Ia-154 | | 2.16 | 548 |
| Ia-155 | | 2.29 | 562 |
| Ia-156 | | 1.97 | 534 |
| Ia-157 | | 1.92 | 576 |

TABLE 1-continued

| Ia-158 | [structure] | 1.61 | 598 |
| Ia-159 | [structure] | 1.60 | 557 |
| Ia-160 | [structure] | 1.57 | 587 |
| Ia-161 | [structure] | 1.57 | 531 |
| Ia-162 | [structure] | 1.61 | 545 |

TABLE 1-continued

| Ia-163 | | 2.07 | 517 |
|---|---|---|---|
| Ia-164 | | 1.97 | 559 |
| Ia-165 | | 1.60 | 628 |
| Ia-166 | | 1.59 | 587 |
| Ia-167 | | 1.56 | 617 |

TABLE 1-continued

| | | | |
|---|---|---|---|
| Ia-168 | [structure] | 1.58 | 575 |
| Ia-169 | [structure] | 1.57 | 547 |
| Ia-170 | [structure] | 1.56 | 589 |
| Ia-171 | [structure] | 1.43 | 595 |
| Ia-172 | [structure] | 1.51 | 556 |

TABLE 1-continued

| | | | |
|---|---|---|---|
| Ia-173 | [structure] | 1.54 | 584 |
| Ia-174 | [structure] | 1.54 | 570 |
| Ia-175 | [structure] | 1.55 | 540 |
| Ia-176 | [structure] | 1.59 | 583 |
| Ia-177 | [structure] | 1.56 | 565 |

TABLE 1-continued

| | | | |
|---|---|---|---|
| Ia-178 | | 1.53 | 526 |
| Ia-179 | | 1.55 | 554 |
| Ia-180 | | 1.56 | 540 |
| Ia-181 | | 1.58 | 556 |
| Ia-182 | | 1.57 | 570 |

TABLE 1-continued

| | | | |
|---|---|---|---|
| Ia-183 | [structure] | 1.59 | 569 |
| Ia-184 | [structure] | 1.60 | 583 |
| Ia-185 | [structure] | 2.23 | 570 |
| Ia-186 | [structure] | 2.10 | 544 |
| Ia-187 | [structure] | 2.20 | 588 |

| | | | |
|---|---|---|---|
| Ia-188 | 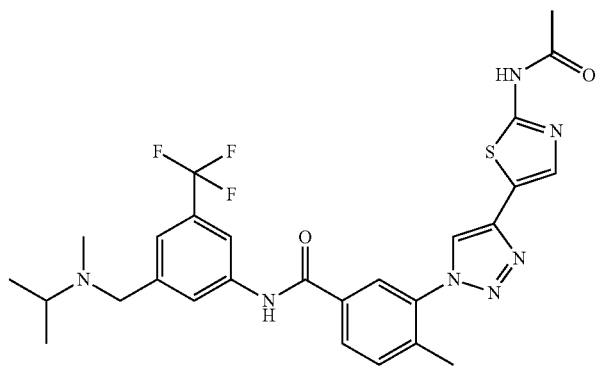 [SMILES: CC(=O)Nc1ncc(-c2cn(-c3cc(C(=O)Nc4cc(CN(C)C(C)C)cc(C(F)(F)F)c4)ccc3C)nn2)s1] | 2.33 | 572 |
| Ia-189 | 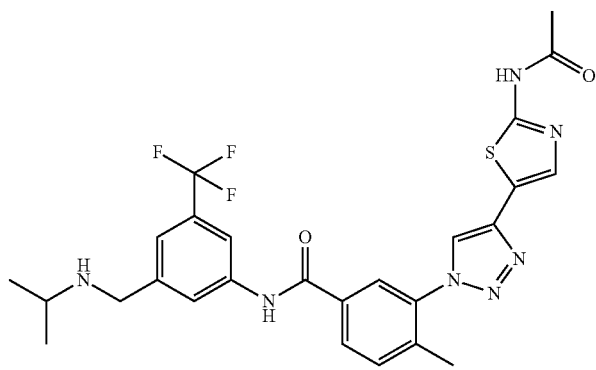 [SMILES: CC(=O)Nc1ncc(-c2cn(-c3cc(C(=O)Nc4cc(CNC(C)C)cc(C(F)(F)F)c4)ccc3C)nn2)s1] | 2.10 | 558 |
| Ia-190 | 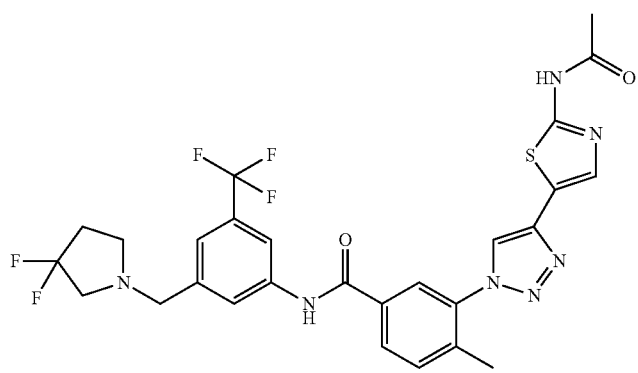 [SMILES: CC(=O)Nc1ncc(-c2cn(-c3cc(C(=O)Nc4cc(CN5CCC(F)(F)C5)cc(C(F)(F)F)c4)ccc3C)nn2)s1] | 2.27 | 606 |
| Ia-191 | 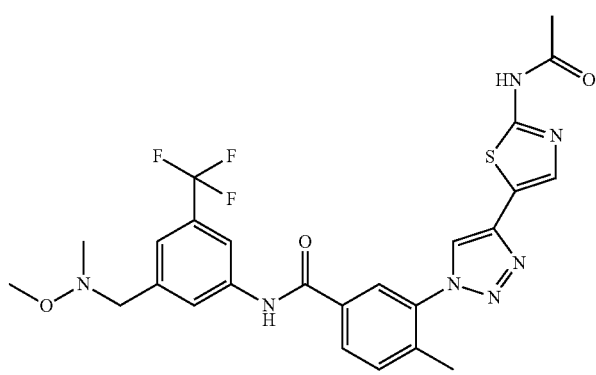 [SMILES: CON(C)Cc1cc(NC(=O)c2ccc(C)c(-n3cc(-c4cnc(NC(C)=O)s4)nn3)c2)cc(C(F)(F)F)c1] | 2.15 | 560 |

| | | | |
|---|---|---|---|
| Ia-192 | 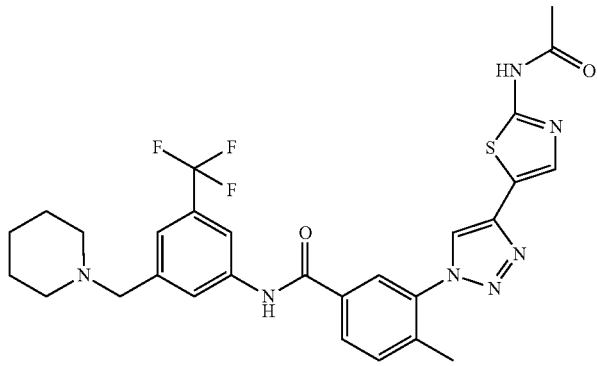 [SMILES: CC(=O)Nc1ncc(-c2cn(-c3cc(C(=O)Nc4cc(CN5CCCCC5)cc(C(F)(F)F)c4)ccc3C)nn2)s1] | 2.33 | 584 |
| Ia-193 | 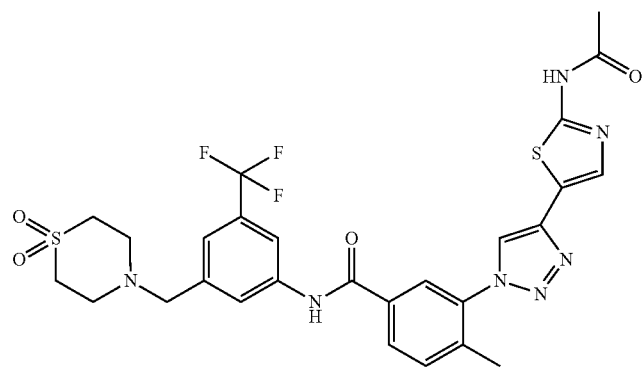 [SMILES: CC(=O)Nc1ncc(-c2cn(-c3cc(C(=O)Nc4cc(CN5CCS(=O)(=O)CC5)cc(C(F)(F)F)c4)ccc3C)nn2)s1] | 2.01 | 634 |
| Ia-194 | 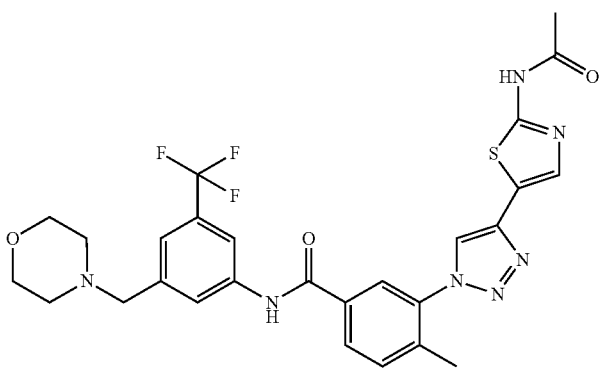 [SMILES: CC(=O)Nc1ncc(-c2cn(-c3cc(C(=O)Nc4cc(CN5CCOCC5)cc(C(F)(F)F)c4)ccc3C)nn2)s1] | 2.06 | 586 |
| Ia-195 | 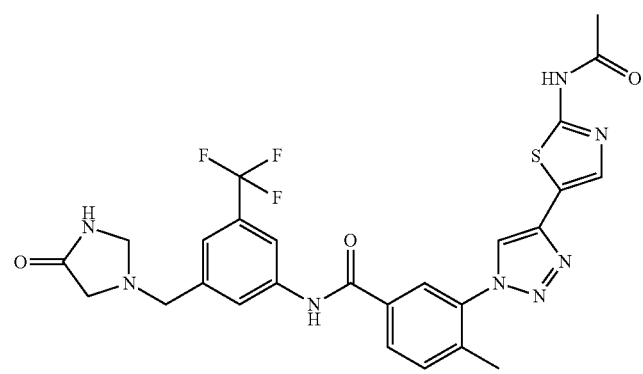 [SMILES: CC(=O)Nc1ncc(-c2cn(-c3cc(C(=O)Nc4cc(CN5CNC(=O)C5)cc(C(F)(F)F)c4)ccc3C)nn2)s1] | 1.84 | 585 |

TABLE 1-continued
| Ia-196 | 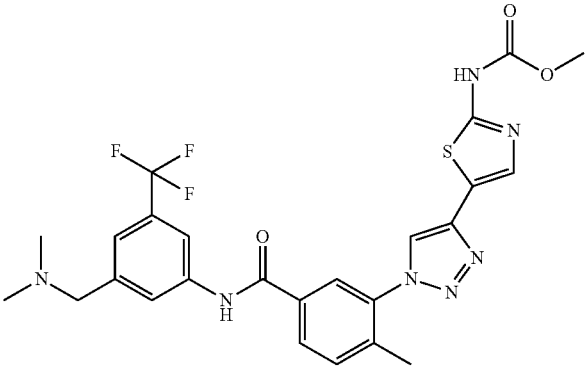 | 2.18 | 560 |
| Ia-197 | 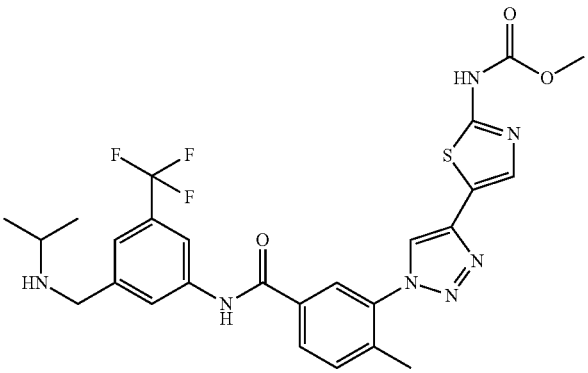 [SMILES: COC(=O)Nc1ncc(-c2cn(-c3cc(C(=O)Nc4cc(CNC(C)C)cc(C(F)(F)F)c4)ccc3C)nn2)s1] | 2.20 | 574 |
| Ia-198 | 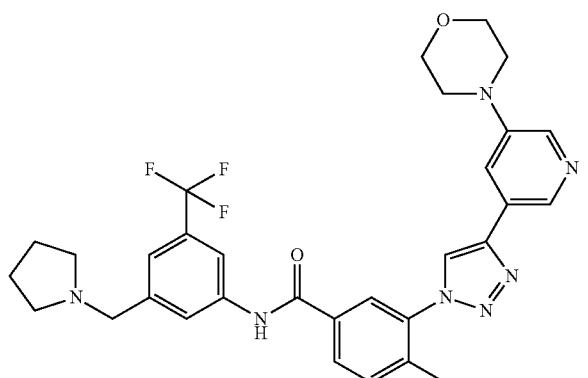 | 2.26 | 592 |
| Ia-199 | 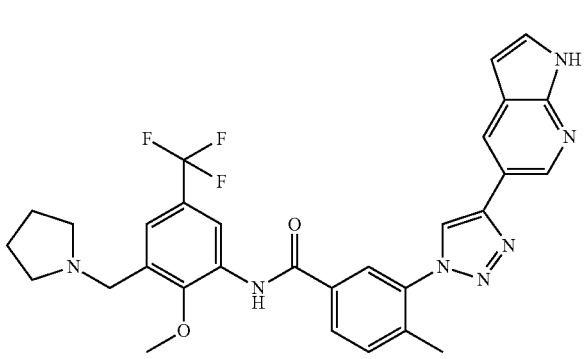 [SMILES: COc1c(CN2CCCC2)cc(C(F)(F)F)cc1NC(=O)c1ccc(C)c(-n2cc(-c3cnc4[nH]ccc4c3)nn2)c1] | 2.36 | 576 |

TABLE 1-continued
| Ia-200 | 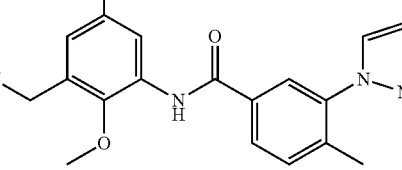 | 2.22 | 550 |
| Ia-201 | 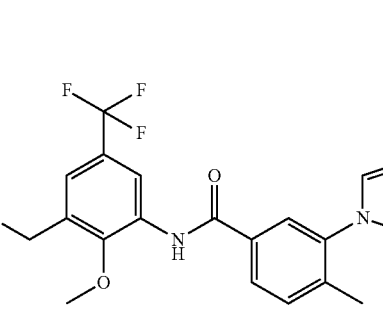 | 2.47 | 578 |
| Ia-202 | 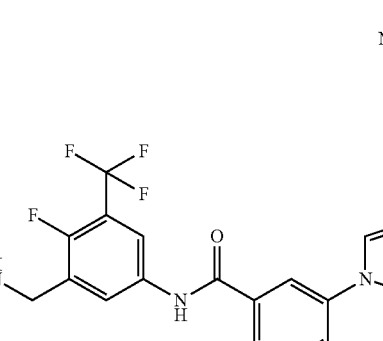 | 2.32 | 538 |
| Ia-203 | 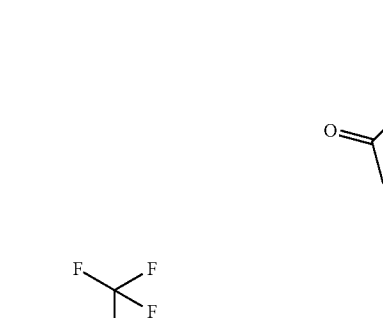 | 2.27 | 600 |

TABLE 1-continued
| Ia-204 | 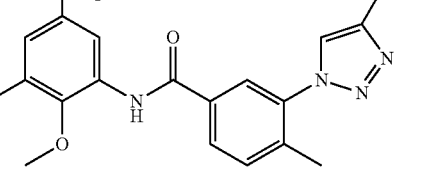 | 2.82 | 550 |
| Ia-205 |  | 2.45 | 583 |
| Ia-206 | 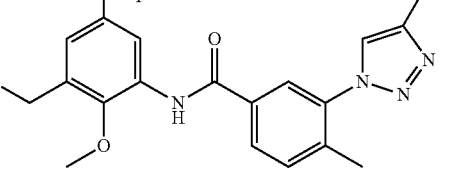 | 2.16 | 587 |
| Ia-207 |  | 2.18 | 510 |
| Ia-208 | 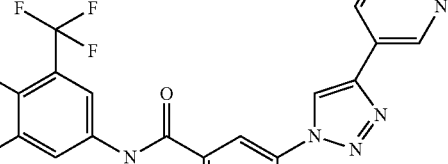 | 2.21 | 531 |

TABLE 1-continued

| Ia-209 | (structure) | 2.13 | 526 |
| Ia-210 | (structure) | 2.15 | 588 |
| Ia-211 | (structure) | 2.27 | 586 |
| Ia-212 | (structure) | 2.12 | 602 |

TABLE 1-continued

| ID | Structure | A | B |
|---|---|---|---|
| Ia-213 | (structure) | 2.10 | 593 |
| Ia-214 | (structure) | 2.23 | 552 |
| Ia-215 | (structure) | 2.23 | 550 |
| Ia-216 | (structure) | 2.29 | 546 |
| Ia-217 | (structure) | 2.34 | 535 |

| | | | |
|---|---|---|---|
| Ia-218 | 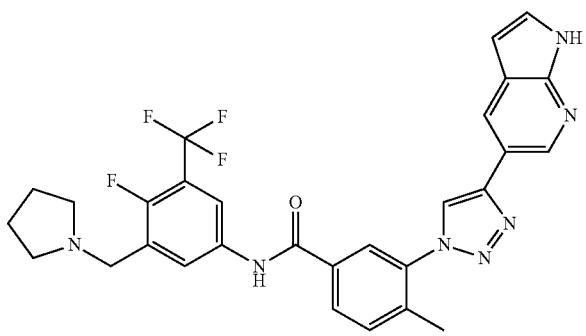 [SMILES: Cc1ccc(C(=O)Nc2cc(CN3CCCC3)c(F)c(C(F)(F)F)c2)cc1-n1cc(-c2cnc3[nH]ccc3c2)nn1] | 2.32 | 564 |
| Ia-219 | 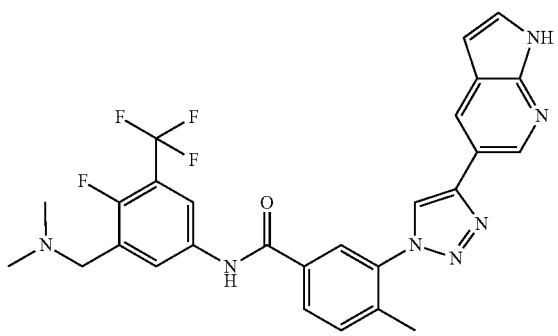 [SMILES: Cc1ccc(C(=O)Nc2cc(CN(C)C)c(F)c(C(F)(F)F)c2)cc1-n1cc(-c2cnc3[nH]ccc3c2)nn1] | 2.20 | 538 |
| Ia-220 | 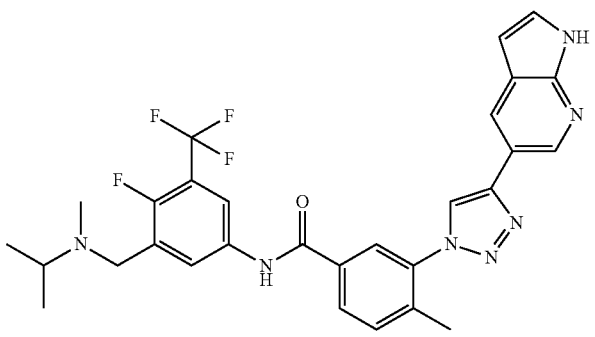 [SMILES: Cc1ccc(C(=O)Nc2cc(CN(C)C(C)C)c(F)c(C(F)(F)F)c2)cc1-n1cc(-c2cnc3[nH]ccc3c2)nn1] | 2.42 | 566 |
| Ia-221 | 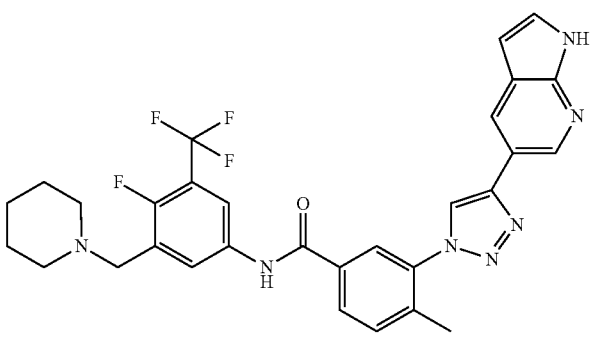 [SMILES: Cc1ccc(C(=O)Nc2cc(CN3CCCCC3)c(F)c(C(F)(F)F)c2)cc1-n1cc(-c2cnc3[nH]ccc3c2)nn1] | 2.43 | 578 |

TABLE 1-continued

| Ia-222 | [structure] | 2.24 | 582 |
| Ia-223 | [structure] | 2.25 | 530 |
| Ia-224 | [structure] | 2.32 | 608 |
| Ia-225 | [structure] | 2.27 | 592 |
| Ia-226 | [structure] | 2.08 | 546 |

| | | | |
|---|---|---|---|
| Ia-227 | 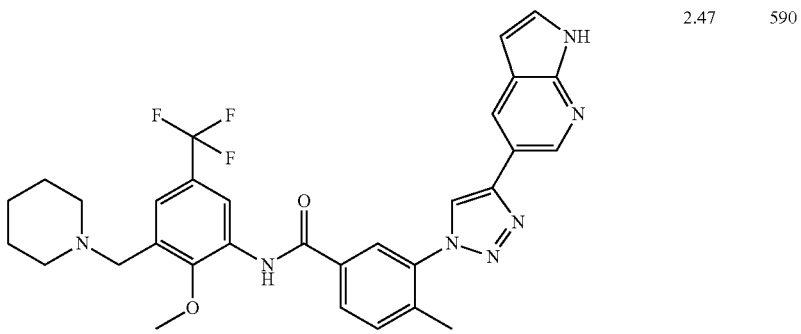 | 2.47 | 590 |
| Ia-228 | 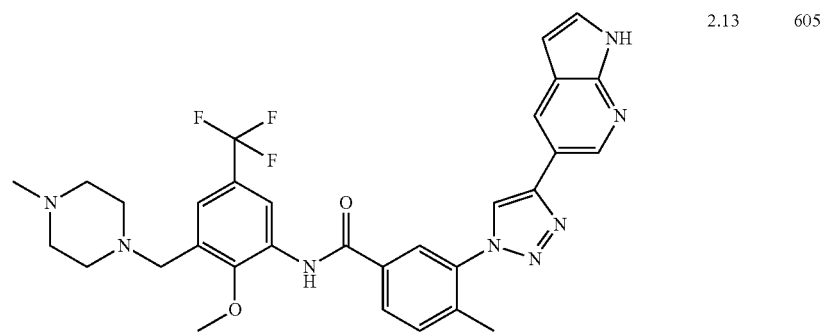 | 2.13 | 605 |
| Ia-229 | 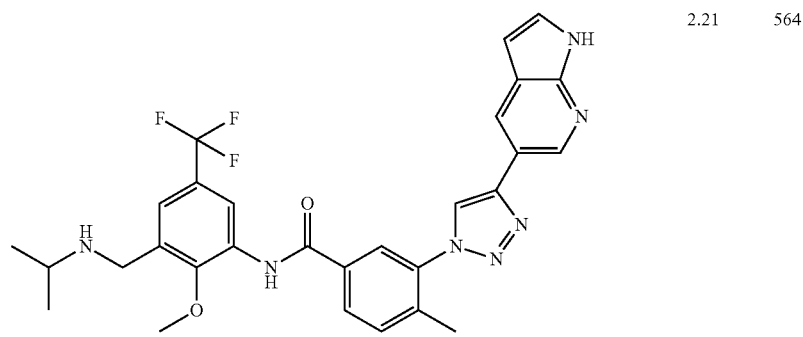 | 2.21 | 564 |
| Ia-230 | 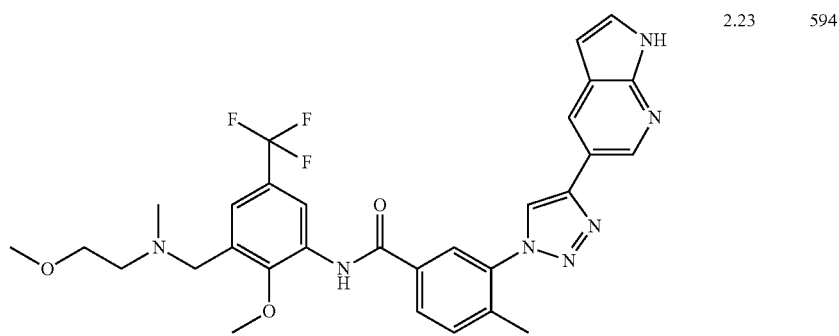 | 2.23 | 594 |

TABLE 1-continued
| Ia-231 | 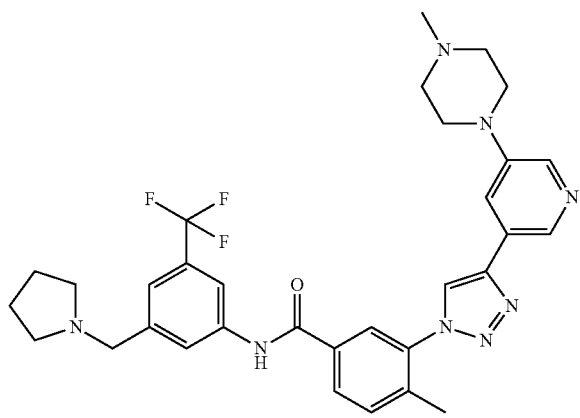 [SMILES: Cc1ccc(C(=O)Nc2cc(CN3CCCC3)cc(C(F)(F)F)c2)cc1-n1cc(-c2cncc(N3CCN(C)CC3)c2)nn1] | 2.21 | 605 |
| Ia-232 | 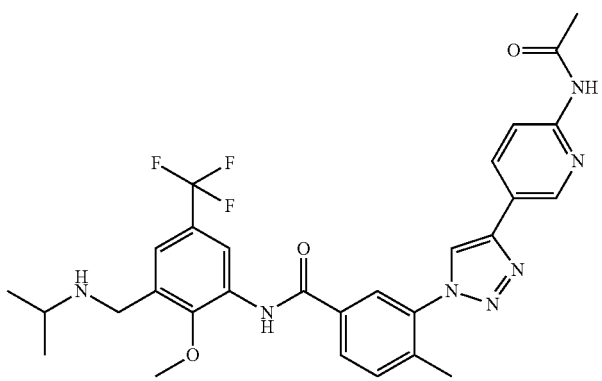 [SMILES: COc1c(CNC(C)C)cc(C(F)(F)F)cc1NC(=O)c1ccc(C)c(-n2cc(-c3ccc(NC(C)=O)nc3)nn2)c1] | 2.14 | 582 |
| Ia-233 | 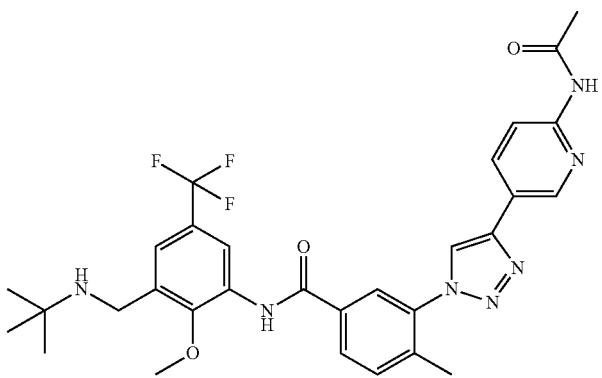 | 2.24 | 596 |
| Ia-234 | 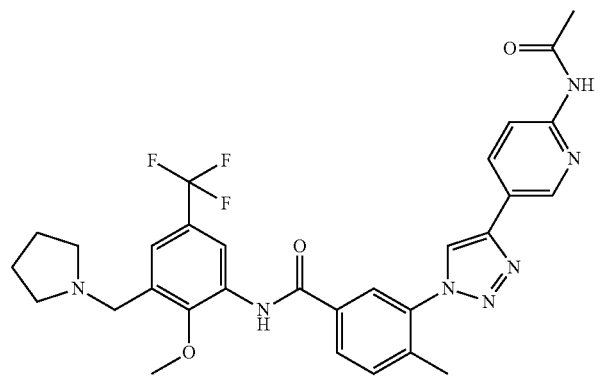 [SMILES: COc1c(CN2CCCC2)cc(C(F)(F)F)cc1NC(=O)c1ccc(C)c(-n2cc(-c3ccc(NC(C)=O)nc3)nn2)c1] | 2.28 | 594 |

TABLE 1-continued
| Ia-235 | 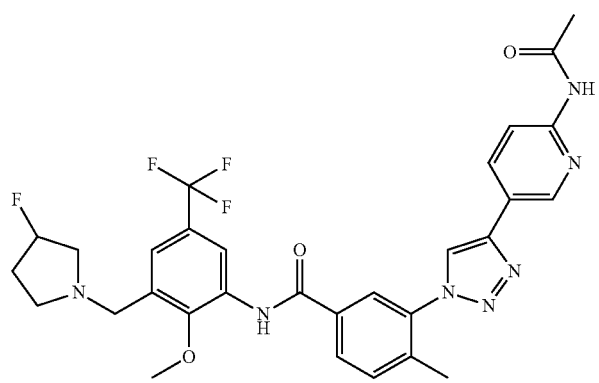 [SMILES: COc1c(CN2CCC(F)C2)cc(C(F)(F)F)cc1NC(=O)c1ccc(C)c(-n2cc(-c3ccc(NC(C)=O)nc3)nn2)c1] | 2.17 | 612 |
| Ia-236 | 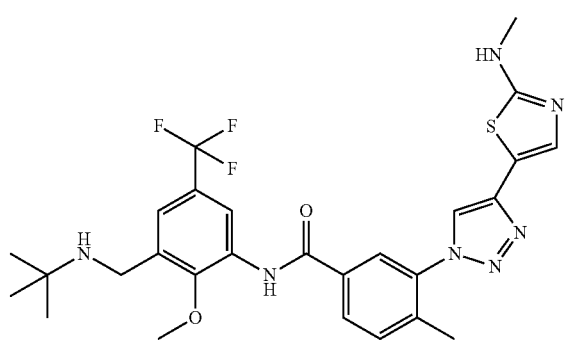 [SMILES: CNc1ncc(-c2cn(-c3cc(C(=O)Nc4cc(C(F)(F)F)cc(CNC(C)(C)C)c4OC)ccc3C)nn2)s1] | 2.28 | 574 |
| Ia-237 | 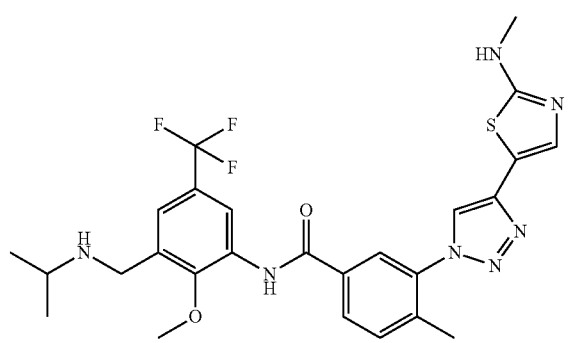 [SMILES: CNc1ncc(-c2cn(-c3cc(C(=O)Nc4cc(C(F)(F)F)cc(CNC(C)C)c4OC)ccc3C)nn2)s1] | 2.17 | 560 |
| Ia-238 | 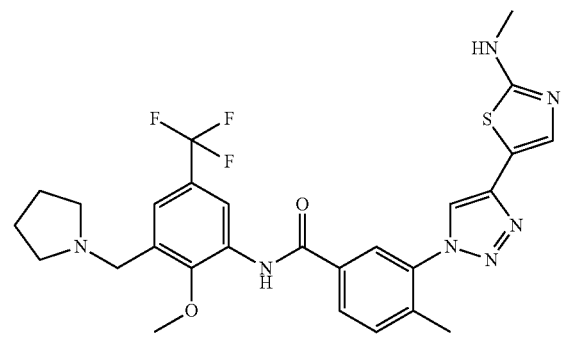 [SMILES: CNc1ncc(-c2cn(-c3cc(C(=O)Nc4cc(C(F)(F)F)cc(CN5CCCC5)c4OC)ccc3C)nn2)s1] | 2.29 | 572 |

TABLE 1-continued
Ia-239 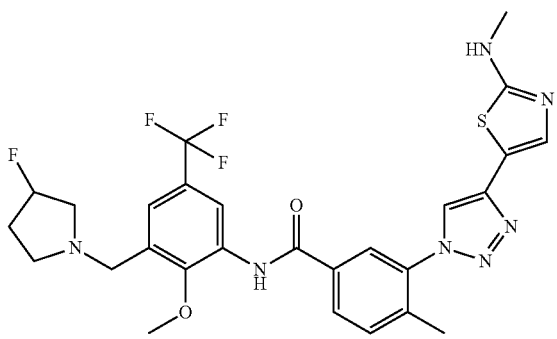 [SMILES: CNc1ncc(-c2cn(-c3cc(C(=O)Nc4cc(C(F)(F)F)cc(CN5CCC(F)C5)c4OC)ccc3C)nn2)s1] 2.23 590
Ia-240 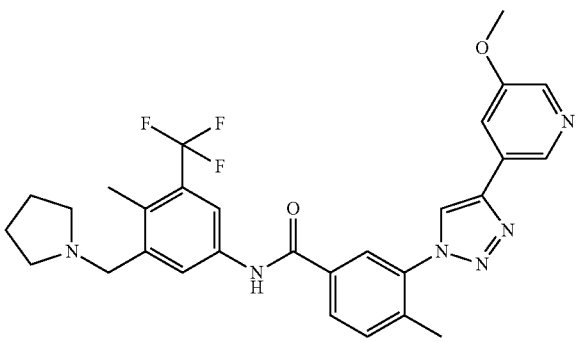 [SMILES: COc1cncc(-c2cn(-c3cc(C(=O)Nc4cc(CN5CCCC5)c(C)c(C(F)(F)F)c4)ccc3C)nn2)c1] 2.50 551
Ia-241 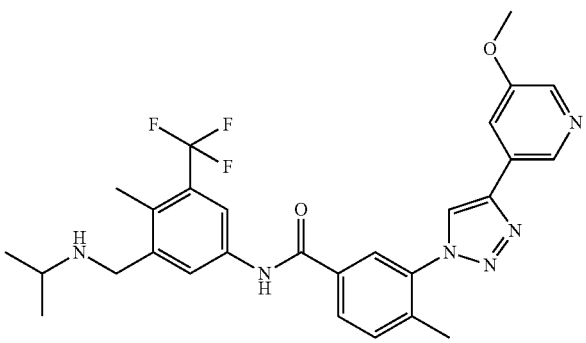 [SMILES: COc1cncc(-c2cn(-c3cc(C(=O)Nc4cc(CNC(C)C)c(C)c(C(F)(F)F)c4)ccc3C)nn2)c1] 2.36 539
Ia-242 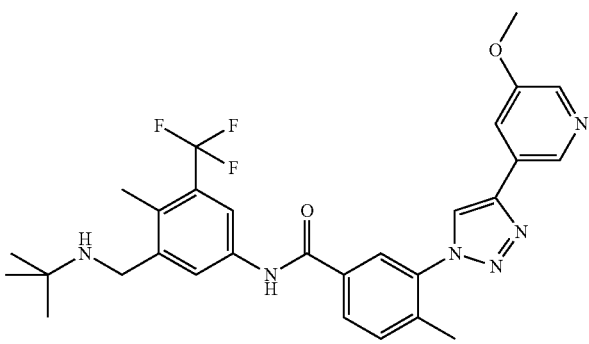 [SMILES: COc1cncc(-c2cn(-c3cc(C(=O)Nc4cc(CNC(C)(C)C)c(C)c(C(F)(F)F)c4)ccc3C)nn2)c1] 2.46 553

| | | | |
|---|---|---|---|
| Ia-243 | 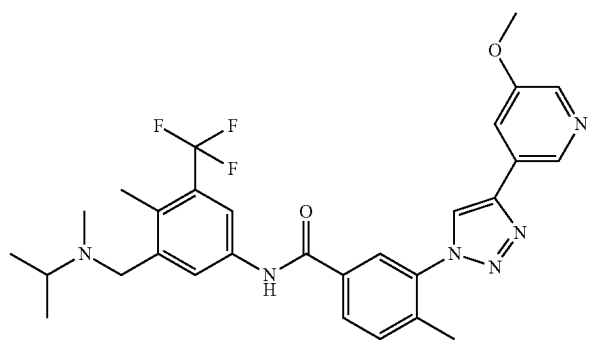 | 2.61 | 553 |
| Ia-244 | 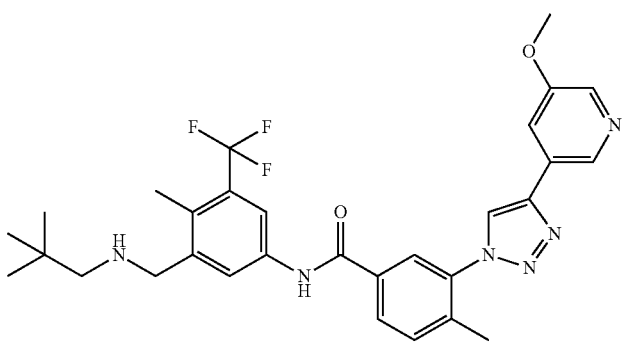 [SMILES: COc1cncc(-c2cn(-c3cc(C(=O)Nc4cc(CNCC(C)(C)C)c(C)c(C(F)(F)F)c4)ccc3C)nn2)c1] | 2.65 | 567 |
| Ia-245 | 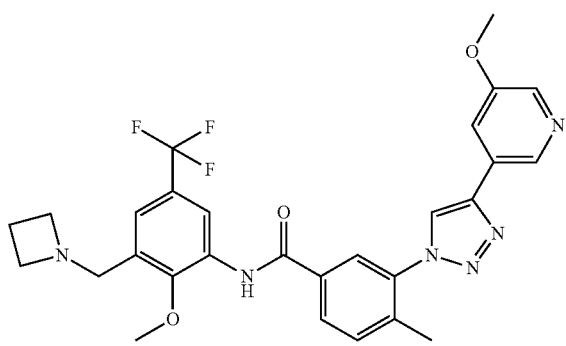 [SMILES: COc1cncc(-c2cn(-c3cc(C(=O)Nc4cc(C(F)(F)F)cc(CN5CCC5)c4OC)ccc3C)nn2)c1] | 2.22 | 553 |
| Ia-246 | 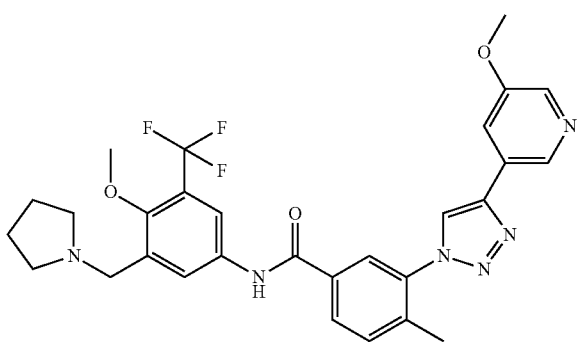 [SMILES: COc1cncc(-c2cn(-c3cc(C(=O)Nc4cc(CN5CCCC5)c(OC)c(C(F)(F)F)c4)ccc3C)nn2)c1] | 2.33 | 567 |

TABLE 1-continued
| Ia-247 | 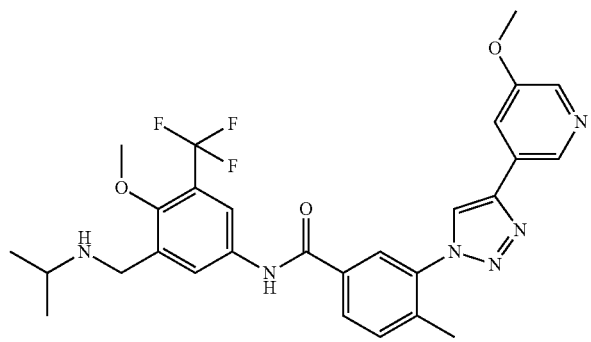 [SMILES: COc1cncc(-c2cn(-c3cc(C(=O)Nc4cc(CNC(C)C)c(OC)c(C(F)(F)F)c4)ccc3C)nn2)c1] | 2.25 | 555 |
| Ia-248 | 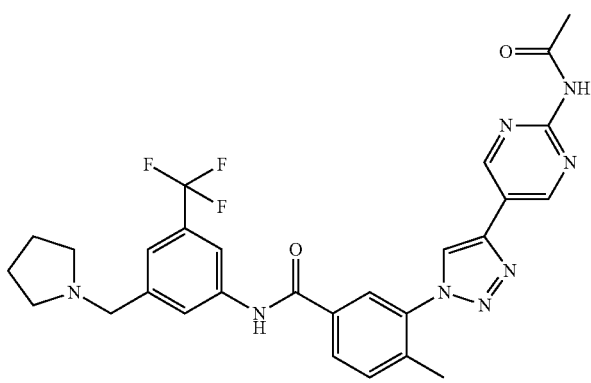 [SMILES: CC(=O)Nc1ncc(-c2cn(-c3cc(C(=O)Nc4cc(CN5CCCC5)cc(C(F)(F)F)c4)ccc3C)nn2)cn1] | 2.15 | 565 |
| Ia-249 | 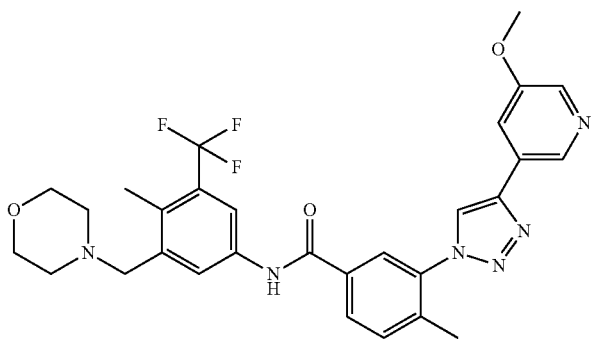 [SMILES: COc1cncc(-c2cn(-c3cc(C(=O)Nc4cc(CN5CCOCC5)c(C)c(C(F)(F)F)c4)ccc3C)nn2)c1] | 2.30 | 567 |
| Ia-250 | 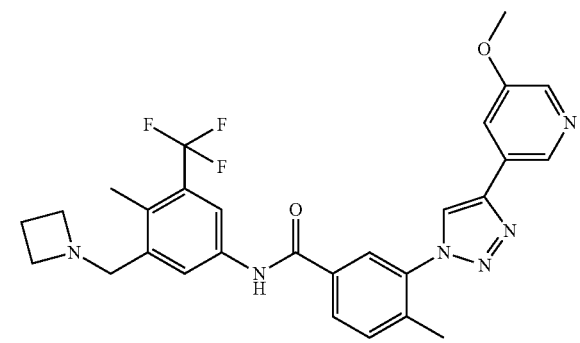 [SMILES: COc1cncc(-c2cn(-c3cc(C(=O)Nc4cc(CN5CCC5)c(C)c(C(F)(F)F)c4)ccc3C)nn2)c1] | 2.29 | 537 |

TABLE 1-continued
| Ia-251 | 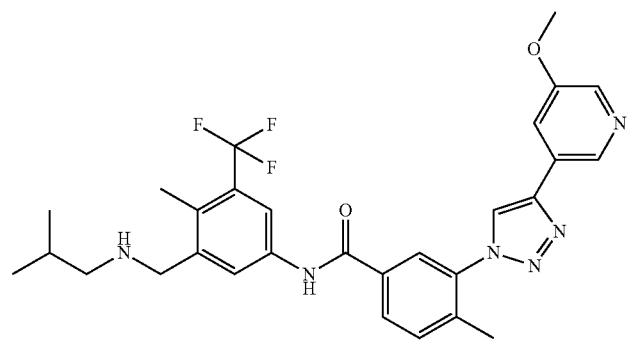 [SMILES: COc1cncc(-c2cn(-c3cc(C(=O)Nc4cc(CNCC(C)C)c(C)c(C(F)(F)F)c4)ccc3C)nn2)c1] | 2.46 | 553 |
| Ia-252 | 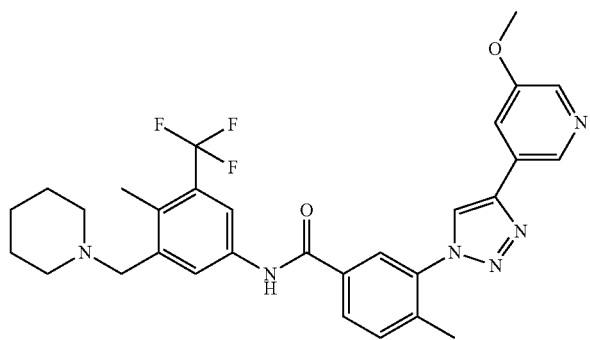 [SMILES: COc1cncc(-c2cn(-c3cc(C(=O)Nc4cc(CN5CCCCC5)c(C)c(C(F)(F)F)c4)ccc3C)nn2)c1] | 2.63 | 565 |
| Ia-253 | 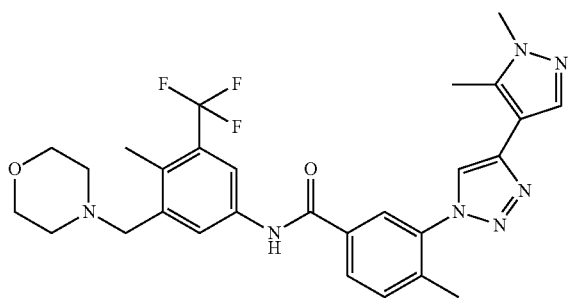 [SMILES: Cc1ccc(C(=O)Nc2cc(CN3CCOCC3)c(C)c(C(F)(F)F)c2)cc1-n1cc(-c2cnn(C)c2C)nn1] | 2.21 | 554 |
| Ia-254 | 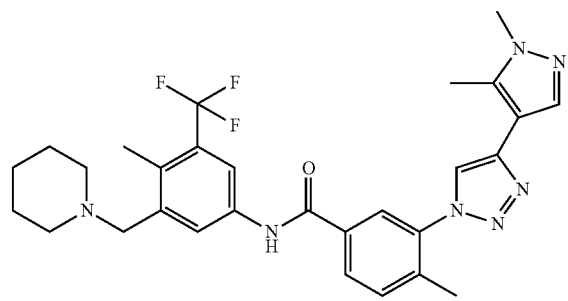 [SMILES: Cc1ccc(C(=O)Nc2cc(CN3CCCCC3)c(C)c(C(F)(F)F)c2)cc1-n1cc(-c2cnn(C)c2C)nn1] | 2.54 | 552 |
| Ia-255 | 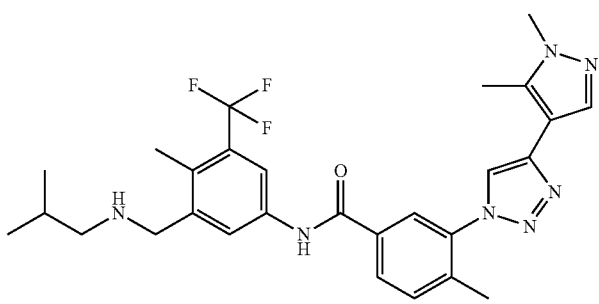 [SMILES: Cc1ccc(C(=O)Nc2cc(CNCC(C)C)c(C)c(C(F)(F)F)c2)cc1-n1cc(-c2cnn(C)c2C)nn1] | 2.38 | 540 |

TABLE 1-continued
| Ia-256 | 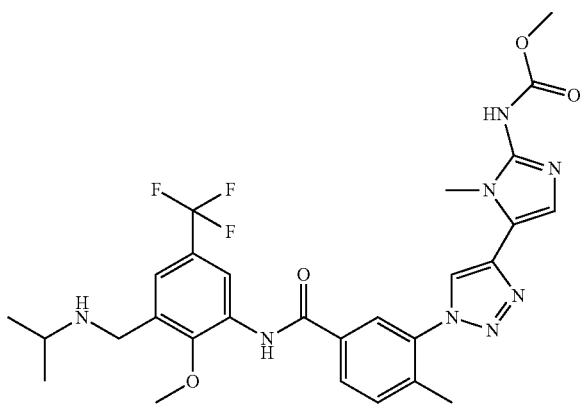 [SMILES: COC(=O)Nc1ncc(-c2cn(-c3cc(C(=O)Nc4cc(C(F)(F)F)cc(CNC(C)C)c4OC)ccc3C)nn2)n1C] | 2.03 | 601 |
| Ia-257 | 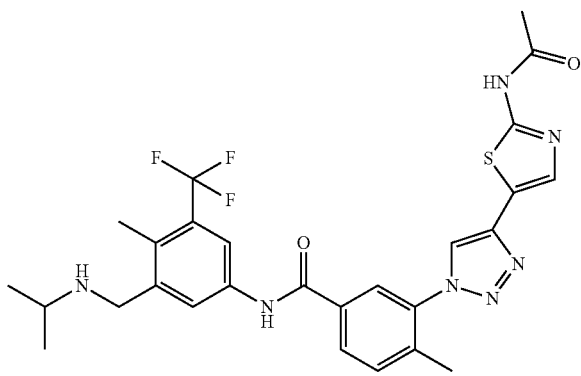 [SMILES: CC(=O)Nc1ncc(-c2cn(-c3cc(C(=O)Nc4cc(CNC(C)C)c(C)c(C(F)(F)F)c4)ccc3C)nn2)s1] | 2.20 | 572 |
| Ia-258 | 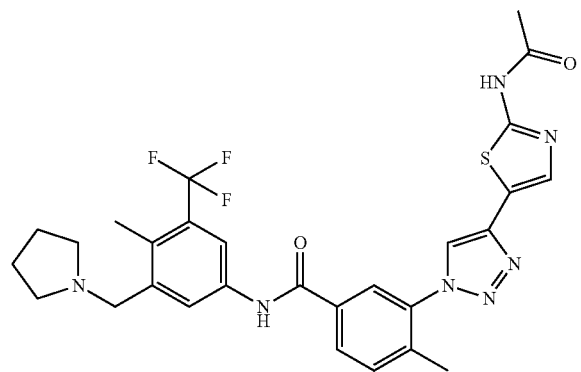 [SMILES: CC(=O)Nc1ncc(-c2cn(-c3cc(C(=O)Nc4cc(CN5CCCC5)c(C)c(C(F)(F)F)c4)ccc3C)nn2)s1] | 2.34 | 584 |
| Ia-259 | 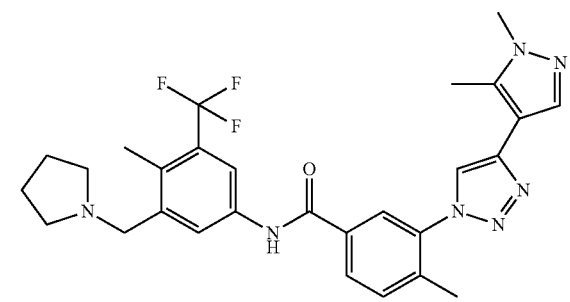 [SMILES: Cc1ccc(C(=O)Nc2cc(CN3CCCC3)c(C)c(C(F)(F)F)c2)cc1-n1cc(-c2cnn(C)c2C)nn1] | 2.30 | 538 |

TABLE 1-continued

| Ia-260 | (structure) | 2.29 | 540 |
| Ia-261 | (structure) | 2.29 | 586 |
| Ia-262 | (structure) | 2.12 | 574 |
| Ia-263 | (structure) | 2.24 | 600 |

TABLE 1-continued
| | | | |
|---|---|---|---|
| Ia-264 | 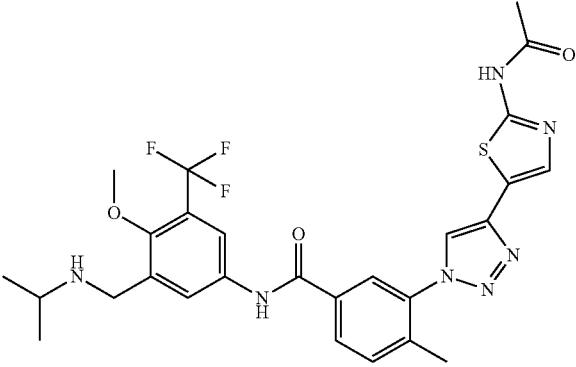 [SMILES: COc1c(CNC(C)C)cc(NC(=O)c2ccc(C)c(-n3cc(-c4cnc(NC(C)=O)s4)nn3)c2)cc1C(F)(F)F] | 2.12 | 588 |
| Ia-265 | 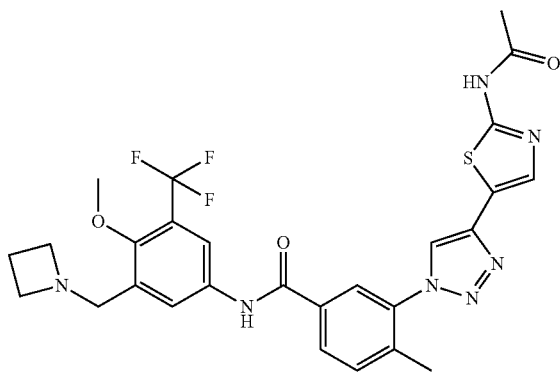 [SMILES: COc1c(CN2CCC2)cc(NC(=O)c2ccc(C)c(-n3cc(-c4cnc(NC(C)=O)s4)nn3)c2)cc1C(F)(F)F] | 2.12 | 586 |
| Ia-266 | 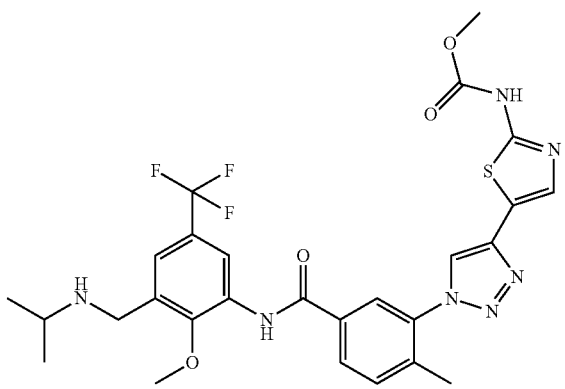 [SMILES: COC(=O)Nc1ncc(-c2cn(-c3cc(C(=O)Nc4cc(C(F)(F)F)cc(CNC(C)C)c4OC)ccc3C)nn2)s1] | 2.19 | 604 |
| Ib-1* | 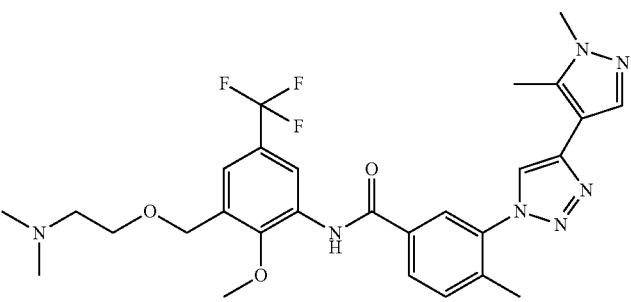 [SMILES: COc1c(COCCN(C)C)cc(C(F)(F)F)cc1NC(=O)c1ccc(C)c(-n2cc(-c3cnn(C)c3C)nn2)c1] | 1.63 | 572 |
*Example compound Ib-1 is synthesised by treating the corresponding benzylalcohol B-3 analogously to the method for synthesising Ia-1 (benzyl chloride route, see above) with thionyl chloride and instead of pyrrolidine adding sodium-2-dimethylaminoethoxide as nucleophil.

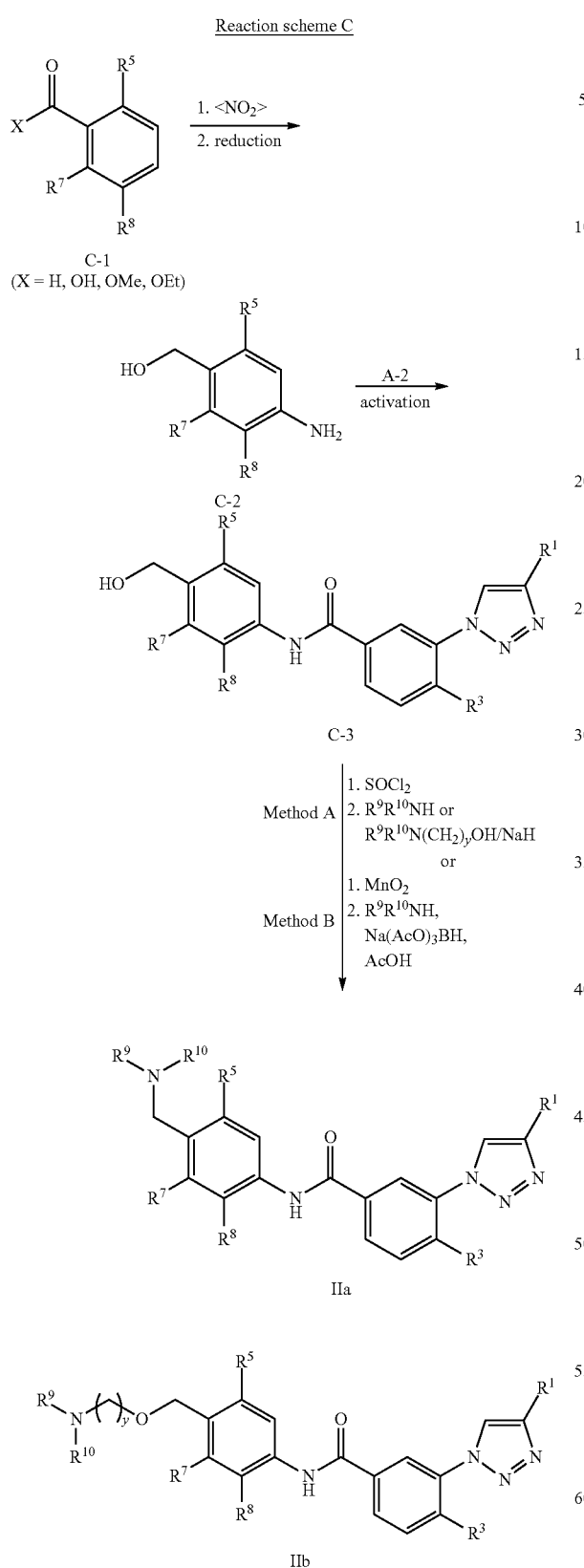

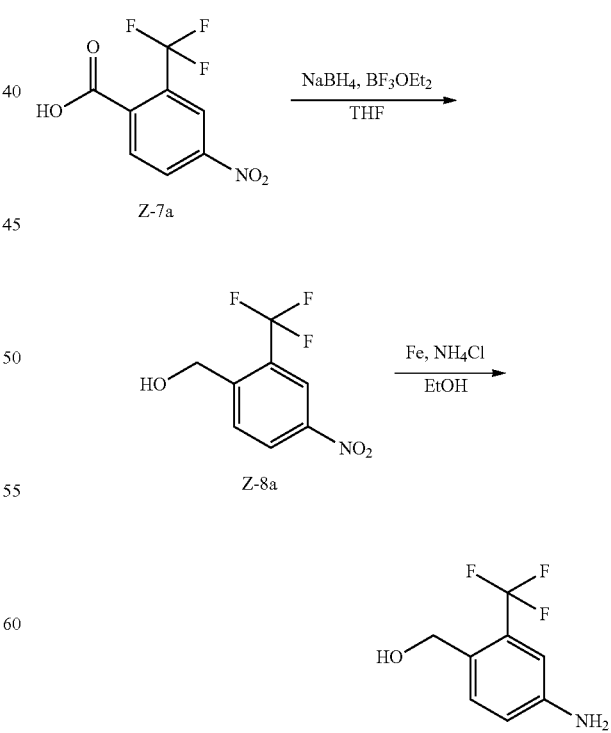

sponding benzyl chloride by means of an amine/hydroxylamine $R^9R^{10}NH$ (type IIa→benzylamine) or aminoalcohol $R^9R^{10}N(CH_2)_yOH$ (or alkoxide, type IIb→benzylether) or by reductive amination of a corresponding aldehyde with an amine $R^9R^{10}NH$ (type IIb→benzylether). In the former case the benzyl alcohols C-3 are reacted by means of thionyl chloride using methods known from the literature to form the corresponding benzyl chloride. In the latter case the benzylalcohols C-3 may be oxidised e.g. with $MnO_2$, Dess-Martin-Periodinane or other common oxidising agents to form the corresponding aldehydes and then reacted in an acetic acid medium with $Na(OAc)_3BH$ or $Na(CN)BH_3$ and an amine $R^9R^{10}NH$ using methods known from the literature to obtain compounds of type IIa. The amines/hydroxylamines/aminoalcohols used are commercially obtainable or are synthesised using methods known from the literature.

The benzylalcohols C-3 are synthesised by an amide coupling reaction of the anilines C-2 (in order to introduce the group $R^2$) and the corresponding benzoic acids A-2 described hereinbefore. The anilines C-2 used are commercially obtainable or are synthesised using methods known from the literature from the corresponding carbonyl compounds C-1 by nitrogenation, e.g. with nitronium tetrafluoroborate, conc. nitric acid, fuming nitric acid or nitrating acid and subsequent reductions with e.g. Pd/C and hydrogen in THF, methanol or ethanol or Fe and ammonium chloride in ethanol via various intermediate products Z. In some cases, already nitrogenated educts Z-7 are available from commercial sources (cf. synthesis of C-2a). Other intermediate steps may also be integrated into the reaction sequence for synthesising the amines C-2, such as the modification of another functional group in the substituents $R^7$ and/or $R^8$.

a) Procedure for Synthesising C-2a:

4-nitro-2-(trifluoromethyl)benzoic acid Z-7a (4.0 g, 17.0 mmol) is taken up in THF (80 mL) and NaBH$_4$ (1.90 g, 50.2 mmol) is added batchwise. The reaction mixture is cooled to 0° C., combined dropwise with boron trifluoride etherate (5.6 mL, 48.37 mmol) and stirred overnight at RT. It is cooled to 0° C. and combined with 1 M NaOH solution with stirring. Then THF is eliminated using the rotary evaporator and the crude product is extracted with EtOAc. The collected organic phases are washed with sat. NaCl solution, dried on Na$_2$SO$_4$, filtered, evaporated down using the rotary evaporator and the intermediate product Z-8a (HPLC-MS: $t_{Ret.}$=1.67 min; MS (M-H)$^+$=220) is further reacted directly.

Benzylalcohol Z-8a (1.0 g, 4.52 mmol) is taken up in EtOH (50 mL), combined with NH$_4$Cl (120 mg, 2.24 mmol) and water (50 mL) and heated to 75° C. Then iron powder (2.5 g, 44.8 mmol) is added batchwise, the reaction mixture is stirred for 15 min and filtered to remove excess iron powder. The solvent is eliminated by distillation using the rotary evaporator, the residue is taken up in EtOAc and the organic phase is washed twice with sat. NaCl solution. The organic phase is dried on MgSO$_4$, filtered, evaporated down using the rotary evaporator and yields the product C-2a (HPLC-MS: $t_{Ret.}$=0.18 min; MS (M+H)$^+$=192).

Analogously to this procedure further anilines C-2 are obtained from the corresponding C-1 intermediates/educts or the corresponding commercially obtainable educt.

b) Procedure for Synthesising C-3a:

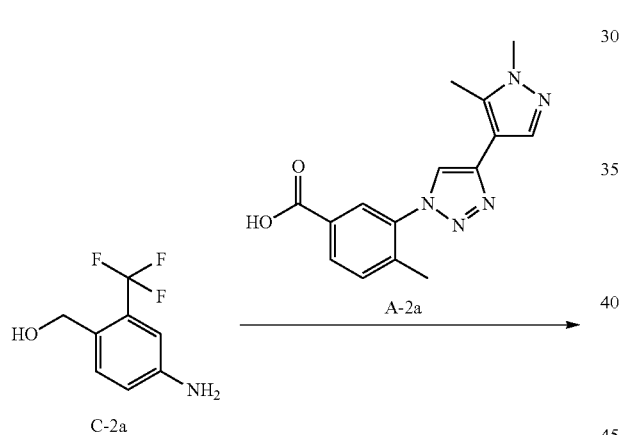

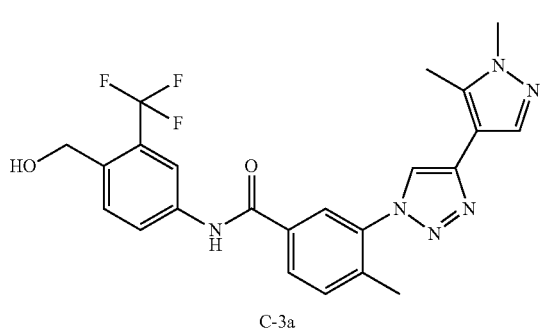

Benzoic acid A-2a (1.0 g, 3.36 mmol) is taken up in thionyl chloride (10 mL, 84 mmol), heated to 65° C. and stirred for 3 h. Then thionyl chloride is eliminated using the rotary evaporator and the reaction mixture is twice azeotroped with toluene. The crude product is taken up in DCM and at 0° C. added dropwise to a solution of C-2a (770 mg, 4.03 mmol) and pyridine (800 μL, 9.90 mmol) in DCM. After the addition is complete the mixture is stirred overnight at RT and the product C-3a is filtered off (HPLC-MS: $t_{Ret.}$=1.92 min; MS (M+H)$^+$=471).

Analogously to this procedure other benzylalcohols C-3 are obtained from the corresponding C-2-and A-2 intermediates.

c) Procedure for synthesising IIa-1 (benzyl chloride route, method A):

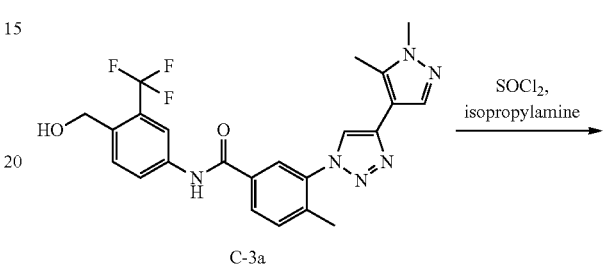

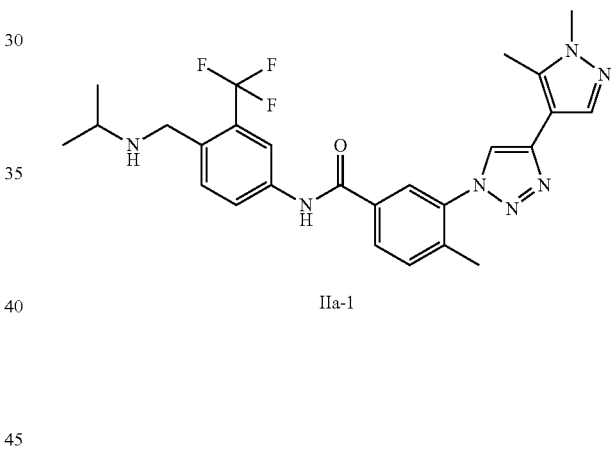

Benzylalcohol C-3a (70 mg, 0.15 mmol) is taken up in 3 mL DCM and combined with thionyl chloride (90 μL, 1.2 mmol) with stirring at RT. The reaction mixture is stirred for 3 h at RT, evaporated down, the residue is taken up in DMF (400 μL), combined with isopropylamine (51 mg, 0.86 mmol) and stirred overnight at 40° C. The reaction mixture is purified by preparative HPLC. The product-containing fractions of IIa-1 (HPLC-MS: $t_{Ret.}$=1.52 min; MS (M+H)$^+$=512) are freeze-dried.

Analogously to this procedure further example compounds of type IIa are obtained from the corresponding C-3 intermediates.

Analogously to the reaction methods a) to c) described above for synthesising Example IIa-1 the following Examples IIa-2 to IIa-24 (Table 2) or comparable further Examples may be obtained from the corresponding precursors, which are either commercially obtainable or are prepared using methods known from the literature.

TABLE 2
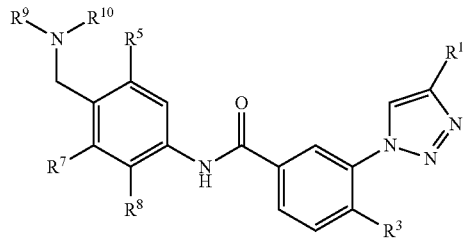
Examples IIa-1 to IIa-24
| # | Structure | $t_{Ret.}$ (HPLC) [min] | MS $(M + H)^+$ |
|---|---|---|---|
| IIa-1 | 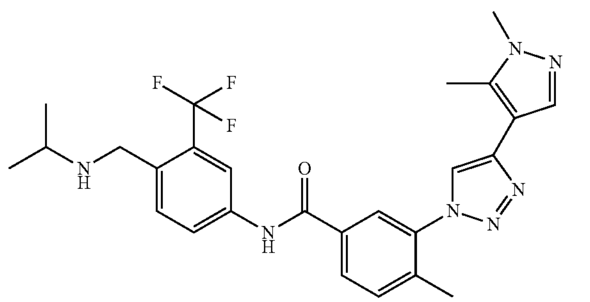 [SMILES: Cc1ccc(C(=O)Nc2ccc(CNC(C)C)c(C(F)(F)F)c2)cc1-n1cc(-c2cnn(C)c2C)nn1] | 1.33 | 481 |
| IIa-2 | 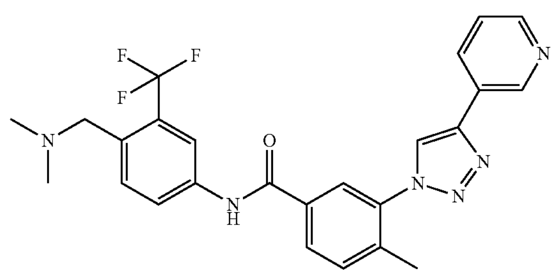 [SMILES: Cc1ccc(C(=O)Nc2ccc(CN(C)C)c(C(F)(F)F)c2)cc1-n1cc(-c2cccnc2)nn1] | 1.43 | 507 |
| IIa-3 | 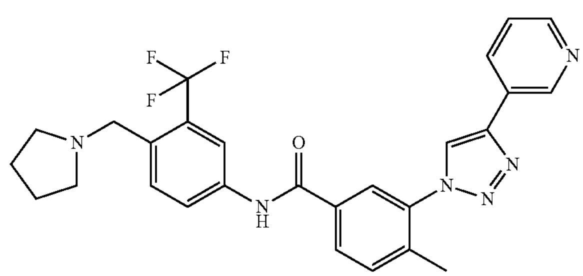 [SMILES: Cc1ccc(C(=O)Nc2ccc(CN3CCCC3)c(C(F)(F)F)c2)cc1-n1cc(-c2cccnc2)nn1] | 1.44 | 524 |
| IIa-4 | 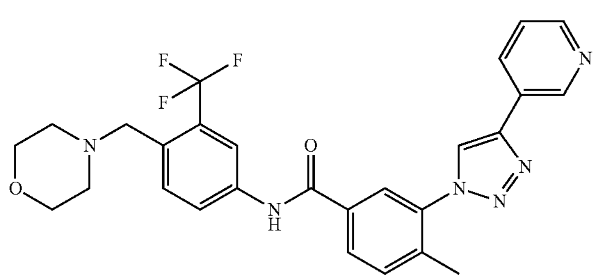 [SMILES: Cc1ccc(C(=O)Nc2ccc(CN3CCOCC3)c(C(F)(F)F)c2)cc1-n1cc(-c2cccnc2)nn1] | 1.75 | 454 |

TABLE 2-continued
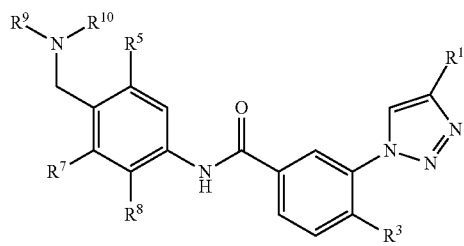
Examples IIa-1 to IIa-24
| # | Structure | t<sub>Ret.</sub> (HPLC) [min] | MS (M + H)+ |
|---|---|---|---|
| IIa-5 | 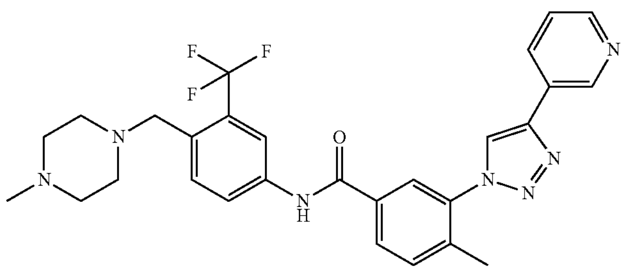 [SMILES: Cc1ccc(C(=O)Nc2ccc(CN3CCN(C)CC3)c(C(F)(F)F)c2)cc1-n1cc(-c2cccnc2)nn1] | 1.55 | 524 |
| IIa-6 | 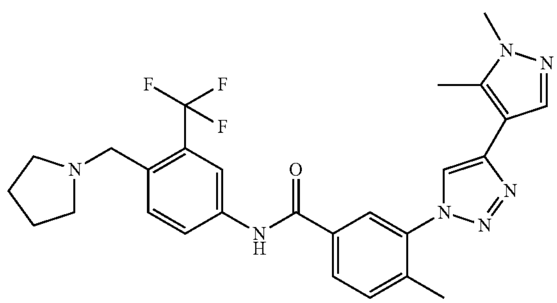 [SMILES: Cc1ccc(C(=O)Nc2ccc(CN3CCCC3)c(C(F)(F)F)c2)cc1-n1cc(-c2cnn(C)c2C)nn1] | 1.52 | 540 |
| IIa-7 | 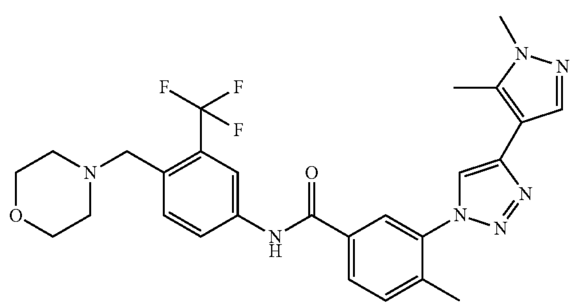 [SMILES: Cc1ccc(C(=O)Nc2ccc(CN3CCOCC3)c(C(F)(F)F)c2)cc1-n1cc(-c2cnn(C)c2C)nn1] | 0.0 | 581 |
| IIa-8 | 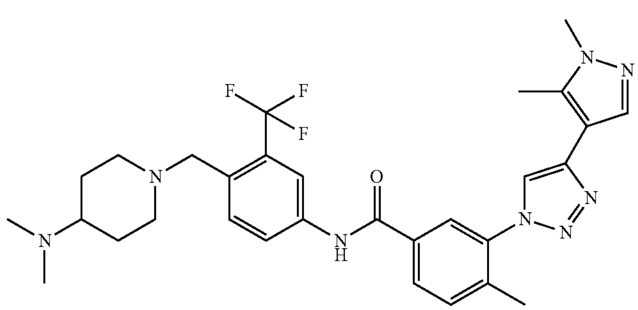 [SMILES: Cc1ccc(C(=O)Nc2ccc(CN3CCC(N(C)C)CC3)c(C(F)(F)F)c2)cc1-n1cc(-c2cnn(C)c2C)nn1] | 0.0 | 498 |

TABLE 2-continued
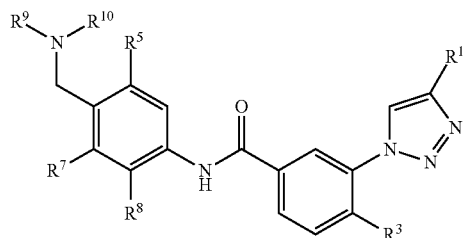
Examples IIa-1 to IIa-24
| # | Structure | t$_{Ret.}$ (HPLC) [min] | MS (M + H)$^+$ |
|---|---|---|---|
| IIa-9 | 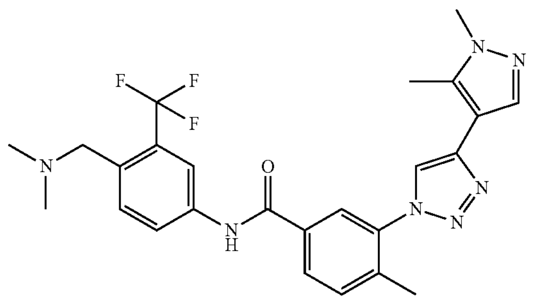 [SMILES: Cc1ccc(C(=O)Nc2ccc(CN(C)C)c(C(F)(F)F)c2)cc1-n1cc(-c2cnn(C)c2C)nn1] | 0.0 | 541 |
| IIa-10 | 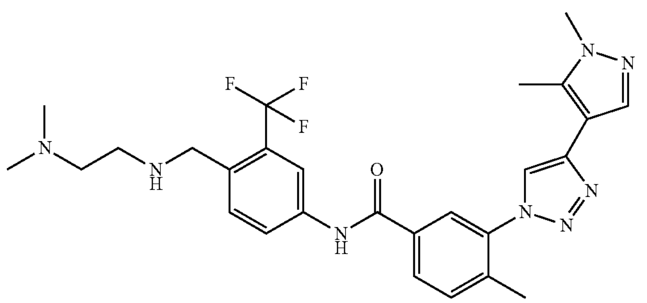 [SMILES: Cc1ccc(C(=O)Nc2ccc(CNCCN(C)C)c(C(F)(F)F)c2)cc1-n1cc(-c2cnn(C)c2C)nn1] | 1.56 | 553 |
| IIa-11 | 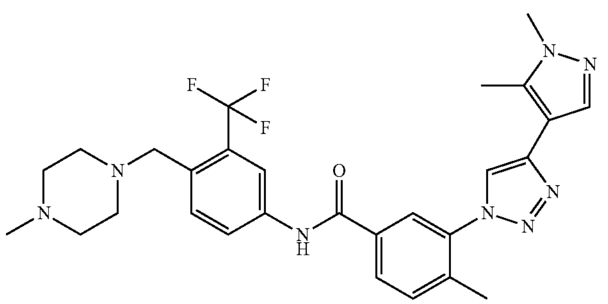 [SMILES: Cc1ccc(C(=O)Nc2ccc(CN3CCN(C)CC3)c(C(F)(F)F)c2)cc1-n1cc(-c2cnn(C)c2C)nn1] | 0.0 | 581 |
| IIa-12 | 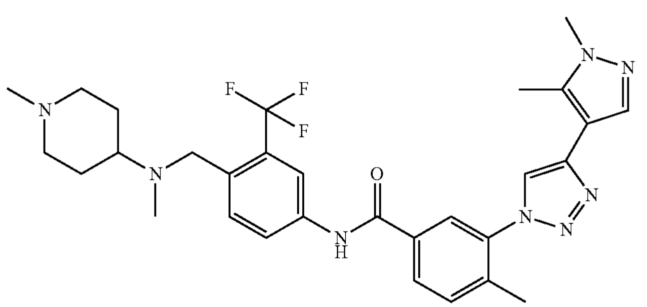 [SMILES: Cc1ccc(C(=O)Nc2ccc(CN(C)C3CCN(C)CC3)c(C(F)(F)F)c2)cc1-n1cc(-c2cnn(C)c2C)nn1] | 0.0 | 513 |

TABLE 2-continued
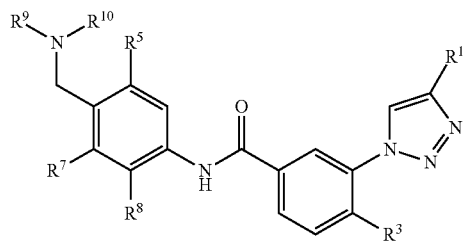
Examples IIa-1 to IIa-24
| # | Structure | t_Ret. (HPLC) [min] | MS (M + H)+ |
|---|---|---|---|
| IIa-13 | 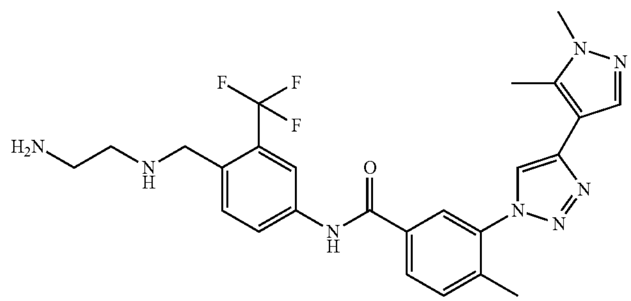 | 1.59 | 538 |
| IIa-14 | 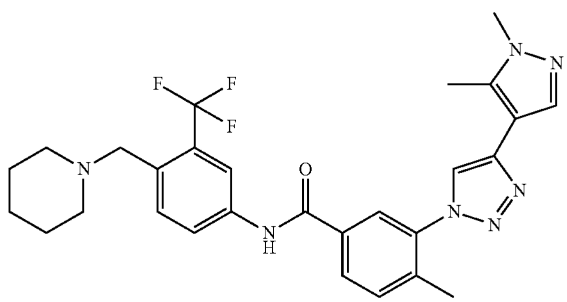 [SMILES: Cc1ccc(C(=O)Nc2ccc(CN3CCCCC3)c(C(F)(F)F)c2)cc1-n1cc(-c2cnn(C)c2C)nn1] | 0.0 | 567 |
| IIa-15 | 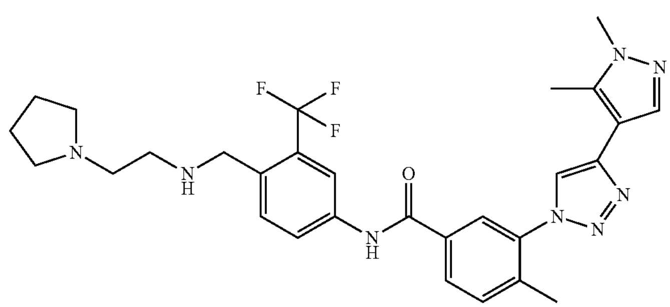 [SMILES: Cc1ccc(C(=O)Nc2ccc(CNCCN3CCCC3)c(C(F)(F)F)c2)cc1-n1cc(-c2cnn(C)c2C)nn1] | 1.48 | 514 |
| IIa-16 | 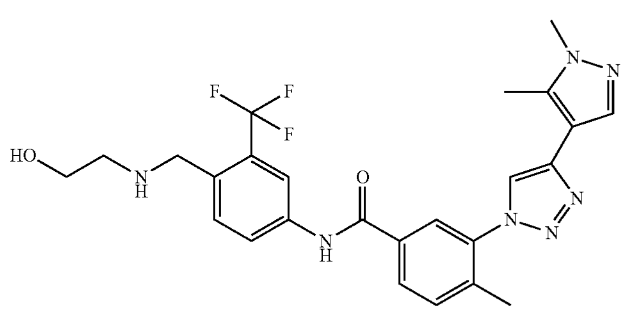 [SMILES: Cc1ccc(C(=O)Nc2ccc(CNCCO)c(C(F)(F)F)c2)cc1-n1cc(-c2cnn(C)c2C)nn1] | 0.0 | 583 |

TABLE 2-continued
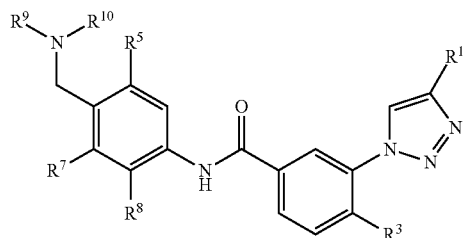
Examples IIa-1 to IIa-24
| # | Structure | t_Ret. (HPLC) [min] | MS (M + H)+ |
|---|---|---|---|
| IIa-17 | 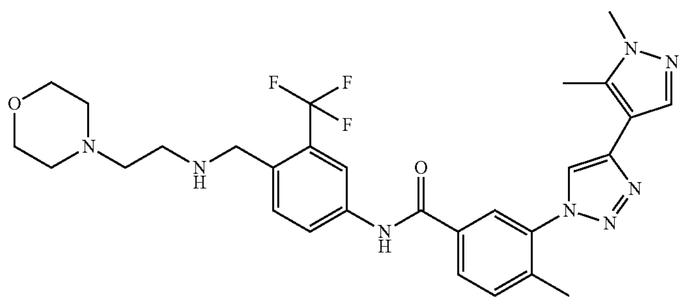 [SMILES: Cc1ccc(C(=O)Nc2ccc(CNCCN3CCOCC3)c(C(F)(F)F)c2)cc1-n1cc(-c2cnn(C)c2C)nn1] | 0.0 | 596 |
| IIa-18 | 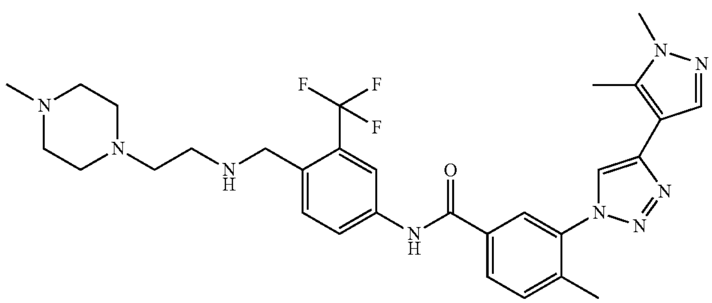 [SMILES: Cc1ccc(C(=O)Nc2ccc(CNCCN3CCN(C)CC3)c(C(F)(F)F)c2)cc1-n1cc(-c2cnn(C)c2C)nn1] | 0.0 | 527 |
| IIa-19 | 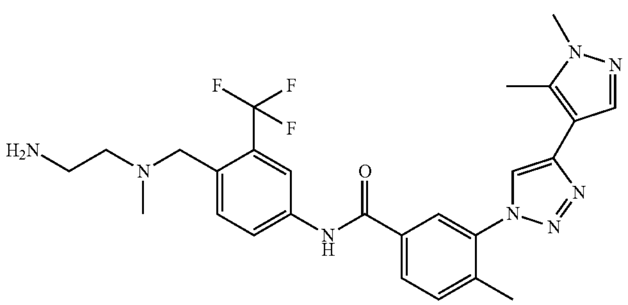 [SMILES: Cc1ccc(C(=O)Nc2ccc(CN(C)CCN)c(C(F)(F)F)c2)cc1-n1cc(-c2cnn(C)c2C)nn1] | 1.34 | 527 |
| IIa-20 | 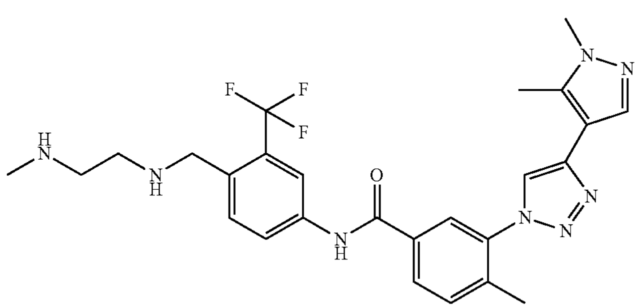 [SMILES: CNCCNCc1ccc(NC(=O)c2ccc(C)c(-n3cc(-c4cnn(C)c4C)nn3)c2)cc1C(F)(F)F] | 1.52 | 581 |

TABLE 2-continued

Examples IIa-1 to IIa-24

| # | Structure | t_Ret. (HPLC) [min] | MS (M + H)+ |
|---|---|---|---|
| IIa-21 | 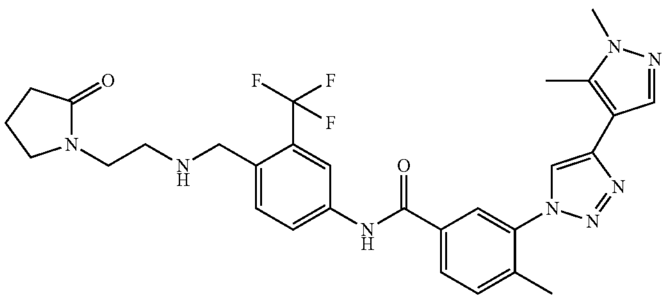 [SMILES: Cc1ccc(C(=O)Nc2ccc(CNCCN3CCCC3=O)c(C(F)(F)F)c2)cc1-n1cc(-c2cnn(C)c2C)nn1] | 0.0 | 526 |
| IIa-22 | 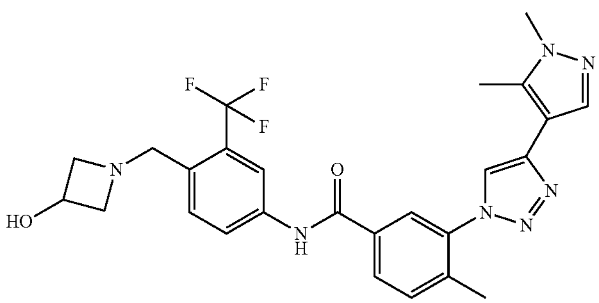 [SMILES: Cc1ccc(C(=O)Nc2ccc(CN3CC(O)C3)c(C(F)(F)F)c2)cc1-n1cc(-c2cnn(C)c2C)nn1] | 0.0 | 510 |
| IIa-23 | 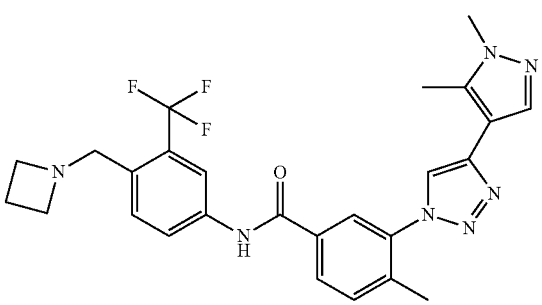 [SMILES: Cc1ccc(C(=O)Nc2ccc(CN3CCC3)c(C(F)(F)F)c2)cc1-n1cc(-c2cnn(C)c2C)nn1] | 1.52 | 512 |
| IIa-24 | 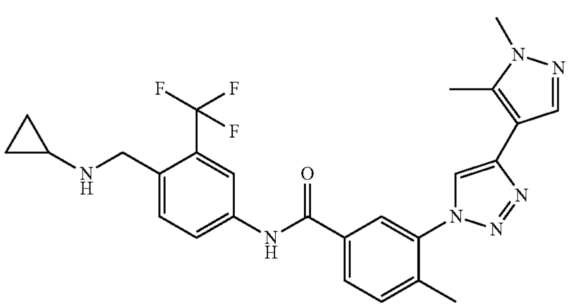 [SMILES: Cc1ccc(C(=O)Nc2ccc(CNC3CC3)c(C(F)(F)F)c2)cc1-n1cc(-c2cnn(C)c2C)nn1] | 1.55 | 510 |

The insertion of a benzylamine, benzylhydroxylamine or aminoalkylbenzylether side chain into the position of the group $R^7$ or $R^6$ as described in reaction scheme B and C can theoretically also be applied to an insertion into the position of the group $R^8$ if a carbonyl compound the carbonyl functionality of which is in position $R^8$ is used as the educt, analogously to B-1 and C-1.

group $R^2$) and the corresponding benzoic acids A-2 described above. The anilines D-2 used are commercially obtainable or are synthesised using methods known from the literature from the corresponding bromides D-1-1 or D-1-2 or also iodides, by nitrogenation, e.g. with nitronium tetrafluoroborate, conc. nitric acid, fuming nitric acid or nitrating acid and subsequent reductions with e.g. Pd/C and hydrogen in THF, methanol or Reaction scheme D-I

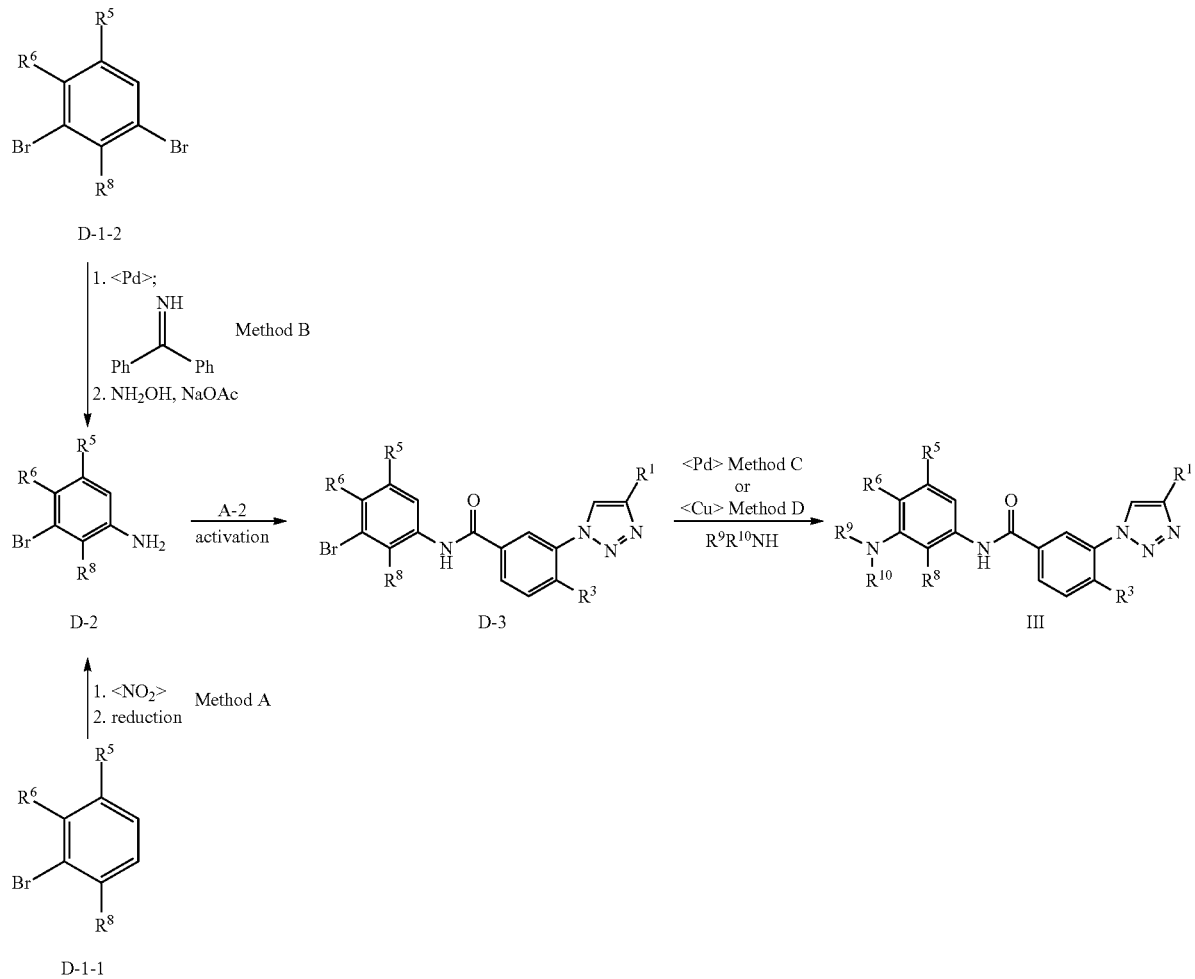

Example compounds of type III (arylamine in the m-position to the amide link→$R^7$) are prepared from arylbromides D-3 either by a palladium-(Buchwald-Hartwig) or copper (Ullmann)-catalysed cross-coupling reaction with an amine or a nitrogen compound of general formula $R^9R^{10}NH$. The palladium-catalysed cross-couplings of D-3 are carried out using methods known from the literature with the aid of common catalysts, such as for example biphenyl-2-yl-di-tent-butylphosphane and tris-(dibenzylideneacetone)-palladium, as well as a base, such as e.g. sodium-tert-butoxide or caesium carbonate, in 1,4-dioxane or toluene with an amine $R^9R^{10}NH$. The copper-catalysed cross-couplings of D-3 are carried out using methods known from the literature with the aid of Cu(I) salts, as well as bases, such as sodium carbonate and ligands, such as L-proline, e.g. in DMSO with a nitrogen compound of general formula $R^9R^{10}NH$. The compounds $R^9R^{10}NH$ used are commercially obtainable or are synthesised using methods known from the literature.

The arylbromides D-3 are synthesised by an amide coupling reaction of the anilines D-2 (in order to introduce the ethanol or Fe and ammonium chloride in ethanol via various intermediate products Z. In some cases, already nitrogenated educts Z-9 are available from commercial sources. Other intermediate steps may also be integrated into the reaction sequence for synthesising the amines D-2, such as the modification of another functional group in the substituents $R^6$ and/or R8.

a) Procedure for Synthesising D-2a (Monobromide Route, Method A):

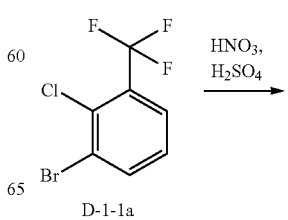

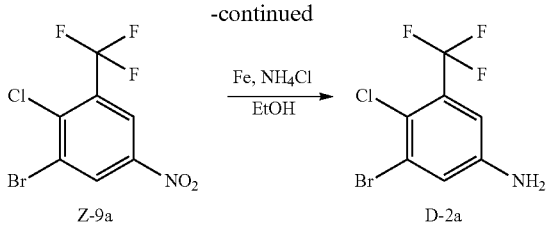

1-Bromo-2-chloro-3-trifluoromethyl-benzene D-1-1a (4.9 g, 18.9 mmol) is taken up in conc. sulphuric acid (20 mL), cooled to 0° C. and combined with an ice-cold mixture of conc. nitric acid (25 mL) and conc. sulphuric acid (20 mL). After 3 h stirring at RT the reaction mixture is poured onto ice water, extracted with EtOAc, the organic phase is washed with sat. NaHCO$_3$ solution and sat. NaCl solution, dried on Na$_2$SO$_4$, filtered and evaporated down using the rotary evaporator and the intermediate product Z-9a obtained (HPLC-MS: $t_{Ret.}$=2.14 min) is further reacted directly.

Nitro compound Z-9a (5.0 g, 16.42 mmol) is taken up in EtOH (22 mL), combined with NH$_4$Cl (440 mg, 8.21 mmol) and water (22 mL) and heated to 75° C. Then iron powder (9.17 g, 164.23 mmol) is added batchwise, the reaction mixture is stirred for 3 h and filtered to remove excess iron powder. The solvent is eliminated by distillation using the rotary evaporator, the residue is taken up in EtOAc and the organic phase is washed twice with sat. NaCl solution. The organic phase is dried on MgSO$_4$, filtered, evaporated down using the rotary evaporator and yields aniline D-2a (HPLC-MS: $t_{Ret.}$=2.03 min; MS (M+H)$^+$=276).

Analogously to this procedure further anilines D-2 are obtained from the corresponding D-1-1 intermediates/educts.

b) Procedure for Synthesising D-2b (Dibromide Route, Method B):

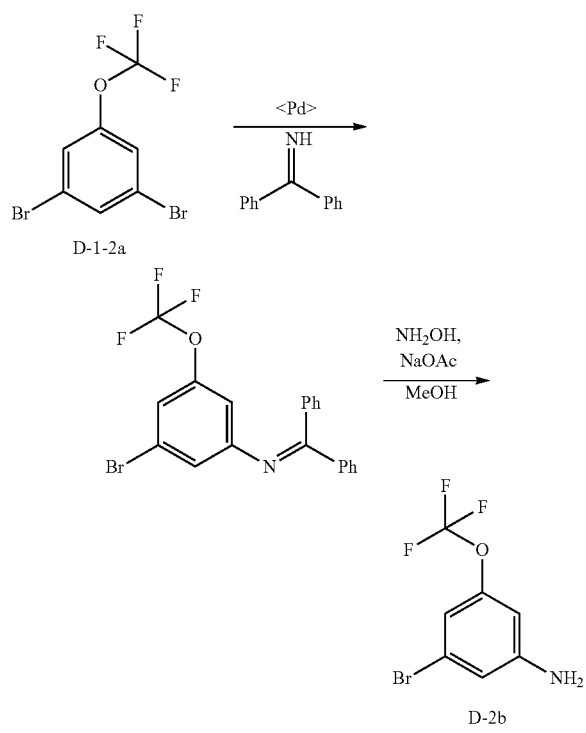

Dibromide D-1-2a (3.0 g, 9.38 mmol), sodium-tert-butoxide (1.26 mg, 13.13 mmol), BINAP (584 mg, 0.938 mmol) and tris-(dibenzylideneacetone)-palladium (85.9 mg, 0.094 mmol) are suspended in 60 mL toluene, combined with benzophenonimine (2.04 g, 11.25 mmol), and refluxed under an argon atmosphere for 3 d. Then the reaction mixture is filtered and the solvent is eliminated by distillation. The residue is taken up in MeOH (20 mL), combined with 1.8 g NaOAc and 1.2 g hydroxylamine hydrochloride, the reaction mixture is stirred overnight at RT, diluted with EtOAc and filtered. The filtrate is evaporated down, taken up in DMF and purified by preparative HPLC. The product-containing fractions of D-2b (HPLC-MS: $t_{Ret.}$=2.15 min; MS (M−H)$^+$=254/256) are freeze-dried.

Analogously to this procedure further anilines D-2 are obtained from the corresponding D-1-2 intermediates/educts.

c) Procedure for Synthesising D-3a:

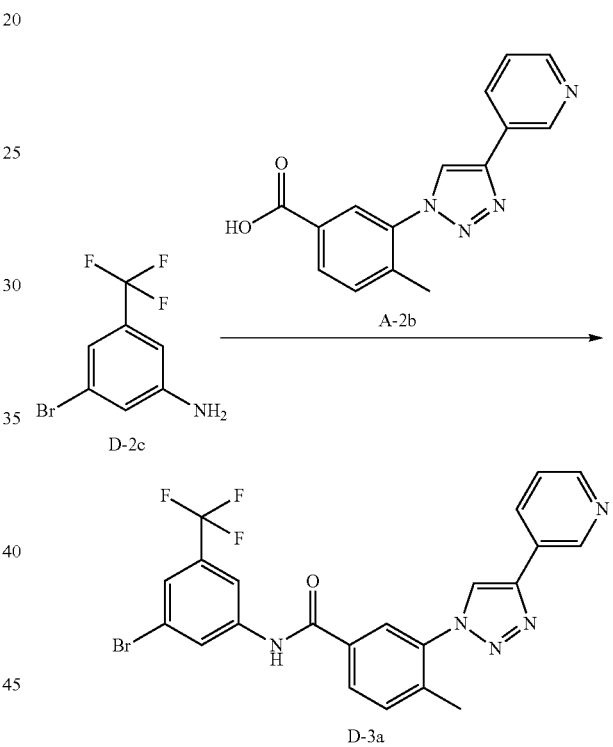

Benzoic acid A-2b (2.56 g, 9.16 mmol) is taken up in 45 mL DCM and 5 mL THF, combined with oxalyl chloride (0.92 mL, 10.5 mmol) and one drop of DMF, stirred for 1 h at RT and then evaporated down using the rotary evaporator. The residue is taken up in 45 mL DCM and 15 mL THF and combined with the aniline D-2c (2.2 g, 9.16 mmol) as well as DIPEA (2.29 mL, 15.6 mmol). The reaction mixture is stirred overnight at RT and then evaporated down using the rotary evaporator. The crude product is taken up in EtOAc and washed with 1 M NaOH solution. The collected organic phases are washed with sat. NaCl solution, dried on Na$_2$SO$_4$, filtered, evaporated down using the rotary evaporator and the product D-3a (HPLC-MS: $t_{Ret.}$=2.23 min; MS (M−H)$^+$=503/505) is further reacted directly.

Analogously to this procedure further arylbromides D-3 are obtained from the corresponding D-2 and A-2 intermediates/educts.

d) Procedure for Synthesising III-1 (Palladium-catalysed Cross-Coupling, Method C):

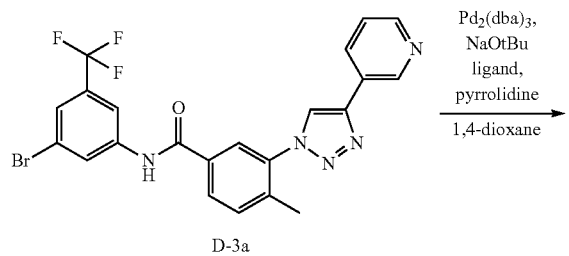

D-3a

Pd$_2$(dba)$_3$, NaOtBu ligand, pyrrolidine
1,4-dioxane
$\longrightarrow$

III-1

Arylbromide D-3a (70 mg, 0.14 mmol), sodium-tert-butoxide (55.2 mg, 0.56 mmol), biphenyl-2-yl-di-tent-butylphosphane (16.6 mg, 0.06 mmol) and tris-(dibenzylideneacetone)-palladium (12.8 mg, 0.014 mmol) are suspended in 1.5 mL of 1,4-dioxane, combined with pyrrolidine (48 μL, 0.56 mmol), heated to 45° C. and stirred for 2 h. Then the reaction mixture is filtered and the solvent is eliminated by distillation. The residue is taken up in DMF and purified by preparative HPLC. The product-containing fractions of III-1 (HPLC-MS: $t_{Ret.}$=2.19 min; MS (M+H)$^+$=493) are freeze-dried.

Analogously to this procedure further example compounds of type III are obtained from the corresponding D-3 intermediates.

e) Procedure for Synthesising III-2 (Copper-catalysed Cross-coupling, Method D):

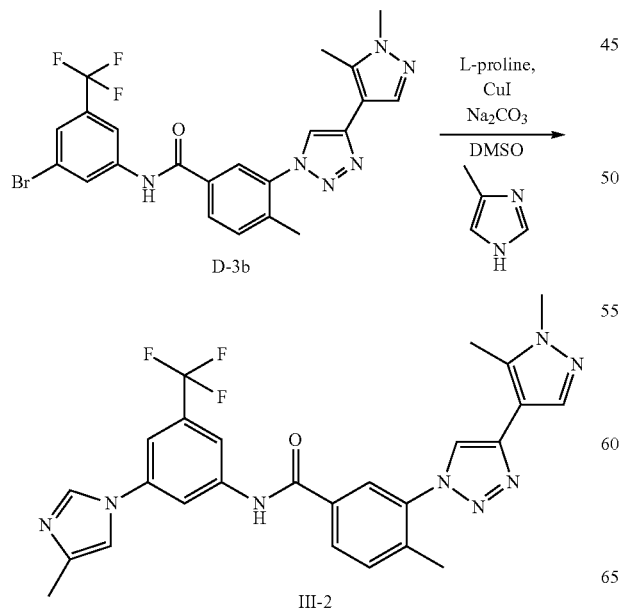

Arylbromide D-3b (50 mg, 0.096 mmol), sodium carbonate (43.7 mg, 0.4 mmol), L-proline (4.6 mg, 0.04 mmol) and copper(I)-iodide (3.8 mg, 0.02 mmol) are taken up in 900 μL DMSO under an argon atmosphere and combined with 4-methylimidazole (33 mg, 0.4 mmol). The reaction mixture is heated to 150° C. using a microwave reactor and stirred for 90 min. Then the reaction mixture is filtered and the reaction mixture is purified by preparative HPLC. The product-containing fractions of III-2 (HPLC-MS: $t_{Ret.}$=1.76 min; MS (M+H)$^+$=521) are freeze-dried.

Reaction scheme D-II

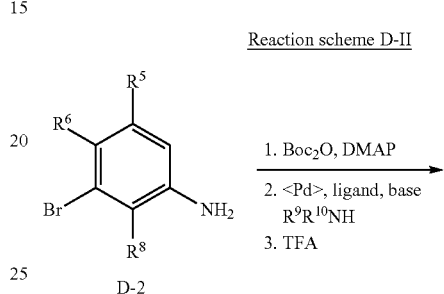

D-2

1. Boc$_2$O, DMAP
2. <Pd>, ligand, base R$^9$R$^{10}$NH
3. TFA

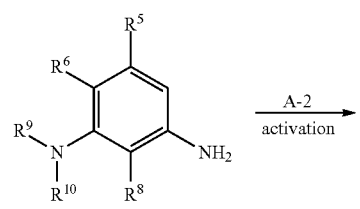

D-4

A-2 activation $\longrightarrow$

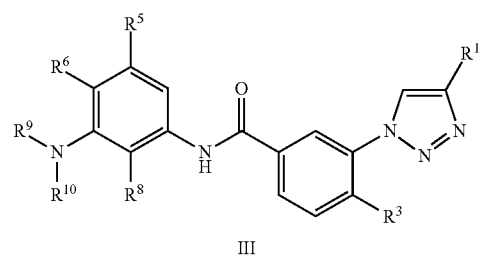

III

Example compounds of type III can also be prepared by a different sequence of the reaction steps shown in reaction scheme D-I ($\rightarrow$reaction scheme D-II), by first synthesising the anilines D-4 using methods known from the literature from the anilines D-2 by protecting the amino function (e.g. by means of the Boc protective group), followed by palladium-catalysed cross-coupling reaction (Buchwald-Hartwig reaction) and cleaving the Boc-protective group (e.g. with TFA or HCl) and then reacting with the components A-2 by standard amide linking methods to form the end compounds III.

f) Procedure for Synthesising D-4a

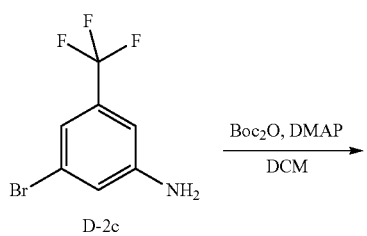

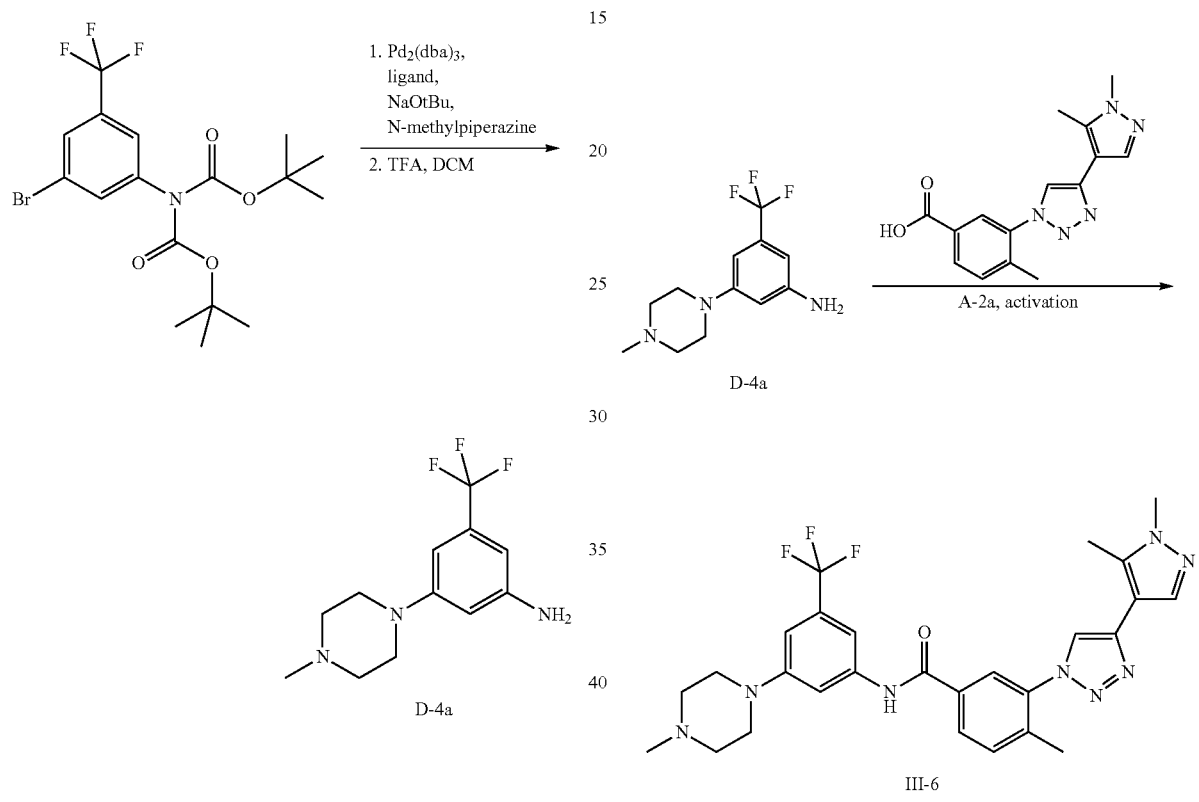

Aniline D-2c (9.00 mL, 63.0 mmol) and DMAP (0.77 g, 6.30 mmol) are placed in DCM (30 mL), cooled to 0° C., combined dropwise with a solution of Boc$_2$O (34.3 g, 157 mmol) in DCM (20 mL) and stirred overnight at RT. The reaction mixture is evaporated down, taken up in EtOAc, washed with saturated NH$_4$Cl solution and saturated NaCl solution, dried on MgSO$_4$, filtered and evaporated down. Some of the resulting crude product of the doubly Boc-protected aniline (14.0 g, 31.8 mmol) is taken up in 1,4-dioxane (300 mL), combined successively with sodium-tert-butoxide (9.45 g, 95.4 mmol), biphenyl-2-yl-di-tert-butylphosphane (2.85 g, 9.54 mmol), tris-(dibenzylideneacetone)-palladium (2.91 g, 3.18 mmol) and N-methylpiperazine (14.1 mL, 127 mmol) and stirred for 4 h at 45° C. The catalyst is filtered off, the filtrate is evaporated down, the residue is taken up in EtOAc and washed with 0.1 N hydrochloric acid. The organic phase is dried on MgSO$_4$, filtered and evaporated down. The crude product thus obtained (15.8 g, 30.8 mmol) is taken up in DCM (250 mL), combined dropwise with TFA (68.6 mL) and stirred for 2 h at RT. Then the reaction mixture is extracted 2× with 200 mL water. The combined aqueous phases are extracted with DCM, adjusted to pH 8 with NaOH and extracted 3× with EtOAc. The combined organic phases are dried on MgSO$_4$, filtered and evaporated down. The residue is dissolved in isopropanol, combined with Et$_2$O and HCl in Et$_2$O (4 M), whereupon the HCl salt of D-4a (6.50 g; 22 mmol) (HPLC-MS: t$_{Ret.}$=1.64 min; MS (M+H)$^+$=260) is precipitated.

Aniline intermediates D-4 (Table 10; R'=—NH$_2$), being another aspect of this invention, can be obtained in analogy with the synthesis of D-4a and process described in scheme L.

g) Procedure for Synthesising III-6

The benzoic acid A-2a (321 mg, 1.08 mmol) is placed in DCM (4 mL) and THF (4 mL), combined with oxalyl chloride (137 µl, 1.62 mmol) and a few drops of DMF, stirred for 2 h at RT and then evaporated down. The residue is taken up in DCM, combined with the aniline D-4a (280 mg, 1.08 mmol) and iPr$_2$EtN (425 µl, 2.48 mmol) and stirred overnight at RT. Then it is evaporated down, the residue is taken up in a little DMF and purified by preparative HPLC. The product-containing fractions of III-6 (HPLC-MS: t$_{Ret.}$=1.58 min; MS (M+H)$^+$=539) are combined and freeze-dried.

Analogously to the reaction procedures a) to g) described above for synthesising Examples III-1, III-2 and III-6, the following Examples III-3 to III-5 and III-7 to III-197 (Table 3) or other comparable Examples may be obtained from the corresponding precursors, which are either commercially obtainable or are prepared using methods known from the literature.

TABLE 3
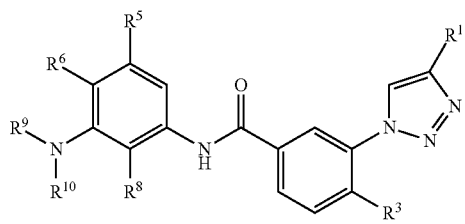
Examples III-1 to III-197
| # | Structure | t_Ret. (HPLC) [min] | MS (M + H)+ |
|---|---|---|---|
| III-1 | 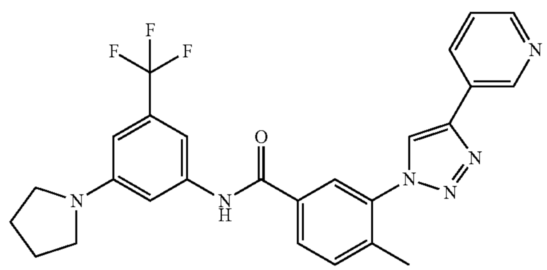 [SMILES: Cc1ccc(C(=O)Nc2cc(N3CCCC3)cc(C(F)(F)F)c2)cc1-n1cc(-c2cccnc2)nn1] | 2.03 | 493 |
| III-2 | 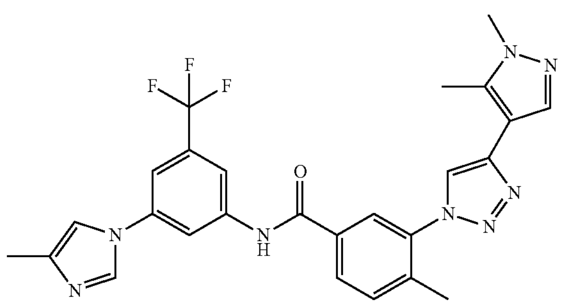 [SMILES: Cc1cn(-c2cc(NC(=O)c3ccc(C)c(-n4cc(-c5cnn(C)c5C)nn4)c3)cc(C(F)(F)F)c2)cn1] | 1.76 | 521 |
| III-3 | 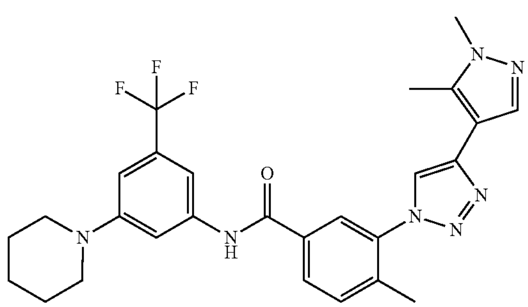 [SMILES: Cc1ccc(C(=O)Nc2cc(N3CCCCC3)cc(C(F)(F)F)c2)cc1-n1cc(-c2cnn(C)c2C)nn1] | 2.39 | 524 |
| III-4 | 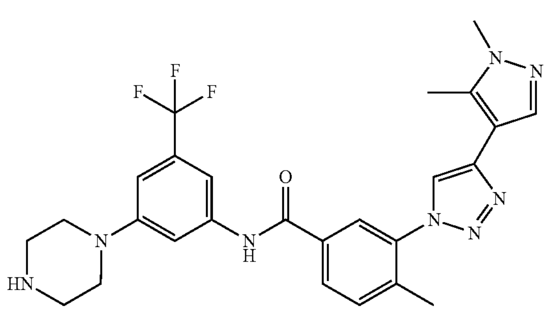 [SMILES: Cc1ccc(C(=O)Nc2cc(N3CCNCC3)cc(C(F)(F)F)c2)cc1-n1cc(-c2cnn(C)c2C)nn1] | 1.60 | 525 |

TABLE 3-continued

Examples III-1 to III-197

| # | Structure | t$_{Ret.}$ (HPLC) [min] | MS (M + H)$^+$ |
|---|---|---|---|
| III-5 | 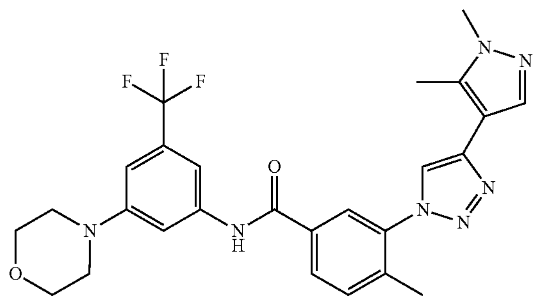 [SMILES: Cc1ccc(C(=O)Nc2cc(N3CCOCC3)cc(C(F)(F)F)c2)cc1-n1cc(-c2cnn(C)c2C)nn1] | 2.16 | 526 |
| III-6 | 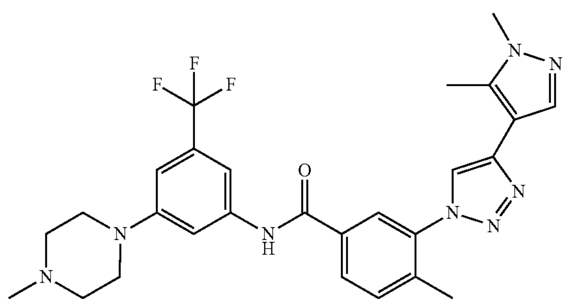 [SMILES: Cc1ccc(C(=O)Nc2cc(N3CCN(C)CC3)cc(C(F)(F)F)c2)cc1-n1cc(-c2cnn(C)c2C)nn1] | 1.58 | 539 |
| III-7 | 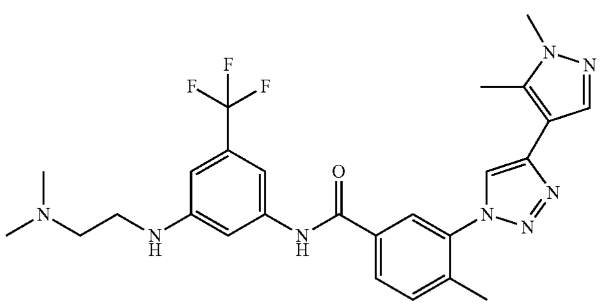 [SMILES: Cc1ccc(C(=O)Nc2cc(NCCN(C)C)cc(C(F)(F)F)c2)cc1-n1cc(-c2cnn(C)c2C)nn1] | 1.59 | 527 |
| III-8 | 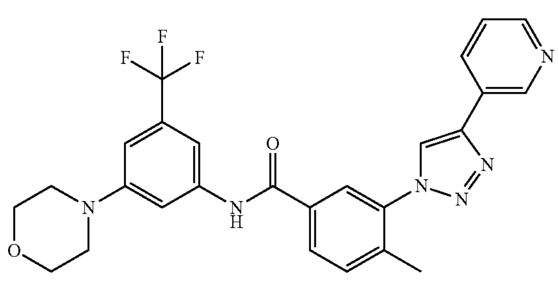 [SMILES: Cc1ccc(C(=O)Nc2cc(N3CCOCC3)cc(C(F)(F)F)c2)cc1-n1cc(-c2cccnc2)nn1] | 1.88 | 509 |

TABLE 3-continued

Examples III-1 to III-197

| # | Structure | t<sub>Ret.</sub> (HPLC) [min] | MS (M + H)⁺ |
|---|---|---|---|
| III-9 | 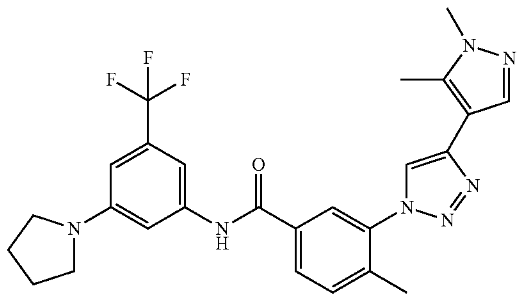 [SMILES: Cc1ccc(C(=O)Nc2cc(N3CCCC3)cc(C(F)(F)F)c2)cc1-n1cc(-c2cnn(C)c2C)nn1] | 2.40 | 510 |
| III-10 | 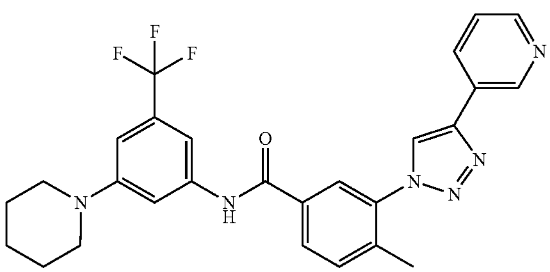 [SMILES: Cc1ccc(C(=O)Nc2cc(N3CCCCC3)cc(C(F)(F)F)c2)cc1-n1cc(-c2cccnc2)nn1] | 2.05 | 507 |
| III-11 | 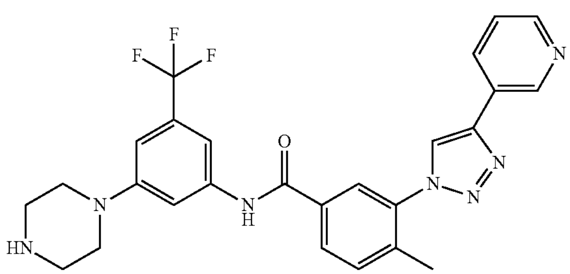 [SMILES: Cc1ccc(C(=O)Nc2cc(N3CCNCC3)cc(C(F)(F)F)c2)cc1-n1cc(-c2cccnc2)nn1] | 1.32 | 508 |
| III-12 | 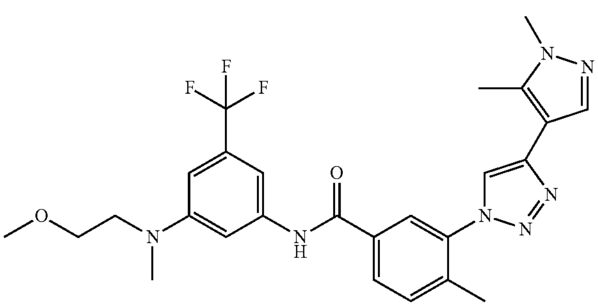 [SMILES: COCCN(C)c1cc(NC(=O)c2ccc(C)c(-n3cc(-c4cnn(C)c4C)nn3)c2)cc(C(F)(F)F)c1] | 1.99 | 528 |

TABLE 3-continued
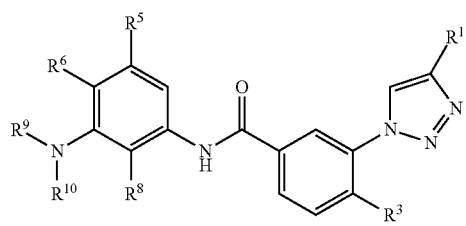
Examples III-1 to III-197
| # | Structure | $t_{Ret.}$ (HPLC) [min] | MS $(M + H)^+$ |
|---|---|---|---|
| III-13 | 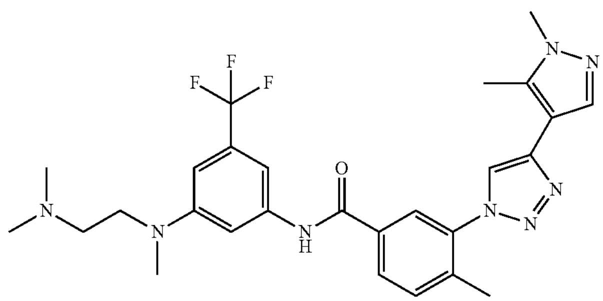 [SMILES: Cc1ccc(C(=O)Nc2cc(N(C)CCN(C)C)cc(C(F)(F)F)c2)cc1-n1cc(-c2cnn(C)c2C)nn1] | 1.44 | 541 |
| III-14 | 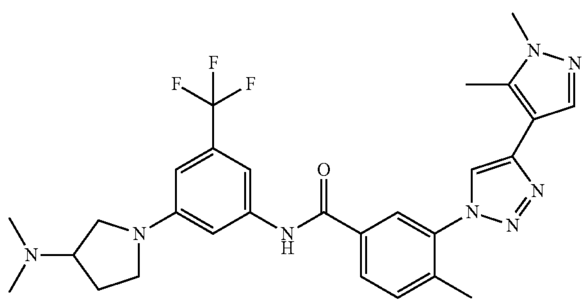 [SMILES: Cc1ccc(C(=O)Nc2cc(N3CCC(N(C)C)C3)cc(C(F)(F)F)c2)cc1-n1cc(-c2cnn(C)c2C)nn1] | 1.44 | 553 |
| III-15 | 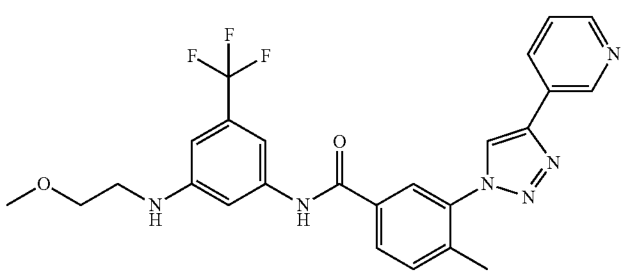 [SMILES: COCCNc1cc(NC(=O)c2ccc(C)c(-n3cc(-c4cccnc4)nn3)c2)cc(C(F)(F)F)c1] | 1.83 | 497 |
| III-16 | 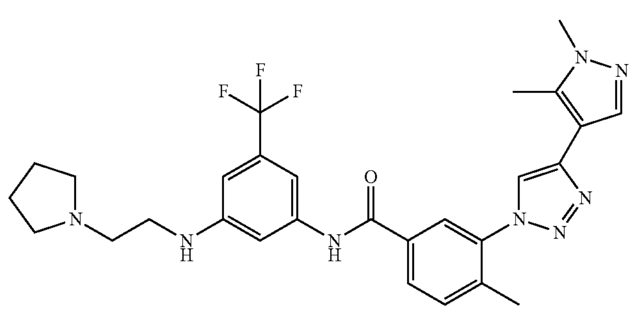 [SMILES: Cc1ccc(C(=O)Nc2cc(NCCN3CCCC3)cc(C(F)(F)F)c2)cc1-n1cc(-c2cnn(C)c2C)nn1] | 1.44 | 553 |

TABLE 3-continued
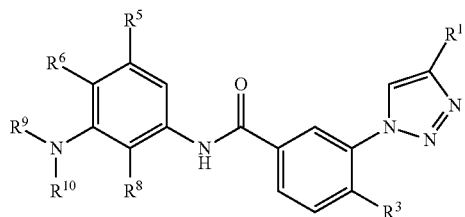
Examples III-1 to III-197
| # | Structure | t_Ret. (HPLC) [min] | MS (M + H)+ |
|---|---|---|---|
| III-17 | 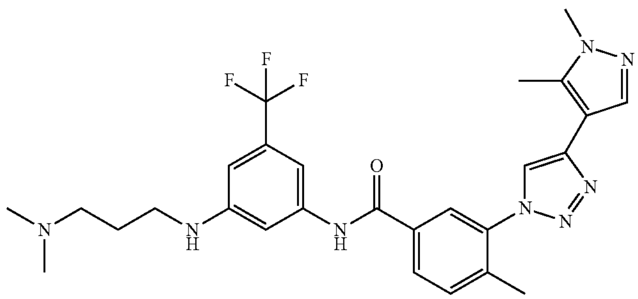 [SMILES: Cc1ccc(C(=O)Nc2cc(NCCCN(C)C)cc(C(F)(F)F)c2)cc1-n1cc(-c2cnn(C)c2C)nn1] | 1.45 | 541 |
| III-18 | 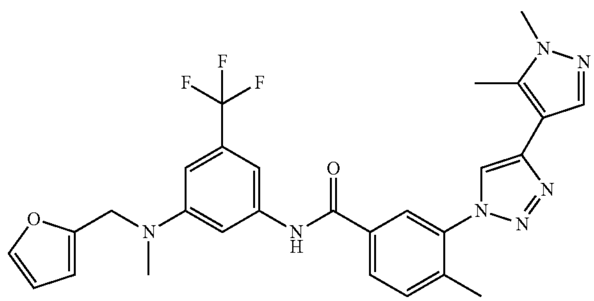 [SMILES: Cc1ccc(C(=O)Nc2cc(N(C)Cc3ccco3)cc(C(F)(F)F)c2)cc1-n1cc(-c2cnn(C)c2C)nn1] | 2.37 | 550 |
| III-19 | 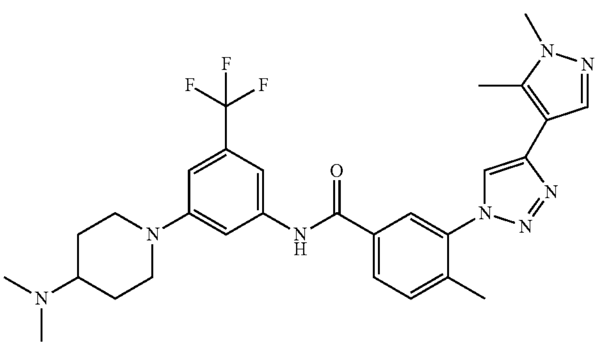 [SMILES: Cc1ccc(C(=O)Nc2cc(N3CCC(N(C)C)CC3)cc(C(F)(F)F)c2)cc1-n1cc(-c2cnn(C)c2C)nn1] | 1.66 | 567 |
| III-20 | 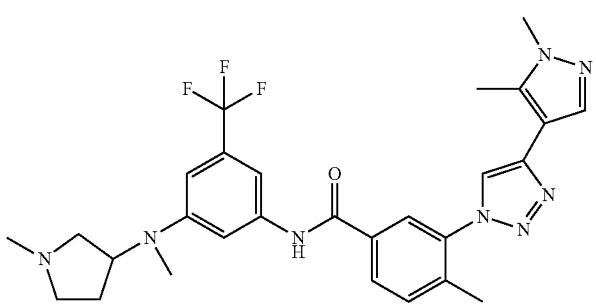 [SMILES: Cc1ccc(C(=O)Nc2cc(N(C)C3CCN(C)C3)cc(C(F)(F)F)c2)cc1-n1cc(-c2cnn(C)c2C)nn1] | 1.65 | 553 |

TABLE 3-continued

Examples III-1 to III-197

| # | Structure | t_Ret. (HPLC) [min] | MS (M + H)+ |
|---|---|---|---|
| III-21 | 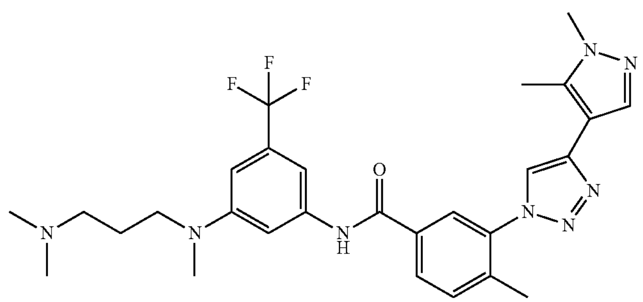 [SMILES: Cc1ccc(C(=O)Nc2cc(N(C)CCCN(C)C)cc(C(F)(F)F)c2)cc1-n1cc(-c2cnn(C)c2C)nn1] | 1.67 | 555 |
| III-22 | 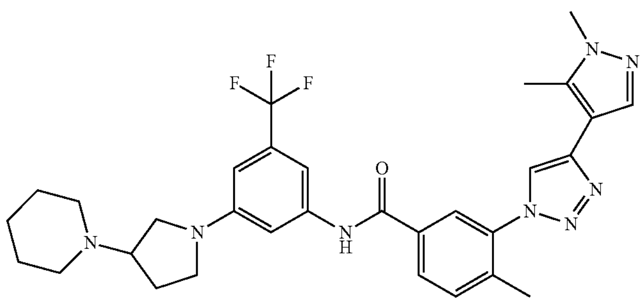 [SMILES: Cc1ccc(C(=O)Nc2cc(N3CCC(N4CCCCC4)C3)cc(C(F)(F)F)c2)cc1-n1cc(-c2cnn(C)c2C)nn1] | 1.68 | 593 |
| III-23 | 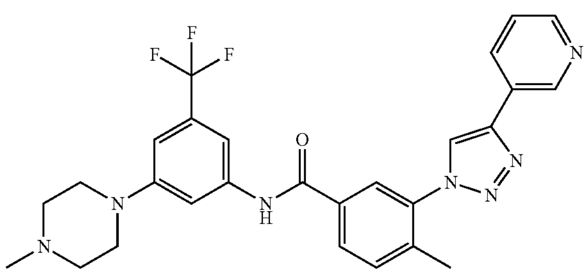 [SMILES: Cc1ccc(C(=O)Nc2cc(N3CCN(C)CC3)cc(C(F)(F)F)c2)cc1-n1cc(-c2cccnc2)nn1] | 1.48 | 522 |
| III-24 | 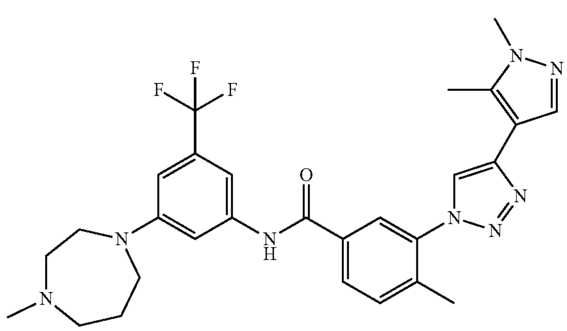 [SMILES: Cc1ccc(C(=O)Nc2cc(N3CCCN(C)CC3)cc(C(F)(F)F)c2)cc1-n1cc(-c2cnn(C)c2C)nn1] | 1.62 | 553 |

TABLE 3-continued

Examples III-1 to III-197

| # | Structure | $t_{Ret.}$ (HPLC) [min] | MS $(M + H)^+$ |
|---|---|---|---|
| III-25 | 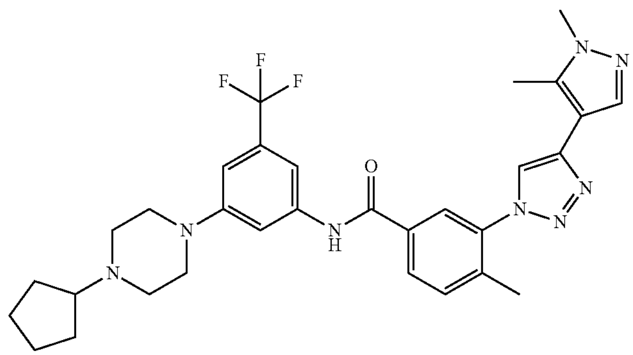 [SMILES: Cc1ccc(C(=O)Nc2cc(N3CCN(C4CCCC4)CC3)cc(C(F)(F)F)c2)cc1-n1cc(-c2cnn(C)c2C)nn1] | 1.67 | 593 |
| III-26 | 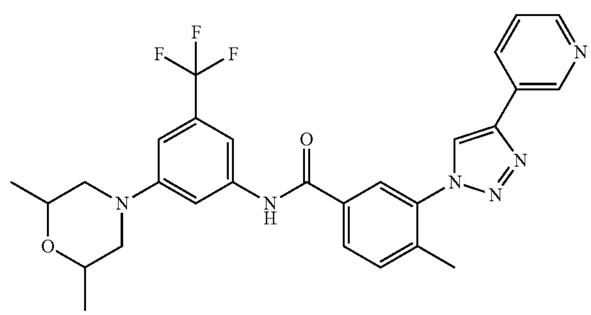 [SMILES: Cc1ccc(C(=O)Nc2cc(N3CC(C)OC(C)C3)cc(C(F)(F)F)c2)cc1-n1cc(-c2cccnc2)nn1] | 2.21 | 537 |
| III-27 | 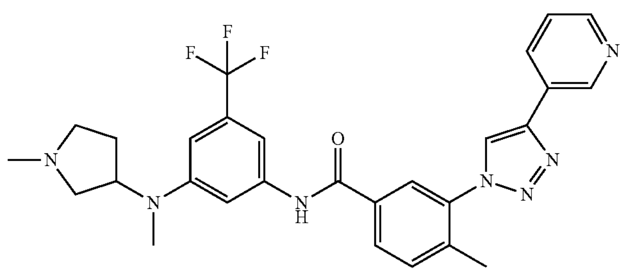 [SMILES: Cc1ccc(C(=O)Nc2cc(N(C)C3CCN(C)C3)cc(C(F)(F)F)c2)cc1-n1cc(-c2cccnc2)nn1] | 1.55 | 536 |
| III-28 | 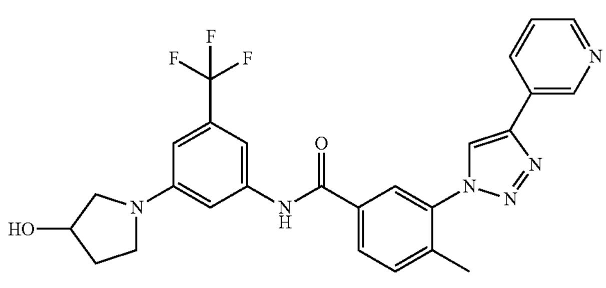 [SMILES: Cc1ccc(C(=O)Nc2cc(N3CCC(O)C3)cc(C(F)(F)F)c2)cc1-n1cc(-c2cccnc2)nn1] | 1.93 | 509 |

TABLE 3-continued
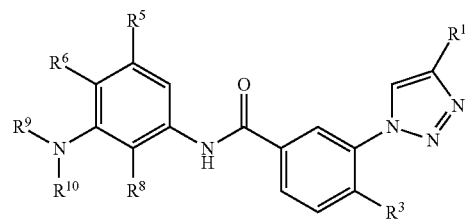
Examples III-1 to III-197
| # | Structure | $t_{Ret.}$ (HPLC) [min] | MS $(M + H)^+$ |
|---|---|---|---|
| III-29 | 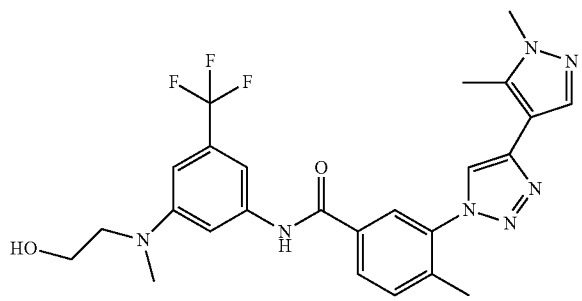 [SMILES: Cc1ccc(C(=O)Nc2cc(N(C)CCO)cc(C(F)(F)F)c2)cc1-n1cc(-c2cnn(C)c2C)nn1] | 2.05 | 514 |
| III-30 | 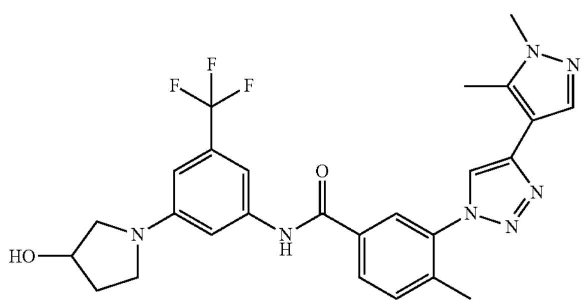 [SMILES: Cc1ccc(C(=O)Nc2cc(N3CCC(O)C3)cc(C(F)(F)F)c2)cc1-n1cc(-c2cnn(C)c2C)nn1] | 2.05 | 526 |
| III-31 | 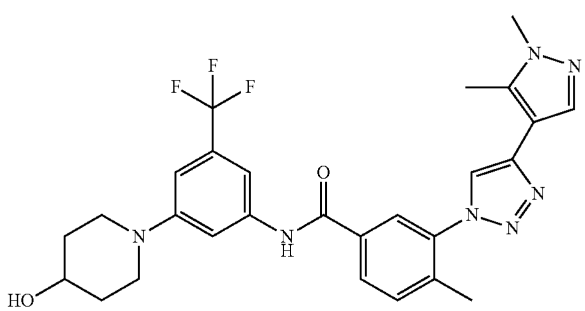 [SMILES: Cc1ccc(C(=O)Nc2cc(N3CCC(O)CC3)cc(C(F)(F)F)c2)cc1-n1cc(-c2cnn(C)c2C)nn1] | 2.04 | 540 |
| III-32 | 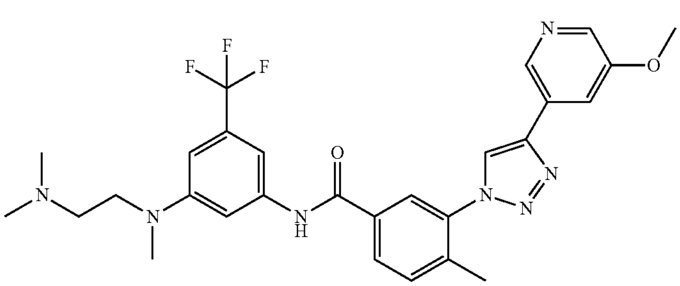 | 1.61 | 554 |

TABLE 3-continued

Examples III-1 to III-197

| # | Structure | t$_{Ret.}$ (HPLC) [min] | MS (M + H)$^+$ |
|---|---|---|---|
| III-33 | 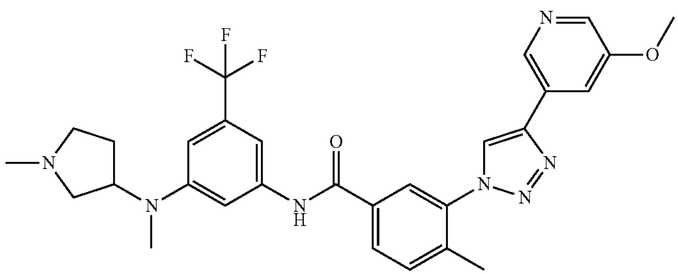 | 1.66 | 566 |
| III-34 | 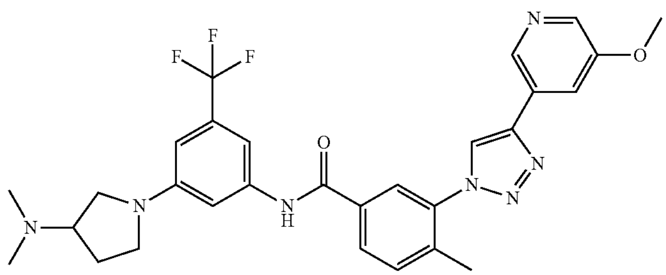 | 1.64 | 566 |
| III-35 | 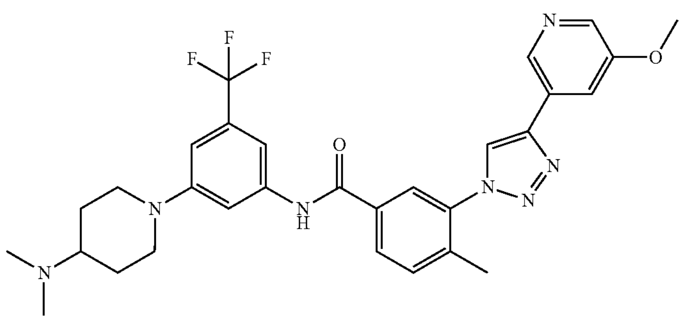 | 1.66 | 580 |
| III-36 | 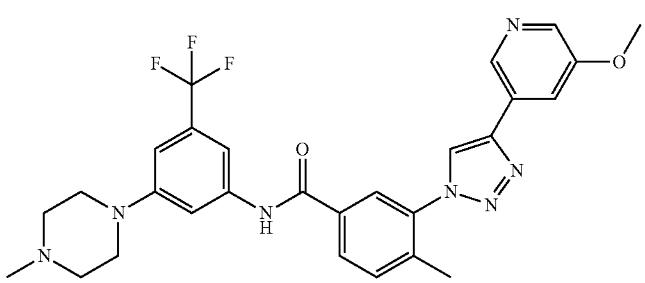 | 2.15 | 552 |

TABLE 3-continued

Examples III-1 to III-197

| # | Structure | t_Ret. (HPLC) [min] | MS (M + H)+ |
|---|---|---|---|
| III-37 | 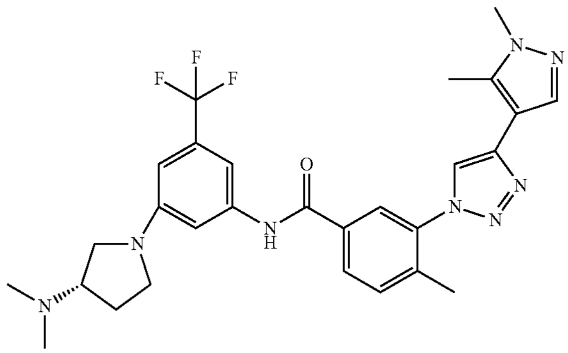 [SMILES: Cc1ccc(C(=O)Nc2cc(N3CC[C@H](N(C)C)C3)cc(C(F)(F)F)c2)cc1-n1cc(-c2cnn(C)c2C)nn1] | 1.60 | 553 |
| III-38 | 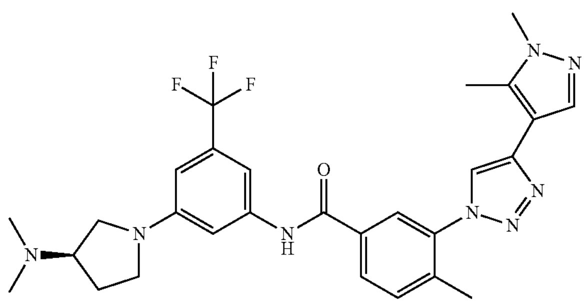 [SMILES: Cc1ccc(C(=O)Nc2cc(N3CC[C@@H](N(C)C)C3)cc(C(F)(F)F)c2)cc1-n1cc(-c2cnn(C)c2C)nn1] | 1.62 | 553 |
| III-39 | 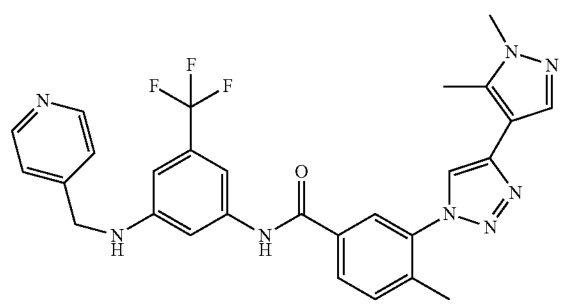 [SMILES: Cc1ccc(C(=O)Nc2cc(NCc3ccncc3)cc(C(F)(F)F)c2)cc1-n1cc(-c2cnn(C)c2C)nn1] | 1.69 | 547 |
| III-40 | 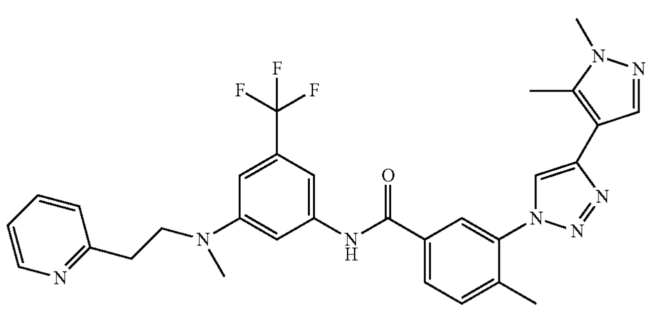 [SMILES: Cc1ccc(C(=O)Nc2cc(N(C)CCc3ccccn3)cc(C(F)(F)F)c2)cc1-n1cc(-c2cnn(C)c2C)nn1] | 1.86 | 575 |

TABLE 3-continued
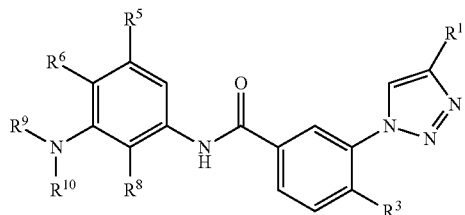
Examples III-1 to III-197
| # | Structure | $t_{Ret.}$ (HPLC) [min] | MS $(M + H)^+$ |
|---|---|---|---|
| III-41 | 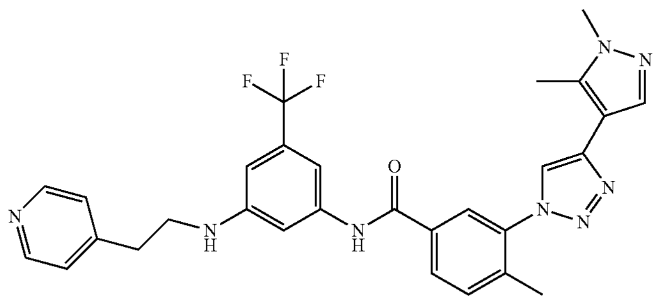 [SMILES: Cc1ccc(C(=O)Nc2cc(NCCc3ccncc3)cc(C(F)(F)F)c2)cc1-n1cc(-c2cnn(C)c2C)nn1] | 1.70 | 561 |
| III-42 | 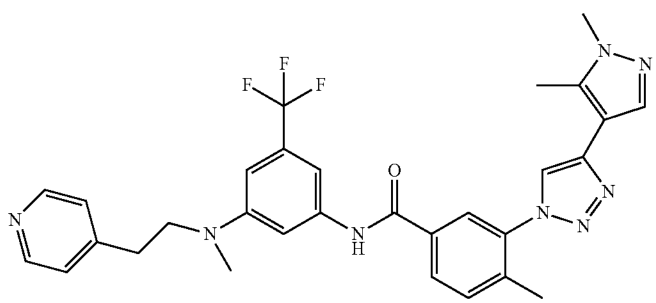 [SMILES: Cc1ccc(C(=O)Nc2cc(N(C)CCc3ccncc3)cc(C(F)(F)F)c2)cc1-n1cc(-c2cnn(C)c2C)nn1] | 1.76 | 575 |
| III-43 | 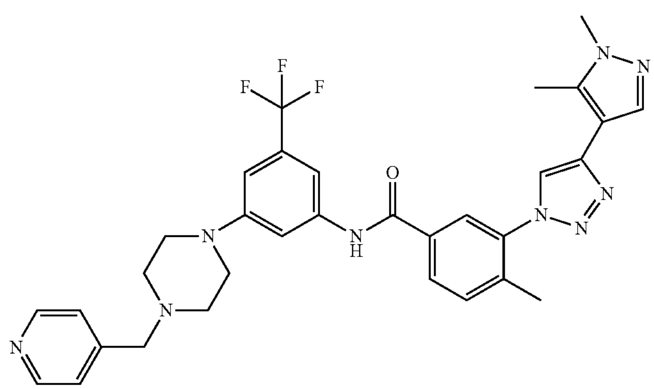 [SMILES: Cc1ccc(C(=O)Nc2cc(N3CCN(Cc4ccncc4)CC3)cc(C(F)(F)F)c2)cc1-n1cc(-c2cnn(C)c2C)nn1] | 1.67 | 616 |

TABLE 3-continued
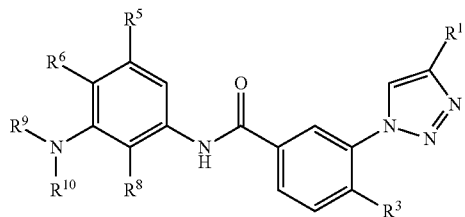
Examples III-1 to III-197
| # | Structure | $t_{Ret.}$ (HPLC) [min] | MS $(M + H)^+$ |
|---|---|---|---|
| III-44 | 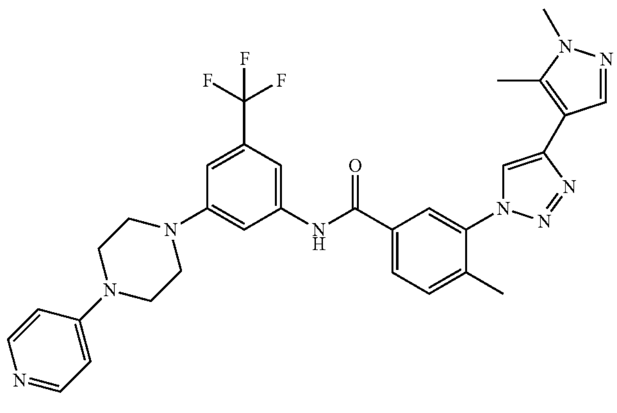 [SMILES: Cc1ccc(C(=O)Nc2cc(N3CCN(c4ccncc4)CC3)cc(C(F)(F)F)c2)cc1-n1cc(-c2cnn(C)c2C)nn1] | 1.72 | 602 |
| III-45 | 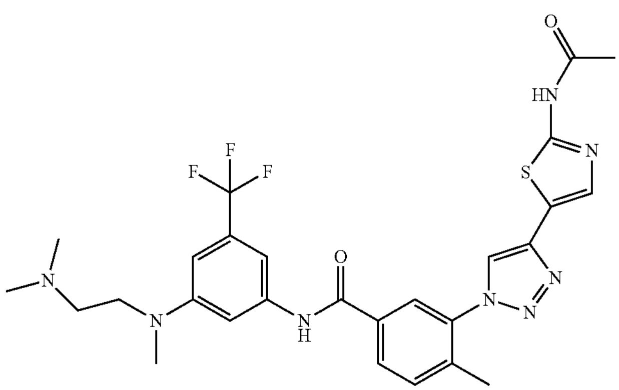 [SMILES: CC(=O)Nc1ncc(-c2cn(-c3cc(C(=O)Nc4cc(N(C)CCN(C)C)cc(C(F)(F)F)c4)ccc3C)nn2)s1] | 2.17 | 587 |
| III-46 | 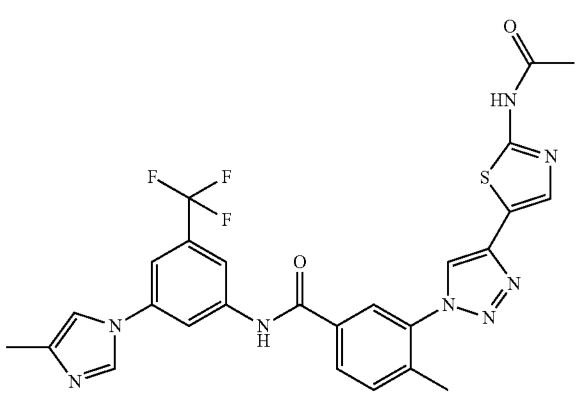 [SMILES: CC(=O)Nc1ncc(-c2cn(-c3cc(C(=O)Nc4cc(-n5cnc(C)c5)cc(C(F)(F)F)c4)ccc3C)nn2)s1] | 2.04 | 567 |

TABLE 3-continued

Examples III-1 to III-197

| # | Structure | t$_{Ret.}$ (HPLC) [min] | MS (M + H)$^+$ |
|---|---|---|---|
| III-47 | 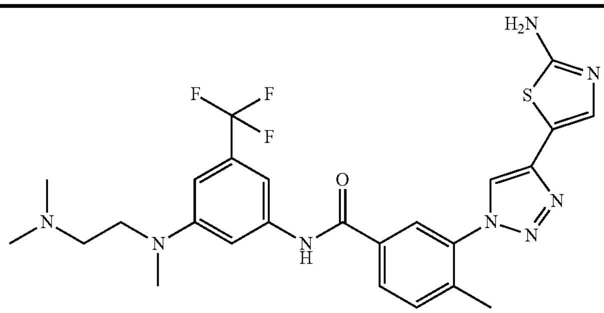 | 2.13 | 545 |
| III-48 | 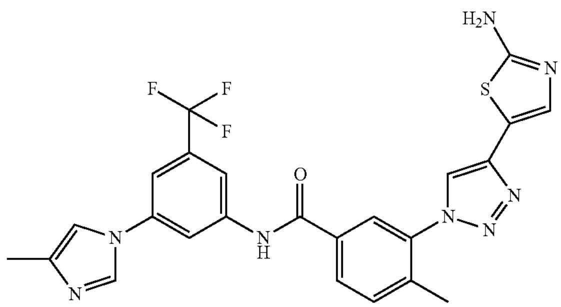 [SMILES: Cc1cn(-c2cc(NC(=O)c3ccc(C)c(-n4cc(-c5cnc(N)s5)nn4)c3)cc(C(F)(F)F)c2)cn1] | 1.99 | 525 |
| III-49 | 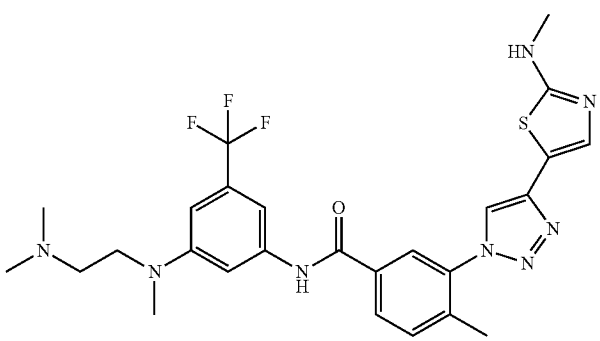 [SMILES: CNc1ncc(-c2cn(-c3cc(C(=O)Nc4cc(N(C)CCN(C)C)cc(C(F)(F)F)c4)ccc3C)nn2)s1] | 2.18 | 559 |
| III-50 | 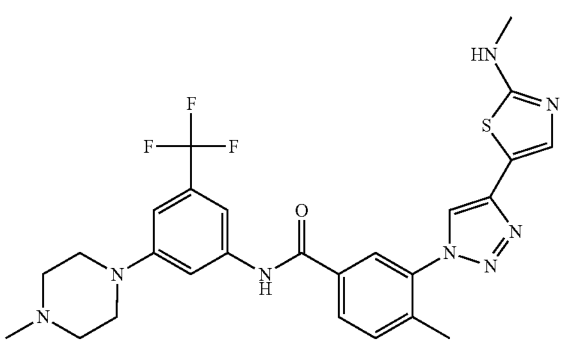 [SMILES: CNc1ncc(-c2cn(-c3cc(C(=O)Nc4cc(N5CCN(C)CC5)cc(C(F)(F)F)c4)ccc3C)nn2)s1] | 2.08 | 557 |

TABLE 3-continued
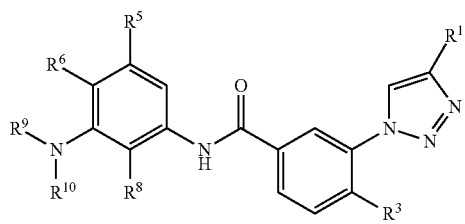
Examples III-1 to III-197
| # | Structure | $t_{Ret.}$ (HPLC) [min] | MS $(M + H)^+$ |
|---|---|---|---|
| III-51 | 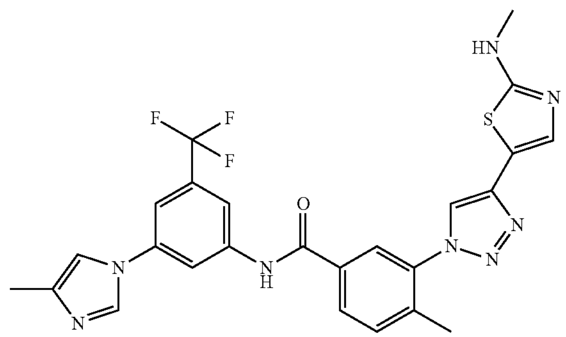 [SMILES: CNc1ncc(-c2cn(-c3cc(C(=O)Nc4cc(-n5cnc(C)c5)cc(C(F)(F)F)c4)ccc3C)nn2)s1] | 2.09 | 539 |
| III-52 | 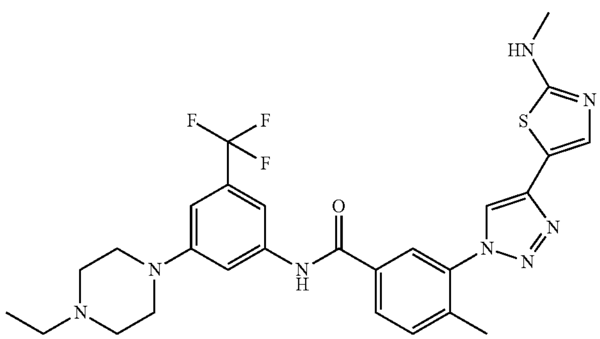 [SMILES: CCN1CCN(c2cc(NC(=O)c3ccc(C)c(-n4cc(-c5cnc(NC)s5)nn4)c3)cc(C(F)(F)F)c2)CC1] | 2.20 | 571 |
| III-53 | 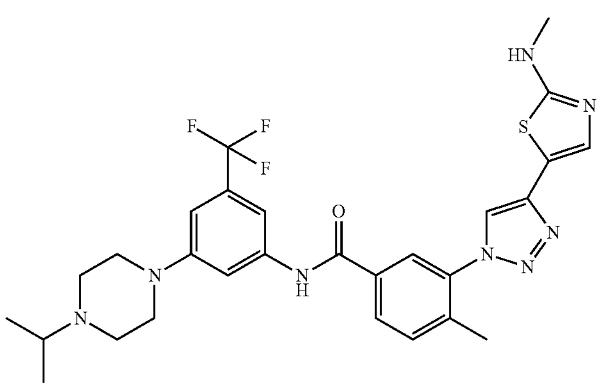 [SMILES: CNc1ncc(-c2cn(-c3cc(C(=O)Nc4cc(N5CCN(C(C)C)CC5)cc(C(F)(F)F)c4)ccc3C)nn2)s1] | 2.29 | 585 |

TABLE 3-continued
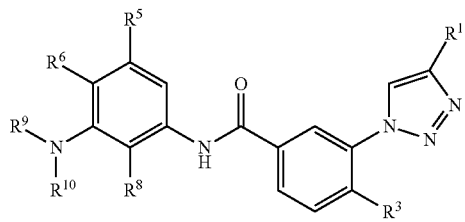
Examples III-1 to III-197
| # | Structure | $t_{Ret.}$ (HPLC) [min] | MS $(M + H)^+$ |
|---|---|---|---|
| III-54 | 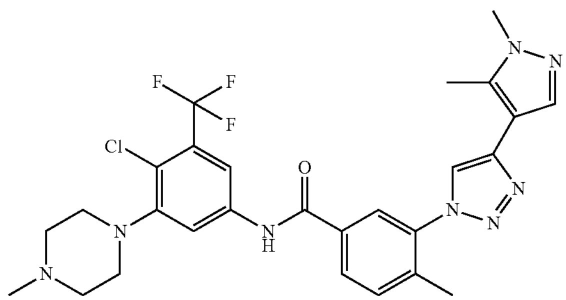 [SMILES: Cc1ccc(C(=O)Nc2cc(N3CCN(C)CC3)c(Cl)c(C(F)(F)F)c2)cc1-n1cc(-c2cnn(C)c2C)nn1] | 1.66 | 573 |
| III-55 | 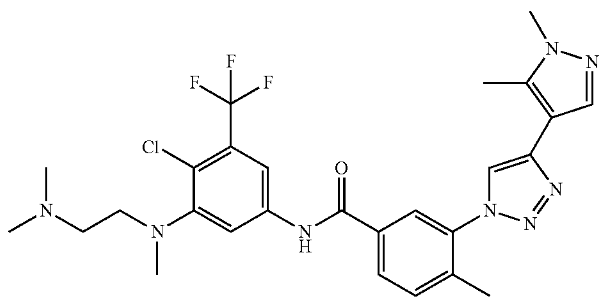 [SMILES: Cc1ccc(C(=O)Nc2cc(N(C)CCN(C)C)c(Cl)c(C(F)(F)F)c2)cc1-n1cc(-c2cnn(C)c2C)nn1] | 1.70 | 575 |
| III-56 | 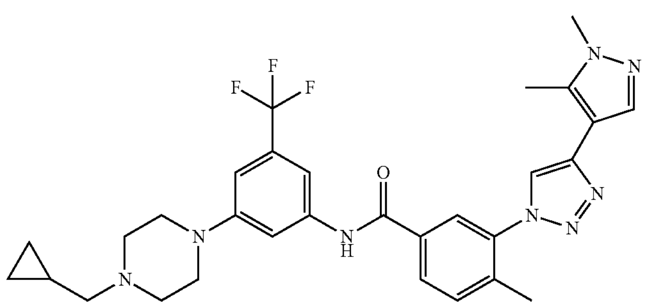 [SMILES: Cc1ccc(C(=O)Nc2cc(N3CCN(CC4CC4)CC3)cc(C(F)(F)F)c2)cc1-n1cc(-c2cnn(C)c2C)nn1] | 1.66 | 579 |
| III-57 | 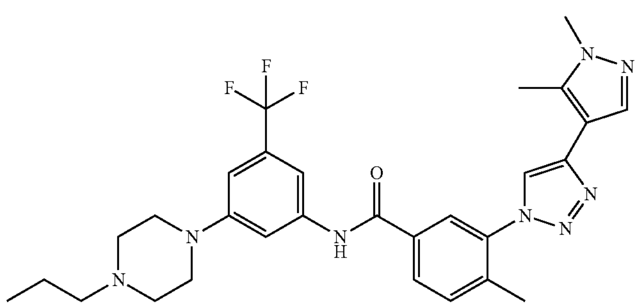 [SMILES: CCCN1CCN(c2cc(NC(=O)c3ccc(C)c(-n4cc(-c5cnn(C)c5C)nn4)c3)cc(C(F)(F)F)c2)CC1] | 1.67 | 567 |

TABLE 3-continued

Examples III-1 to III-197
| # | Structure | $t_{Ret.}$ (HPLC) [min] | MS $(M + H)^+$ |
|---|---|---|---|
| III-58 | 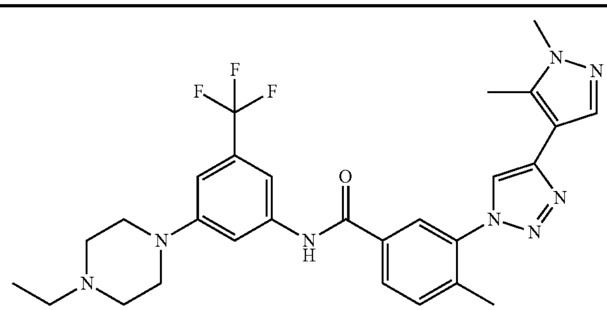 | 2.17 | 553 |
| III-59 | 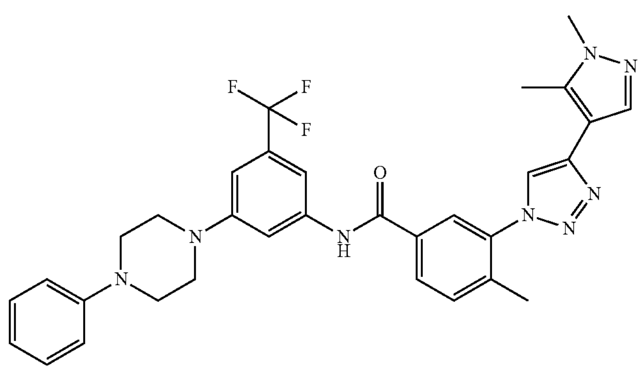 [SMILES: Cc1ccc(C(=O)Nc2cc(N3CCN(c4ccccc4)CC3)cc(C(F)(F)F)c2)cc1-n1cc(-c2cnn(C)c2C)nn1] | 2.49 | 601 |
| III-60 | 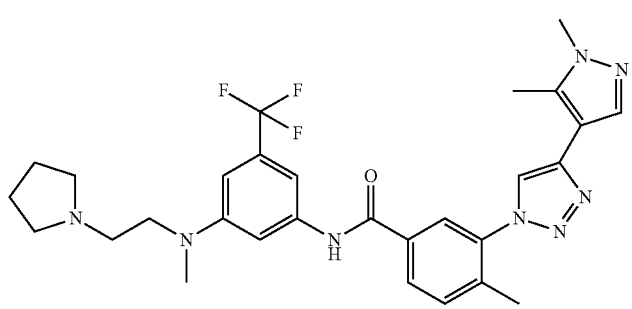 [SMILES: Cc1ccc(C(=O)Nc2cc(N(C)CCN3CCCC3)cc(C(F)(F)F)c2)cc1-n1cc(-c2cnn(C)c2C)nn1] | 2.24 | 567 |
| III-61 | 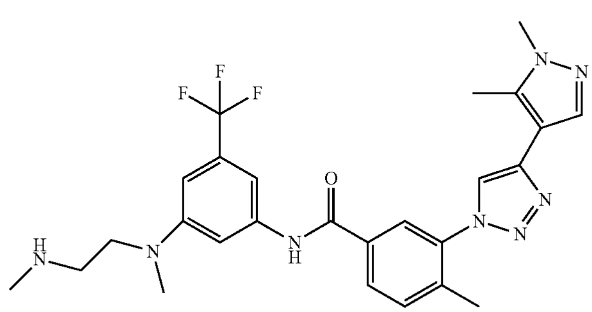 [SMILES: CNCCN(C)c1cc(NC(=O)c2ccc(C)c(-n3cc(-c4cnn(C)c4C)nn3)c2)cc(C(F)(F)F)c1] | 2.08 | 527 |

TABLE 3-continued
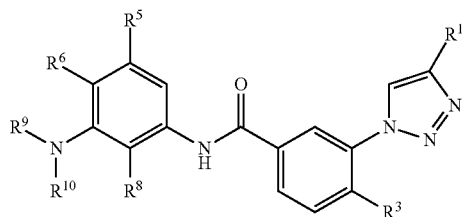
Examples III-1 to III-197
| # | Structure | t_Ret. (HPLC) [min] | MS (M + H)+ |
|---|---|---|---|
| III-62 | 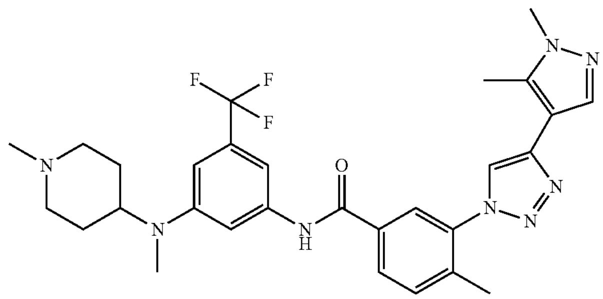 [SMILES: Cc1ccc(C(=O)Nc2cc(N(C)C3CCN(C)CC3)cc(C(F)(F)F)c2)cc1-n1cc(-c2cnn(C)c2C)nn1] | 2.14 | 567 |
| III-63 | 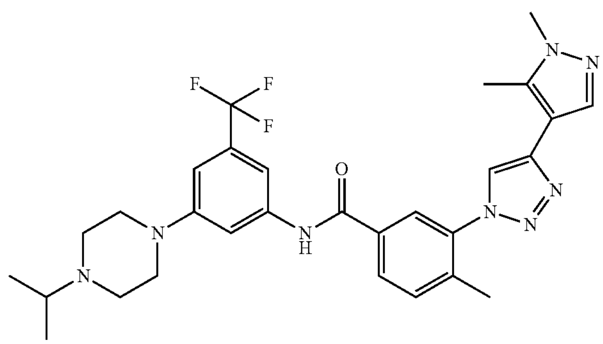 [SMILES: Cc1ccc(C(=O)Nc2cc(N3CCN(C(C)C)CC3)cc(C(F)(F)F)c2)cc1-n1cc(-c2cnn(C)c2C)nn1] | 2.27 | 567 |
| III-64 | 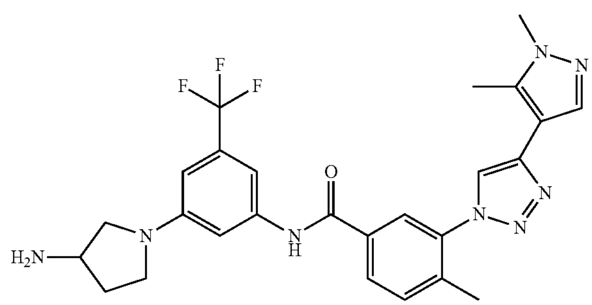 [SMILES: Cc1ccc(C(=O)Nc2cc(N3CCC(N)C3)cc(C(F)(F)F)c2)cc1-n1cc(-c2cnn(C)c2C)nn1] | 2.03 | 525 |
| III-65 | 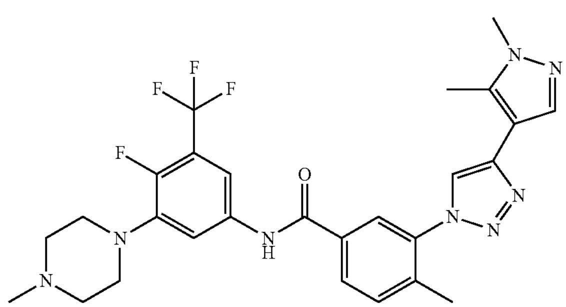 [SMILES: Cc1ccc(C(=O)Nc2cc(N3CCN(C)CC3)c(F)c(C(F)(F)F)c2)cc1-n1cc(-c2cnn(C)c2C)nn1] | 2.10 | 557 |

TABLE 3-continued
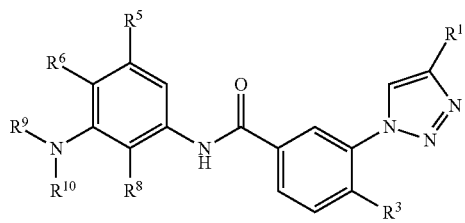
Examples III-1 to III-197
| # | Structure | $t_{Ret.}$ (HPLC) [min] | MS $(M + H)^+$ |
|---|---|---|---|
| III-66 | 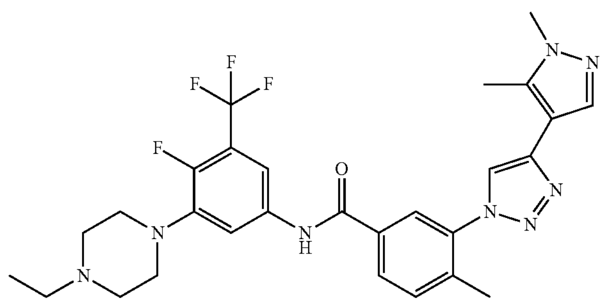 [SMILES: CCN1CCN(c2cc(NC(=O)c3ccc(C)c(-n4cc(-c5cnn(C)c5C)nn4)c3)cc(C(F)(F)F)c2F)CC1] | 2.22 | 571 |
| III-67 | 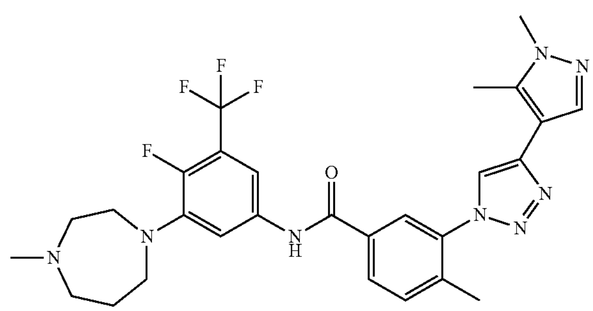 [SMILES: Cc1ccc(C(=O)Nc2cc(N3CCCN(C)CC3)c(F)c(C(F)(F)F)c2)cc1-n1cc(-c2cnn(C)c2C)nn1] | 2.22 | 571 |
| III-68 | 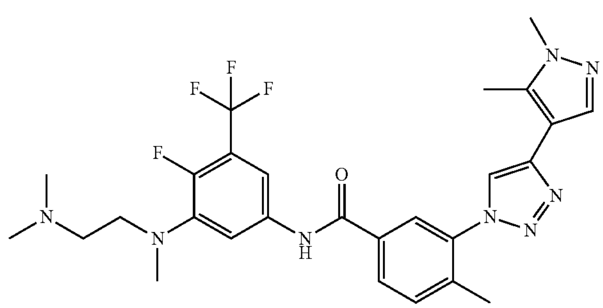 [SMILES: Cc1ccc(C(=O)Nc2cc(N(C)CCN(C)C)c(F)c(C(F)(F)F)c2)cc1-n1cc(-c2cnn(C)c2C)nn1] | 2.18 | 559 |
| III-69 | 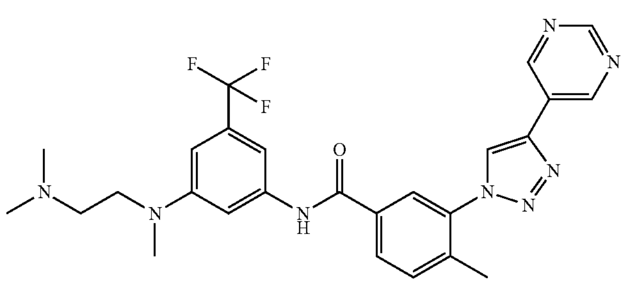 [SMILES: Cc1ccc(C(=O)Nc2cc(N(C)CCN(C)C)cc(C(F)(F)F)c2)cc1-n1cc(-c2cncnc2)nn1] | 2.15 | 525 |

TABLE 3-continued
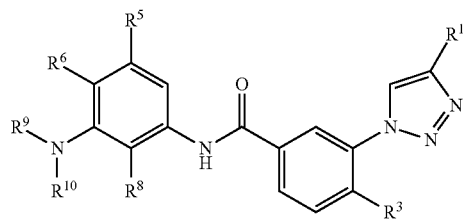
Examples III-1 to III-197
| # | Structure | $t_{Ret.}$ (HPLC) [min] | MS $(M + H)^+$ |
|---|---|---|---|
| III-70 | 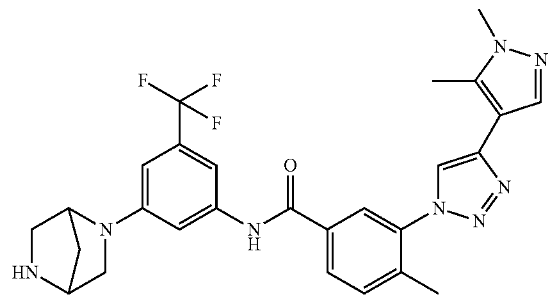 [SMILES: Cc1ccc(C(=O)Nc2cc(N3CC4CC3CN4)cc(C(F)(F)F)c2)cc1-n1cc(-c2cnn(C)c2C)nn1] | 1.96 | 537 |
| III-71 | 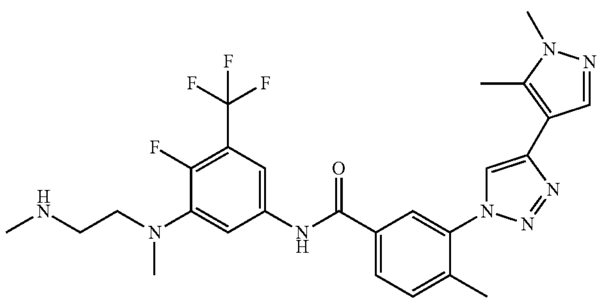 [SMILES: CNCCN(C)c1cc(NC(=O)c2ccc(C)c(-n3cc(-c4cnn(C)c4C)nn3)c2)cc(C(F)(F)F)c1F] | 2.03 | 545 |
| III-72 | 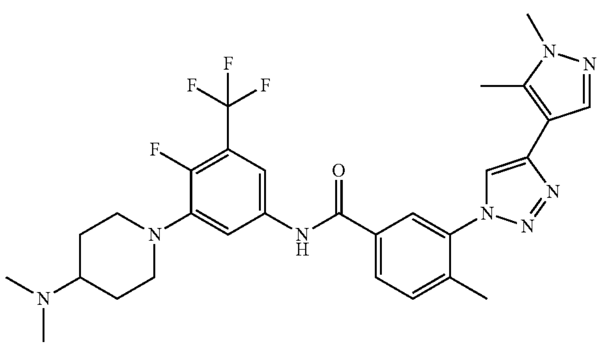 [SMILES: Cc1ccc(C(=O)Nc2cc(N3CCC(N(C)C)CC3)c(F)c(C(F)(F)F)c2)cc1-n1cc(-c2cnn(C)c2C)nn1] | 2.21 | 585 |
| III-73 | 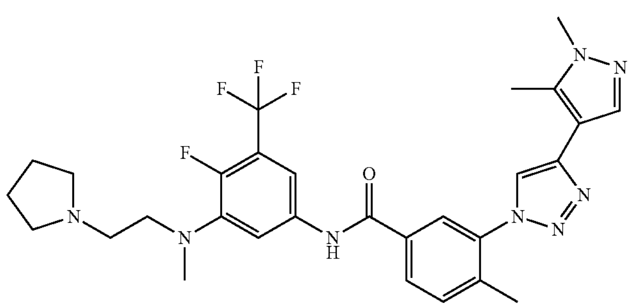 [SMILES: Cc1ccc(C(=O)Nc2cc(N(C)CCN3CCCC3)c(F)c(C(F)(F)F)c2)cc1-n1cc(-c2cnn(C)c2C)nn1] | 2.30 | 585 |

TABLE 3-continued
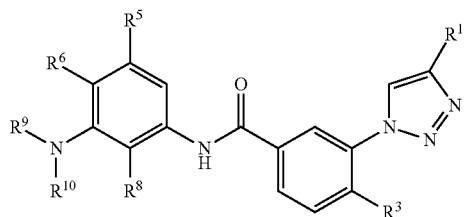
Examples III-1 to III-197
| # | Structure | $t_{Ret.}$ (HPLC) [min] | MS $(M + H)^+$ |
|---|---|---|---|
| III-74 | 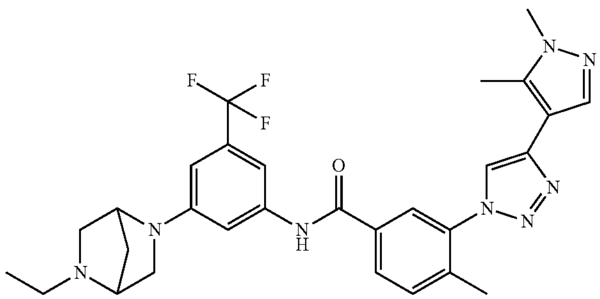 [SMILES: CCN1CC2CC1CN2c1cc(NC(=O)c2ccc(C)c(-n3cc(-c4cnn(C)c4C)nn3)c2)cc(C(F)(F)F)c1] | 2.18 | 565 |
| III-75 | 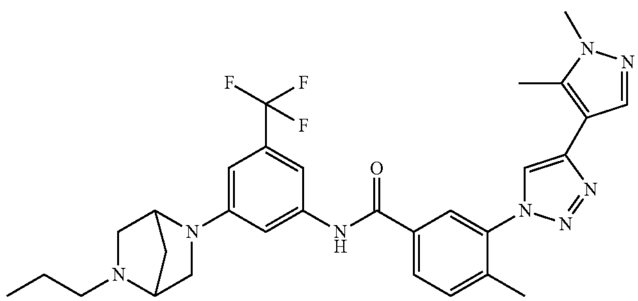 [SMILES: CCCN1CC2CC1CN2c1cc(NC(=O)c2ccc(C)c(-n3cc(-c4cnn(C)c4C)nn3)c2)cc(C(F)(F)F)c1] | 2.25 | 579 |
| III-76 | 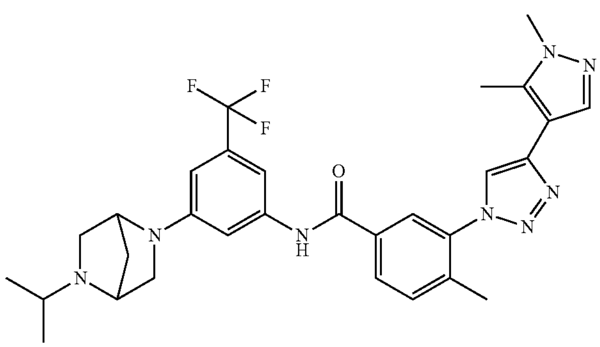 [SMILES: Cc1ccc(C(=O)Nc2cc(N3CC4CC3CN4C(C)C)cc(C(F)(F)F)c2)cc1-n1cc(-c2cnn(C)c2C)nn1] | 2.19 | 579 |
| III-77 | 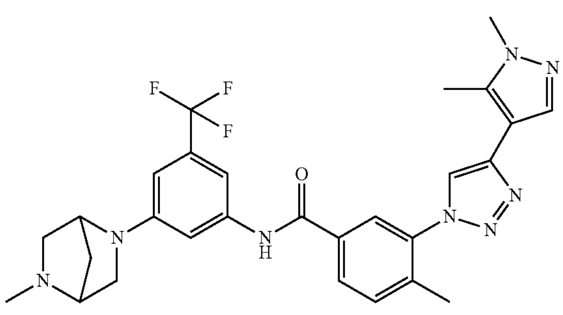 [SMILES: Cc1ccc(C(=O)Nc2cc(N3CC4CC3CN4C)cc(C(F)(F)F)c2)cc1-n1cc(-c2cnn(C)c2C)nn1] | 2.07 | 551 |

TABLE 3-continued
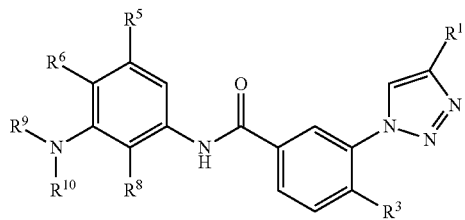
Examples III-1 to III-197
| # | Structure | $t_{Ret.}$ (HPLC) [min] | MS $(M + H)^+$ |
|---|---|---|---|
| III-78 | 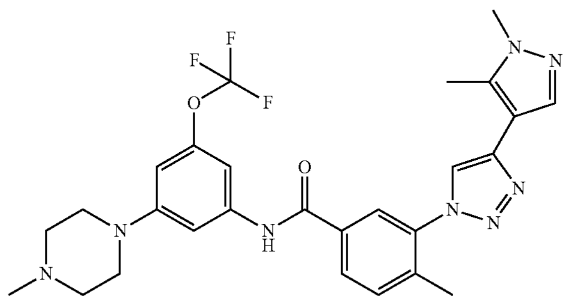 [SMILES: Cc1ccc(C(=O)Nc2cc(OC(F)(F)F)cc(N3CCN(C)CC3)c2)cc1-n1cc(-c2cnn(C)c2C)nn1] | 2.13 | 555 |
| III-79 | 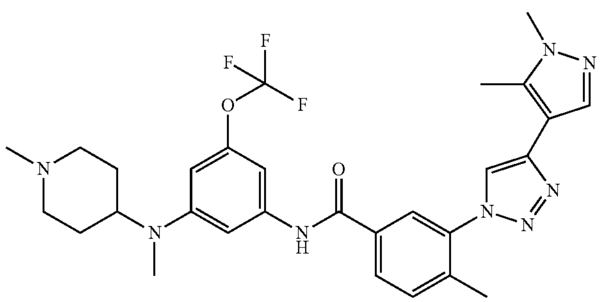 [SMILES: Cc1ccc(C(=O)Nc2cc(OC(F)(F)F)cc(N(C)C3CCN(C)CC3)c2)cc1-n1cc(-c2cnn(C)c2C)nn1] | 1.55 | 583 |
| III-80 | 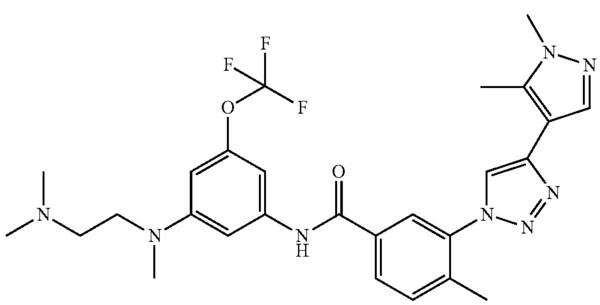 [SMILES: Cc1ccc(C(=O)Nc2cc(OC(F)(F)F)cc(N(C)CCN(C)C)c2)cc1-n1cc(-c2cnn(C)c2C)nn1] | 2.21 | 557 |
| III-81 | 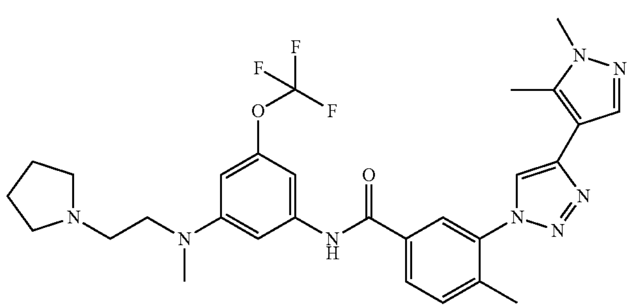 [SMILES: Cc1ccc(C(=O)Nc2cc(OC(F)(F)F)cc(N(C)CCN3CCCC3)c2)cc1-n1cc(-c2cnn(C)c2C)nn1] | 2.30 | 583 |

TABLE 3-continued

Examples III-1 to III-197

| # | Structure | t_Ret. (HPLC) [min] | MS (M + H)+ |
|---|---|---|---|
| III-82 | 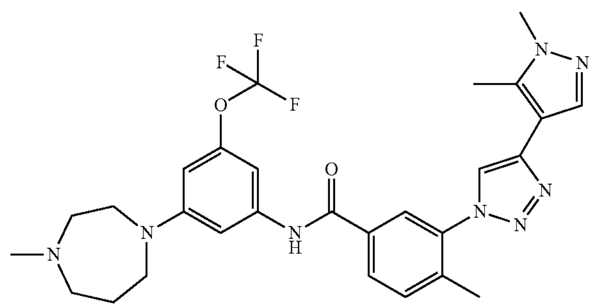 [SMILES: Cc1ccc(C(=O)Nc2cc(OC(F)(F)F)cc(N3CCCN(C)CC3)c2)cc1-n1cc(-c2cnn(C)c2C)nn1] | 2.17 | 569 |
| III-83 | 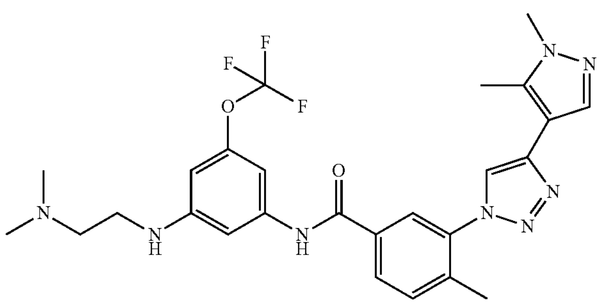 [SMILES: Cc1ccc(C(=O)Nc2cc(NCCN(C)C)cc(OC(F)(F)F)c2)cc1-n1cc(-c2cnn(C)c2C)nn1] | 2.13 | 543 |
| III-84 | 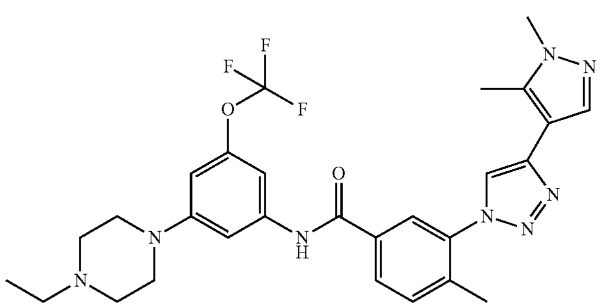 [SMILES: CCN1CCN(c2cc(NC(=O)c3ccc(C)c(-n4cc(-c5cnn(C)c5C)nn4)c3)cc(OC(F)(F)F)c2)CC1] | 2.22 | 569 |
| III-85 | 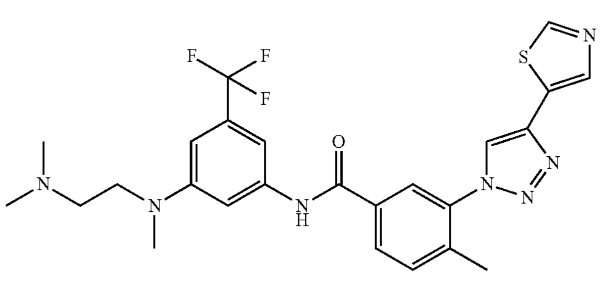 [SMILES: Cc1ccc(C(=O)Nc2cc(N(C)CCN(C)C)cc(C(F)(F)F)c2)cc1-n1cc(-c2cncs2)nn1] | 2.22 | 530 |

TABLE 3-continued

Examples III-1 to III-197

| # | Structure | $t_{Ret.}$ (HPLC) [min] | MS $(M + H)^+$ |
|---|---|---|---|
| III-86 | 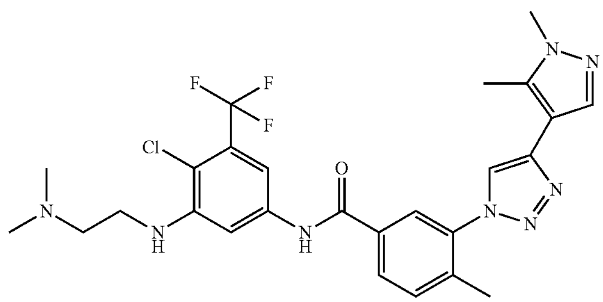 [SMILES: Cc1ccc(C(=O)Nc2cc(NCCN(C)C)c(Cl)c(C(F)(F)F)c2)cc1-n1cc(-c2cnn(C)c2C)nn1] | 1.63 | 561/563 |
| III-87 | 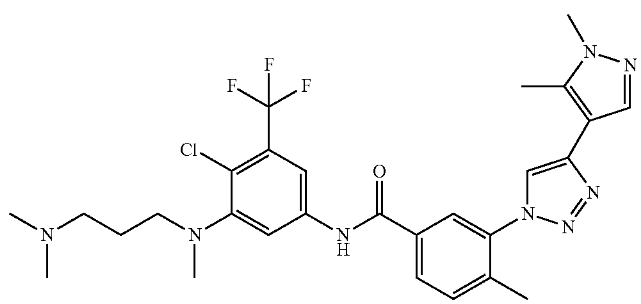 [SMILES: Cc1ccc(C(=O)Nc2cc(N(C)CCCN(C)C)c(Cl)c(C(F)(F)F)c2)cc1-n1cc(-c2cnn(C)c2C)nn1] | 1.69 | 589/591 |
| III-88 | 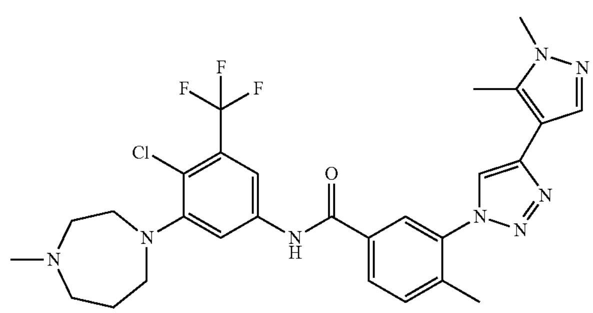 [SMILES: Cc1ccc(C(=O)Nc2cc(N3CCCN(C)CC3)c(Cl)c(C(F)(F)F)c2)cc1-n1cc(-c2cnn(C)c2C)nn1] | 1.69 | 587/589 |
| III-89 | 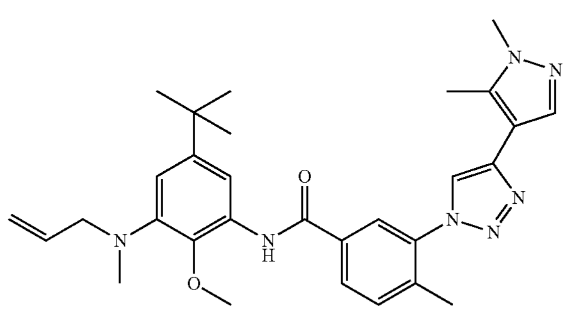 [SMILES: C=CCN(C)c1cc(C(C)(C)C)cc(NC(=O)c2ccc(C)c(-n3cc(-c4cnn(C)c4C)nn3)c2)c1OC] | 2.53 | 528 |

TABLE 3-continued

Examples III-1 to III-197

| # | Structure | $t_{Ret.}$ (HPLC) [min] | MS $(M + H)^+$ |
|---|---|---|---|
| III-90 | 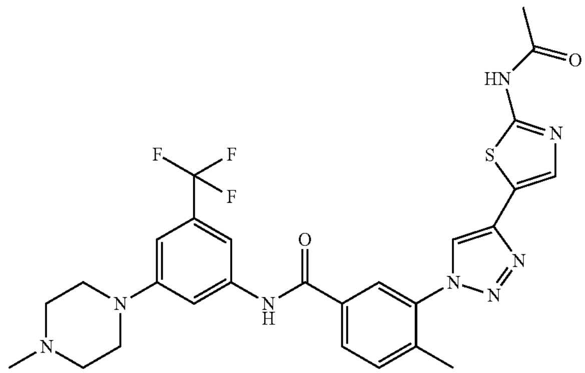 [SMILES: CC(=O)Nc1ncc(-c2cn(-c3cc(C(=O)Nc4cc(N5CCN(C)CC5)cc(C(F)(F)F)c4)ccc3C)nn2)s1] | 2.06 | 585 |
| III-91 | 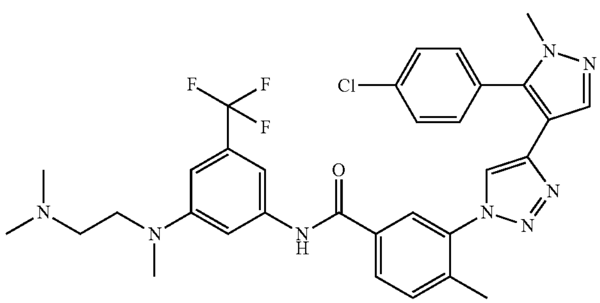 [SMILES: Cc1ccc(C(=O)Nc2cc(N(C)CCN(C)C)cc(C(F)(F)F)c2)cc1-n1cc(-c2cnn(C)c2-c2ccc(Cl)cc2)nn1] | 2.45 | 637 |
| III-92 | 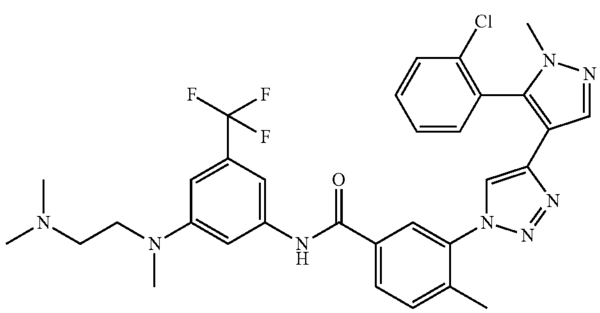 [SMILES: Cc1ccc(C(=O)Nc2cc(N(C)CCN(C)C)cc(C(F)(F)F)c2)cc1-n1cc(-c2cnn(C)c2-c2ccccc2Cl)nn1] | 2.42 | 637 |
| III-93 | 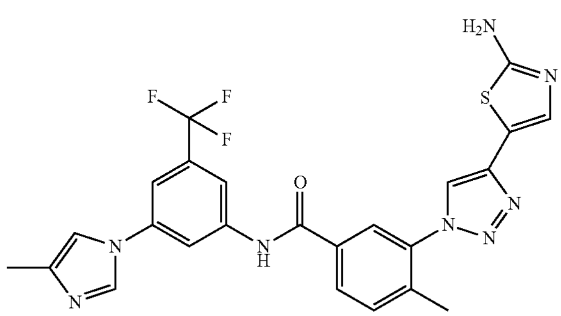 [SMILES: Cc1cn(-c2cc(NC(=O)c3ccc(C)c(-n4cc(-c5cnc(N)s5)nn4)c3)cc(C(F)(F)F)c2)cn1] | 1.99 | 525 |

TABLE 3-continued
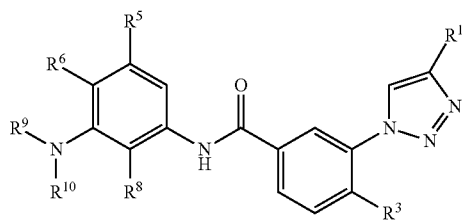
Examples III-1 to III-197
| # | Structure | t_Ret. (HPLC) [min] | MS (M + H)+ |
|---|---|---|---|
| III-94 | 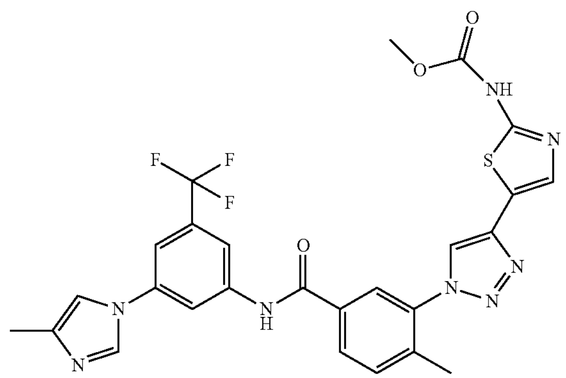 [SMILES: CCC(=O)Nc1ncc(-c2cn(-c3cc(C(=O)Nc4cc(-n5cnc(C)c5)cc(C(F)(F)F)c4)ccc3C)nn2)s1] | 2.10 | 583 |
| III-95 | 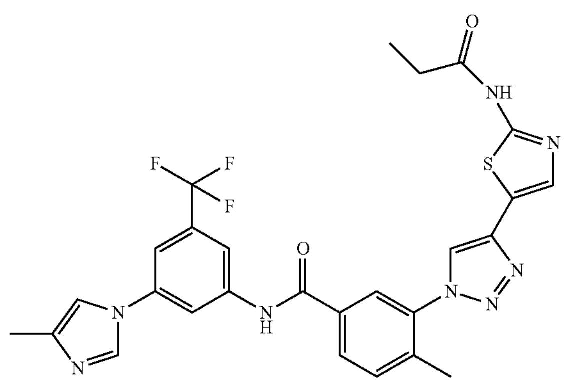 | 2.12 | 581 |
| III-96 | 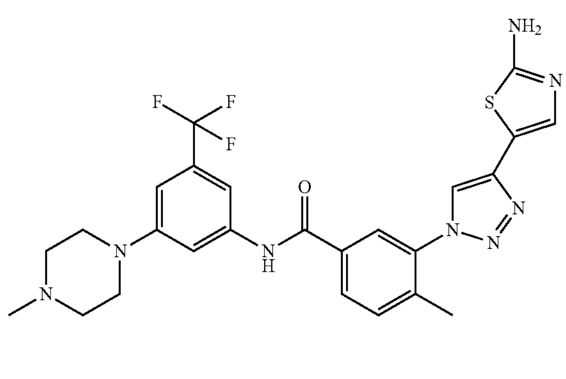 [SMILES: Cc1ccc(C(=O)Nc2cc(N3CCN(C)CC3)cc(C(F)(F)F)c2)cc1-n1cc(-c2cnc(N)s2)nn1] | 2.04 | 543 |

TABLE 3-continued
Examples III-1 to III-197
| # | Structure | $t_{Ret.}$ (HPLC) [min] | MS $(M + H)^+$ |
|---|---|---|---|
| III-97 | 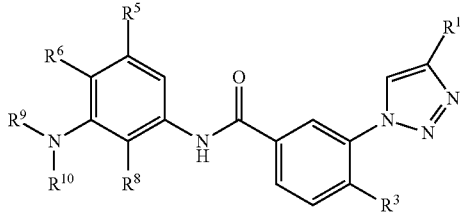 | 2.15 | 601 |
| III-98 | 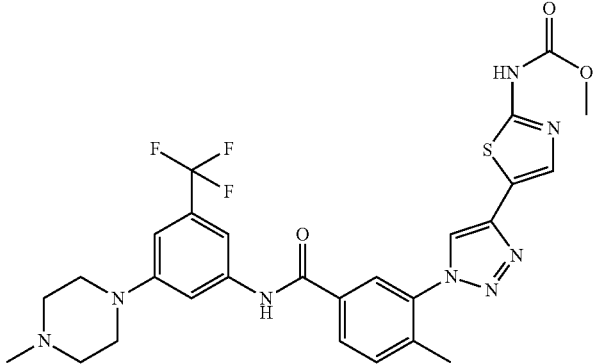 | 2.17 | 599 |
| III-99 | 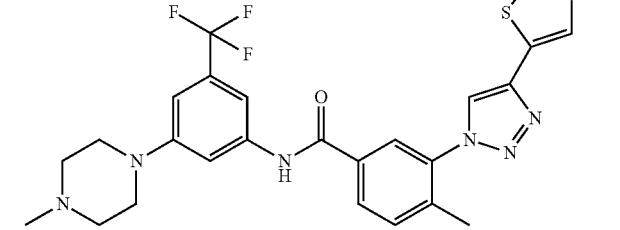 | 2.18 | 599 |

TABLE 3-continued
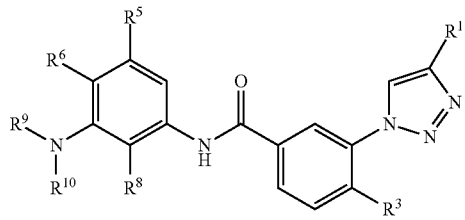
Examples III-1 to III-197
| # | Structure | $t_{Ret.}$ (HPLC) [min] | MS $(M + H)^+$ |
|---|---|---|---|
| III-100 | 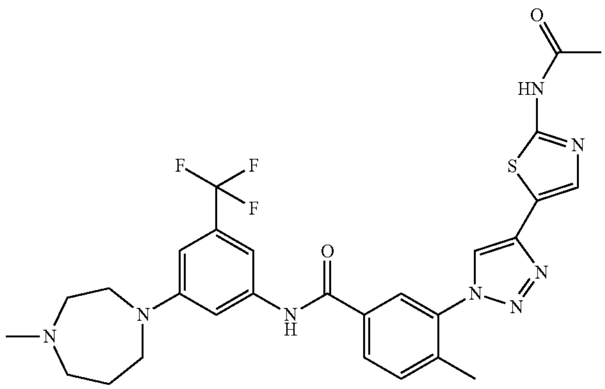 [SMILES: CC(=O)Nc1ncc(-c2cn(-c3cc(C(=O)Nc4cc(N5CCCN(C)CC5)cc(C(F)(F)F)c4)ccc3C)nn2)s1] | 2.14 | 599 |
| III-101 | 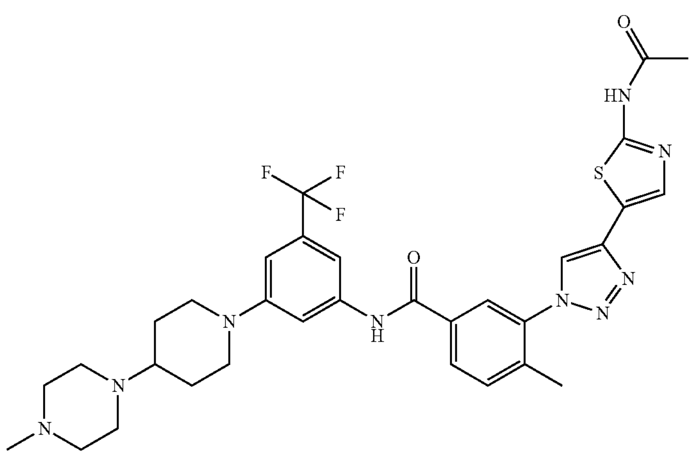 [SMILES: CC(=O)Nc1ncc(-c2cn(-c3cc(C(=O)Nc4cc(N5CCC(N6CCN(C)CC6)CC5)cc(C(F)(F)F)c4)ccc3C)nn2)s1] | 2.06 | 668 |
| III-102 | 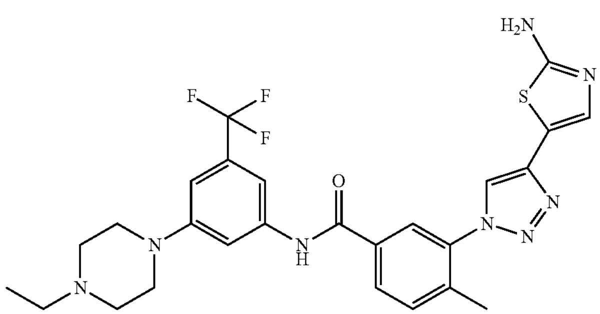 [SMILES: CCN1CCN(c2cc(NC(=O)c3ccc(C)c(-n4cc(-c5cnc(N)s5)nn4)c3)cc(C(F)(F)F)c2)CC1] | 2.12 | 557 |

US 8,889,665 B2
TABLE 3-continued
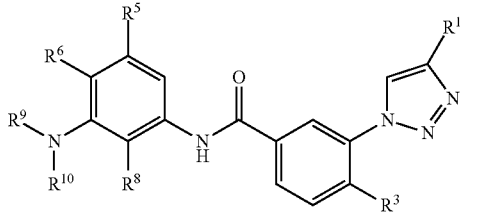
Examples III-1 to III-197
| # | Structure | t<sub>Ret.</sub> (HPLC) [min] | MS (M + H)+ |
|---|---|---|---|
| III-103 | 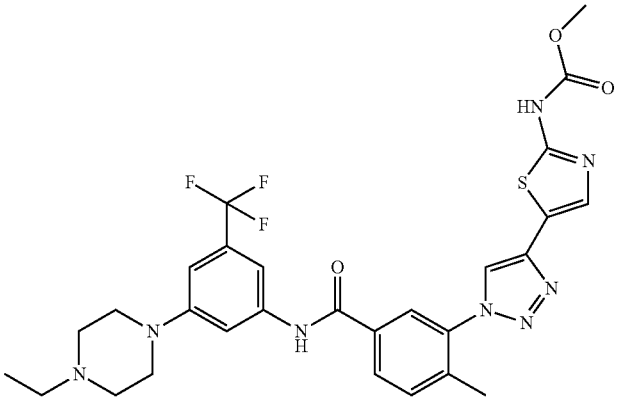 [SMILES: CCN1CCN(c2cc(NC(=O)c3ccc(C)c(-n4cc(-c5cnc(NC(=O)OC)s5)nn4)c3)cc(C(F)(F)F)c2)CC1] | 2.14 | 615 |
| III-104 | 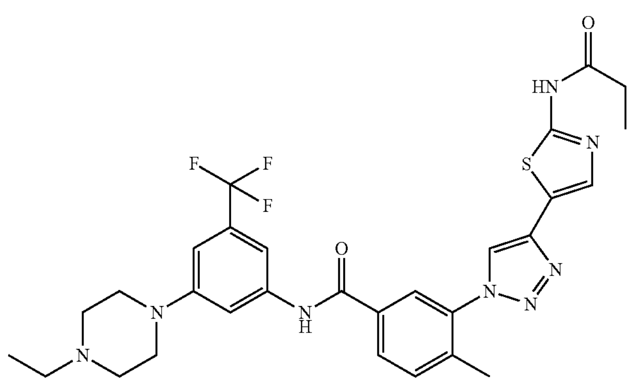 [SMILES: CCC(=O)Nc1ncc(-c2cn(-c3cc(C(=O)Nc4cc(N5CCN(CC)CC5)cc(C(F)(F)F)c4)ccc3C)nn2)s1] | 2.22 | 613 |
| III-105 | 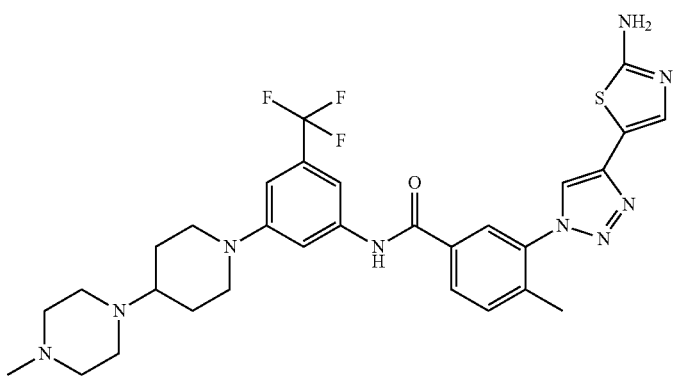 [SMILES: Cc1ccc(C(=O)Nc2cc(N3CCC(N4CCN(C)CC4)CC3)cc(C(F)(F)F)c2)cc1-n1cc(-c2cnc(N)s2)nn1] | 1.97 | 626 |

TABLE 3-continued
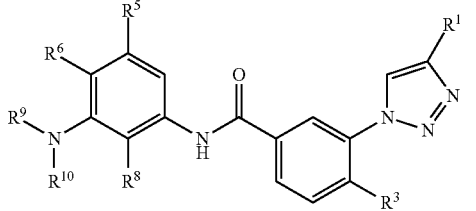
Examples III-1 to III-197
| # | Structure | t_Ret. (HPLC) [min] | MS (M + H)+ |
|---|---|---|---|
| III-106 | 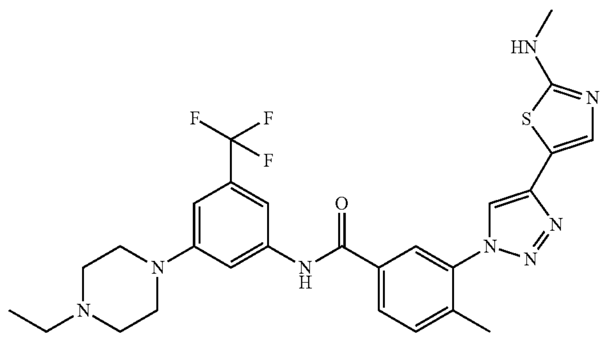 [SMILES: CCN1CCN(c2cc(NC(=O)c3ccc(C)c(-n4cc(-c5cnc(NC)s5)nn4)c3)cc(C(F)(F)F)c2)CC1] | 2.20 | 571 |
| III-107 | 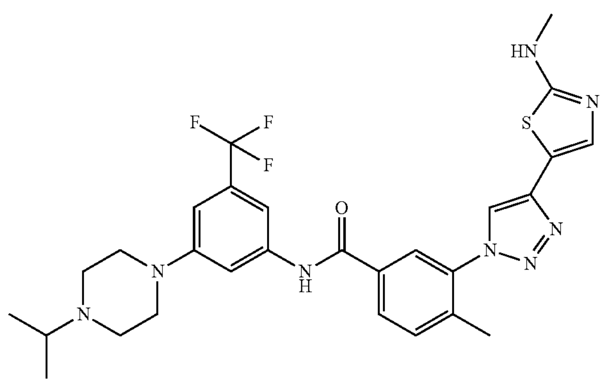 [SMILES: CNc1ncc(-c2cn(-c3cc(C(=O)Nc4cc(N5CCN(C(C)C)CC5)cc(C(F)(F)F)c4)ccc3C)nn2)s1] | 2.29 | 585 |
| III-108 | 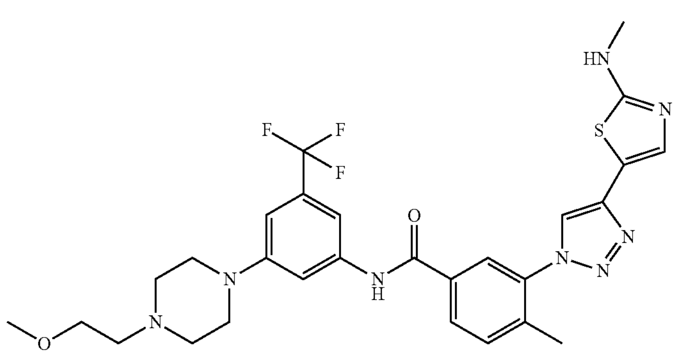 [SMILES: CNc1ncc(-c2cn(-c3cc(C(=O)Nc4cc(N5CCN(CCOC)CC5)cc(C(F)(F)F)c4)ccc3C)nn2)s1] | 2.09 | 601 |

TABLE 3-continued
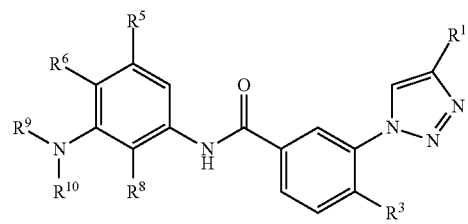
Examples III-1 to III-197
| # | Structure | $t_{Ret.}$ (HPLC) [min] | MS $(M + H)^+$ |
|---|---|---|---|
| III-109 | 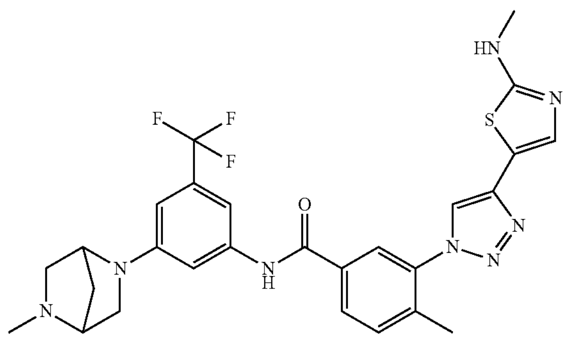 [SMILES: CNc1ncc(-c2cn(-c3cc(C(=O)Nc4cc(N5CC6CC5CN6C)cc(C(F)(F)F)c4)ccc3C)nn2)s1] | 2.07 | 569 |
| III-110 | 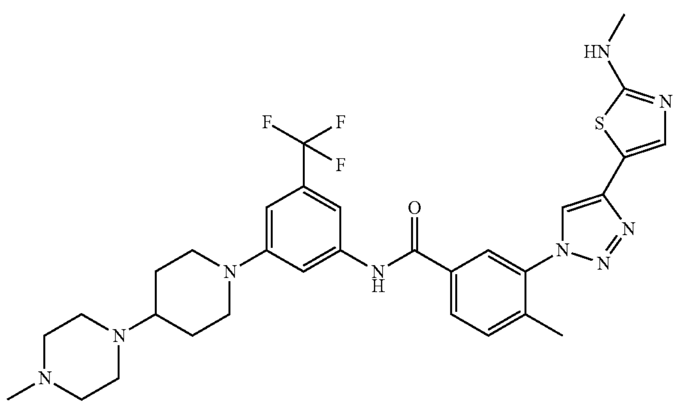 [SMILES: CNc1ncc(-c2cn(-c3cc(C(=O)Nc4cc(N5CCC(N6CCN(C)CC6)CC5)cc(C(F)(F)F)c4)ccc3C)nn2)s1] | 2.05 | 641 |
| III-111 | 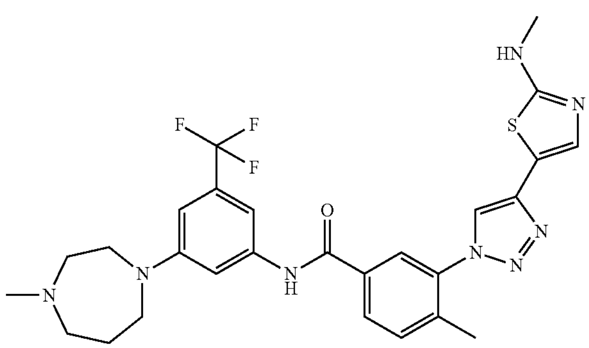 [SMILES: CNc1ncc(-c2cn(-c3cc(C(=O)Nc4cc(N5CCCN(C)CC5)cc(C(F)(F)F)c4)ccc3C)nn2)s1] | 2.13 | 571 |

TABLE 3-continued
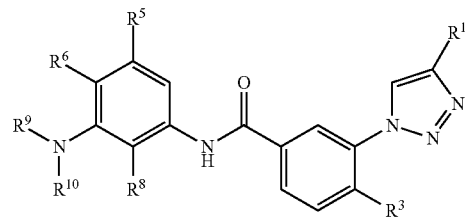
Examples III-1 to III-197
| # | Structure | t_Ret. (HPLC) [min] | MS (M + H)+ |
|---|---|---|---|
| III-112 | 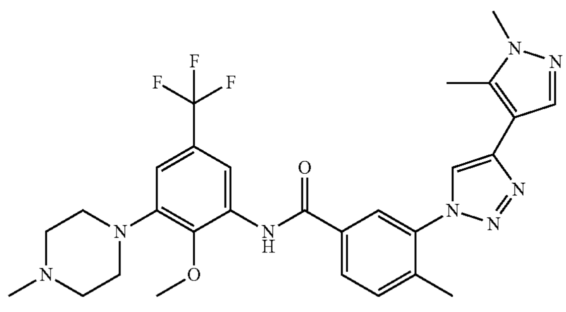 [SMILES: COc1c(NC(=O)c2ccc(C)c(-n3cc(-c4cnn(C)c4C)nn3)c2)cc(C(F)(F)F)cc1N1CCN(C)CC1] | 2.18 | 569 |
| III-113 | 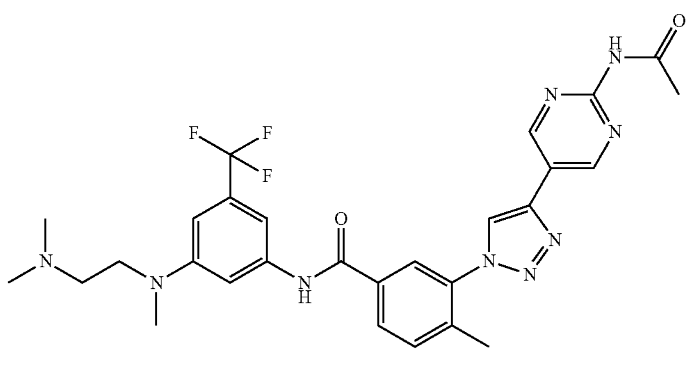 [SMILES: CC(=O)Nc1ncc(-c2cn(-c3cc(C(=O)Nc4cc(N(C)CCN(C)C)cc(C(F)(F)F)c4)ccc3C)nn2)cn1] | 2.06 | 582 |
| III-114 | 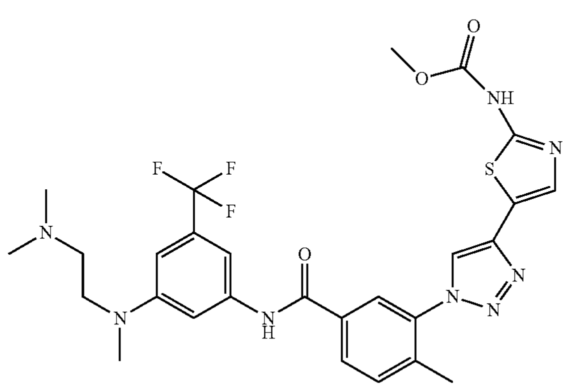 [SMILES: COC(=O)Nc1ncc(-c2cn(-c3cc(C(=O)Nc4cc(N(C)CCN(C)C)cc(C(F)(F)F)c4)ccc3C)nn2)s1] | 2.15 | 603 |

TABLE 3-continued

Examples III-1 to III-197

| # | Structure | t_Ret. (HPLC) [min] | MS (M + H)+ |
|---|---|---|---|
| III-115 | 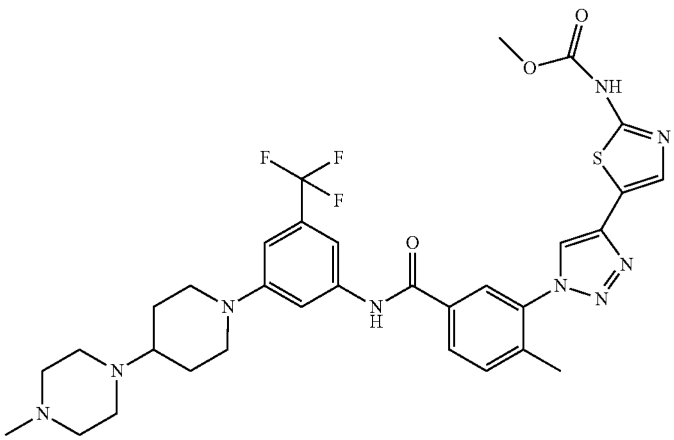 [SMILES: COC(=O)Nc1ncc(-c2cn(-c3cc(C(=O)Nc4cc(N5CCC(N6CCN(C)CC6)CC5)cc(C(F)(F)F)c4)ccc3C)nn2)s1] | 2.07 | 684 |
| III-116 | 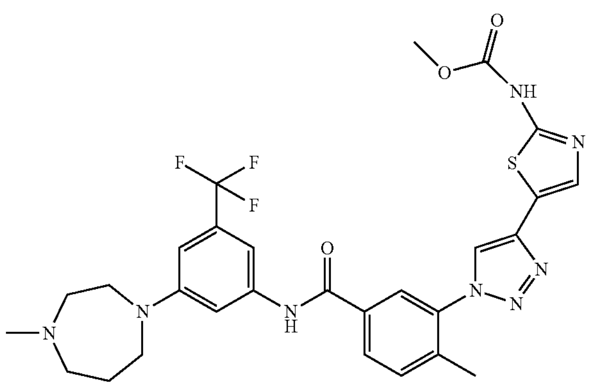 [SMILES: COC(=O)Nc1ncc(-c2cn(-c3cc(C(=O)Nc4cc(N5CCCN(C)CC5)cc(C(F)(F)F)c4)ccc3C)nn2)s1] | 2.15 | 615 |
| III-117 | 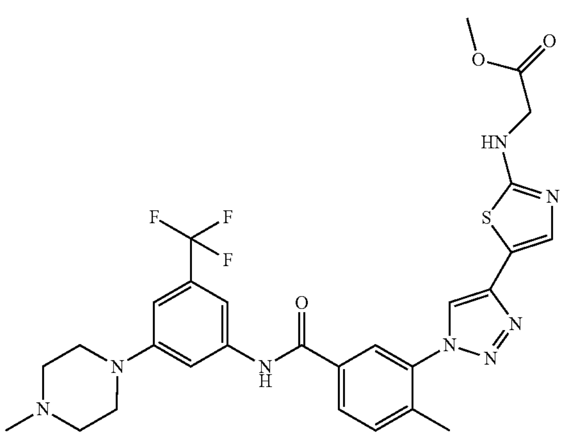 [SMILES: COC(=O)CNc1ncc(-c2cn(-c3cc(C(=O)Nc4cc(N5CCN(C)CC5)cc(C(F)(F)F)c4)ccc3C)nn2)s1] | 2.12 | 615 |

TABLE 3-continued
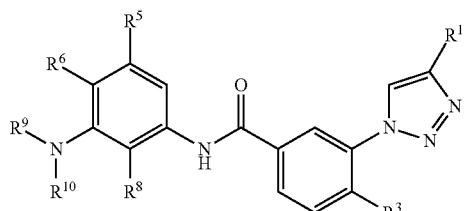
Examples III-1 to III-197
| # | Structure | t$_{Ret.}$ (HPLC) [min] | MS (M + H)$^+$ |
|---|---|---|---|
| III-118 | 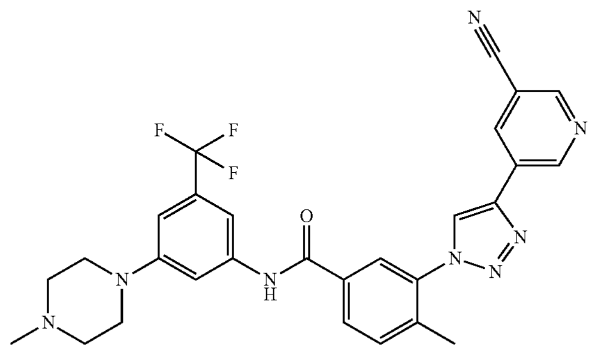 [SMILES: Cc1ccc(C(=O)Nc2cc(N3CCN(C)CC3)cc(C(F)(F)F)c2)cc1-n1cc(-c2cncc(C#N)c2)nn1] | 2.21 | 547 |
| III-119 | 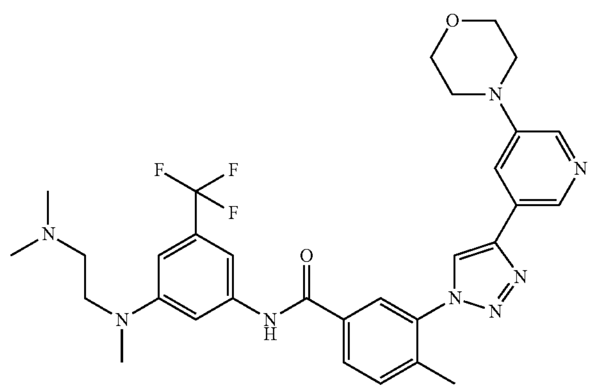 [SMILES: Cc1ccc(C(=O)Nc2cc(N(C)CCN(C)C)cc(C(F)(F)F)c2)cc1-n1cc(-c2cncc(N3CCOCC3)c2)nn1] | 2.20 | 609 |
| III-120 | 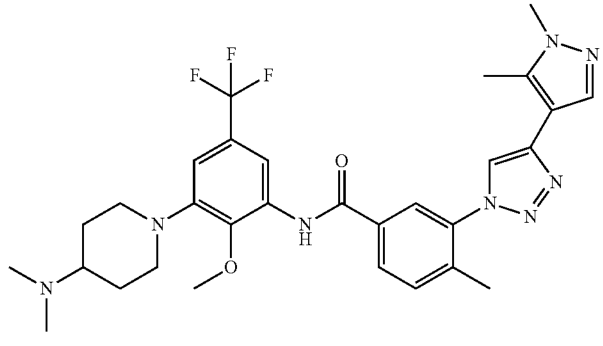 [SMILES: COc1c(NC(=O)c2ccc(C)c(-n3cc(-c4cnn(C)c4C)nn3)c2)cc(C(F)(F)F)cc1N1CCC(N(C)C)CC1] | 2.26 | 597 |

US 8,889,665 B2
TABLE 3-continued
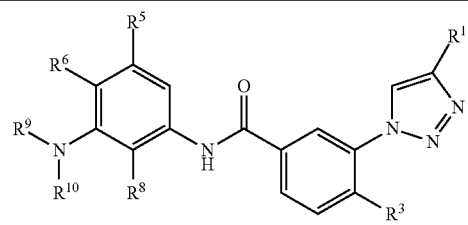
Examples III-1 to III-197
| # | Structure | $t_{Ret.}$ (HPLC) [min] | MS $(M + H)^+$ |
|---|---|---|---|
| III-121 | 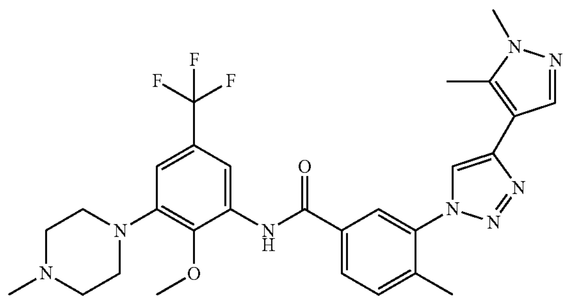 [SMILES: COc1c(NC(=O)c2ccc(C)c(-n3cc(-c4cnn(C)c4C)nn3)c2)cc(C(F)(F)F)cc1N1CCN(C)CC1] | 2.26 | 583 |
| III-122 | 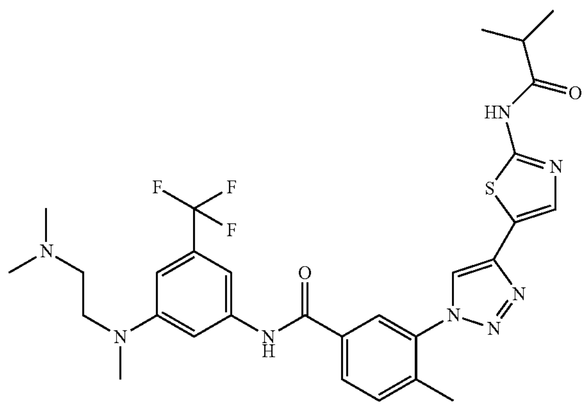 [SMILES: Cc1ccc(C(=O)Nc2cc(N(C)CCN(C)C)cc(C(F)(F)F)c2)cc1-n1cc(-c2cnc(NC(=O)C(C)C)s2)nn1] | 2.25 | 615 |
| III-123 | 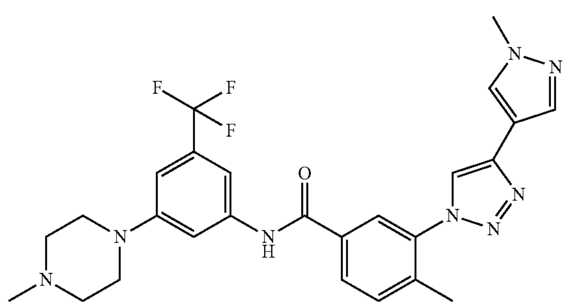 [SMILES: Cc1ccc(C(=O)Nc2cc(N3CCN(C)CC3)cc(C(F)(F)F)c2)cc1-n1cc(-c2cnn(C)c2)nn1] | 2.04 | 525 |
| III-124 | 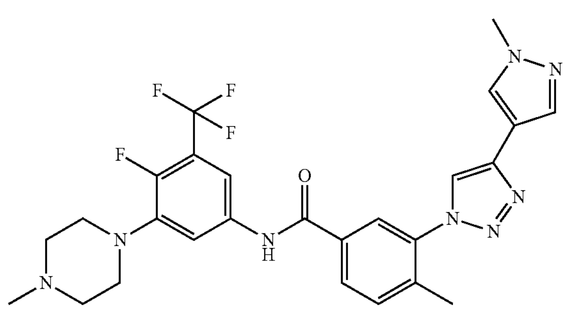 [SMILES: Cc1ccc(C(=O)Nc2cc(N3CCN(C)CC3)c(F)c(C(F)(F)F)c2)cc1-n1cc(-c2cnn(C)c2)nn1] | 2.10 | 543 |

TABLE 3-continued

Examples III-1 to III-197

| # | Structure | t<sub>Ret.</sub> (HPLC) [min] | MS (M + H)⁺ |
|---|---|---|---|
| III-125 | 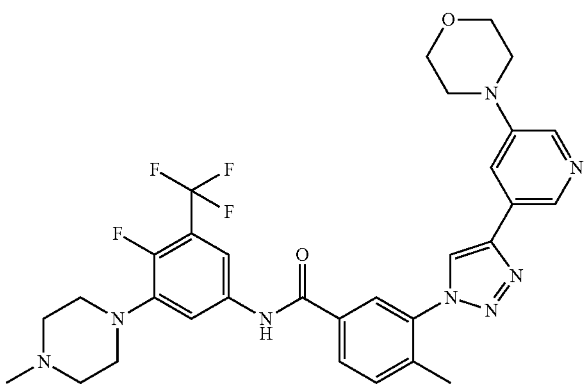 [SMILES: Cc1ccc(C(=O)Nc2cc(N3CCN(C)CC3)c(F)c(C(F)(F)F)c2)cc1-n1cc(-c2cncc(N3CCOCC3)c2)nn1] | 2.18 | 625 |
| III-126 | 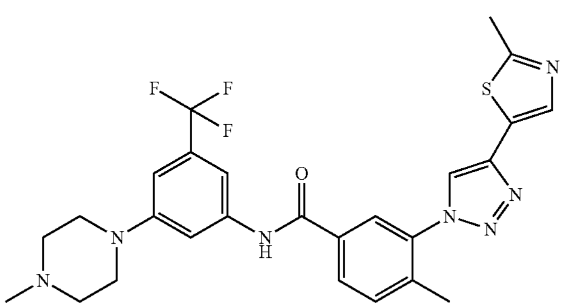 [SMILES: Cc1ncc(-c2cn(-c3cc(C(=O)Nc4cc(N5CCN(C)CC5)cc(C(F)(F)F)c4)ccc3C)nn2)s1] | 2.16 | 542 |
| III-127 | 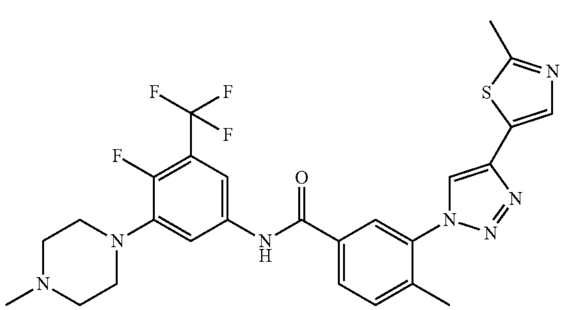 [SMILES: Cc1ncc(-c2cn(-c3cc(C(=O)Nc4cc(N5CCN(C)CC5)c(F)c(C(F)(F)F)c4)ccc3C)nn2)s1] | 2.23 | 560 |

TABLE 3-continued
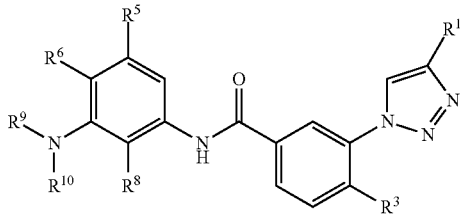
Examples III-1 to III-197
| # | Structure | t_{Ret.} (HPLC) [min] | MS (M + H)+ |
|---|---|---|---|
| III-128 | 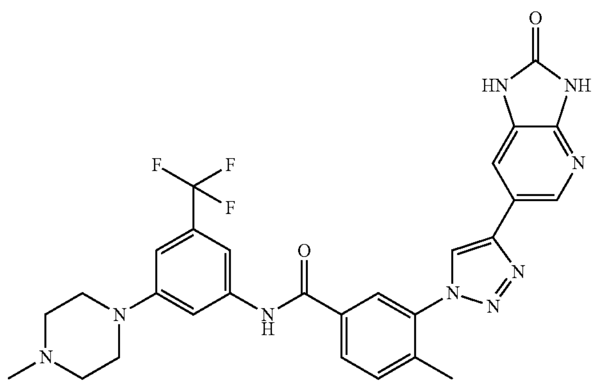 [SMILES: Cc1ccc(C(=O)Nc2cc(N3CCN(C)CC3)cc(C(F)(F)F)c2)cc1-n1cc(-c2cnc3[nH]c(=O)[nH]c3c2)nn1] | 1.65 | 578 |
| III-129 | 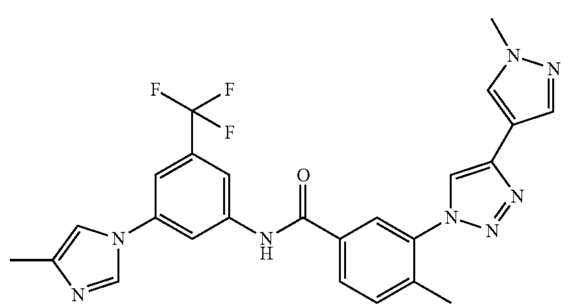 [SMILES: Cc1cn(-c2cc(NC(=O)c3ccc(C)c(-n4cc(-c5cnn(C)c5)nn4)c3)cc(C(F)(F)F)c2)cn1] | 1.98 | 507 |
| III-130 | 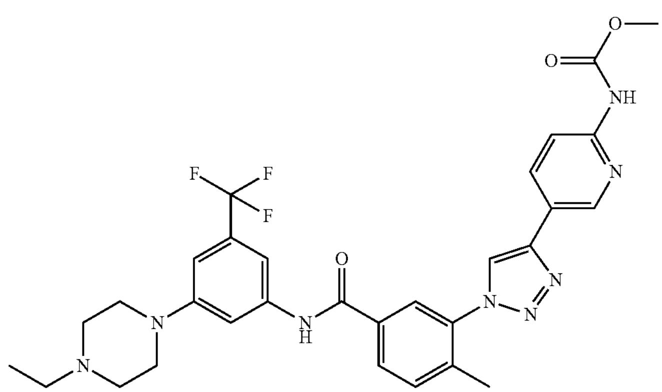 [SMILES: CCN1CCN(c2cc(NC(=O)c3ccc(C)c(-n4cc(-c5ccc(NC(=O)OC)nc5)nn4)c3)cc(C(F)(F)F)c2)CC1] | 2.28 | 609 |

TABLE 3-continued
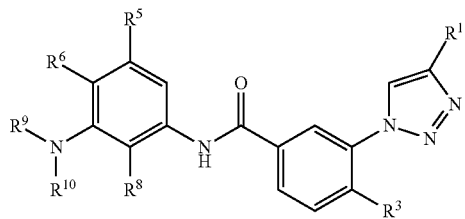
Examples III-1 to III-197
| # | Structure | $t_{Ret.}$ (HPLC) [min] | MS $(M + H)^+$ |
|---|---|---|---|
| III-131 | 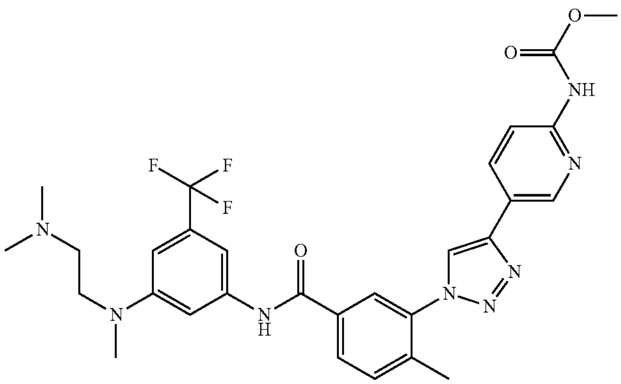 | 2.30 | 597 |
| III-132 | 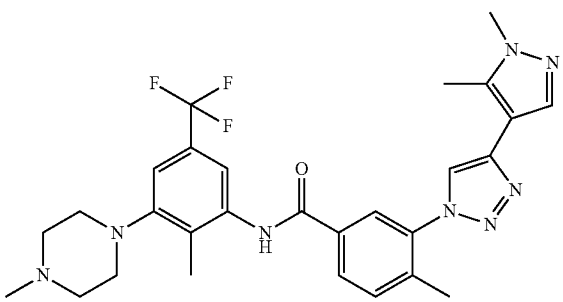 [SMILES: Cc1ccc(C(=O)Nc2cc(C(F)(F)F)cc(N3CCN(C)CC3)c2C)cc1-n1cc(-c2cnn(C)c2C)nn1] | 1.99 | 553 |
| III-133 | 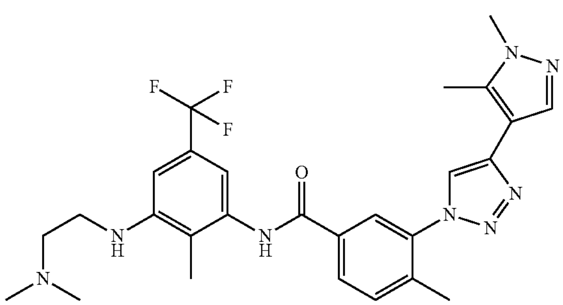 [SMILES: Cc1ccc(C(=O)Nc2cc(C(F)(F)F)cc(NCCN(C)C)c2C)cc1-n1cc(-c2cnn(C)c2C)nn1] | 2.08 | 541 |
| III-134 | 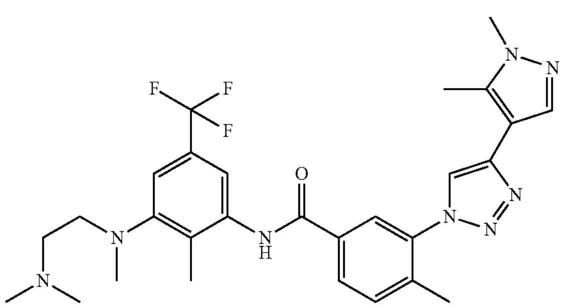 [SMILES: Cc1ccc(C(=O)Nc2cc(C(F)(F)F)cc(N(C)CCN(C)C)c2C)cc1-n1cc(-c2cnn(C)c2C)nn1] | 2.15 | 555 |

TABLE 3-continued
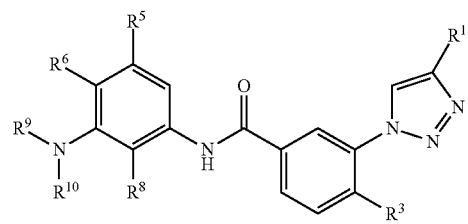
Examples III-1 to III-197
| # | Structure | $t_{Ret.}$ (HPLC) [min] | MS $(M + H)^+$ |
|---|---|---|---|
| III-135 | 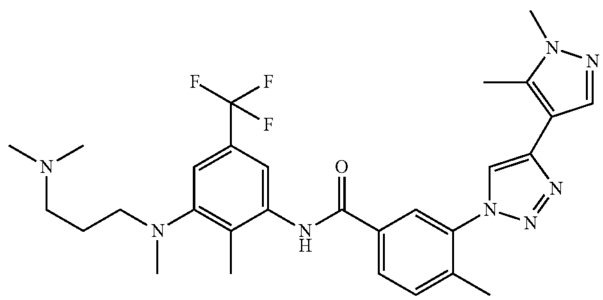 [SMILES: Cc1ccc(C(=O)Nc2cc(C(F)(F)F)cc(N(C)CCCN(C)C)c2C)cc1-n1cc(-c2cnn(C)c2C)nn1] | 2.19 | 569 |
| III-136 | 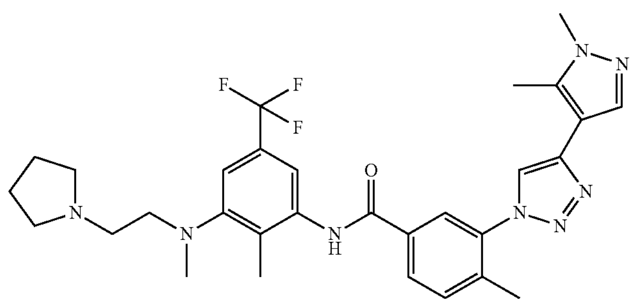 [SMILES: Cc1ccc(C(=O)Nc2cc(C(F)(F)F)cc(N(C)CCN3CCCC3)c2C)cc1-n1cc(-c2cnn(C)c2C)nn1] | 2.26 | 581 |
| III-137 | 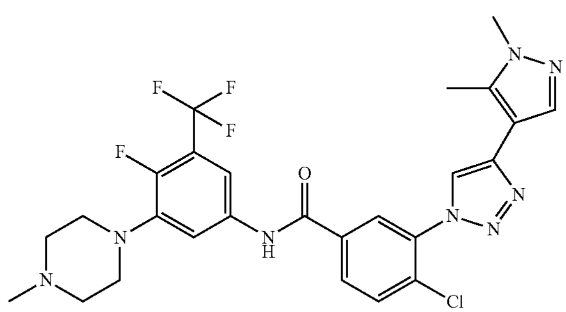 [SMILES: Cc1c(-c2cn(-c3cc(C(=O)Nc4cc(N5CCN(C)CC5)c(F)c(C(F)(F)F)c4)ccc3Cl)nn2)cnn1C] | 2.19 | 577 |
| III-138 | 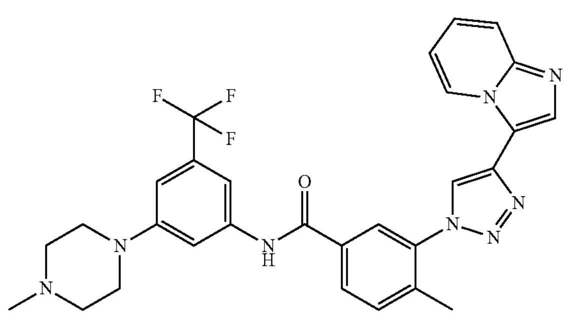 [SMILES: Cc1ccc(C(=O)Nc2cc(N3CCN(C)CC3)cc(C(F)(F)F)c2)cc1-n1cc(-c2cnc3ccccn23)nn1] | 2.17 | 561 |

TABLE 3-continued
Examples III-1 to III-197
| # | Structure | t_Ret. (HPLC) [min] | MS (M + H)+ |
|---|---|---|---|
| III-139 | 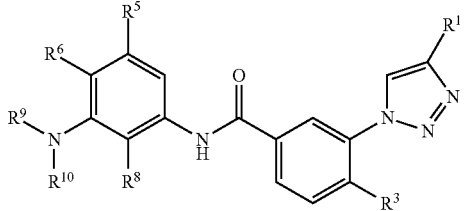 | 2.06 | 562 |
| III-140 | 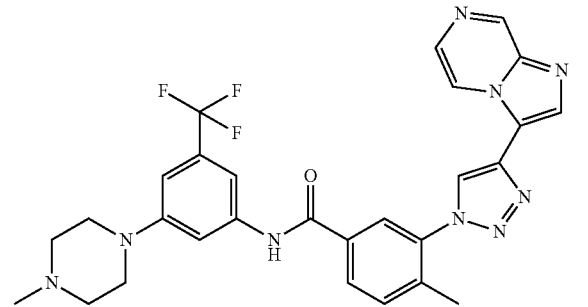 [SMILES: Cc1ccc(C(=O)Nc2cc(N3CCN(C)CC3)cc(C(F)(F)F)c2)cc1-n1cc(-c2cnc3cnccn23)nn1] | 2.22 | 563 |
| III-141 | 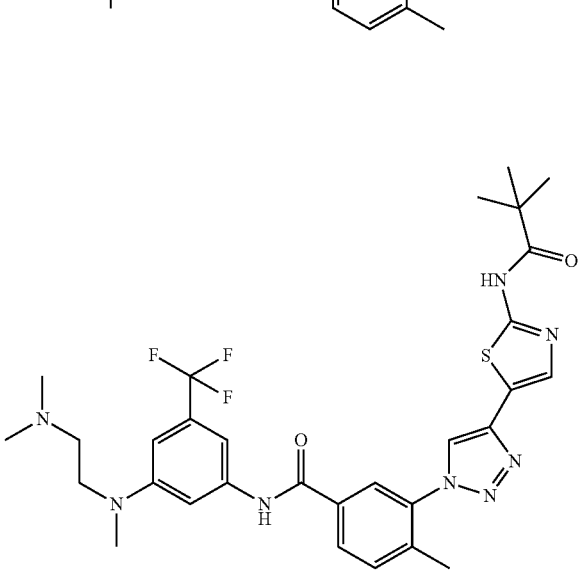 | 2.40 | 629 |

US 8,889,665 B2
253                                                                          254
TABLE 3-continued
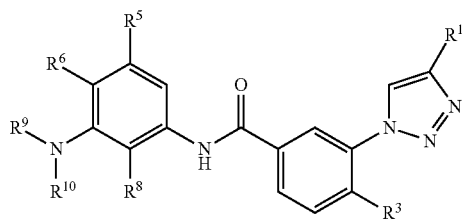
Examples III-1 to III-197
| # | Structure | t<sub>Ret.</sub> (HPLC) [min] | MS (M + H)<sup>+</sup> |
|---|---|---|---|
| III-142 | 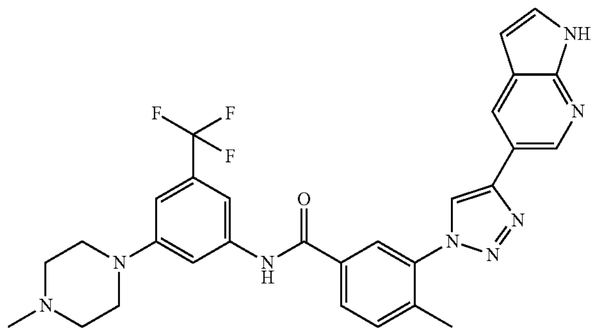 [SMILES: Cc1ccc(C(=O)Nc2cc(N3CCN(C)CC3)cc(C(F)(F)F)c2)cc1-n1cc(-c2cnc3[nH]ccc3c2)nn1] | 2.14 | 561 |
| III-143 | 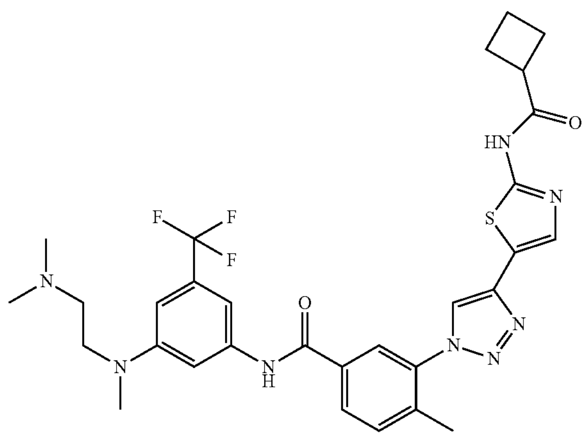 [SMILES: Cc1ccc(C(=O)Nc2cc(N(C)CCN(C)C)cc(C(F)(F)F)c2)cc1-n1cc(-c2cnc(NC(=O)C3CCC3)s2)nn1] | 2.29 | 627 |
| III-144 | 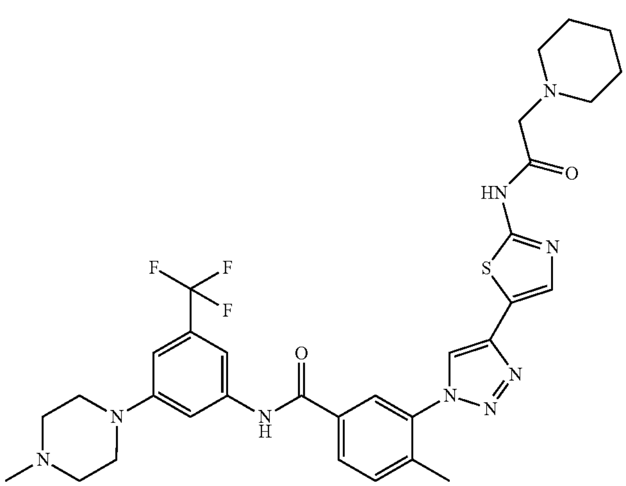 [SMILES: Cc1ccc(C(=O)Nc2cc(N3CCN(C)CC3)cc(C(F)(F)F)c2)cc1-n1cc(-c2cnc(NC(=O)CN3CCCCC3)s2)nn1] | 2.30 | 668 |

TABLE 3-continued
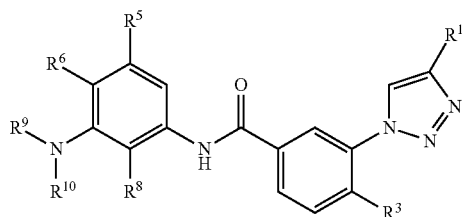
Examples III-1 to III-197
| # | Structure | t_Ret. (HPLC) [min] | MS (M + H)+ |
|---|---|---|---|
| III-145 | 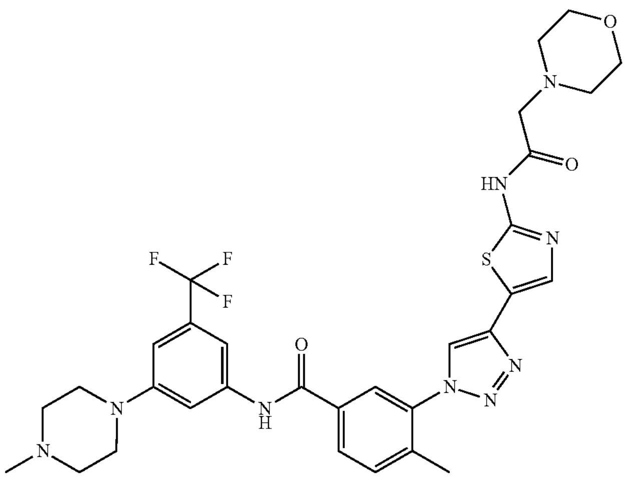 [SMILES: Cc1ccc(C(=O)Nc2cc(N3CCN(C)CC3)cc(C(F)(F)F)c2)cc1-n1cc(-c2cnc(NC(=O)CN3CCOCC3)s2)nn1] | 1.97 | 670 |
| III-146 | 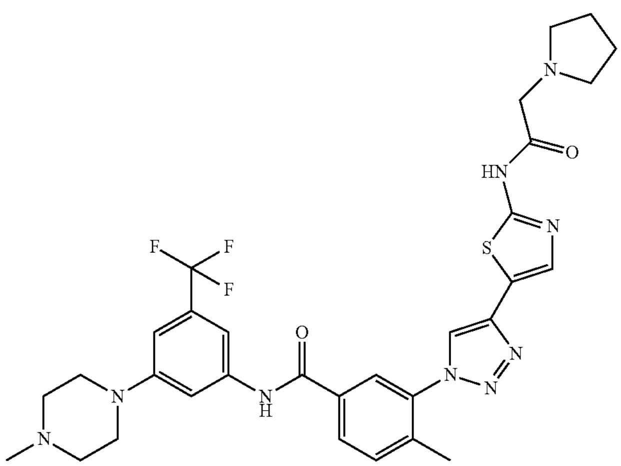 [SMILES: Cc1ccc(C(=O)Nc2cc(N3CCN(C)CC3)cc(C(F)(F)F)c2)cc1-n1cc(-c2cnc(NC(=O)CN3CCCC3)s2)nn1] | 2.11 | 654 |
| III-147 | 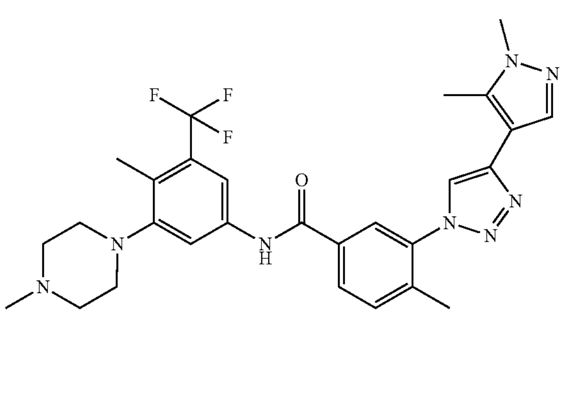 [SMILES: Cc1ccc(C(=O)Nc2cc(N3CCN(C)CC3)c(C)c(C(F)(F)F)c2)cc1-n1cc(-c2cnn(C)c2C)nn1] | 2.23 | 553 |

TABLE 3-continued

Examples III-1 to III-197

| # | Structure | t_Ret. (HPLC) [min] | MS (M + H)+ |
|---|---|---|---|
| III-148 | 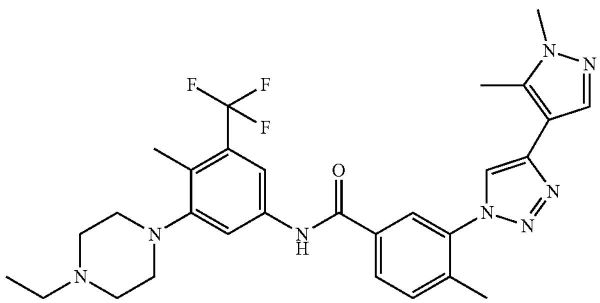 [SMILES: CCN1CCN(c2cc(NC(=O)c3ccc(C)c(-n4cc(-c5cnn(C)c5C)nn4)c3)cc(C(F)(F)F)c2C)CC1] | 2.31 | 567 |
| III-149 | 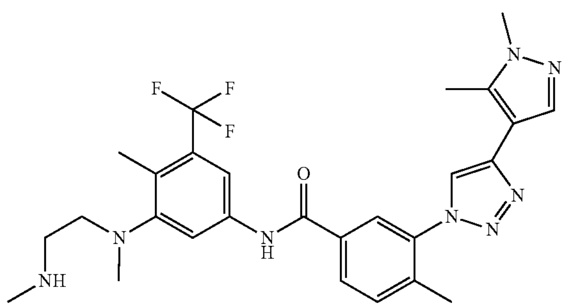 [SMILES: CNCCN(C)c1cc(NC(=O)c2ccc(C)c(-n3cc(-c4cnn(C)c4C)nn3)c2)cc(C(F)(F)F)c1C] | 2.07 | 541 |
| III-150 | 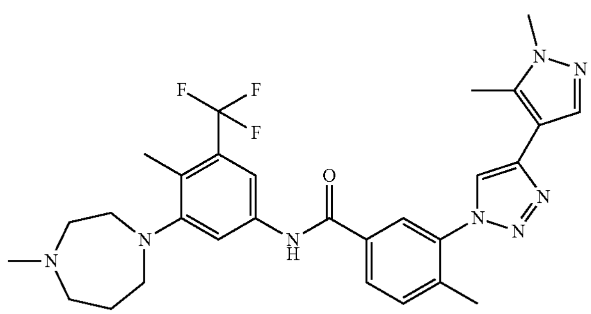 [SMILES: Cc1ccc(C(=O)Nc2cc(N3CCCN(C)CC3)c(C)c(C(F)(F)F)c2)cc1-n1cc(-c2cnn(C)c2C)nn1] | 2.24 | 567 |
| III-151 | 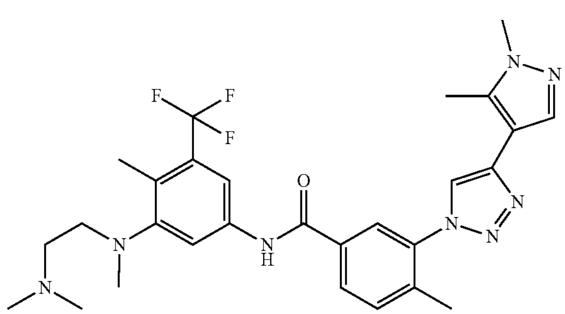 [SMILES: Cc1ccc(C(=O)Nc2cc(N(C)CCN(C)C)c(C)c(C(F)(F)F)c2)cc1-n1cc(-c2cnn(C)c2C)nn1] | 2.24 | 555 |

TABLE 3-continued

Examples III-1 to III-197

| # | Structure | $t_{Ret.}$ (HPLC) [min] | MS $(M + H)^+$ |
|---|---|---|---|
| III-152 | 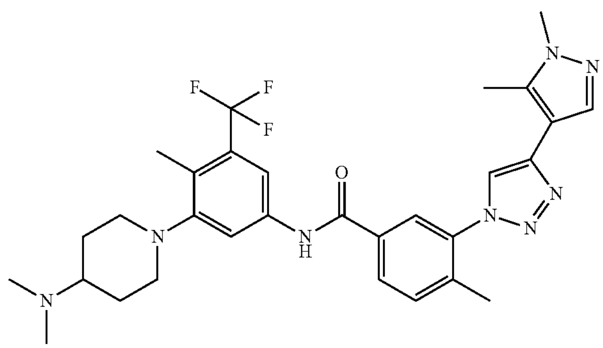 [SMILES: Cc1ccc(C(=O)Nc2cc(N3CCC(N(C)C)CC3)c(C)c(C(F)(F)F)c2)cc1-n1cc(-c2cnn(C)c2C)nn1] | 2.24 | 581 |
| III-153 | 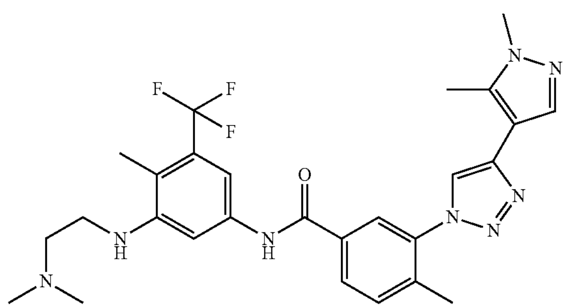 | 2.16 | 541 |
| III-154 | 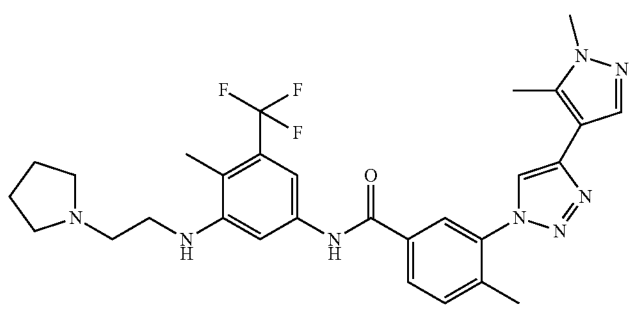 [SMILES: Cc1ccc(C(=O)Nc2cc(NCCN3CCCC3)c(C)c(C(F)(F)F)c2)cc1-n1cc(-c2cnn(C)c2C)nn1] | 2.25 | 567 |
| III-155 | 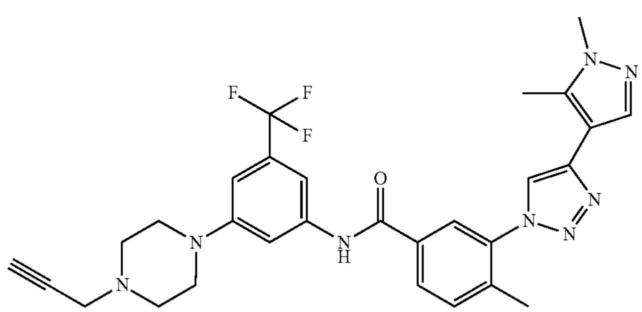 [SMILES: C#CCN1CCN(c2cc(NC(=O)c3ccc(C)c(-n4cc(-c5cnn(C)c5C)nn4)c3)cc(C(F)(F)F)c2)CC1] | 2.18 | 563 |

TABLE 3-continued
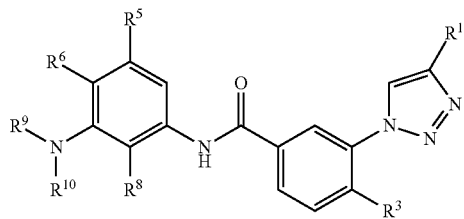
Examples III-1 to III-197
| # | Structure | t_Ret. (HPLC) [min] | MS (M + H)+ |
|---|---|---|---|
| III-156 | 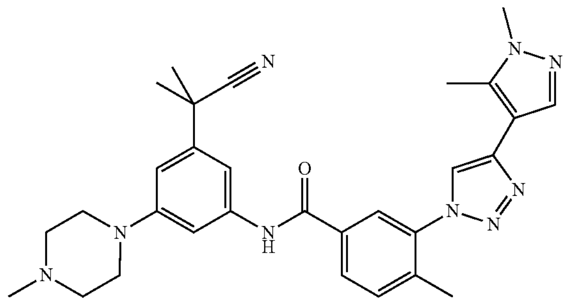 [SMILES: Cc1ccc(C(=O)Nc2cc(N3CCN(C)CC3)cc(C(C)(C)C#N)c2)cc1-n1cc(-c2cnn(C)c2C)nn1] | 1.93 | 538 |
| III-157 | 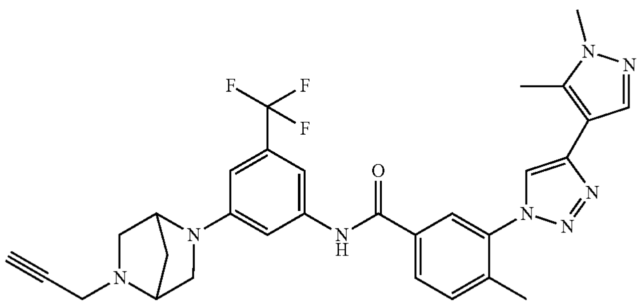 [SMILES: C#CCN1CC2CC1CN2c1cc(NC(=O)c2ccc(C)c(-n3cc(-c4cnn(C)c4C)nn3)c2)cc(C(F)(F)F)c1] | 2.15 | 575 |
| III-158 | 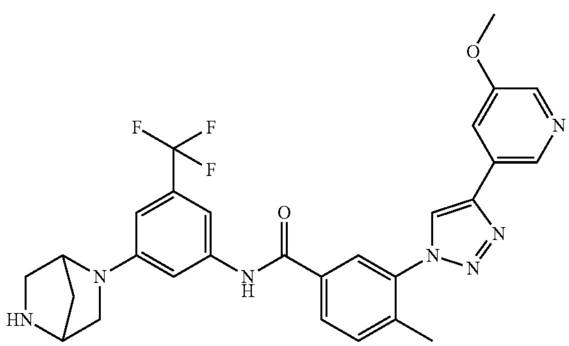 [SMILES: COc1cncc(-c2cn(-c3cc(C(=O)Nc4cc(N5CC6CC5CN6)cc(C(F)(F)F)c4)ccc3C)nn2)c1] | 2.07 | 550 |
| III-159 | 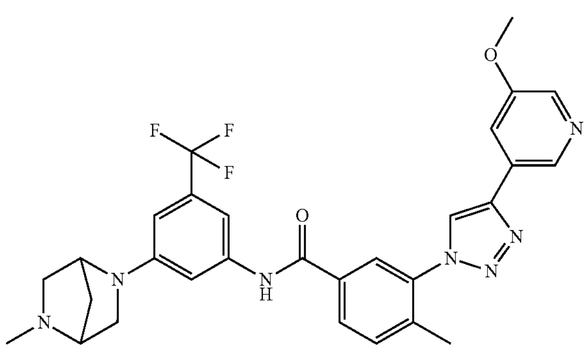 [SMILES: COc1cncc(-c2cn(-c3cc(C(=O)Nc4cc(N5CC6CC5CN6C)cc(C(F)(F)F)c4)ccc3C)nn2)c1] | 2.12 | 564 |

TABLE 3-continued
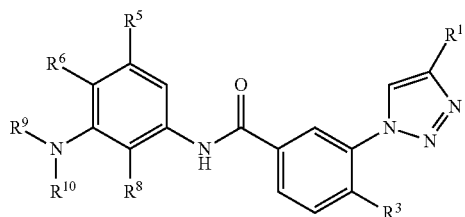
Examples III-1 to III-197
| # | Structure | t$_{Ret.}$ (HPLC) [min] | MS (M + H)$^+$ |
|---|---|---|---|
| III-160 | 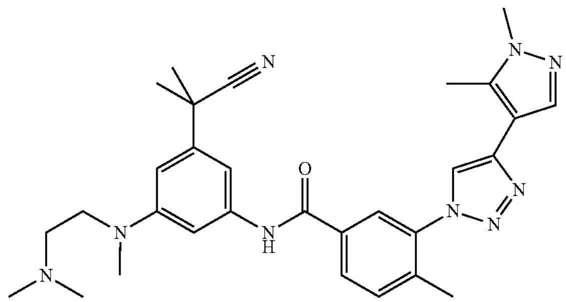 | 2.01 | 540 |
| III-161 | 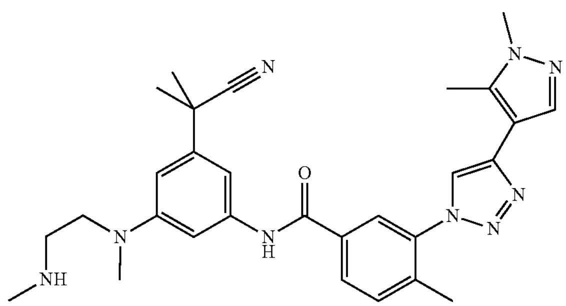 [SMILES: CNCCN(C)c1cc(NC(=O)c2ccc(C)c(-n3cc(-c4cnn(C)c4C)nn3)c2)cc(C(C)(C)C#N)c1] | 1.89 | 526 |
| III-162 | 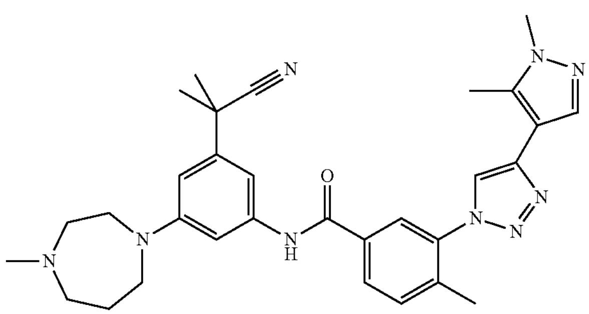 [SMILES: Cc1ccc(C(=O)Nc2cc(N3CCCN(C)CC3)cc(C(C)(C)C#N)c2)cc1-n1cc(-c2cnn(C)c2C)nn1] | 1.98 | 552 |
| III-163 | 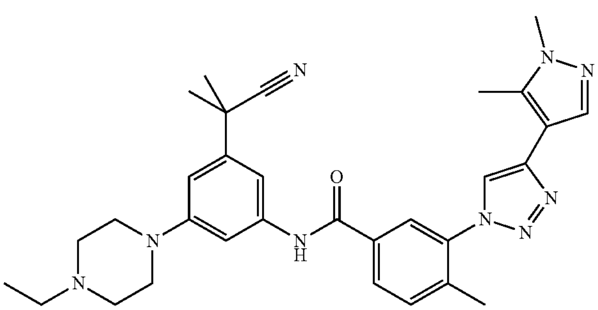 [SMILES: CCN1CCN(c2cc(NC(=O)c3ccc(C)c(-n4cc(-c5cnn(C)c5C)nn4)c3)cc(C(C)(C)C#N)c2)CC1] | 2.01 | 552 |

TABLE 3-continued
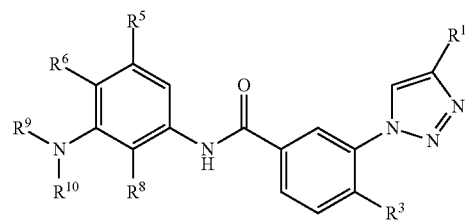
Examples III-1 to III-197
| # | Structure | $t_{Ret.}$ (HPLC) [min] | MS $(M + H)^+$ |
|---|---|---|---|
| III-164 | 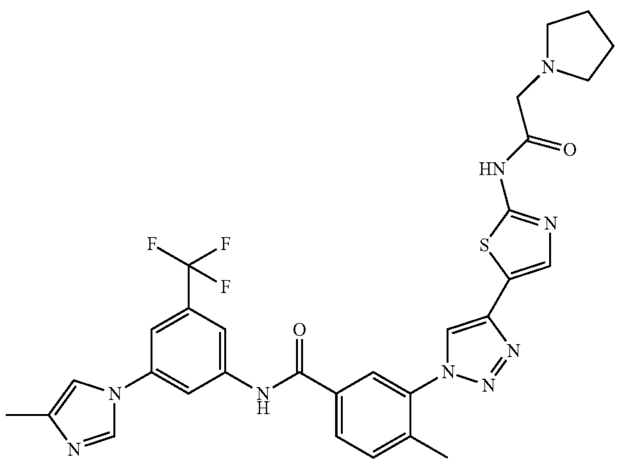 [SMILES: Cc1cn(-c2cc(NC(=O)c3ccc(C)c(-n4cc(-c5cnc(NC(=O)CN6CCCC6)s5)nn4)c3)cc(C(F)(F)F)c2)cn1] | 2.12 | 636 |
| III-165 | 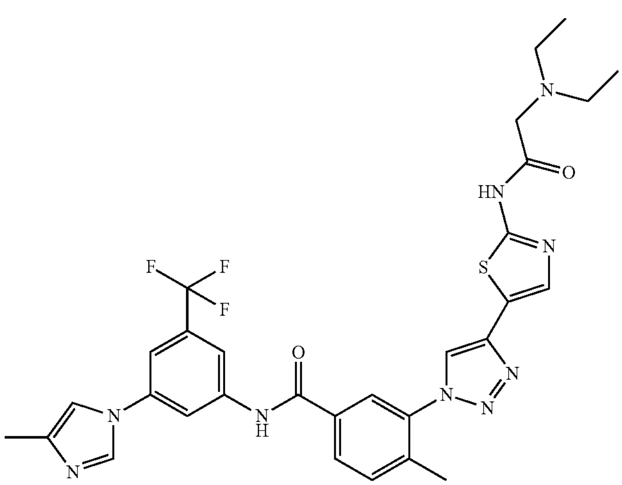 [SMILES: CCN(CC)CC(=O)Nc1ncc(-c2cn(-c3cc(C(=O)Nc4cc(-n5cnc(C)c5)cc(C(F)(F)F)c4)ccc3C)nn2)s1] | 2.26 | 638 |

TABLE 3-continued
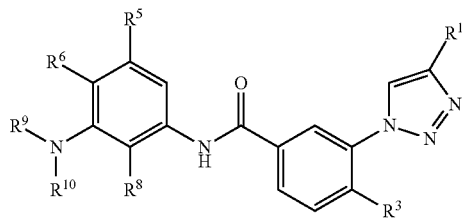
Examples III-1 to III-197
| # | Structure | t_Ret. (HPLC) [min] | MS (M + H)+ |
|---|---|---|---|
| III-166 | 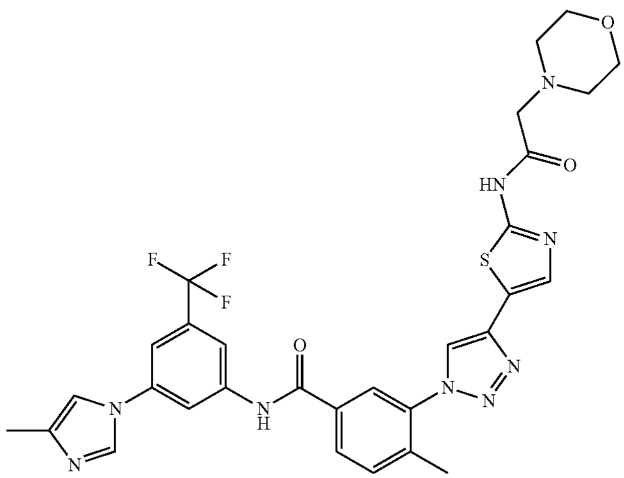 [SMILES: Cc1cn(-c2cc(NC(=O)c3ccc(C)c(-n4cc(-c5cnc(NC(=O)CN6CCOCC6)s5)nn4)c3)cc(C(F)(F)F)c2)cn1] | 2.05 | 652 |
| III-167 | 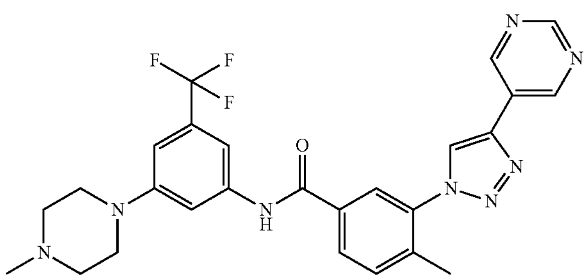 [SMILES: Cc1ccc(C(=O)Nc2cc(N3CCN(C)CC3)cc(C(F)(F)F)c2)cc1-n1cc(-c2cncnc2)nn1] | 2.04 | 523 |
| III-168 | 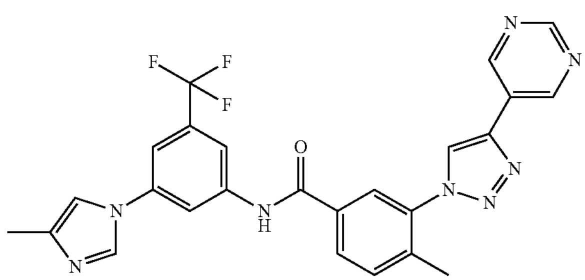 [SMILES: Cc1cn(-c2cc(NC(=O)c3ccc(C)c(-n4cc(-c5cncnc5)nn4)c3)cc(C(F)(F)F)c2)cn1] | 2.00 | 505 |
| III-169 | 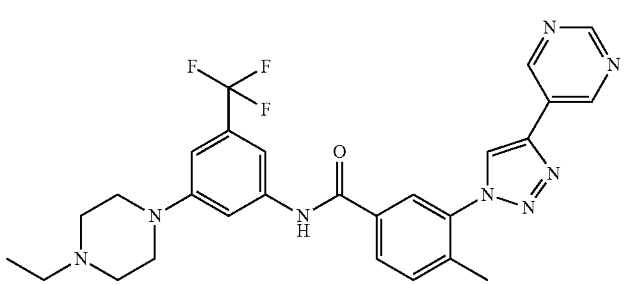 [SMILES: CCN1CCN(c2cc(NC(=O)c3ccc(C)c(-n4cc(-c5cncnc5)nn4)c3)cc(C(F)(F)F)c2)CC1] | 2.13 | 537 |

TABLE 3-continued

Examples III-1 to III-197

| # | Structure | t_Ret. (HPLC) [min] | MS (M + H)+ |
|---|---|---|---|
| III-170 | 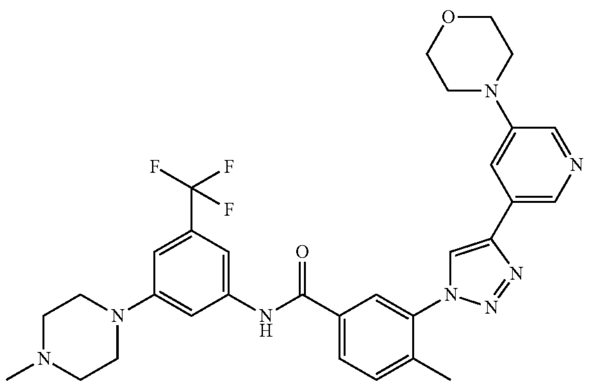 [SMILES: Cc1ccc(C(=O)Nc2cc(N3CCN(C)CC3)cc(C(F)(F)F)c2)cc1-n1cc(-c2cncc(N3CCOCC3)c2)nn1] | 2.12 | 607 |
| III-171 | 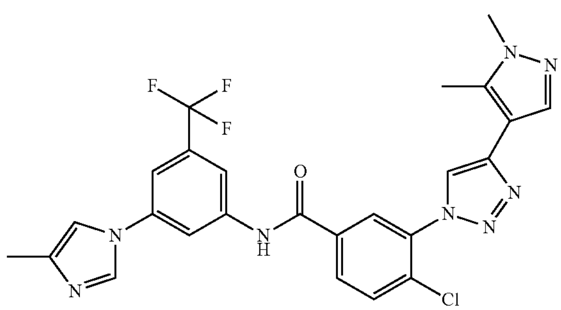 [SMILES: Cc1cn(-c2cc(NC(=O)c3ccc(Cl)c(-n4cc(-c5cnn(C)c5C)nn4)c3)cc(C(F)(F)F)c2)cn1] | 2.06 | 541 |
| III-172 | 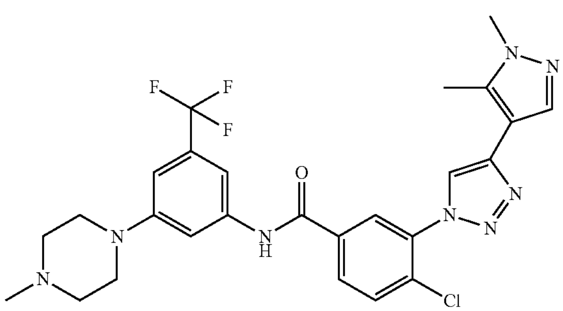 [SMILES: Cc1c(-c2cn(-c3cc(C(=O)Nc4cc(N5CCN(C)CC5)cc(C(F)(F)F)c4)ccc3Cl)nn2)cnn1C] | 2.12 | 559 |

TABLE 3-continued
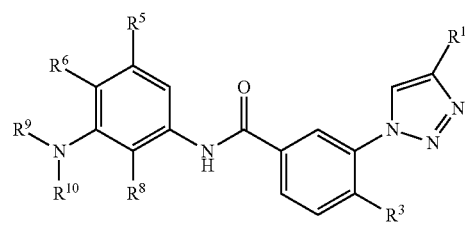
Examples III-1 to III-197
| # | Structure | $t_{Ret.}$ (HPLC) [min] | MS $(M + H)^+$ |
|---|---|---|---|
| III-173 | 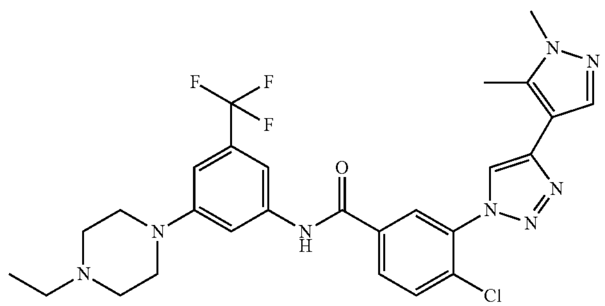 [SMILES: CCN1CCN(c2cc(NC(=O)c3ccc(Cl)c(-n4cc(-c5cnn(C)c5C)nn4)c3)cc(C(F)(F)F)c2)CC1] | 2.19 | 573 |
| III-174 | 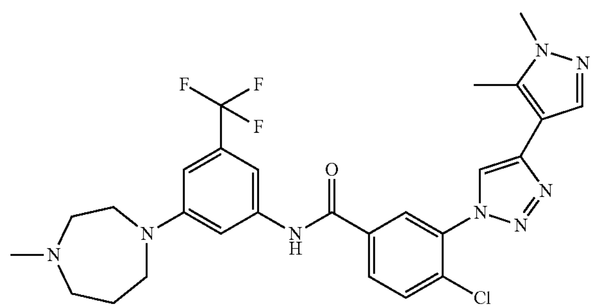 [SMILES: Cc1c(-c2cn(-c3cc(C(=O)Nc4cc(N5CCCN(C)CC5)cc(C(F)(F)F)c4)ccc3Cl)nn2)cnn1C] | 2.18 | 573 |
| III-175 | 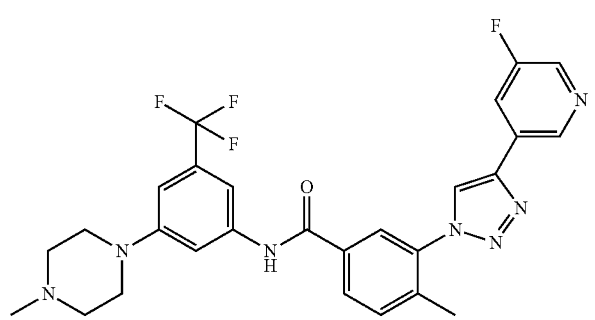 [SMILES: Cc1ccc(C(=O)Nc2cc(N3CCN(C)CC3)cc(C(F)(F)F)c2)cc1-n1cc(-c2cncc(F)c2)nn1] | 2.21 | 540 |
| III-176 | 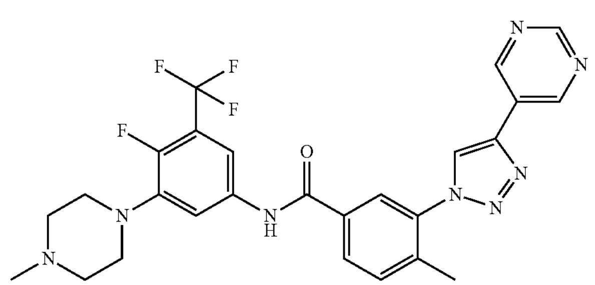 [SMILES: Cc1ccc(C(=O)Nc2cc(N3CCN(C)CC3)c(F)c(C(F)(F)F)c2)cc1-n1cc(-c2cncnc2)nn1] | 2.09 | 541 |

TABLE 3-continued
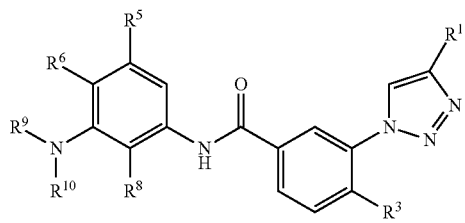
Examples III-1 to III-197
| # | Structure | t_Ret. (HPLC) [min] | MS (M + H)+ |
|---|---|---|---|
| III-177 | 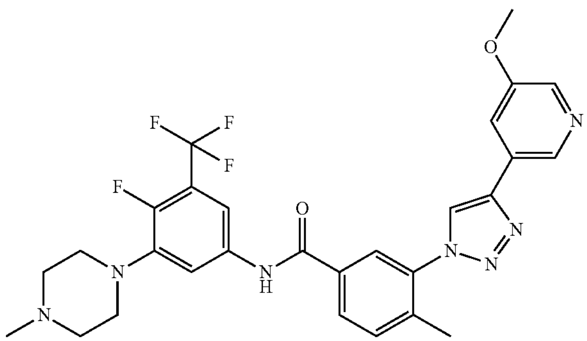 [SMILES: COc1cncc(-c2cn(-c3cc(C(=O)Nc4cc(N5CCN(C)CC5)c(F)c(C(F)(F)F)c4)ccc3C)nn2)c1] | 2.23 | 570 |
| III-178 | 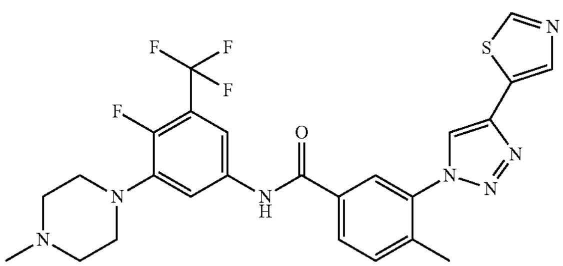 [SMILES: Cc1ccc(C(=O)Nc2cc(N3CCN(C)CC3)c(F)c(C(F)(F)F)c2)cc1-n1cc(-c2cncs2)nn1] | 2.18 | 546 |
| III-179 | 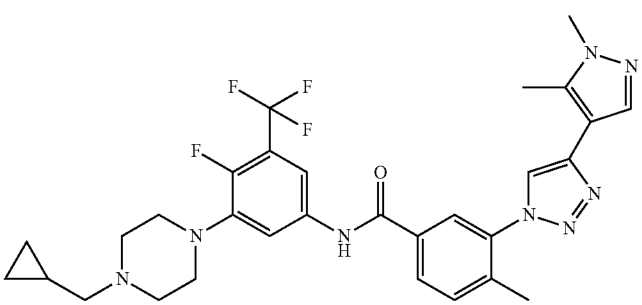 [SMILES: Cc1ccc(C(=O)Nc2cc(N3CCN(CC4CC4)CC3)c(F)c(C(F)(F)F)c2)cc1-n1cc(-c2cnn(C)c2C)nn1] | 2.37 | 597 |
| III-180 | 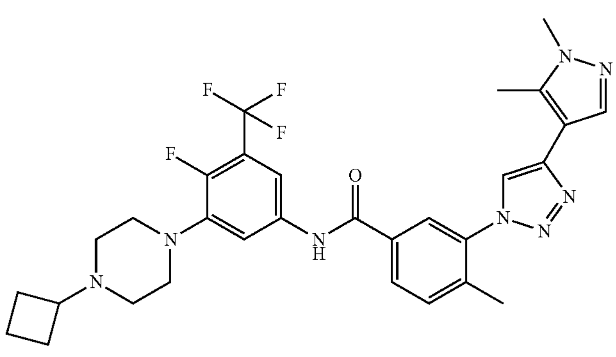 [SMILES: Cc1ccc(C(=O)Nc2cc(N3CCN(C4CCC4)CC3)c(F)c(C(F)(F)F)c2)cc1-n1cc(-c2cnn(C)c2C)nn1] | 2.41 | 597 |

TABLE 3-continued
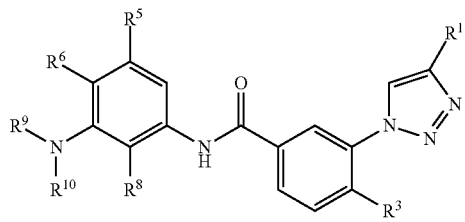
Examples III-1 to III-197
| # | Structure | $t_{Ret.}$ (HPLC) [min] | MS $(M + H)^+$ |
|---|---|---|---|
| III-181 | 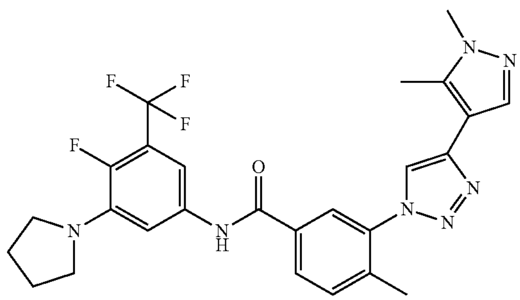 [SMILES: Cc1ccc(C(=O)Nc2cc(N3CCCC3)c(F)c(C(F)(F)F)c2)cc1-n1cc(-c2cnn(C)c2C)nn1] | 2.40 | 528 |
| III-182 | 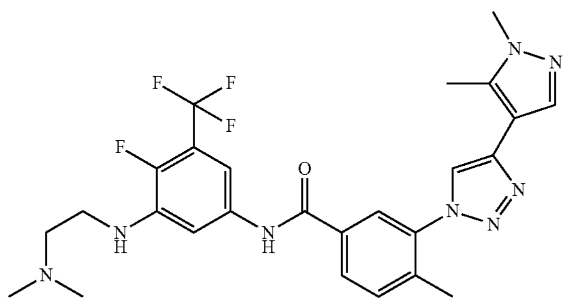 [SMILES: Cc1ccc(C(=O)Nc2cc(NCCN(C)C)c(F)c(C(F)(F)F)c2)cc1-n1cc(-c2cnn(C)c2C)nn1] | 2.17 | 545 |
| III-183 | 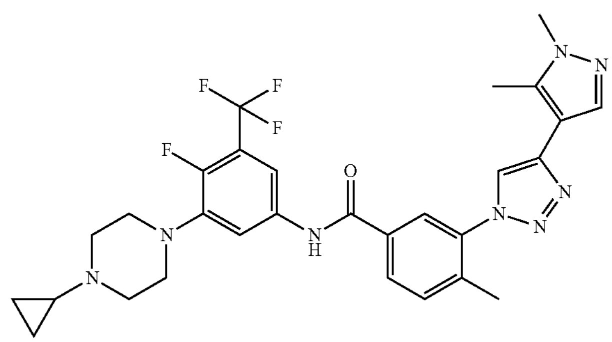 [SMILES: Cc1ccc(C(=O)Nc2cc(N3CCN(C4CC4)CC3)c(F)c(C(F)(F)F)c2)cc1-n1cc(-c2cnn(C)c2C)nn1] | 2.36 | 583 |
| III-184 | 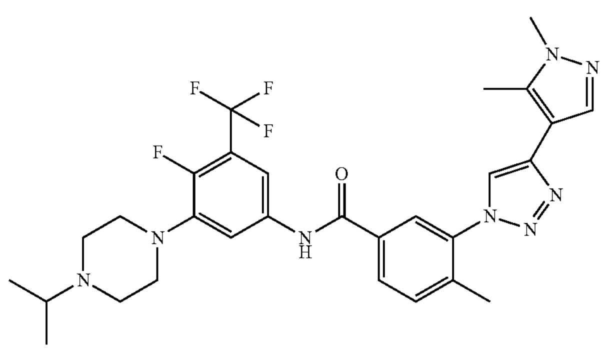 [SMILES: Cc1ccc(C(=O)Nc2cc(N3CCN(C(C)C)CC3)c(F)c(C(F)(F)F)c2)cc1-n1cc(-c2cnn(C)c2C)nn1] | 2.34 | 585 |

TABLE 3-continued
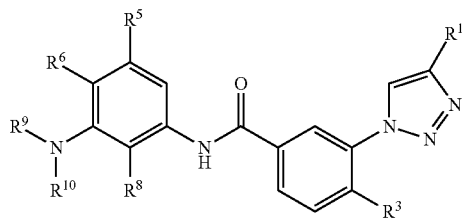
Examples III-1 to III-197
| # | Structure | $t_{Ret.}$ (HPLC) [min] | MS $(M + H)^+$ |
|---|---|---|---|
| III-185 | 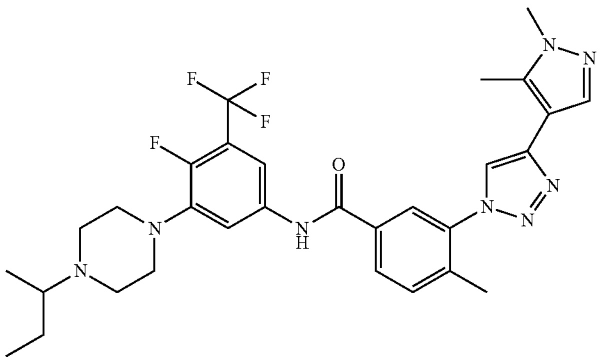 [SMILES: CCC(C)N1CCN(c2cc(NC(=O)c3ccc(C)c(-n4cc(-c5cnn(C)c5C)nn4)c3)cc(C(F)(F)F)c2F)CC1] | 2.51 | 599 |
| III-186 | 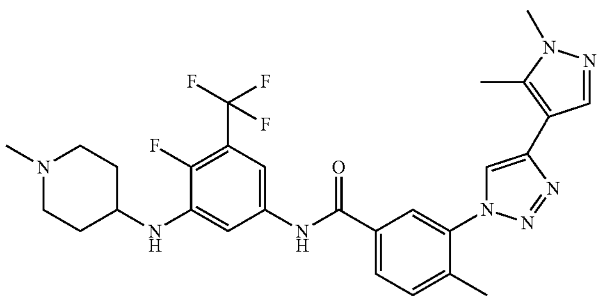 [SMILES: Cc1ccc(C(=O)Nc2cc(NC3CCN(C)CC3)c(F)c(C(F)(F)F)c2)cc1-n1cc(-c2cnn(C)c2C)nn1] | 2.15 | 571 |
| III-187 | 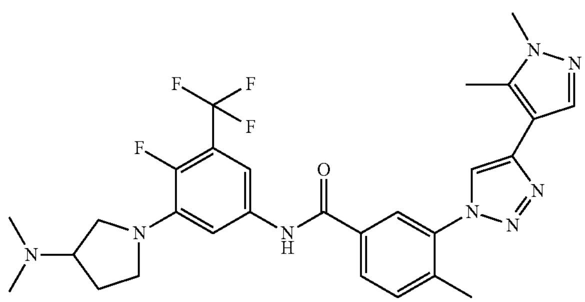 [SMILES: Cc1ccc(C(=O)Nc2cc(N3CCC(N(C)C)C3)c(F)c(C(F)(F)F)c2)cc1-n1cc(-c2cnn(C)c2C)nn1] | 2.21 | 571 |
| III-188 | 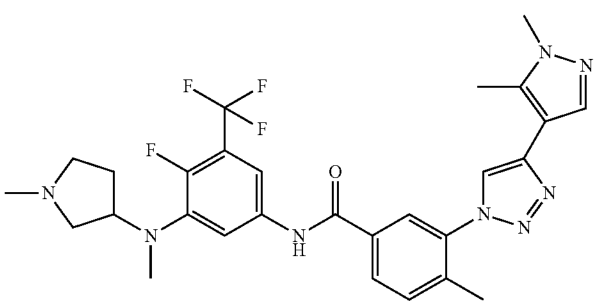 [SMILES: Cc1ccc(C(=O)Nc2cc(N(C)C3CCN(C)C3)c(F)c(C(F)(F)F)c2)cc1-n1cc(-c2cnn(C)c2C)nn1] | 2.22 | 571 |

TABLE 3-continued
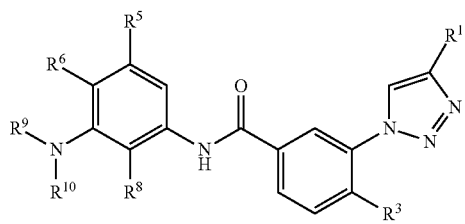
Examples III-1 to III-197
| # | Structure | $t_{Ret.}$ (HPLC) [min] | MS $(M + H)^+$ |
|---|---|---|---|
| III-189 | 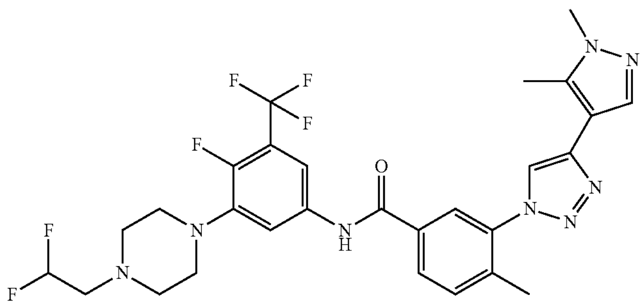 [SMILES: Cc1ccc(C(=O)Nc2cc(N3CCN(CC(F)F)CC3)c(F)c(C(F)(F)F)c2)cc1-n1cc(-c2cnn(C)c2C)nn1] | 2.33 | 607 |
| III-190 | 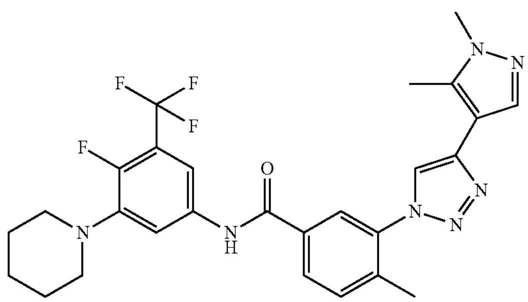 [SMILES: Cc1ccc(C(=O)Nc2cc(N3CCCCC3)c(F)c(C(F)(F)F)c2)cc1-n1cc(-c2cnn(C)c2C)nn1] | 2.47 | 542 |
| III-191 | 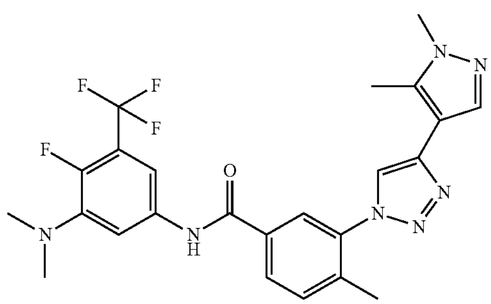 [SMILES: Cc1ccc(C(=O)Nc2cc(N(C)C)c(F)c(C(F)(F)F)c2)cc1-n1cc(-c2cnn(C)c2C)nn1] | 2.24 | 502 |
| III-192 | 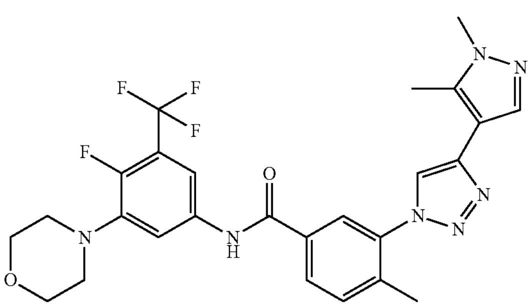 [SMILES: Cc1ccc(C(=O)Nc2cc(N3CCOCC3)c(F)c(C(F)(F)F)c2)cc1-n1cc(-c2cnn(C)c2C)nn1] | 2.18 | 544 |

TABLE 3-continued
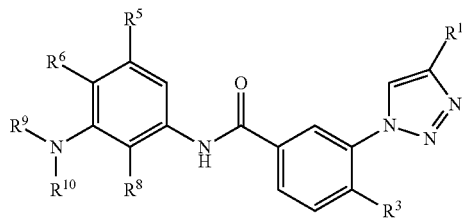
Examples III-1 to III-197
| # | Structure | $t_{Ret.}$ (HPLC) [min] | MS $(M + H)^+$ |
|---|---|---|---|
| III-193 | 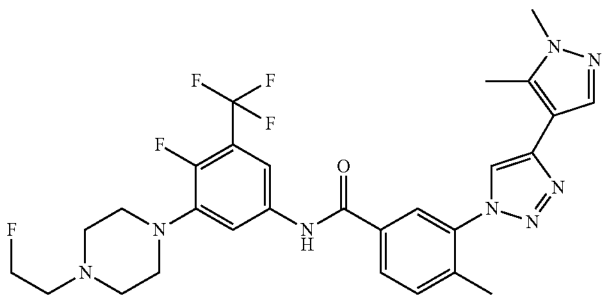 [SMILES: Cc1ccc(C(=O)Nc2cc(N3CCN(CCF)CC3)c(F)c(C(F)(F)F)c2)cc1-n1cc(-c2cnn(C)c2C)nn1] | 2.21 | 589 |
| III-194 | 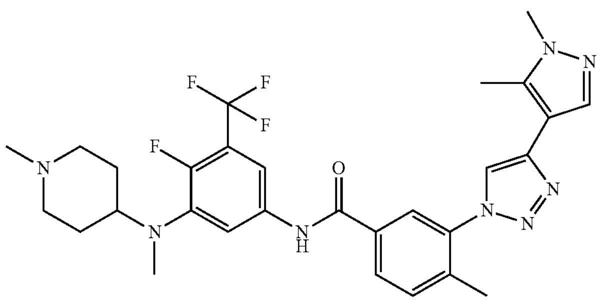 [SMILES: Cc1ccc(C(=O)Nc2cc(N(C)C3CCN(C)CC3)c(F)c(C(F)(F)F)c2)cc1-n1cc(-c2cnn(C)c2C)nn1] | 2.20 | 585 |
| III-195 | 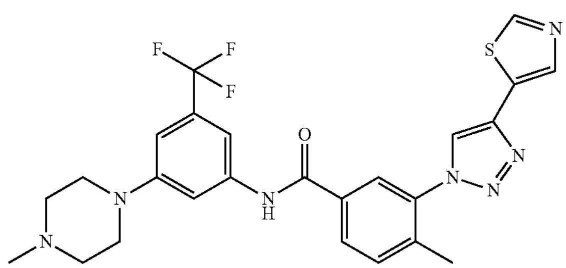 [SMILES: Cc1ccc(C(=O)Nc2cc(N3CCN(C)CC3)cc(C(F)(F)F)c2)cc1-n1cc(-c2cncs2)nn1] | 2.12 | 528 |
| III-196 | 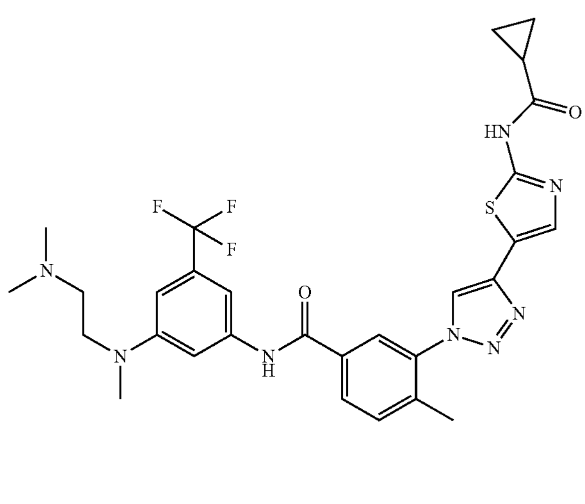 [SMILES: Cc1ccc(C(=O)Nc2cc(N(C)CCN(C)C)cc(C(F)(F)F)c2)cc1-n1cc(-c2cnc(NC(=O)C3CC3)s2)nn1] | 2.26 | 613 |

TABLE 3-continued
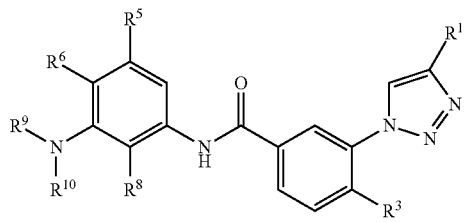
Examples III-1 to III-197
| # | Structure | t_Ret. (HPLC) [min] | MS (M + H)+ |
|---|---|---|---|
| III-197 | 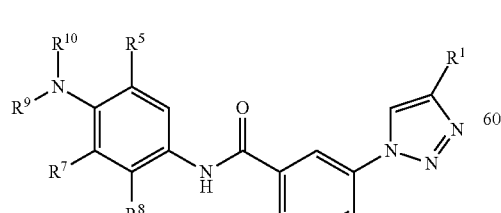 | 2.09 | 620 |
Reaction scheme E
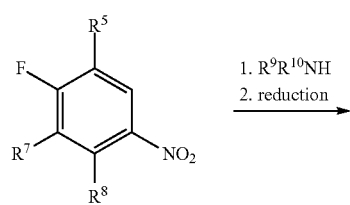
E-1
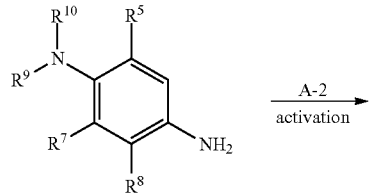
E-2
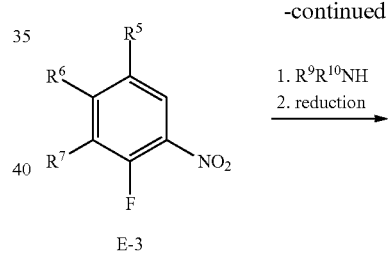
E-3
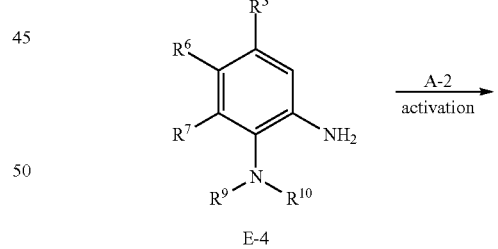
E-4
-continued
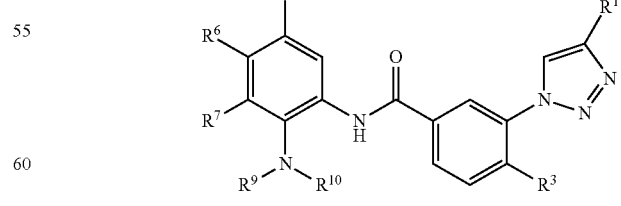
IV
V
Example compounds of type IV (arylamines in the p-position to the amide link→$R^6$) and type V (arylamines in the o-position to the amide link→$R^8$) are synthesised by an amide coupling reaction of the anilines E-2 or E-4 (in order to introduce the group R²) and the corresponding benzoic acids A-2 described above. The anilines E-2 or E-4 used are commercially obtainable or are synthesised using methods known from the literature from the corresponding fluoronitroaromatic compounds E-1 or E-3 by nucleophilic aromatic substitution with an amine R⁹R¹⁰NH and subsequent reduction via the intermediate products Z-10 or Z-11. The nucleophilic aromatic substitutions at E-1 and E-3 are carried out using methods known from the literature in common solvents, such as for example NMP, DMSO or DMF. The amines R⁹R¹⁰NH used are commercially obtainable or are synthesised using methods known from the literature.

The reaction conditions for the nucleophilic substitution and reduction are essentially independent of whether the starting material is an educt E-1 (4-fluoronitrobenzene) or E-3 (2-fluoro-nitrobenzene). Therefore only the synthesis of E-2 and hence of examples of type IV will be described hereinafter. The reaction conditions can be applied to the synthesis of E-4 and Examples of type V.

a) Procedure for Synthesising E-2a:

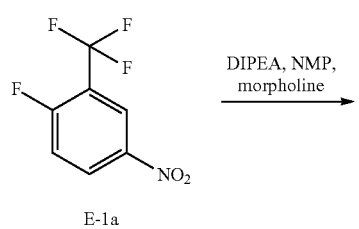

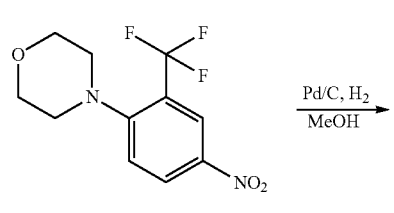

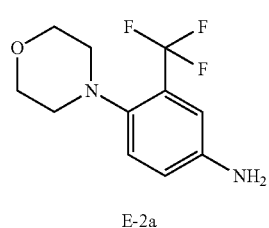

1-fluoro-4-nitro-2-trifluoromethylbenzene E-1a (250 µL, 1.82 mmol) and DIPEA (443 µL, 30 mmol) are taken up in 1 mL NMP, combined with morpholine (160 µL, 1.84 mmol), the reaction mixture is stirred for 1.5 h at RT and for 4 h at 40° C. (→intermediate product Z-10a). Then it is diluted with 8 mL MeOH and transferred into a hydrogenation reactor. Pd/C (20 mg) is added and the mixture is stirred for 18 h under a H₂ atmosphere (5 bar) at RT. The reaction mixture is filtered through Celite, the filtrate is evaporated down using the rotary evaporator and the product E-2a (HPLC-MS: $t_{Ret.}$=5.66 min; MS (M−H)⁺=245) is further reacted directly.

Analogously to this procedure further anilines E-2 and E-4 are obtained from the corresponding E-1- or E-3 intermediates/educts.

b) Procedure for Synthesising IV-1:

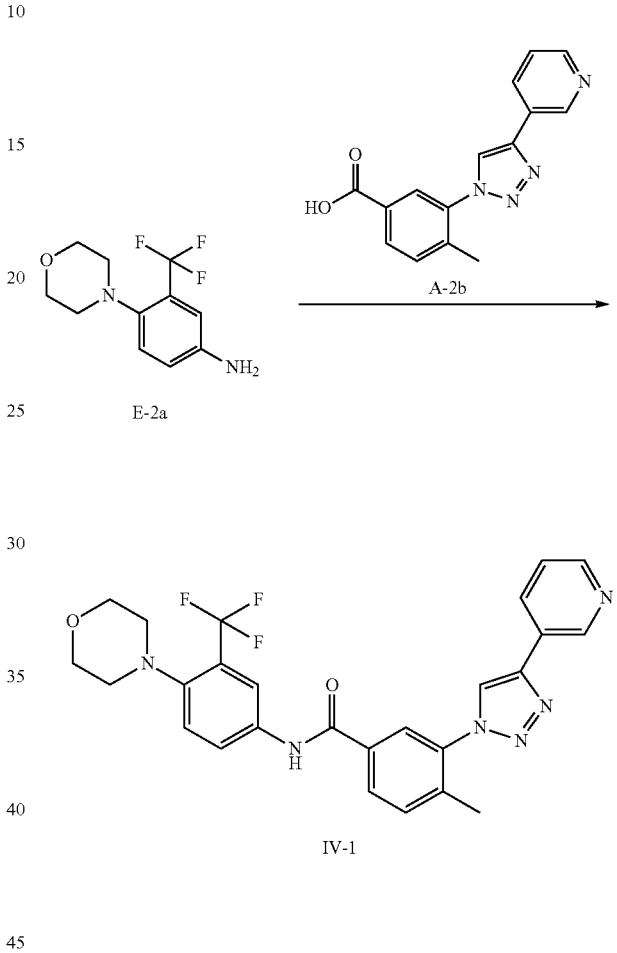

Benzoic acid A-2b (50 mg, 0.178 mmol) is taken up in 1 mL THF, combined with HATU (69 mg, 0.214 mmol) and DIPEA (68 µL, 0.395 mmol), and stirred for 20 min at RT. Then aniline E-2a (96.6 mg, 0.196 mmol) is added and the reaction mixture is stirred overnight at RT. The crude product is taken up in EtOAc and washed with water. The organic phase is washed with sat. NaCl solution, dried on Na₂SO₄, filtered, evaporated down using the rotary evaporator and the crude product is purified by preparative HPLC. The product-containing fractions of IV-1 (HPLC-MS: $t_{Ret.}$=2.03 min; MS (M+H)⁺=509) are freeze-dried.

Analogously to procedures a) and b) described hereinbefore, Examples IV-1 to IV-21 and V-1 to V-18 (Table 4) or comparable further examples may be obtained from the corresponding precursors, which are either commercially obtainable or are prepared using methods known from the literature.

TABLE 4
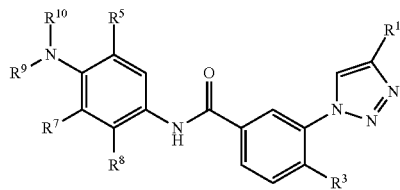
Examples IV-1 to IV-21
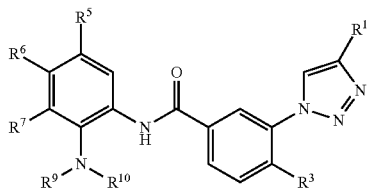
Examples V-1 to V-18
| # | Structure | $t_{Ret.}$ (HPLC) [min] | MS $(M + H)^+$ |
|---|---|---|---|
| IV-1 | 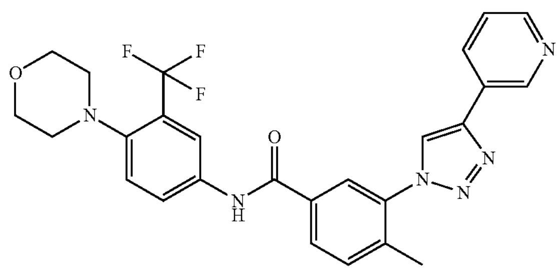 [SMILES: Cc1ccc(C(=O)Nc2ccc(N3CCOCC3)c(C(F)(F)F)c2)cc1-n1cc(-c2cccnc2)nn1] | 2.03 | 509 |
| IV-2 | 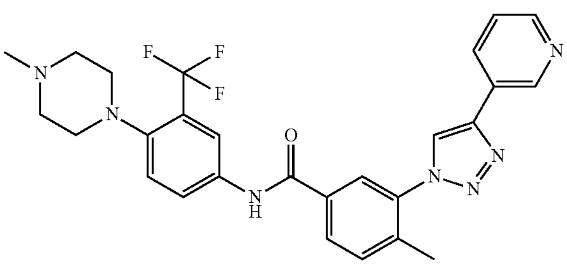 [SMILES: Cc1ccc(C(=O)Nc2ccc(N3CCN(C)CC3)c(C(F)(F)F)c2)cc1-n1cc(-c2cccnc2)nn1] | 1.46 | 522 |
| IV-3 | 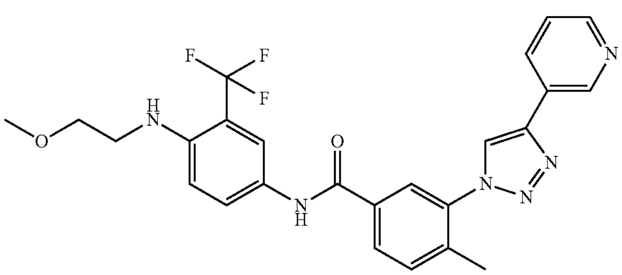 [SMILES: COCCNc1ccc(NC(=O)c2ccc(C)c(-n3cc(-c4cccnc4)nn3)c2)cc1C(F)(F)F] | 1.97 | 497 |
| IV-4 | 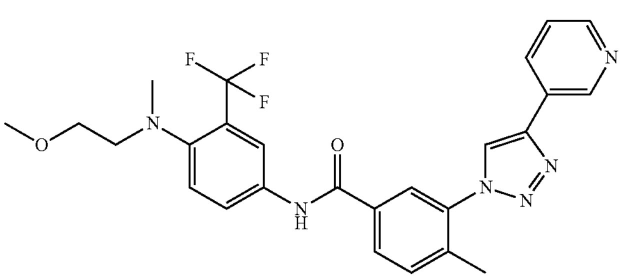 [SMILES: COCCN(C)c1ccc(NC(=O)c2ccc(C)c(-n3cc(-c4cccnc4)nn3)c2)cc1C(F)(F)F] | 2.06 | 511 |

TABLE 4-continued
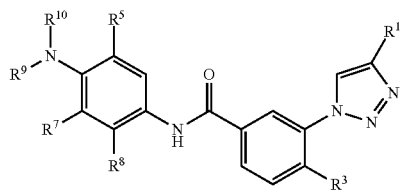
Examples IV-1 to IV-21
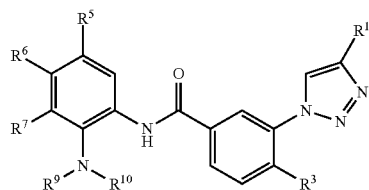
Examples V-1 to V-18
| # | Structure | $t_{Ret.}$ (HPLC) [min] | MS $(M + H)^+$ |
|---|---|---|---|
| IV-5 | 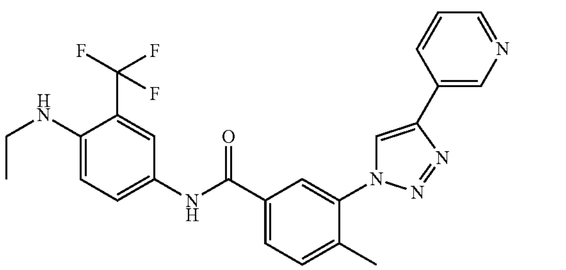 [SMILES: CCNc1ccc(NC(=O)c2ccc(C)c(-n3cc(-c4cccnc4)nn3)c2)cc1C(F)(F)F] | 2.06 | 467 |
| IV-6 | 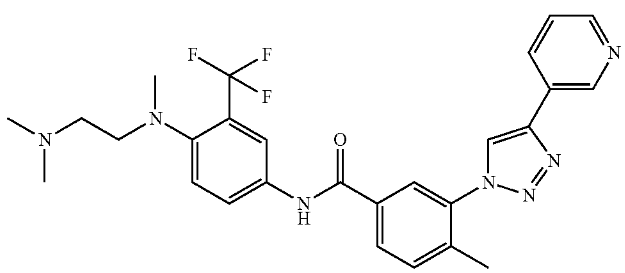 [SMILES: Cc1ccc(C(=O)Nc2ccc(N(C)CCN(C)C)c(C(F)(F)F)c2)cc1-n1cc(-c2cccnc2)nn1] | 1.48 | 524 |
| IV-7 | 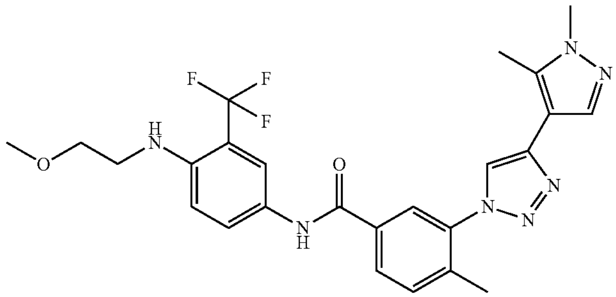 [SMILES: COCCNc1ccc(NC(=O)c2ccc(C)c(-n3cc(-c4cnn(C)c4C)nn3)c2)cc1C(F)(F)F] | 2.11 | 514 |

TABLE 4-continued
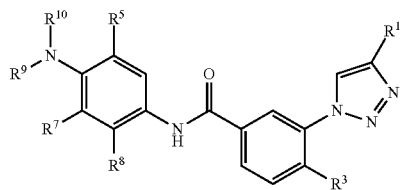
Examples IV-1 to IV-21
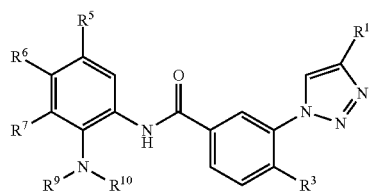
Examples V-1 to V-18
| # | Structure | $t_{Ret.}$ (HPLC) [min] | MS $(M + H)^+$ |
|---|---|---|---|
| IV-8 | 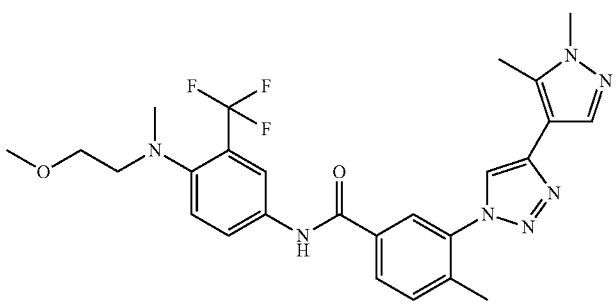 [SMILES: COCCN(C)c1ccc(NC(=O)c2ccc(C)c(-n3cc(-c4cnn(C)c4C)nn3)c2)cc1C(F)(F)F] | 2.05 | 528 |
| IV-9 | 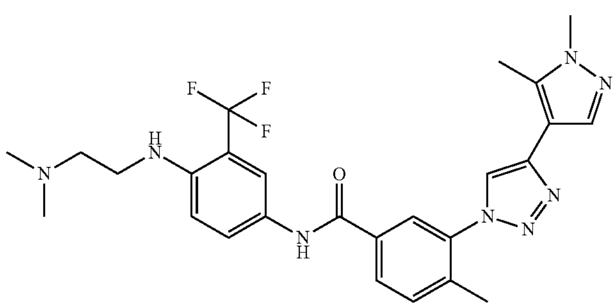 [SMILES: Cc1ccc(C(=O)Nc2ccc(NCCN(C)C)c(C(F)(F)F)c2)cc1-n1cc(-c2cnn(C)c2C)nn1] | 1.54 | 527 |
| IV-10 | 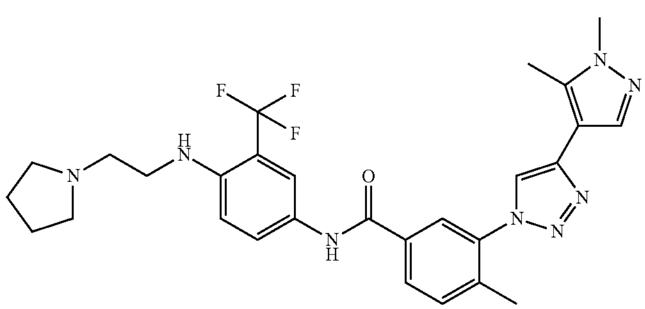 [SMILES: Cc1ccc(C(=O)Nc2ccc(NCCN3CCCC3)c(C(F)(F)F)c2)cc1-n1cc(-c2cnn(C)c2C)nn1] | 1.53 | 553 |

TABLE 4-continued
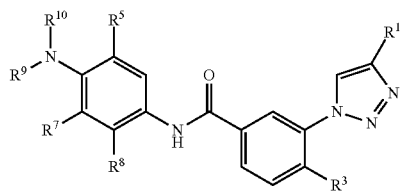
Examples IV-1 to IV-21
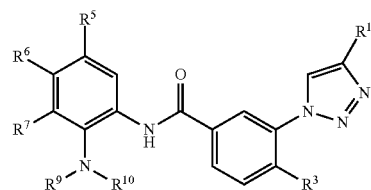
Examples V-1 to V-18
| # | Structure | $t_{Ret.}$ (HPLC) [min] | MS $(M + H)^+$ |
|---|---|---|---|
| IV-11 | 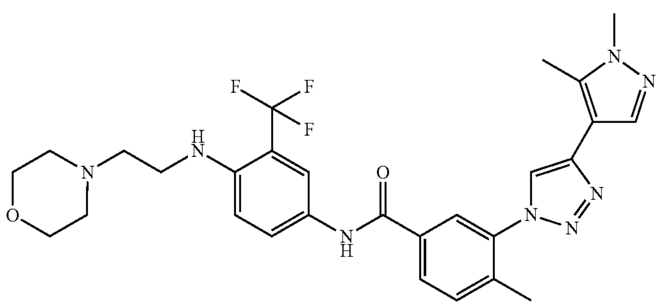 [SMILES: Cc1ccc(C(=O)Nc2ccc(NCCN3CCOCC3)c(C(F)(F)F)c2)cc1-n1cc(-c2cnn(C)c2C)nn1] | 1.55 | 569 |
| IV-12 | 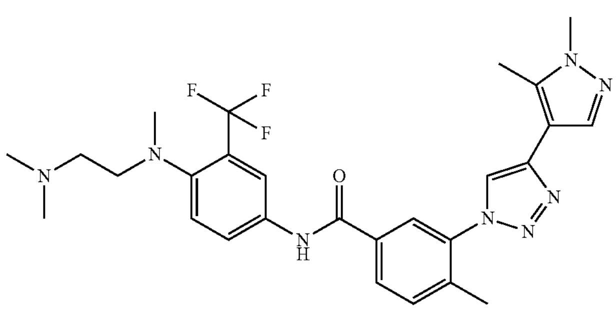 [SMILES: Cc1ccc(C(=O)Nc2ccc(N(C)CCN(C)C)c(C(F)(F)F)c2)cc1-n1cc(-c2cnn(C)c2C)nn1] | 1.57 | 541 |
| IV-13 | 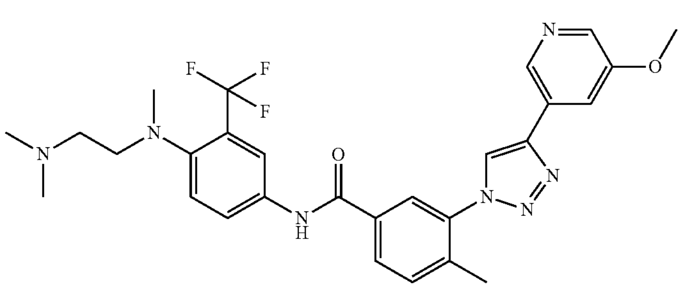 | 1.44 | 554 |

TABLE 4-continued
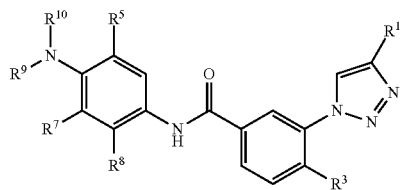
Examples IV-1 to IV-21
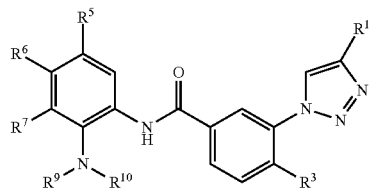
Examples V-1 to V-18
| # | Structure | $t_{Ret.}$ (HPLC) [min] | MS $(M + H)^+$ |
|---|---|---|---|
| IV-14 | 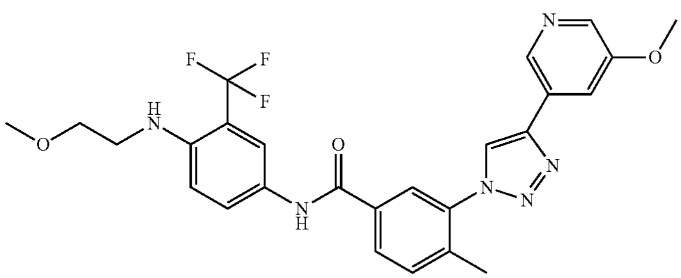 | 2.01 | 527 |
| IV-15 | 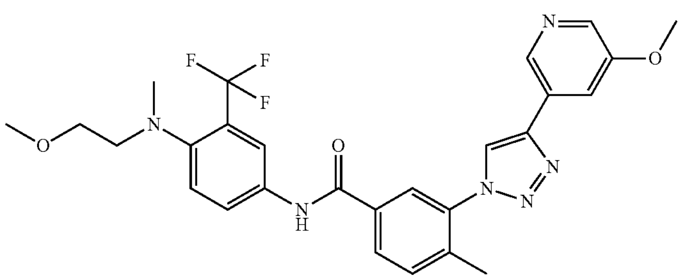 | 2.12 | 541 |
| IV-16 | 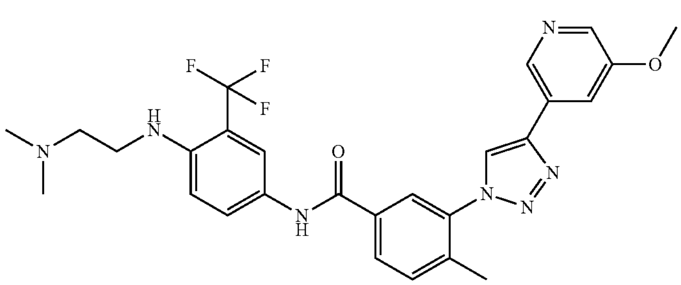 | 1.37 | 540 |

TABLE 4-continued
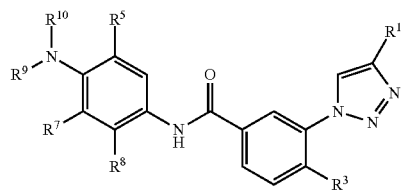
Examples IV-1 to IV-21
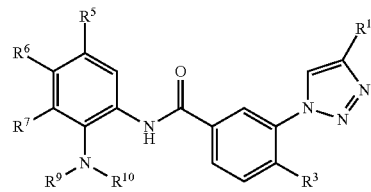
Examples V-1 to V-18
| # | Structure | $t_{Ret.}$ (HPLC) [min] | MS $(M + H)^+$ |
|---|---|---|---|
| IV-17 | 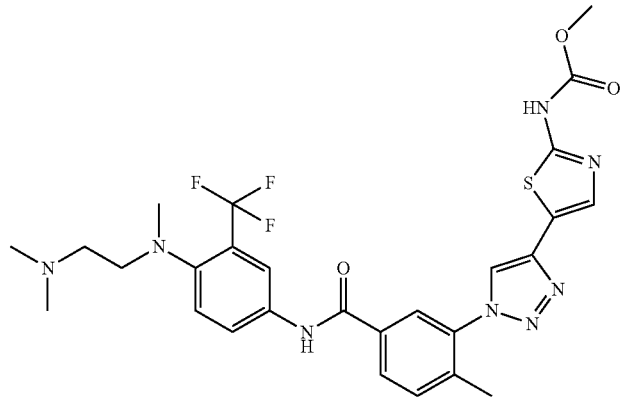 [SMILES: COC(=O)Nc1ncc(-c2cn(-c3cc(C(=O)Nc4ccc(N(C)CCN(C)C)c(C(F)(F)F)c4)ccc3C)nn2)s1] | 2.10 | 603 |
| IV-18 | 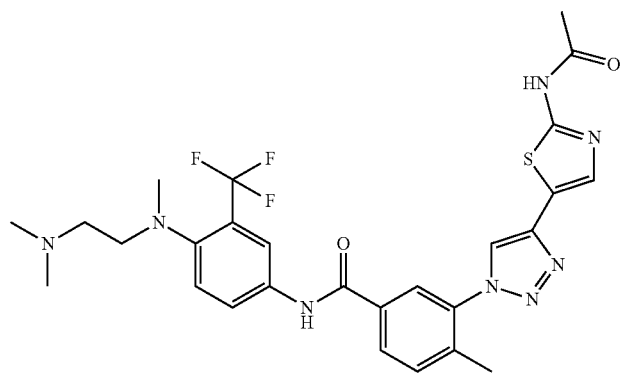 [SMILES: CC(=O)Nc1ncc(-c2cn(-c3cc(C(=O)Nc4ccc(N(C)CCN(C)C)c(C(F)(F)F)c4)ccc3C)nn2)s1] | 2.07 | 587 |

TABLE 4-continued
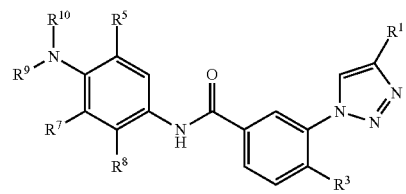
Examples IV-1 to IV-21
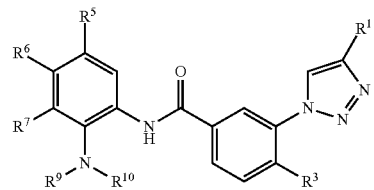
Examples V-1 to V-18
| # | Structure | t$_{Ret.}$ (HPLC) [min] | MS (M + H)$^+$ |
|---|---|---|---|
| IV-19 | 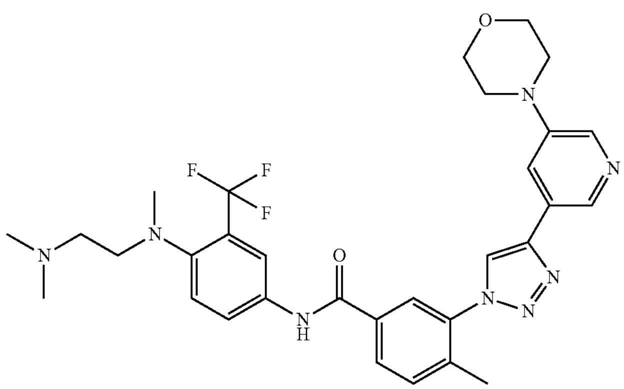 [SMILES: Cc1ccc(C(=O)Nc2ccc(N(C)CCN(C)C)c(C(F)(F)F)c2)cc1-n1cc(-c2cncc(N3CCOCC3)c2)nn1] | 2.15 | 609 |
| IV-20 | 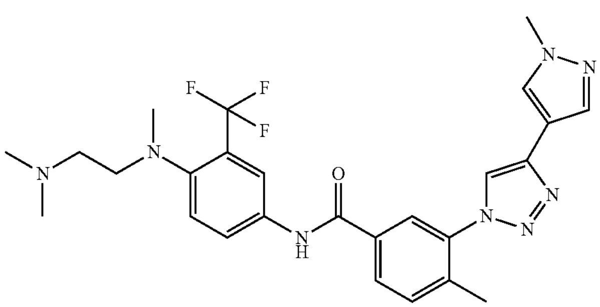 [SMILES: Cc1ccc(C(=O)Nc2ccc(N(C)CCN(C)C)c(C(F)(F)F)c2)cc1-n1cc(-c2cnn(C)c2)nn1] | 2.08 | 527 |
| IV-21 | 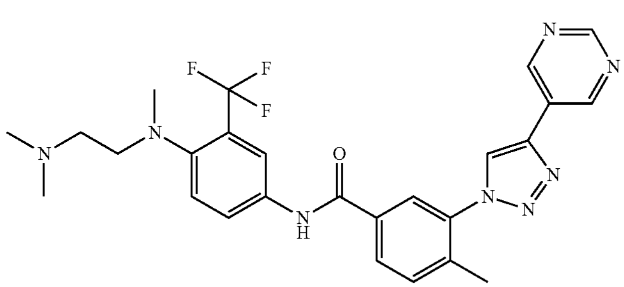 [SMILES: Cc1ccc(C(=O)Nc2ccc(N(C)CCN(C)C)c(C(F)(F)F)c2)cc1-n1cc(-c2cncnc2)nn1] | 2.05 | 525 |

TABLE 4-continued
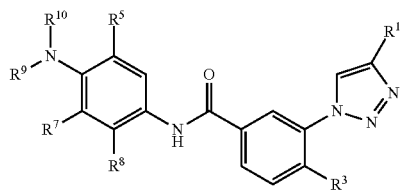
Examples IV-1 to IV-21
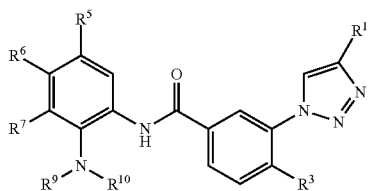
Examples V-1 to V-18
| # | Structure | t$_{Ret.}$ (HPLC) [min] | MS (M + H)$^+$ |
|---|---|---|---|
| V-1 | 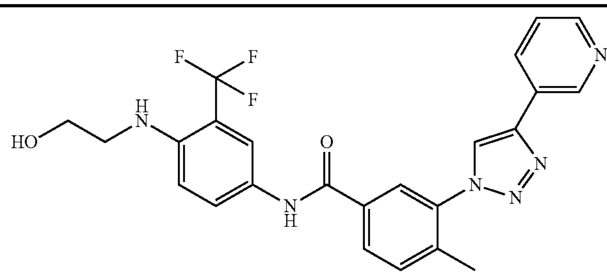 | 1.72 | 483 |
| V-2 | 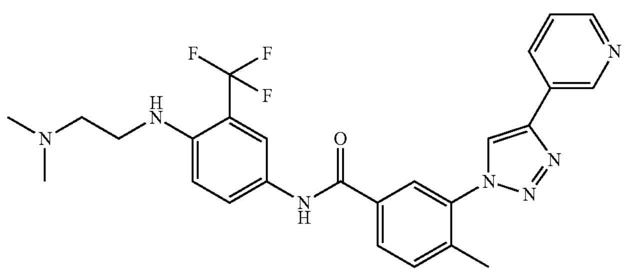 [SMILES: Cc1ccc(C(=O)Nc2ccc(NCCN(C)C)c(C(F)(F)F)c2)cc1-n1cc(-c2cccnc2)nn1] | 1.40 | 510 |
| V-3 | 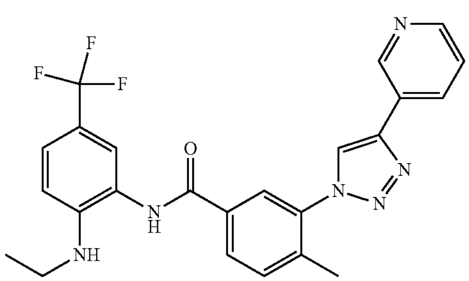 [SMILES: CCNc1ccc(C(F)(F)F)cc1NC(=O)c1ccc(C)c(-n2cc(-c3cccnc3)nn2)c1] | 2.03 | 467 |
| V-4 | 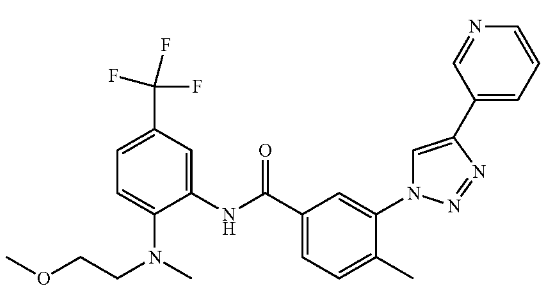 [SMILES: COCCN(C)c1ccc(C(F)(F)F)cc1NC(=O)c1ccc(C)c(-n2cc(-c3cccnc3)nn2)c1] | 2.23 | 511 |

TABLE 4-continued
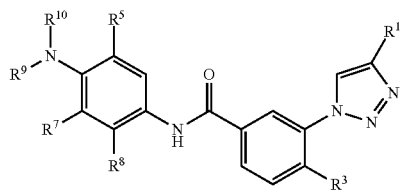
Examples IV-1 to IV-21
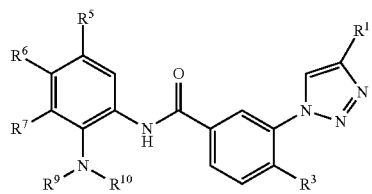
Examples V-1 to V-18
| # | Structure | t_Ret. (HPLC) [min] | MS (M + H)+ |
|---|-----------|---------------------|-------------|
| V-5 | 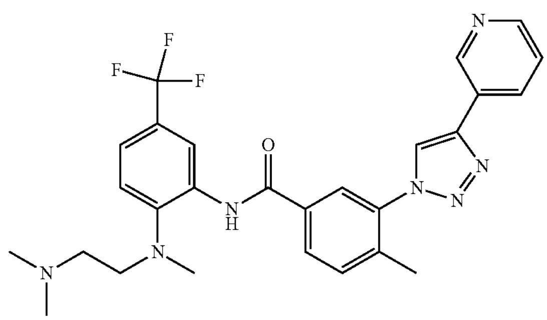 [SMILES: Cc1ccc(C(=O)Nc2cc(C(F)(F)F)ccc2N(C)CCN(C)C)cc1-n1cc(-c2cccnc2)nn1] | 1.50 | 524 |
| V-6 | 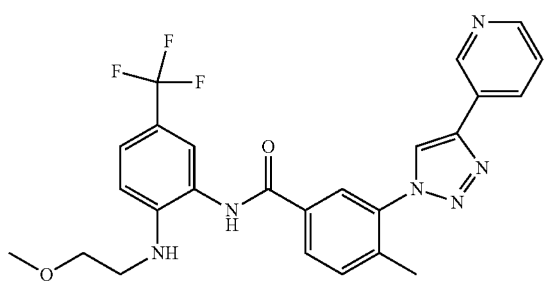 [SMILES: COCCNc1ccc(C(F)(F)F)cc1NC(=O)c1ccc(C)c(-n2cc(-c3cccnc3)nn2)c1] | 1.94 | 497 |
| V-7 | 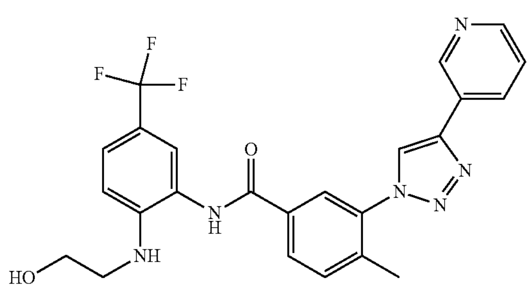 [SMILES: Cc1ccc(C(=O)Nc2cc(C(F)(F)F)ccc2NCCO)cc1-n1cc(-c2cccnc2)nn1] | 1.81 | 483 |

TABLE 4-continued
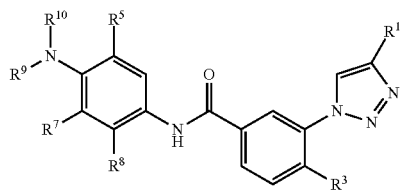
Examples IV-1 to IV-21
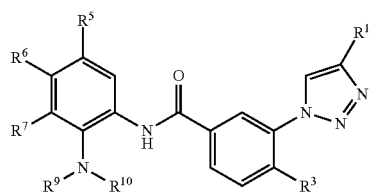
Examples V-1 to V-18
| # | Structure | t$_{Ret.}$ (HPLC) [min] | MS (M + H)$^+$ |
|---|---|---|---|
| V-8 | 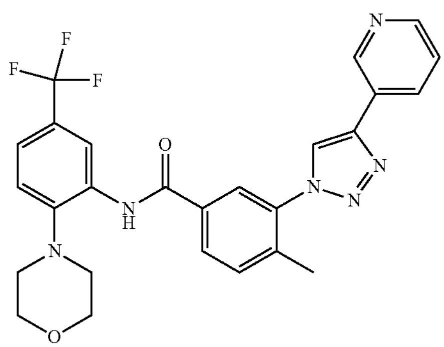 [SMILES: Cc1ccc(C(=O)Nc2cc(C(F)(F)F)ccc2N2CCOCC2)cc1-n1cc(-c2cccnc2)nn1] | 2.09 | 509 |
| V-9 | 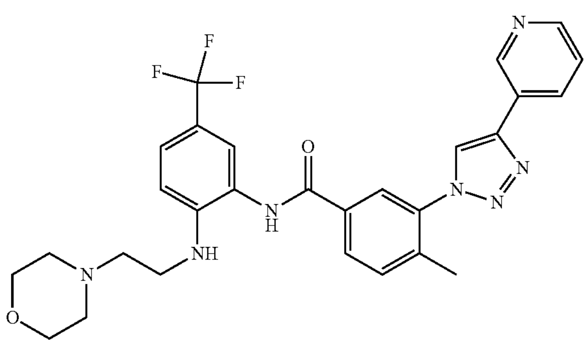 [SMILES: Cc1ccc(C(=O)Nc2cc(C(F)(F)F)ccc2NCCN2CCOCC2)cc1-n1cc(-c2cccnc2)nn1] | 1.50 | 552 |
| V-10 | 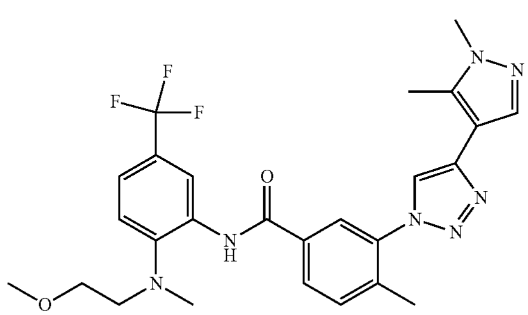 [SMILES: COCCN(C)c1ccc(C(F)(F)F)cc1NC(=O)c1ccc(C)c(-n2cc(-c3cnn(C)c3C)nn2)c1] | 2.34 | 528 |

TABLE 4-continued
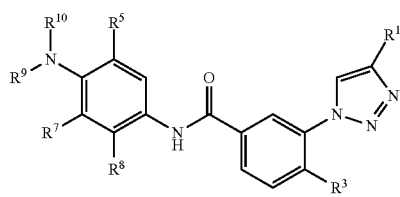
Examples IV-1 to IV-21
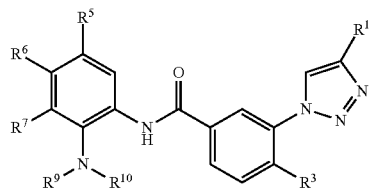
Examples V-1 to V-18
| # | Structure | t_{Ret.} (HPLC) [min] | MS (M + H)+ |
|---|---|---|---|
| V-11 | 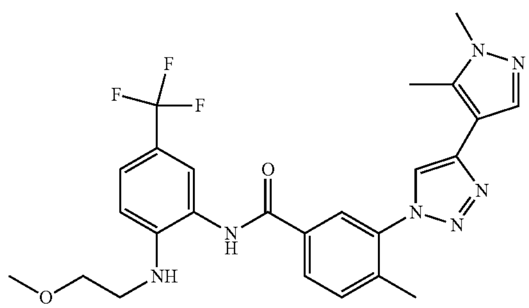 [SMILES: COCCNc1ccc(C(F)(F)F)cc1NC(=O)c1ccc(C)c(-n2cc(-c3cnn(C)c3C)nn2)c1] | 2.08 | 514 |
| V-12 | 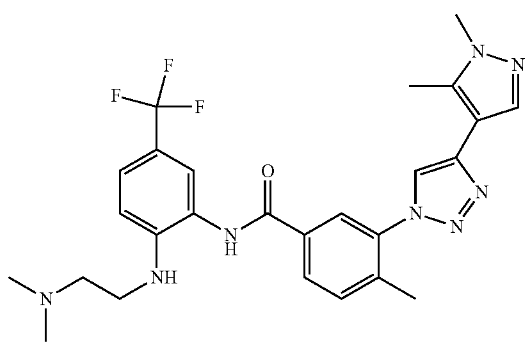 [SMILES: Cc1ccc(C(=O)Nc2cc(C(F)(F)F)ccc2NCCN(C)C)cc1-n1cc(-c2cnn(C)c2C)nn1] | 1.57 | 527 |
| V-13 | 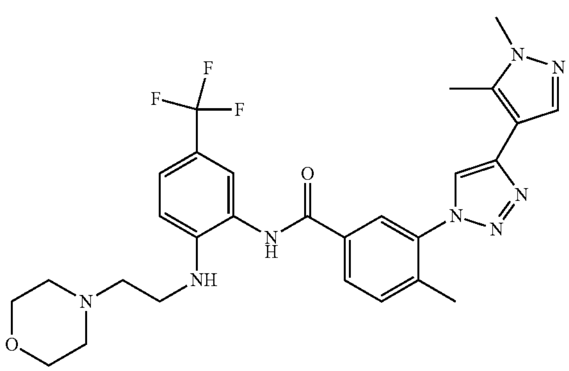 [SMILES: Cc1ccc(C(=O)Nc2cc(C(F)(F)F)ccc2NCCN2CCOCC2)cc1-n1cc(-c2cnn(C)c2C)nn1] | 1.59 | 569 |

TABLE 4-continued
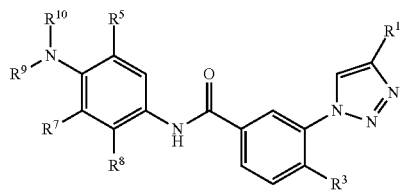
Examples IV-1 to IV-21
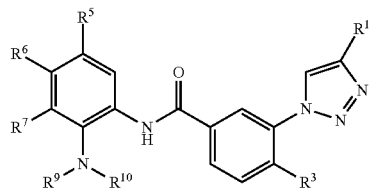
Examples V-1 to V-18
| # | Structure | $t_{Ret.}$ (HPLC) [min] | MS $(M + H)^+$ |
|---|---|---|---|
| V-14 | 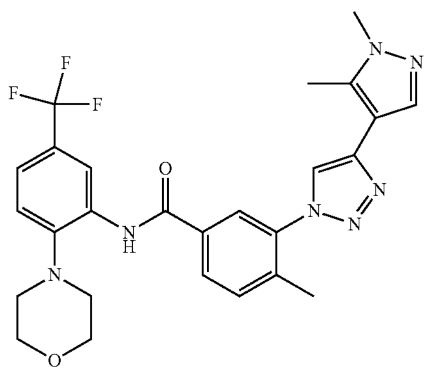 [SMILES: Cc1ccc(C(=O)Nc2cc(C(F)(F)F)ccc2N2CCOCC2)cc1-n1cc(-c2cnn(C)c2C)nn1] | 2.21 | 526 |
| V-15 | 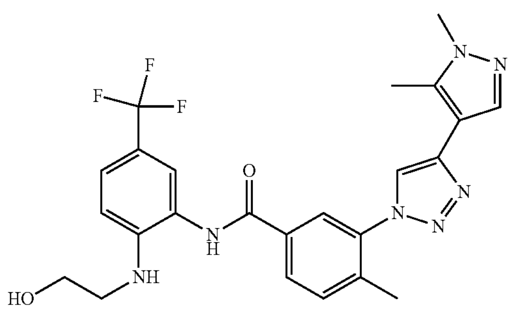 [SMILES: Cc1ccc(C(=O)Nc2cc(C(F)(F)F)ccc2NCCO)cc1-n1cc(-c2cnn(C)c2C)nn1] | 1.93 | 500 |
| V-16 | 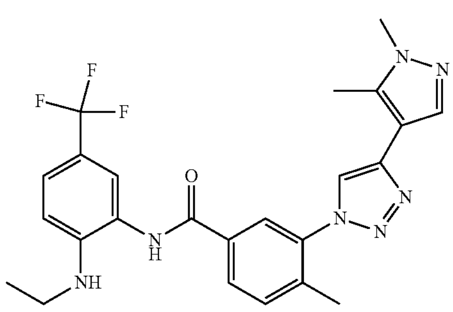 [SMILES: CCNc1ccc(C(F)(F)F)cc1NC(=O)c1ccc(C)c(-n2cc(-c3cnn(C)c3C)nn2)c1] | 2.16 | 484 |

TABLE 4-continued
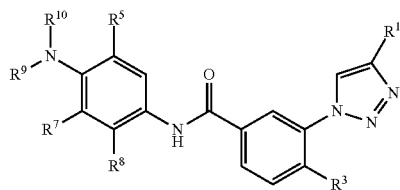
Examples IV-1 to IV-21
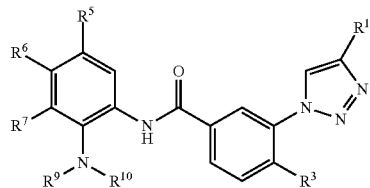
Examples V-1 to V-18
| # | Structure | $t_{Ret.}$ (HPLC) [min] | MS $(M + H)^+$ |
|---|---|---|---|
| V-17 | 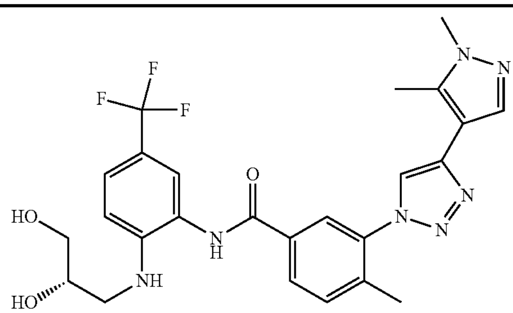 | 1.87 | 530 |
| V-18 | 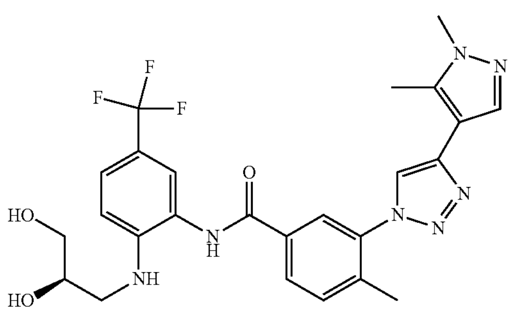 [SMILES: Cc1ccc(C(=O)Nc2cc(C(F)(F)F)ccc2NC[C@@H](O)CO)cc1-n1cc(-c2cnn(C)c2C)nn1] | 1.85 | 530 |
Reaction scheme F
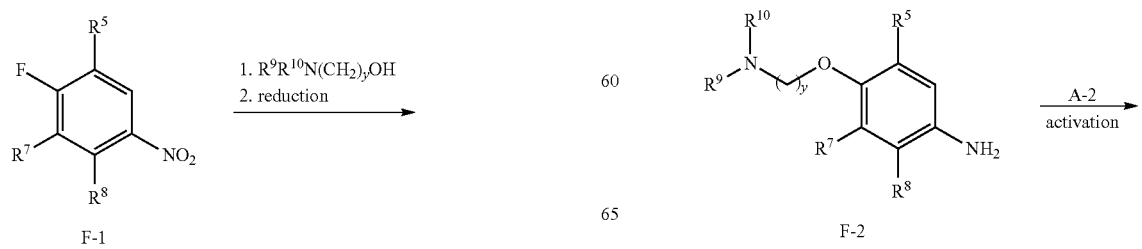

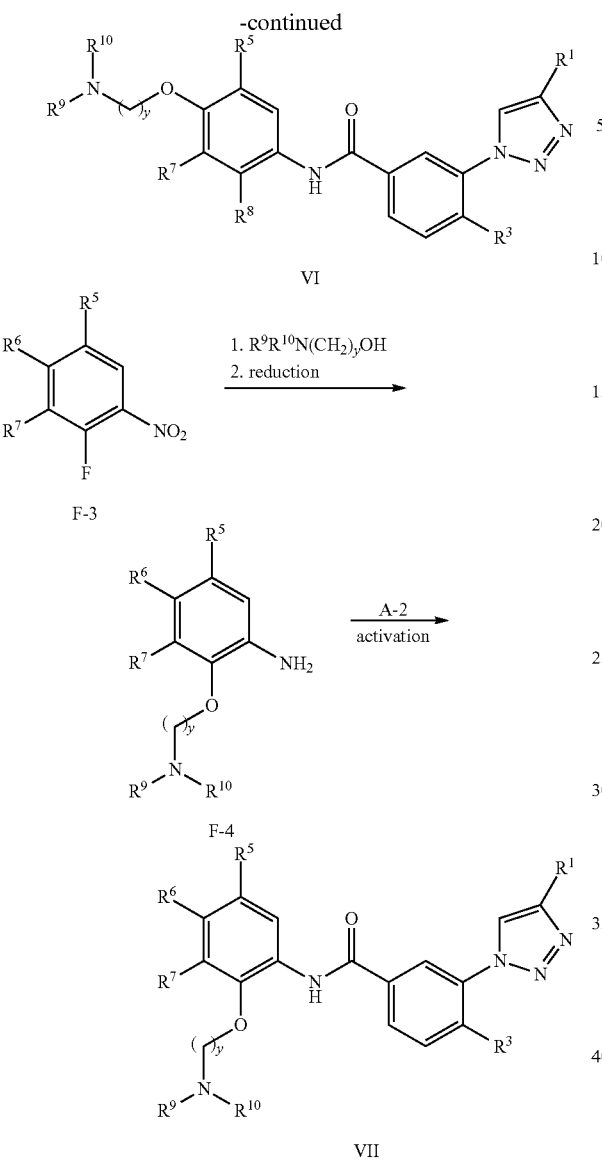

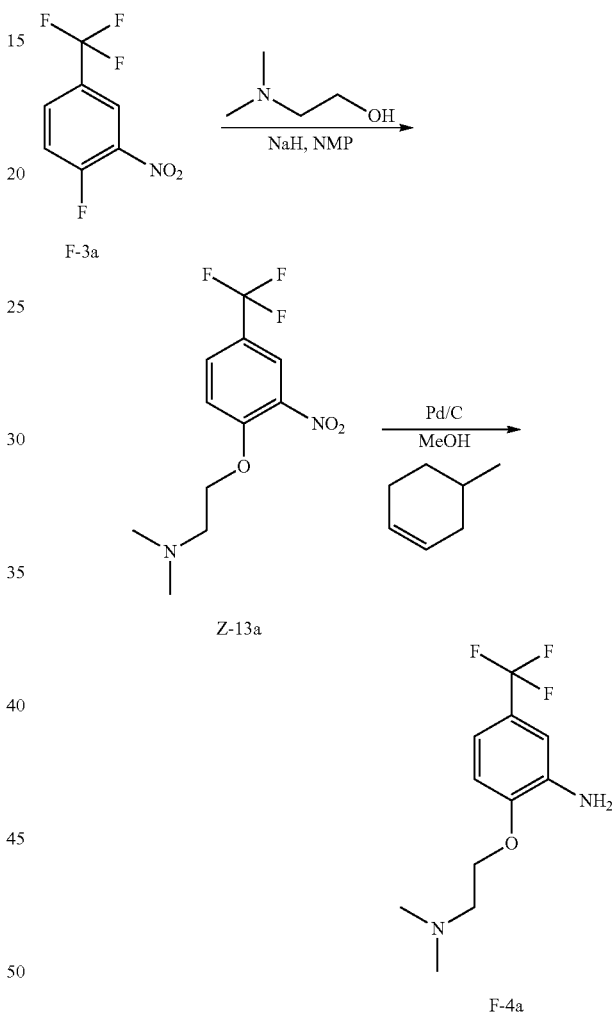

Example compounds of type VI (arylethers in the p-position to the amide link→$R^6$) and type VII (arylethers in the o-position to the amide link→$R^8$) are synthesised by a reaction of amide coupling of the anilines F-2 or F-4 (in order to introduce the group $R^2$) and the corresponding benzoic acid A-2 described hereinbefore. The anilines used are commercially obtainable or are synthesised using methods known from the literature from the corresponding fluoronitroaromatic compounds F-1 or F-3 by nucleophilic aromatic substitution with an aminoalcohol $R^9R^{10}N(CH_2)_yOH$ (or the corresponding alkoxide) and subsequent reduction via the intermediate products Z-12 and Z-13.

If the aminoalcohol $R^9R^{10}N(CH_2)_yOH$ that is to be used is unobtainable or difficult to obtain, there is the alternative possibility of carrying out the nucleophilic substitution with a functionalised alcohol or a corresponding alkoxide and to generate an aldehyde function CHO from the second functional group via corresponding intermediate stages, in order to finally introduce the group $NR^9R^{10}$ by reductive amination.

The nucleophilic aromatic substitutions at F-1 and F-3 are carried out using methods known from the literature in common solvents, such as e.g. NMP, DMSO or DMF, using a base such as NaH or $K_2CO_3$. The aminoalcohols $R^9R^{10}N(CH_2)_yOH$ used are commercially obtainable or are synthesised using methods known from the literature.

The reaction conditions for the nucleophilic substitution and reduction are essentially dependent on whether the starting material is an educt F-1 (4-fluoronitrobenzene) or F-3 (2-fluoro-nitrobenzene). Therefore, only the synthesis of F-4 and hence of examples of type VII will be described hereinafter by way of example. The reaction conditions can be applied to the synthesis of F-2 and Examples of type VI.

a) Procedure for Synthesising F-4a:

1-fluoro-2-nitro-4-(trifluoromethyl)-benzene F-3a (250 μL, 1.82 mmol) is taken up in NMP (500 μL), combined with NaH (80 mg, 2.0 mmol) and 2-dimethylaminoethanol (158 mg, 1.82 mmol) and stirred overnight at RT. The reaction mixture is purified by silica gel chromatography. The product-containing fractions are evaporated down and the residue (→intermediate product Z-13a, HPLC-MS: $t_{Ret.}$=0 min; MS $(M+H)^-$=279) is taken up in 6 mL MeOH in a microwave vial. Pd/C (20 mg) and 4-methyl-1-cyclohexene are added and the mixture is stirred for 1 h at 100° C. The reaction mixture is filtered through Celite, the filtrate is evaporated down using the rotary evaporator and the product F-4a (HPLC-MS: $t_{Ret.}$=0.56 min; MS $(M+H)^+$=249) obtained is further reacted directly.

Analogously to this procedure further anilines F-2 and F-4 are obtained from the corresponding F-1- or F-3 intermediates/educts.

b) Procedure for Synthesising VII-1:

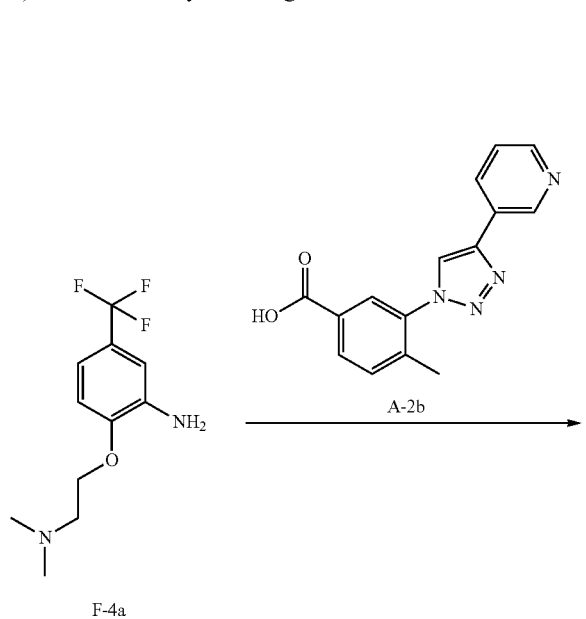

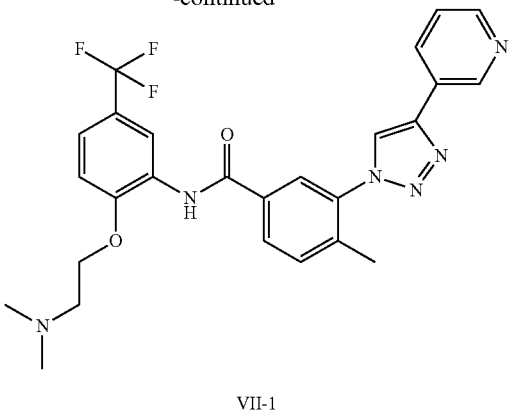

VII-1

Benzoic acid A-2b (50 mg, 0.178 mmol) is taken up in 800 μL NMP, combined with HATU (73 mg, 0.225 mmol) and DIPEA (62 mg, 0.474 mmol) and stirred for 20 min at RT. Then the aniline F-4a (48.7 mg, 0.196 mmol) is added and the reaction mixture is stirred overnight at RT. The crude product is purified by preparative HPLC. The product-containing fractions of VII-1 (HPLC-MS: $t_{Ret.}$=1.45 min; MS (M+H)$^+$=511) are freeze-dried.

Analogously to reaction methods a) and b) described above Examples VI-1 to VI-2 and VII-1 to VII-3 (Table 5) or comparable further examples may be obtained from the corresponding precursors, which are either commercially obtainable or are prepared using methods known from the literature.

TABLE 5

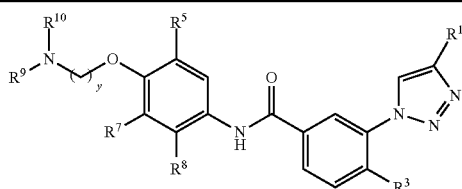

Examples VI-1 to VI-2

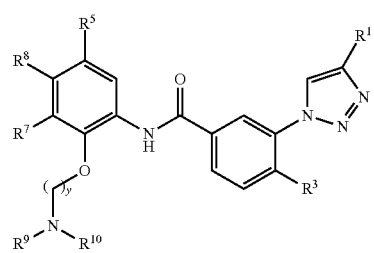

Examples VII-1 to VII-3

| # | Structure | $t_{Ret.}$ (HPLC) [min] | MS (M + H)$^+$ |
|---|-----------|------------------------|----------------|
| VI-1 | 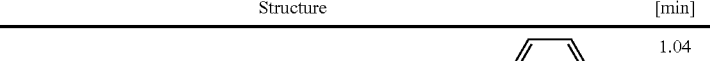 | 1.04 | 256 |

TABLE 5-continued
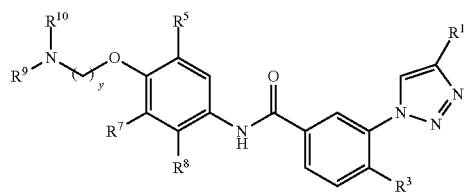
Examples VI-1 to VI-2
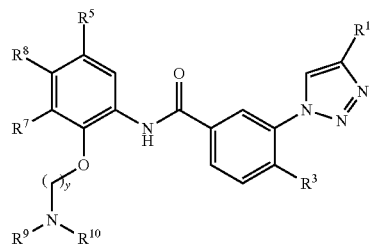
Examples VII-1 to VII-3
| # | Structure | t$_{Ret.}$ (HPLC) [min] | MS (M + H)$^+$ |
|---|---|---|---|
| VI-2 | 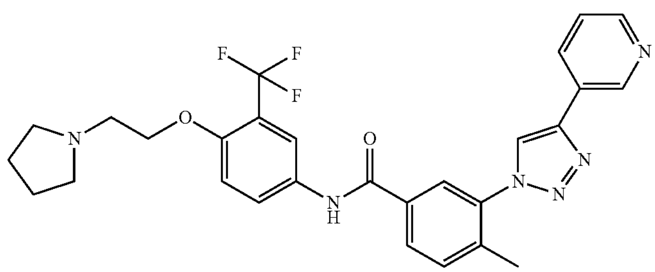 [SMILES: Cc1ccc(C(=O)Nc2ccc(OCCN3CCCC3)c(C(F)(F)F)c2)cc1-n1cc(-c2cccnc2)nn1] | 1.68 | 537 |
| VII-1 | 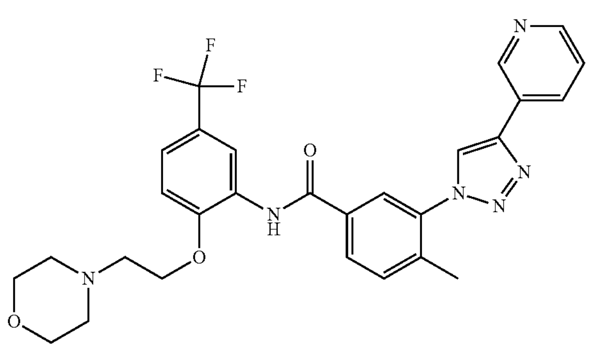 [SMILES: Cc1ccc(C(=O)Nc2cc(C(F)(F)F)ccc2OCCN2CCOCC2)cc1-n1cc(-c2cccnc2)nn1] | 1.51 | 553 |
| VII-2 | 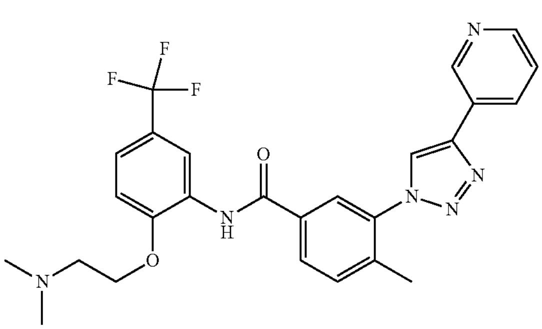 [SMILES: Cc1ccc(C(=O)Nc2cc(C(F)(F)F)ccc2OCCN(C)C)cc1-n1cc(-c2cccnc2)nn1] | 1.48 | 511 |

TABLE 5-continued
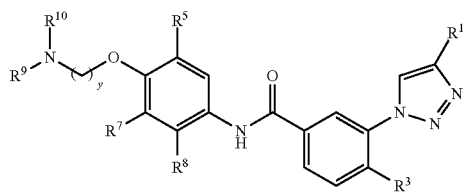
Examples VI-1 to VI-2
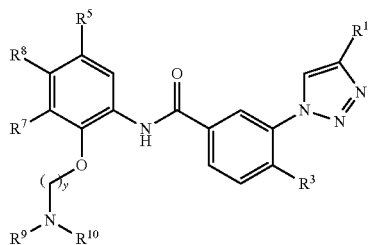
Examples VII-1 to VII-3
| # | Structure | $t_{Ret.}$ (HPLC) [min] | MS $(M + H)^+$ |
|---|-----------|-------------------------|----------------|
| VII-3 | 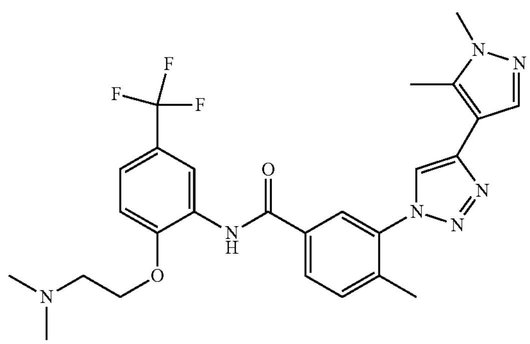 | 1.57 | 528 |
Reaction scheme G
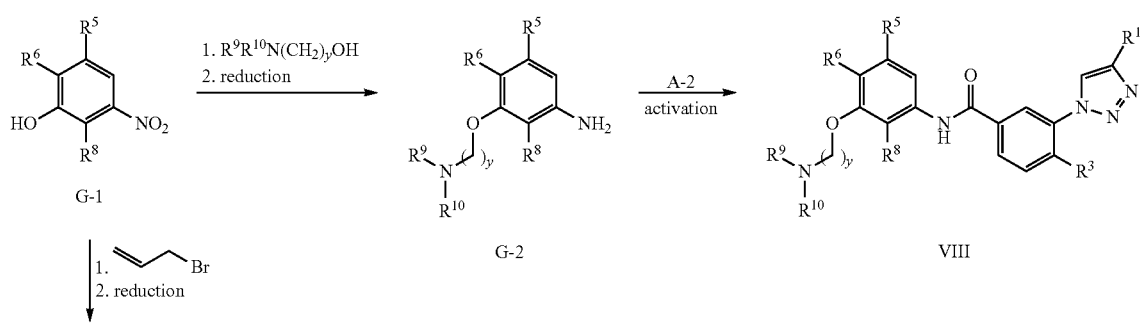

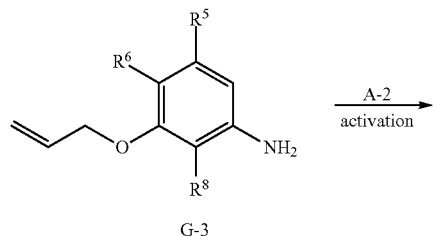

G-3

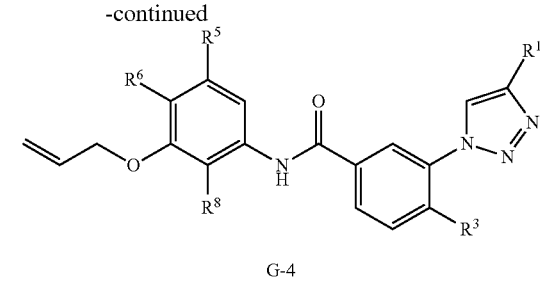

G-4

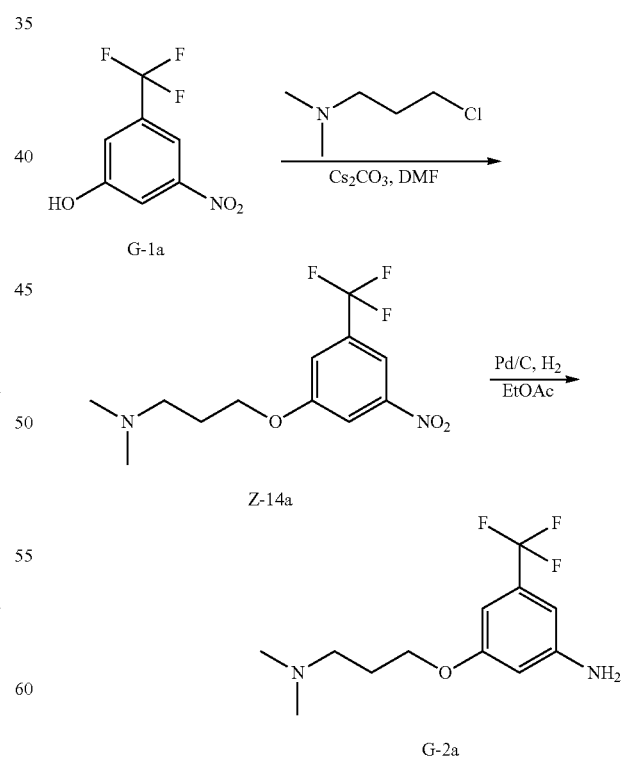

VIII (y = 2)

Example compounds of type VIII (arylethers in the m-position to the amide link→$R^7$) are synthesised by an amide coupling reaction of the aniline G-2 and the corresponding, benzoic acid A-2 described hereinbefore. The anilines G-2 used are commercially obtainable or are synthesised using methods known from the literature from the corresponding nitrophenols G-1 by nucleophilic substitution at an aminoalkylhalide $R^9R^{10}N(CH_2)_yX$ and subsequent reduction via the intermediate product Z-14. The aminoalkylhalides $R^9R^{10}N(CH_2)_yX$ used are commercially obtainable or are synthesised using methods known from the literature.

Alternatively, certain example compounds of type VIII (y=2) may be prepared by reductive amination of a corresponding aldehyde intermediate product Z-16 with an amine $R^9R^{10}NH$. The corresponding aldehydes Z-16 are obtained for example by ozonolysis of allylarylethers G-4 in methanolic medium, the reductive amination is carried out in acetic acid medium with $Na(OAc)_3BH$ or $Na(CN)BH_3$ using methods known from the literature. The amines $R^9R^{10}NH$ used are commercially obtainable or are synthesised using methods known from the literature. Allylarylethers G-4 are synthesised by an amide coupling reaction of the aniline G-3 with the corresponding benzoic acid A-2 described hereinbefore, while aniline G-3 may be obtained by allylation of the nitrophenols G-1 and subsequent reduction via the intermediate product Z-15.

The nucleophilic substitution to obtain the intermediate products Z-14 and Z-15 is carried out using methods known from the literature in common solvents, such as e.g. NMP, DMSO or DMF, using a base such as e.g. caesium carbonate, NaH or $K_2CO_3$.

a) Procedure for Synthesising G-2a:

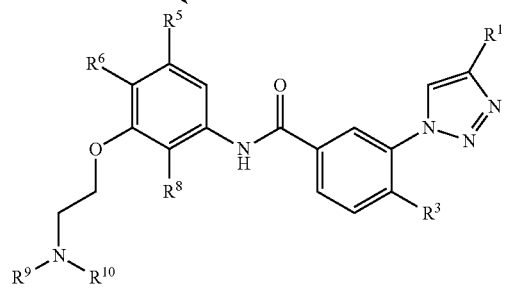

3-nitro-5-(trifluoromethyl)-phenol G-1a (500 mg, 2.41 mmol), 3-dimethylaminopropyl-chloride hydrochloride (573 mg, 3.62 mmol) and caesium carbonate (3.93 g, 12.07 mmol)

are taken up in DMF (10 mL) and heated to 120° C. for 60 min in a microwave reactor. Then the solvent is evaporated down using the rotary evaporator, the reaction mixture is diluted with EtOAc and extracted twice with water. The organic phase is dried on MgSO$_4$, filtered, evaporated down using the rotary evaporator and the resulting intermediate product Z-14a (HPLC-MS: t$_{Ret.}$=0.67 min; MS (M+H)$^+$=293) is further reacted directly.

The nitro compound Z-14a (700 mg, 1.80 mmol) is taken up in 15 mL EtOAc and transferred into a hydrogenation reactor. Pd/C (20 mg) is added and the mixture is stirred for 18 h under a H$_2$ atmosphere (4 bar) at RT. The reaction mixture is filtered through Celite, the filtrate is evaporated down using the rotary evaporator and the product obtained G-2a (HPLC-MS: t$_{Ret.}$=1.88 min; MS (M+H)$^+$=263) is further reacted directly.

Analogously to this procedure further anilines G-2 are obtained from the corresponding G-1 intermediates/educts.

b) Procedure for Synthesising VIII-1:

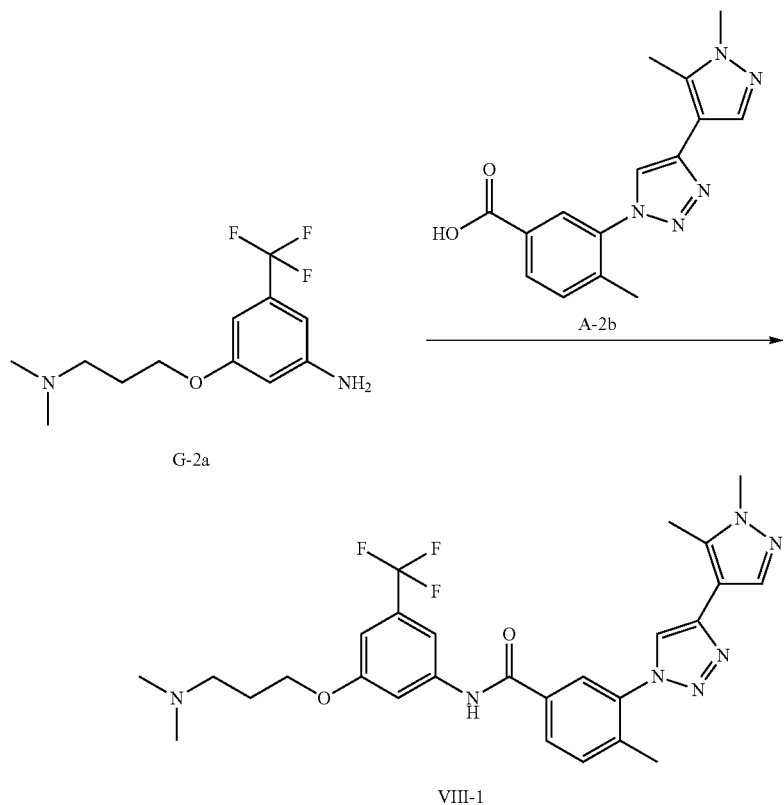

Benzoic acid A-2a (50 mg, 0.16 mmol) is taken up in 1 mL DCM and 1 mL THF, combined with oxalyl chloride (0.15 µL, 0.19 mmol) and one drop of DMF, stirred for 3 h at RT and then evaporated down using the rotary evaporator. The residue is taken up in 1 mL DCM, cooled to 0° C. in the ice bath and combined with the amine G-2a (50 mg, 0.16 mmol) as well as pyridine (40 µL, 0.49 mmol) and stirred overnight at RT. The crude product is purified by preparative HPLC. The product-containing fractions of VIII-1 (HPLC MS: t$_{Ret.}$=2.21 min; MS (M+H)$^+$=542) are freeze-dried.

Further Example compounds VIII may be synthesised analogously to this procedure from the corresponding G-2 and A-2 intermediates/educts.

c) Procedure for Synthesising G-3a:

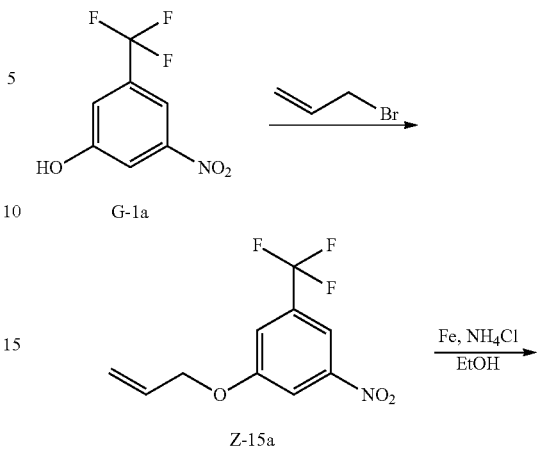

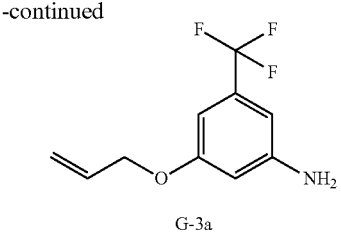

3-Nitro-5-(trifluoromethyl)-phenol G-1a (2.5 g, 12.08 mmol) and potassium carbonate (2.00 g, 14.5 mmol) are taken up in acetone (10 mL), combined dropwise with allylbromide (1.15 mL, 13 mmol) and stirred overnight at 80° C. Then the solvent is evaporated down using the rotary evaporator, the reaction mixture is diluted with EtOAc and extracted twice with water. The organic phase is dried on MgSO$_4$, filtered, evaporated down using the rotary evaporator and the intermediate product Z-15a (HPLC-MS: t$_{Ret.}$=2.13 min) obtained is further reacted directly.

Nitro compound Z-15a (1.5 g, 6.07 mmol) is taken up in EtOH (30 mL), combined with NH$_4$Cl (163 mg, 3.03 mmol) and water (30 mL) and heated to 75° C. Then iron powder (3.39 g, 60.68 mmol) is added batchwise, the reaction mixture is stirred for 3 h and filtered to remove excess iron powder. The solvent is eliminated by distillation using the rotary evaporator, the residue is taken up in EtOAc and the organic phase is washed twice with sat. NaCl solution. The organic phase is dried on MgSO$_4$, filtered, evaporated down using the rotary evaporator and yields aniline G-3a (HPLC-MS: t$_{Ret.}$=1.95 min; MS (M+H)$^+$=218).

Analogously to this procedure further anilines G-3 are obtained from the corresponding G-1 intermediates/educts.

d) Procedure for Synthesising G-4a:

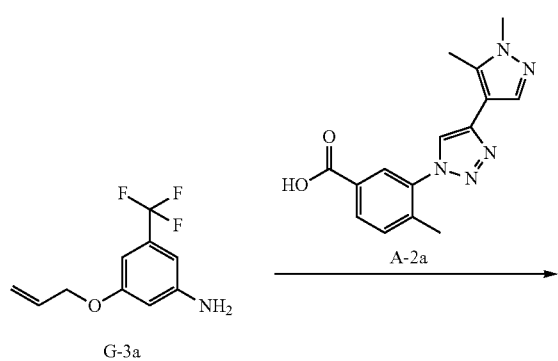

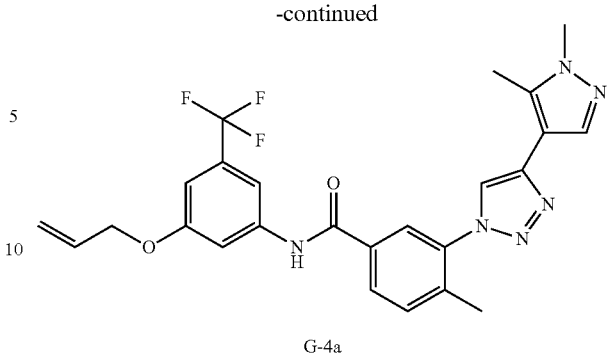

G-4a

Benzoic acid A-2a (1.5 g, 5.1 mmol) is taken up in 32 mL DCM and 10 mL THF, combined with oxalyl chloride (0.49 mL, 5.5 mmol) and one drop of DMF, stirred for 3 h at RT and then evaporated down using the rotary evaporator. The residue is taken up in 15 mL THF, cooled to 0° C. in the ice bath and combined with the aniline G-3a (1.21 g, 5.5 mmol) as well as DIPEA (2.6 mL, 15.1 mmol). The reaction mixture is stirred overnight at RT, evaporated down using the rotary evaporator and the residue is taken up in EtOAc. The organic phase is washed with water, dilute KHSO$_4$ solution and dilute NaHCO$_3$ solution, dried on MgSO$_4$ and evaporated down using the rotary evaporator. The product obtained G-4a (HPLC-MS: t$_{Ret.}$=2.06 min; MS (M+H)$^+$=497) is reacted further without any additional purification.

Analogously to this procedure further allylarylethers G-4 may be synthesised from the corresponding G-3 and A-2 intermediates/educts.

e) Procedure for Synthesising VIII-10:

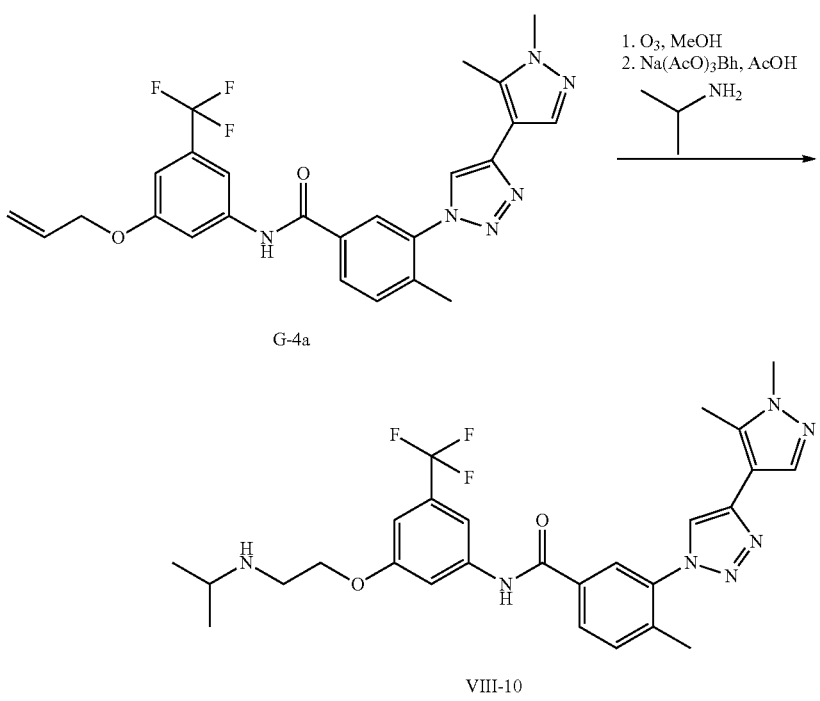

Allylaryl ether G-4a (1.0 g, 2.01 mmol) is taken up in 40 mL DCM and 4 mL MeOH and cooled to −78° C. Then a mixture of O$_3$/O$_2$ is piped through until the solution turns slightly blue. The reaction mixture is combined with dimethylsulphide (520 μL, 7.05 mmol), stirred overnight at RT, extracted with dilute NaHCO$_3$ solution, dried on MgSO$_4$ and concentrated by rotary evaporation. The intermediate product Z-16a obtained (HPLC-MS: t$_{Ret.}$=1.83 min; MS (M+H)$^+$=499) is further reacted directly.

The intermediate product Z-16a (100 mg, 0.2 mmol) is taken up in 3 ml DCM, combined with isopropylamine (15 mg, 0.20 mmol) and stirred for 15 min. Then glacial acetic acid (17 μL, 0.3 mmol) is added and Na(AcO)$_3$BH (64 mg, 0.3 mmol) is added batchwise. The reaction mixture is stirred overnight at RT, evaporated down using the rotary evaporator, the residue is taken up in a little DMF and purified by preparative HPLC. The product-containing fractions of VIII-10 (HPLC-MS: t$_{Ret.}$=2.20 min; MS (M+H)$^+$=554) are freeze-dried.

Analogously to the methods a) to e) described above Examples VIII-1 to VIII-10 (Table 6) or comparable further examples may be obtained from the corresponding precursors.

TABLE 6

Examples VIII-1 to VIII-10

| # | Structure | t$_{Ret.}$ (HPLC) [min] | MS (M + H)$^+$ |
|---|---|---|---|
| VIII-1 | 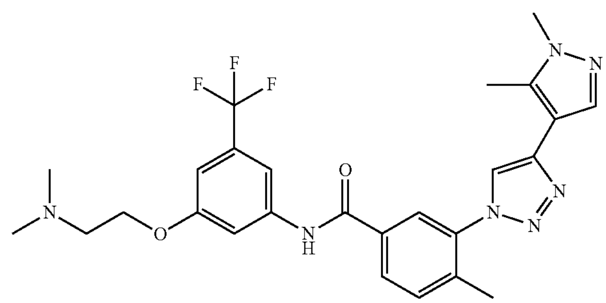 [SMILES: Cc1ccc(C(=O)Nc2cc(OCCN(C)C)cc(C(F)(F)F)c2)cc1-n1cc(-c2cnn(C)c2C)nn1] | 2.11 | 528 |
| VIII-2 | 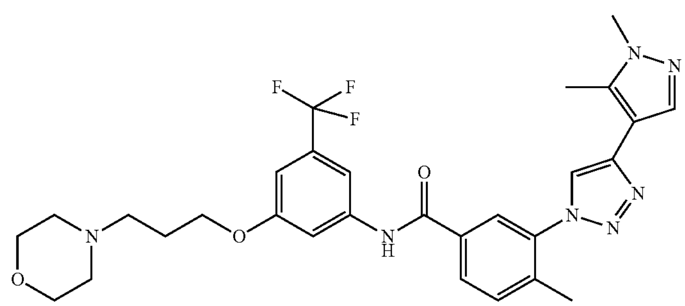 [SMILES: Cc1ccc(C(=O)Nc2cc(OCCCN3CCOCC3)cc(C(F)(F)F)c2)cc1-n1cc(-c2cnn(C)c2C)nn1] | 2.13 | 584 |
| VIII-3 | 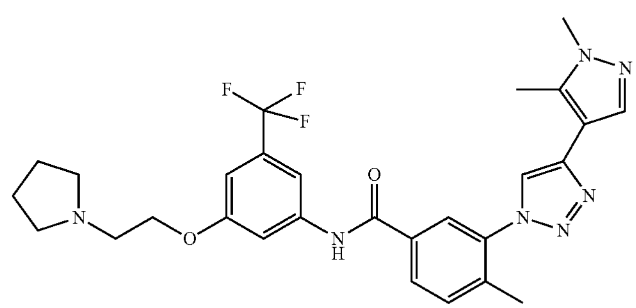 [SMILES: Cc1ccc(C(=O)Nc2cc(OCCN3CCCC3)cc(C(F)(F)F)c2)cc1-n1cc(-c2cnn(C)c2C)nn1] | 2.20 | 554 |

TABLE 6-continued

Examples VIII-1 to VIII-10

| # | Structure | t_Ret. (HPLC) [min] | MS (M + H)+ |
|---|---|---|---|
| VIII-4 | 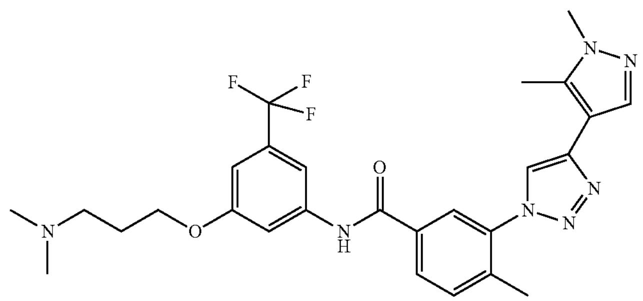 [SMILES: Cc1ccc(C(=O)Nc2cc(OCCCN(C)C)cc(C(F)(F)F)c2)cc1-n1cc(-c2cnn(C)c2C)nn1] | 2.21 | 542 |
| VIII-5 | 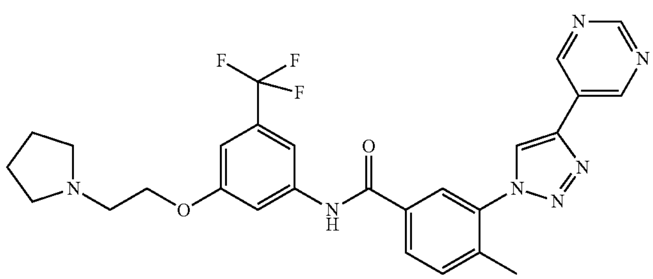 [SMILES: Cc1ccc(C(=O)Nc2cc(OCCN3CCCC3)cc(C(F)(F)F)c2)cc1-n1cc(-c2cncnc2)nn1] | 2.21 | 538 |
| VIII-6 | 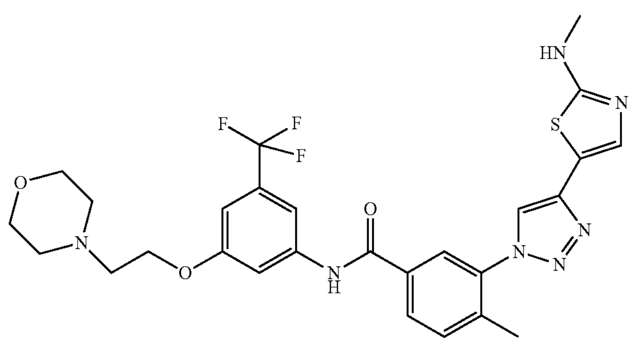 [SMILES: CNc1ncc(-c2cn(-c3cc(C(=O)Nc4cc(OCCN5CCOCC5)cc(C(F)(F)F)c4)ccc3C)nn2)s1] | 2.10 | 588 |
| VIII-7 | 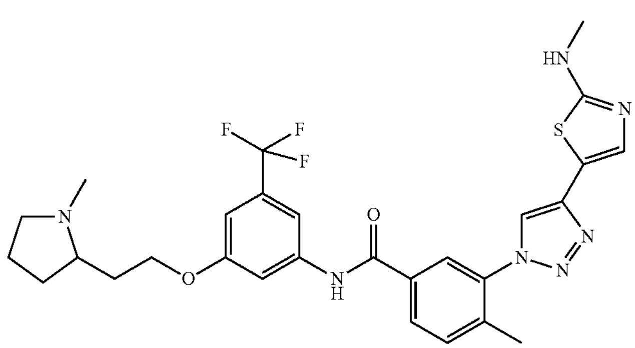 [SMILES: CNc1ncc(-c2cn(-c3cc(C(=O)Nc4cc(OCCC5CCCN5C)cc(C(F)(F)F)c4)ccc3C)nn2)s1] | 2.29 | 586 |

TABLE 6-continued
Examples VIII-1 to VIII-10
| # | Structure | $t_{Ret.}$ (HPLC) [min] | MS $(M + H)^+$ |
|---|---|---|---|
| VIII-8 | 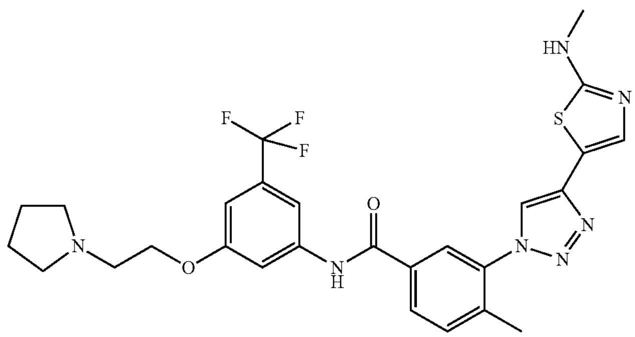 [SMILES: CNc1ncc(-c2cn(-c3cc(C(=O)Nc4cc(OCCN5CCCC5)cc(C(F)(F)F)c4)ccc3C)nn2)s1] | 2.25 | 572 |
| VIII-9 | 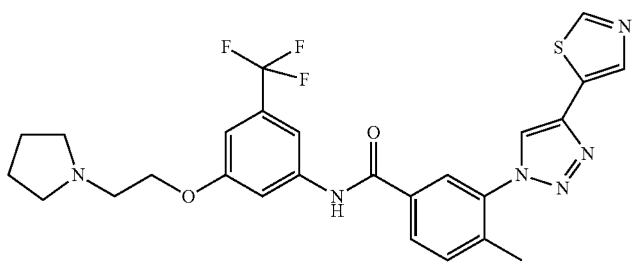 [SMILES: Cc1ccc(C(=O)Nc2cc(OCCN3CCCC3)cc(C(F)(F)F)c2)cc1-n1cc(-c2cncs2)nn1] | 2.31 | 543 |
| VIII-10 | 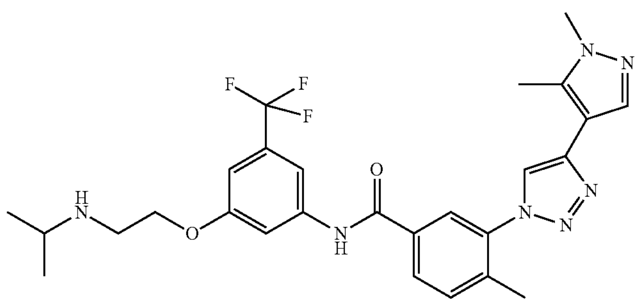 [SMILES: Cc1ccc(C(=O)Nc2cc(OCCNC(C)C)cc(C(F)(F)F)c2)cc1-n1cc(-c2cnn(C)c2C)nn1] | 2.14 | 542 |
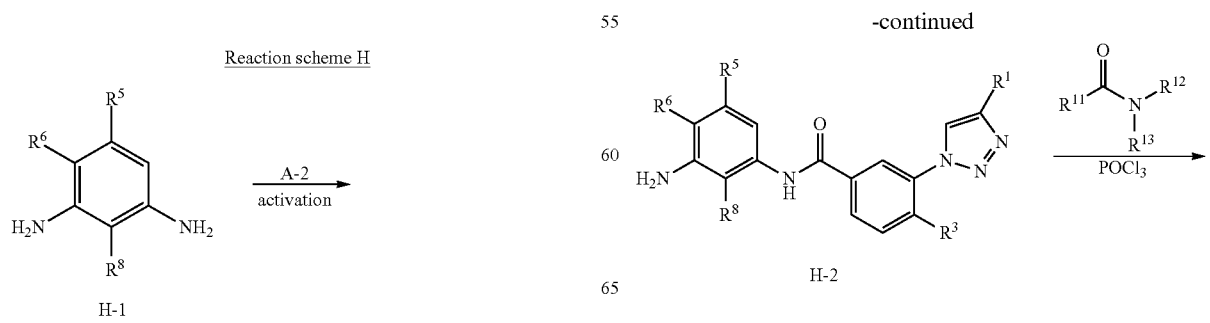

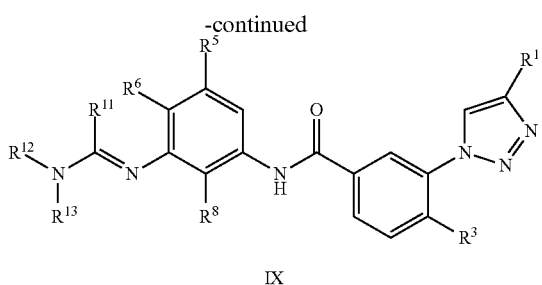

Example compounds of type IX (amidines in the in-position to the amide link→$R^7$) are synthesised from the anilines H-2 by amidine formation with the corresponding amide.

The amides used are activated using methods known from the literature with acid chlorides, such as e.g. phosphoryl chloride or oxalyl chloride, and the reaction is carried out in ethereal solvents, such as dioxane or THF, for example. If desired the amides used may also serve as solvents.

The anilines H-2 are synthesised by an amide coupling reaction of the 1,3-dianilines H-1 and the corresponding benzoic acids A-2 described hereinbefore. The dianilines used are commercially obtainable or may be synthesised using methods known from the literature.

To introduce amidine groups in the o- or p-position to the amide link (→$R^6$, $R^8$), the corresponding 1,2- or 1,4-dianilines may be used analogously instead of H-1.

a) Procedure for Synthesising H-2a:

Benzoic acid A-2a (2.0 g, 6.73 mmol) is taken up in 60 mL THF, combined with HATU (2.38 g, 7.40 mmol) and DIPEA (2.59 mL, 15.47 mmol), and stirred for 20 min at RT. Then 5-(trifluoromethyl)-benzene-1,3-diamine H-1a (1.18 g, 6.73 mmol) is added and the reaction mixture is stirred overnight at RT. The reaction mixture is concentrated by rotary evaporation, the crude product is taken up in DMF and purified by preparative HPLC. The product-containing fractions of H-2a (HPLC-MS: $t_{Ret.}$=1.81 min; MS $(M+H)^+$=456) are freeze-dried.

Analogously to this procedure further anilines H-2 may be synthesised from the corresponding H-1 and A-2 intermediates/educts.

b) Procedure for Synthesising IX-1

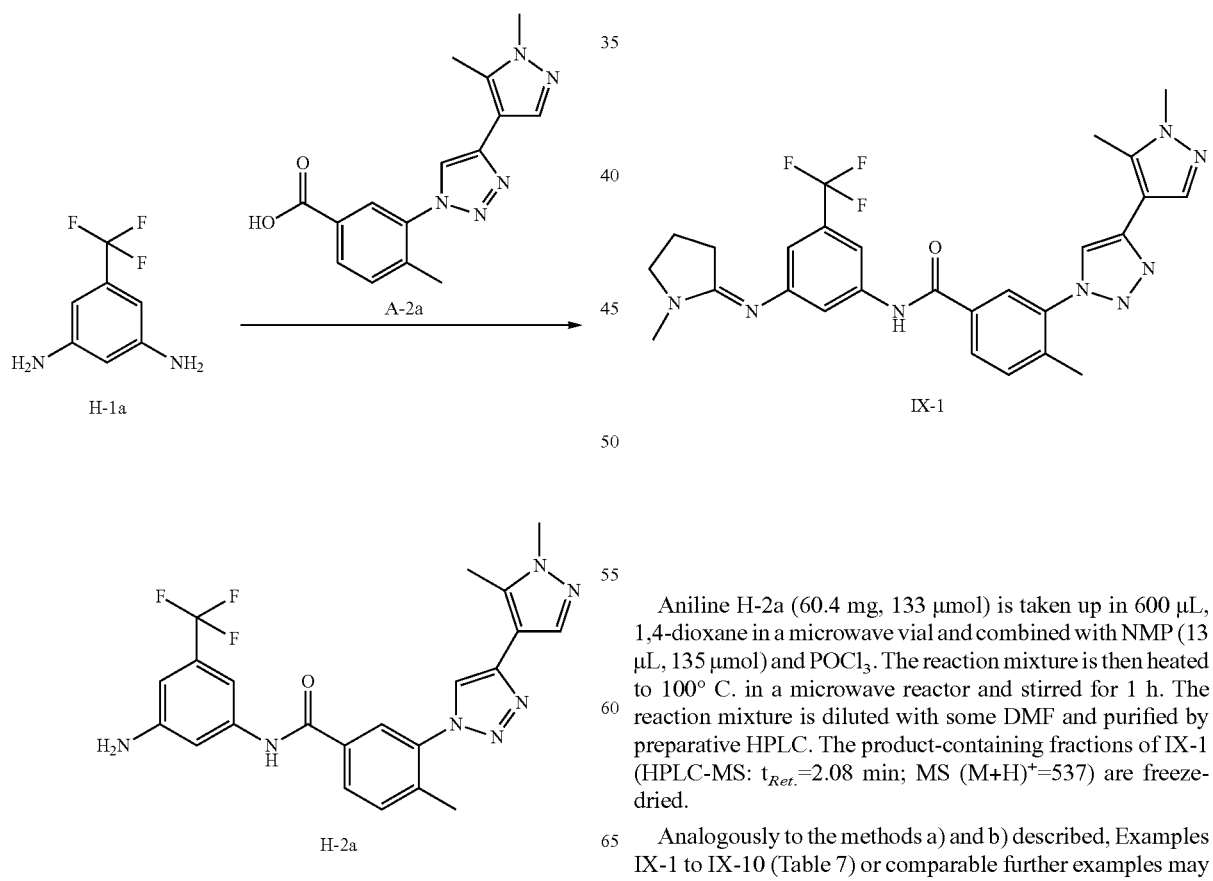

Aniline H-2a (60.4 mg, 133 μmol) is taken up in 600 μL, 1,4-dioxane in a microwave vial and combined with NMP (13 μL, 135 μmol) and POCl$_3$. The reaction mixture is then heated to 100° C. in a microwave reactor and stirred for 1 h. The reaction mixture is diluted with some DMF and purified by preparative HPLC. The product-containing fractions of IX-1 (HPLC-MS: $t_{Ret.}$=2.08 min; MS $(M+H)^+$=537) are freeze-dried.

Analogously to the methods a) and b) described, Examples IX-1 to IX-10 (Table 7) or comparable further examples may be obtained from the corresponding precursors.

TABLE 7

Examples IX-1 to IX-10
| # | Structure | t_Ret. (HPLC) [min] | MS (M + H)+ |
|---|---|---|---|
| IX-1 | 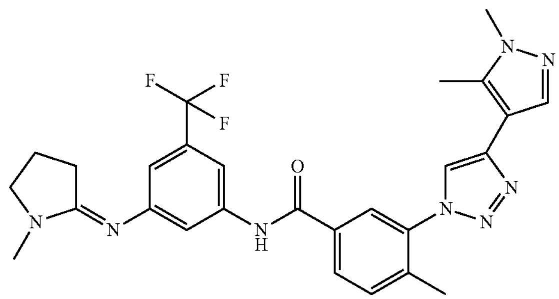 [SMILES: Cc1ccc(C(=O)Nc2cc(/N=C3\CCCN3C)cc(C(F)(F)F)c2)cc1-n1cc(-c2cnn(C)c2C)nn1] | 2.08 | 537 |
| IX-2 | 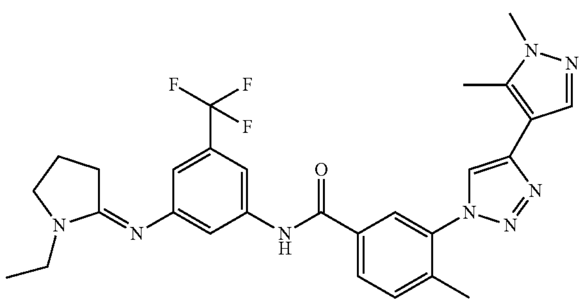 [SMILES: CCN1CCC/C1=N\c1cc(NC(=O)c2ccc(C)c(-n3cc(-c4cnn(C)c4C)nn3)c2)cc(C(F)(F)F)c1] | 2.09 | 551 |
| IX-3 | 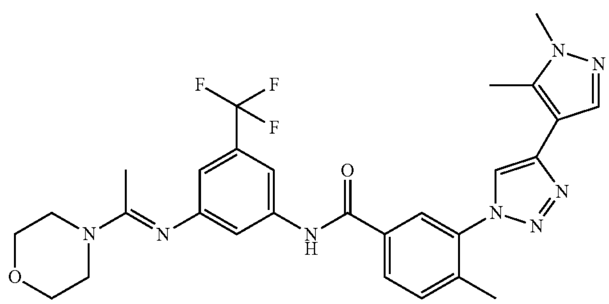 [SMILES: C/C(=N\c1cc(NC(=O)c2ccc(C)c(-n3cc(-c4cnn(C)c4C)nn3)c2)cc(C(F)(F)F)c1)N1CCOCC1] | 2.08 | 567 |
| IX-4 | 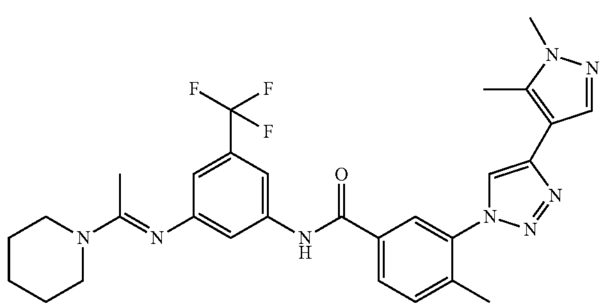 [SMILES: C/C(=N\c1cc(NC(=O)c2ccc(C)c(-n3cc(-c4cnn(C)c4C)nn3)c2)cc(C(F)(F)F)c1)N1CCCCC1] | 2.37 | 565 |

TABLE 7-continued

Examples IX-1 to IX-10
| # | Structure | t_Ret. (HPLC) [min] | MS (M + H)+ |
|---|---|---|---|
| IX-5 | 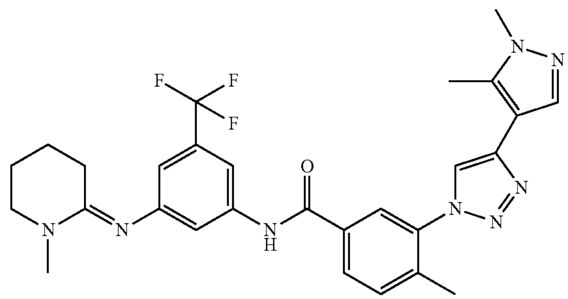 [SMILES: Cc1ccc(C(=O)Nc2cc(/N=C3\CCCCN3C)cc(C(F)(F)F)c2)cc1-n1cc(-c2cnn(C)c2C)nn1] | 2.23 | 551 |
| IX-6 | 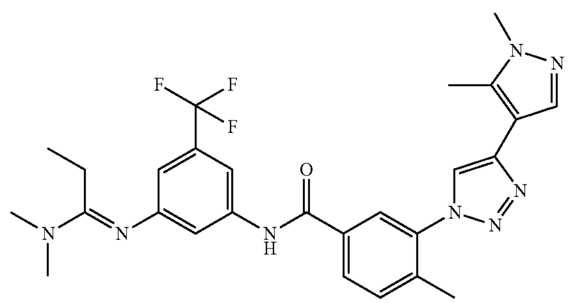 [SMILES: CC/C(=N\c1cc(NC(=O)c2ccc(C)c(-n3cc(-c4cnn(C)c4C)nn3)c2)cc(C(F)(F)F)c1)N(C)C] | 2.18 | 537 |
| IX-7 | 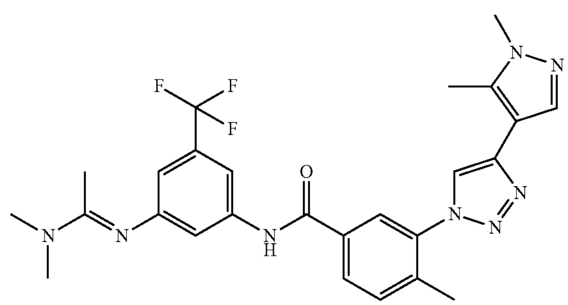 [SMILES: C/C(=N\c1cc(NC(=O)c2ccc(C)c(-n3cc(-c4cnn(C)c4C)nn3)c2)cc(C(F)(F)F)c1)N(C)C] | 2.13 | 525 |
| IX-8 | 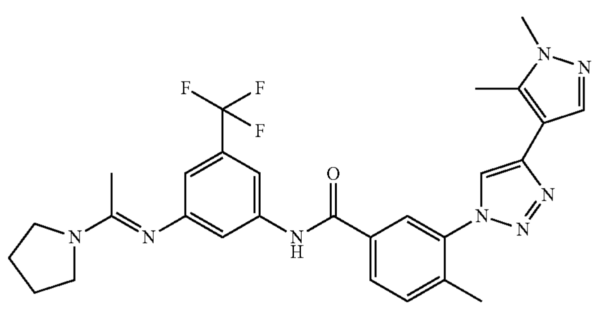 [SMILES: C/C(=N\c1cc(NC(=O)c2ccc(C)c(-n3cc(-c4cnn(C)c4C)nn3)c2)cc(C(F)(F)F)c1)N1CCCC1] | 2.17 | 551 |

TABLE 7-continued
Examples IX-1 to IX-10
| # | Structure | $t_{Ret.}$ (HPLC) [min] | MS (M + H)⁺ |
|---|---|---|---|
| IX-9 | 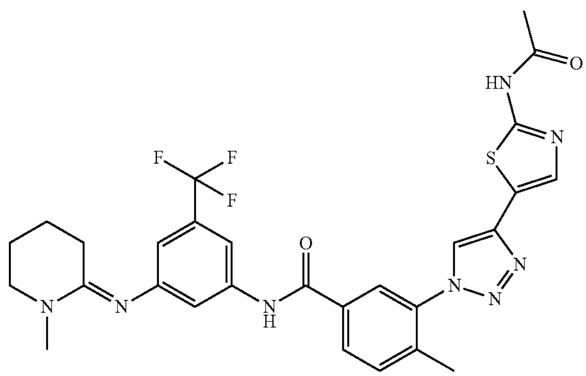 [SMILES: CC(=O)Nc1ncc(-c2cn(-c3cc(C(=O)Nc4cc(/N=C5\CCCCN5C)cc(C(F)(F)F)c4)ccc3C)nn2)s1] | 2.20 | 597 |
| IX-10 | 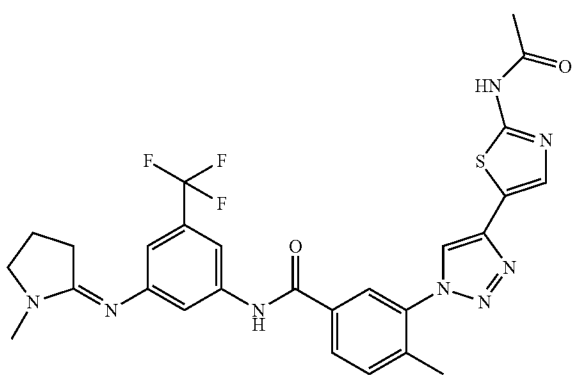 [SMILES: CC(=O)Nc1ncc(-c2cn(-c3cc(C(=O)Nc4cc(/N=C5\CCCN5C)cc(C(F)(F)F)c4)ccc3C)nn2)s1] | 2.08 | 583 |
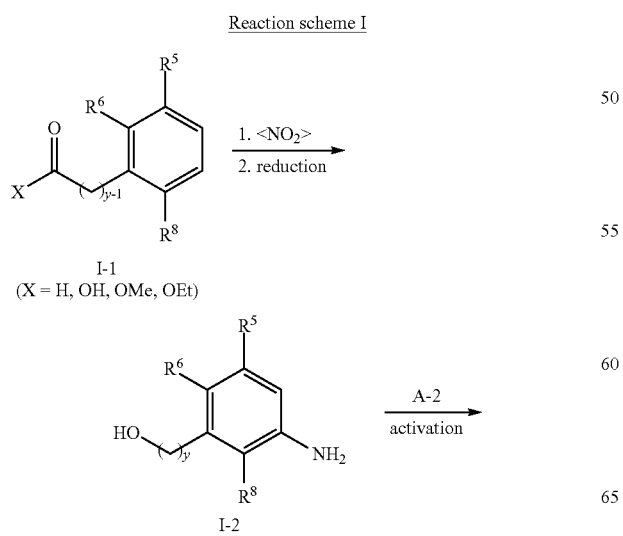
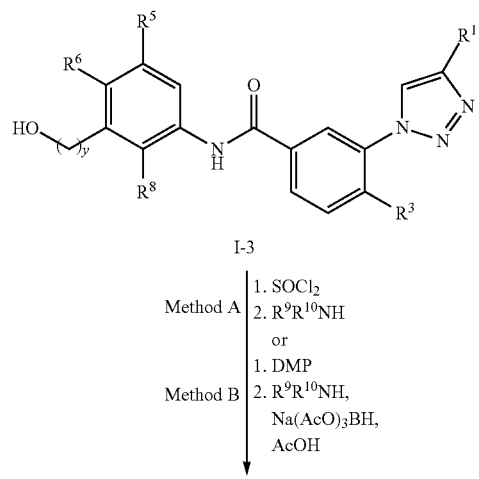

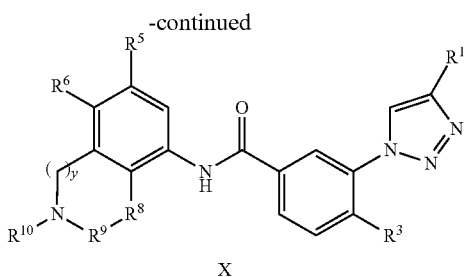

X

Example compounds of type X (amines with Cy linkers in the m-position to the amide link→$R^7$) are obtained from compounds I-3 either by substitution of the corresponding phenylalkyl chloride by means of an amine $R^9R^{10}NH$ or by reductive amination of a corresponding aldehyde with an amine $R^9R^{10}NH$. In the former case the phenylalkyl-alcohols I-3 are reacted by means of thionyl chloride using methods known from the literature to obtain the corresponding chlorides. In the latter case the phenylalkylalcohols I-3 may be oxidised e.g. with DMP, $MnO_2$ or other common oxidising agents to form the corresponding aldehydes and then reacted in an acetic acid medium with $Na(OAc)_3BH$ or $Na(CN)BH_3$ and an amine $R^9R^{10}NH$ using methods known from the literature to form compounds of type X. The amines $R^9R^{10}NH$ used are commercially obtainable or are synthesised using methods known from the literature.

The phenylalkylalcohols I-3 are synthesised by an amide coupling reaction of the anilines I-2 (in order to introduce the group $R^2$) and the corresponding benzoic acid A-2 described hereinbefore. The anilines I-2 used are commercially obtainable or are synthesised using methods known from the literature from the corresponding carbonyl compounds I-1, e.g. phenylacetic acids, by nitrogenation and subsequent reductions via various intermediate products Z.

a) Procedure for Synthesising I-2a:

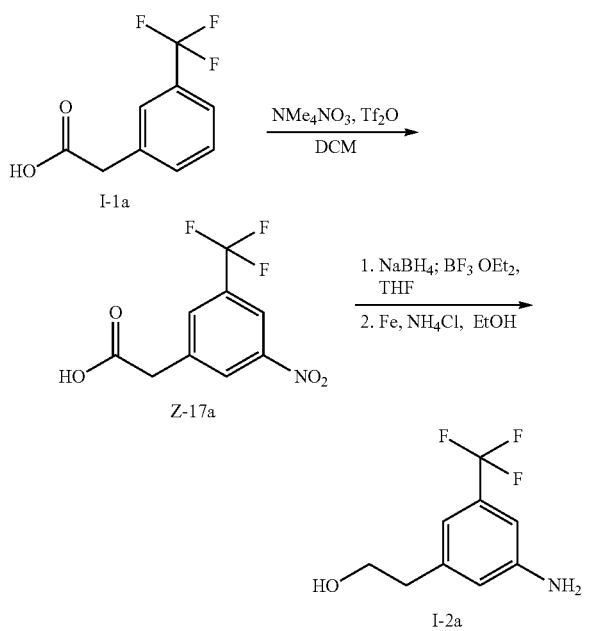

3-(trifluoromethyl)-phenylacetic acid I-1a (8.0 g, 36.7 mmol) and tetramethylammonium nitrate (7.47 g, 54.87 mmol) are taken up in DCM (90 mL), combined with trifluorosulphonic acid anhydride (15.52 g, 55.0 mmol) in 30 mL DCM and stirred for 2 h at RT as well as for a further 12 h at 45° C. The reaction mixture is neutralised with sat. $NaHCO_3$ solution, the organic phase is washed with water, dried on $Na_2SO_4$, filtered and evaporated down using the rotary evaporator. The reaction mixture is further reacted directly as a mixture of regioisomers, including the intermediate product Z-17a (HPLC-MS: $t_{Ret.}$=1.92/1.96 min; MS $(M-H)^+$=262).

The mixture of regioisomers containing Z-17a (1.04 g, 3.50 mmol) is taken up in THF (10 mL), $NaBH_4$ (198 mg, 5.23 mmol) is added batchwise, the mixture is cooled to 0° C., boron trifluoride etherate (627 μL, 5.41 mmol) is added dropwise and the mixture is stirred overnight at RT. After cooling to 0° C. it is combined with 10 mL 1 M NaOH solution with stirring, the THF is eliminated using the rotary evaporator and the crude product is extracted with EtOAc. The organic phases collected are washed with sat. NaCl solution, dried on $Na_2SO_4$, filtered and evaporated down using the rotary evaporator. The residue is purified by silica gel chromatography (HPLC-MS: $t_{Ret.}$=1.74 min) and the isomerically pure phenylethylalcohol Z-18a is further reacted directly.

Intermediate product Z-18a (100 mg, 0.425 mmol) is taken up in EtOH (2.5 mL), combined with $NH_4Cl$ (11 mg, 0.211 mmol) and water (2.5 mL) and heated to 75° C. Then iron powder (235 mg, 4.21 mmol) is added batchwise, the reaction mixture is stirred for 1 h and the excess iron powder is filtered off. The solvent is eliminated by distillation using the rotary evaporator, the residue is taken up in EtOAc and the organic phase is washed twice with sat. NaCl solution. The organic phase is dried on $MgSO_4$, filtered and evaporated down using the rotary evaporator and yields product I-2a (HPLC-MS: $t_{Ret.}$=1.54 min; MS $(M+H)^+$=206).

Analogously to this procedure further anilines I-2 may be synthesised from the corresponding I-1 intermediates/educts.

b) Procedure for Synthesising I-3a:

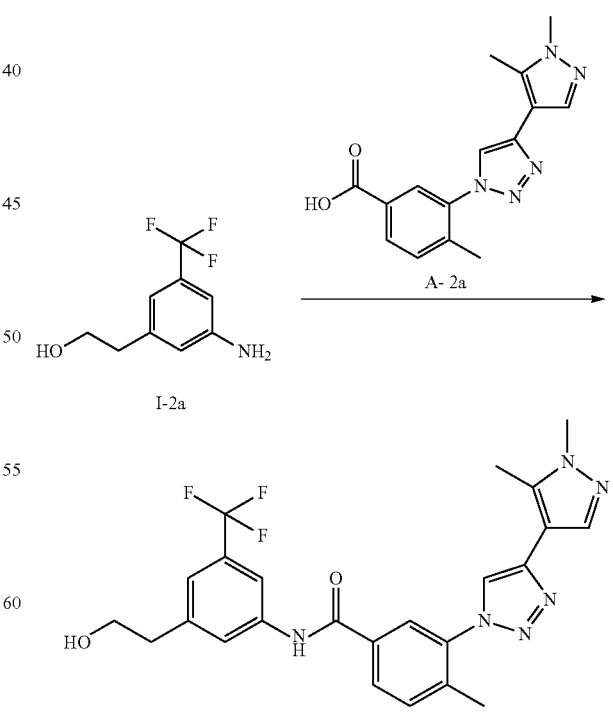

Benzoic acid A-2a (680 mg, 2.29 mmol) is taken up in 4 mL DCM and 4 mL THF, combined with oxalyl chloride (0.3 mL, 3.5 mmol) and one drop of DMF, stirred for 1 h at RT and then evaporated down using the rotary evaporator. The residue is taken up in 10 mL DCM and combined with the aniline I-2a (492 mg, 2.40 mmol) as well as DIPEA (0.7 mL, 4 mmol). The reaction mixture is stirred overnight at RT, evaporated down using the rotary evaporator, the residue is taken up in DMF and purified by preparative HPLC. The product-containing fractions of I-3a (HPLC-MS: $t_{Ret.}$=1.79 min; MS $(M+H)^+$=485) are freeze-dried.

Analogously to this procedure further phenylalkylalcohols I-3 are obtained from the corresponding I-2 intermediates/educts.

c) Procedure for Synthesising X-1 (Oxidation-reductive Amination, Method B):

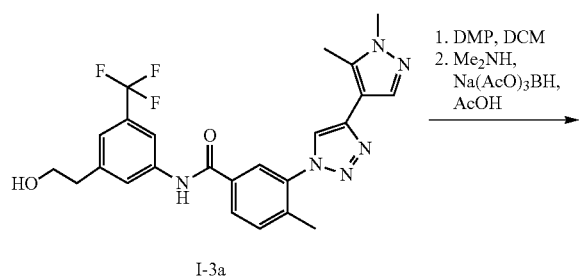

I-3a

1. DMP, DCM
2. Me$_2$NH, Na(AcO)$_3$BH, AcOH

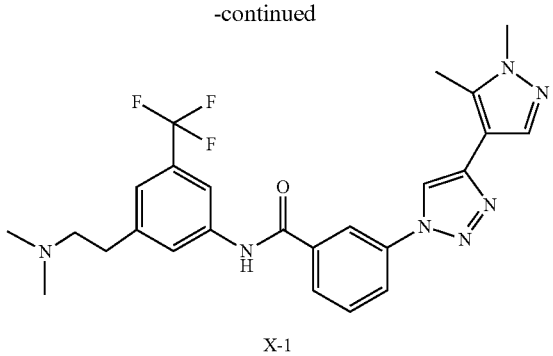

X-1

Phenylalkylalcohol I-3a (226 mg, 0.467 mmol) is taken up in DCM, combined at RT with DMP (237 mg, 0.558 mmol) and stirred for 1.5 h. Then 1 g Na$_2$S$_2$O$_3$ and 1 g NaHCO$_3$ dissolved in 10 mL water are added to the solution and the reaction mixture is stirred for 20 min at RT. The organic phase is separated off and the aqueous phase is extracted twice more with DCM. The combined organic phases are again washed with sat. NaHCO$_3$ solution, dried on MgSO$_4$, filtered off, evaporated down using the rotary evaporator and the intermediate product Z-19a is ob, which is further reacted directly.

Z-19a (109 mg, 0.226 mmol) is taken up in 3 ml DCM, combined with dimethylamine (125 μL, 2.0 M in THF, 0.25 mmol) and stirred for 15 min. Then glacial acetic acid (20 μL, 0.34 mmol) is added and Na(AcO)$_3$BH (72 mg, 0.34 mmol) is added batchwise. The reaction mixture is stirred overnight at RT, evaporated down using the rotary evaporator, the residue is taken up in a little DMF and purified by preparative HPLC. The product-containing fractions of X-1 (HPLC-MS: $t_{Ret.}$=2.15 min; MS $(M+H)^+$=512) are freeze-dried.

Analogously to methods a) to c) described, Examples X-1 to X-6 (Table 8) or comparable further examples may be obtained from the corresponding precursors.

TABLE 8

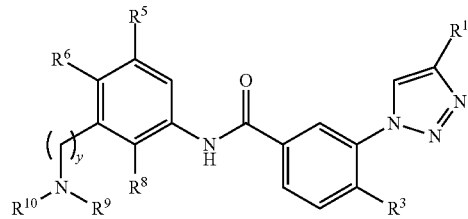

Examples X-1 to X-6

| # | Structure | $t_{Ret.}$ (HPLC) [min] | MS (M + H)$^+$ |
|---|---|---|---|
| X-1 | 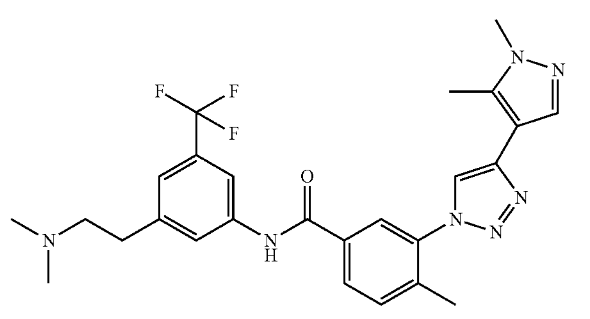 [SMILES: Cc1ccc(C(=O)Nc2cc(CCN(C)C)cc(C(F)(F)F)c2)cc1-n1cc(-c2cnn(C)c2C)nn1] | 2.15 | 512 |

TABLE 8-continued

Examples X-1 to X-6

| # | Structure | t$_{Ret.}$ (HPLC) [min] | MS (M + H)$^+$ |
|---|---|---|---|
| X-2 | 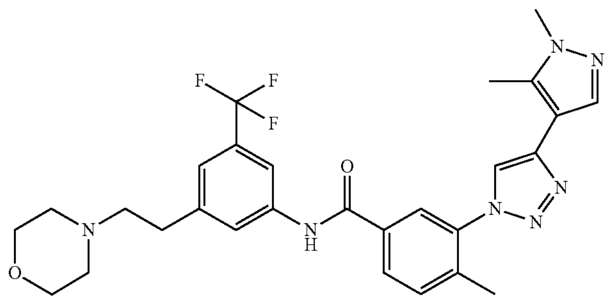 [SMILES: Cc1ccc(C(=O)Nc2cc(CCN3CCOCC3)cc(C(F)(F)F)c2)cc1-n1cc(-c2cnn(C)c2C)nn1] | 1.55 | 554 |
| X-3 | 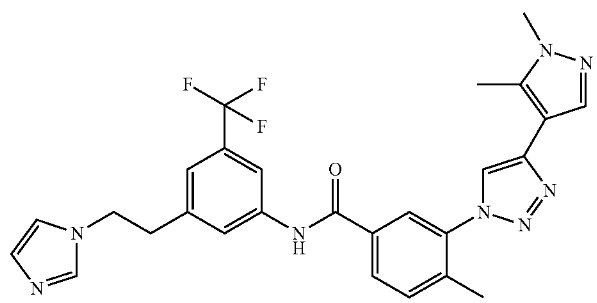 [SMILES: Cc1ccc(C(=O)Nc2cc(CCn3ccnc3)cc(C(F)(F)F)c2)cc1-n1cc(-c2cnn(C)c2C)nn1] | 1.62 | 535 |
| X-4 | 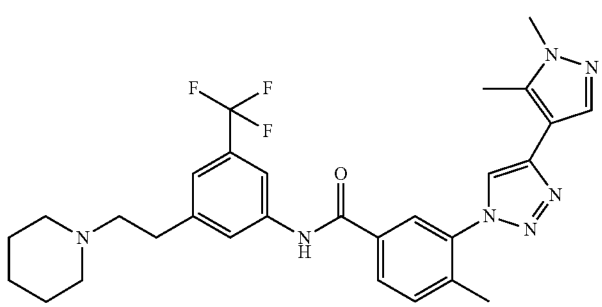 [SMILES: Cc1ccc(C(=O)Nc2cc(CCN3CCCCC3)cc(C(F)(F)F)c2)cc1-n1cc(-c2cnn(C)c2C)nn1] | 2.30 | 552 |
| X-5 | 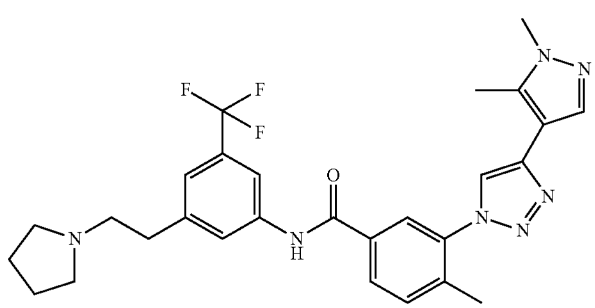 [SMILES: Cc1ccc(C(=O)Nc2cc(CCN3CCCC3)cc(C(F)(F)F)c2)cc1-n1cc(-c2cnn(C)c2C)nn1] | 2.18 | 538 |

TABLE 8-continued

Examples X-1 to X-6

| # | Structure | $t_{Ret.}$ (HPLC) [min] | MS (M + H)$^+$ |
|---|---|---|---|
| X-6 | 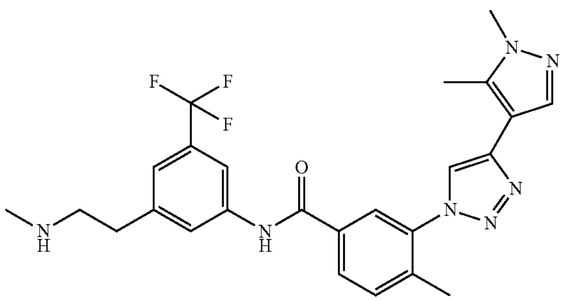 [SMILES: CNCCc1cc(NC(=O)c2ccc(C)c(-n3cc(-c4cnn(C)c4C)nn3)c2)cc(C(F)(F)F)c1] | 2.00 | 498 |

The introduction of an aminoalkyl side chain into the position of the group R$^7$ in reaction scheme I can theoretically also be applied to an introduction into the position of the group R$^6$ and R$^8$ if carbonyl compounds whose carbonyl functionality is in position R$^6$ or R$^8$ are used as educt, analogously to I-1.

Reaction scheme J

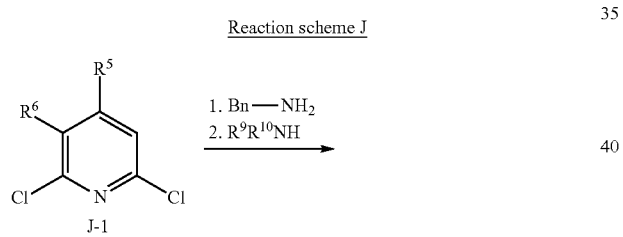

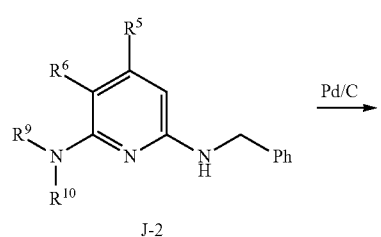

Example compounds of type XI are synthesised from the diaminopyridines J-3 by an amide coupling reaction with the corresponding benzoic acids A-2 described hereinbefore. The diaminopyridines J-3 used are commercially obtainable or are synthesised using methods known from the literature from the corresponding dichloropyridines J-1 by twofold nucleophilic aromatic substitution with amines R$^9$R$^{10}$NH and protected ammonia equivalents (e.g. benzylamine) via the intermediate stages Z-20 and J-2 and subsequent selective cleaving of protective groups. The nucleophilic aromatic substitutions are carried out in common solvents, such as e.g. NMP, DMSO or DMF, with a base, such as pyridine or DIPEA, for example. The amines R$^9$R$^{10}$NH used are commercially obtainable or are synthesised using methods known from the literature.

a) Procedure for Synthesising J-3a:

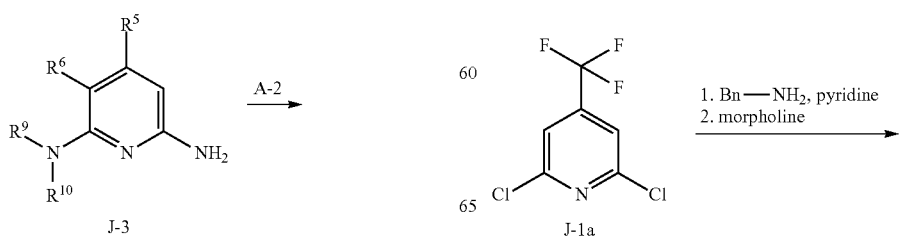

-continued

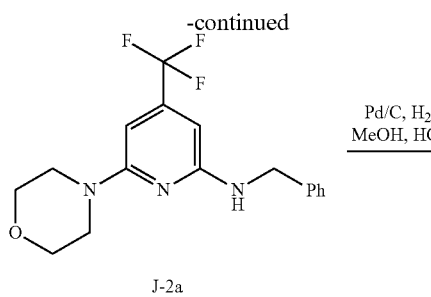

J-2a

Pd/C, H₂
MeOH, HCl
→

J-3a 2,6-dichloro-4-trifluoromethylpyridine J-1a (1.51 g, 6.99 mmol) is taken up in 1 mL pyridine, combined with benzylamine (1.0 mL, 9.16 mmol) and stirred overnight at 45° C. The reaction mixture is diluted with water, combined with 2 N HCl and extracted three times with EtOAc. The organic phases collected are dried on Na₂SO₄, filtered, evaporated down using the rotary evaporator and the intermediate product Z-20a obtained (HPLC-MS: $t_{Ret.}$=2.44 min; MS $(M+H)^+$=287) is further reacted directly.

Z-20a (165 mg, 0.573 mmol) is taken up in morpholine (1.02 g, 11.5 mmol) and heated to 160° C. for 1 h in a microwave reactor. The precipitate is filtered off and the filtrate is purified by preparative HPLC. The product-containing fractions of J-2a (HPLC-MS: $t_{Ret.}$=2.40 min; MS $(M+H)^+$=338) are freeze-dried.

Diaminopyridine J-2a (95 mg, 0.282 mmol) is taken up in 5 mL MeOH and 1 mL 1 N HCl and transferred into a hydrogenating reactor. Pd/C (20 mg) is added and the mixture is stirred for 18 h under an H₂ atmosphere (4 bar) at RT. The reaction mixture is filtered through Celite, the filtrate is evaporated down using the rotary evaporator, J-3a is lyophilised from dioxane/HCl (HPLC-MS: $t_{Ret.}$=1.74 min; MS $(M+H)^+$=248) and further reacted directly.

Analogously to this procedure further diaminopyridines J-3 may be synthesised from the corresponding K-1-or K-2 intermediates/educts.

b) Procedure for Synthesising XI-1:

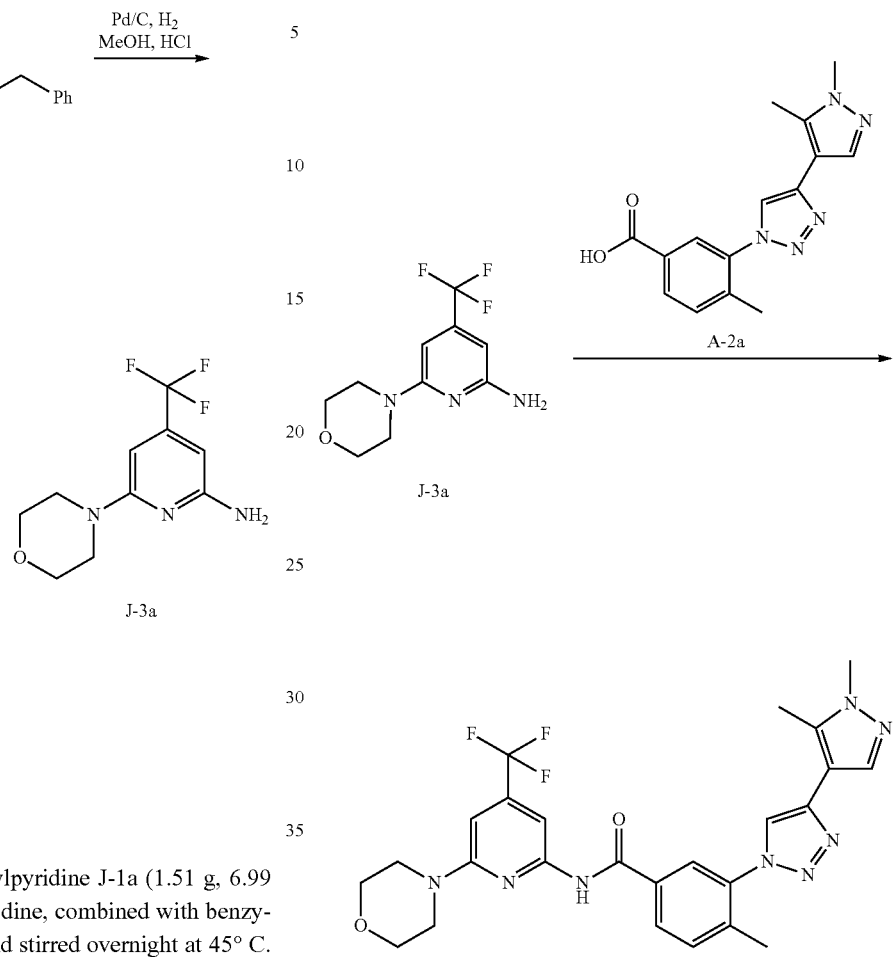

Benzoic acid A-2a (48 mg, 0.16 mmol) is taken up in 2 mL DCM and 2 mL THF, combined with 1 mL thionyl chloride, stirred for 3 h at RT and then evaporated down using the rotary evaporator. The residue is taken up in 3 ml DCM and combined with the diaminopyridine J-3a (100 mg, 0.41 mmol) and pyridine (100 µL, 0.78 mmol). The reaction mixture is stirred overnight at RT, evaporated down using the rotary evaporator, the residue is taken up in DMF and purified by preparative HPLC. The product-containing fractions of XI-1 (HPLC-MS: $t_{Ret.}$=2.31 min; MS $(M+H)^+$=527) are freeze-dried.

Analogously to methods a) and b) described, Examples XI-1 to XI-5 (Table 9) or comparable further examples may be obtained from the corresponding precursors, which are either commercially obtainable or are prepared using methods known from the literature.

TABLE 9
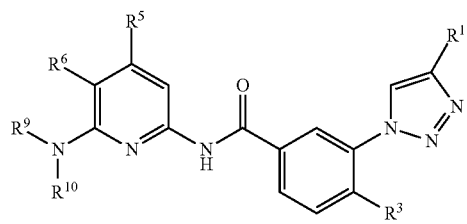
Examples XI-1 to XI-5
| # | Structure | t$_{Ret.}$ (HPLC) [min] | MS (M + H)$^+$ |
|---|---|---|---|
| XI-1 | 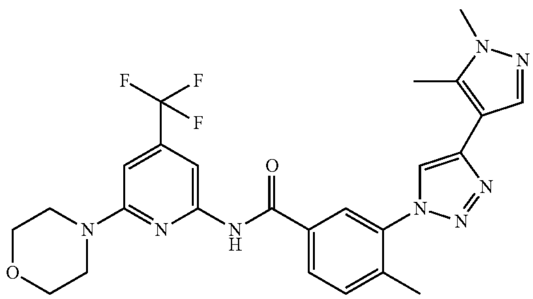 [SMILES: Cc1ccc(C(=O)Nc2cc(C(F)(F)F)cc(N3CCOCC3)n2)cc1-n1cc(-c2cnn(C)c2C)nn1] | 2.16 | 527 |
| XI-2 | 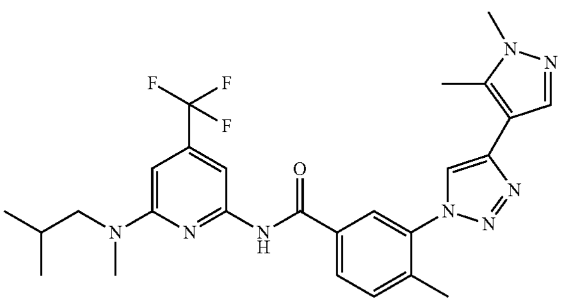 [SMILES: Cc1ccc(C(=O)Nc2cc(C(F)(F)F)cc(N(C)CC(C)C)n2)cc1-n1cc(-c2cnn(C)c2C)nn1] | 2.51 | 527 |
| XI-3 | 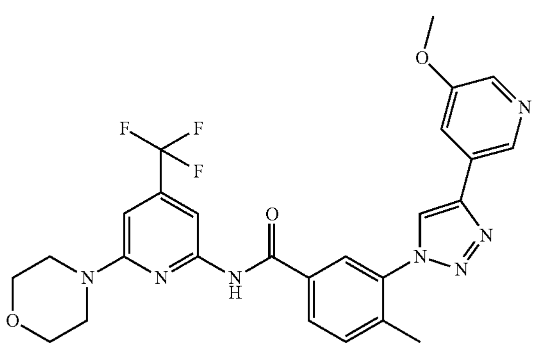 [SMILES: COc1cncc(-c2cn(-c3cc(C(=O)Nc4cc(C(F)(F)F)cc(N5CCOCC5)n4)ccc3C)nn2)c1] | 2.26 | 540 |
| XI-4 | 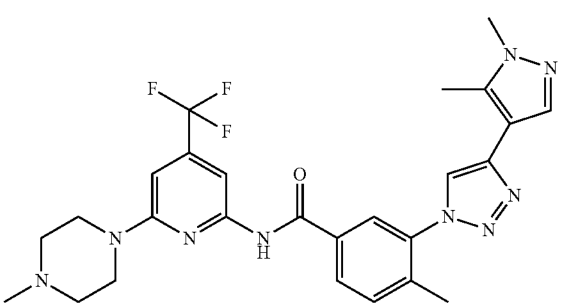 [SMILES: Cc1ccc(C(=O)Nc2cc(C(F)(F)F)cc(N3CCN(C)CC3)n2)cc1-n1cc(-c2cnn(C)c2C)nn1] | 2.13 | 540 |

TABLE 9-continued

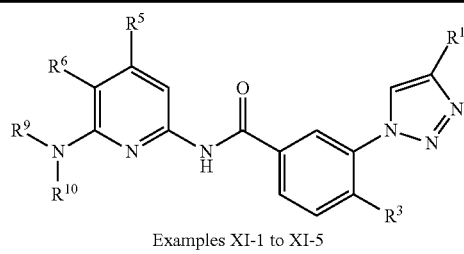

Examples XI-1 to XI-5

| # | Structure | $t_{Ret.}$ (HPLC) [min] | MS $(M + H)^+$ |
|---|---|---|---|
| XI-5 | 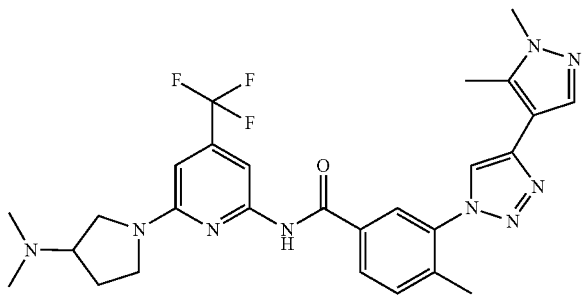 [SMILES: Cc1ccc(C(=O)Nc2cc(C(F)(F)F)cc(N3CCC(N(C)C)C3)n2)cc1-n1cc(-c2cnn(C)c2C)nn1] | 2.18 | 554 |

Reaction scheme K

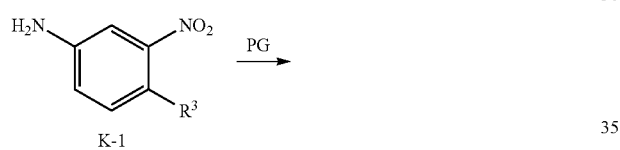

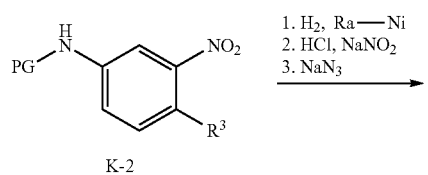

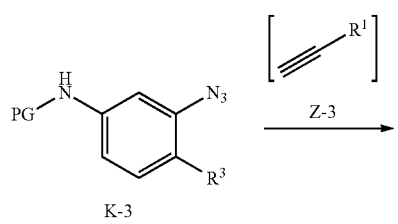

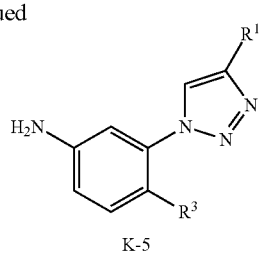

Anilines K-5 are obtained using methods known from the literature, by reacting protected m-nitroanilines K-2 by reduction of the nitro group, diazotisation in hydrochloric NaNO$_2$ solution and reaction with sodium azide via the intermediate product Z-21 to form the aromatic azides K-3. The protected nitroanilines K-2 are obtained from the free nitroanilines K-1 by introducing the corresponding protective group (PG). The protective groups used may be any amino protective groups that are stable under the following reaction conditions and are known for example from peptide synthesis, preferably the group Cbz (introduced using the acid chloride Cbz-Cl). The cycloaddition (in order to introduce the group R$^1$) of the azides K-3 is carried out by methods known from the literature using a corresponding alkyne Z-3, CuSO$_4$ and sodium ascorbate and K-4. The protected anilines K-4 are deprotected in the last step by cleaving the protective group under the respective conditions known from the literature to obtain the free aniline K-5 (Cbz→Pd/C, H$_2$).

The alkynes Z-3 used to introduce the groups R$^1$ are either commercially obtainable or are prepared from aldehydes Z-2 that are commercially obtainable or synthesised by methods known from the literature, e.g. using the Bestmann-Ohira reagent. In addition, the alkynes used may also be prepared from the aryl bromides and iodides and trimethylsilylacetylene that are commercially obtainable or synthesised using methods known from the literature by palladium-catalysed cross-coupling (Sonogashira) and subsequent cleaving of the silyl protective group. Experimental procedures for the incorporation of substituted imidazoles as groups $R^1$ (via halo imidazoles) are disclosed in WO 2007/121390 and references cited therein. Analogously, other heteroaryls can be incorporated. Sonogashira couplings with halo pyridyls, halo imidazolyls, halo pyrazolyls, halo thiazolyls, halo pyrimidyls result in intermediates like e.g. 2-cyclopropyl-1-methyl-5-trimethylsilanylethynyl-1H-imidazole, 2-cyclopropyl-1-methyl-4-trimethylsilanylethynyl-1H-imidazole, 2-trimethylsilanylethynyl-pyridine, 5-trimethylsilanylethynyl-pyrimidine, 1,5-dimethyl-4-trimethylsilanylethynyl-1H-pyrazole and 5-trimethylsilanylethynyl-thiazole.

The anilines K-5 that are obtainable directly by these reaction methods may then be further modified in $R^1$ in a manner known from the literature or analogously to the literature to obtain further anilines K-5. Thus, for example, the groups $R^1$ of directly obtainable anilines K-5, consisting of a halogen- or amino-substituted heteroaryl, can be modified by reactions of substitution (at the heteroaryl itself), alkylation, acylation or addition (at the amino group of the heteroaryls). In particular, transition metal-catalysed cross-coupling reactions (Ullmann, Buchwald-Hartwig, Sonogashira etc.) may be carried out on heteroarylbromides in $R^1$ in order to introduce various substituents.

Procedure for Synthesising K-3a

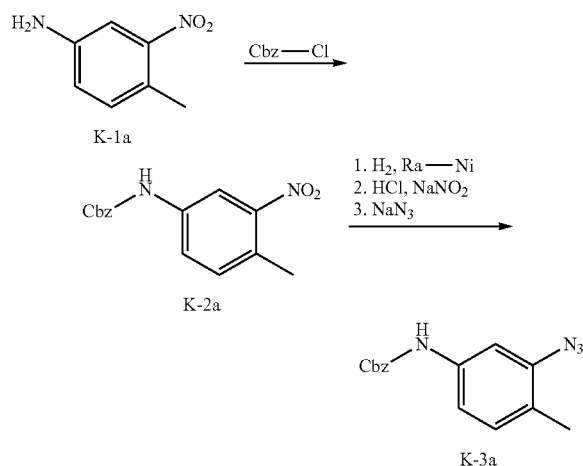

4-methyl-3-nitroaniline K-1a (51.0 g, 335 mmol) is taken up in THF (300 mL), combined with DIPEA (73.6 mL, 402 mmol), benzyl chloroformate (52.4 mL, 369 mmol) dissolved in 50 mL THF is added while cooling with ice and the mixture is stirred overnight at RT. The reaction mixture is mixed with water and the THF is eliminated using the rotary evaporator. The crude product is filtered off, recrystallised from methanol/water (25:1) and K-2a is obtained and further reacted directly (HPLC-MS: $t_{Ret.}$=2.25 min; MS (M–H)$^+$=285).

The protected nitroaniline K-2a (5.00 g, 17.5 mmol) is taken up in methanol (30 mL), mixed with Raney nickel (500 mg) and stirred under a hydrogen pressure of 8 bar for 18 h at RT. The reaction mixture is then filtered through a silica gel frit, the filtrate is evaporated down, recrystallised from n-pentane and the monoprotected phenylenediamine Z-21a is obtained and further reacted directly (HPLC-MS: $t_{Ret.}$=1.86 min; MS (M+H)$^+$=257).

The protected phenylenediamine Z-21a (3.90 g, 15.2 mmol) is taken up in 2N HCl (300 mL), cooled to 0° C., combined with a solution of sodium nitrite (1.58 g, 22.8 mmol) in 50 mL water and stirred for 30 min. Then a solution of sodium azide (2.18 g, 33.5 mmol) in 30 mL water is added dropwise, after the addition is complete the mixture is stirred for another 30 min and then heated to RT. The precipitate of K-3a formed is filtered off, washed repeatedly with water and then freeze-dried (HPLC-MS: $t_{Ret.}$=2.35 min; MS (M–H)$^+$=281).

Analogously to this procedure further azides K-3 are obtained from the corresponding 3-nitroanilines K-1.

Procedure for Synthesising K-4a

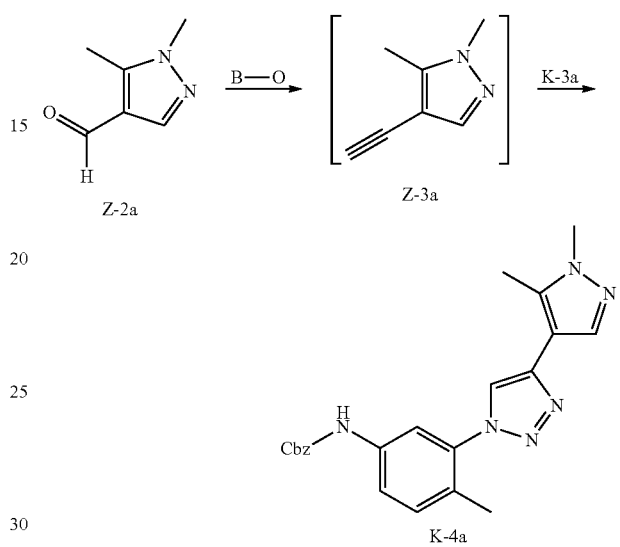

1,5-dimethyl-1H-pyrazole-4-carbaldehyde Z-2a (2.8 g, 23.0 mmol) and the Bestmann-Ohira reagent (B-O, 6.0 g, 31.0 mmol) are placed in MeOH (100 mL) and combined with potassium carbonate (6.27 g, 45.3 mmol). After 12 h stirring at RT the azide K-4a (4.0 g, 14.2 mmol) is added and stirred in. 16 mL of a 1 M sodium ascorbate sln. (16 mmol) and 28.4 mL of a 0.1M CuSO$_4$ sln. (2.84 mmol) are added and the mixture is stirred for 3 d at 40° C. For working up the mixture is evaporated down under reduced pressure, mixed with water and adjusted to an acid pH by the addition of 2M HCl sln. The mixture is then extracted several times with EE, the combined organic phases are dried on MgSO$_4$, filtered and evaporated down under reduced pressure. K-4a (HPLC-MS: $t_{Ret.}$=2.01 min; MS (M+H)$^+$=403) is obtained by chromatographic purification by silica gel chromatography.

Analogously to this procedure other protected anilines K-4 are obtained from the corresponding K-3- or Z-2 intermediates/educts.

Procedure for Synthesising K-5a

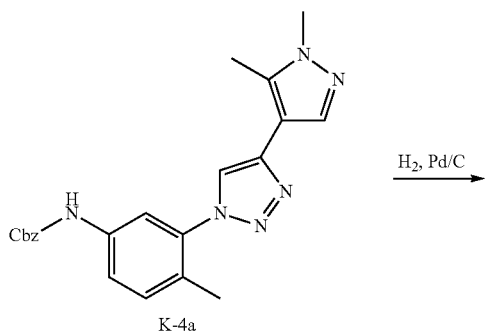

-continued

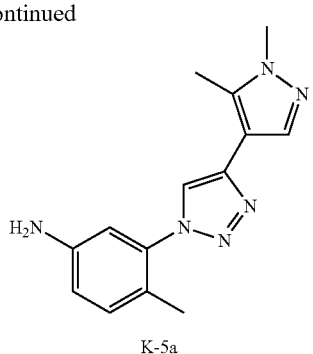

K-5a

The Cbz-protected aniline K-4a (4.0 g, 9.94 mmol) is taken up in 100 mL THF, mixed with Pd/C (2.0 g) and water (2 mL) and stirred overnight under a hydrogen pressure of 8 bar at 60° C. The reaction mixture is filtered through a silica gel frit, the filtrate is evaporated down and the residue of K-5a is taken up in diethyl ether, filtered off and dried (HPLC-MS: $t_{Ret.}$=1.46 min; MS (M+H)$^+$=269).

The anilines K-5 described are used as synthesis components in all the following reaction sequences (schemes L and M) and in each case are coupled to benzoic acids (introduction of $R^2$). These amide couplings are carried out using methods known from the literature with the aid of common coupling reagents, such as e.g. HATU or TBTU, or the respective benzoic acids are activated by thionyl chloride, oxalyl chloride or Ghosez reagent using methods known from the literature to form the corresponding acid chloride and then reacted with the anilines K-5. Examples of reaction methods can be found there.

Alternatively, first of all the m-nitroanilines K-1 may be coupled with benzoic acids (introduction of $R^2$) and only then are the reduction, diazotisation, introduction of the azide group and cycloaddition according to Scheme K carried out. Using this sequence it is possible to avoid using a protective group (PG).

Example compounds of type XII (arylamines in the m-position to the amide link→$R^7$), prepared according to general Scheme L, have an inverse amide bond, in relation to those of type III (reaction scheme D).

Example compounds of type XII are synthesised by an amide coupling reaction of the benzoic acids L-3 (in order to introduce the group $R^2$) and the corresponding anilines K-5 described hereinbefore. The benzoic acids L-3 used are commercially obtainable or are synthesised by methods known from the literature from the corresponding benzoic acids L-1 or benzonitriles L-2.

The compounds XII according to the invention thus obtained may be modified in le (analogously to the anilines K-5 described above) to obtain other compounds XII according to the invention (cf. explanations relating to reaction scheme K).

The benzoic acids L-3 are prepared starting from arylhalides L-1 by a palladium-catalysed cross-coupling reaction (Buchwald-Hartwig) with an amine $R^9R^{10}NH$ using methods known from the literature with the aid of common catalysts, such as for example biphenyl-2-yl-di-tert-butylphosphane and tris-(dibenzylidene-acetone)-palladium, as well as a base, such as sodium-tert-butoxide or caesium carbonate, in 1,4-dioxane or toluene. The amines $R^9R^{10}NH$ used are commercially obtainable or are synthesised using methods known from the literature.

Alternatively benzoic acids L-3 may also be synthesised starting from the corresponding fluorobenzonitriles L-2 by nucleophilic aromatic substitution with an amine or a nitrogen compound of general formula $R^9R^{10}NH$ using methods known from the literature in common solvents, such as e.g. dimethylacetamide, NMP, DMSO or DMF. The substitution to obtain the intermediate product Z-22 in this case follows a nitrile saponification. The compounds $R^9R^{10}NH$ are commercially obtainable or are synthesised using methods known from the literature Reaction scheme L-1

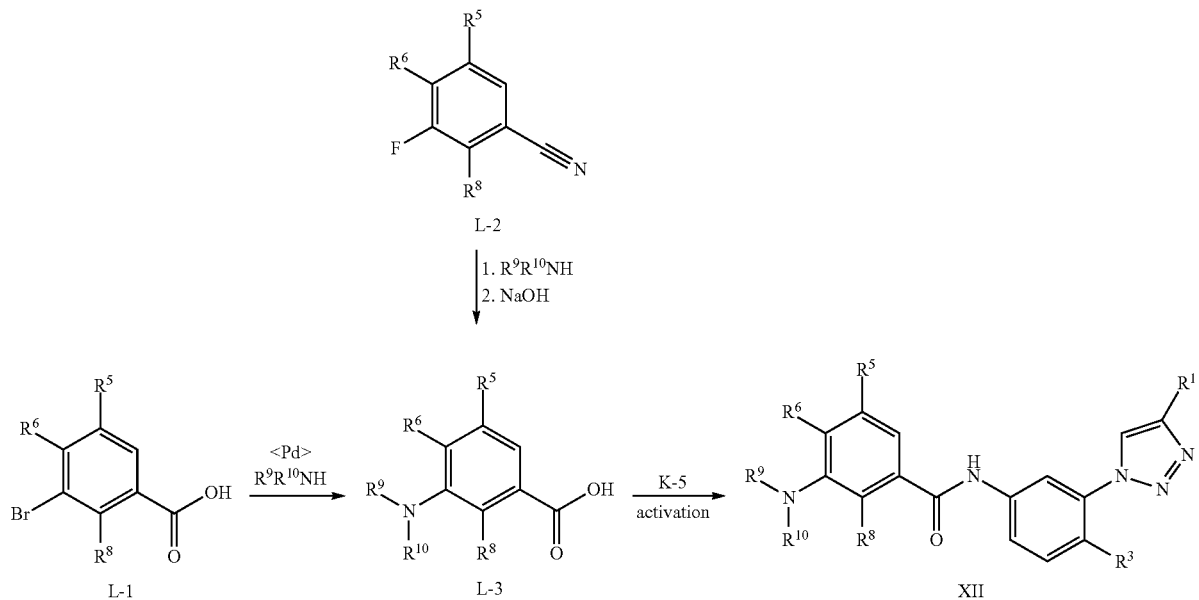

a) Procedure for Synthesising L-3a (Palladium-Catalysed Cross-Coupling):

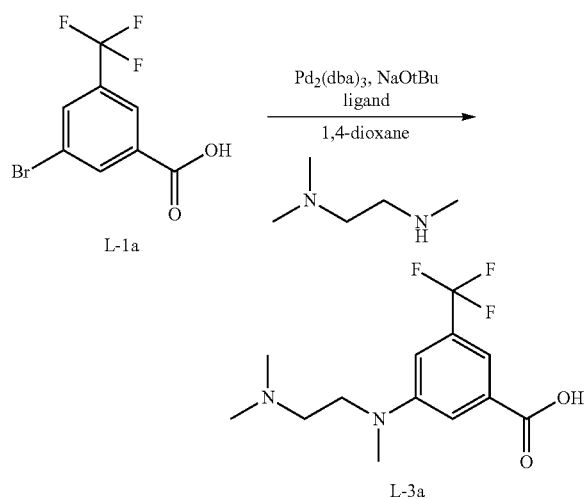

m-Bromobenzoic acid L-1a (500 mg, 1.86 mmol), sodium-tert-butoxide (737 mg, 7.44 mmol), biphenyl-2-yl-di-tert-butylphosphane (444 mg, 1.49 mmol) and tris-(dibenzylidene-acetone)-palladium (170 mg, 0.186 mmol) are suspended in 4 mL 1,4-dioxane, combined with N,N,N'-tr imethyl-ethylenediamine (760 mg, 7.44 mmol), heated to 45° C. and stirred for 3 h. Then the reaction mixture is filtered and the solvent is eliminated by distillation. The residue is taken up in water and the precipitate is filtered off. The filtrate is acidified with 1 N HCl and the product-containing precipitate (HPLC-MS: $t_{Ret.}$=0 min; MS (M+H)$^+$=291) is filtered off and freeze-dried.

b) Procedure for Synthesising L-3b (Aromatic Nucleophilic Substitution):

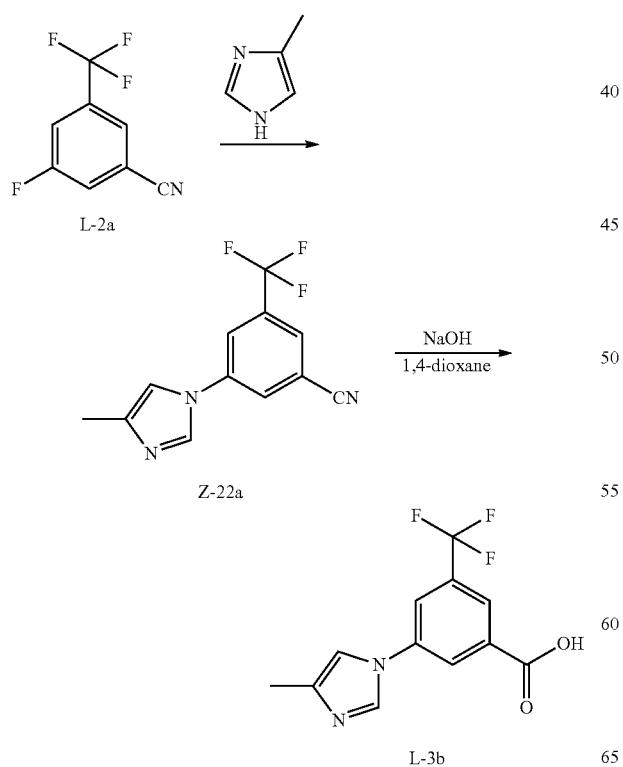

A mixture of 3-fluoro-5-(trifluoromethyl)-benzonitrile L-2a (17 g, 89 mmol) and 2-methylimidazole (22.2 g, 270 mmol) in 80 mL dimethylacetamide is stirred for 24 h at 145° C. Then the solvent is eliminated by distillation and the residue is taken up in EtOAc. The solution is washed with sat. NaCl solution, dried on Na$_2$SO$_4$, filtered, evaporated down using the rotary evaporator and the intermediate product Z-22a (HPLC-MS: $t_{Ret.}$=3.16 min; MS (M+H)$^+$=252) is further reacted directly.

Intermediate product Z-22a (25 g, 99 mmol) is taken up in 1,4-dioxane (400 mL), combined dropwise with 1 N NaOH solution (400 mL) and stirred for 20 h at 95° C. Then the solvent is eliminated by distillation. The residue is neutralised with 1 N HCl and extracted with n-butanol. The combined organic phases are dried on Na$_2$SO$_4$, filtered, evaporated down using the rotary evaporator and das crude product of L-3b is washed with acetone and a little water (HPLC-MS: $t_{Ret.}$=3.56 min; MS (M+H)$^+$=271).

Benzoic acid intermediates L-3 (Table 10; R'=—COOH), being another aspect of this invention, can be obtained in analogy with the procedures a) or b)

Benzoic acids L-3 can be used as starting materials for the synthesis of anilines D-4 (Table 10; R'=—NH$_2$), which are intermediates of compounds of type III (reaction scheme D-II). For that purpose, benzoic acids L-3 are converted to the corresponding acid azides by reaction with diphenyl phosphoryl azide (DPPA). The Curtius rearrangement/degradation reaction is carried out under heating in a toluene/base/alcohol solvent system; in which the isocyanate generated initially, is scavenged by the alcoholic co-solvent to yield the corresponding carbamate. Preferred alcohols used as co-solvents allowing for an easy cleavage of the carbamate to yield the free anilines D-4 (see also Ninomiya et al., *Tetrahedron* 1974, Vol. 30, 2151-2157 and Lebel et al., *Org. Lett.* 2006, Vol. 8, No. 25, 5717-5720)., include tBuOH or tert-amylalcohol. The carbamates in Table 10 are a further aspect of this invention.

TABLE 10

Anilines D-4, Benzoic acids L-3 and Carbamates*

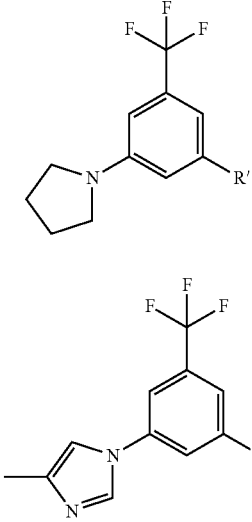

TABLE 10-continued
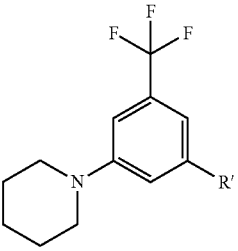
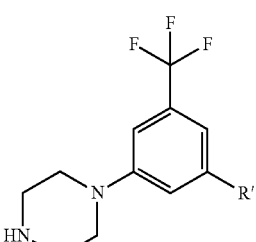
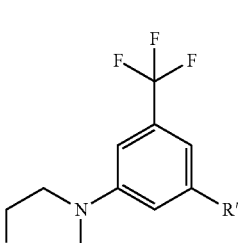
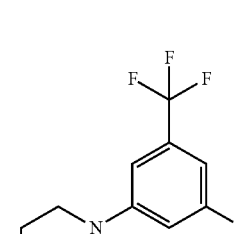
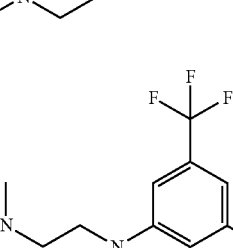
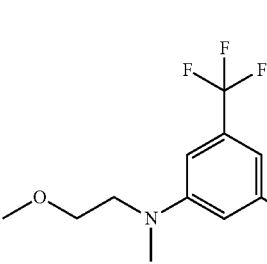
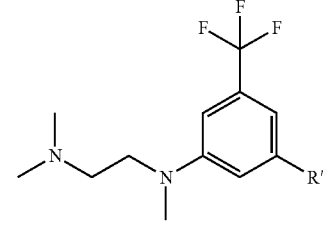
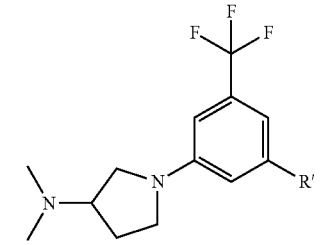

TABLE 10-continued
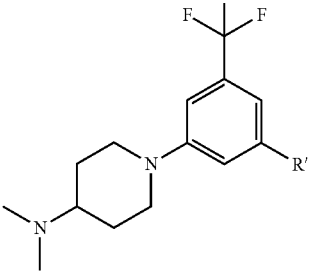
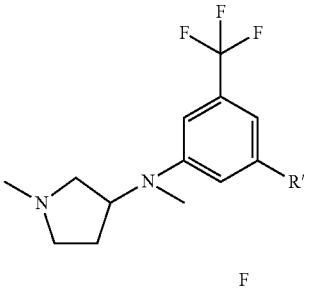
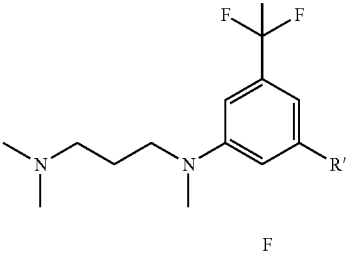
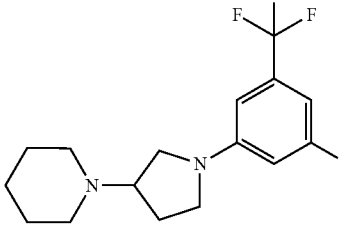
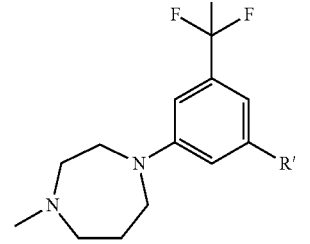
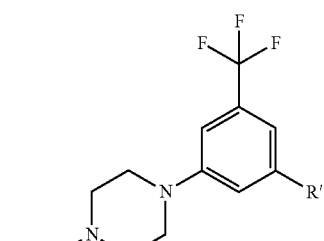
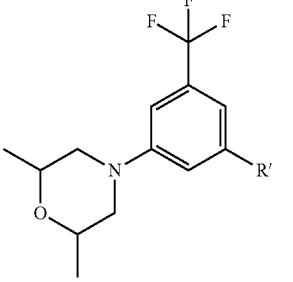
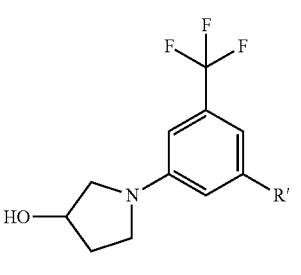
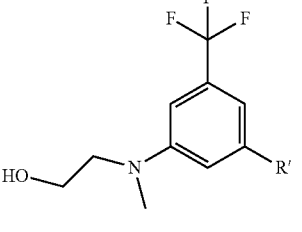
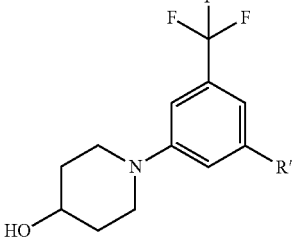
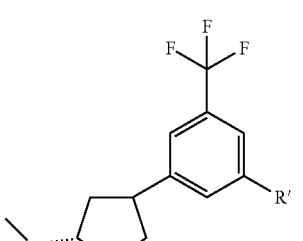
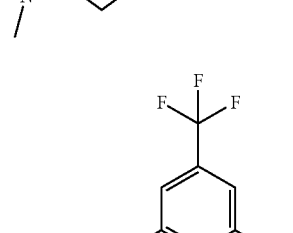
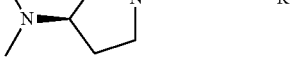

TABLE 10-continued
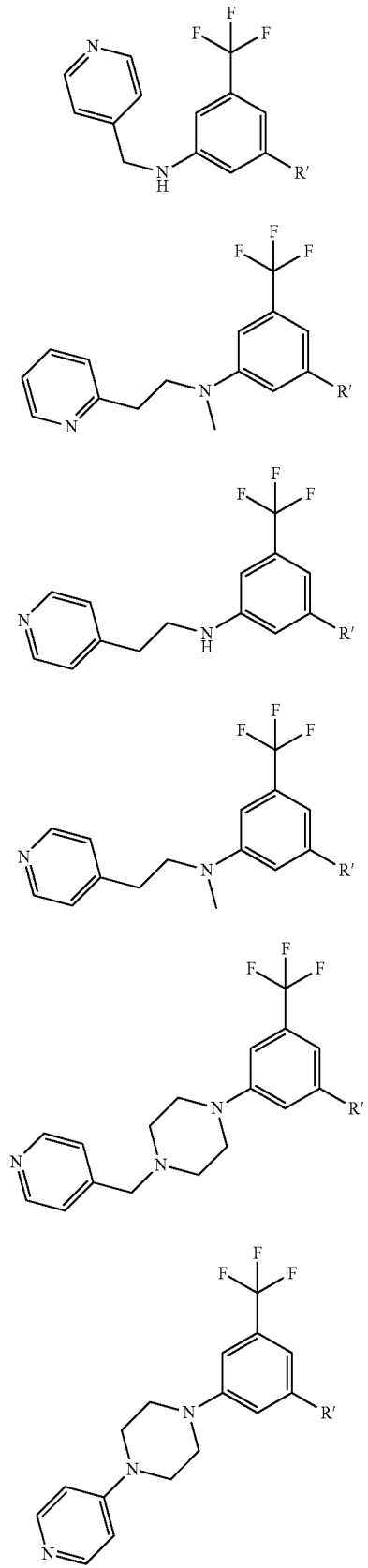
TABLE 10-continued
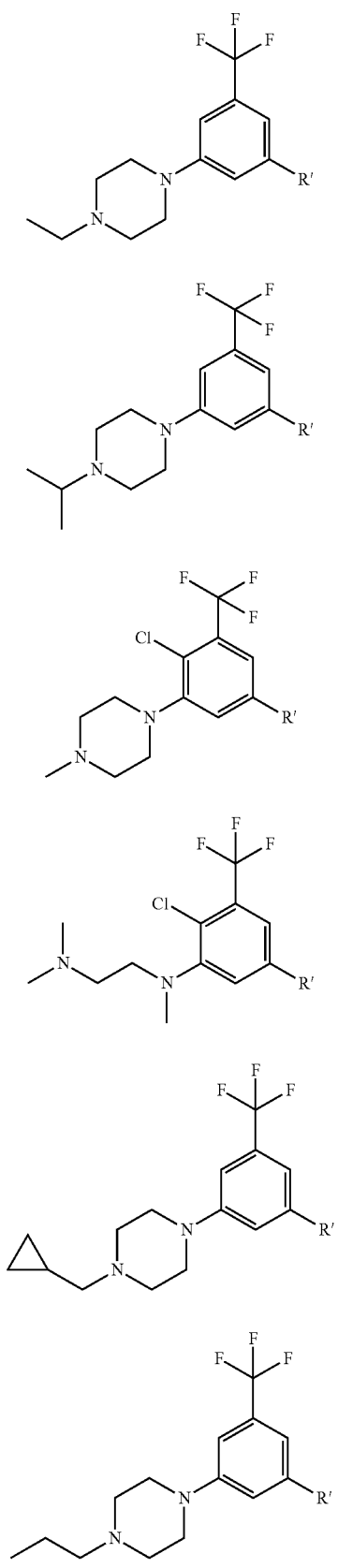

TABLE 10-continued
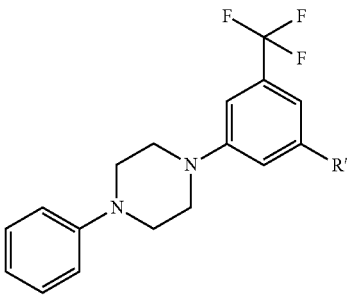
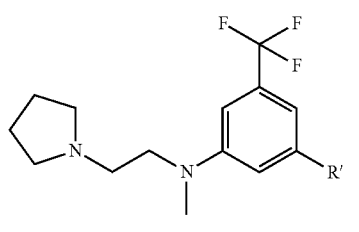
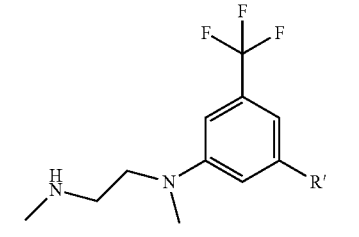
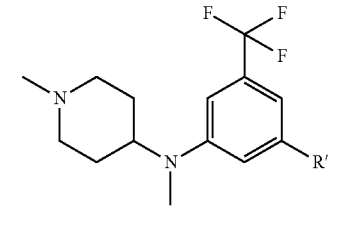
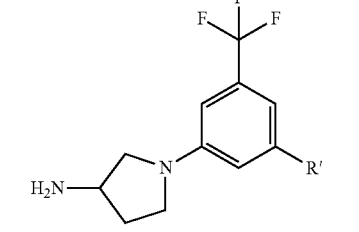
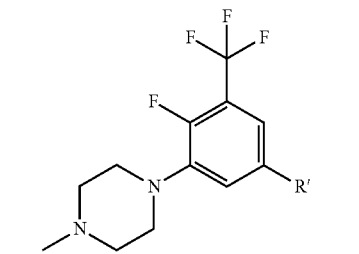
TABLE 10-continued
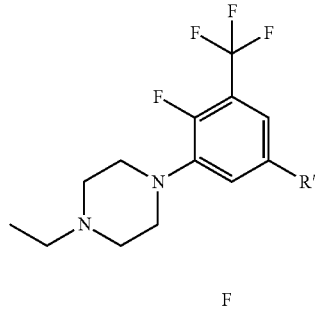
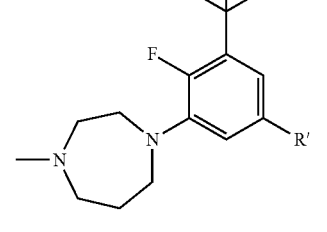

TABLE 10-continued
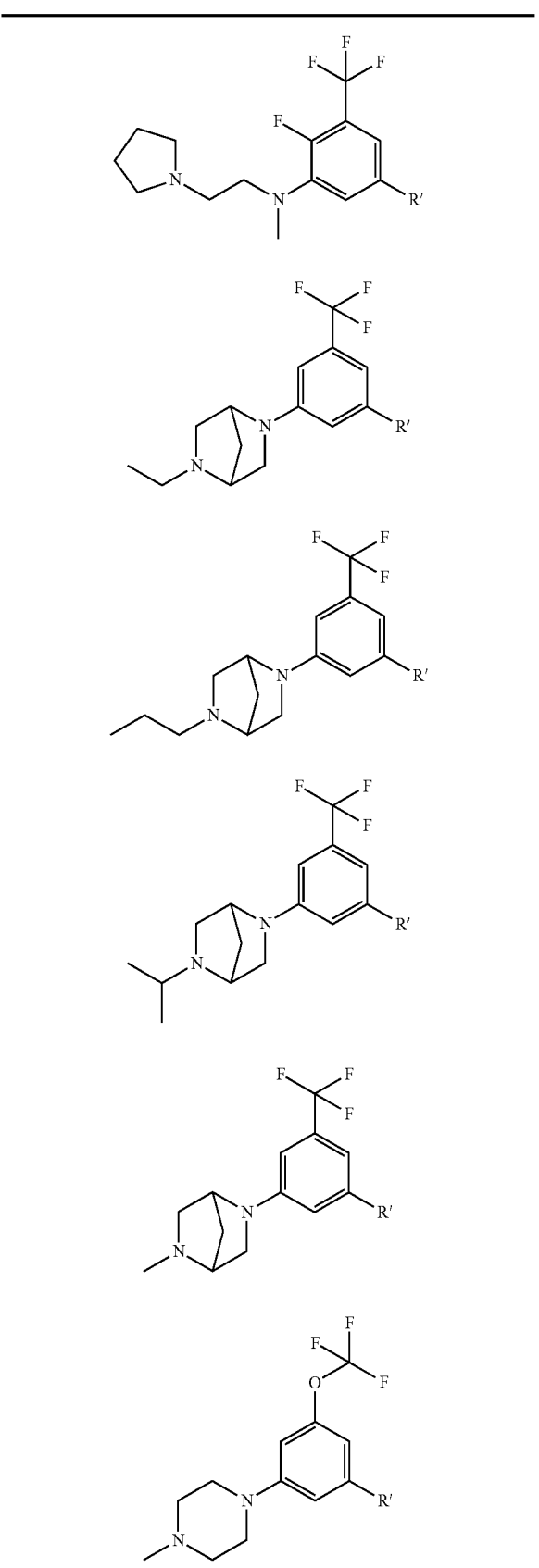
TABLE 10-continued
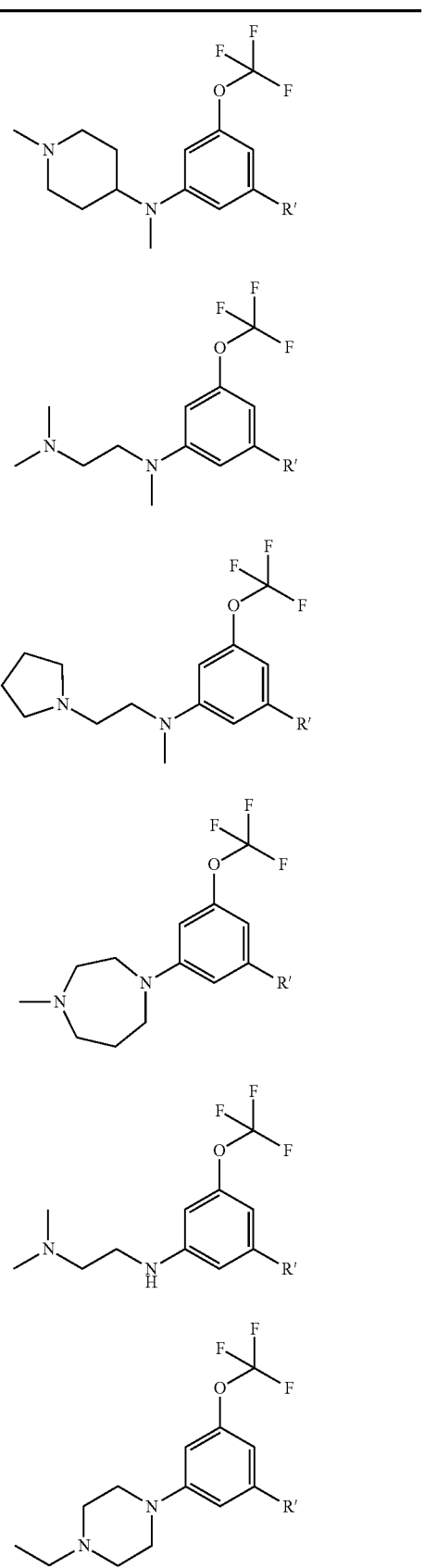

TABLE 10-continued

TABLE 10-continued
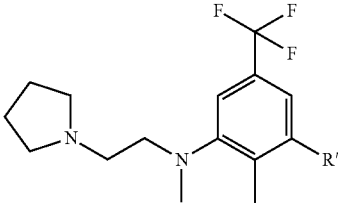
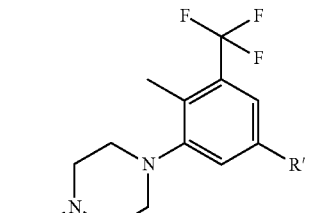
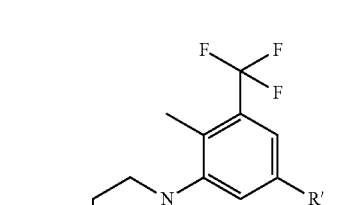
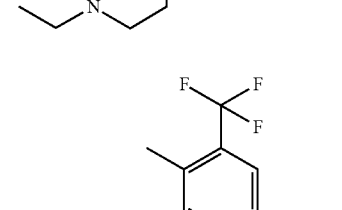
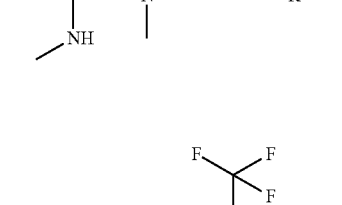
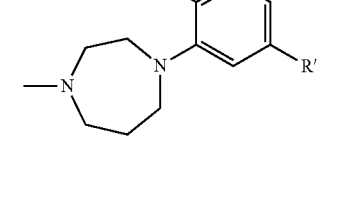
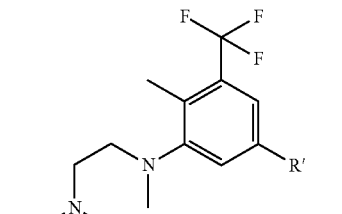
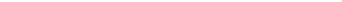
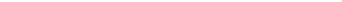
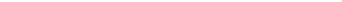
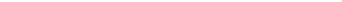
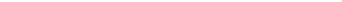
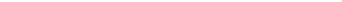

TABLE 10-continued
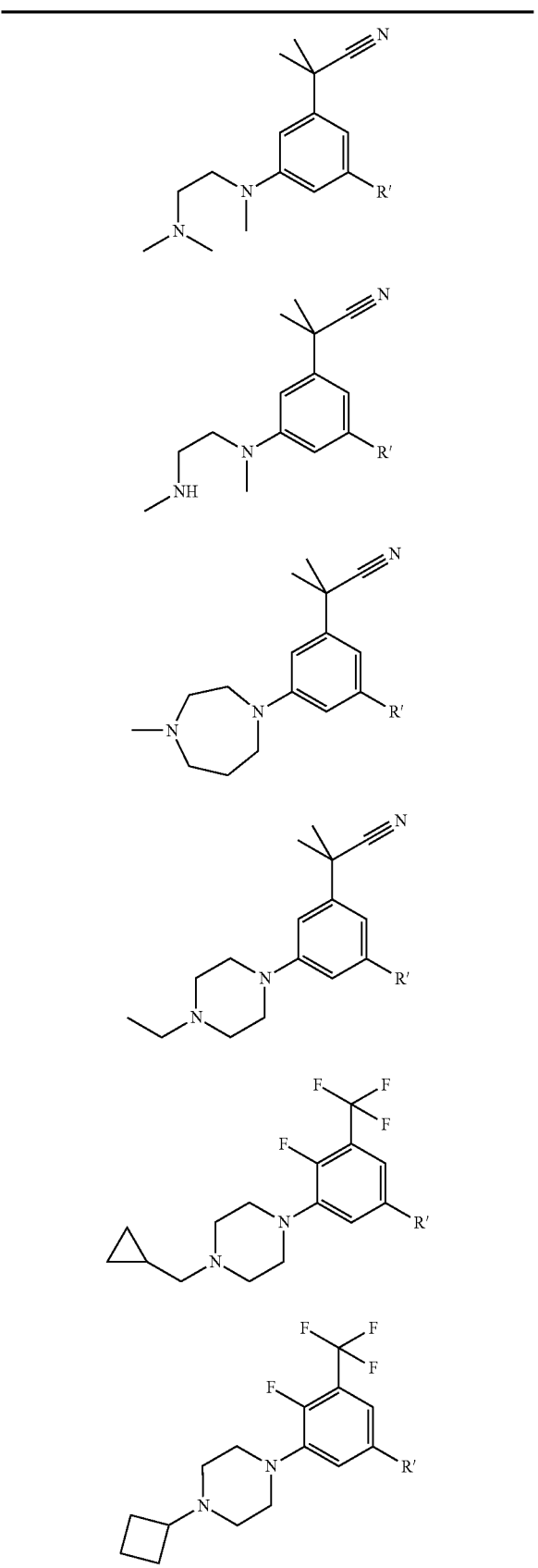
TABLE 10-continued
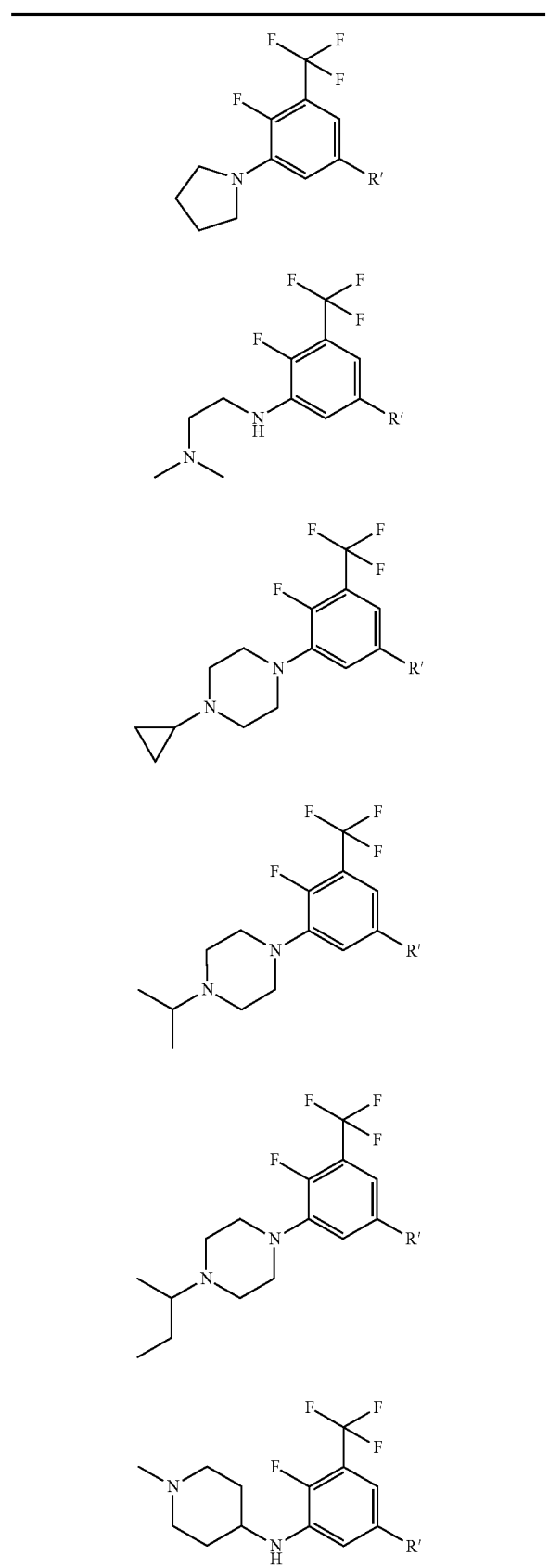

TABLE 10-continued
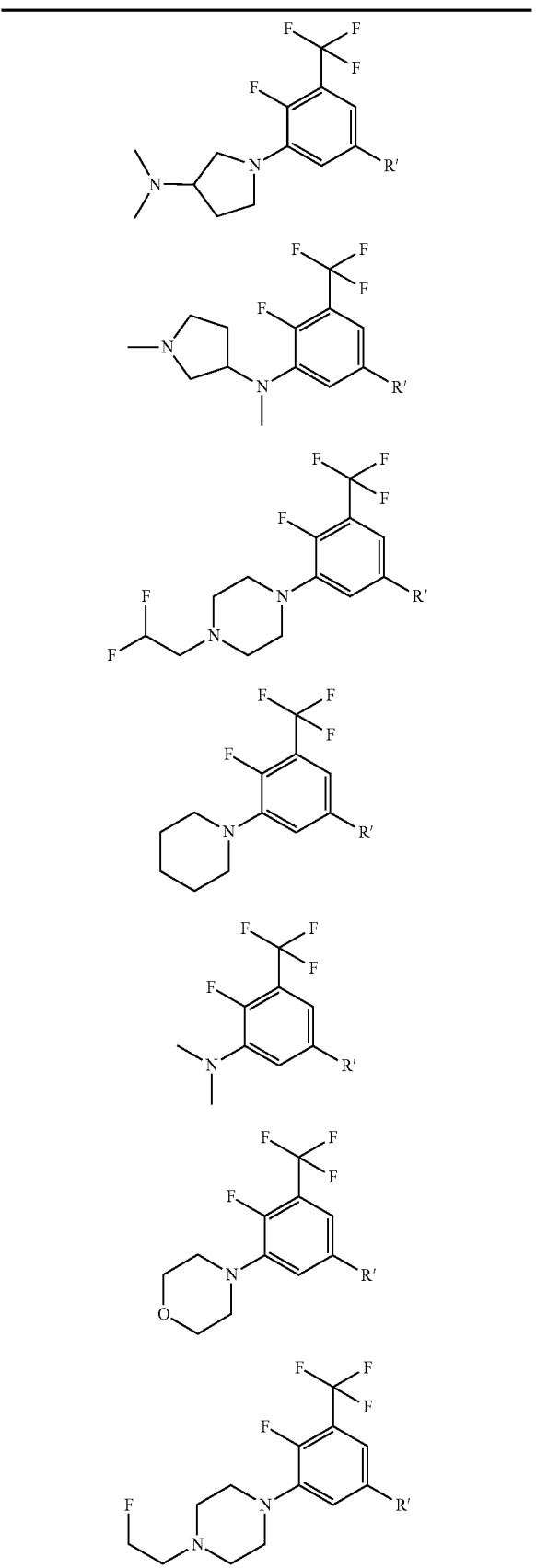
TABLE 10-continued
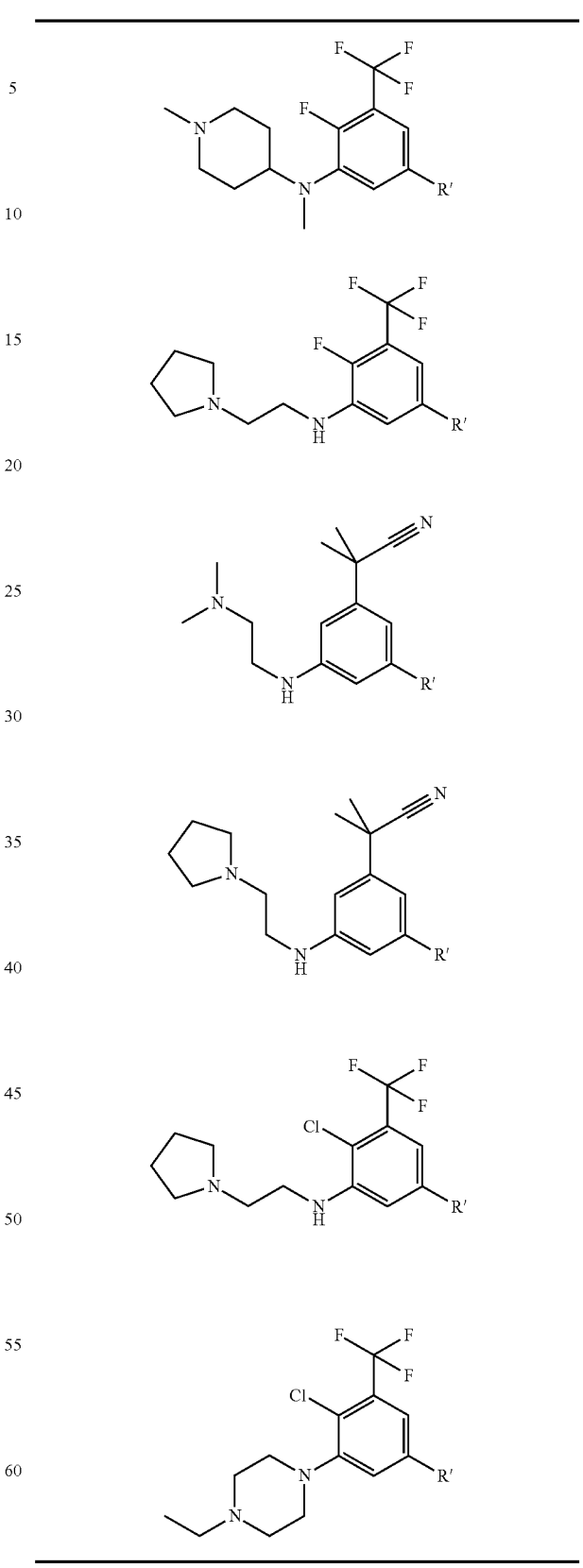
*R' = —NH₂ for anilines D-4, R' = —COOH for benzoic acids L-3, R' = —NHBoc or R' = —NHC(O)OCH(CH₃)₂C₂H₅ for carbamates.

c) Procedure for Synthesising XII-1:

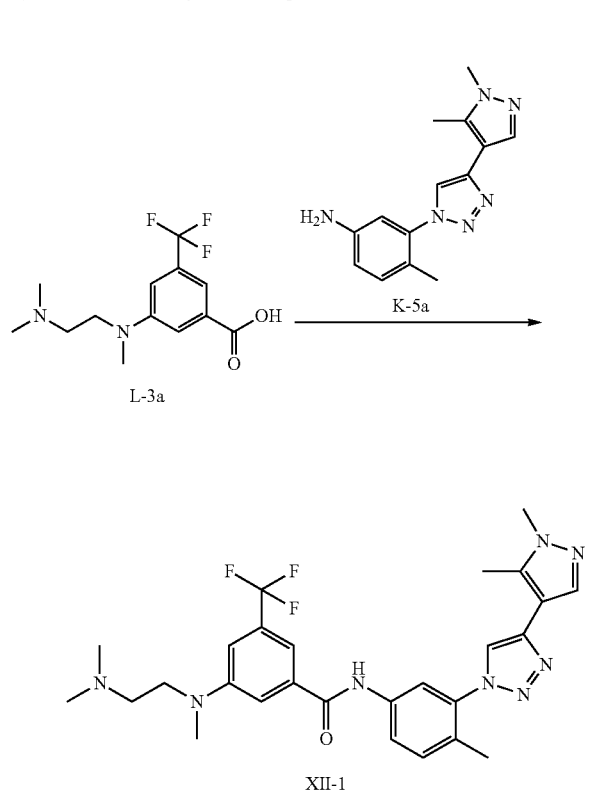 [SMILES: CN(C)CCN(C)c1cc(C(=O)O)cc(C(F)(F)F)c1 ; Cc1ccc(N)cc1-n1cc(-c2cnn(C)c2C)nn1 ; Cc1ccc(NC(=O)c2cc(N(C)CCN(C)C)cc(C(F)(F)F)c2)cc1-n1cc(-c2cnn(C)c2C)nn1]

Benzoic acid L-3a (1.00 g, 3.45 mmol) is taken up in 10 mL NMP, combined with HATU (1.11 g, 3.45 mmol) and DIPEA (891 mg, 6.89 mmol) and stirred for 40 min at RT. Then aniline K-5a (925 mg, 3.45 mmol) is added and the reaction mixture is stirred overnight at RT. The crude product is taken up in EtOAc and washed with water. The combined organic phases are washed with sat. NaCl solution, dried on $Na_2SO_4$, filtered, evaporated down using the rotary evaporator and the crude product is purified by preparative HPLC. The product-containing fractions of XII-1 (HPLC-MS: $t_{Ret.}$=2.19 min; MS $(M+H)^+$=541) are freeze-dried.

Reaction scheme L-II

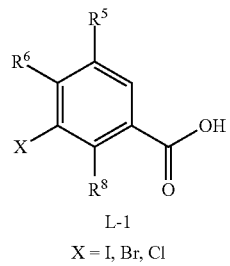

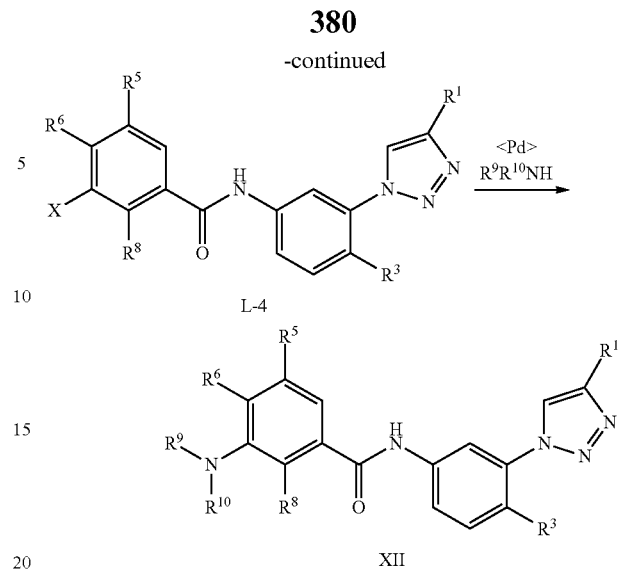

Example compounds of type XII can also be prepared by altering the sequence of the reaction steps shown in reaction scheme L-I (→reaction scheme L-II), by first synthesising the amide coupling products L-4 using methods known from the literature from the benzoic acids L-1 and the anilines K-5 and then reacting them with an amine $R^9R^{10}NH$ by a palladium-catalysed cross-coupling reaction (Buchwald-Hartwig) using methods known from the literature with the aid of common catalysts, such as for example biphenyl-2-yl-di-tent-butylphosphane and tris-(dibenzylidene-acetone)-palladium, and a base, such as sodium-tert-butoxide or caesium carbonate, in 1,4-dioxane or toluene, to obtain the end compounds XII. Preferably, bromine or iodine compounds are used, while corresponding chlorine compounds may also be used. The amines $R^9R^{10}NH$ used are commercially obtainable or are synthesised using methods known from the literature.

The compounds XII according to the invention obtained in this way may be modified in $R^1$ (analogously to the anilines K-5 described above) to form other compounds according to the invention XII (cf. explanations relating to reaction scheme K).

d) Procedure for Synthesising L-1b

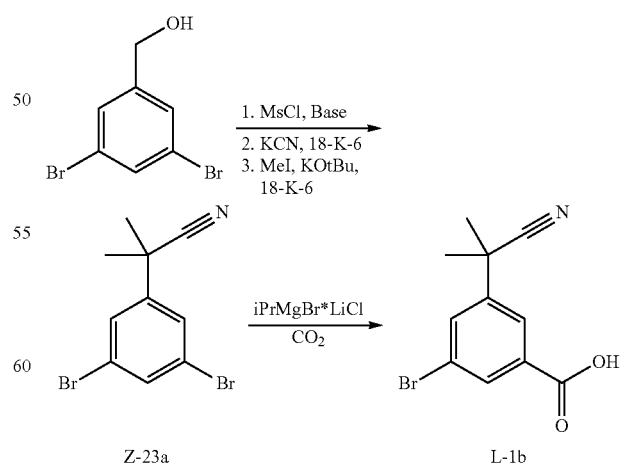

$NEt_3$ (4.69 mL, 33.8 mmol) is added to 3,5-dibromobenzylalcohol (3.00 g, 11.3 mmol) in THF (100 mL), then at 0° C.

methanesulphonic acid chloride (1.75 mL, 22.6 mmol) is slowly added dropwise and the mixture is stirred overnight. The reaction mixture is evaporated down, the residue is taken up in 1 M NaOH and extracted with EtOAc. The combined organic phases are washed with saturated NaCl solution, dried on MgSO$_4$, filtered and evaporated down using the rotary evaporator.

The activated benzylalcohol thus obtained is taken up as a crude product (4.09 g, 11.9 mmol) in MeCN (30 mL), mixed with KCN (3.88 g, 59.5 mmol) and crown ether (18 K-6; 315 mg, 1.19 mmol) and stirred for 18 h at RT. The reaction mixture is diluted with water and extracted 2× with DCM. The combined organic phases are washed with saturated NaCl solution, dried on MgSO$_4$, filtered and evaporated down using the rotary evaporator.

The nitrile thus obtained is placed as a crude product (3.27 g, 11.9 mmol) in THF (120 mL), cooled to -78° C., mixed with MeI (1.64 mL, 26.2 mmol), potassium-tert.-butoxide (3.13 g, 26.2 mmol) and crown ether (18-K-6; 635 mg, 2.38 mmol) and stirred for 30 min at this temperature. The reaction mixture is left to thaw overnight at RT, combined with saturated NH$_4$Cl solution (100 mL) and the aqueous phase is extracted 3× with EtOAc. The combined organic phases are dried on MgSO$_4$, filtered and evaporated down using the rotary evaporator.

The nitrile Z-23a thus obtained (2.00 g, 6.60 mmol) is taken up in THF (50 mL), cooled to −40° C., combined with isopropylmagnesium chloride/LiCl solution (0.9 M; 11.5 mL, 9.90 mmol) and stirred overnight at this temperature. Then CO$_2$ gas is piped through the reaction mixture and in the mean time the mixture is allowed to thaw to RT. EtOAc is added and the mixture is extracted 3× with 1 M NaOH. The combined aqueous phase is acidified with conc. hydrochloric acid and extracted 3× with EtOAc. The combined organic phases are dried on MgSO$_4$, filtered and evaporated down using the rotary evaporator. The benzoic acid L-1b thus obtained is used in the following reactions without any further purification.

e) Procedure for Synthesising L-4a

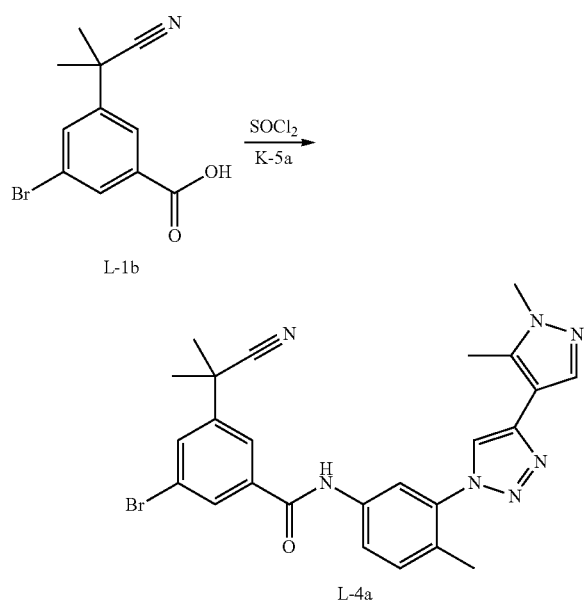

The benzoic acid L-1b (725 mg, 2.70 mmol) is placed in toluene (10 mL), mixed with SOCl$_2$ (0.37 mL, 5.14 mmol) and refluxed for 2 h. The mixture is left to cool, the aniline K-5a (725 mg, 2.70 mmol) and diisopropylethylamine (1.4 mL, 8.11 mmol; dissolved in 5 mL toluene) are added and the mixture is refluxed for 1 h. It is diluted with 2 M NaOH, cooled to RT and the aqueous phase is extracted 3× with DCM. The combined organic phases are washed with 1N hydrochloric acid and saturated NaCl solution, dried on MgSO$_4$, filtered and evaporated down using the rotary evaporator. The crude product is taken up in EtOAc and combined with cyclohexane, whereupon L-4a (HPLC-MS: t$_{Ret.}$=2.14 min; MS (M+H)$^+$=518/520) is precipitated as a solid.

f) Procedure for Synthesising XII-40

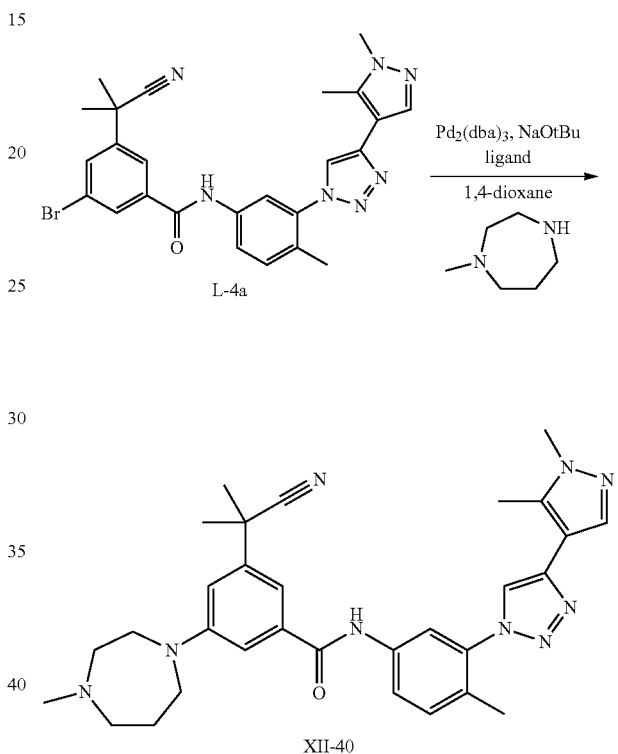

The bromine compound L-4a (100 mg, 0.19 mmol), sodium-tert-butoxide (76.5 mg; 0.77 mmol), biphenyl-2-yl-di-tent-butylphosphane (23.0 mg; 77.2 μmol) and tris(dibenzylideneacetone)-palladium (17.6 mg, 19.3 μmol) are suspended in 2 mL of 1,4-dioxane, combined with 1-methylhomopiperazine, heated to 45° C. and stirred for 3 h. Then the reaction mixture is filtered through Celite, washed with MeCN and evaporated down. The residue is taken up in a little DCM and chromatographed on silica gel. The product-containing fractions of XII-40 (HPLC-MS: t$_{Ret.}$=2.00 min; MS (M+H)$^+$=552) are evaporated down and freeze-dried.

Analogously to the methods a)-g) described above Examples XII-1 to XII-66 (Table 11) or comparable further examples may be obtained from the corresponding precursors, which are either commercially obtainable or are prepared using methods known from the literature.

TABLE 11
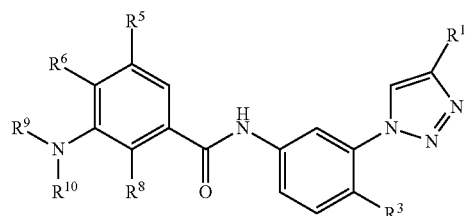
Examples XII-1 to XII-66
| # | Structure | $t_{Ret.}$(HPLC) [min] | MS (M + H)$^+$ |
|---|---|---|---|
| XII-1 | 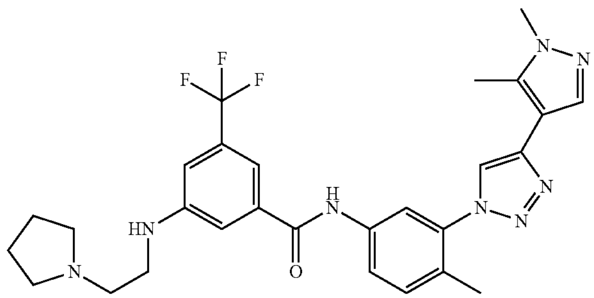 [SMILES: Cc1ccc(NC(=O)c2cc(NCCN3CCCC3)cc(C(F)(F)F)c2)cc1-n1cc(-c2cnn(C)c2C)nn1] | 1.63 | 553 |
| XII-2 | 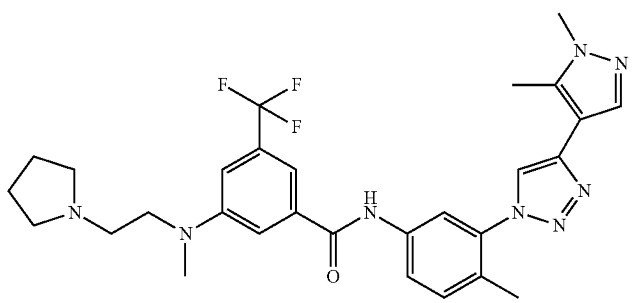 [SMILES: Cc1ccc(NC(=O)c2cc(N(C)CCN3CCCC3)cc(C(F)(F)F)c2)cc1-n1cc(-c2cnn(C)c2C)nn1] | 1.65 | 567 |
| XII-3 | 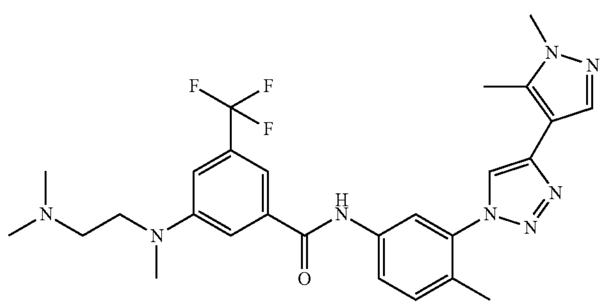 [SMILES: Cc1ccc(NC(=O)c2cc(N(C)CCN(C)C)cc(C(F)(F)F)c2)cc1-n1cc(-c2cnn(C)c2C)nn1] | 1.62 | 541 |
| XII-4 | 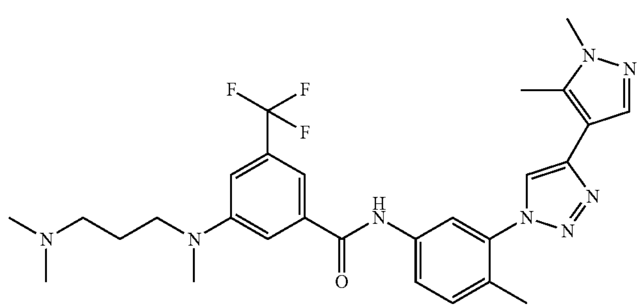 [SMILES: Cc1ccc(NC(=O)c2cc(N(C)CCCN(C)C)cc(C(F)(F)F)c2)cc1-n1cc(-c2cnn(C)c2C)nn1] | 1.68 | 555 |

TABLE 11-continued
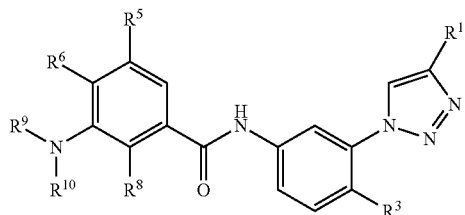
Examples XII-1 to XII-66
| # | Structure | $t_{Ret.}$(HPLC) [min] | MS (M + H)+ |
|---|---|---|---|
| XII-5 | 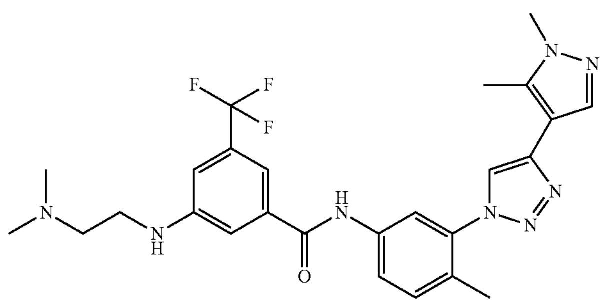 | 1.60 | 527 |
| XII-6 | 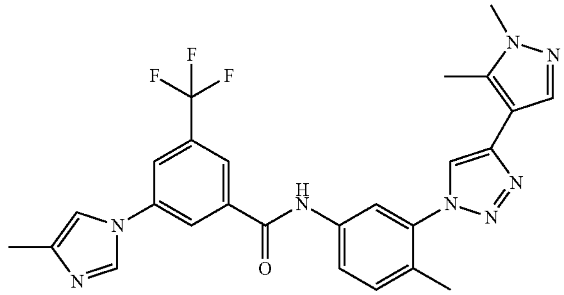 [SMILES: Cc1cn(-c2cc(C(=O)Nc3ccc(C)c(-n4cc(-c5cnn(C)c5C)nn4)c3)cc(C(F)(F)F)c2)cn1] | 2.03 | 521 |
| XII-7 | 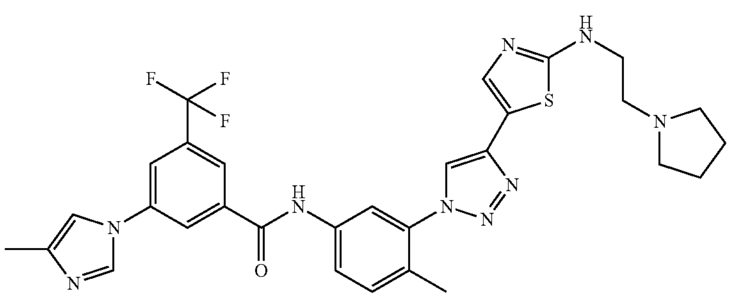 [SMILES: Cc1cn(-c2cc(C(=O)Nc3ccc(C)c(-n4cc(-c5cnc(NCCN6CCCC6)s5)nn4)c3)cc(C(F)(F)F)c2)cn1] | 2.14 | 622 |
| XII-8 | 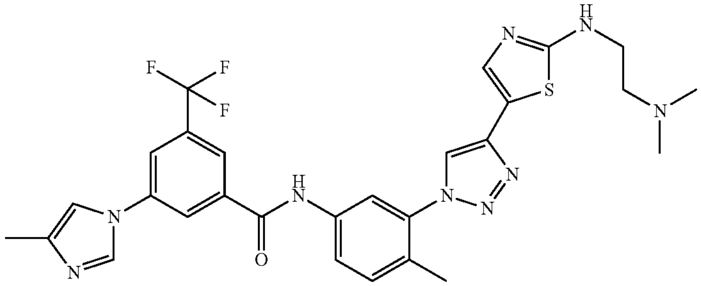 | 2.04 | 596 |

TABLE 11-continued
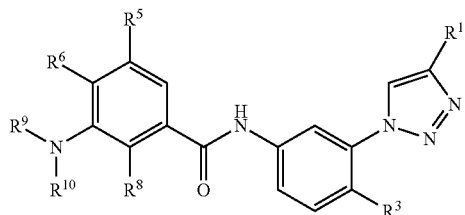
Examples XII-1 to XII-66
| # | Structure | $t_{Ret.}$(HPLC) [min] | MS (M + H)+ |
|---|---|---|---|
| XII-9 | 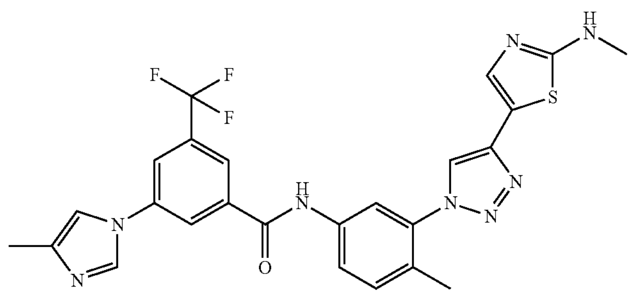 | 2.02 | 539 |
| XII-10 | 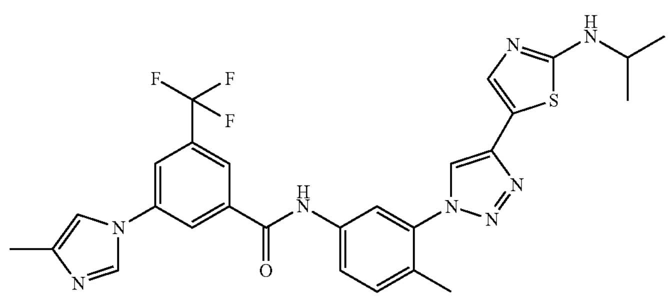 [SMILES: Cc1cn(-c2cc(C(=O)Nc3ccc(C)c(-n4cc(-c5cnc(NC(C)C)s5)nn4)c3)cc(C(F)(F)F)c2)cn1] | 2.16 | 567 |
| XII-11 | 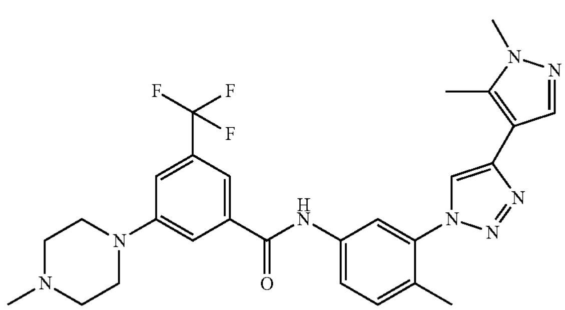 [SMILES: Cc1ccc(NC(=O)c2cc(N3CCN(C)CC3)cc(C(F)(F)F)c2)cc1-n1cc(-c2cnn(C)c2C)nn1] | 1.63 | 539 |
| XII-12 | 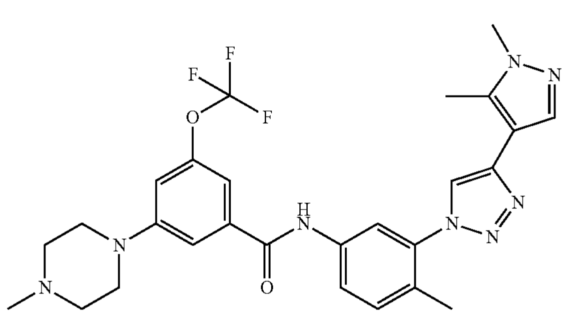 [SMILES: Cc1ccc(NC(=O)c2cc(OC(F)(F)F)cc(N3CCN(C)CC3)c2)cc1-n1cc(-c2cnn(C)c2C)nn1] | 2.12 | 555 |

TABLE 11-continued
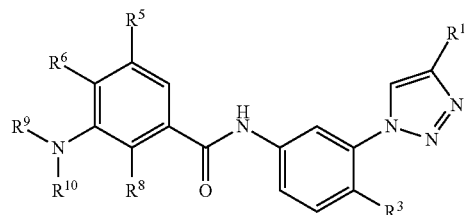
Examples XII-1 to XII-66
| # | Structure | t<sub>Ret.</sub>(HPLC) [min] | MS (M + H)+ |
|---|---|---|---|
| XII-13 | 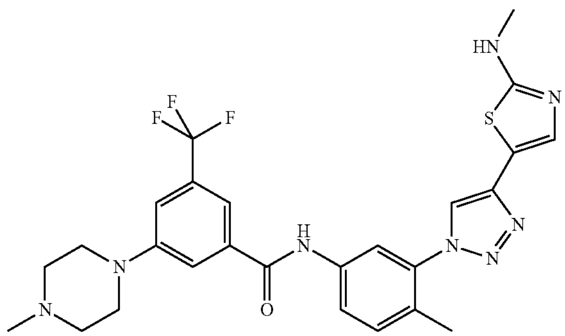 [SMILES: CNc1ncc(-c2cn(-c3cc(NC(=O)c4cc(N5CCN(C)CC5)cc(C(F)(F)F)c4)ccc3C)nn2)s1] | 2.11 | 557 |
| XII-14 | 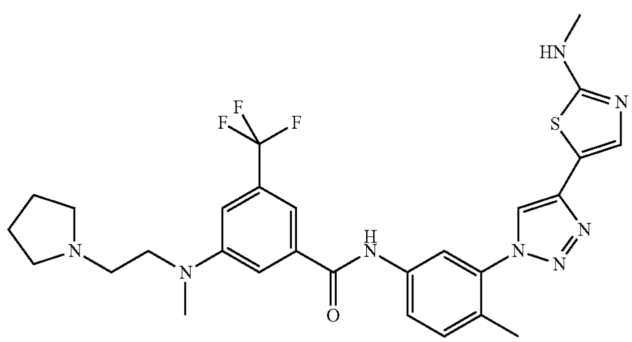 [SMILES: CNc1ncc(-c2cn(-c3cc(NC(=O)c4cc(N(C)CCN5CCCC5)cc(C(F)(F)F)c4)ccc3C)nn2)s1] | 2.28 | (M − H)−: 584 |
| XII-15 | 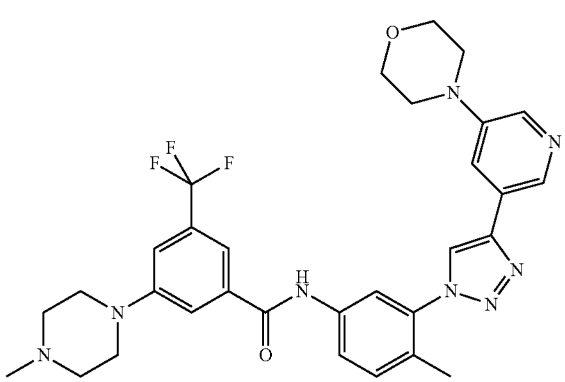 [SMILES: Cc1ccc(NC(=O)c2cc(N3CCN(C)CC3)cc(C(F)(F)F)c2)cc1-n1cc(-c2cncc(N3CCOCC3)c2)nn1] | 2.12 | 607 |

TABLE 11-continued
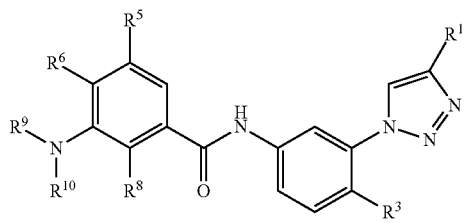
Examples XII-1 to XII-66
| # | Structure | t$_{Ret.}$(HPLC) [min] | MS (M + H)$^+$ |
|---|---|---|---|
| XII-16 | 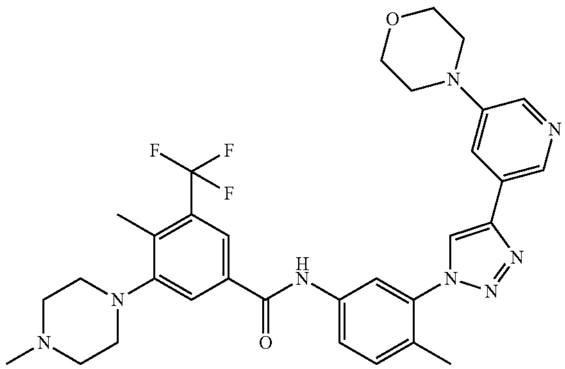 | 2.27 | 621 |
| XII-17 | 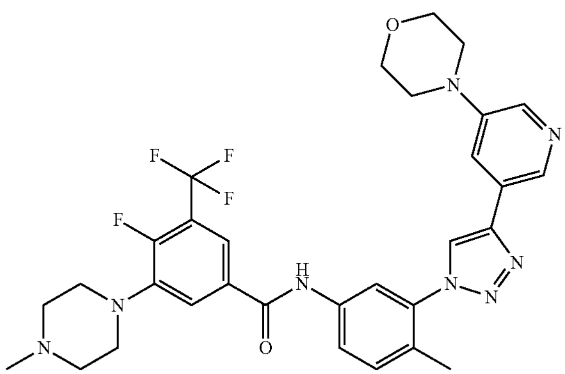 [SMILES: Cc1ccc(NC(=O)c2cc(N3CCN(C)CC3)c(C)c(C(F)(F)F)c2)cc1-n1cc(-c2cncc(N3CCOCC3)c2)nn1] | 2.18 | 625 |
| XII-18 | 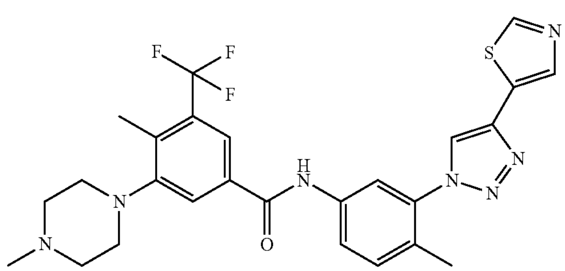 [SMILES: Cc1ccc(NC(=O)c2cc(N3CCN(C)CC3)c(C)c(C(F)(F)F)c2)cc1-n1cc(-c2cncs2)nn1] | 2.19 | 542 |
| XII-19 | 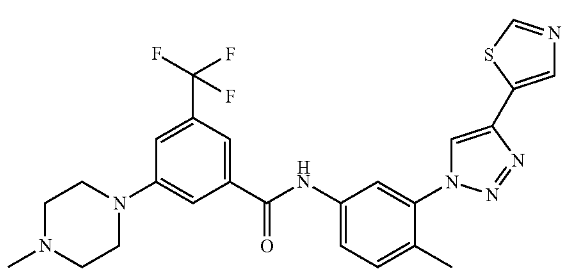 [SMILES: Cc1ccc(NC(=O)c2cc(N3CCN(C)CC3)cc(C(F)(F)F)c2)cc1-n1cc(-c2cncs2)nn1] | 2.09 | 528 |

TABLE 11-continued
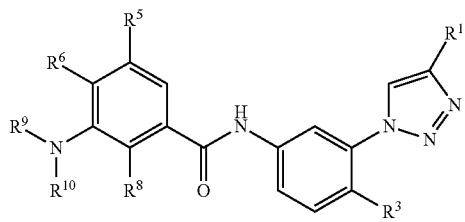
Examples XII-1 to XII-66
| # | Structure | $t_{Ret.}$(HPLC) [min] | MS (M + H)+ |
|---|---|---|---|
| XII-20 | 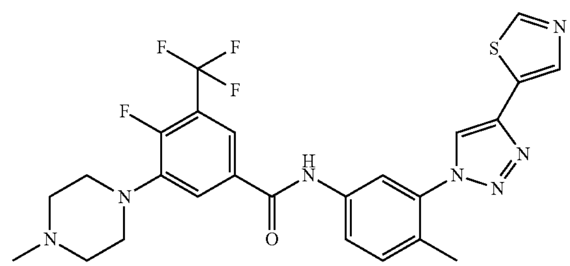 [SMILES: Cc1ccc(NC(=O)c2cc(N3CCN(C)CC3)c(F)c(C(F)(F)F)c2)cc1-n1cc(-c2cncs2)nn1] | 2.12 | 546 |
| XII-21 | 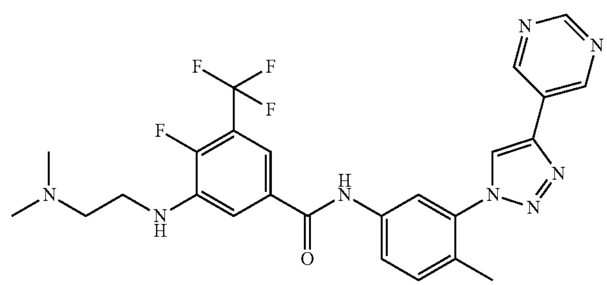 [SMILES: Cc1ccc(NC(=O)c2cc(NCCN(C)C)c(F)c(C(F)(F)F)c2)cc1-n1cc(-c2cncnc2)nn1] | 2.14 | 529 |
| XII-22 | 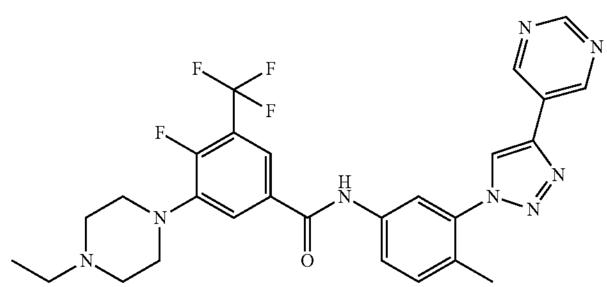 [SMILES: CCN1CCN(c2cc(C(=O)Nc3ccc(C)c(-n4cc(-c5cncnc5)nn4)c3)cc(C(F)(F)F)c2F)CC1] | 2.20 | 555 |
| XII-23 | 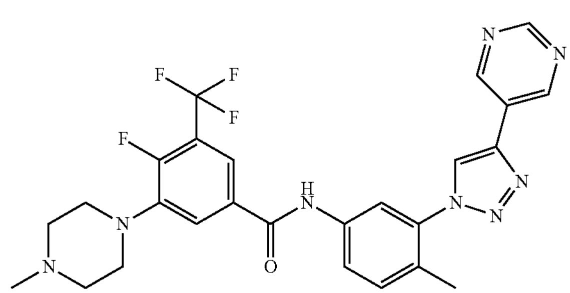 | 2.10 | 541 |

TABLE 11-continued
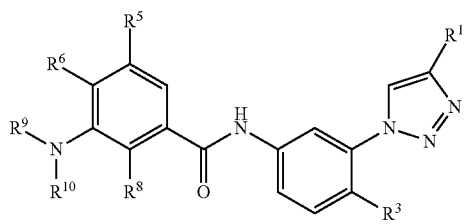
Examples XII-1 to XII-66
| # | Structure | $t_{Ret.}$(HPLC) [min] | MS (M + H)+ |
|---|---|---|---|
| XII-24 | 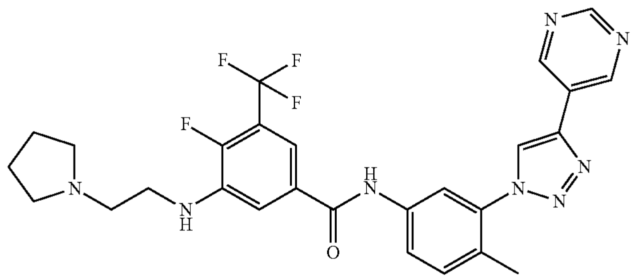 [SMILES: Cc1ccc(NC(=O)c2cc(NCCN3CCCC3)c(F)c(C(F)(F)F)c2)cc1-n1cc(-c2cncnc2)nn1] | 2.25 | 555 |
| XII-25 | 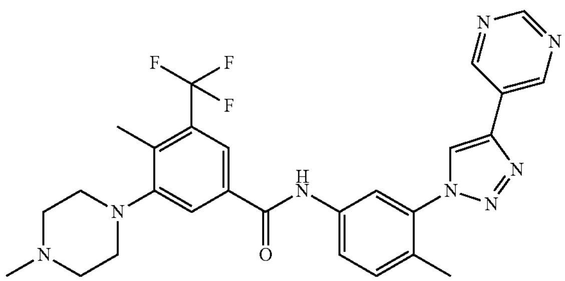 [SMILES: Cc1ccc(NC(=O)c2cc(N3CCN(C)CC3)c(C)c(C(F)(F)F)c2)cc1-n1cc(-c2cncnc2)nn1] | 2.19 | 537 |
| XII-26 | 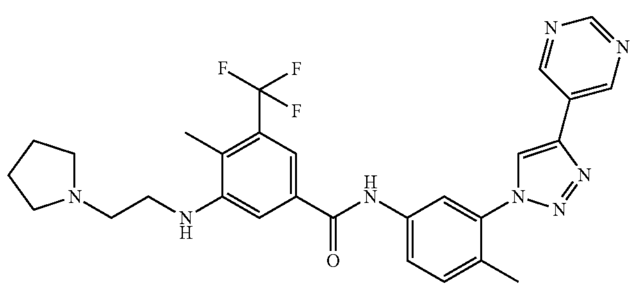 [SMILES: Cc1ccc(NC(=O)c2cc(NCCN3CCCC3)c(C)c(C(F)(F)F)c2)cc1-n1cc(-c2cncnc2)nn1] | 2.29 | 551 |
| XII-27 | 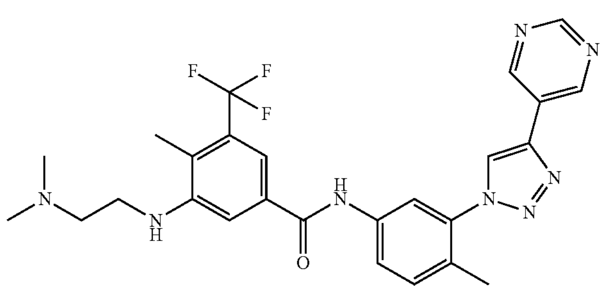 [SMILES: Cc1ccc(NC(=O)c2cc(NCCN(C)C)c(C)c(C(F)(F)F)c2)cc1-n1cc(-c2cncnc2)nn1] | 2.14 | 525 |

TABLE 11-continued
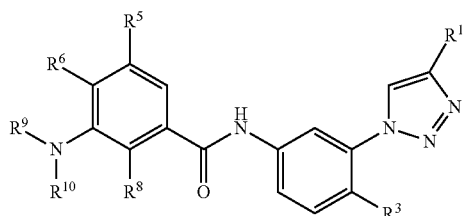
Examples XII-1 to XII-66
| # | Structure | $t_{Ret.}$(HPLC) [min] | MS (M + H)⁺ |
|---|---|---|---|
| XII-28 | 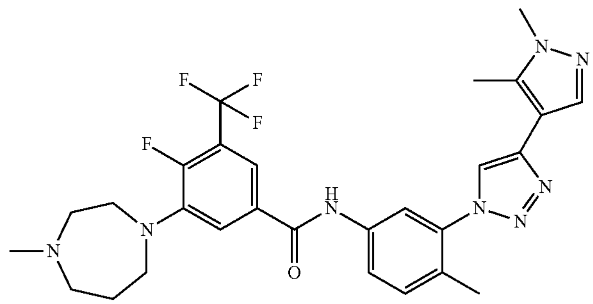 [SMILES: Cc1ccc(NC(=O)c2cc(N3CCCN(C)CC3)c(F)c(C(F)(F)F)c2)cc1-n1cc(-c2cnn(C)c2C)nn1] | 2.20 | 571 |
| XII-29 | 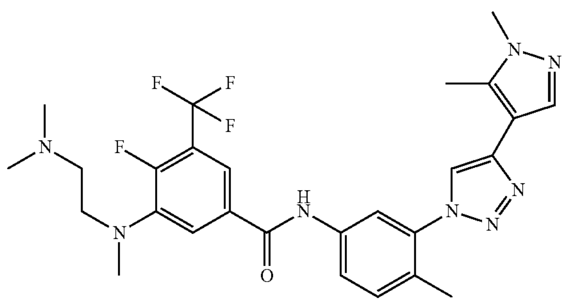 [SMILES: Cc1ccc(NC(=O)c2cc(N(C)CCN(C)C)c(F)c(C(F)(F)F)c2)cc1-n1cc(-c2cnn(C)c2C)nn1] | 2.21 | 559 |
| XII-30 | 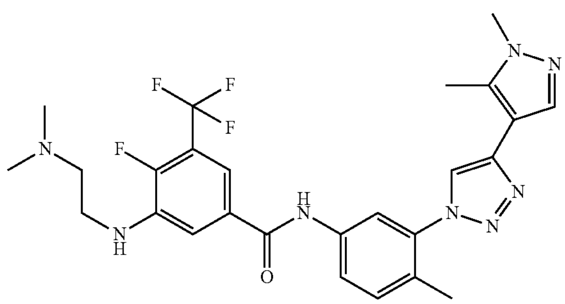 [SMILES: Cc1ccc(NC(=O)c2cc(NCCN(C)C)c(F)c(C(F)(F)F)c2)cc1-n1cc(-c2cnn(C)c2C)nn1] | 2.16 | 545 |
| XII-31 | 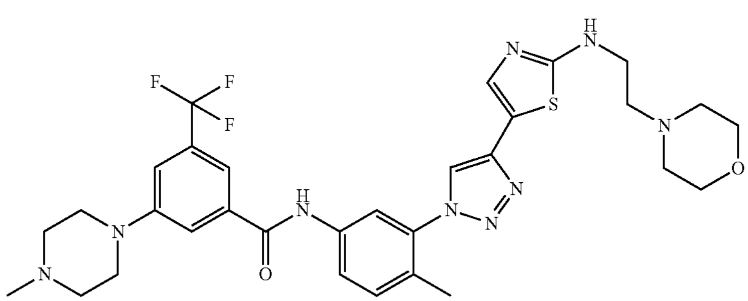 [SMILES: Cc1ccc(NC(=O)c2cc(N3CCN(C)CC3)cc(C(F)(F)F)c2)cc1-n1cc(-c2cnc(NCCN3CCOCC3)s2)nn1] | 2.08 | 656 |

TABLE 11-continued
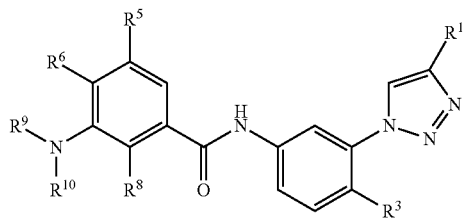
Examples XII-1 to XII-66
| # | Structure | t_Ret.(HPLC) [min] | MS (M + H)+ |
|---|---|---|---|
| XII-32 | 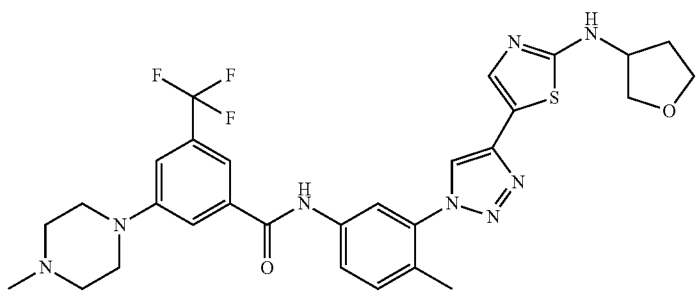 [SMILES: Cc1ccc(NC(=O)c2cc(N3CCN(C)CC3)cc(C(F)(F)F)c2)cc1-n1cc(-c2cnc(NC3CCOC3)s2)nn1] | 2.10 | 613 |
| XII-33 | 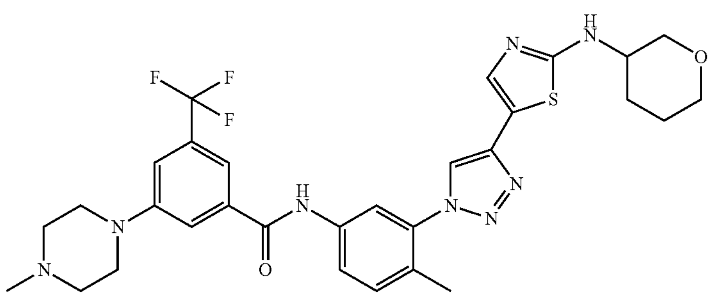 [SMILES: Cc1ccc(NC(=O)c2cc(N3CCN(C)CC3)cc(C(F)(F)F)c2)cc1-n1cc(-c2cnc(NC3CCCOC3)s2)nn1] | 2.19 | 641 |
| XII-34 | 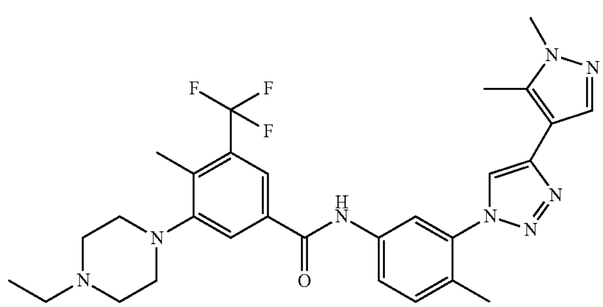 [SMILES: CCN1CCN(c2cc(C(=O)Nc3ccc(C)c(-n4cc(-c5cnn(C)c5C)nn4)c3)cc(C(F)(F)F)c2C)CC1] | 2.32 | 567 |
| XII-35 | 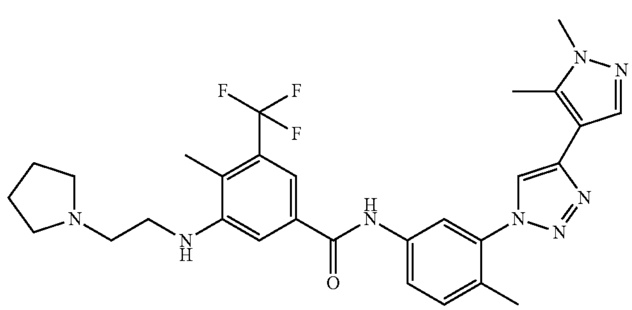 [SMILES: Cc1ccc(NC(=O)c2cc(NCCN3CCCC3)c(C)c(C(F)(F)F)c2)cc1-n1cc(-c2cnn(C)c2C)nn1] | 2.28 | 567 |

TABLE 11-continued
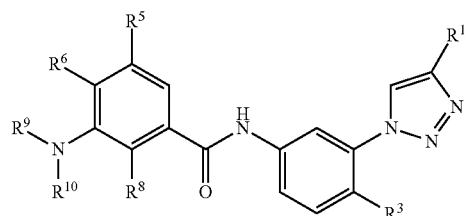
Examples XII-1 to XII-66
| # | Structure | $t_{Ret.}$(HPLC) [min] | MS (M + H)⁺ |
|---|---|---|---|
| XII-36 | 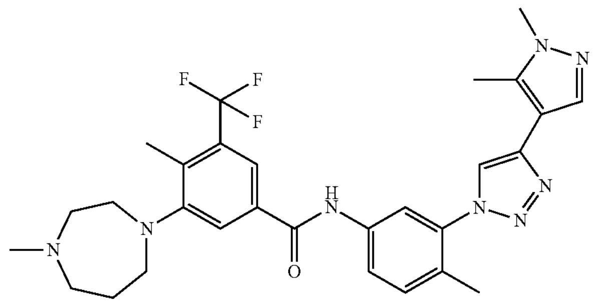 [SMILES: Cc1ccc(NC(=O)c2cc(N3CCCN(C)CC3)c(C)c(C(F)(F)F)c2)cc1-n1cc(-c2cnn(C)c2C)nn1] | 2.26 | 567 |
| XII-37 | 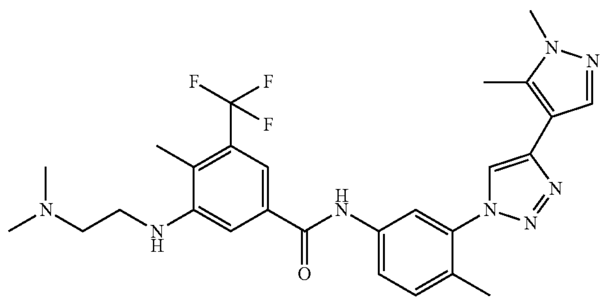 [SMILES: Cc1ccc(NC(=O)c2cc(NCCN(C)C)c(C)c(C(F)(F)F)c2)cc1-n1cc(-c2cnn(C)c2C)nn1] | 2.17 | 541 |
| XII-38 | 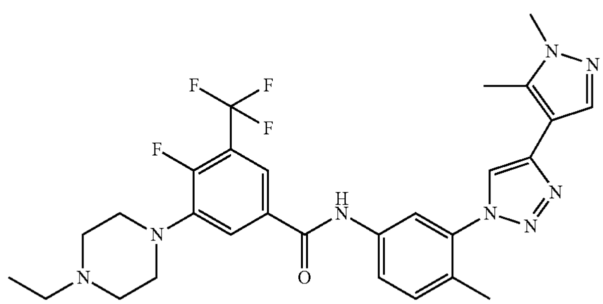 [SMILES: CCN1CCN(c2cc(C(=O)Nc3ccc(C)c(-n4cc(-c5cnn(C)c5C)nn4)c3)cc(C(F)(F)F)c2F)CC1] | 2.24 | 571 |
| XII-39 | 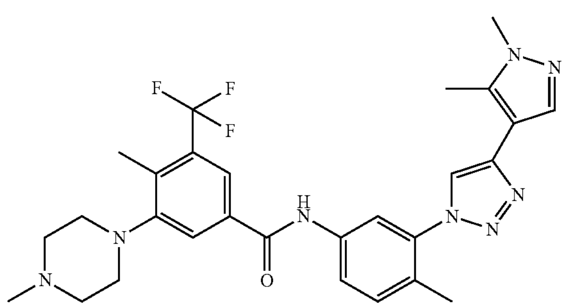 [SMILES: Cc1ccc(NC(=O)c2cc(N3CCN(C)CC3)c(C)c(C(F)(F)F)c2)cc1-n1cc(-c2cnn(C)c2C)nn1] | 2.21 | 553 |

TABLE 11-continued
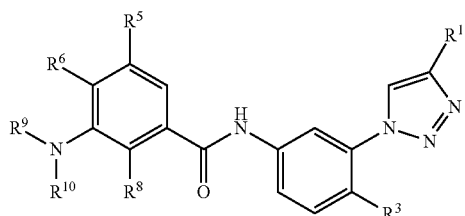
Examples XII-1 to XII-66
| # | Structure | $t_{Ret.}$(HPLC) [min] | MS (M + H)+ |
|---|---|---|---|
| XII-40 | 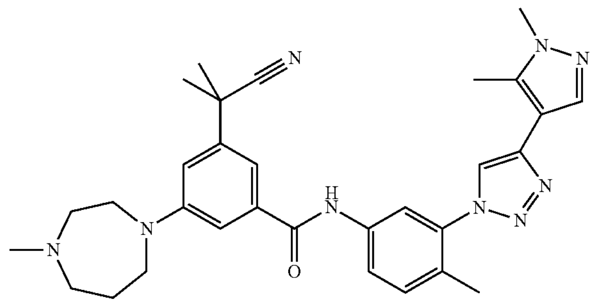 [SMILES: Cc1ccc(NC(=O)c2cc(N3CCCN(C)CC3)cc(C(C)(C)C#N)c2)cc1-n1cc(-c2cnn(C)c2C)nn1] | 2.00 | 552 |
| XII-41 | 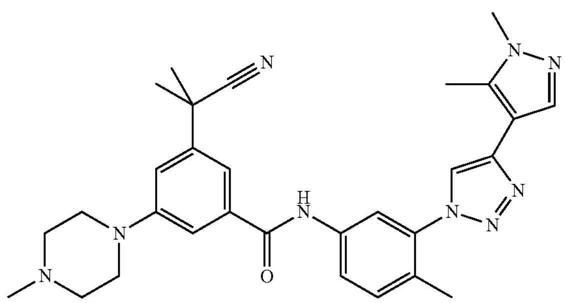 [SMILES: Cc1ccc(NC(=O)c2cc(N3CCN(C)CC3)cc(C(C)(C)C#N)c2)cc1-n1cc(-c2cnn(C)c2C)nn1] | 1.94 | 538 |
| XII-42 | 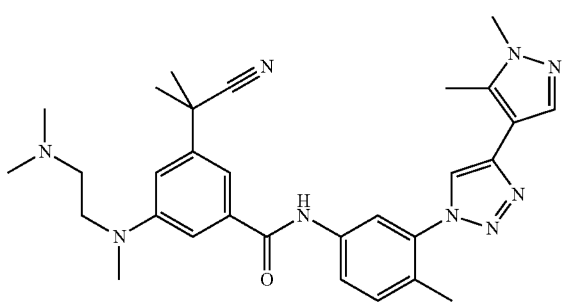 [SMILES: Cc1ccc(NC(=O)c2cc(N(C)CCN(C)C)cc(C(C)(C)C#N)c2)cc1-n1cc(-c2cnn(C)c2C)nn1] | 2.04 | 540 |
| XII-43 | 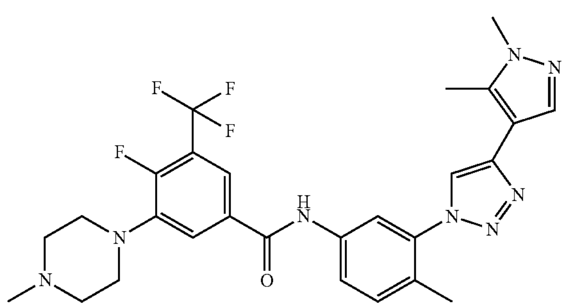 | 2.13 | 557 |

TABLE 11-continued
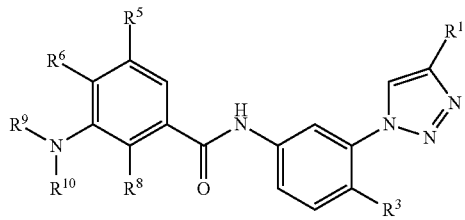
Examples XII-1 to XII-66
| # | Structure | t$_{Ret.}$(HPLC) [min] | MS (M + H)$^+$ |
|---|---|---|---|
| XII-44 | 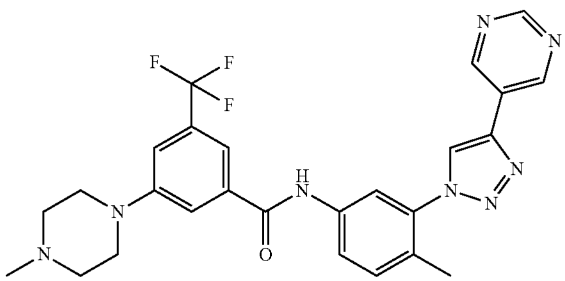 [SMILES: Cc1ccc(NC(=O)c2cc(N3CCN(C)CC3)cc(C(F)(F)F)c2)cc1-n1cc(-c2cncnc2)nn1] | 2.02 | 523 |
| XII-45 | 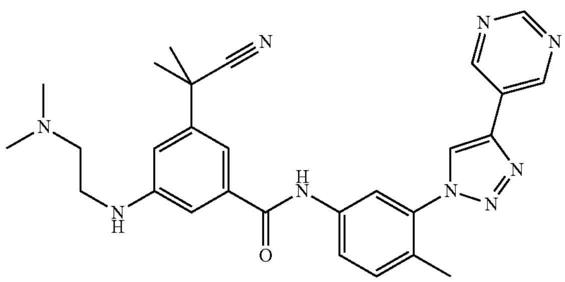 [SMILES: Cc1ccc(NC(=O)c2cc(NCCN(C)C)cc(C(C)(C)C#N)c2)cc1-n1cc(-c2cncnc2)nn1] | 1.92 | 510 |
| XII-46 | 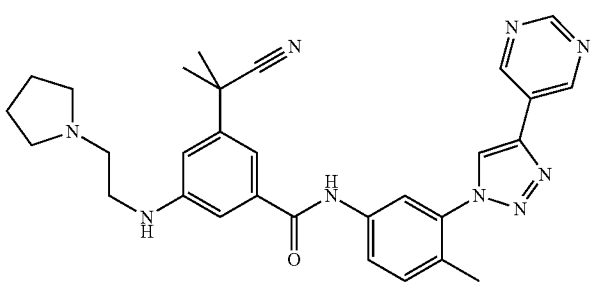 [SMILES: Cc1ccc(NC(=O)c2cc(NCCN3CCCC3)cc(C(C)(C)C#N)c2)cc1-n1cc(-c2cncnc2)nn1] | 2.03 | 536 |
| XII-47 | 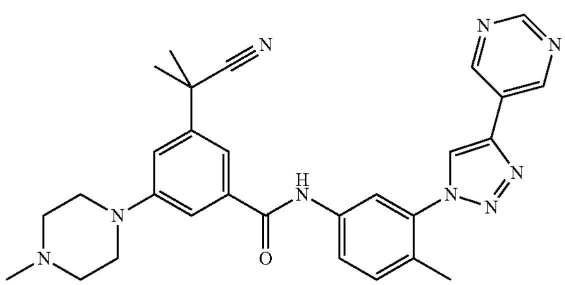 [SMILES: Cc1ccc(NC(=O)c2cc(N3CCN(C)CC3)cc(C(C)(C)C#N)c2)cc1-n1cc(-c2cncnc2)nn1] | 1.90 | 522 |

TABLE 11-continued
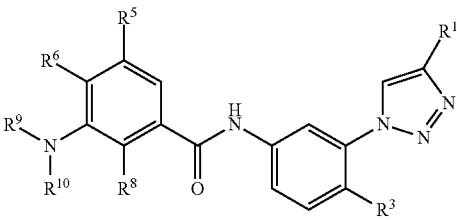
Examples XII-1 to XII-66
| # | Structure | t$_{Ret.}$(HPLC) [min] | MS (M + H)$^+$ |
|---|---|---|---|
| XII-48 | 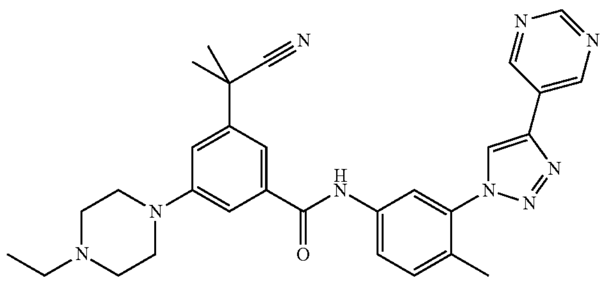 [SMILES: CCN1CCN(c2cc(C(=O)Nc3ccc(C)c(-n4cc(-c5cncnc5)nn4)c3)cc(C(C)(C)C#N)c2)CC1] | 1.98 | 536 |
| XII-49 | 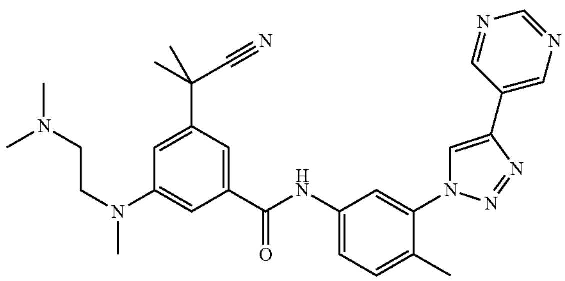 [SMILES: Cc1ccc(NC(=O)c2cc(N(C)CCN(C)C)cc(C(C)(C)C#N)c2)cc1-n1cc(-c2cncnc2)nn1] | 2.00 | 524 |
| XII-50 | 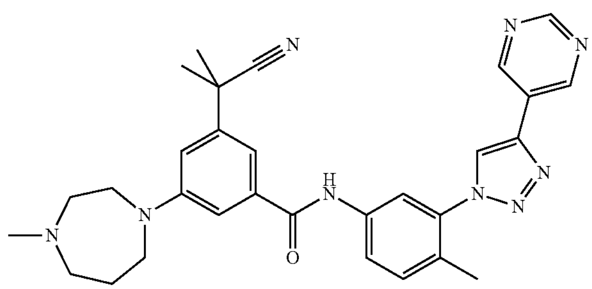 [SMILES: Cc1ccc(NC(=O)c2cc(N3CCCN(C)CC3)cc(C(C)(C)C#N)c2)cc1-n1cc(-c2cncnc2)nn1] | 1.96 | 536 |
| XII-51 | 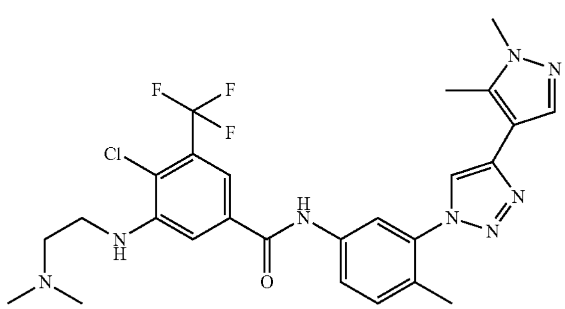 [SMILES: Cc1ccc(NC(=O)c2cc(NCCN(C)C)c(Cl)c(C(F)(F)F)c2)cc1-n1cc(-c2cnn(C)c2C)nn1] | 2.21 | 561 |

TABLE 11-continued
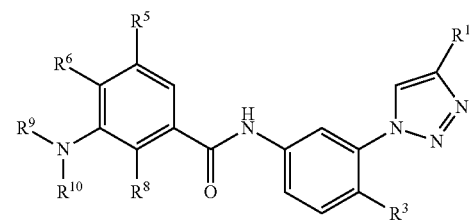
Examples XII-1 to XII-66
| # | Structure | $t_{Ret.}$(HPLC) [min] | MS (M + H)+ |
|---|---|---|---|
| XII-52 | 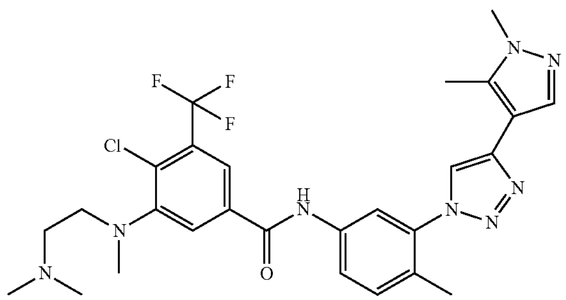 [SMILES: Cc1ccc(NC(=O)c2cc(N(C)CCN(C)C)c(Cl)c(C(F)(F)F)c2)cc1-n1cc(-c2cnn(C)c2C)nn1] | 2.25 | 575 |
| XII-53 | 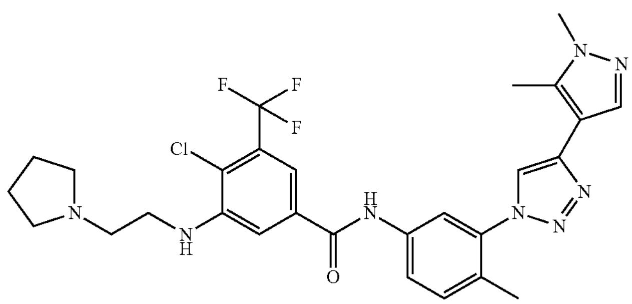 [SMILES: Cc1ccc(NC(=O)c2cc(NCCN3CCCC3)c(Cl)c(C(F)(F)F)c2)cc1-n1cc(-c2cnn(C)c2C)nn1] | 2.37 | 587 |
| XII-54 | 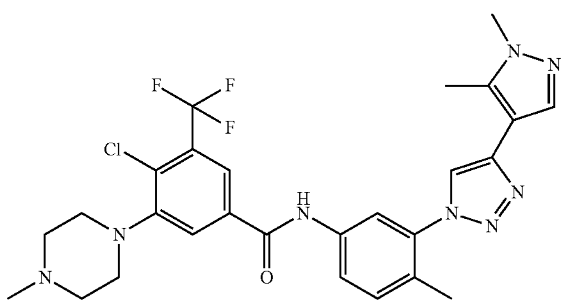 | 2.21 | 573 |
| XII-55 | 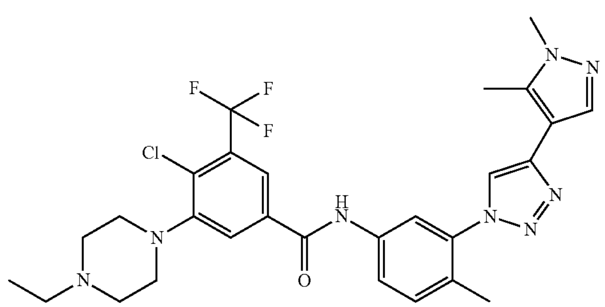 | 2.31 | 587 |

TABLE 11-continued
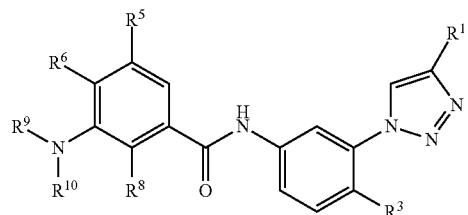
Examples XII-1 to XII-66
| # | Structure | $t_{Ret.}$(HPLC) [min] | MS (M + H)+ |
|---|---|---|---|
| XII-56 | 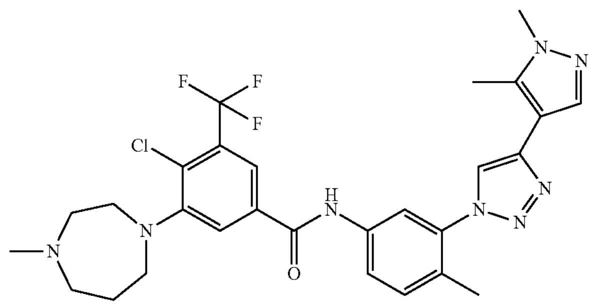 | 2.26 | 587 |
| XII-57 | 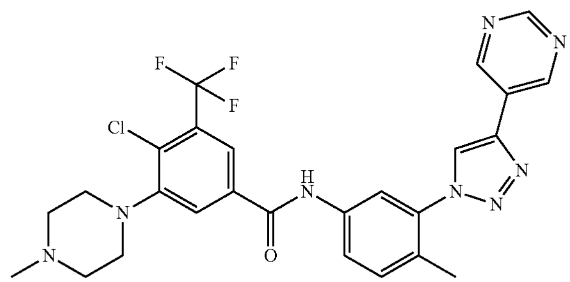 | 2.18 | 557 |
| XII-58 | 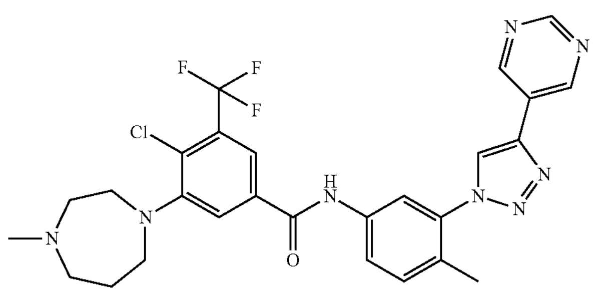 [SMILES: Cc1ccc(NC(=O)c2cc(N3CCCN(C)CC3)c(Cl)c(C(F)(F)F)c2)cc1-n1cc(-c2cncnc2)nn1] | 2.23 | 571 |
| XII-59 | 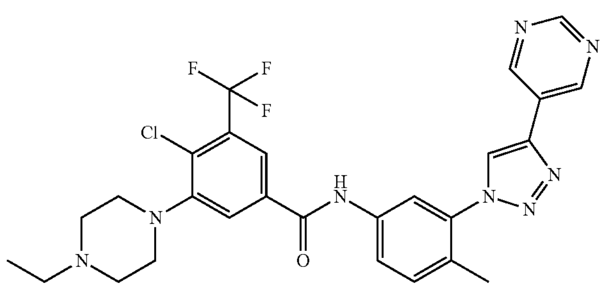 [SMILES: CCN1CCN(c2cc(C(=O)Nc3ccc(C)c(-n4cc(-c5cncnc5)nn4)c3)cc(C(F)(F)F)c2Cl)CC1] | 2.28 | 571 |

TABLE 11-continued
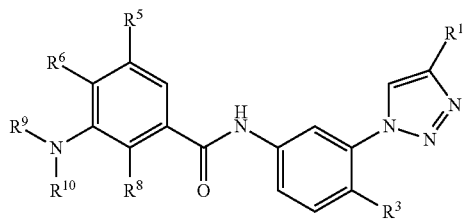
Examples XII-1 to XII-66
| # | Structure | $t_{Ret.}$(HPLC) [min] | MS (M + H)$^+$ |
|---|---|---|---|
| XII-60 | 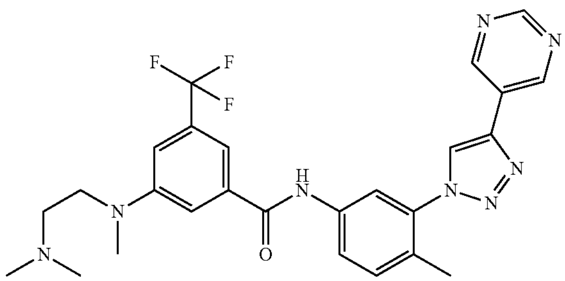 [SMILES: Cc1ccc(NC(=O)c2cc(N(C)CCN(C)C)cc(C(F)(F)F)c2)cc1-n1cc(-c2cncnc2)nn1] | 2.13 | 525 |
| XII-61 | 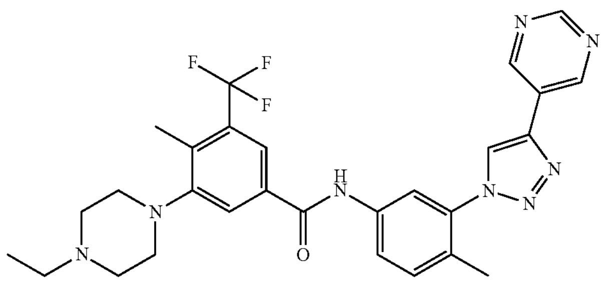 [SMILES: CCN1CCN(c2cc(C(=O)Nc3ccc(C)c(-n4cc(-c5cncnc5)nn4)c3)cc(C(F)(F)F)c2C)CC1] | 1.98 | 551 |
| XII-62 | 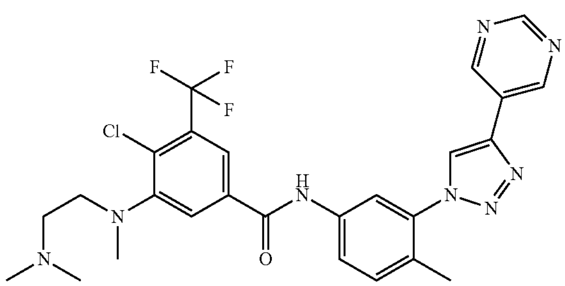 [SMILES: Cc1ccc(NC(=O)c2cc(N(C)CCN(C)C)c(Cl)c(C(F)(F)F)c2)cc1-n1cc(-c2cncnc2)nn1] | 1.89 | 559 |
| XII-63 | 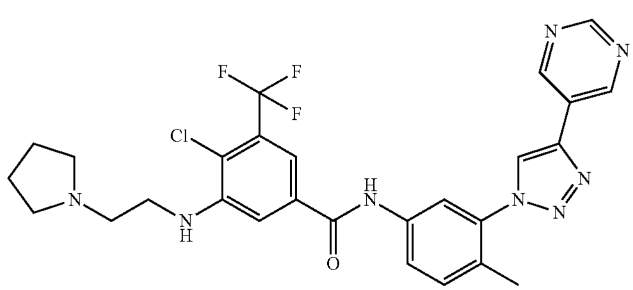 [SMILES: Cc1ccc(NC(=O)c2cc(NCCN3CCCC3)c(Cl)c(C(F)(F)F)c2)cc1-n1cc(-c2cncnc2)nn1] | 2.04 | 571/573 |

TABLE 11-continued
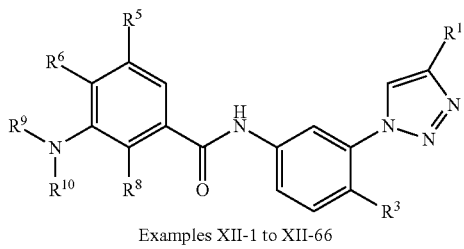
Examples XII-1 to XII-66
| # | Structure | t_Ret.(HPLC) [min] | MS (M + H)+ |
|---|---|---|---|
| XII-64 | 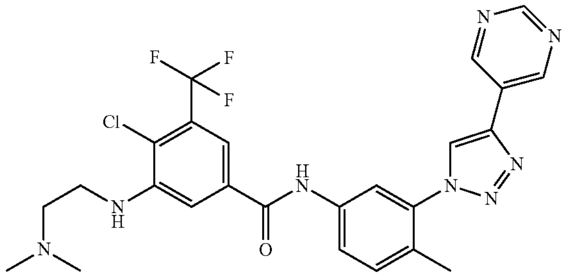 [SMILES: Cc1ccc(NC(=O)c2cc(NCCN(C)C)c(Cl)c(C(F)(F)F)c2)cc1-n1cc(-c2cncnc2)nn1] | 1.77 | 511 |
| XII-65 | 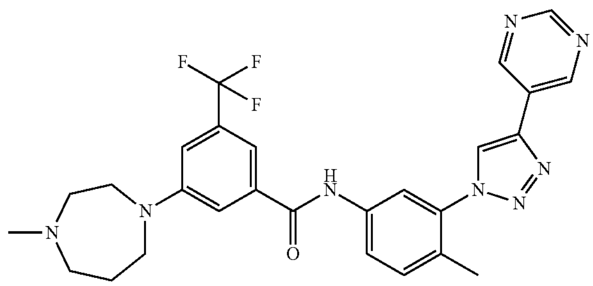 [SMILES: Cc1ccc(NC(=O)c2cc(N3CCCN(C)CC3)cc(C(F)(F)F)c2)cc1-n1cc(-c2cncnc2)nn1] | 1.78 | 537 |
| XII-66 | 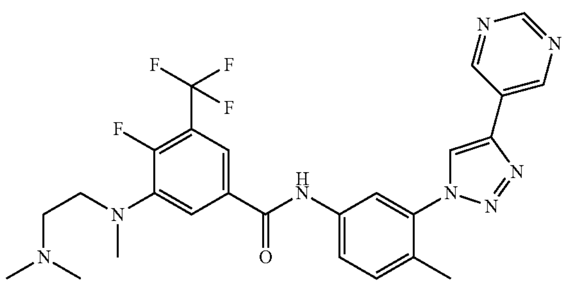 [SMILES: Cc1ccc(NC(=O)c2cc(N(C)CCN(C)C)c(F)c(C(F)(F)F)c2)cc1-n1cc(-c2cncnc2)nn1] | 1.85 | 543 |
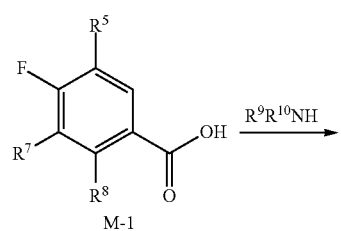
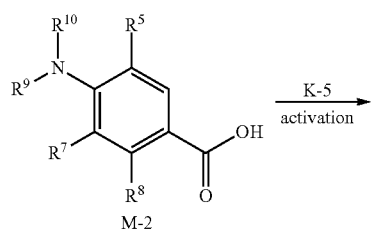

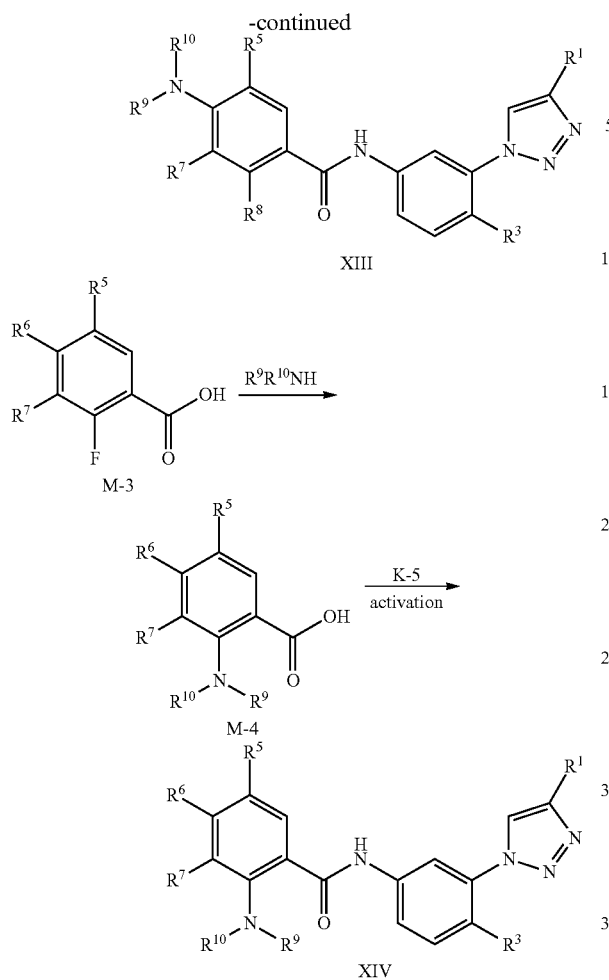

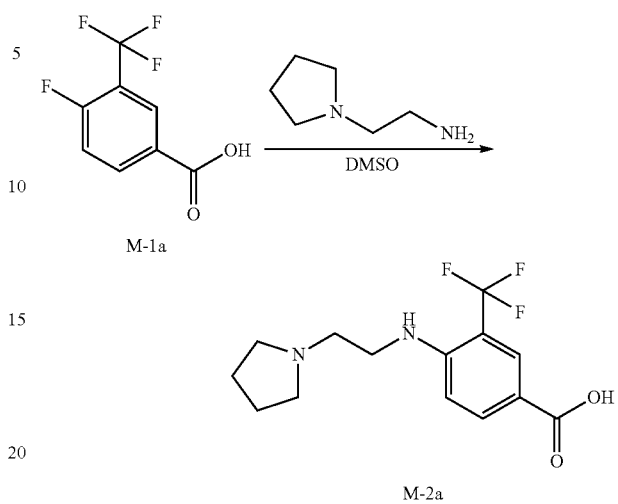

a) Procedure for Synthesising M-2a:

In a microwave vial 4-fluoro-3-(trifluoromethyl)-benzoic acid M-1a (150 mg, 0.721 mmol) and N-(2-aminoethyl)pyrrolidine (99 mg, 0.865 mmol) are taken up in 1.5 mL DMSO. The reaction mixture is heated to 120° C. using a microwave reactor, stirred for 4 h, then diluted with EtOAc, washed twice with water and with sat. NaCl solution, dried on $Na_2SO_4$, filtered and evaporated down using the rotary evaporator. The crude product is purified by preparative HPLC. The product-containing fractions of M-2a (HPLC-MS: $t_{Ret.}$=0 Min; MS $(M+H)^+$=303) are freeze-dried.

Analogously to this procedure further benzoic acids M-2 and M-4 are obtained from the corresponding M-1 or M-3 intermediates/educts.

b) Procedure for Synthesising XIII-1:

Example compounds of type XIII (arylamines in the p-position to the amide link→$R^6$) and type XVI (arylamines in the o-position to the amide link→$R^8$), which are prepared according to general scheme M, have an inverse amide bond, compared with the compounds of type IV or V (reaction scheme E).

Example compounds of type XIII and type XIV are synthesised by an amide coupling reaction of the benzoic acids M-2 or M-4 (in order to introduce the group $R^2$) and the corresponding anilines K-5 described hereinbefore. The benzoic acids M-2 or M-4 used are commercially obtainable or are synthesised using methods known from the literature from the corresponding fluorobenzoic acids M-1 or M-3 by nucleophilic aromatic substitution with an amine $R^9R^{10}NH$ in common solvents such as e.g. NMP, DMSO or DMF. The amines $R^9R^{10}NH$ used are commercially obtainable or are synthesised using methods known from the literature.

The reaction conditions for the nucleophilic substitution are essentially independent of whether the starting material is an educt M-1 (4-fluorobenzoic acid) or M-3 (2-fluorobenzoic acid). Therefore the following is a description by way of example of only the synthesis of M-2 and hence of examples of type XIII The reaction conditions can also be applied to the synthesis of M-4 and examples of type XVI.

Alternatively to the educts M-1 and M-3, L-1-analogous o- and p-bromobenzoic acids which are functionalised by palladium-catalysed cross-couplings (Buchwald-Hartwig) with the amines $R^9R^{10}NH$ may also be used.

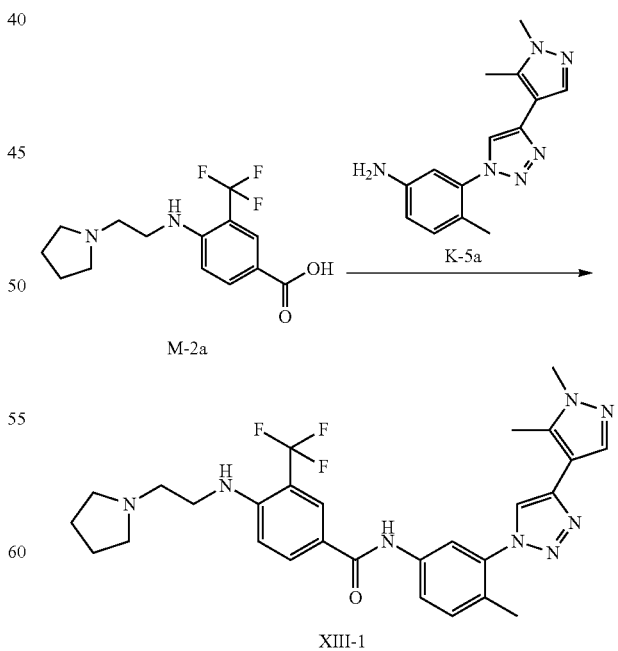

Benzoic acid M-2a (40 mg, 0.132 mmol) is taken up in 500 μL NMP, combined with HATU (43 mg, 0.132 mmol) and DIPEA (20.5 mg, 0.159 mmol) and stirred for 20 min at RT. Then the aniline K-5a (51 mg, 0.132 mmol) is added and the reaction mixture is stirred overnight at RT. The reaction mixture is filtered and the residue is purified by preparative HPLC. The product-containing fractions of XIII-1 (HPLC-MS: $t_{Ret.}$=1.58 min; MS (M+H)$^+$=553) are freeze-dried.

Analogously to reaction methods a) and b) described above, Examples XIII-2 and XIV-1 to XIV-3 (Table 12) or comparable further examples may also be obtained from the corresponding precursors, which are either commercially obtainable or are prepared using methods known from the literature.

TABLE 12

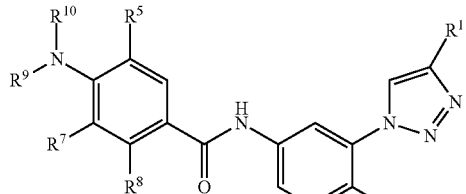

Examples XIII-1 to XIII-2

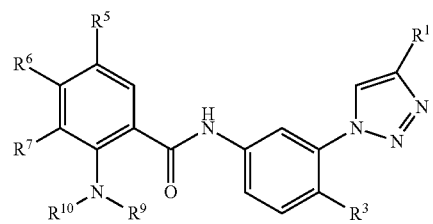

Examples XIV-1 to XIV-3

| # | Structure | $t_{Ret}$ (HPLC) [min] | MS (M + H)$^+$ |
|---|---|---|---|
| XIII-1 | 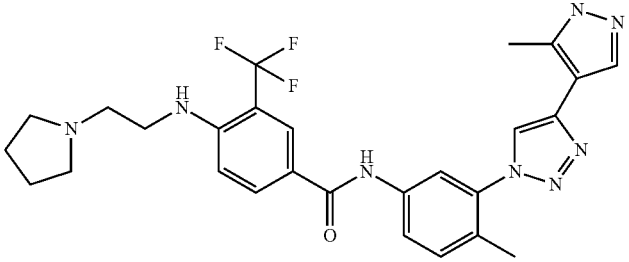 | 1.58 | 553 |
| XIII-2 | 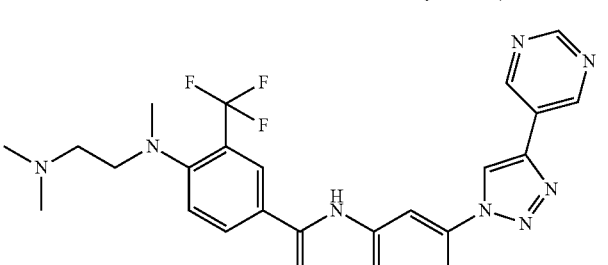 | 2.06 | 525 |
| XIV-1 | 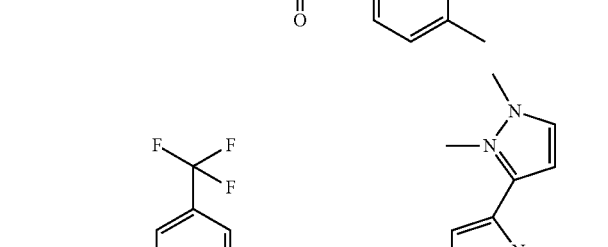 | 1.46 | 541 |

TABLE 12-continued
| | | | |
|---|---|---|---|
| XIV-2 | 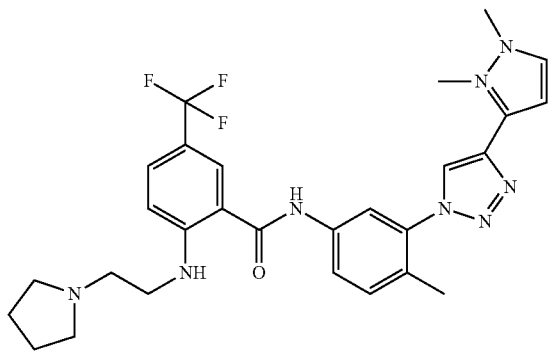 | 1.51 | 553 |
| XIV-3 | 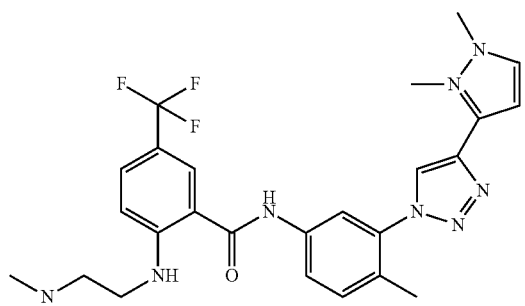 | 1.47 | 527 |
Reaction scheme N-I
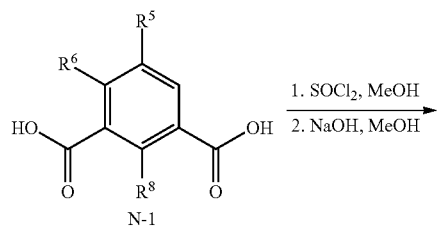 1. SOCl$_2$, MeOH
2. NaOH, MeOH
→ 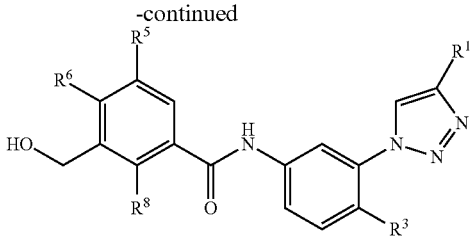
N-3
Method A: 1. SOCl$_2$
2. R$^9$R$^{10}$NH or R$^9$R$^{10}$N(CH$_2$)$_y$OH/NaH
or
Method B: 1. MnO$_2$
2. R$^9$R$^{10}$NH, Na(AcO)$_3$BH, AcOH
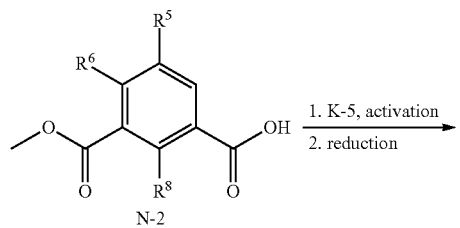 1. K-5, activation
2. reduction
→ 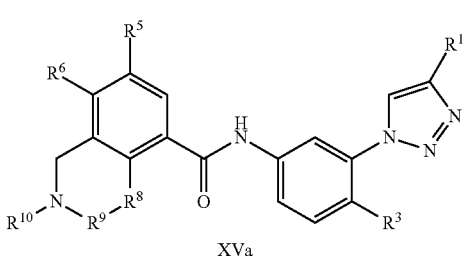
XVa

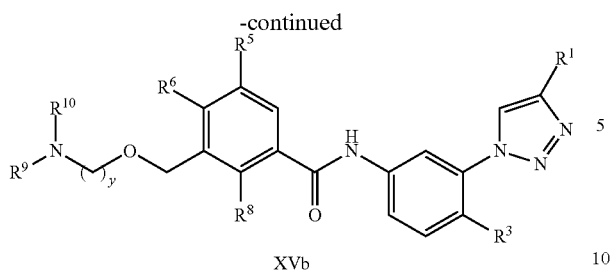

XVb

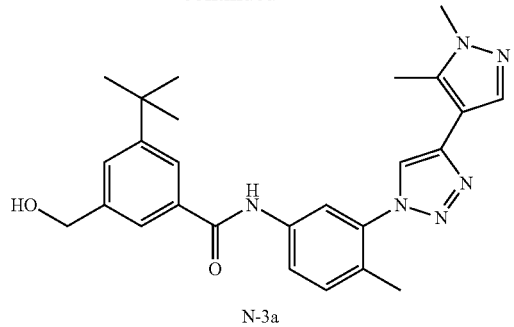

N-3a

Example compounds of type XV (benzylethers or benzylamines in the m-position to the amide link→$R^7$), prepared according to general Scheme N-I, have an inverse amide bond, compared with the compounds of type I (reaction scheme B-I).

Example compounds of type XV are prepared from benzylalcohols N-3 either by substitution of the corresponding benzyl chloride by means of an amine/hydroxylamine $R^9R^{10}NH$ (type XVa→benzylamine) or aminoalcohol $R^9R^{10}N(CH_2)_yOH$ (or alkoxide, type XVb→benzylether) or by reductive amination of a corresponding aldehyde with an amine $R^9R^{10}NH$ (type XVa→benzylamine). In the former case the benzyl alcohols N-3 are reacted for this purpose by means of thionyl chloride using methods known from the literature to obtain the corresponding benzyl chloride. In the latter case the benzylalcohols N-3 may be oxidised e.g. with $MnO_2$, Dess-Martin-Periodinane or other common oxidising agents to form the corresponding aldehydes and then reacted in acetic acid medium with $Na(OAc)_3BH$ or $Na(CN)BH_3$ and an amine $R^9R^{10}NH$ using methods known from the literature to obtain compounds of type XVa. The amines/hydroxylamines/aminoalcohols used are commercially obtainable or are synthesised using methods known from the literature.

The benzylalcohols N-3 are synthesised by an amide coupling reaction of the isophthalic acid monoesters N-2 (in order to introduce the group $R^2$) and the corresponding anilines K-5 described above, and subsequent reduction of the ester function. The isophthalic acid monoesters N-2 used are commercially obtainable or are synthesised using methods known from the literature from the corresponding isophthalic acids N-1 by esterification, e.g. with thionyl chloride in MeOH and subsequent monosaponification, e.g. with NaOH in MeOH via various intermediate products Z.

a) Procedure for Synthesising N-3a:

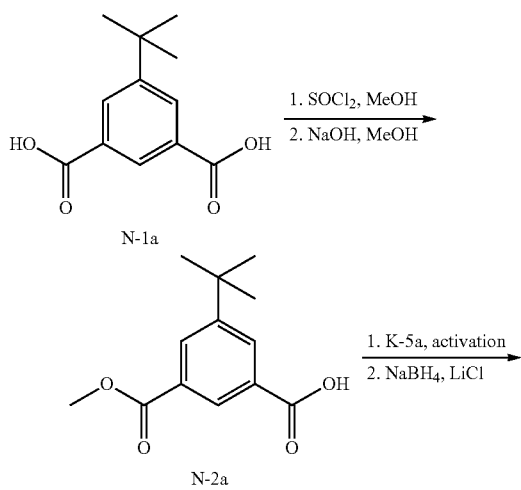

5-tert-butyl-isophthalic acid N-1a (5.00 g, 22.5 mmol) is taken up in 13 mL MeOH, cooled to −15° C. and thionyl chloride is added dropwise. After the addition is complete, the reaction mixture is stirred overnight at RT and then refluxed for 24 h. The volatile constituents are eliminated using the rotary evaporator, the residue is taken up in EtOAc and washed with sat. $NaHCO_3$ solution. The organic phase is dried with $MgSO_4$, filtered, evaporated down and the intermediate product Z-24a thus obtained (HPLC-MS: $t_{Ret.}$=2.30 min; MS $(M+H)^+$=251) is further reacted directly.

Intermediate product Z-24a (5.54 g, 22.15 mmol) is taken up in 45 mL acetone and at RT a solution of NaOH (877 mg, 21.9 mmol) in 10 mL MeOH is added dropwise. The reaction mixture is stirred for 16 h at RT and then evaporated down. The residue is combined with $NaHCO_3$ solution and extracted with EtOAc. The organic phase is extracted again with $NaHCO_3$ solution and the aqueous phases are then acidified with 4 N HCl. The precipitate is filtered off, washed with water, dried and isophthalic acid monoester N-2a (HPLC-MS: $t_{Ret.}$=1.26 min; MS $(M-H)^-$=235) is further reacted directly.

Isophthalic acid monoester N-2a (504 mg, 2.132 mmol) is taken up in 10 mL THF, combined with HATU (754 mg, 2.34 mmol) and DIPEA (814 μL, 4.87 mmol) and stirred for 20 min at RT. Then the aniline K-5a (570 mg, 2.123 mmol) is added and the reaction mixture is stirred overnight at 40° C. The reaction mixture is filtered and the solvent is eliminated by distillation. The residue is taken up in EtOAc and extracted with sat. $NaHCO_3$ solution. The organic phase is washed with sat. NaCl solution, dried on $Na_2SO_4$, filtered and evaporated down using the rotary evaporator. The crude product is purified by preparative HPLC. The product-containing fractions of Z-25a (HPLC-MS: $t_{Ret.}$=2.03 min; MS $(M+H)^+$=487) are freeze-dried.

Methyl benzoate Z-25a (423 mg, 0.87 mmol) is taken up in THF (8 mL), and $NaBH_4$ (190 g, 5.02 mmol) and then LiCl (154 mg, 3.63 mmol) are added batchwise. The reaction mixture is heated to 50° C. and stirred for 72 h. Then it is cooled to 0° C. and combined with stirring with 1 M NaOH solution. THF is eliminated using the rotary evaporator and the crude product is extracted with EtOAc. The combined organic phases are washed with sat. NaCl solution, dried on $MgSO_4$, filtered, evaporated down using the rotary evaporator, the residue is taken up in DMF and purified by preparative HPLC. The product-containing fractions of benzylalcohol N-3a (HPLC-MS: $t_{Ret.}$=1.81 min; MS $(M+H)^+$=459) are freeze-dried.

b) Procedure for Synthesising XVa-1 (benzyl chloride Route, Method A):

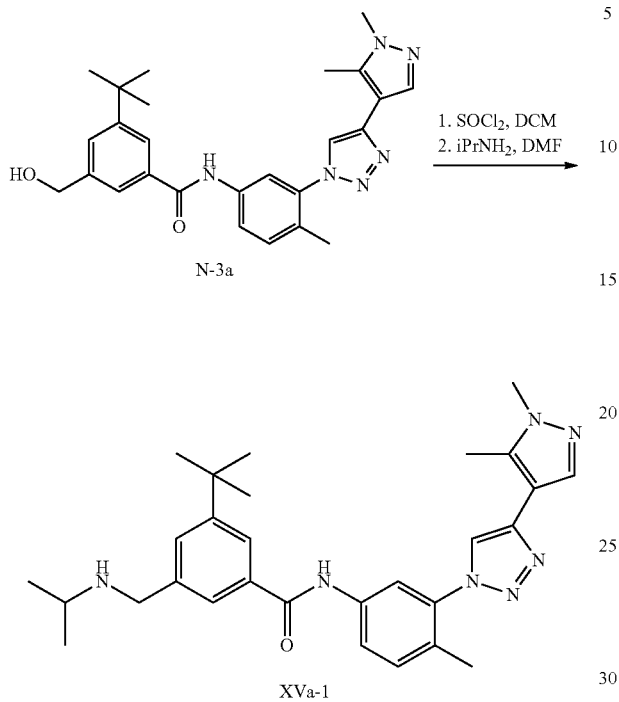

Benzylalcohol N-3a (40 mg, 0.09 mmol) is taken up in 3 ml DCM and combined with thionyl chloride (27 μL, 0.37 mmol) with stirring at RT. The reaction mixture is stirred for 3 h at RT, evaporated down, the residue is taken up in DMF (300 μL), combined with i-propylamine (30 μL, 0.35 mmol) and stirred for 3 h at RT. The volatile constituents are eliminated using the rotary evaporator and the residue is purified by preparative HPLC. The product-containing fractions of XVa-1 (HPLC-MS: $t_{Ret.}$=2.19 min; MS (M+H)$^+$=500) are freeze-dried.

Reaction scheme N-II

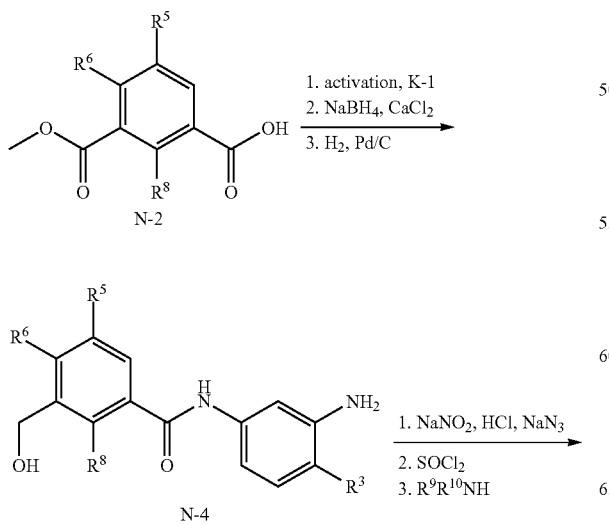

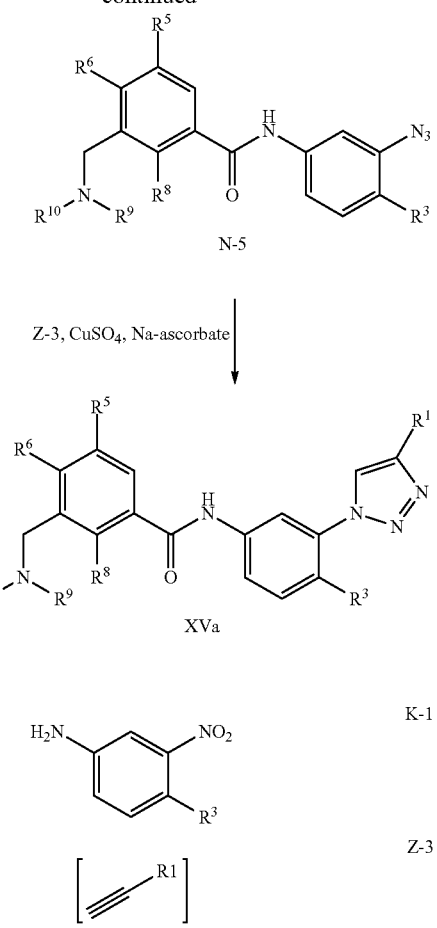

Example compounds of type XVa may also be synthesised by a slightly modified method according to reaction scheme N-II from the azides N-5 by cycloaddition with alkynes Z-3, CuSO$_4$ and sodium ascorbate. The azides N-5 may be obtained from the corresponding benzylalcohols N-4 by diazotisation with for example NaNO$_2$ in hydrochloric acid, subsequent reaction with sodium azide, activation of the benzylalcohol using thionyl chloride, for example, followed by reaction with an amine R$^9$R$^{10}$NH. The benzylalcohols N-4 are in turn synthesised by amide linking of the isophthalic acid monoester N-2 with nitroanilines K-1, subsequent reduction of the ester function, for example with NaBH$_4$ in the presence of CaCl$_2$, and subsequent reduction of the nitro group, for example with hydrogen and Pd/C or with Fe in the presence of NH$_4$Cl.

c) Procedure for Synthesising N-4a

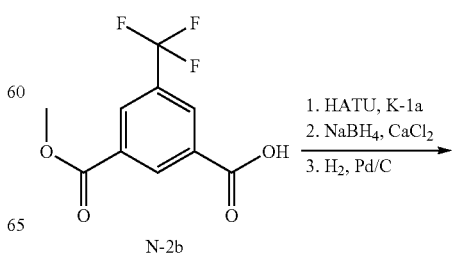

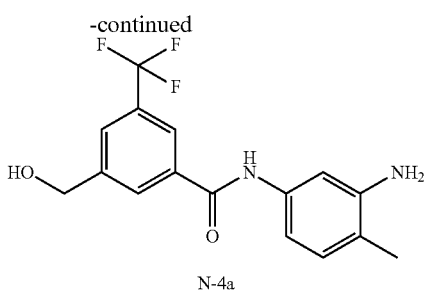

N-4a

The isophthalic acid monoester N-2b (3.76 g, 15.2 mmol) is dissolved in DMF (8 mL) and stirred for 10 min at RT with HATU (6.01 g, 16.6 mmol) and iPr$_2$EtNH (5.8 mL, 34.9 mmol). After the addition of aniline K-1a (2.31 g, 15.2 mmol) the mixture is stirred overnight at 40° C. The reaction mixture is purified by preparative RP-MPLC (gradient: water/acetonitrile=80:20 to 2:98; 45 min). The product-containing fractions (HPLC-MS: $t_{Ret.}$=2.35 min; MS (M+H)$^+$=383) are combined and freeze-dried.

The amide intermediate product (3.9 g, 10.1 mmol) is placed in EtOH (70 mL), combined with CaCl$_2$ (2.24 g, 20.3 mmol) and briefly stirred in the ultrasound bath. Then the mixture is cooled to 0° C. and NaBH$_4$ (1.53 g, 40.5 mmol) in THF (70 mL) is added thereto. The mixture is left at this temperature for 1.5 h with stirring and then 1 N hydrochloric acid is carefully added. The aqueous phase is extracted with DCM (4×75 mL), the combined organic phase is dried on MgSO$_4$, filtered off and evaporated down.

The benzylalcohol thus obtained (2.86 g, 8.07 mmol) is placed in MeOH (50 mL), combined with Pd/C (10%, 775 mg) and hydrogenated for 3 h at RT (p=50 PSI). After the catalyst has been filtered off and the mixture has been evaporated down the benzylalcohol N-4a is obtained, which is used for the next reaction without any further purification steps.

d) Procedure for Synthesising N-5a

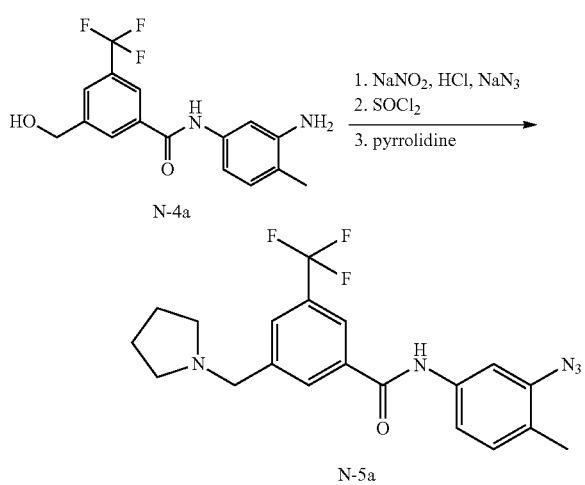

The benzylalcohol N-4a (2.21 g, 6.82 mmol) placed at 0° C. in 2 N hydrochloric acid (29 mL) and dioxane (5 mL) is combined dropwise with a cooled solution of sodium nitrite (567 mg, 8.22 mmol) in water (2.2 mL). After the addition has ended the mixture is left for 30 min with stirring, then sodium azide (495 mg, 7.54 mmol) in cooled water (2.2 mL) is added and the mixture is stirred for a further 2.5 h. For working up the mixture is diluted with water and extracted with EtOAc (3×50 mL). The combined organic phase is dried on MgSO$_4$, filtered and evaporated down. The azide thus obtained is used for the next reaction without any further purification.

The azide (602 mg, 1.72 mmol) is placed in DCM (5 mL), combined with thionyl chloride (497 μL, 6.85 mmol) and stirred for 3 h at RT. The reaction mixture is evaporated down, the residue is taken up in DMF (3 mL), combined with pyrrolidine (710 μl, 8.59 mmol) and stirred overnight at 40° C. The reaction mixture is purified by preparative HPLC. The product-containing fractions of N-5a (HPLC-MS: $t_{Ret.}$=1.79 min; MS (M+H)$^+$=404) are freeze-dried.

e) Procedure for Synthesising XVa-4

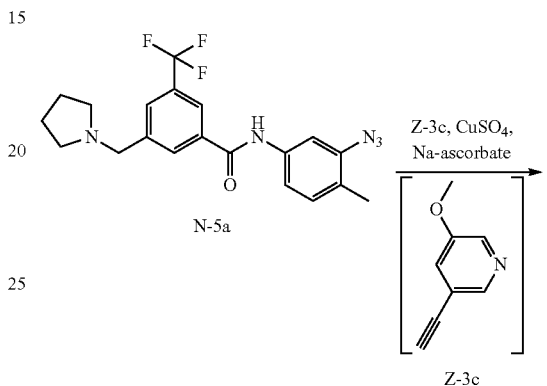

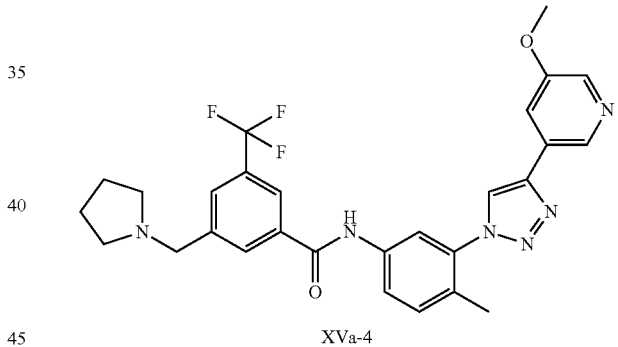

XVa-4

The azide N-5a (50.8 mg, 0.13 mmol), sodium ascorbate solution (40 mg; 0.20 mmol in 1 mL water) and CuSO$_4$ solution (20.3 μl, 0.8 M) are added successively to the alkyne Z-3c, which is generated in situ from the trimethylsilyl-protected precursor (75.5 mg, 0.37 mmol) by reaction with K$_2$CO$_3$ (57.3 mg, 0.42 mmol) in MeOH (3 mL) at RT (30 min). The reaction mixture is stirred overnight at 40° C. and then evaporated down. The residue is taken up in a little DMF and purified by preparative HPLC. The product-containing fractions of XVa-4 (HPLC-MS: $t_{Ret.}$=2.32 min; MS (M+H)$^+$=537) are freeze-dried.

Analogously to reaction methods a) and b) or c) to e) described above, Examples XVa-2 and XVa-3 and Examples XVa-5-XVa-33 (Table 13) or comparable further examples may be obtained from the corresponding precursors, which are either commercially obtainable or are prepared using methods known from the literature.

TABLE 13
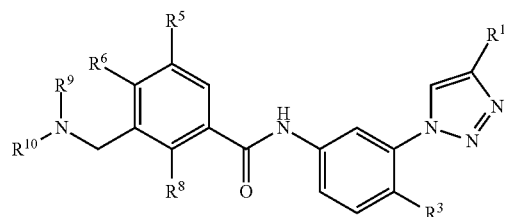
Examples XVa-1 to XVa-33
| # | Structure | $t_{Ret}$ (HPLC) [min] | MS (M + H)⁺ |
|---|---|---|---|
| XVa-1 | 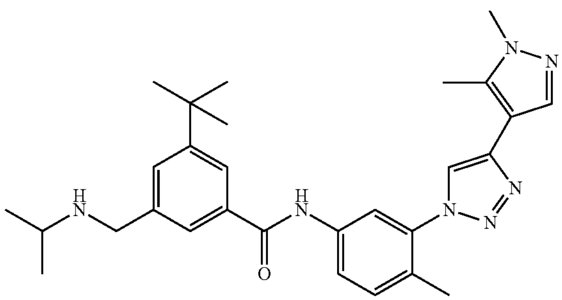 [SMILES: Cc1ccc(NC(=O)c2cc(CNC(C)C)cc(C(C)(C)C)c2)cc1-n1cc(-c2cnn(C)c2C)nn1] | 2.19 | 500 |
| XVa-2 | 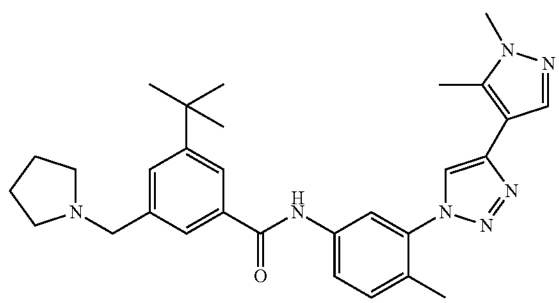 [SMILES: Cc1ccc(NC(=O)c2cc(CN3CCCC3)cc(C(C)(C)C)c2)cc1-n1cc(-c2cnn(C)c2C)nn1] | 2.26 | 512 |
| XVa-3 | 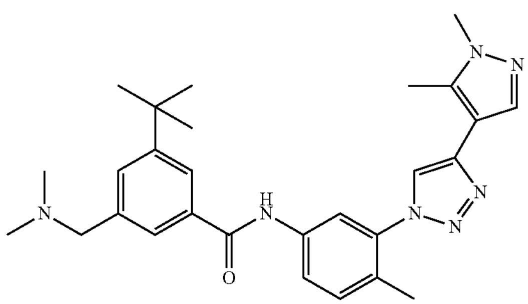 [SMILES: Cc1ccc(NC(=O)c2cc(CN(C)C)cc(C(C)(C)C)c2)cc1-n1cc(-c2cnn(C)c2C)nn1] | 2.13 | 486 |
| XVa-4 | 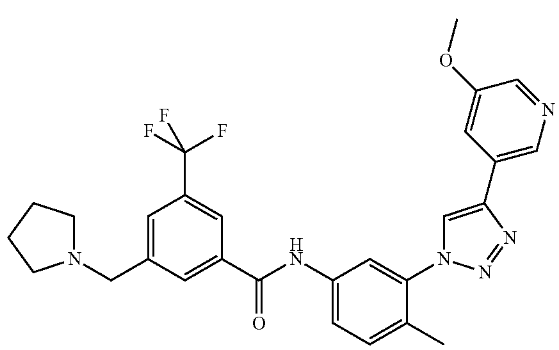 [SMILES: COc1cncc(-c2cn(-c3cc(NC(=O)c4cc(CN5CCCC5)cc(C(F)(F)F)c4)ccc3C)nn2)c1] | 2.32 | 537 |

TABLE 13-continued

Examples XVa-1 to XVa-33

| # | Structure | $t_{Ret}$ (HPLC) [min] | MS (M + H)+ |
|---|---|---|---|
| XVa-5 | 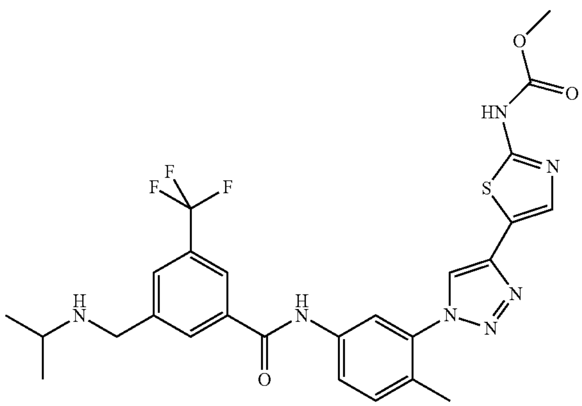 [SMILES: COC(=O)Nc1ncc(-c2cn(-c3cc(NC(=O)c4cc(CNC(C)C)cc(C(F)(F)F)c4)ccc3C)nn2)s1] | 2.22 | 562 |
| XVa-6 | 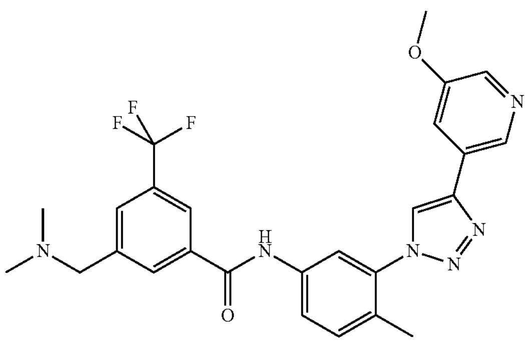 [SMILES: COc1cncc(-c2cn(-c3cc(NC(=O)c4cc(CN(C)C)cc(C(F)(F)F)c4)ccc3C)nn2)c1] | 2.20 | 511 |
| XVa-7 | 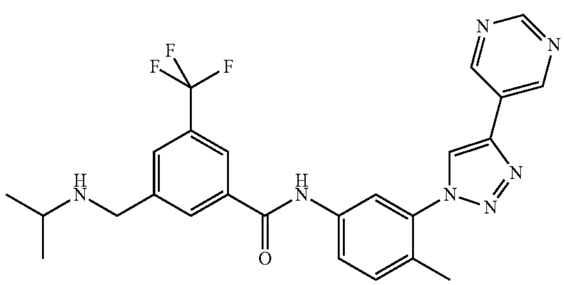 [SMILES: Cc1ccc(NC(=O)c2cc(CNC(C)C)cc(C(F)(F)F)c2)cc1-n1cc(-c2cncnc2)nn1] | 2.21 | 484 |
| XVa-8 | 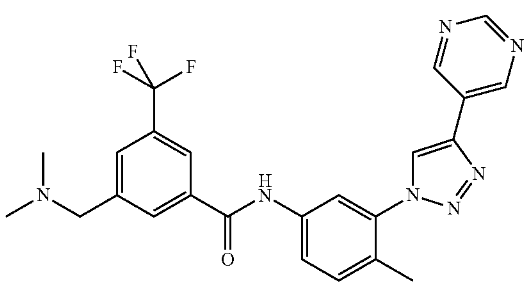 [SMILES: Cc1ccc(NC(=O)c2cc(CN(C)C)cc(C(F)(F)F)c2)cc1-n1cc(-c2cncnc2)nn1] | 2.06 | 482 |

TABLE 13-continued
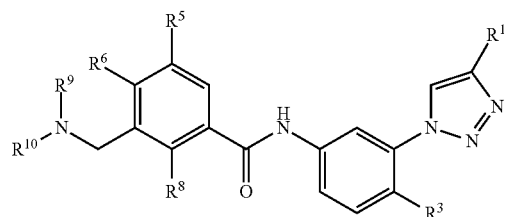
Examples XVa-1 to XVa-33
| # | Structure | t$_{Ret}$ (HPLC) [min] | MS (M + H)$^+$ |
|---|---|---|---|
| XVa-9 | 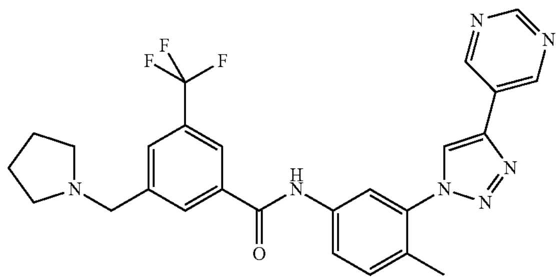 [SMILES: Cc1ccc(NC(=O)c2cc(CN3CCCC3)cc(C(F)(F)F)c2)cc1-n1cc(-c2cncnc2)nn1] | 2.19 | 508 |
| XVa-10 | 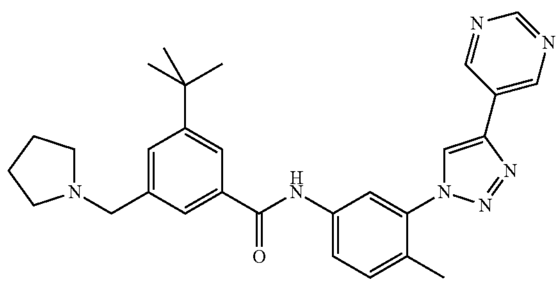 [SMILES: Cc1ccc(NC(=O)c2cc(CN3CCCC3)cc(C(C)(C)C)c2)cc1-n1cc(-c2cncnc2)nn1] | 2.28 | 496 |
| XVa-11 | 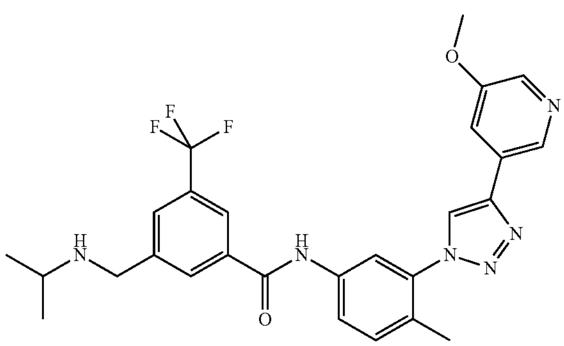 [SMILES: COc1cncc(-c2cn(-c3cc(NC(=O)c4cc(CNC(C)C)cc(C(F)(F)F)c4)ccc3C)nn2)c1] | 2.24 | 525 |
| XVa-12 | 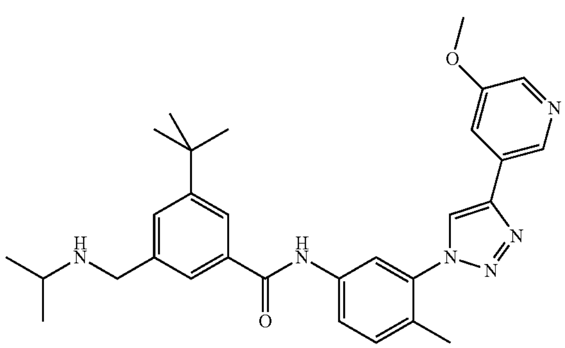 [SMILES: COc1cncc(-c2cn(-c3cc(NC(=O)c4cc(CNC(C)C)cc(C(C)(C)C)c4)ccc3C)nn2)c1] | 2.34 | 513 |

TABLE 13-continued
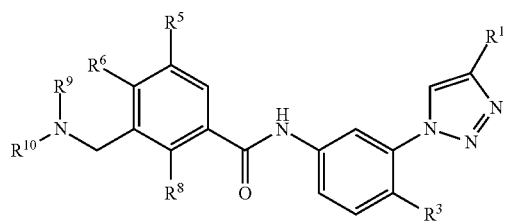
Examples XVa-1 to XVa-33
| # | Structure | $t_{Ret}$ (HPLC) [min] | MS (M + H)⁺ |
|---|---|---|---|
| XVa-13 | 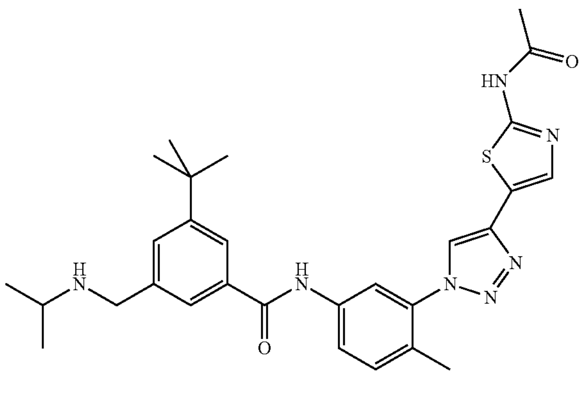 [SMILES: CC(=O)Nc1ncc(-c2cn(-c3cc(NC(=O)c4cc(CNC(C)C)cc(C(C)(C)C)c4)ccc3C)nn2)s1] | 2.20 | 546 |
| XVa-14 | 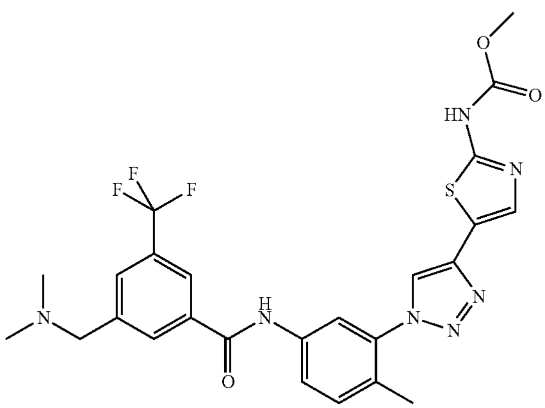 [SMILES: COC(=O)Nc1ncc(-c2cn(-c3cc(NC(=O)c4cc(CN(C)C)cc(C(F)(F)F)c4)ccc3C)nn2)s1] | 2.12 | 560 |
| XVa-15 | 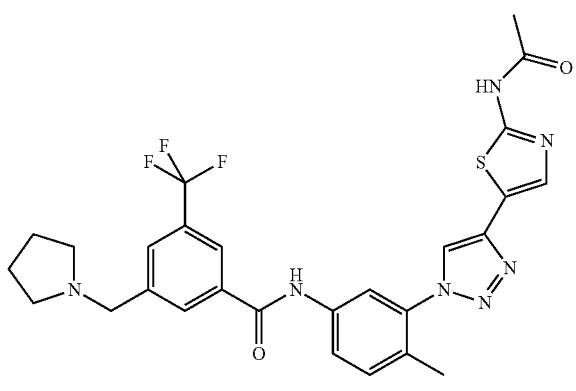 [SMILES: CC(=O)Nc1ncc(-c2cn(-c3cc(NC(=O)c4cc(CN5CCCC5)cc(C(F)(F)F)c4)ccc3C)nn2)s1] | 1.23 | 570 |

TABLE 13-continued
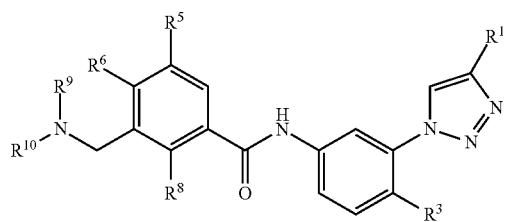
Examples XVa-1 to XVa-33
| # | Structure | t$_{Ret}$ (HPLC) [min] | MS (M + H)$^+$ |
|---|---|---|---|
| XVa-16 | 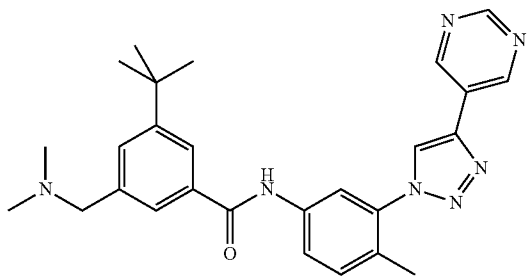 [SMILES: Cc1ccc(NC(=O)c2cc(CN(C)C)cc(C(C)(C)C)c2)cc1-n1cc(-c2cncnc2)nn1] | 2.14 | 470 |
| XVa-17 | 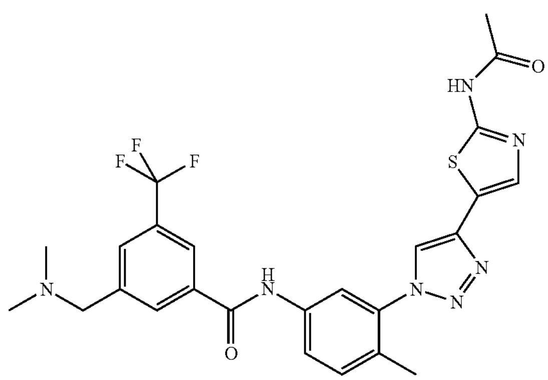 [SMILES: CC(=O)Nc1ncc(-c2cn(-c3cc(NC(=O)c4cc(CN(C)C)cc(C(F)(F)F)c4)ccc3C)nn2)s1] | 2.10 | 544 |
| XVa-18 | 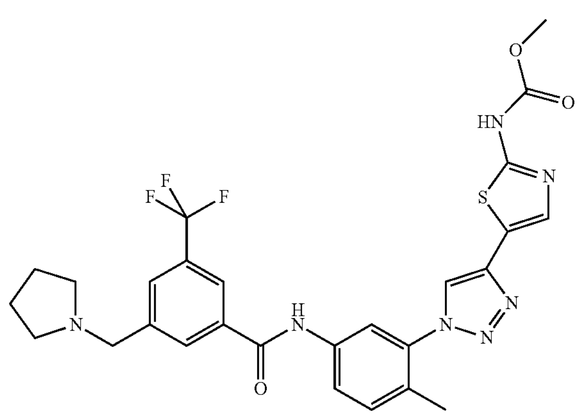 | 2.24 | 586 |

TABLE 13-continued
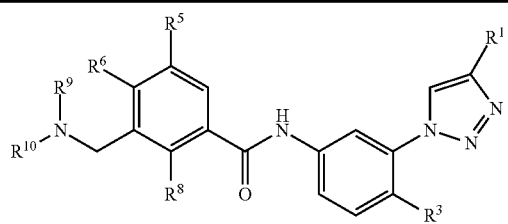
Examples XVa-1 to XVa-33
| # | Structure | t_Ret (HPLC) [min] | MS (M + H)+ |
|---|---|---|---|
| XVa-19 | 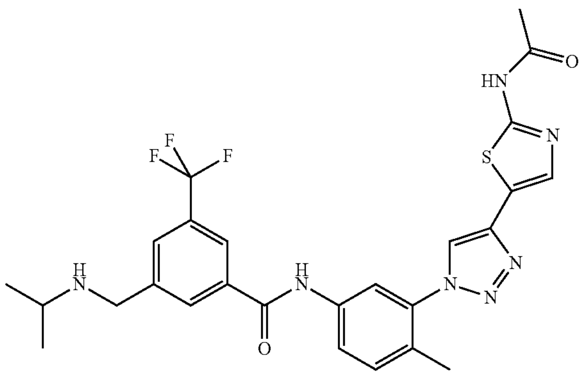 | 2.13 | 558 |
| XVa-20 | 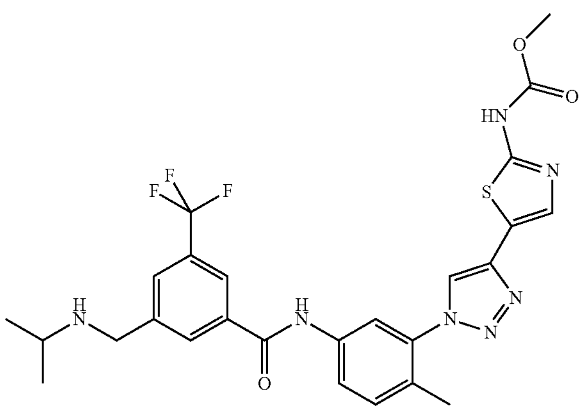 [SMILES: COC(=O)Nc1ncc(-c2cn(-c3cc(NC(=O)c4cc(CNC(C)C)cc(C(F)(F)F)c4)ccc3C)nn2)s1] | 2.16 | 574 |
| XVa-21 | 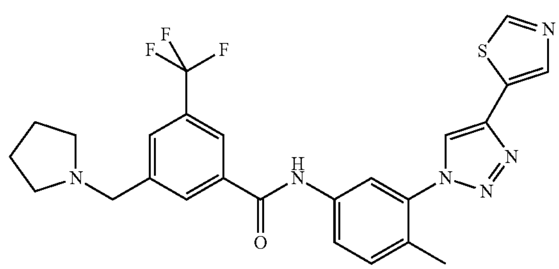 [SMILES: Cc1ccc(NC(=O)c2cc(CN3CCCC3)cc(C(F)(F)F)c2)cc1-n1cc(-c2cncs2)nn1] | 2.30 | 513 |
| XVa-22 | 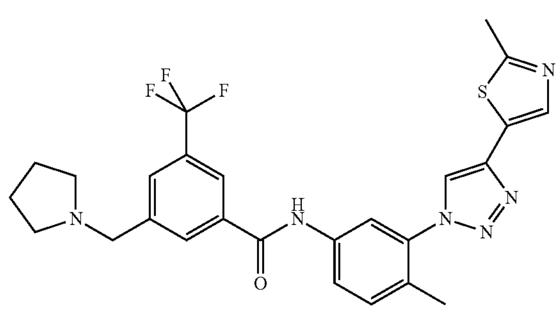 [SMILES: Cc1ncc(-c2cn(-c3cc(NC(=O)c4cc(CN5CCCC5)cc(C(F)(F)F)c4)ccc3C)nn2)s1] | 2.34 | 527 |

TABLE 13-continued
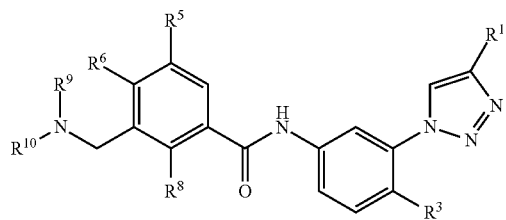
Examples XVa-1 to XVa-33
| # | Structure | $t_{Ret}$ (HPLC) [min] | MS (M + H)+ |
|---|---|---|---|
| XVa-23 | 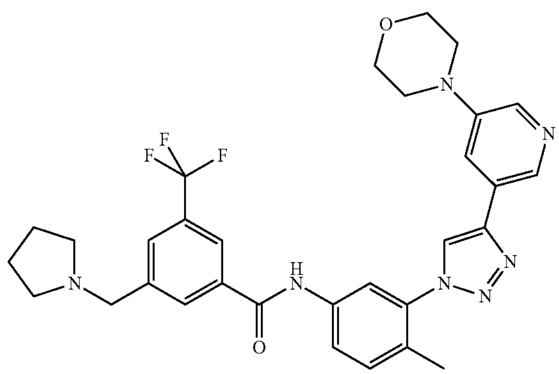 [SMILES: Cc1ccc(NC(=O)c2cc(CN3CCCC3)cc(C(F)(F)F)c2)cc1-n1cc(-c2cncc(N3CCOCC3)c2)nn1] | 2.28 | 592 |
| XVa-24 | 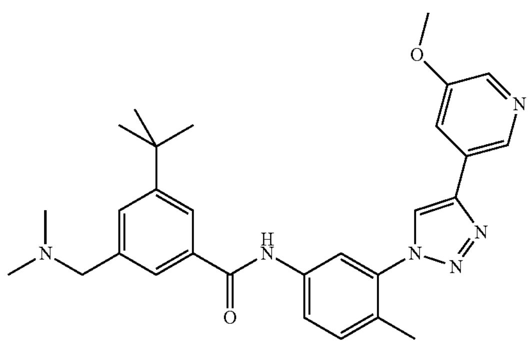 [SMILES: COc1cncc(-c2cn(-c3cc(NC(=O)c4cc(CN(C)C)cc(C(C)(C)C)c4)ccc3C)nn2)c1] | 2.26 | 499 |
| XVa-25 | 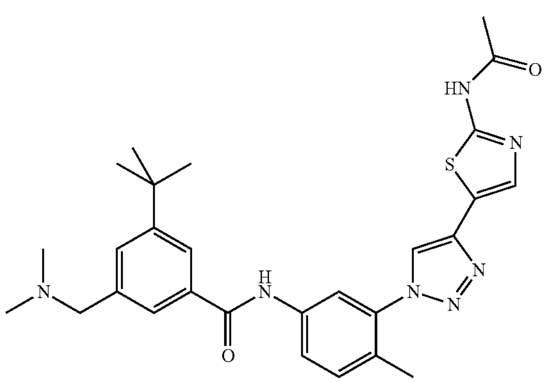 [SMILES: CC(=O)Nc1ncc(-c2cn(-c3cc(NC(=O)c4cc(CN(C)C)cc(C(C)(C)C)c4)ccc3C)nn2)s1] | 2.15 | 532 |

TABLE 13-continued
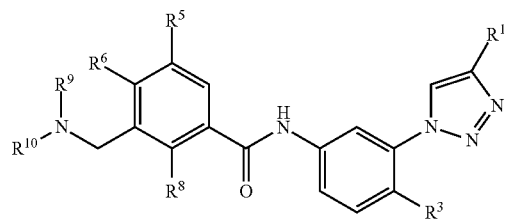
Examples XVa-1 to XVa-33
| # | Structure | $t_{Ret}$ (HPLC) [min] | MS (M + H)+ |
|---|---|---|---|
| XVa-26 | 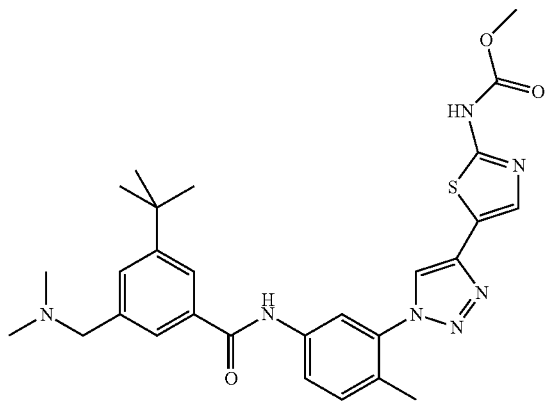 [SMILES: COC(=O)Nc1ncc(-c2cn(-c3cc(NC(=O)c4cc(CN(C)C)cc(C(C)(C)C)c4)ccc3C)nn2)s1] | 2.00 | 548 |
| XVa-27 | 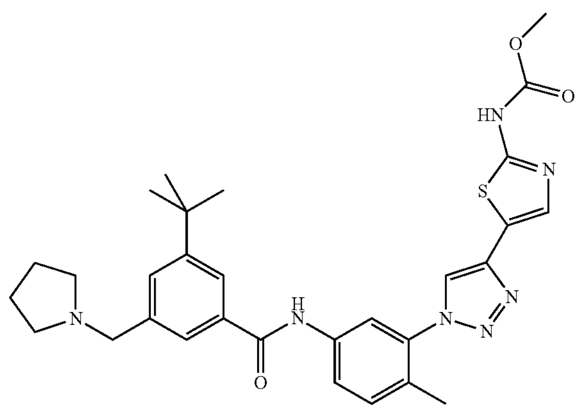 [SMILES: COC(=O)Nc1ncc(-c2cn(-c3cc(NC(=O)c4cc(CN5CCCC5)cc(C(C)(C)C)c4)ccc3C)nn2)s1] | 2.14 | 574 |
| XVa-28 | 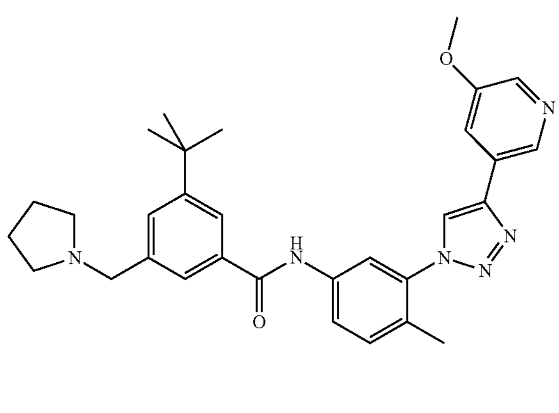 [SMILES: COc1cncc(-c2cn(-c3cc(NC(=O)c4cc(CN5CCCC5)cc(C(C)(C)C)c4)ccc3C)nn2)c1] | 2.40 | 525 |

TABLE 13-continued
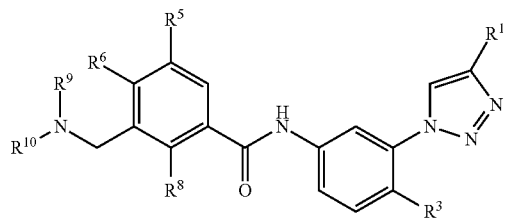
Examples XVa-1 to XVa-33
| # | Structure | t_Ret (HPLC) [min] | MS (M + H)+ |
|---|---|---|---|
| XVa-29 | 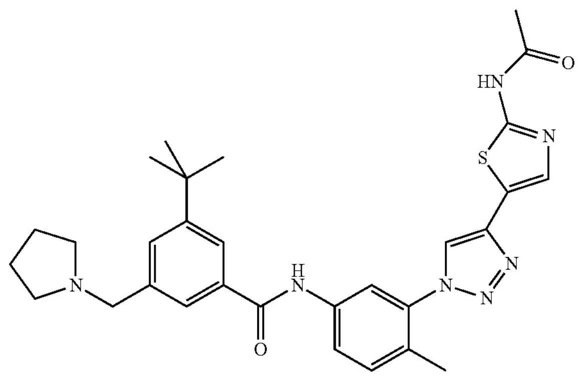 [SMILES: CC(=O)Nc1ncc(-c2cn(-c3cc(NC(=O)c4cc(CN5CCCC5)cc(C(C)(C)C)c4)ccc3C)nn2)s1] | 2.24 | 558 |
| XVa-30 | 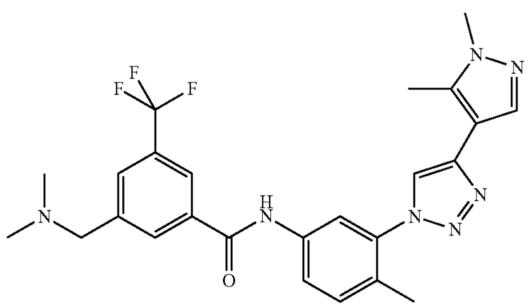 [SMILES: Cc1ccc(NC(=O)c2cc(CN(C)C)cc(C(F)(F)F)c2)cc1-n1cc(-c2cnn(C)c2C)nn1] | 2.10 | 498 |
| XVa-31 | 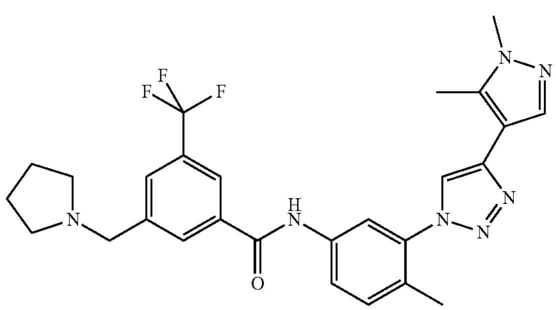 [SMILES: Cc1ccc(NC(=O)c2cc(CN3CCCC3)cc(C(F)(F)F)c2)cc1-n1cc(-c2cnn(C)c2C)nn1] | 2.23 | 524 |
| XVa-32 | 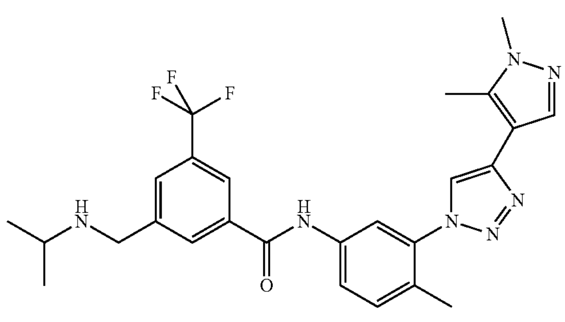 [SMILES: Cc1ccc(NC(=O)c2cc(CNC(C)C)cc(C(F)(F)F)c2)cc1-n1cc(-c2cnn(C)c2C)nn1] | 2.12 | 512 |

TABLE 13-continued

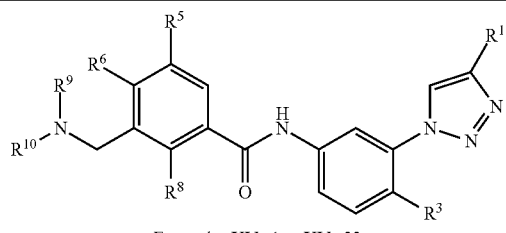

Examples XVa-1 to XVa-33

| # | Structure | $t_{Ret}$ (HPLC) [min] | MS (M + H)⁺ |
|---|---|---|---|
| XVa-33 | 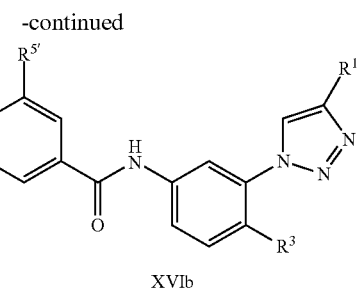 | 2.10 | 496 |

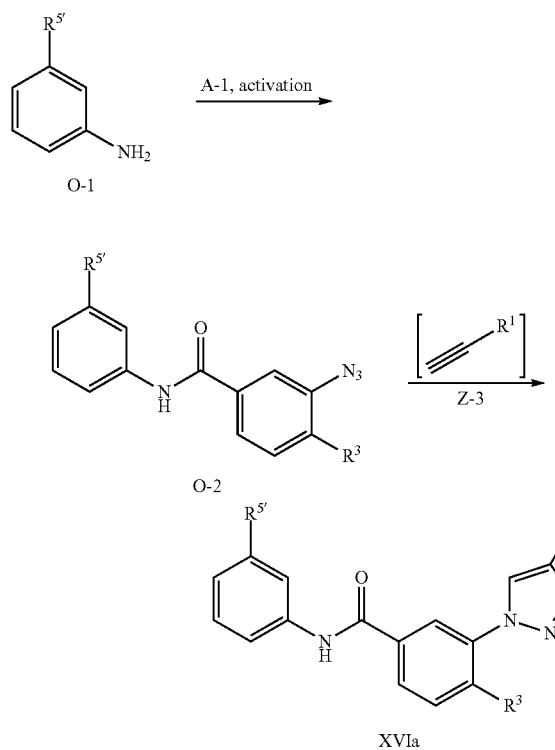

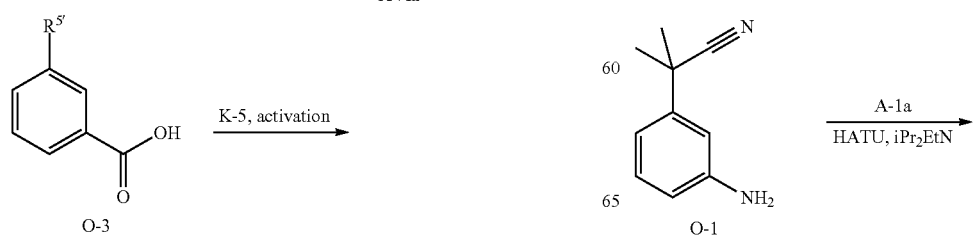

$R^{5'}$ = $C_{1-6}$Alkyl or $C_{3-4}$Cycloalkyl, each substituted with -CN

Example compounds of type XVIa are synthesised according to reaction scheme O by a reaction of cycloaddition from the corresponding azides O-2 with suitable alkynes Z-3 in the presence of CuSO$_4$ and sodium ascorbate using methods known from the literature. The azide compounds O-2 may be obtained by amide coupling from the anilines O-1 and the benzoic acids A-1 using methods known from the literature.

Example compounds of type XVIb, which have an inverse amide bond, compared with the compounds XVIa, may be synthesised from the corresponding benzoic acids O-3 with the anilines K-5 described hereinbefore. The benzoic acids O-3 are synthesised using methods known from the literature.

a) Procedure for Synthesising O-2a

-continued

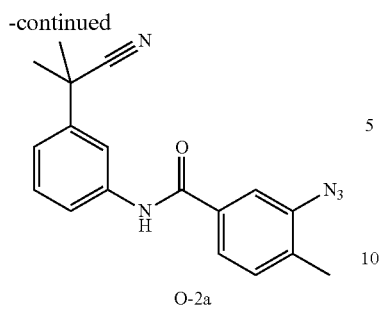

O-2a

The benzoic acid A-1a (500 mg, 2.82 mmol) is placed in DMF (15 mL), combined with HATU (1.19 g, 3.11 mmol) and iPr$_2$EtN (1.5 mL), stirred for 30 min at RT and then combined with the aniline O-1a (450 mg, 2.84 mmol). The reaction mixture is stirred overnight at RT and then evaporated down completely. The residue is taken up in a little DMF and purified by RP-MPLC. The product-containing fractions of O-2a (HPLC-MS: t$_{Ret.}$=2.29 min; MS (M+H)$^+$=320) are freeze-dried.

b) Procedure for Synthesising XVIa-1

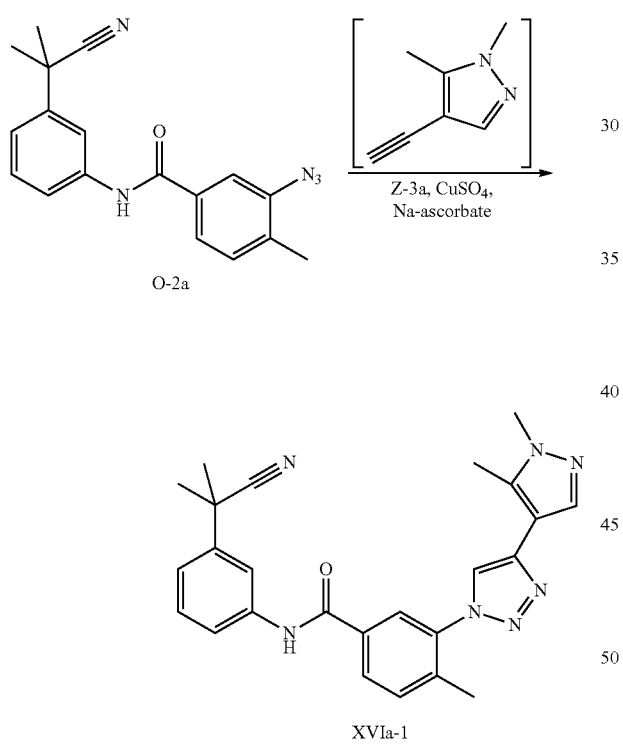

1,5-dimethyl-1H-pyrazole-4-carbaldehyde Z-2a (120 mg, 0.97 mmol) and the Bestmann-Ohira reagent (S. Müller et al. Synlett 1996, 521-522) (B-O, 360 mg, 1.87 mmol) are placed in MeOH (5 mL) and combined with potassium carbonate (260 mg, 1.88 mmol). After 3 d stirring at RT the azide O-2a (100 mg, 0.31 mmol) is added. Then sodium ascorbate stn. (1 M; 0.32 mL), CuSO$_4$ sln. (0.1 M; 0.44 mL) and NEt$_3$ (0.1 mL, 0.72 mmol) are added and the mixture is stirred for 3 d at RT. For working up the mixture is evaporated down, diluted with water, extracted 3× with EtOAc and the combined organic phases are evaporated down again. The residue is taken up in a little DMF and purified by preparative HPLC. The product-containing fractions of XVIa-1 (HPLC-MS: t$_{Ret.}$=2.02 min; MS (M+H)$^+$=440) are freeze-dried.

c) Procedure for Synthesising XVIb-1

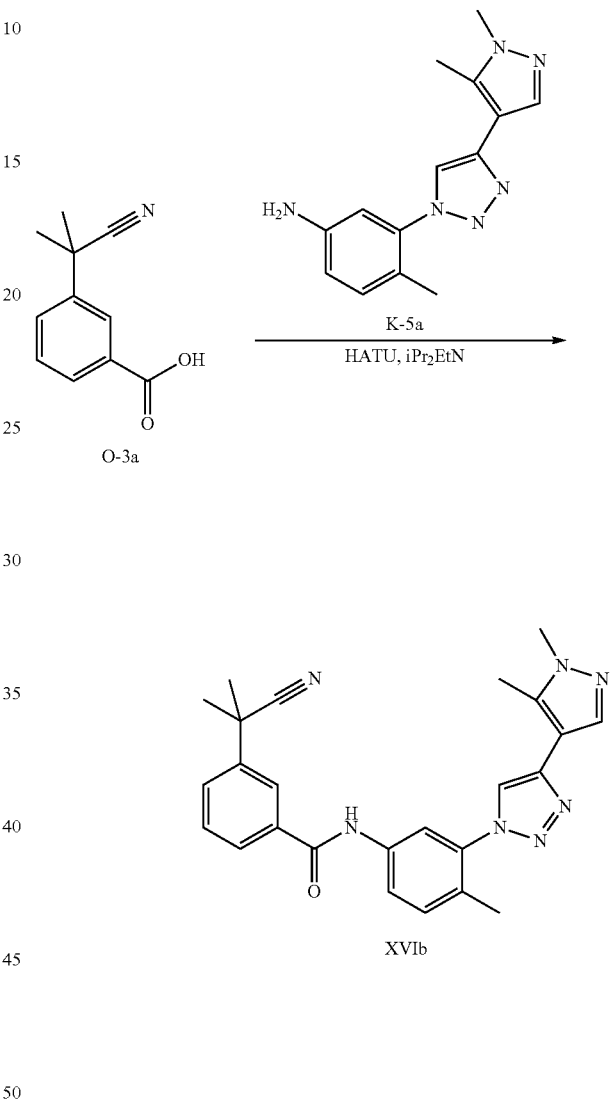

The benzoic acid O-3a (50 mg, 0.26 mmol) is placed in DMF (3.5 mL), combined with HATU (110 mg, 0.29 mmol) and iPr$_2$EtN (51 µl, 0.29 mmol), stirred for 30 min at RT and then the aniline K-5a (78 mg; 0.29 mmol) is added. The reaction mixture is stirred overnight at RT and then evaporated down completely. The residue is taken up in a little DMF and purified by preparative HPLC. The product-containing fractions of XVIb-1 (HPLC-MS: t$_{Ret.}$=1.95 min; MS (M+H)$^+$=440) are freeze-dried.

Analogously to reaction methods a) to c) described above, Examples XVIa-2 to XVIa-18 and Examples XVIb-2 to XVIb-7 (Table 14) or comparable further examples may be obtained from the corresponding precursors, which are either commercially obtainable or are prepared using methods known from the literature.

TABLE 14
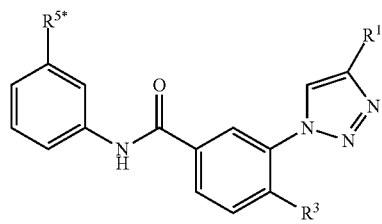
Examples XVIa-1 to Examples XVIa-18
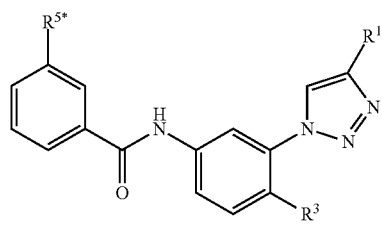
Examples XVIb-1 to XVIb-7
| # | Structure | $t_{Ret}$(HPLC) [min] | MS (M + H)⁺ |
|---|---|---|---|
| XVIa-1 | 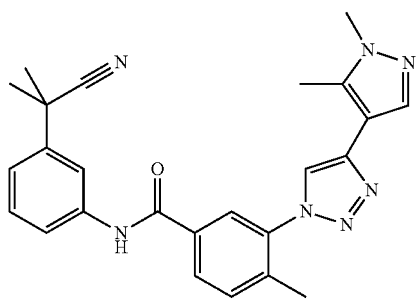 [SMILES: Cc1ccc(C(=O)Nc2cccc(C(C)(C)C#N)c2)cc1-n1cc(-c2cnn(C)c2C)nn1] | 2.02 | 440 |
| XVIa-2 | 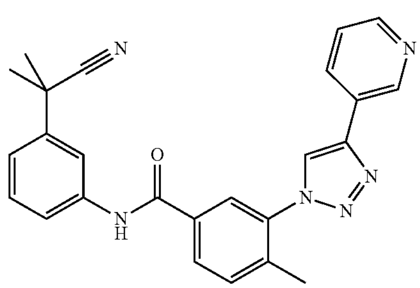 [SMILES: Cc1ccc(C(=O)Nc2cccc(C(C)(C)C#N)c2)cc1-n1cc(-c2cccnc2)nn1] | 1.88 | 423 |
| XVIa-3 | 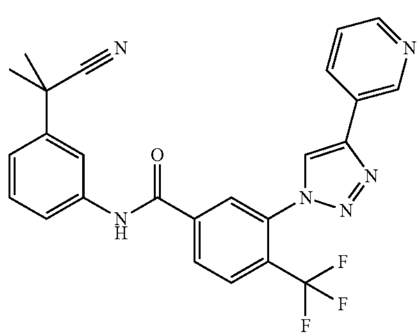 [SMILES: CC(C)(C#N)c1cccc(NC(=O)c2ccc(C(F)(F)F)c(-n3cc(-c4cccnc4)nn3)c2)c1] | 2.00 | 477 |

TABLE 14-continued
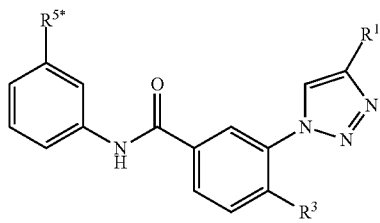
Examples XVIa-1 to Examples XVIa-18
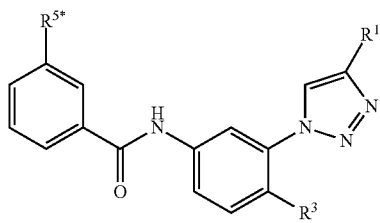
Examples XVIb-1 to XVIb-7
| # | Structure | $t_{Ret}$(HPLC) [min] | MS (M + H)⁺ |
|---|---|---|---|
| XVIa-4 | 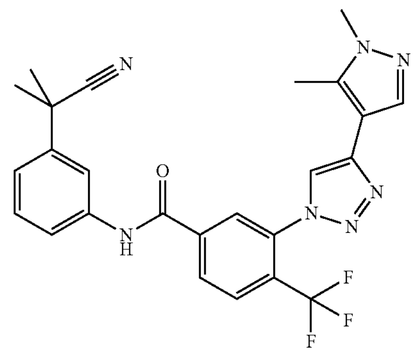 [SMILES: Cc1c(-c2cn(-c3cc(C(=O)Nc4cccc(C(C)(C)C#N)c4)ccc3C(F)(F)F)nn2)cnn1C] | 2.10 | 494 |
| XVIa-5 | 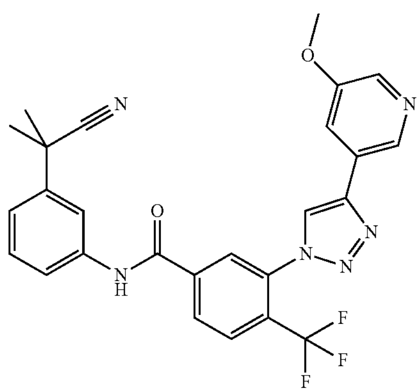 [SMILES: COc1cncc(-c2cn(-c3cc(C(=O)Nc4cccc(C(C)(C)C#N)c4)ccc3C(F)(F)F)nn2)c1] | 2.13 | 507 |
| XVIa-6 | 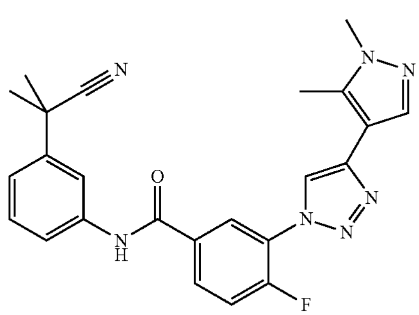 [SMILES: Cc1c(-c2cn(-c3cc(C(=O)Nc4cccc(C(C)(C)C#N)c4)ccc3F)nn2)cnn1C] | 2.01 | 444 |

TABLE 14-continued
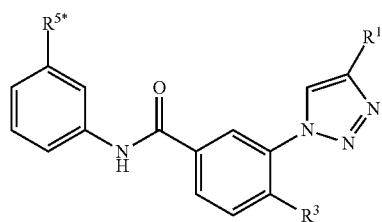
Examples XVIa-1 to Examples XVIa-18
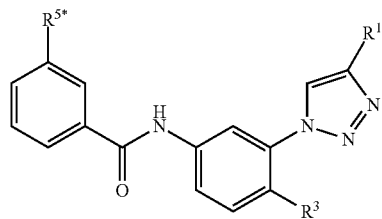
Examples XVIb-1 to XVIb-7
| # | Structure | $t_{Ret}$(HPLC) [min] | MS (M + H)⁺ |
|---|---|---|---|
| XVIa-7 | 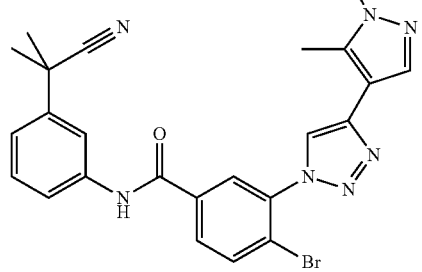 | 2.07 | 504/506 |
| XVIa-8 | 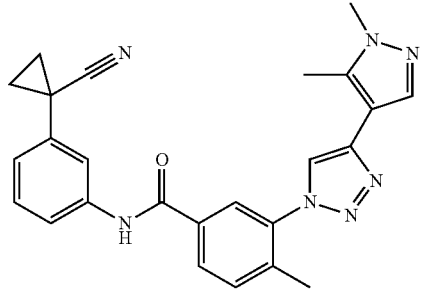 [SMILES: Cc1ccc(C(=O)Nc2cccc(C3(C#N)CC3)c2)cc1-n1cc(-c2cnn(C)c2C)nn1] | 1.98 | 438 |
| XVIa-9 | 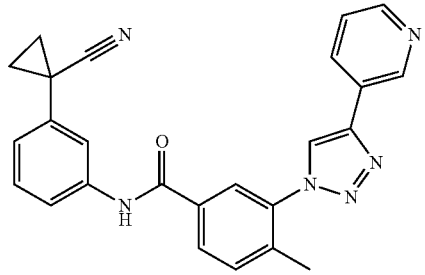 [SMILES: Cc1ccc(C(=O)Nc2cccc(C3(C#N)CC3)c2)cc1-n1cc(-c2cccnc2)nn1] | 1.83 | 421 |

TABLE 14-continued
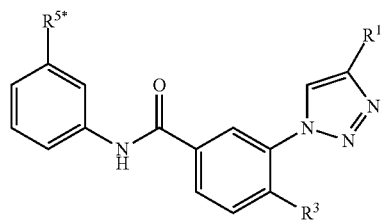
Examples XVIa-1 to Examples XVIa-18
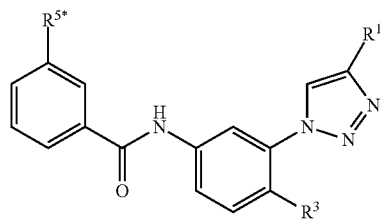
Examples XVIb-1 to XVIb-7
| # | Structure | $t_{Ret}$(HPLC) [min] | MS (M + H)⁺ |
|---|---|---|---|
| XVIa-10 | 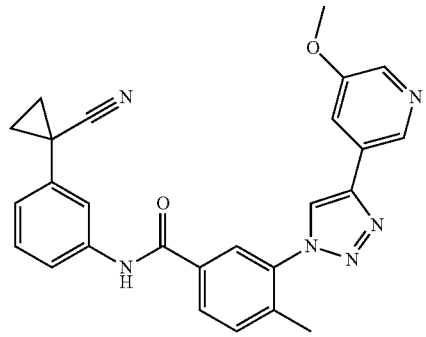 [SMILES: COc1cncc(-c2cn(-c3cc(C(=O)Nc4cccc(C5(C#N)CC5)c4)ccc3C)nn2)c1] | 2.00 | 451 |
| XVIa-11 | 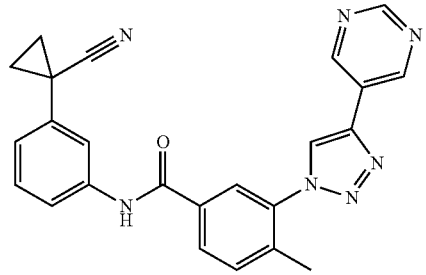 [SMILES: Cc1ccc(C(=O)Nc2cccc(C3(C#N)CC3)c2)cc1-n1cc(-c2cncnc2)nn1] | 1.93 | 422 |
| XVIa-12 | 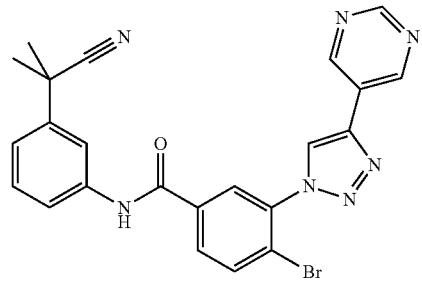 [SMILES: CC(C)(C#N)c1cccc(NC(=O)c2ccc(Br)c(-n3cc(-c4cncnc4)nn3)c2)c1] | 2.01 | 488/490 |

TABLE 14-continued
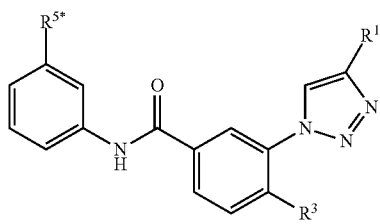
Examples XVIa-1 to Examples XVIa-18
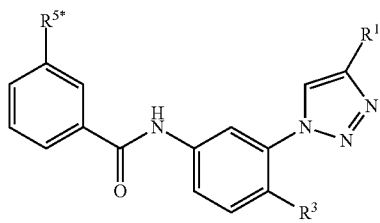
Examples XVIb-1 to XVIb-7
| # | Structure | $t_{Ret}$(HPLC) [min] | MS (M + H)⁺ |
|---|---|---|---|
| XVIa-13 | 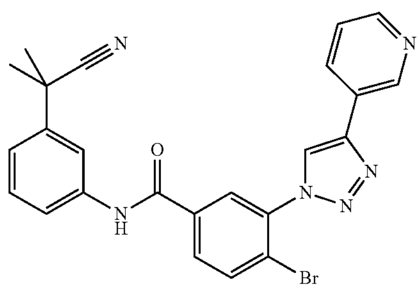 [SMILES: CC(C)(C#N)c1cccc(NC(=O)c2ccc(Br)c(-n3cc(-c4cccnc4)nn3)c2)c1] | 1.94 | 487/489 |
| XVIa-14 | 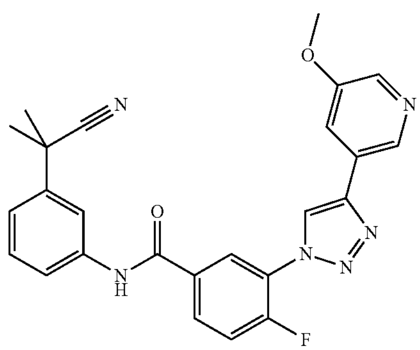 [SMILES: COc1cncc(-c2cn(-c3cc(C(=O)Nc4cccc(C(C)(C)C#N)c4)ccc3F)nn2)c1] | 2.08 | 457 |
| XVIa-15 | 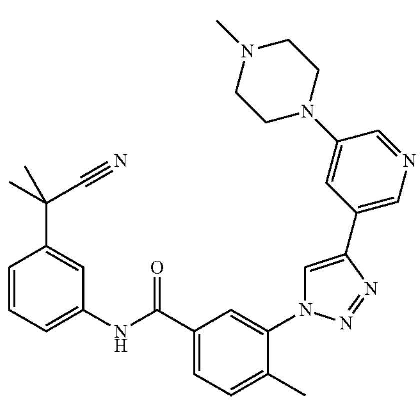 [SMILES: Cc1ccc(C(=O)Nc2cccc(C(C)(C)C#N)c2)cc1-n1cc(-c2cncc(N3CCN(C)CC3)c2)nn1] | 2.00 | 521 |

TABLE 14-continued
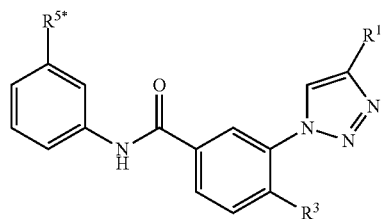
Examples XVIa-1 to Examples XVIa-18
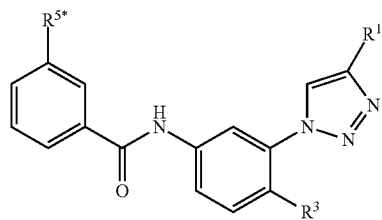
Examples XVIb-1 to XVIb-7
| # | Structure | $t_{Ret}$(HPLC) [min] | MS (M + H)$^+$ |
|---|---|---|---|
| XVIa-16 | 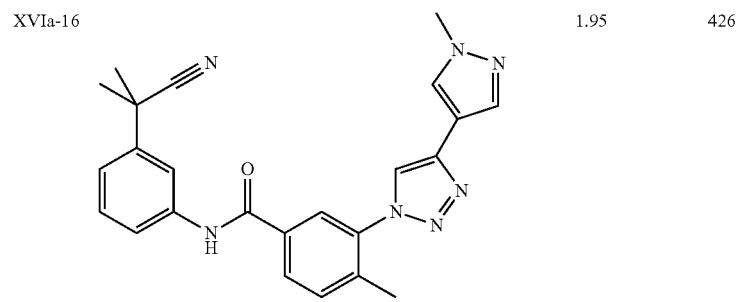 | 1.95 | 426 |
| XVIa-17 | 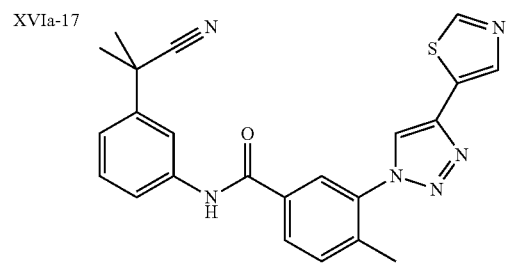 | | |
| XVIa-18 | 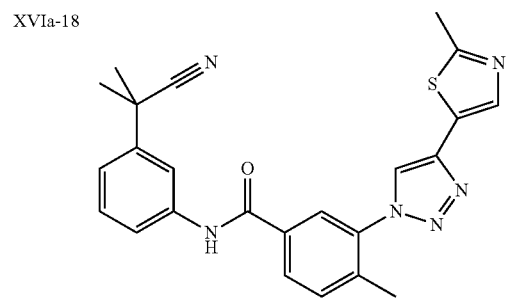 | | |

TABLE 14-continued
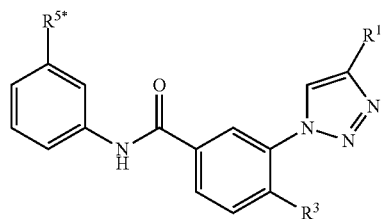
Examples XVIa-1 to Examples XVIa-18
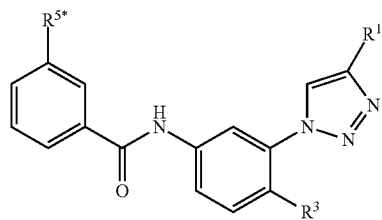
Examples XVIb-1 to XVIb-7
| # | Structure | $t_{Ret}$ (HPLC) [min] | MS (M + H)⁺ |
|---|---|---|---|
| XVIb-1 | 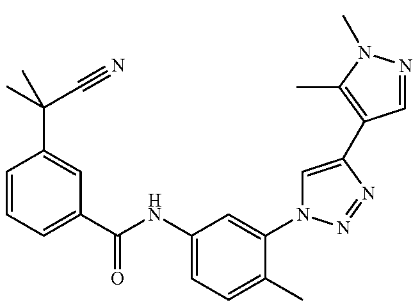 [SMILES: Cc1ccc(NC(=O)c2cccc(C(C)(C)C#N)c2)cc1-n1cc(-c2cnn(C)c2C)nn1] | 1.95 | 440 |
| XVIb-2 | 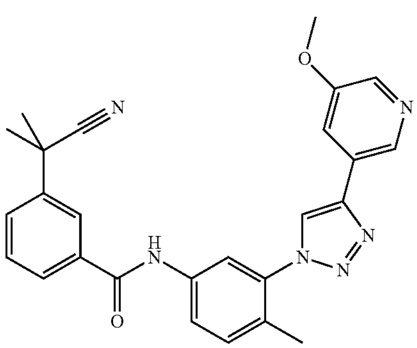 [SMILES: COc1cncc(-c2cn(-c3cc(NC(=O)c4cccc(C(C)(C)C#N)c4)ccc3C)nn2)c1] | 2.00 | 453 |
| XVIb-3 | 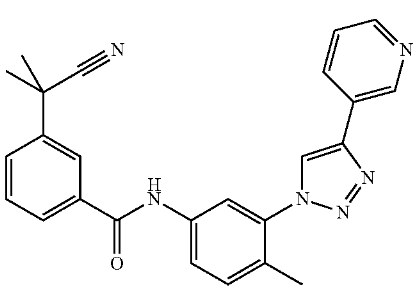 | 1.83 | 423 |

TABLE 14-continued
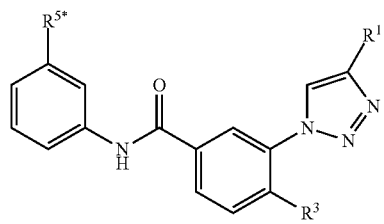
Examples XVIa-1 to Examples XVIa-18
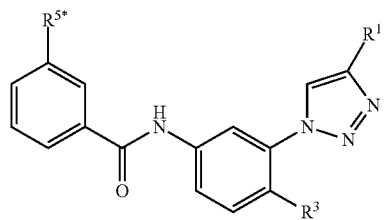
Examples XVIb-1 to XVIb-7
| # | Structure | t_Ret (HPLC) [min] | MS (M + H)+ |
|---|---|---|---|
| XVIb-4 | 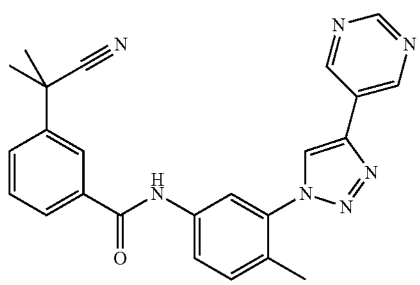 [SMILES: Cc1ccc(NC(=O)c2cccc(C(C)(C)C#N)c2)cc1-n1cc(-c2cncnc2)nn1] | 1.91 | 424 |
| XVIb-5 | 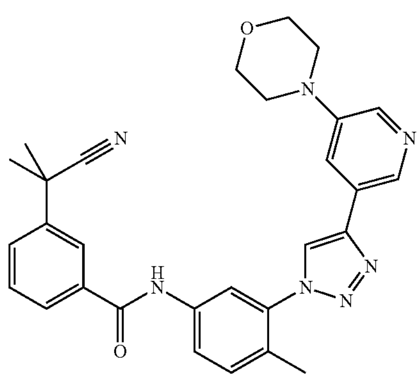 [SMILES: Cc1ccc(NC(=O)c2cccc(C(C)(C)C#N)c2)cc1-n1cc(-c2cncc(N3CCOCC3)c2)nn1] | 2.01 | 508 |
| XVIb-6 | 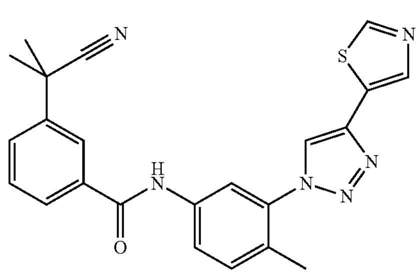 [SMILES: Cc1ccc(NC(=O)c2cccc(C(C)(C)C#N)c2)cc1-n1cc(-c2cncs2)nn1] | 1.69 | 429 |

TABLE 14-continued

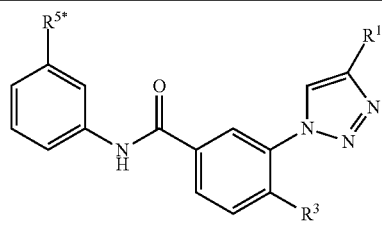

Examples XVIa-1 to Examples XVIa-18

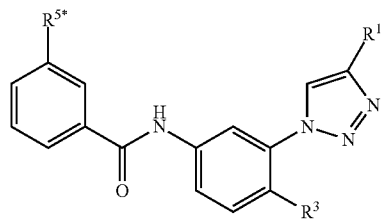

Examples XVIb-1 to XVIb-7

| # | Structure | $t_{Ret}$(HPLC) [min] | MS (M + H)$^+$ |
|---|---|---|---|
| XVIb-7 | (structure shown) | 1.81 | 443 |

As novel compounds with an inverse amide bond (compared with the amide bonds of example types I to XI) only example types XII to XVI (aryl- and benzylamines, cyanoalkyls, cyanocycloalkyls) are represented by specific example compounds. In principle, however, it is also possible to synthesise all the other compound types I to XI with an inverse amide bond by modification of the methods of synthesis described herein and by using the corresponding educts.

In order to synthesise compounds according to the invention wherein the group L is different from —C(O)NH— and —NHC(O)—, in a departure from the benzoic acids A-2, the anilines K-5 or the respective benzoic acids and anilines used as coupling partners, components with other functional groups may also be synthesised and used in the reactions (benzoic acids, arylalcohols→esters; sulphonic acids, anilines→sulphonamides, etc.).

The following Examples describe the biological activity of the compounds according to the invention without restricting the invention to these Examples.

Compounds of general formula (1) are characterised by their wide range of applications in the therapeutic field. Particular mention should be made of those applications in which the inhibition of specific signal enzymes, particularly the inhibiting effect on the proliferation of cultivated human tumour cells but also the proliferation of other cells, such as endothelial cells, for example, plays a part.

Kinase Test B-Raf (V600E)

In a dilution series, 10 µL aliquots of test substance solution are placed in a multiwell plate. The dilution series is selected so as to cover a range of concentrations from 2 µM to 0.128 or 0.017 nM. If necessary the initial concentration is changed from 2 µM to 10 or 0.4 µM and further dilution is carried out accordingly. The final concentration of DMSO is 5%. 10 µL of the B-Raf (V600E) kinase solution are pipetted in (containing 2.5 ng B-Raf (V600E)-kinase in 20 mM TrisHCl pH 7.5, 0.1 mM EDTA, 0.1 mM EGTA, 0.286 mM sodium orthovanadate, 10% glycerol, 1 mg/mL bovine serum albumin, 1 mM dithiothreitol) and incubated for 1 h at RT with agitation. The kinase reaction is started by the addition of 20 µL ATP solution [final concentration: 250 µM ATP, 30 mM Tris-HCl pH 7.5, 0.02% Brij, 0.2 mM sodium-orthovanadate, 10 mM magnesium acetate, phosphatase cocktail (Sigma, #P2850, dilution recommended by the manufacturer), 0.1 mM EGTA] and 10 µL MEK1 solution [containing 50 ng biotinylated MEK1 (prepared from purified MEK1 according to standard procedure, e.g. with reagent EZ-Link Sulfo-NHS-LC-Biotin, Pierce, #21335) in 50 mM Hepes pH 7.5, 150 mM NaCl, 10% glycerol, 0.02% Brij-35, 0.2 mM PMSF, 0.2 mM benzamidine] and carried out for 60 min at RT with constant agitation. The reaction is stopped by the addition of 12 µL of a 100 mM EDTA solution and incubated for a further 5 min. 55 µL of the reaction solution are transferred into a strepta-vidine-coated plate (e.g. Streptawell HighBond, Roche, #11989685001) and shaken gently for 1 h at RT, in order to bind biotinylated MEK1 to the plate. After removal of the liquid the plate is washed five times with 200 µL of 1× PBS, and 100 µL solution of primary antibody plus europium-labelled secondary antibody [Anti Phospho-MEK (Ser2171221), Cell Signaling #9121 and Eu—N1 labeled goat-anti-rabbit antibody, Perkin Elmer #AD01015], the primary antibody is diluted 1:2000 and the secondary antibody is added to 0.4-0.5 µg/mL diluted in Delfia Assay Buffer (Perkin Elmer, #1244-111). After 1 h agitation at RT the solution is poured away and washed five times with 200 µL Delfia Wash Buffer (Perkin Elmer #4010-00101244-114). After the addition of 200 µL Enhancement Solution (Perkin Elmer #4001-00101244-105) the preparation is shaken for 10 min at RT and then measured in a Wallac Victor using the programme "Delfia Time Resolved Fluorescence (Europium)". $IC_{50}$ values are determined from these dosage-activity curves using the software programme (GraphPad-Prizm). Most example compounds of type I to XVI exhibit a good to very good inhibitory effect in this B-Raf (V600E) inhibition test, i.e. they have an $IC_{50}$ value of less than 0.3 µM, generally less than 100 nM.

Measurement of the Inhibition of Proliferation on Cultivated Human Melanoma Cells (SK-MEL28)

To measure proliferation on cultivated human tumour cells, cells of melanoma cell line SK-MEL28 [American Type Culture Collection (ATCC)] are cultivated in MEM medium, supplemented with 10% foetal calf serum, 2% sodium bicarbonate, 1 mM sodium pyruvate, 1% non-essential amino acids (e.g. from Cambrex, #BE13-114E) and 2 mM glutamine. SK-MEL28 cells are placed in 96-well flat-bottomed plates at a density of 2500 cells per well in supplemented MEM medium (see above) and incubated overnight in an incubator (at 37° C. and 5% $CO_2$). The active substances are added to the cells in various concentrations so as to cover a range of concentrations from 50 µM to 3.2 nM. If necessary the initial concentration is changed from 50 µM to 10 µM or 2 µM and further dilution (to 0.6 nM or 0.12 nM) is carried out accordingly. After a further 72 hours incubation, 20 µl AlamarBlue reagent (Serotec Ltd., #BUF012B) is added to each well, and the cells are incubated for a further 3-6 hours. The colour change of the AlamarBlue reagent is determined in a fluorescence spectrophotometer (e.g. Gemini, Molecular Devices). $EC_{50}$ values are calculated using the software programme (GraphPadPrizm).

Most of the example compounds of type I to XVI exhibit a good to very good activity in the cellular SK-MEL28 assay, i.e. they have an $EC_{50}$ value of less than 5 µM, generally less than 2 µM.

Measurement of the Inhibition of Proliferation on Cultivated Human Melanoma Cells (A375)

To measure proliferation on cultivated human tumour cells, cells of melanoma cell line A375 [American Type Culture Collection (ATCC)] are cultivated in MEM medium, supplemented with 10% foetal calf serum and 2% sodium bicarbonate. Test substances are tested on A375 cells according to the method described for SK-MEL28 cells (see above).

Most of the example compounds of type I to XVI exhibit a good to very good activity in the cellular A375 assay, i.e. they have an $EC_{50}$ value of less than 3 µM, generally less than 1 µM.

The substances of the present invention are B-Raf kinase inhibitors. As can be demonstrated by DNA staining followed by FACS or Cellomics Array Scan analysis, the inhibition of proliferation achieved by the compounds according to the invention is brought about primarily by preventing entry into the DNA synthesis phase. The treated cells arrest in the G1 phase of the cell cycle. Accordingly, the compounds according to the invention are also tested on other tumour cells. For example these compounds are active on the colon carcinoma cell line Colo205 and the breast cancer cell line DU4475 and can be used for these indications. This demonstrates the usefulness of the compounds according to the invention for treating various types of tumours.

Because of their biological properties the compounds of general formula (1) according to the invention, the tautomers, racemates, enantiomers, diastereomers, mixtures, polymorphs and the salts of all the above-mentioned forms are suitable for the treatment of diseases characterised by excessive or abnormal cell proliferation.

Such diseases include for example: viral infections (e.g. HIV and Kaposi's sarcoma); inflammatory and autoimmune diseases (e.g. colitis, arthritis, Alzheimer's disease, glomerulonephritis and wound healing); bacterial, fungal and/or parasitic infections; leukaemias, lymphomas and solid tumours (e.g. carcinomas and sarcomas), skin diseases (e.g. psoriasis); diseases based on hyperplasia which are characterised by an increase in the number of cells (e.g. fibroblasts, hepatocytes, bones and bone marrow cells, cartilage or smooth muscle cells or epithelial cells (e.g. endometrial hyperplasia)); bone diseases and cardiovascular diseases (e.g. restenosis and hypertrophy). They are also useful for protecting proliferating cells (e.g. hair, intestinal, blood and progenitor cells) from DNA damage caused by radiation, UV treatment and/or cytostatic treatment.

For example, the following cancers may be treated with compounds according to the invention, without being restricted thereto: brain tumours such as for example acoustic neurinoma, astrocytomas such as pilocytic astrocytomas, fibrillary astrocytoma, protoplasmic astrocytoma, gemistocytary astrocytoma, anaplastic astrocytoma and glioblastoma, brain lymphomas, brain metastases, hypophyseal tumour such as prolactinoma, HGH (human growth hormone) producing tumour and ACTH producing tumour (adrenocorticotropic hormone), craniopharyngiomas, medulloblastomas, meningeomas and oligodendrogliomas; nerve tumours (neoplasms) such as for example tumours of the vegetative nervous system such as neuroblastoma sympathicum, ganglioneuroma, paraganglioma (pheochromocytoma, chromaffinoma) and glomus-caroticum tumour, tumours on the peripheral nervous system such as amputation neuroma, neurofibroma, neurinoma (neurilemmoma, Schwannoma) and malignant Schwannoma, as well as tumours of the central nervous system such as brain and bone marrow tumours; intestinal cancer such as for example carcinoma of the rectum, colon, anus, small intestine and duodenum; eyelid tumours such as basalioma or basal cell carcinoma; pancreatic cancer or carcinoma of the pancreas; bladder cancer or carcinoma of the bladder; lung cancer (bronchial carcinoma) such as for example small-cell bronchial carcinomas (oat cell carcinomas) and non-small cell bronchial carcinomas such as plate epithelial carcinomas, adenocarcinomas and large-cell bronchial carcinomas; breast cancer such as for example mammary carcinoma such as infiltrating ductal carcinoma, colloid carcinoma, lobular invasive carcinoma, tubular carcinoma, adenocystic carcinoma and papillary carcinoma; non-Hodgkin's lymphomas (NHL) such as for example Burkitt's lymphoma, low-malignancy non-Hodgkin's lymphomas (NHL) and mucosis fungoides; uterine cancer or endometrial carcinoma or corpus carcinoma; CUP syndrome (Cancer of Unknown Primary); ovarian cancer or ovarian carcinoma such as mucinous, endometrial or serous cancer; gall bladder cancer; bile duct cancer such as for example Klatskin tumour; testicular cancer such as for example seminomas and non-seminomas; lymphoma (lymphosarcoma) such as for example malignant lymphoma, Hodgkin's disease, non-Hodgkin's lymphomas (NHL) such as chronic lymphatic leukaemia, leukaemic reticuloendotheliosis, immunocytoma, plasmocytoma (multiple myeloma), immuno-blastoma, Burkitt's lymphoma, T-zone mycosis fungoides, large-cell anaplastic lymphoblastoma and lymphoblastoma; laryngeal cancer such as for example tumours of the vocal cords, supraglottal, glottal and subglottal laryngeal tumours; bone cancer such as for example osteochondroma, chondroma, chondroblastoma, chondromyxoid fibroma, osteoma, osteoid osteoma, osteoblastoma, eosinophilic granuloma, giant cell tumour, chondrosarcoma, osteosarcoma, Ewing's sarcoma, reticulo-sarcoma, plasmocytoma, fibrous dysplasia, juvenile bone cysts and aneurysmatic bone cysts; head and neck tumours such as for example tumours of the lips, tongue, floor of the mouth, oral cavity, gums, palate, salivary glands, throat, nasal cavity, paranasal sinuses, larynx and middle ear; liver cancer such as for example liver cell carcinoma or hepatocellular carcinoma (HCC); leukaemias, such as for example acute leukaemias such as acute lymphatic/lymphoblastic leukaemia (ALL), acute myeloid leukaemia (AML); chronic leukaemias such as chronic lymphatic leukaemia (CLL), chronic myeloid leukaemia (CML); stomach cancer or gastric carcinoma such as for example papillary, tubular and mucinous adenocarcinoma, signet ring cell carcinoma, adenosquamous carcinoma, small-cell carcinoma and undifferentiated carcinoma; melanomas such as for example superficially spreading, nodular, lentigo-maligna and acral-lentiginous melanoma; renal cancer such as for example kidney cell carcinoma or hypernephroma or Grawitz's tumour; oesophageal cancer or carcinoma of the oesophagus; penile cancer; prostate cancer; throat cancer or carcinomas of the pharynx such as for example nasopharynx carcinomas, oropharynx carcinomas and hypopharynx carcinomas; retinoblastoma; vaginal cancer or vaginal carcinoma; plate epithelial carcinomas, adenocarcinomas, in situ carcinomas, malignant melanomas and sarcomas; thyroid carcinomas such as for example papillary, follicular and medullary thyroid carcinoma, as well as anaplastic carcinomas; spinalioma, epidormoid carcinoma and plate epithelial carcinoma of the skin; thymomas, cancer of the urethra and cancer of the vulva.

The new compounds may be used for the prevention, short-term or long-term treatment of the above-mentioned diseases, optionally also in combination with radiotherapy or other "state-of-the-art" compounds, such as e.g. cytostatic or cytotoxic substances, cell proliferation inhibitors, anti-angiogenic substances, steroids or antibodies.

The compounds of general formula (1) may be used on their own or in combination with other active substances according to the invention, optionally also in combination with other pharmacologically active substances.

Chemotherapeutic agents which may be administered in combination with the compounds according to the invention include, without being restricted thereto, hormones, hormone analogues and antihormones (e.g. tamoxifen, toremifene, raloxifene, fulvestrant, megestrol acetate, flutamide, nilutamide, bicalutamide, aminoglutethimide, cyproterone acetate, finasteride, buserelin acetate, fludrocortisone, fluoxymesterone, medroxyprogesterone, octreotide), aromatase inhibitors (e.g. anastrozole, letrozole, liarozole, vorozole, exemestane, atamestane), LHRH agonists and antagonists (e.g. goserelin acetate, luprolide), inhibitors of growth factors (growth factors such as for example "platelet derived growth factor" and "hepatocyte growth factor", inhibitors are for example "growth factor" antibodies, "growth factor receptor" antibodies and tyrosinekinase inhibitors, such as for example gefitinib, imatinib, lapatinib and trastuzumab); antimetabolites (e.g. antifolates such as methotrexate, raltitrexed, pyrimidine analogues such as 5-fluorouracil, capecitabin and gemcitabin, purine and adenosine analogues such as mercaptopurine, thioguanine, cladribine and pentostatin, cytarabine, fludarabine); antitumour antibiotics (e.g. anthracyclins such as doxorubicin, daunorubicin, epirubicin and idarubicin, mitomycin-C, bleomycin, dactinomycin, plicamycin, streptozocin); platinum derivatives (e.g. cisplatin, oxaliplatin, carboplatin); alkylation agents (e.g. estramustin, meclorethamine, melphalan, chlorambucil, busulphan, dacarbazin, cyclophosphamide, ifosfamide, temozolomide, nitrosoureas such as for example carmustin and lomustin, thiotepa); antimitotic agents (e.g. Vinca alkaloids such as for example vinblastine, vindesin, vinorelbin and vincristine; and taxanes such as paclitaxel, docetaxel); topoisomerase inhibitors (e.g. epipodophyllotoxins such as for example etoposide and etopophos, teniposide, amsacrin, topotecan, irinotecan, mitoxantron) and various chemotherapeutic agents such as amifostin, anagrelid, clodronat, filgrastin, interferon alpha, leucovorin, rituximab, procarbazine, levamisole, mesna, mitotane, pamidronate and porfimer.

Suitable preparations include for example tablets, capsules, suppositories, solutions—particularly solutions for injection (s.c., i.v., i.m.) and infusion—, elixirs, emulsions or dispersible powders. The content of the pharmaceutically active compound(s) should be in the range from 0.1 to 90 wt.-%, preferably 0.5 to 50 wt.-% of the composition as a whole, i.e. in amounts which are sufficient to achieve the dosage range specified below. The doses specified may, if necessary, be given several times a day.

Suitable tablets may be obtained, for example, by mixing the active substance(s) with known excipients, for example inert diluents such as calcium carbonate, calcium phosphate or lactose, disintegrants such as corn starch or alginic acid, binders such as starch or gelatine, lubricants such as magnesium stearate or talc and/or agents for delaying release, such as carboxymethyl cellulose, cellulose acetate phthalate, or polyvinyl acetate. The tablets may also comprise several layers.

Coated tablets may be prepared accordingly by coating cores produced analogously to the tablets with substances normally used for tablet coatings, for example collidone or shellac, gum arabic, talc, titanium dioxide or sugar. To achieve delayed release or prevent incompatibilities the core may also consist of a number of layers. Similarly the tablet coating may consist of a number of layers to achieve delayed release, possibly using the excipients mentioned above for the tablets.

Syrups or elixirs containing the active substances or combinations thereof according to the invention may additionally contain a sweetener such as saccharine, cyclamate, glycerol or sugar and a flavour enhancer, e.g. a flavouring such as vanillin or orange extract. They may also contain suspension adjuvants or thickeners such as sodium carboxymethyl cellulose, wetting agents such as, for example, condensation products of fatty alcohols with ethylene oxide, or preservatives such as p-hydroxybenzoates.

Solutions for injection and infusion are prepared in the usual way, e.g. with the addition of isotonic agents, preservatives such as p-hydroxybenzoates, or stabilisers such as alkali metal salts of ethylenediamine tetraacetic acid, optionally using emulsifiers and/or dispersants, whilst if water is used as the diluent, for example, organic solvents may optionally be used as solvating agents or dissolving aids, and transferred into injection vials or ampoules or infusion bottles.

Capsules containing one or more active substances or combinations of active substances may for example be prepared by mixing the active substances with inert carriers such as lactose or sorbitol and packing them into gelatine capsules.

Suitable suppositories may be made for example by mixing with carriers provided for this purpose, such as neutral fats or polyethyleneglycol or the derivatives thereof.

Excipients which may be used include, for example, water, pharmaceutically acceptable organic solvents such as paraffins (e.g. petroleum fractions), vegetable oils (e.g. groundnut or sesame oil), mono- or polyfunctional alcohols (e.g. ethanol or glycerol), carriers such as e.g. natural mineral powders (e.g. kaolins, clays, talc, chalk), synthetic mineral powders (e.g. highly dispersed silicic acid and silicates), sugars (e.g. cane sugar, lactose and glucose) emulsifiers (e.g. lignin, spent sulphite liquors, methylcellulose, starch and polyvinylpyrrolidone) and lubricants (e.g. magnesium stearate, talc, stearic acid and sodium lauryl sulphate).

The preparations are administered by the usual methods, preferably by oral or transdermal route, most preferably by oral route. For oral administration the tablets may, of course contain, apart from the abovementioned carriers, additives such as sodium citrate, calcium carbonate and dicalcium phosphate together with various additives such as starch, preferably potato starch, gelatine and the like. Moreover, lubricants such as magnesium stearate, sodium lauryl sulphate and talc may be used at the same time for the tabletting process. In the case of aqueous suspensions the active substances may be combined with various flavour enhancers or colourings in addition to the excipients mentioned above.

For parenteral use, solutions of the active substances with suitable liquid carriers may be used.

The dosage for intravenous use is from 1-1000 mg per hour, preferably between 5 and 500 mg per hour.

However, it may sometimes be necessary to depart from the amounts specified, depending on the body weight, the route of administration, the individual response to the drug, the nature of its formulation and the time or interval over which the drug is administered. Thus, in some cases it may be sufficient to use less than the minimum dose given above, whereas in other cases the upper limit may have to be exceeded. When administering large amounts it may be advisable to divide them up into a number of smaller doses spread over the day.

The formulation examples that follow illustrate the present invention without restricting its scope:

Examples of Pharmaceutical Formulations

| A) | Tablets | per tablet |
|---|---|---|
| | active substance according to formula (1) | 100 mg |
| | lactose | 140 mg |
| | corn starch | 240 mg |
| | polyvinylpyrrolidone | 15 mg |
| | magnesium stearate | 5 mg |
| | | 500 mg |

The finely ground active substance, lactose and some of the corn starch are mixed together. The mixture is screened, then moistened with a solution of polyvinylpyrrolidone in water, kneaded, wet-granulated and dried. The granules, the remaining corn starch and the magnesium stearate are screened and mixed together. The mixture is compressed to produce tablets of suitable shape and size.

| B) | Tablets | per tablet |
|---|---|---|
| | active substance according to formula (1) | 80 mg |
| | lactose | 55 mg |
| | corn starch | 190 mg |
| | microcrystalline cellulose | 35 mg |
| | polyvinylpyrrolidone | 15 mg |
| | sodium-carboxymethyl starch | 23 mg |
| | magnesium stearate | 2 mg |
| | | 400 mg |

The finely ground active substance, some of the corn starch, lactose, microcrystalline cellulose and polyvinylpyrrolidone are mixed together, the mixture is screened and worked with the remaining corn starch and water to form a granulate which is dried and screened. The sodiumcarboxymethyl starch and the magnesium stearate are added and mixed in and the mixture is compressed to form tablets of a suitable size.

| C) | Ampoule solution | |
|---|---|---|
| | active substance according to formula (1) | 50 mg |
| | sodium chloride | 50 mg |
| | water for inj. | 5 mL |

The active substance is dissolved in water at its own pH or optionally at pH 5.5 to 6.5 and sodium chloride is added to make it isotonic. The solution obtained is filtered free from pyrogens and the filtrate is transferred under aseptic conditions into ampoules which are then sterilised and sealed by fusion. The ampoules contain 5 mg, 25 mg and 50 mg of active substance.

The invention claimed is:

1. A compound of the formula (1)

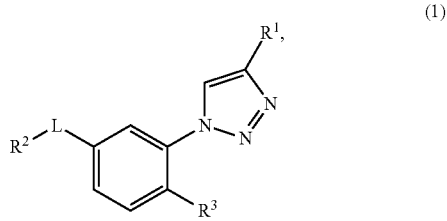

wherein $R^1$ denotes

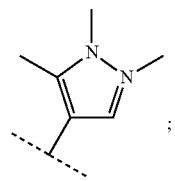

$R^2$ has the partial structure (i)

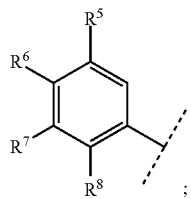

(i)

$R^3$ is selected from among methyl, trifluoromethyl, ethyl, iso-propyl, 1-propyl, 1-butyl, 2-butyl, tert-butyl, fluorine, chlorine and bromine;

$R^5$ is selected from among $C_{1-6}$alkyl, —$OC_{1-6}$alkyl, $C_{1-6}$haloalkyl, —$OC_{1-6}$haloalkyl, $C_{3-7}$cycloalkyl, 3-7 membered heterocycloalkyl, all the above-mentioned groups optionally being substituted by $C_{1-6}$alkyl, —CN or —OH;

$R^7$ has one of the partial structures (iii-a) to (iii-h)

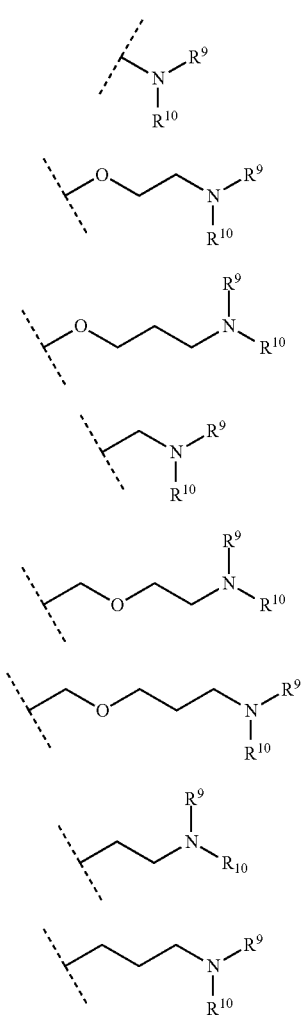

$R^6$ is selected from among hydrogen, $C_{1-6}$alkyl, —$OC_{1-6}$alkyl, chlorine and fluorine and $R^8$ is selected from among hydrogen, $C_{1-6}$alkyl and —$OC_{1-6}$alkyl;

$R^9$ is selected from among hydrogen and $C_{1-6}$alkyl, $R^{10}$ is selected from among $R^a$ and —$OR^a$, or the group —$NR^9R^{10}$ in all denotes a nitrogen-containing, 3-14 membered heterocycloalkyl or 5-12 membered heteroaryl, optionally substituted by one or more identical or different group(s) selected from among $R^a$ and $R^b$;

L is selected from among —C(O)NH— and —NHC(O)

each $R^a$ independently of one another in each case denotes hydrogen or a group optionally substituted by one or more identical or different $R^b$ and/or $R^c$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered heteroaryl, 6-18 membered heteroarylalkyl, 3-14 membered heterocycloalkyl and 4-14 membered heterocycloalkylalkyl;

each $R^b$ denotes a suitable substituent and is independently selected in each case from among —$OR^c$, —$SR^c$, —$NR^cR^c$, —$ONR^cR^c$, —$N(OR^c)R^c$, —$NR^gNR^cR^c$, halogen, —CN, —NC, —OCN, —SCN, —NO, —$NO_2$, —$N_3$, —C(O)$R^c$, —C(O)O$R^c$, —C(O)N$R^cR^c$, —C(O)S$R^c$, —C(O)N$R^g$N$R^cR^c$, —C(O)N$R^g$O$R^c$, —[C(O)]$_2$N$R^cR^c$, —[C(O)N$R^g$]$_2R^c$, —C(S)$R^c$, —C(S)O$R^c$, —C(S)N$R^cR^c$, —C(S)S$R^c$, —C(N$R^g$)$R^c$, —N═C$R^cR^c$, —C(N$R^g$)O$R^c$, —C(N$R^g$)N$R^cR^c$, —C(N$R^g$)S$R^c$, —C(N$R^g$)N$R^g$N$R^cR^c$, —C(NO$R^g$)$R^c$, —C(NO$R^g$)N$R^cR^c$, —C(NN$R^gR^g$)$R^c$, —C[NN$R^g$C(O)N$R^gR^g$]$R^c$, —OS(O)$R^c$, —OS(O)O$R^c$, —OS(O)N$R^cR^c$, —OS(O)$_2R^c$, —OS(O)$_2$O$R^c$, —OS(O)$_2$N$R^cR^c$, —OC(O)$R^c$, —OC(O)O$R^c$, —OC(O)S$R^c$, —OC(O)N$R^cR^c$, —O[C(O)]$_2$N$R^cR^c$, —O[C(O)N$R^g$]$_2$N$R^cR^c$, —OC(S)$R^c$, —OC(N$R^g$)$R^c$, —OC(N$R^g$)N$R^cR^c$, —ON$R^g$C(O)$R^c$, —S(O)$R^c$, —S(O)O$R^c$, —S(O)N$R^cR^c$, —S(O)$_2R^c$, —S(O)$_2$O$R^c$, —S(O)$_2$N$R^cR^c$, —[S(O)$_2$]$_2$N$R^cR^c$, —SC(O)$R^c$, —SC(O)O$R^c$, —SC(O)N$R^cR^c$, —SC(S)$R^c$, —SC(N$R^g$)$R^c$, —SC(N$R^g$)N$R^cR^c$, —N$R^g$C(O)$R^c$, —N$R^g$C(O)O$R^c$, —N$R^g$C(O)N$R^cR^c$, —N$R^g$C(O)S$R^c$, —N$R^g$C(O)N$R^g$N$R^cR^c$, —N$R^g$C(S)$R^c$, —N$R^g$C(S)N$R^cR^c$, —N$R^g$C(N$R^g$)$R^c$, —N═C$R^g$N$R^cR^c$, —N$R^g$C(N$R^g$)O$R^c$, —N$R^g$C(N$R^g$)N$R^cR^c$, —N$R^g$C(N$R^g$)S$R^c$, —N$R^g$C(NO$R^g$)$R^c$, —N$R^g$S(O)$R^c$, —N$R^g$S(O)O$R^c$, —N$R^g$S(O)$_2R^c$, —N$R^g$S(O)$_2$O$R^c$, —N$R^g$S(O)$_2$N$R^cR^c$, —N$R^g$N$R^g$C(O)$R^c$, —N$R^g$N$R^g$C(O)N$R^cR^c$, —N$R^g$N$R^g$C(N$R^g$)$R^c$, —N$R^g$[C(O)]$_2R^c$, —N$R^g$[C(O)]$_2$O$R^c$, —N$R^g$[C(O)]$_2$N$R^cR^c$, —[N$R^g$C(O)]$_2R^c$, —[N$R^g$C(O)]$_2$O$R^c$, —N$R^g$[S(O)$_2$]$_2R^c$, —N(O$R^g$)C(O)$R^c$, —N[C(O)$R^c$]N$R^cR^c$, —N[C(O)$R^c$]$_2$, —N[S(O)$_2R^c$]$_2$, —N{[C(O)]$_2R^c$}$_2$, —N{[C(O)]$_2$O$R^c$}$_2$ and —N{[C(O)]$_2$N$R^cR^c$}$_2$ as well as the bivalent substituents ═O, ═S, ═N$R^g$, ═NO$R^g$, ═NN$R^gR^g$ and ═NN$R^g$C(O)N$R^gR^g$, while these bivalent substituents may only be substituents in non-aromatic ring systems;

each $R^c$ independently of one another in each case denotes hydrogen or a group optionally substituted by one or more identical or different $R^d$ and/or $R^e$, selected from among $C_{1-6}$alkyl, 2-6 membered heteroalkyl, $C_{1-6}$haloalkyl, $C_{3-10}$cycloalkyl, $C_{4-16}$cycloalkylalkyl, $C_{6-10}$aryl, $C_{7-16}$arylalkyl, 5-12 membered hetero-aryl, 6-18 membered heteroarylalkyl, 3-14 membered heterocycloalkyl and 4-14 membered heterocycloalkylalkyl;

each $R^d$ is a suitable substituent and is independently selected in each case from among —$OR^e$, —$SR^e$, —NR$^e$R$^e$, —ONR$^e$R$^e$, —N(OR$^e$)R$^e$, —N(R$^g$)NR$^e$R$^e$, halogen, —CN, —NC, —OCN, —SCN, —NO, —NO$_2$, —N$_3$, —C(O)R$^e$, —C(O)OR$^e$, —C(O)NR$^e$R$^e$, —C(O)SR$^e$, —C(O)NR$^g$NR$^e$R$^e$, —C(O)NR$^g$OR$^e$, —[C(O)]$_2$NR$^e$R$^e$, —[C(O)NR$^g$]$_2$R$^e$, —C(S)R$^e$, —C(S)OR$^e$, —C(S)NR$^e$R$^e$, —C(S)SR$^e$, —C(NR$^g$)R$^e$, —N=CR$^e$R$^e$, —C(NR$^g$)OR$^e$, —C(NR$^g$)NR$^e$R$^e$, —C(NR$^g$)SR$^e$, —C(NR$^g$)NR$^g$NR$^e$R$^e$, —C(NOR$^g$)R$^e$, —C(NOR$^g$)NR$^e$R$^e$, —C(NNR$^g$R$^g$)R$^e$, —C[NNR$^g$C(O)NR$^g$R$^g$]R$^e$, —OS(O)R$^e$, —OS(O)OR$^e$, —OS(O)NR$^e$R$^e$, —OS(O)$_2$R$^e$, —OS(O)$_2$OR$^e$, —OS(O)$_2$NR$^e$R$^e$, —OC(O)R$^e$, —OC(O)OR$^e$, —OC(O)SR$^e$, —OC(O)NR$^e$R$^e$, —O[C(O)]$_2$NR$^e$R$^e$, —O[C(O)NR$^g$]$_2$NR$^e$R$^e$, —OC(S)R$^e$, —OC(NR$^g$)R$^e$, —OC(NR$^g$)NR$^e$R$^e$, —ONR$^g$C(O)R$^e$, —S(O)R$^e$, —S(O)OR$^e$, —S(O)NR$^e$R$^e$, —S(O)$_2$R$^e$, —S(O)$_2$OR$^e$, —S(O)$_2$NR$^e$R$^e$, —[S(O)$_2$]$_2$NR$^e$R$^e$, —SC(O)R$^e$, —SC(O)OR$^e$, —SC(O)NR$^e$R$^e$, —SC(S)R$^e$, —SC(NR$^g$)R$^e$, —SC(NR$^g$)NR$^e$R$^e$, —NR$^g$C(O)R$^e$, —NR$^g$C(O)OR$^e$, —NR$^g$C(O)NR$^e$R$^e$, —NR$^g$C(O)SR$^e$, —NR$^g$C(O)NR$^g$NR$^e$R$^e$, —NR$^g$C(S)R$^e$, —NR$^g$C(S)NR$^e$R$^e$, —NR$^g$C(NR$^g$)R$^e$, —N=CR$^e$NR$^e$R$^e$, —NR$^g$C(NR$^g$)OR$^e$, —NR$^g$C(NR$^g$)NR$^e$R$^e$, —NR$^g$C(NR$^g$)SR$^e$, —NR$^g$C(NOR$^g$)R$^e$, —NR$^g$S(O)R$^e$, —NR$^g$S(O)OR$^e$, —NR$^g$S(O)$_2$R$^e$, —NR$^g$S(O)$_2$OR$^e$, —NR$^g$S(O)$_2$NR$^e$R$^e$, —NR$^g$NR$^g$C(O)R$^e$, —NR$^g$NR$^g$C(O)NR$^e$R$^e$, —NR$^g$NR$^g$C(NR$^g$)R$^e$, —NR$^g$[C(O)]$_2$R$^e$, —NR$^g$[C(O)]$_2$OR$^e$, —NR$^g$[C(O)]$_2$NR$^e$R$^e$, —[NR$^g$C(O)]$_2$R$^e$, 13 [NR$^g$C(O)]$_2$OR$^e$, —NR$^g$[S(O)$_2$]$_2$R$^e$, —N(OR$^g$)C(O)R$^e$, —N[C(O)R$^e$]NR$^e$R$^e$, —N[C(O)R$^e$]$_2$, —N[S(O)$_2$R$^e$]$_2$, —N{[C(O)]$_2$R$^e$}$_2$, —N{[C(O)]$_2$OR$^e$} and —N{[C(O)]$_2$NR$^e$R$^e$}$_2$ as well as the bivalent substituents =O, =S, =NR$^g$, =NOR$^g$, =NNR$^g$R$^g$ and =NNR$^g$C(O)NR$^g$R$^g$, while these bivalent substituents may only be substituents in non-aromatic ring systems;

each R$^e$ independently of one another in each case denotes hydrogen or a group optionally substituted by one or more identical or different R$^f$ and/or R$^g$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl;

each R$^f$ is a suitable substituent and is independently selected in each case from among —OR$^g$, —SR$^g$, —NR$^g$R$^g$, —ONR$^g$R$^g$, —N(OR$^g$)R$^g$, —N(R$^h$)NR$^g$R$^g$, halogen, —CN, —NC, —OCN, —SCN, —NO, —NO$_2$, —N$_3$, —C(O)R$^g$, —C(O)OR$^g$, —C(O)NR$^g$R$^g$, —C(O)SR$^g$, —C(O)NR$^h$NR$^g$R$^g$, —C(O)NR$^h$OR$^g$, —[C(O)]$_2$NR$^g$R$^g$, —[C(O)NR$^h$]$_2$R$^g$, —C(S)R$^g$, —C(S)OR$^g$, —C(S)NR$^g$R$^g$, —C(S)SR$^g$, —C(NR$^h$)R$^g$, —N=CR$^g$R$^g$, —C(NR$^h$)OR$^g$, —C(NR$^h$)NR$^g$R$^g$, —C(NR$^h$)SR$^g$, —C(NR$^h$)NR$^h$NR$^g$R$^g$, —C(NOR$^h$)R$^g$, —C(NOR$^h$)NR$^g$R$^g$, —C(NNR$^h$R$^h$)R$^g$, —C[NNR$^h$C(O)NR$^g$R$^h$]R$^g$, —OS(O)R$^g$, —OS(O)OR$^g$, —OS(O)NR$^g$R$^g$, —OS(O)$_2$R$^g$, —OS(O)$_2$OR$^g$, —OS(O)$_2$NR$^g$R$^g$, —OC(O)R$^g$, —OC(O)OR$^g$, —OC(O)SR$^g$, —OC(O)NR$^g$R$^g$, —O[C(O)]$_2$NR$^g$R$^g$, —O[C(O)NR$^h$]$_2$NR$^g$R$^g$, —OC(S)R$^g$, —OC(NR$^h$)R$^g$, —OC(NR$^h$)NR$^g$R$^g$, —ONR$^h$C(O)R$^g$, —S(O)R$^g$, —S(O)OR$^g$, —S(O)NR$^g$R$^g$, —S(O)$_2$R$^g$, —S(O)$_2$OR$^g$, —S(O)$_2$NR$^g$R$^g$, —[S(O)$_2$]$_2$NR$^g$R$^g$, —SC(O)R$^g$, —SC(O)OR$^g$, —SC(O)NR$^g$R$^g$, —SC(S)R$^g$, —SC(NR$^h$)R$^g$, —SC(NR$^h$)NR$^g$R$^g$, —NR$^h$C(O)R$^g$, —NR$^h$C(O)OR$^g$, —NR$^h$C(O)NR$^g$R$^g$, —NR$^h$C(O)SR$^g$, —NR$^h$C(O)NR$^h$NR$^g$R$^g$, —NR$^h$C(S)R$^g$, —NR$^h$C(S)NR$^g$R$^g$, —NR$^h$C(NR$^h$)R$^g$, —N=CR$^g$NR$^g$R$^g$, —NR$^h$C(NR$^h$)OR$^g$, —NR$^h$C(NR$^h$)NR$^g$R$^g$, —NR$^h$C(NR$^h$)SR$^g$, —NR$^h$C(NOR$^h$)R$^g$, —NR$^h$S(O)R$^g$, —NR$^h$S(O)OR$^g$, —NR$^h$S(O)$_2$R$^g$, —NR$^h$S(O)$_2$OR$^g$, —NR$^h$S(O)$_2$NR$^g$R$^g$, —NR$^h$NR$^h$C(O)R$^g$, —NR$^h$NR$^h$C(O)NR$^g$R$^g$, —NR$^h$NR$^h$C(NR$^h$)R$^g$, —NR$^h$[C(O)]$_2$R$^g$, —NR$^h$[C(O)]$_2$OR$^g$, —NR$^h$[C(O)]$_2$NR$^g$R$^g$, —[NR$^h$C(O)]$_2$R$^g$, —[NR$^h$C(O)]$_2$OR$^g$, —NR$^h$[S(O)$_2$]$_2$R$^g$, —N(OR$^h$)C(O)R$^g$, —N[C(O)R$^g$]NR$^g$R$^g$, —N[C(O)R$^g$]$_2$, —N[S(O)$_2$R$^g$]$_2$, —N{[C(O)]$_2$R$^g$}$_2$, —N{[C(O)]$_2$OR$^g$}$_2$ and —N{[C(O)]$_2$NR$^g$R$^g$}$_2$ as well as the bivalent substituents =O, =S, =NR$^h$, =NOR$^h$, =NNR$^h$R$^h$ and =NNR$^h$C(O)NR$^h$R$^h$, while these bivalent substituents may only be substituents in non-aromatic ring systems;

each R$^g$ in each case independently of one another denote hydrogen or a group optionally substituted by one or more identical or different R$^h$, selected from among C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered hetero-aryl, 6-18 membered heteroarylalkyl, 3-14 membered heterocycloalkyl and 4-14 membered heterocycloalkylalkyl;

each R$^h$ is selected independently of one another in each case from among hydrogen, C$_{1-6}$alkyl, 2-6 membered heteroalkyl, C$_{1-6}$haloalkyl, C$_{3-10}$cycloalkyl, C$_{4-16}$cycloalkylalkyl, C$_{6-10}$aryl, C$_{7-16}$arylalkyl, 5-12 membered heteroaryl, 6-18 membered heteroarylalkyl, 3-14 membered heterocycloalkyl and 4-14 membered heterocycloalkylalkyl;

while the compounds (1) may optionally also be present in the form of the tautomers, the racemates, the enantiomers, the diastereomers, the mixtures thereof, or as pharmacologically acceptable salts of all the above-mentioned forms.

2. The compound according to claim 1, wherein R$^5$ is selected from among

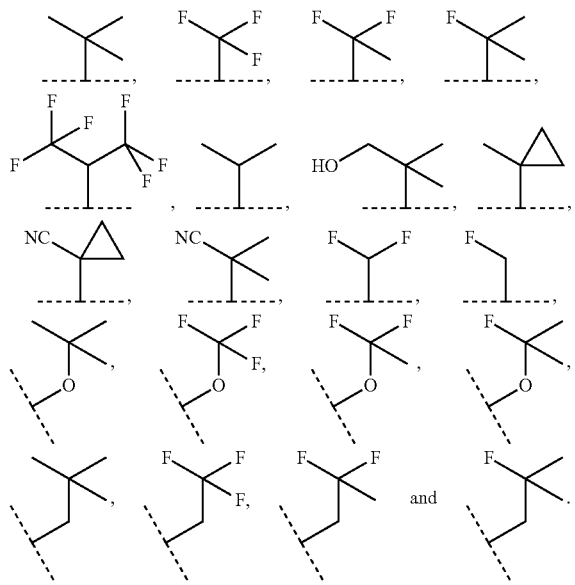

3. The compound according to claim 1, wherein R$^6$ and R$^8$ each denote hydrogen.

4. The compound according to claim 1, wherein R$^{10}$ is selected from among R$^{a1}$ and —OC$_{1-6}$alkyl;

R$^{a1}$ denotes hydrogen or a group optionally substituted by one or more identical or different R$^{b1}$ and/or R$^{c1}$, selected from among $C_{1-6}$alkyl, $C_{3-10}$cycloalkyl, 6-18 membered heteroarylalkyl, 3-14 membered heterocycloalkyl and 4-14 membered heterocycloalkylalkyl;

each $R^{b1}$ denotes a suitable substituent and is independently selected in each case from among —$OR^{c1}$, —$NR^{c1}R^{e1}$, —$C(O)R^{c1}$, —$C(O)NR^{c1}R^{e1}$, —$NHC(O)R^{c1}$ as well as the bivalent substituent =O, while the latter may only be a substituent in non-aromatic ring systems;

each $R^{c1}$ denotes, independently of one another in each case, hydrogen or a group optionally substituted by one or more identical or different $R^{d1}$ and/or $R^{e1}$, selected from among $C_{1-6}$alkyl, 5-12 membered heteroaryl and 3-14 membered heterocycloalkyl;

each $R^{d1}$ denotes the bivalent substituent =O, which may only be a substituent in non-aromatic ring systems; and each $R^{e1}$ is selected independently in each case from among hydrogen, $C_{1-6}$alkyl and 3-14 membered heterocycloalkyl;

or the group —$NR^9R^{10}$ altogether represents in each case a nitrogen-containing, 3-14 membered heterocycloalkyl or 5-12 membered heteroaryl, in each case optionally substituted by one or more identical or different group(s) selected from among $R^{a2}$ and $R^{b2}$;

each $R^{a2}$ denotes a group optionally substituted by one or more identical or different $R^{b2}$ and/or $R^{c2}$, selected from among $C_{1-6}$alkyl, $C_{3-10}$cycloalkyl, $C_{4-16}$cycloalkylalkyl, $C_{6-10}$aryl, 5-12 membered heteroaryl, 6-18 membered heteroarylalkyl and 3-14 membered heterocycloalkyl;

each $R^{b2}$ denotes a suitable substituent and is independently selected in each case from among —$OR^{c2}$, —$NR^{c2}R^{c2}$, halogen as well as the bivalent substituent =O, while the latter may only be a substituent in non-aromatic ring systems;

each $R^{c2}$ is selected independently in each case from among hydrogen, $C_{1-6}$alkyl, $C_{3-10}$cycloalkyl and 5-12 membered heteroaryl.

5. The compound according to claim 1, wherein
$R^{10}$ is selected from among methyl; ethyl; allyl; 2-propyl; 2-hydroxyethyl; 2-aminoethyl; 2-methoxyethyl; 2,2-dimethoxyethyl; 2,3-dihydroxypropyl; 2-methylpropyl; cyclopropyl; cyclobutyl; cyclopentyl; 1,1-dimethylethyl; methoxy; 2,2-dimethylpropyl;

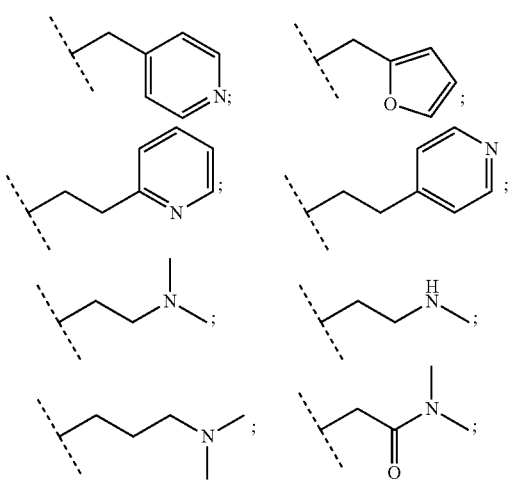

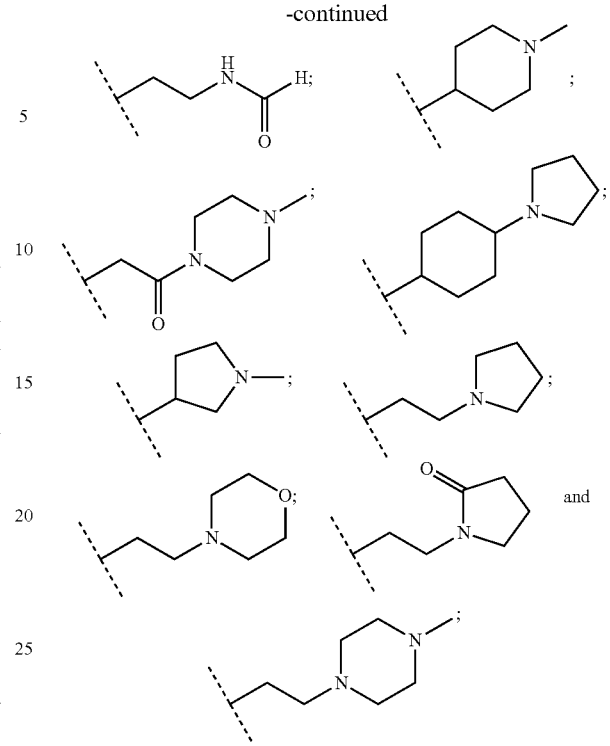

or
the group —$NR^9R^{10}$ altogether denotes

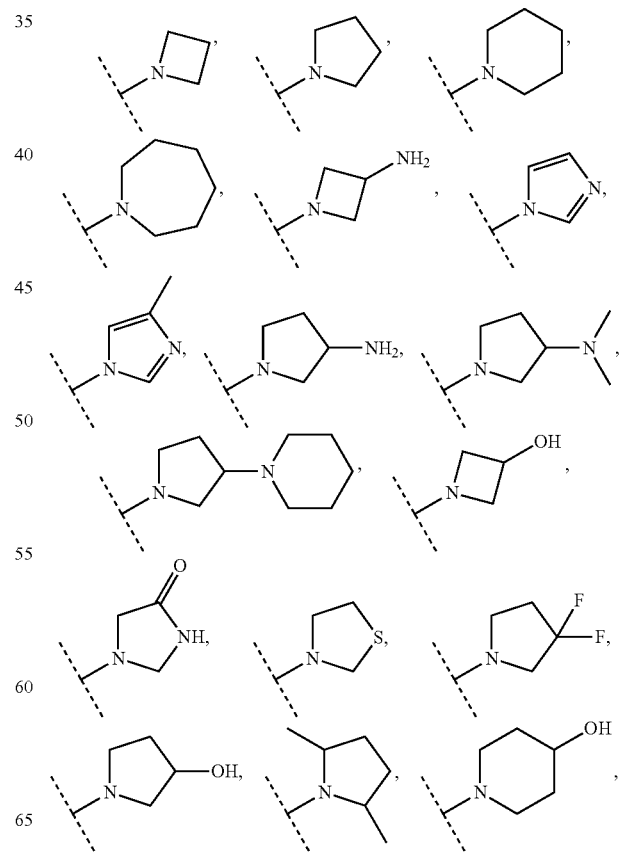

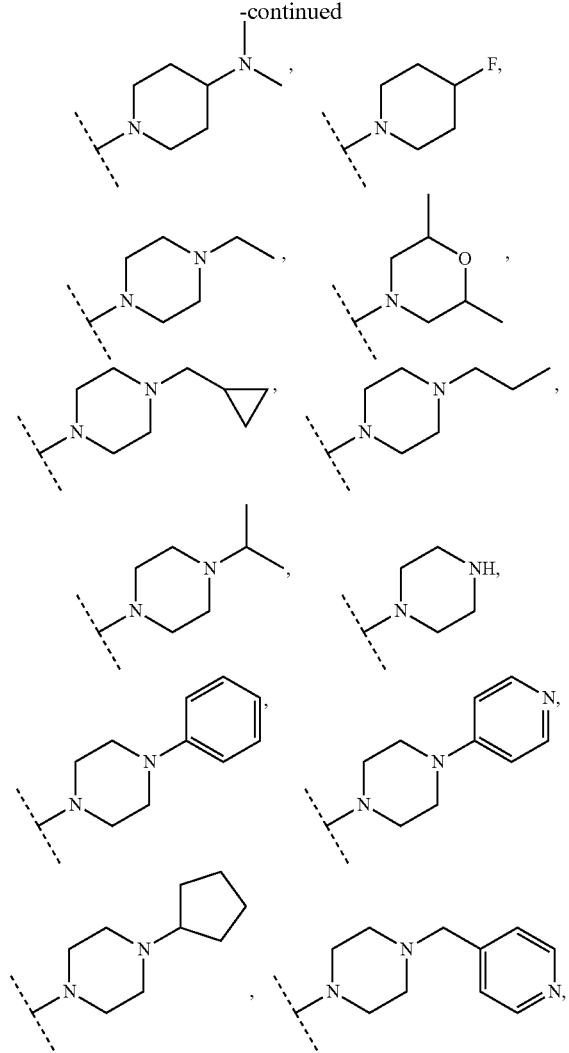
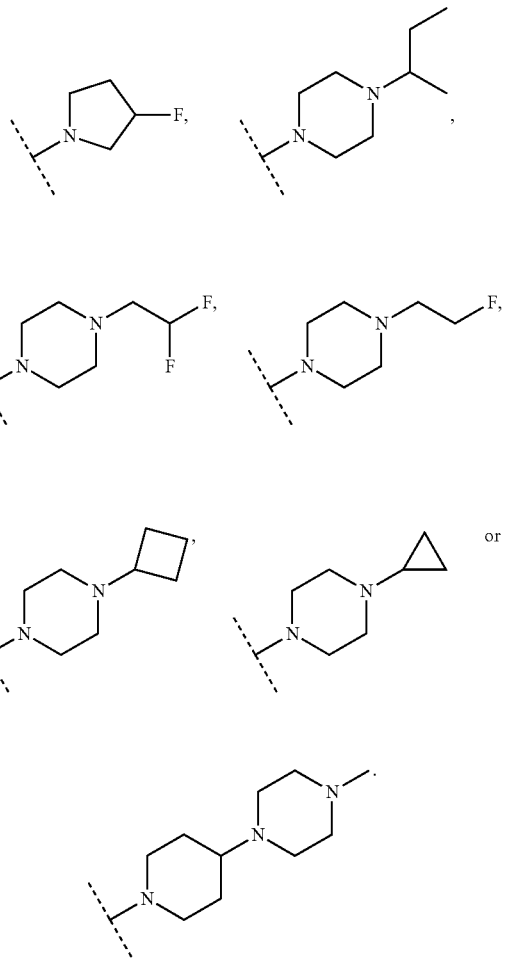
6. A compound selected from among:
Ia-5
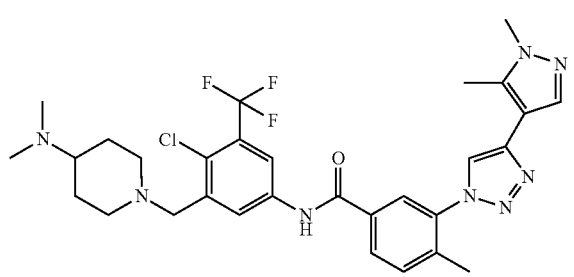
Ia-6
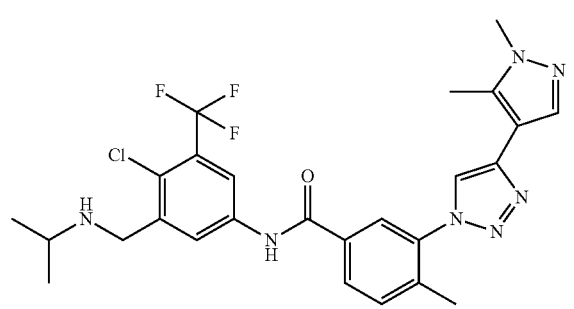

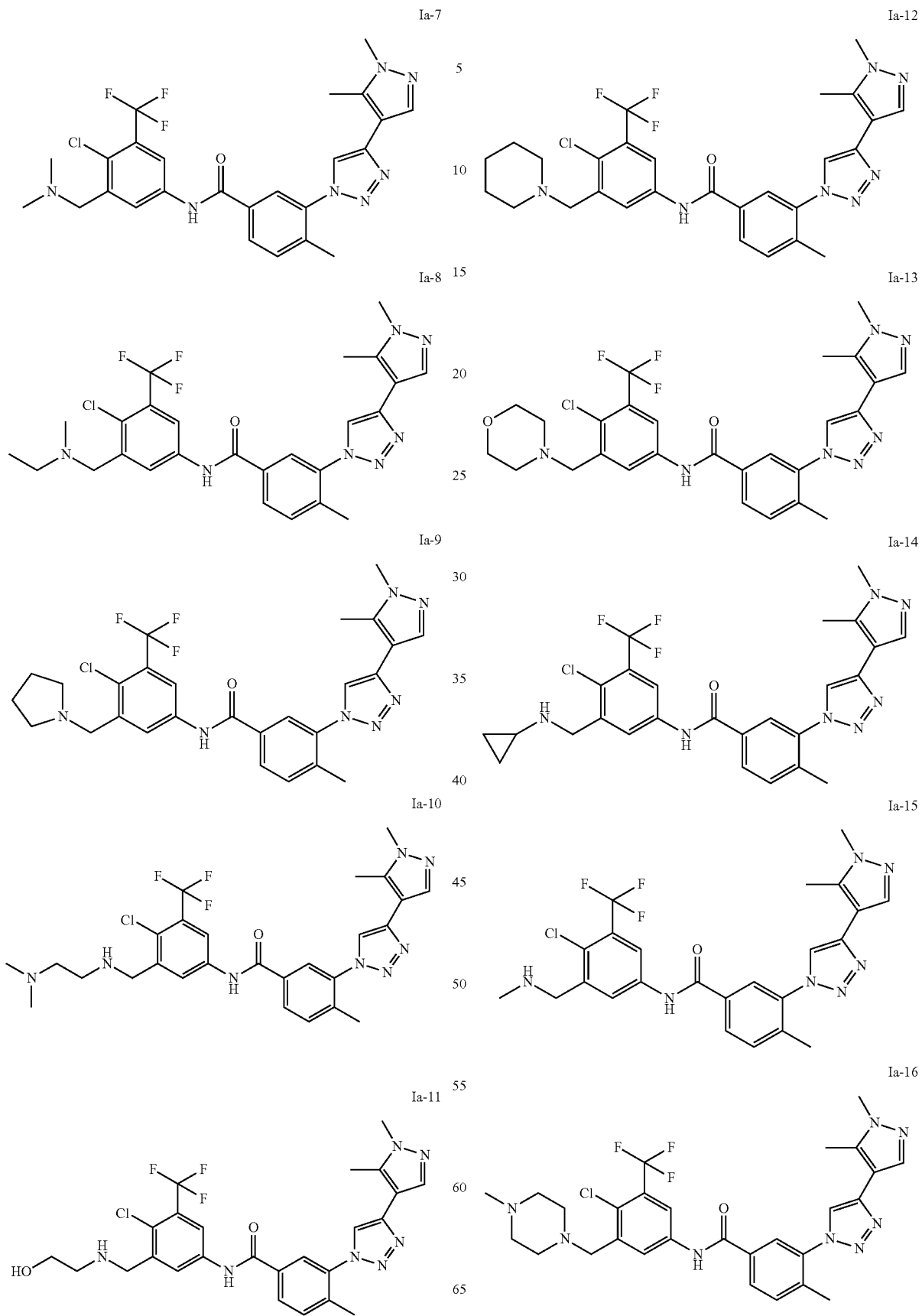

Ia-17
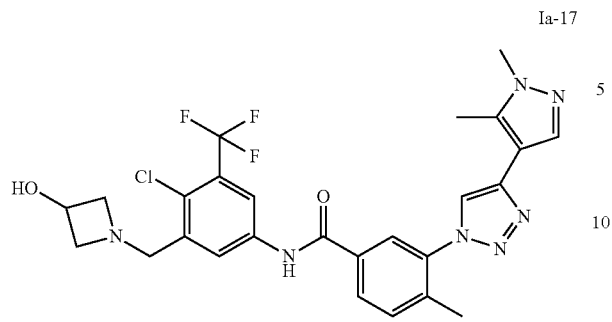
Ia-18
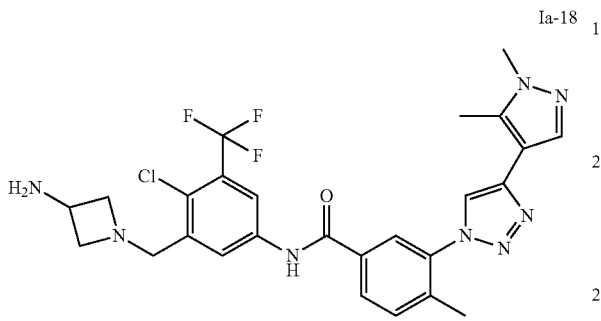
Ia-19
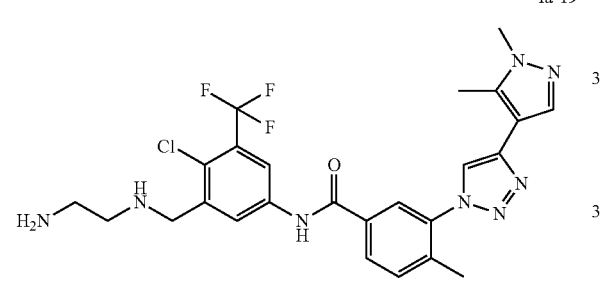
Ia-20
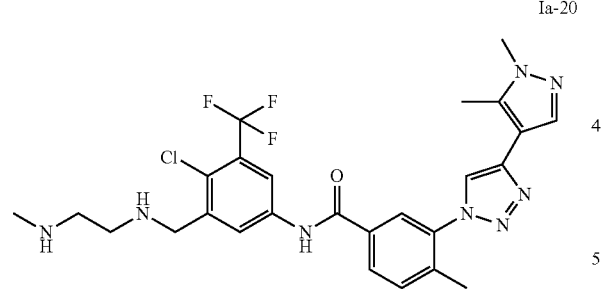
Ia-21
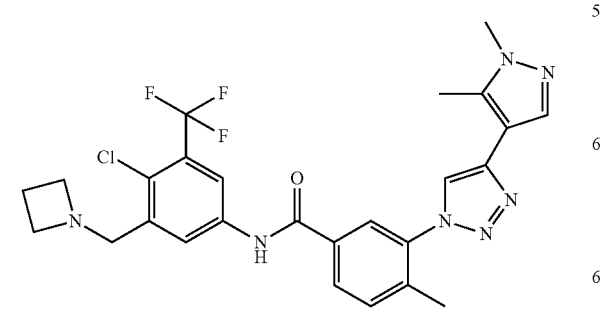
Ia-22
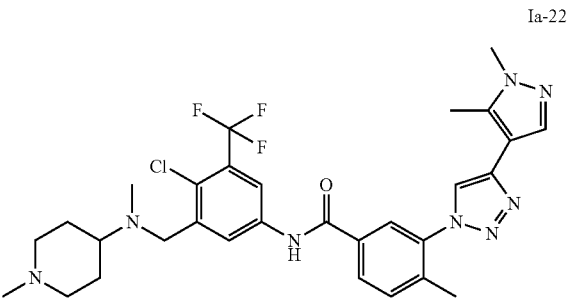
Ia-23
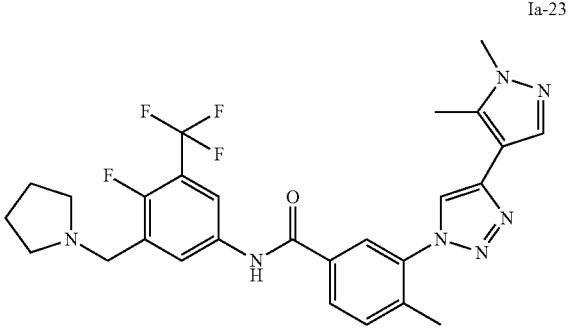
Ia-24
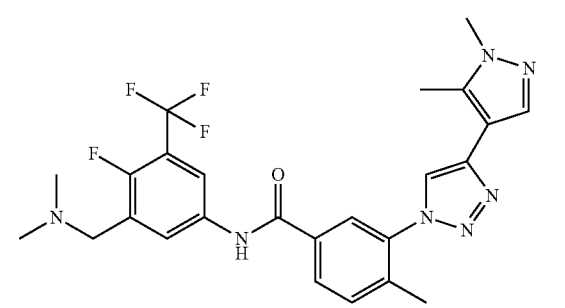
Ia-25
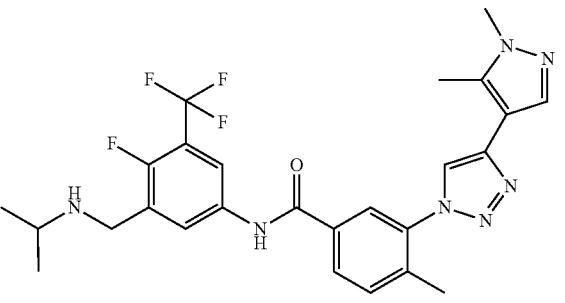
Ia-32
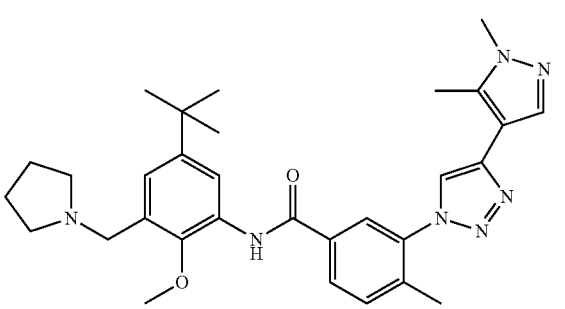

Ia-33
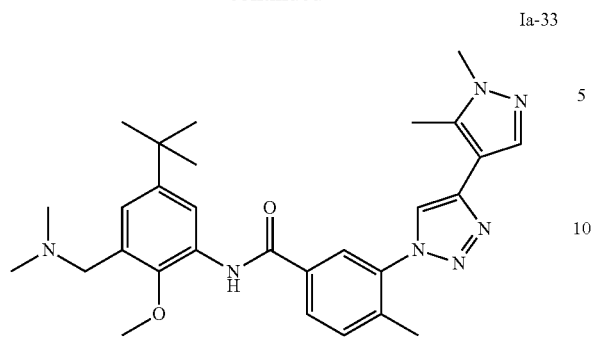
Ia-39
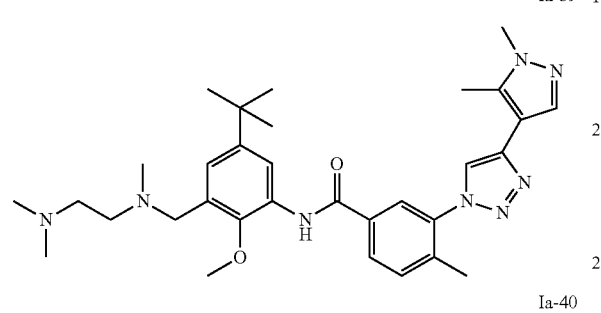
Ia-40
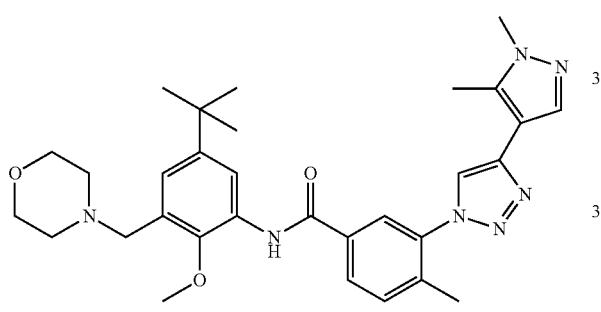
Ia-47
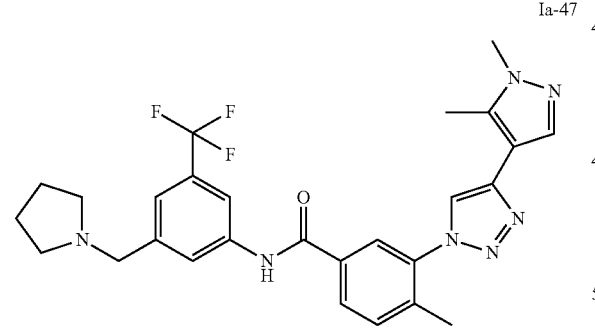
Ia-48
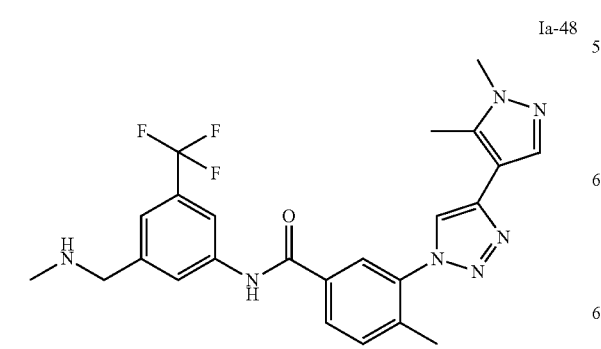
Ia-49
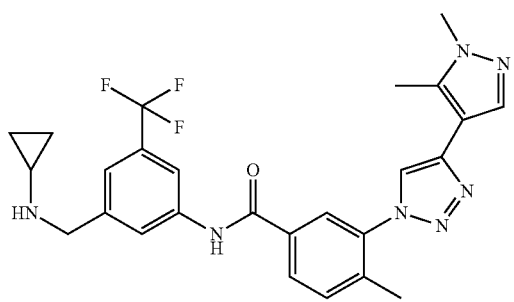
Ia-50
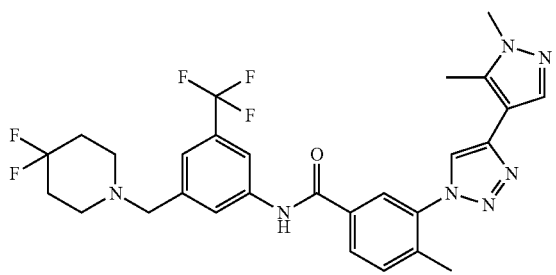
Ia-51
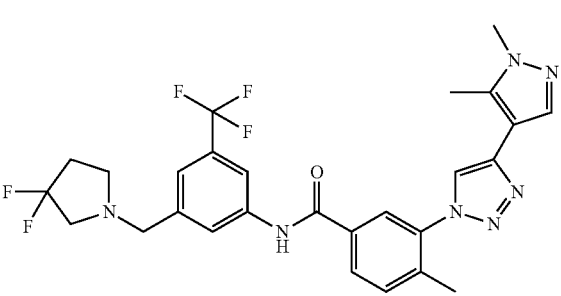
Ia-52
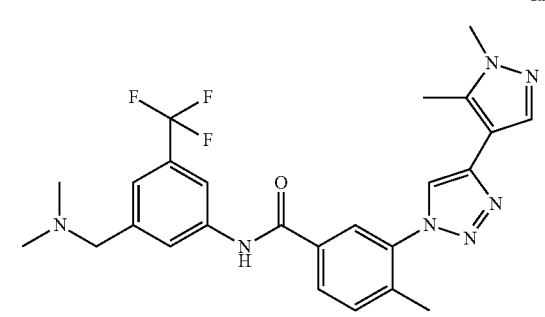
Ia-53
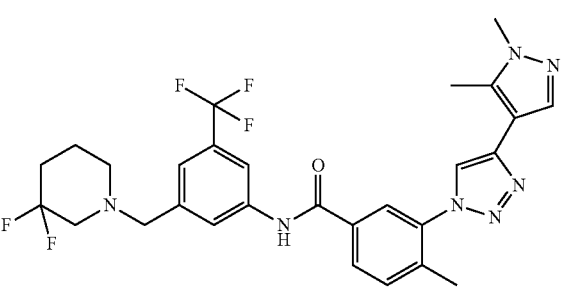

Ia-54
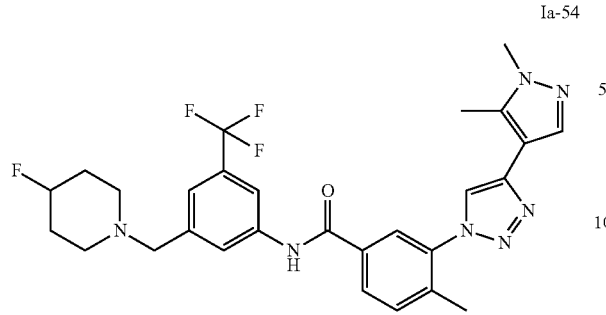
Ia-55
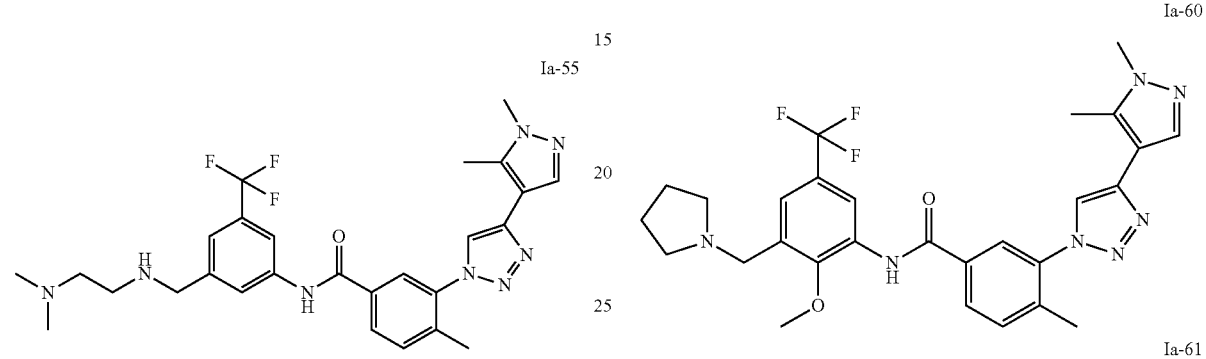
Ia-56
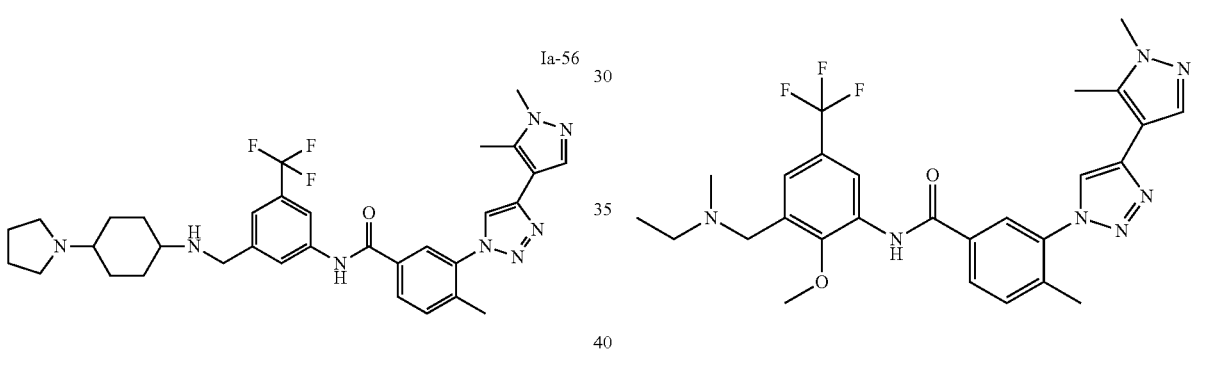
Ia-57
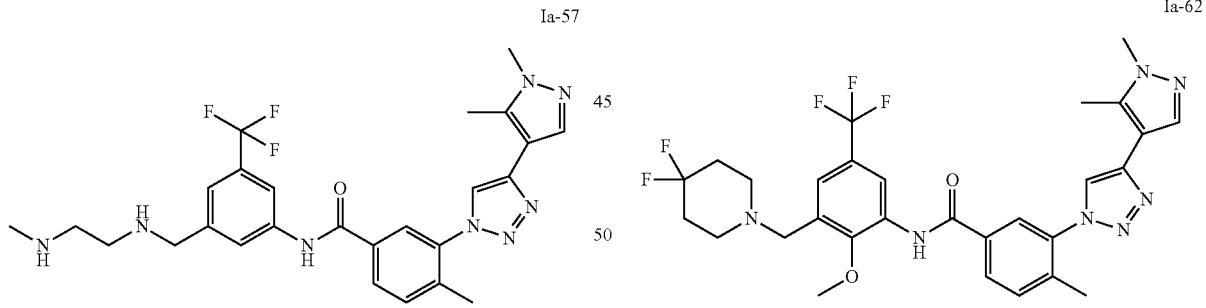
Ia-58
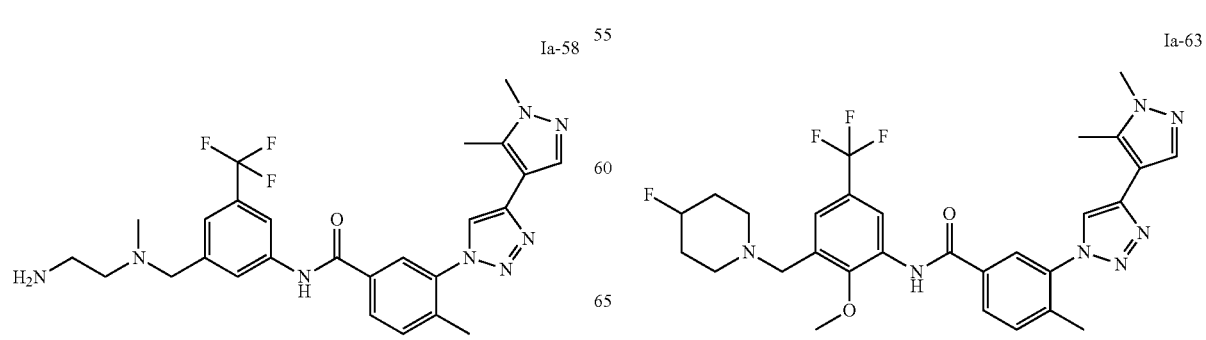
Ia-59
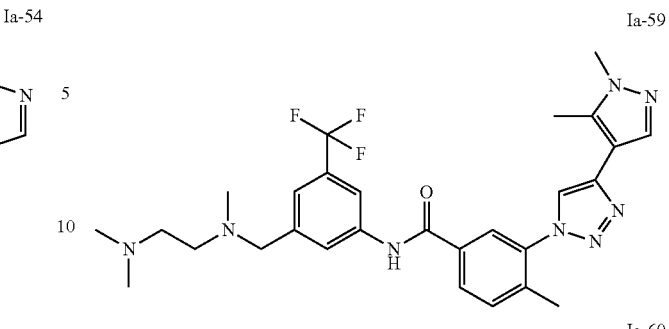
Ia-60
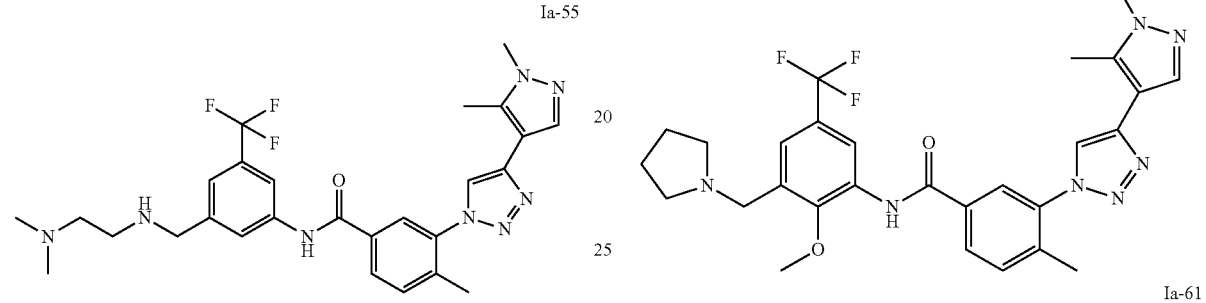
Ia-61
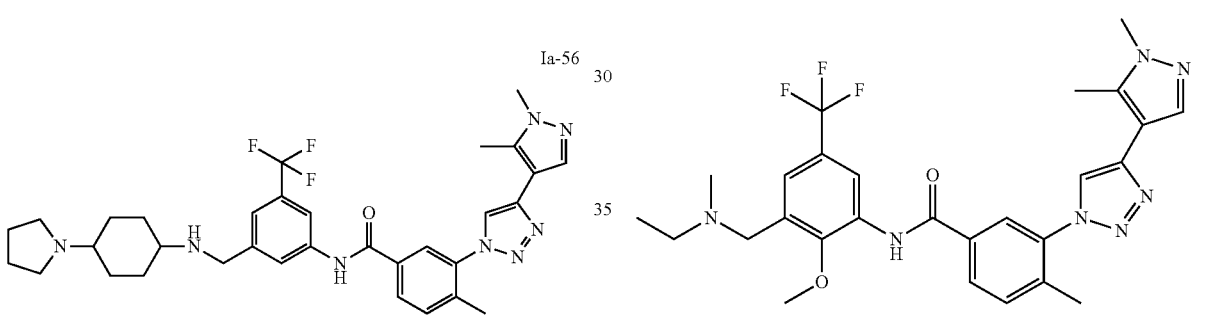
Ia-62
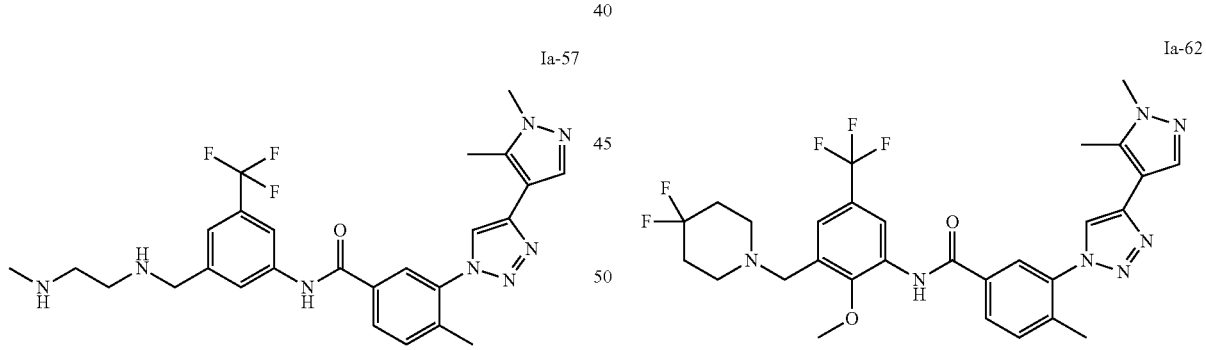
Ia-63
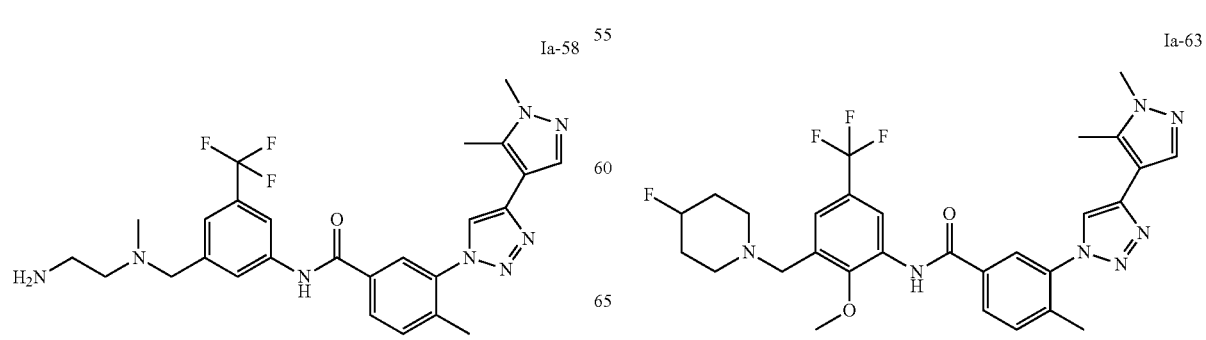

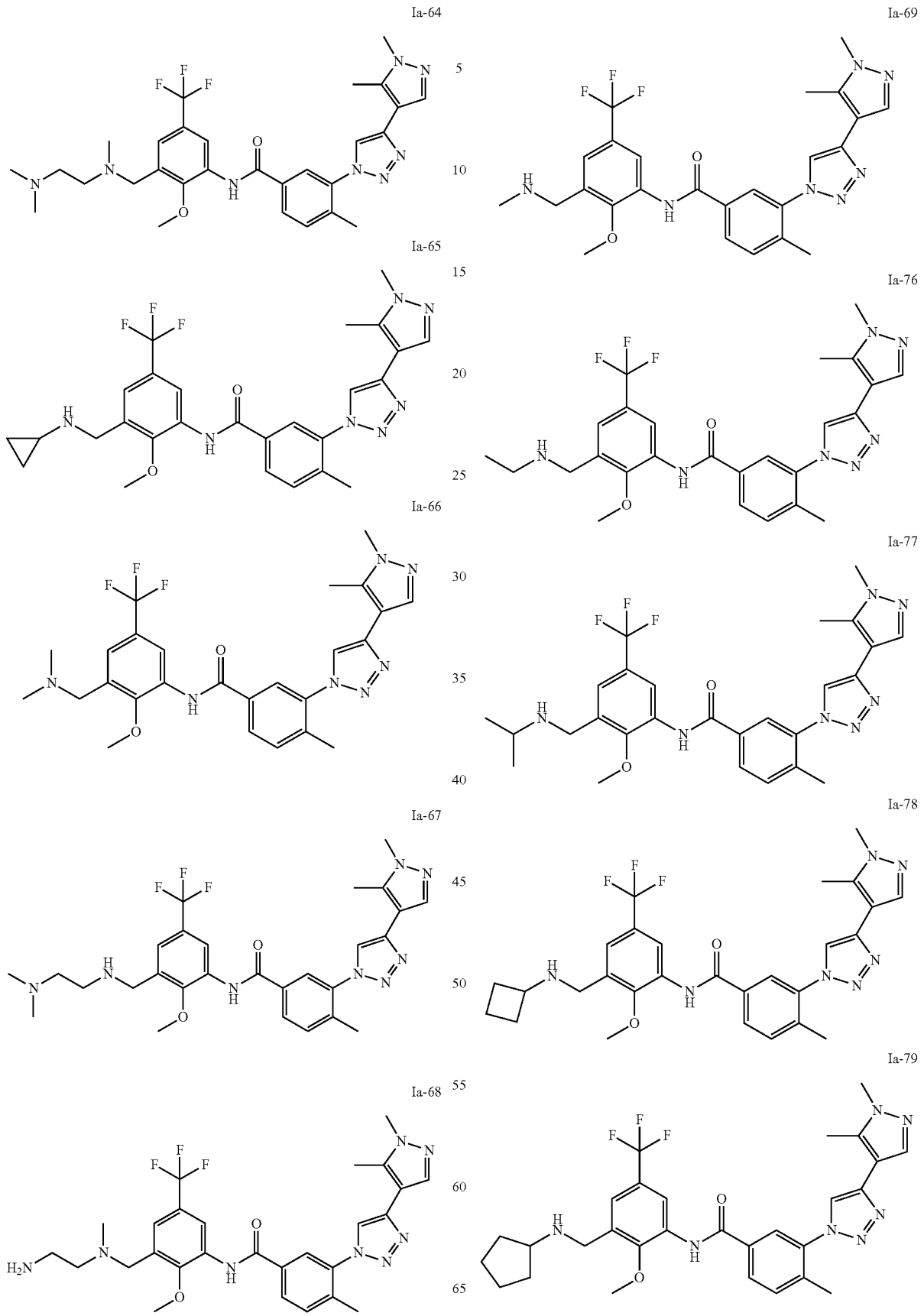

Ia-80
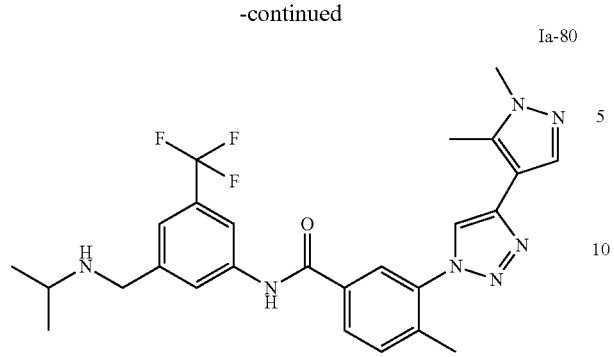
Ia-81
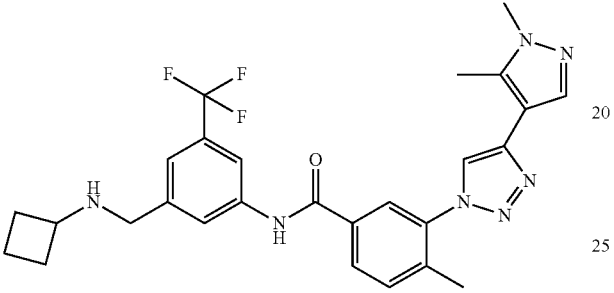
Ia-82
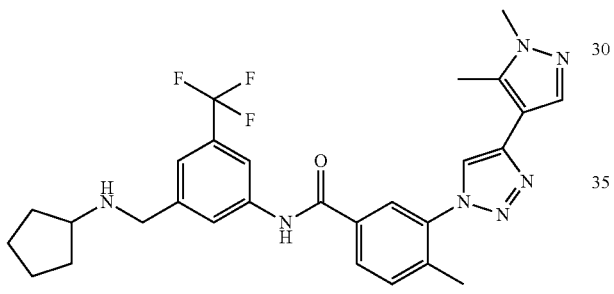
Ia-83
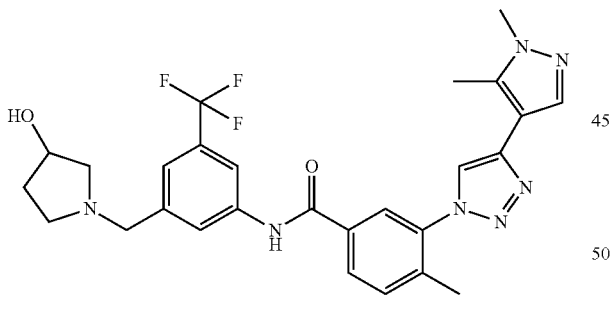
Ia-88
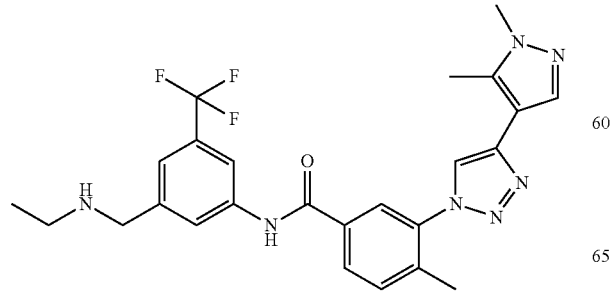
Ia-90
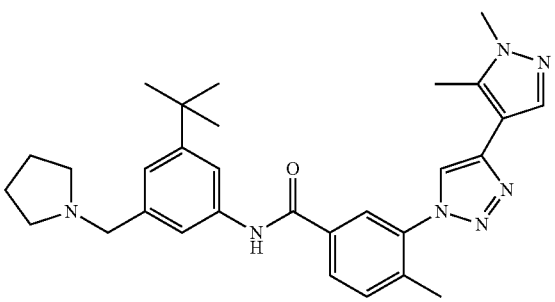
Ia-91
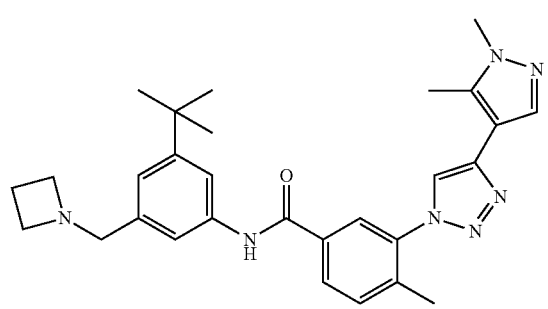
Ia-92
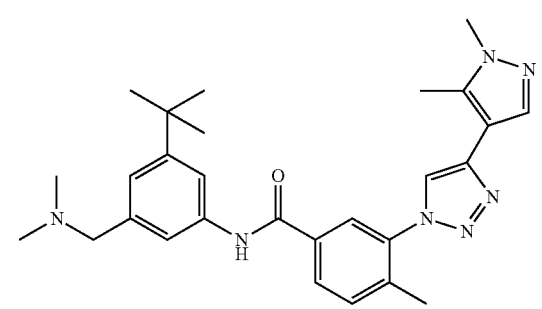
Ia-93
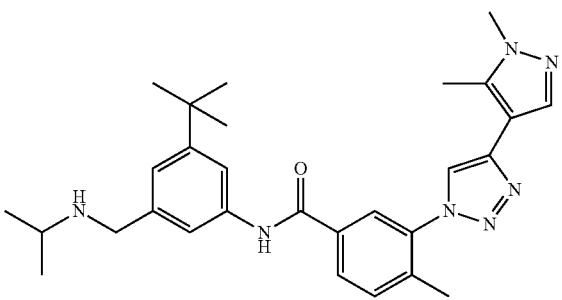
Ia-94
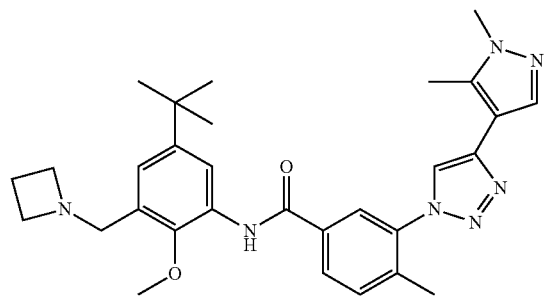

Ia-95
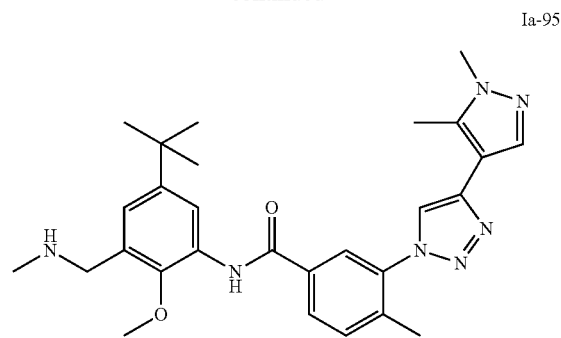 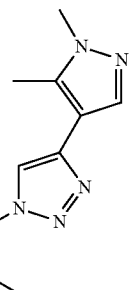
Ia-100
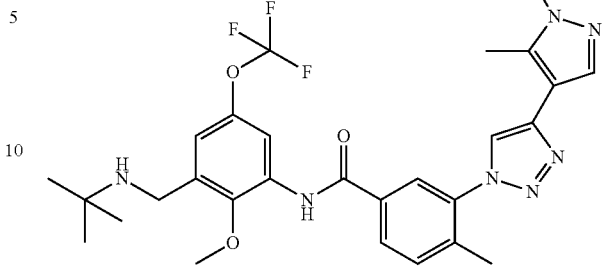
Ia-96
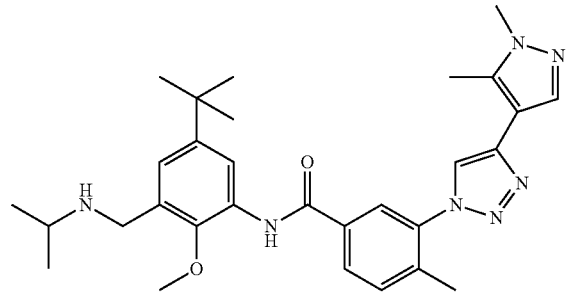 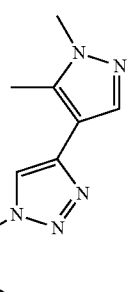
Ia-102
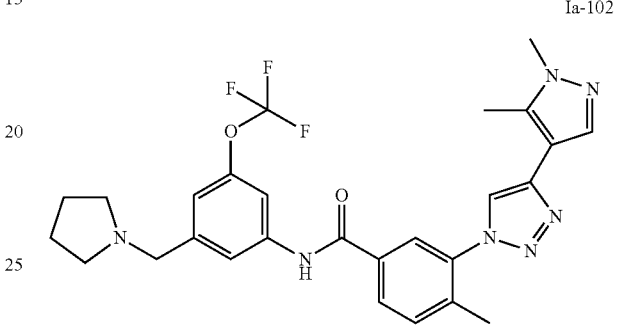
Ia-97
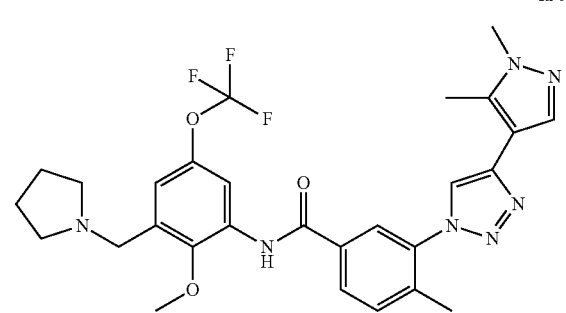 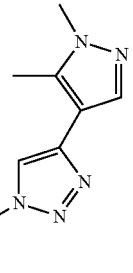
Ia-103
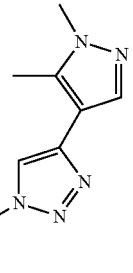
Ia-98
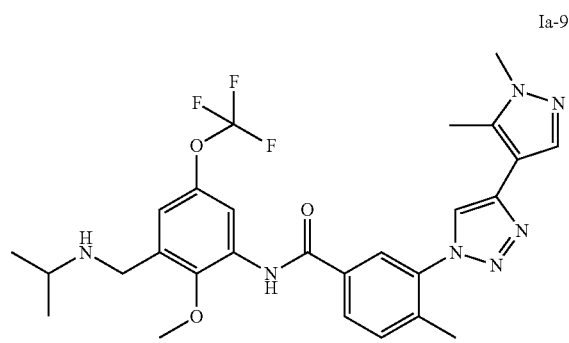 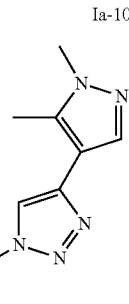
Ia-104
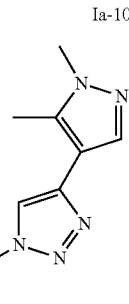
Ia-99
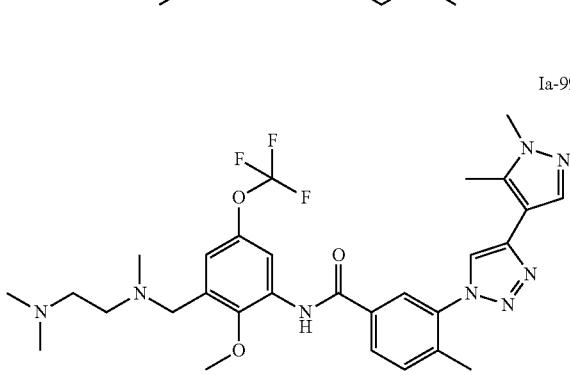 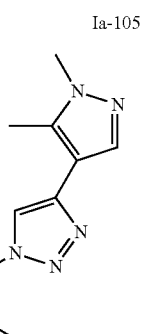
Ia-105
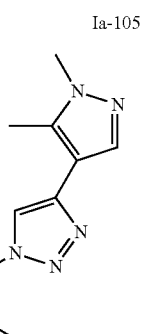

Ia-106
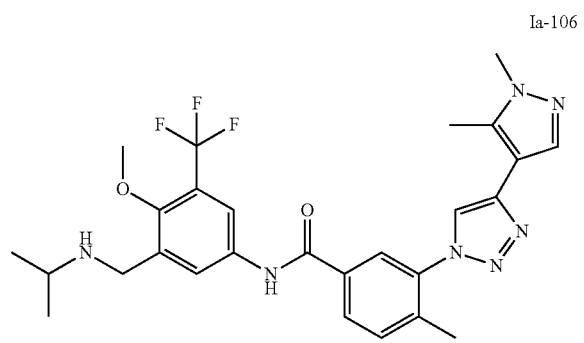 [SMILES: CNCCc1cc(NC(=O)c2ccc(C)c(-n3cc(-c4cnn(C)c4C)nn3)c2)cc(C(F)(F)F)c1]
Ia-107
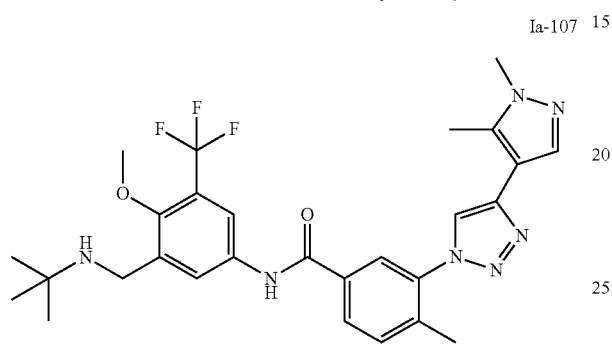
Ia-108
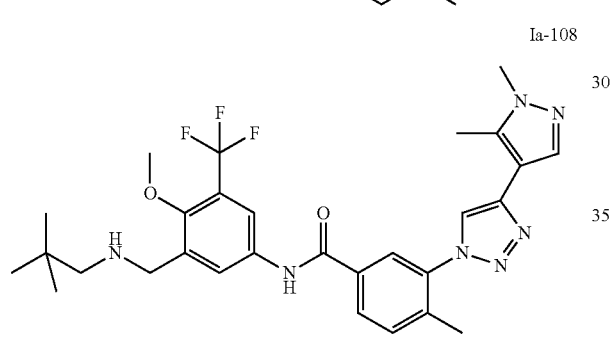
Ia-109
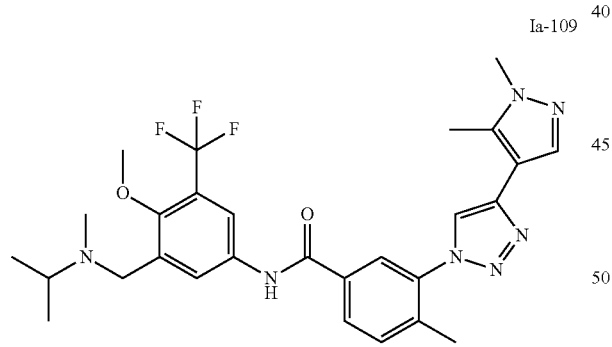
Ia-110
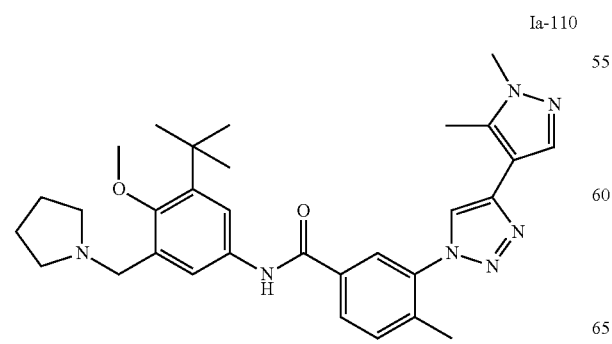
Ia-111
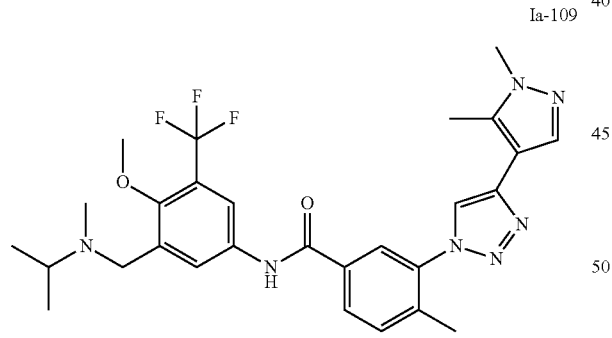
Ia-112
Ia-113
Ia-114
Ia-115

-continued
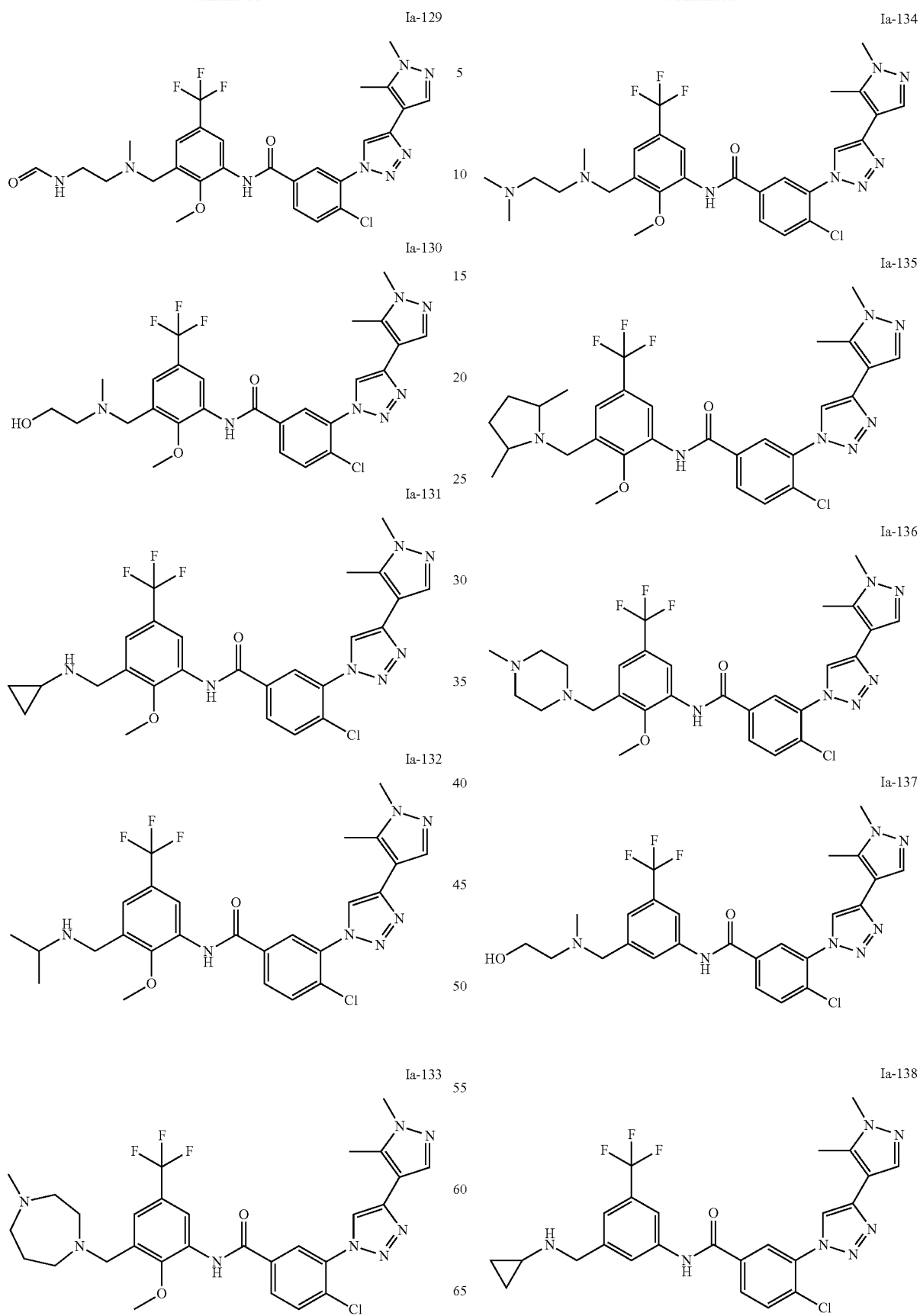

Ia-139
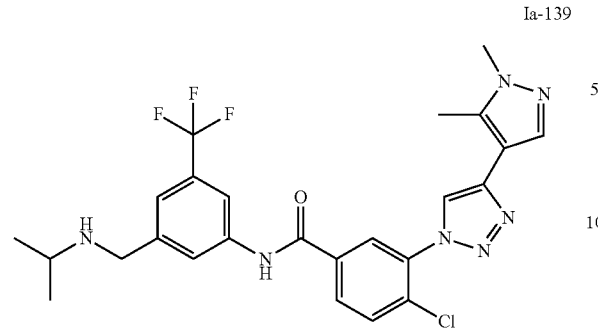
Ia-140
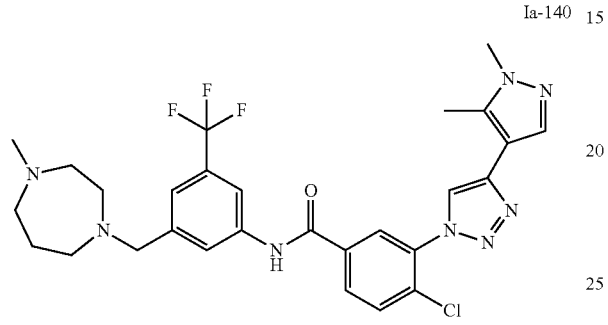
Ia-141
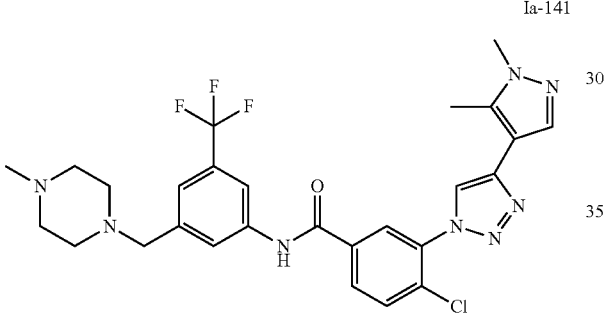
Ia-142
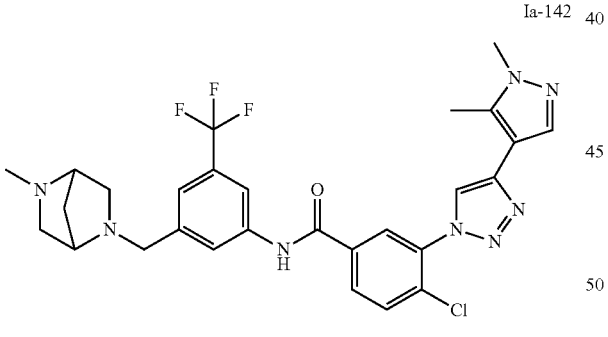
Ia-143
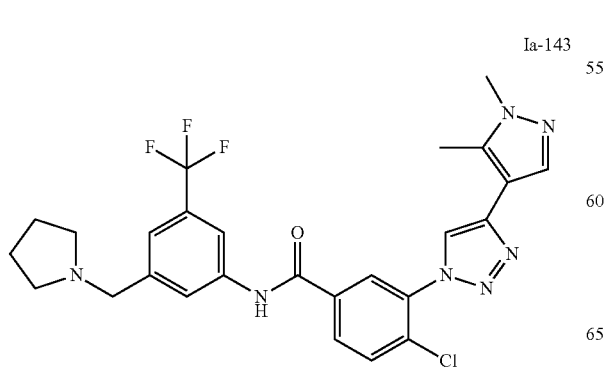
Ia-144
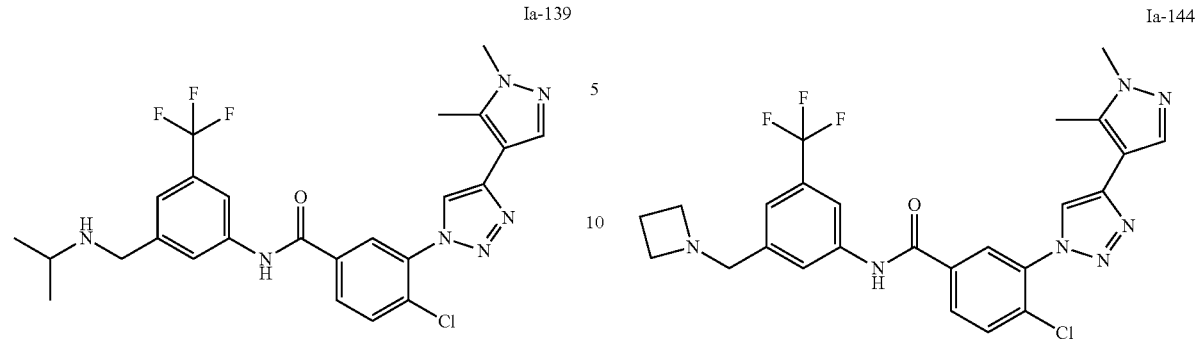
Ia-145
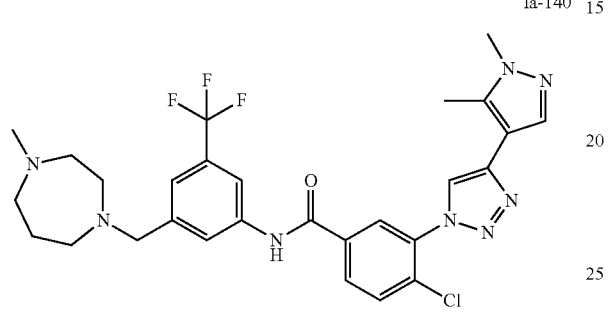
Ia-146
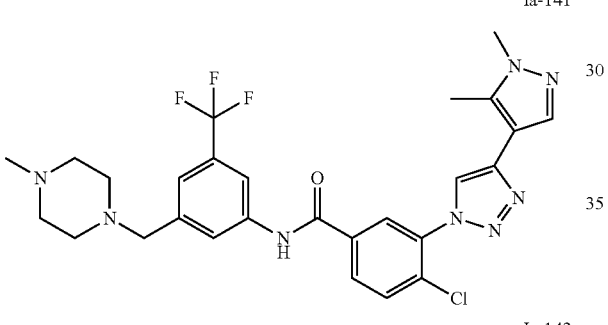
Ia-147
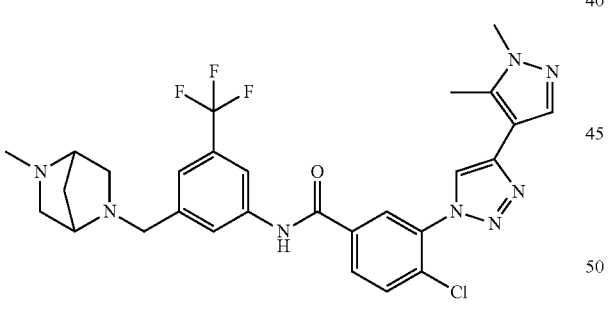
Ia-148
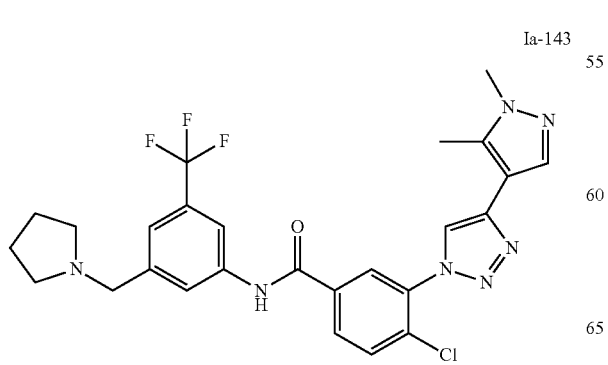

503
-continued
Ia-149
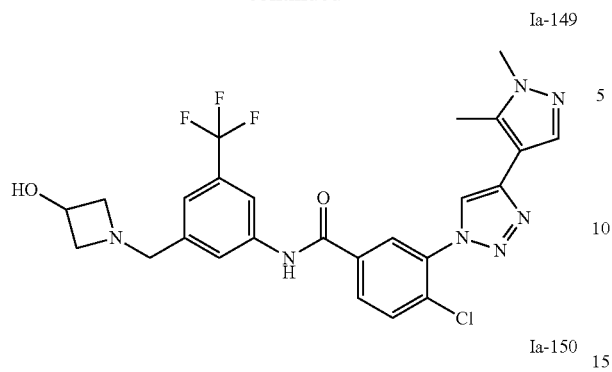
Ia-150
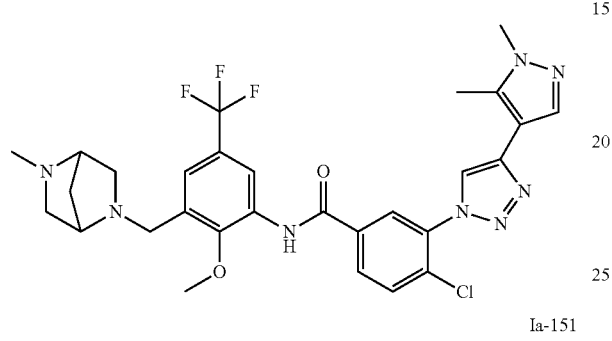
Ia-151
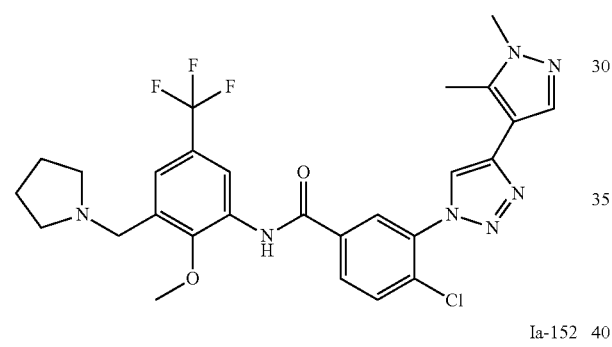
Ia-152
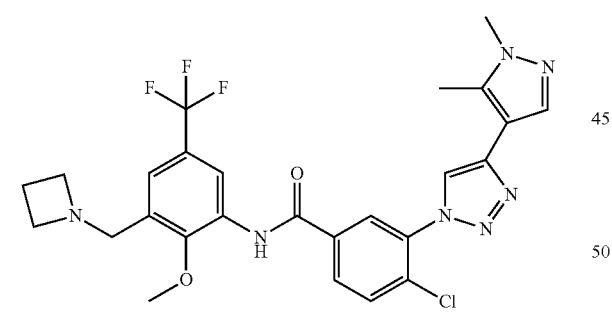
Ia-153
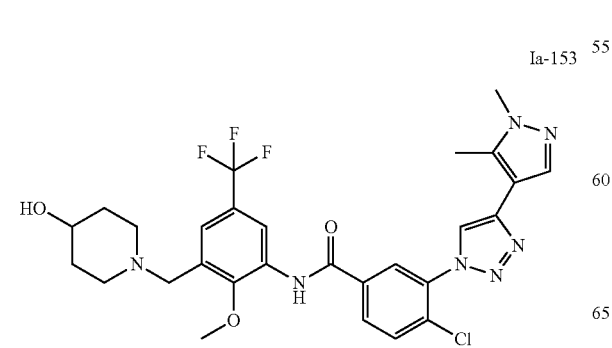
504
-continued
Ia-154
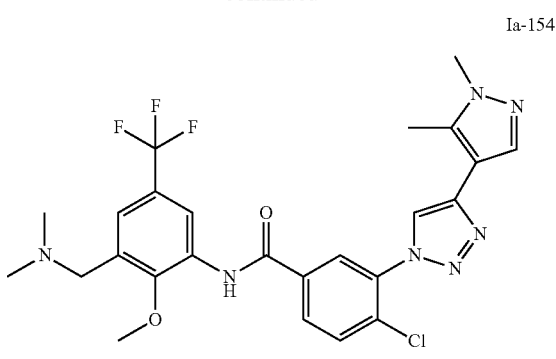
Ia-155
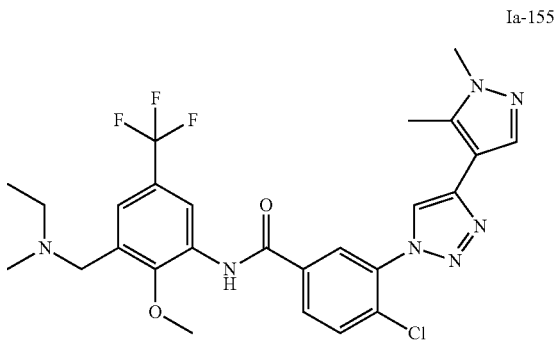
Ia-156
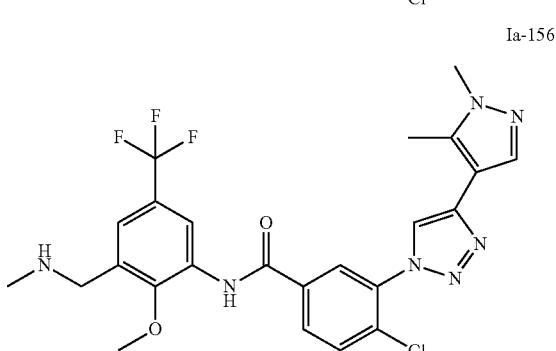
Ia-157
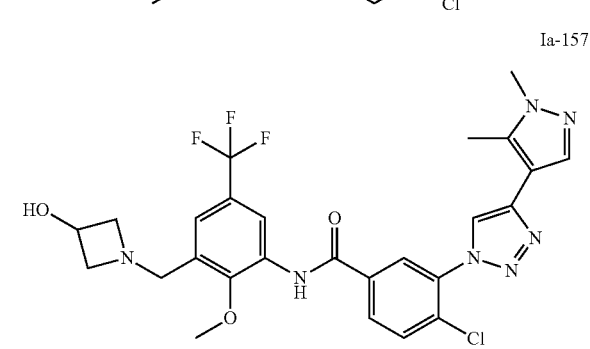
Ia-171
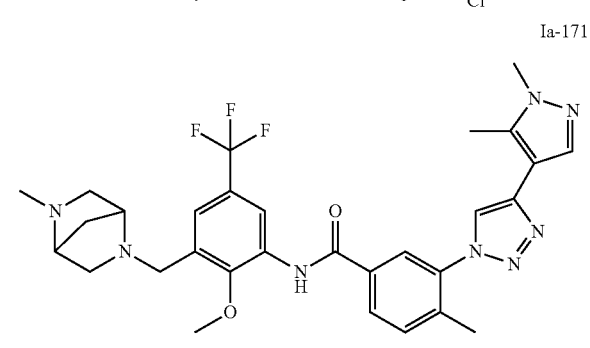

Ia-172
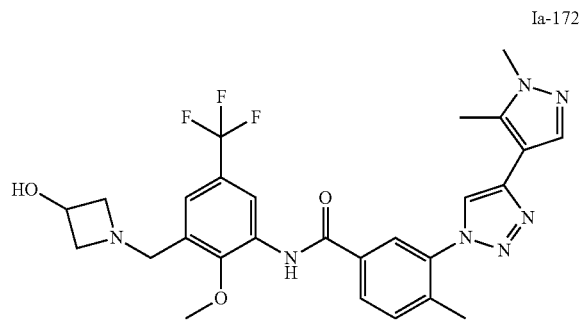
Ia-173
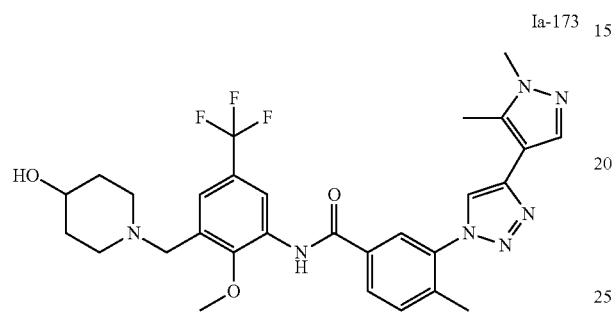
Ia-174
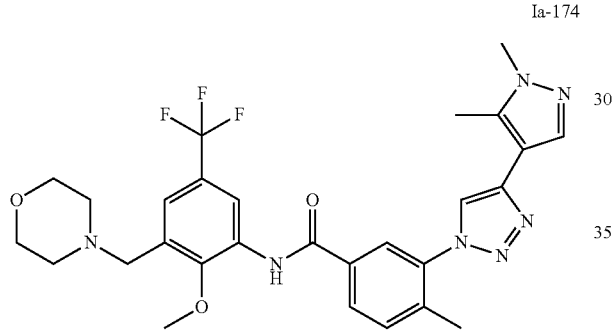
Ia-175
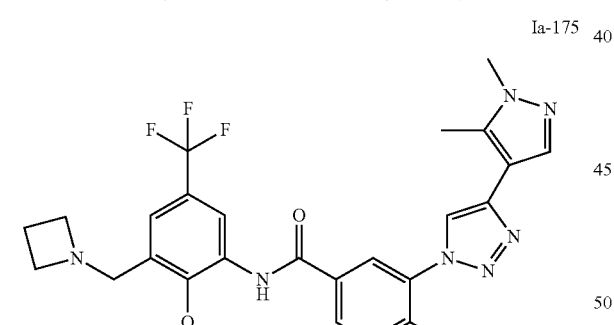
Ia-176
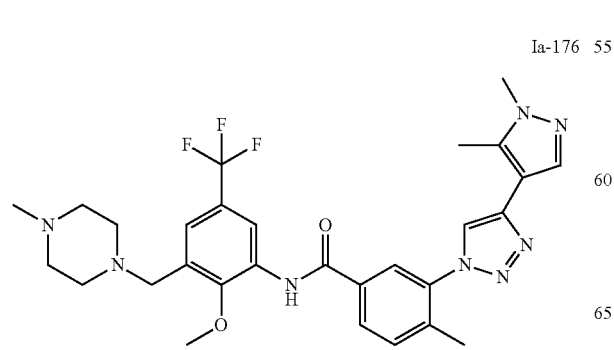
Ia-177
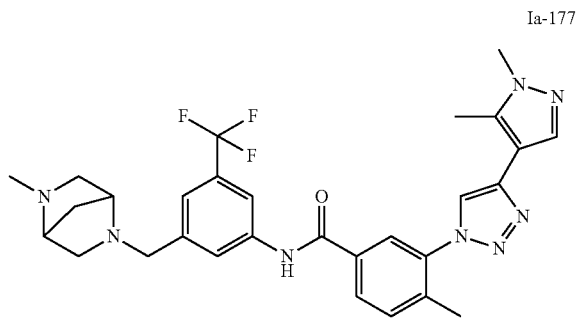
Ia-178
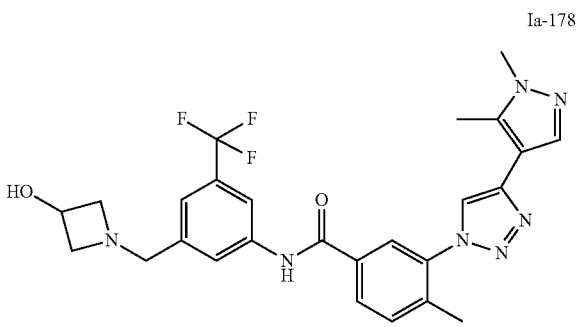
Ia-179
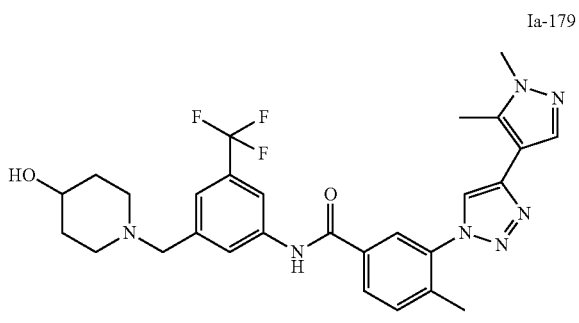
Ia-180
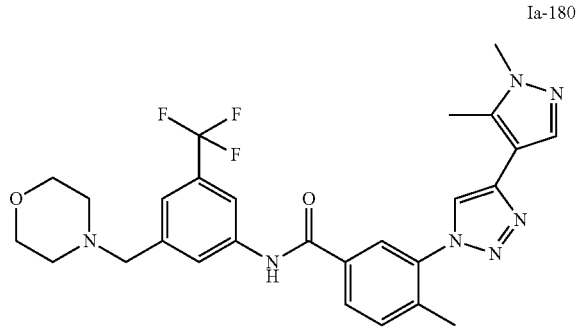
Ia-181
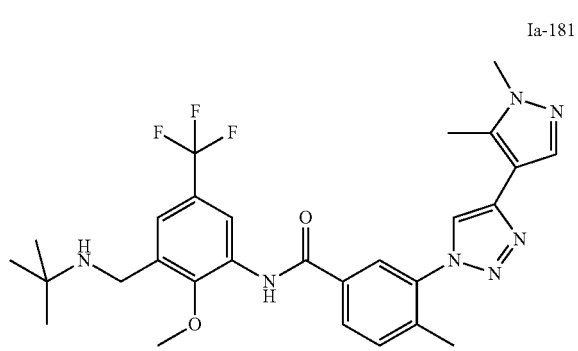 [SMILES: COc1c(NC(=O)c2ccc(C)c(-n3cc(-c4cnn(C)c4C)nn3)c2)cc(C(F)(F)F)cc1N1CCN(C)CC1]

Ia-182
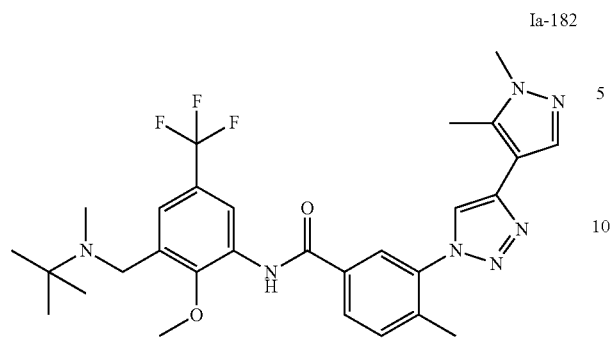
Ia-253
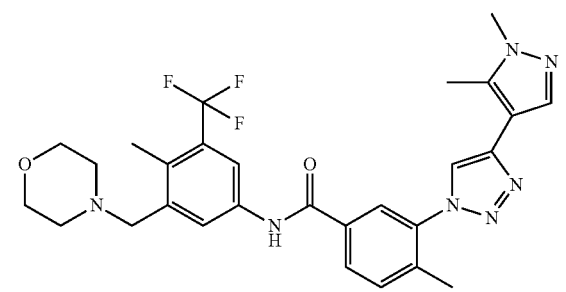
Ia-254
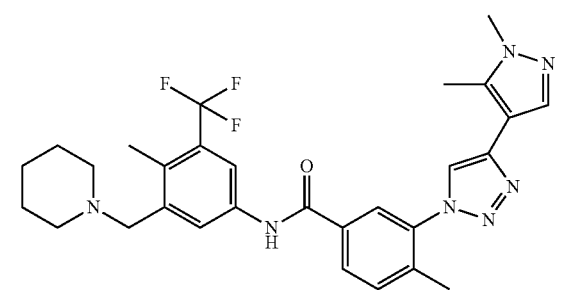
Ia-255
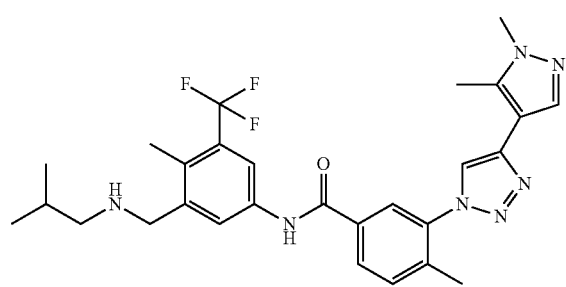
Ia-259
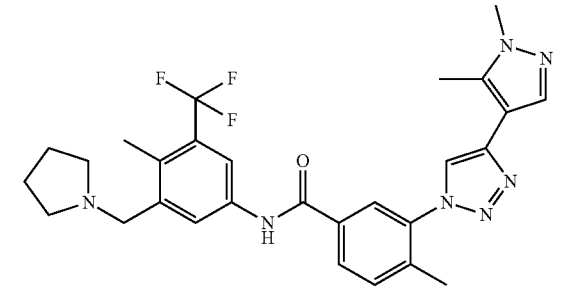
Ia-260
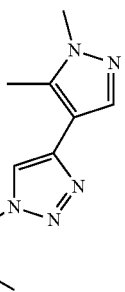
X-1
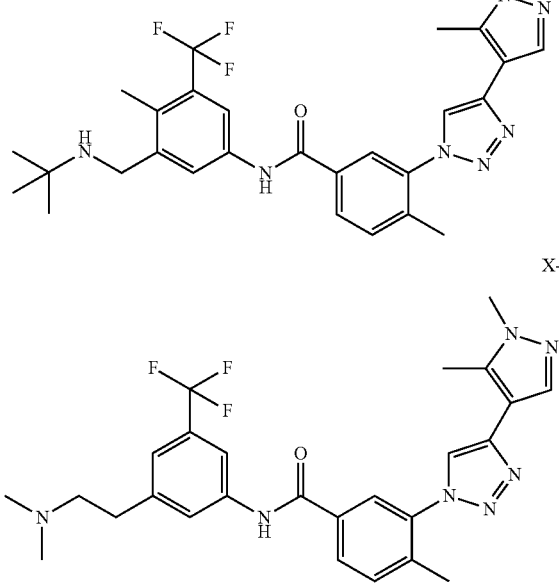
X-2
X-3
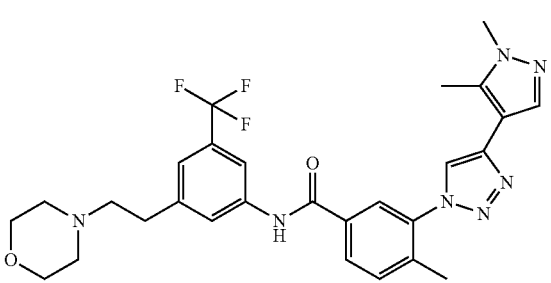
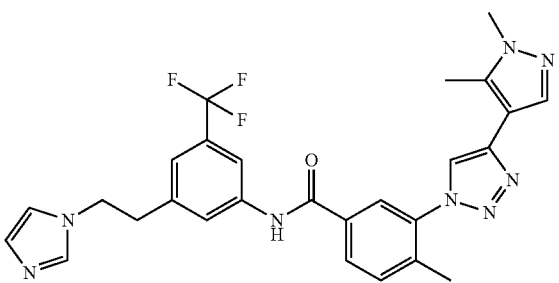
X-4
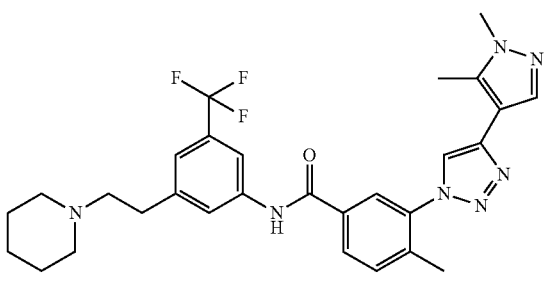

X-5
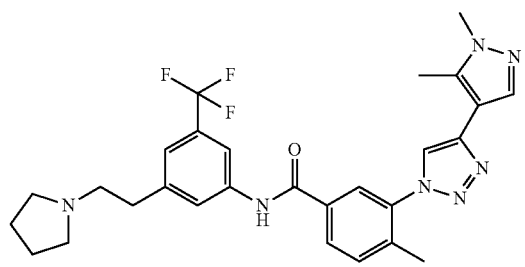
X-6
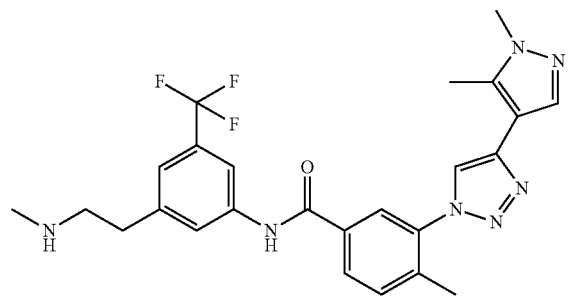
or pharmacologically acceptable salt thereof.
7. A compound selected from among:
III-2
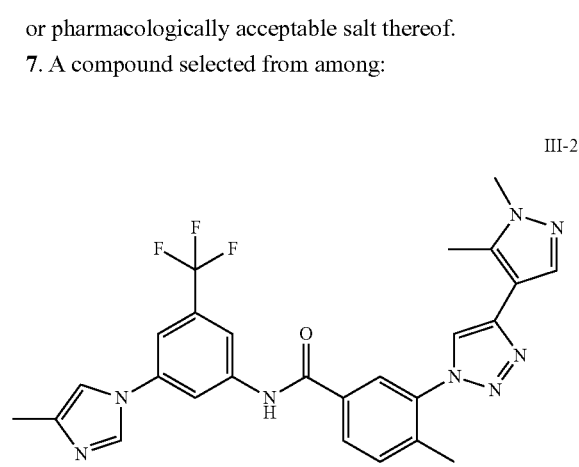
III-3
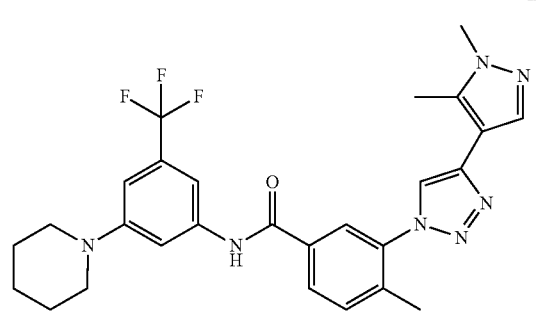
III-4
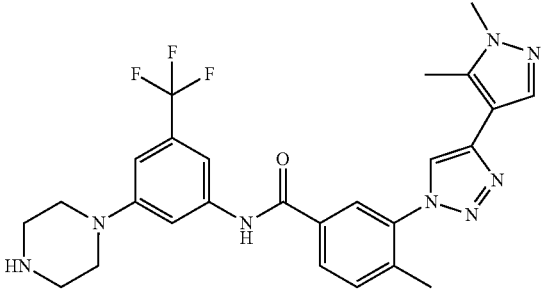
and
III-5
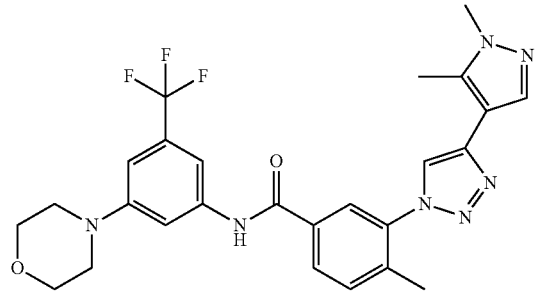
III-6
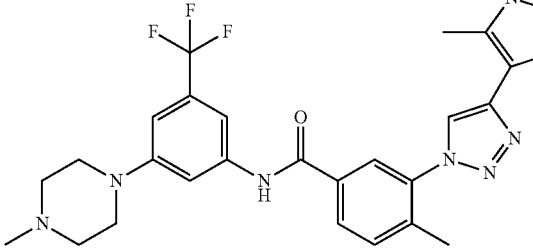
III-7
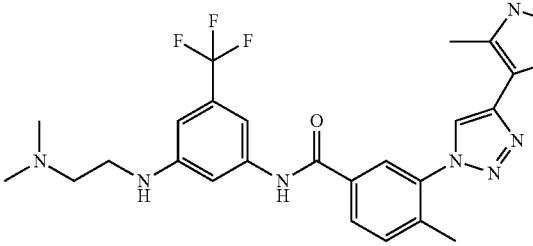
III-9
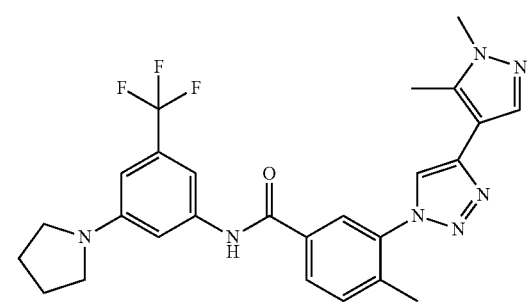

-continued
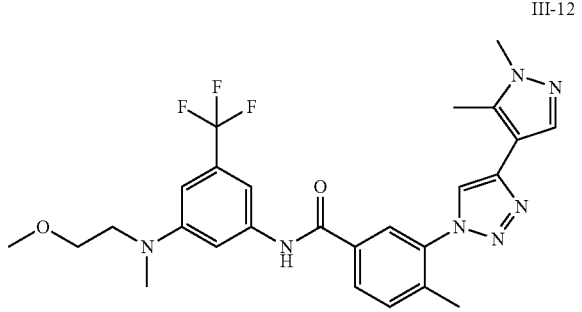
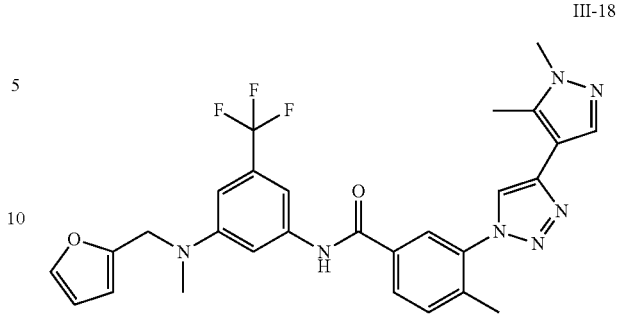

III-24
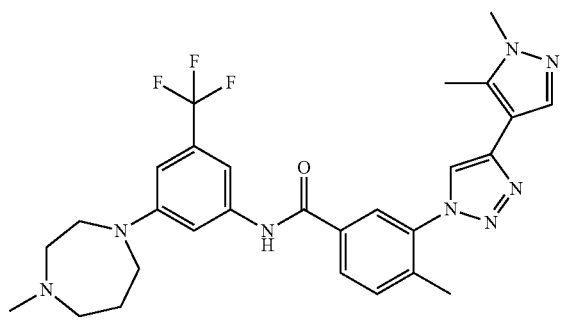
III-25
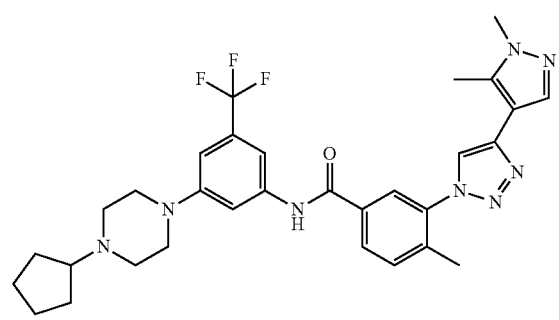
III-29
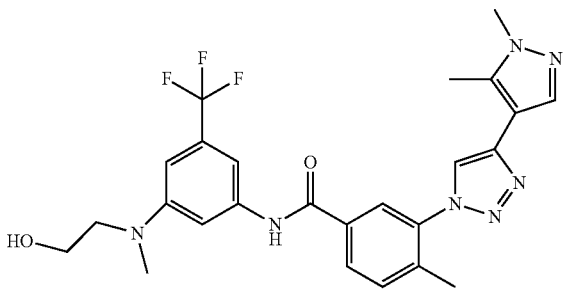
III-30
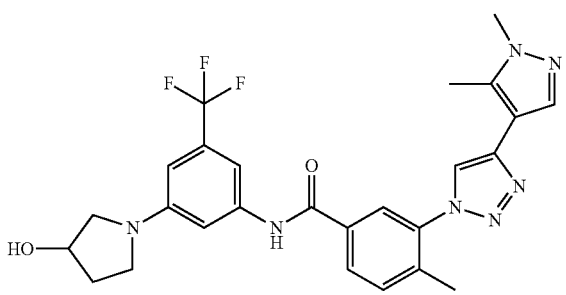
III-31
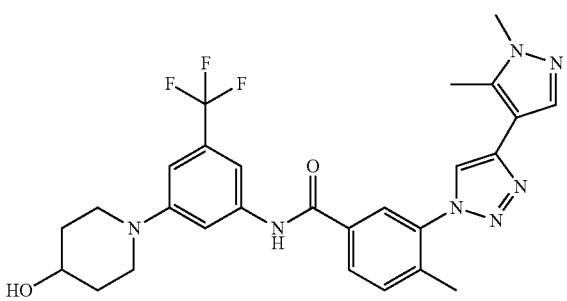
III-37
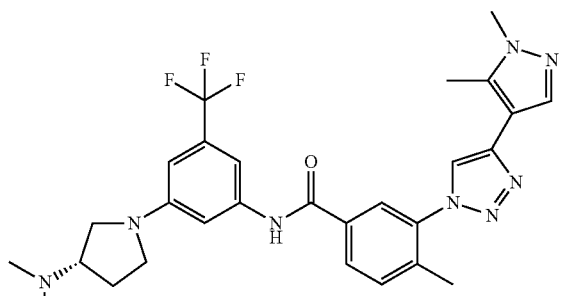
III-38
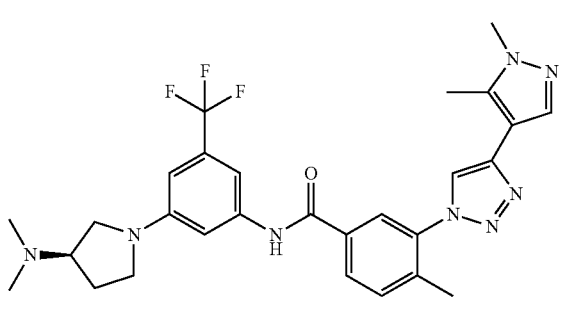
III-39
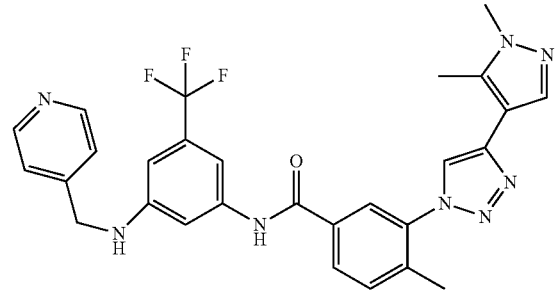
III-40
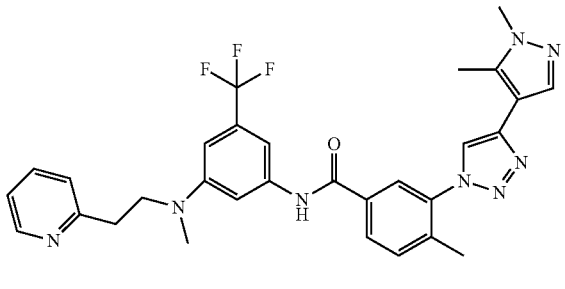
III-41
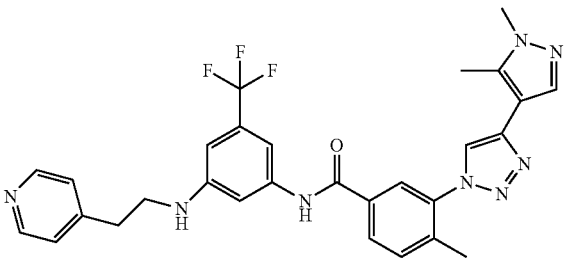

III-42
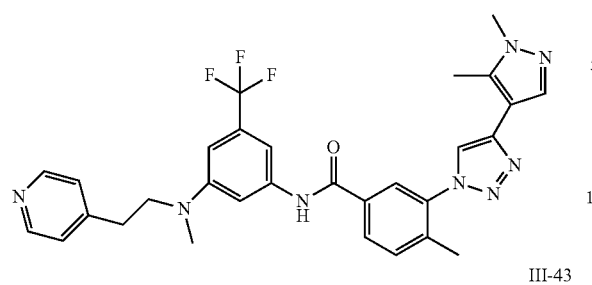
III-43
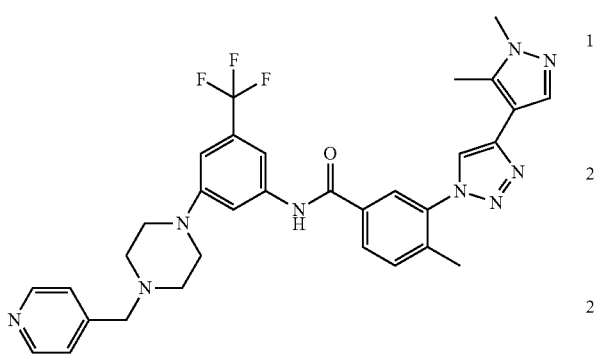
III-44
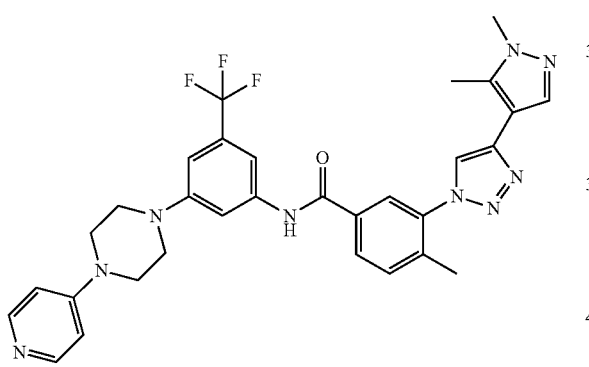
III-54
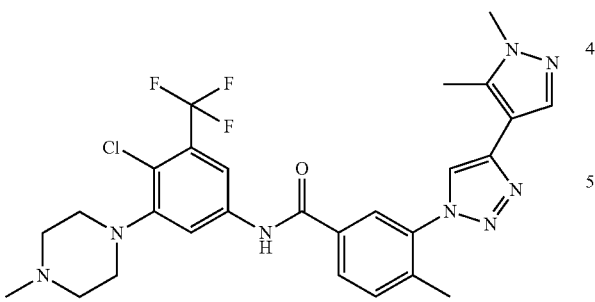
III-55
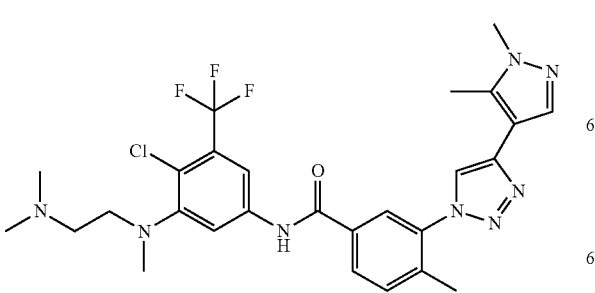
III-56
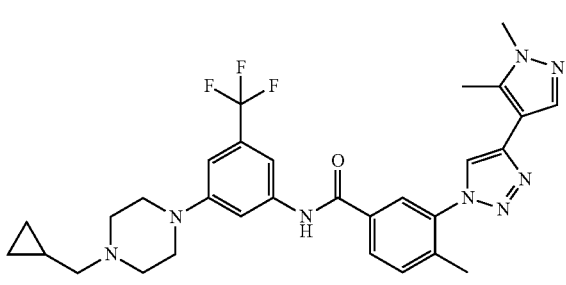
III-57
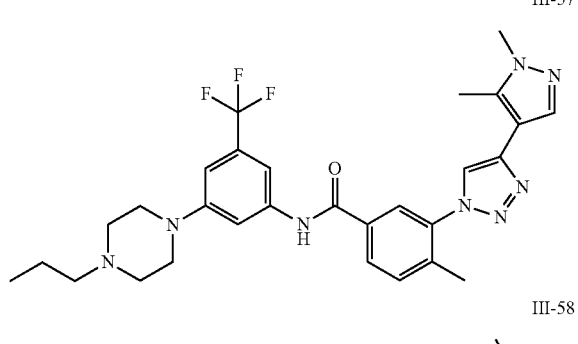
III-58
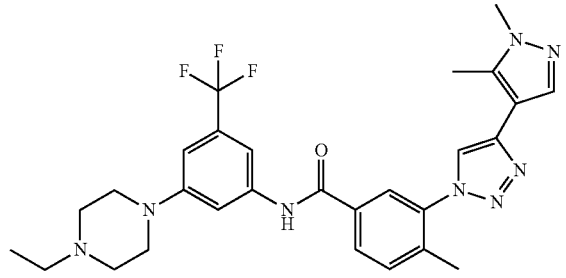
III-59
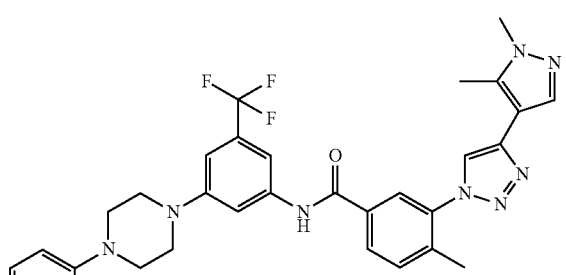
III-60
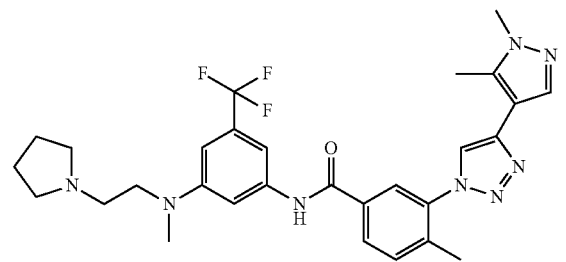

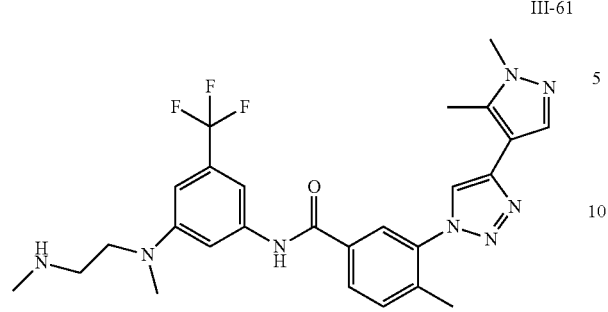
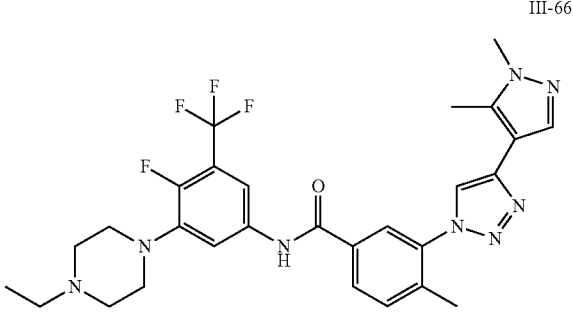

III-72
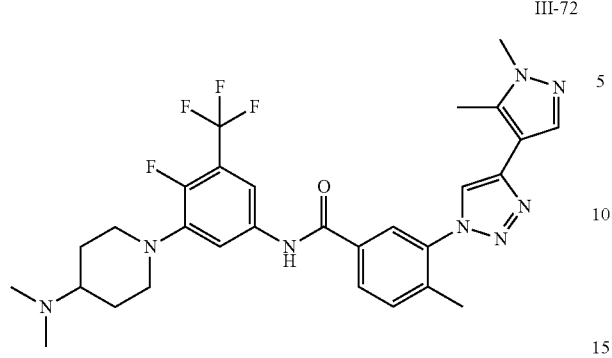
III-77
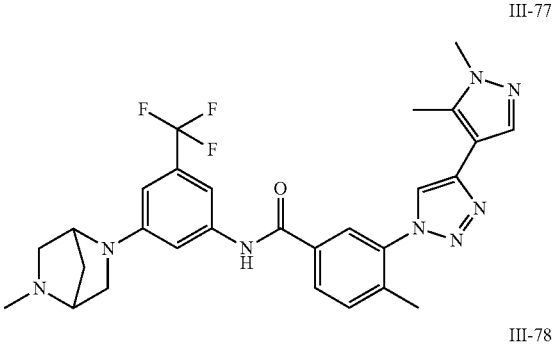
III-73
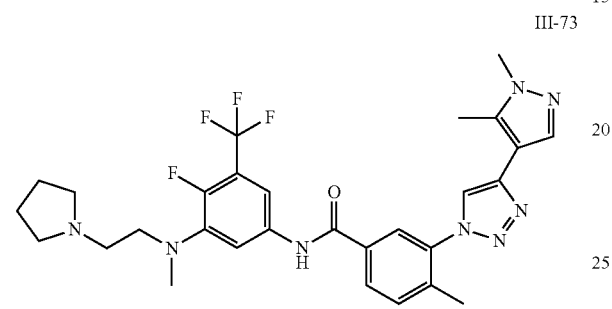
III-78
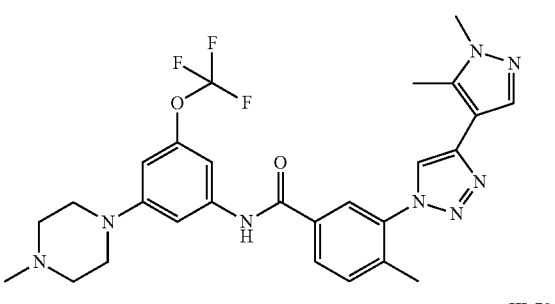
III-74
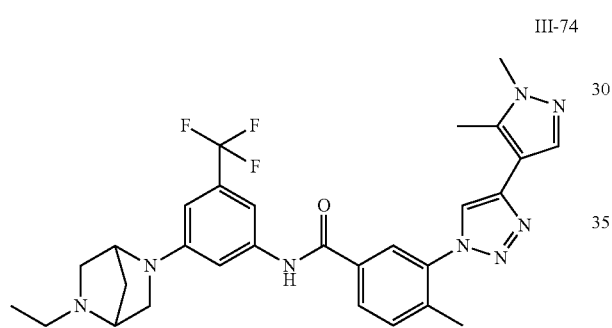
III-79
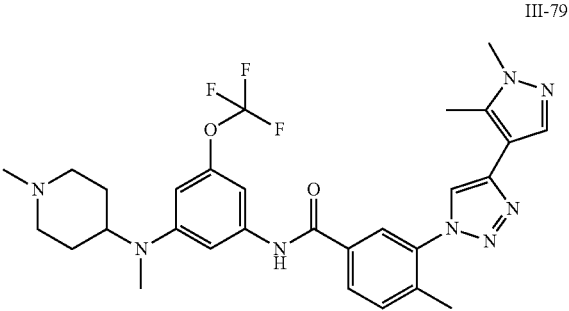
III-75
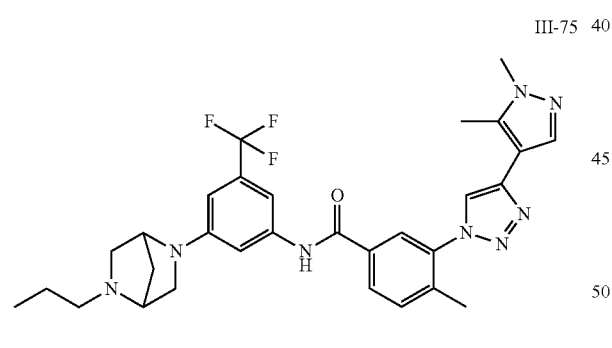
III-80
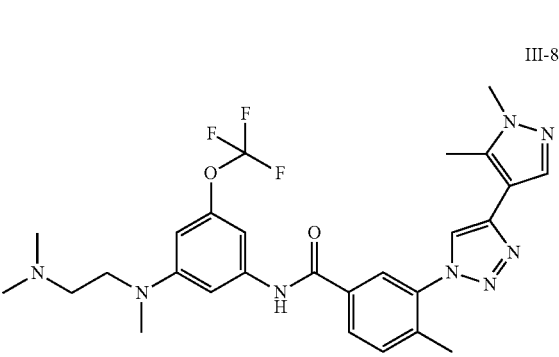
III-76
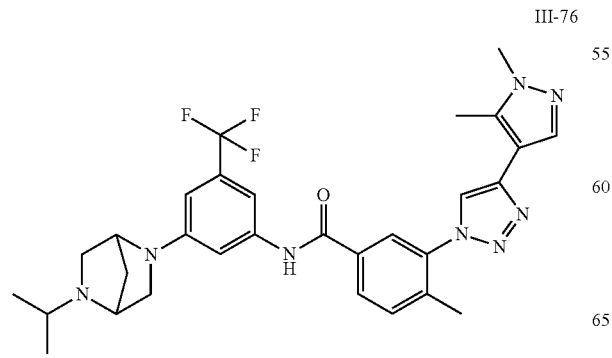
III-81
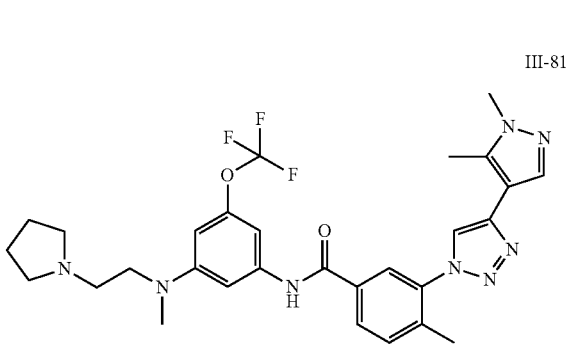

521
-continued
III-82
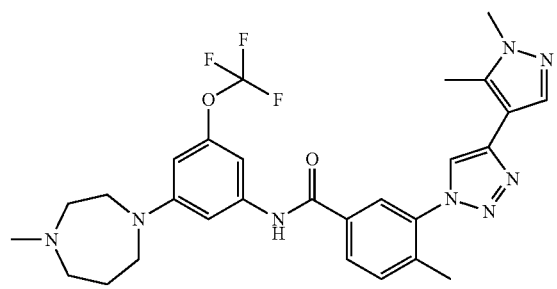
III-83
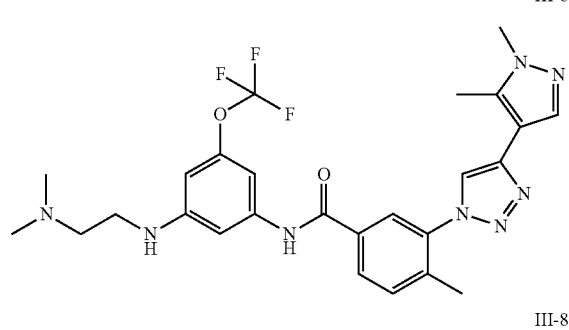
III-84
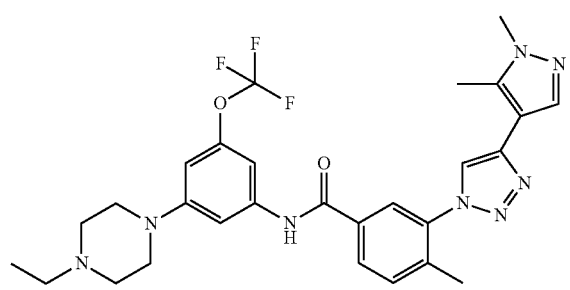
III-86
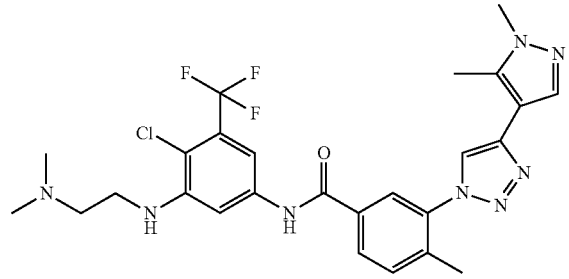
III-87
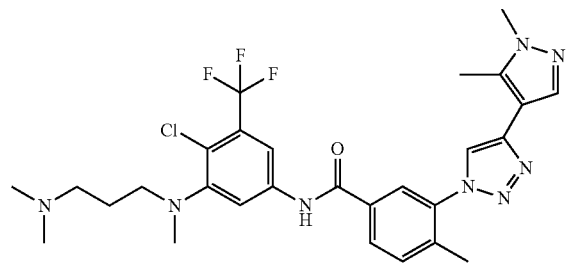
522
-continued
III-88
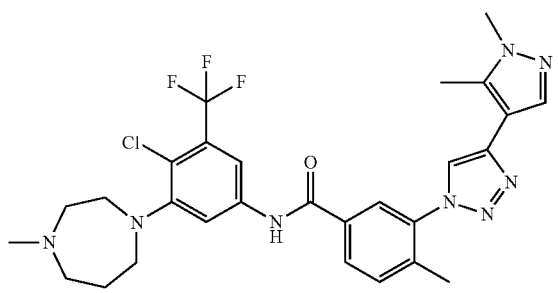
III-89
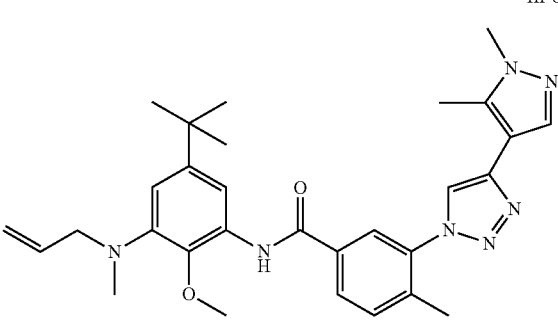
III-112
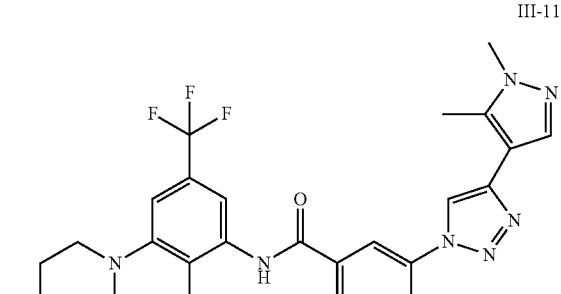
III-120
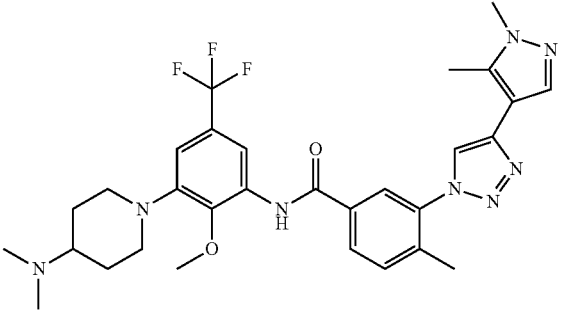
III-121
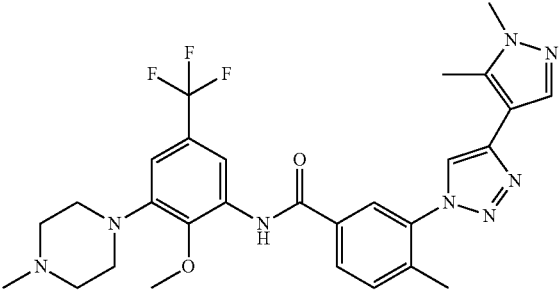

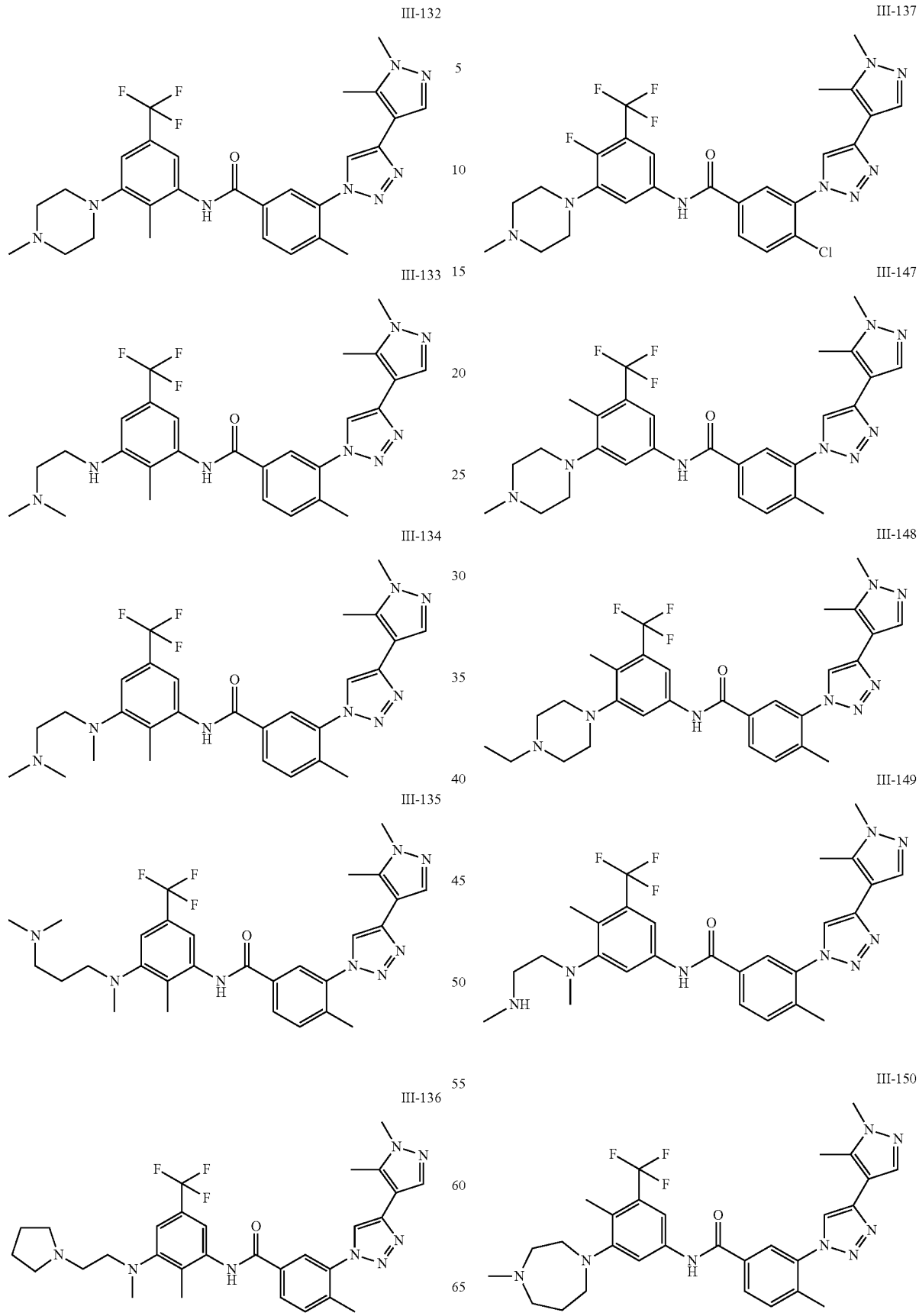

III-151
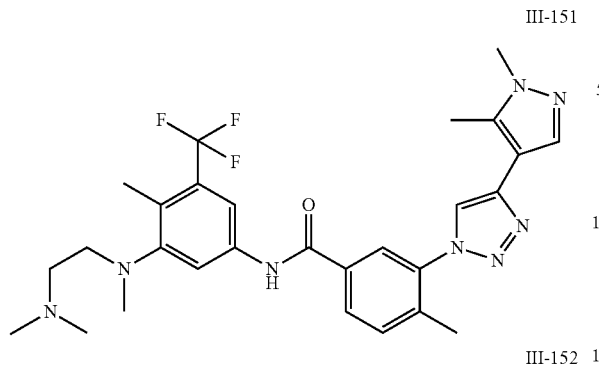
III-152
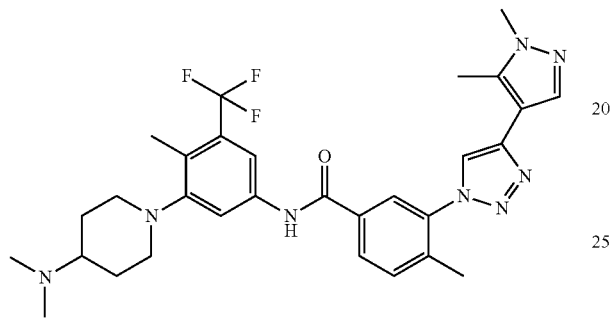
III-153
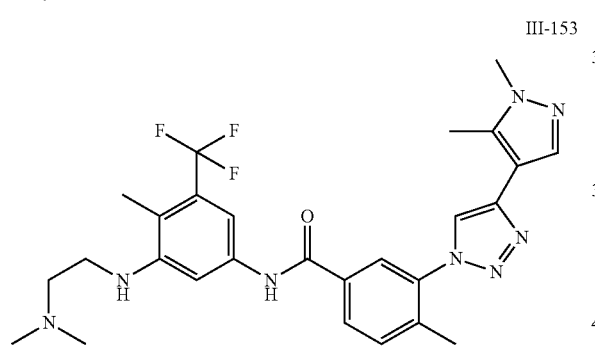
III-154
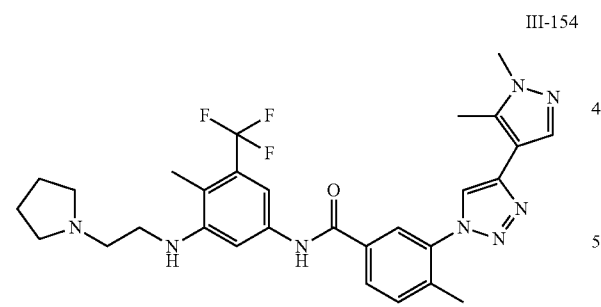
III-155
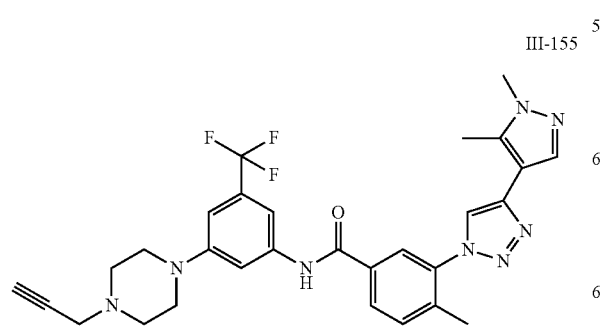
III-156
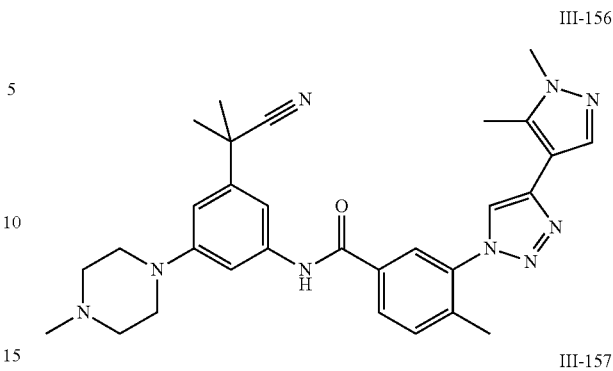
III-157
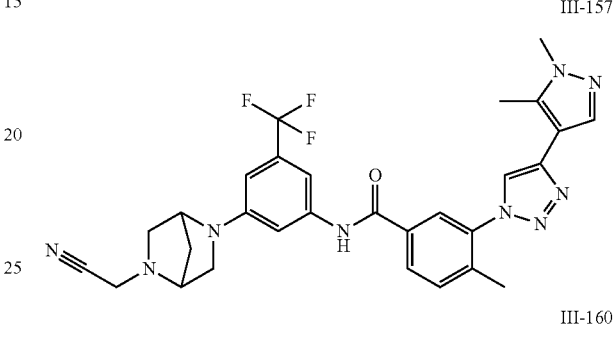
III-160
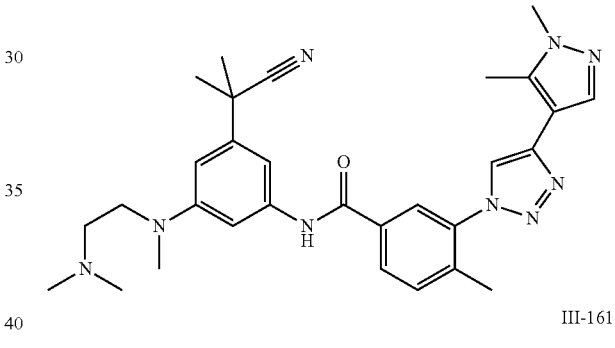
III-161
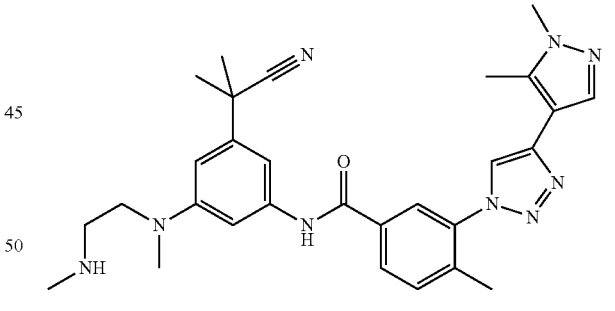
III-162
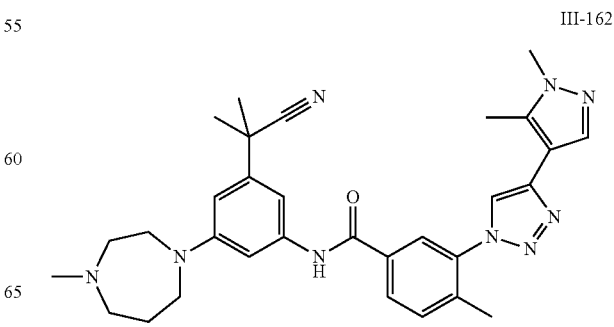

III-163
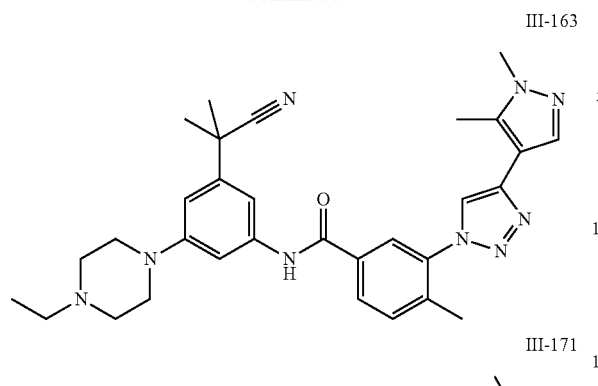
III-171
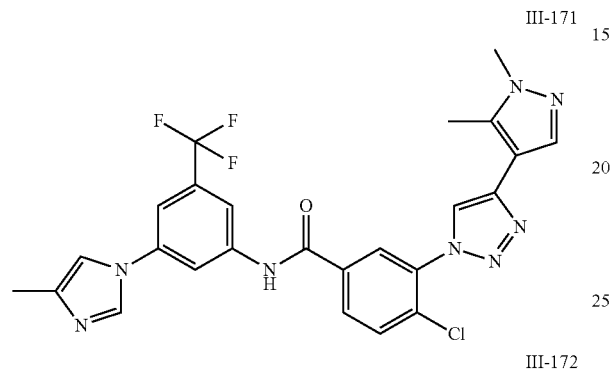
III-172
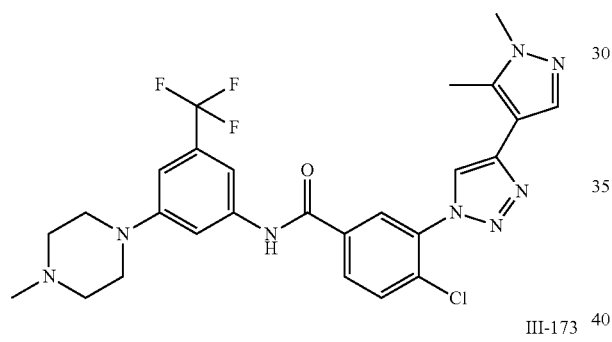
III-173
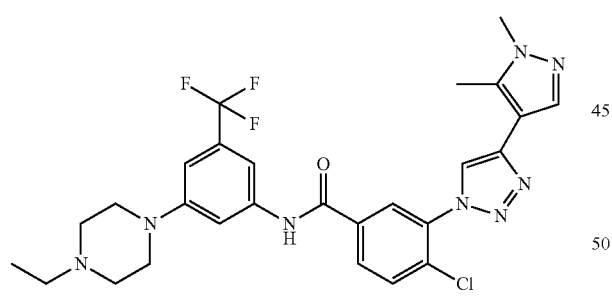
III-174
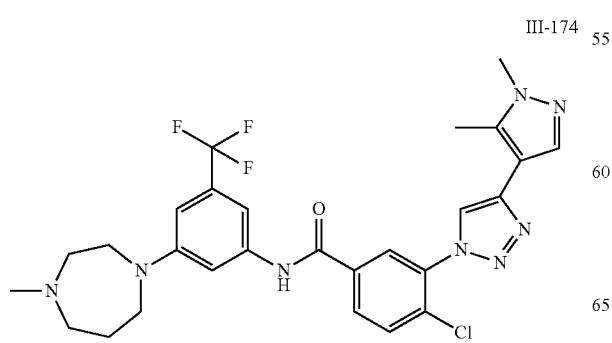
III-179
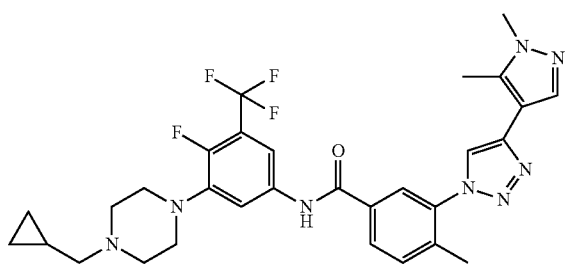
III-180
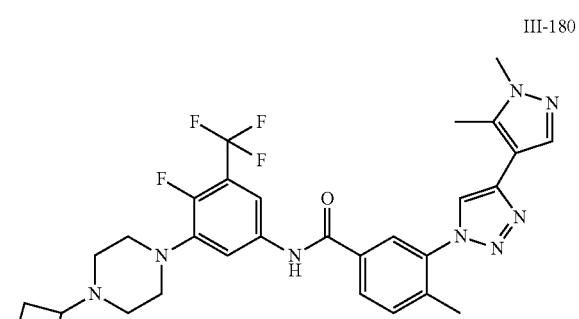
III-181
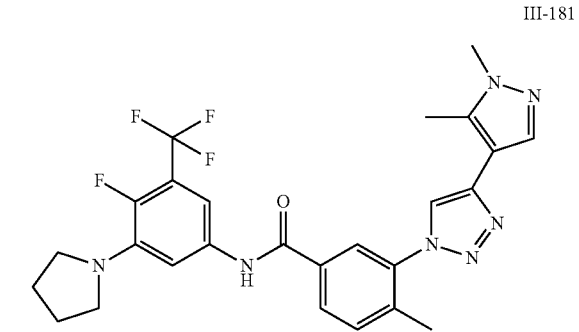
III-182
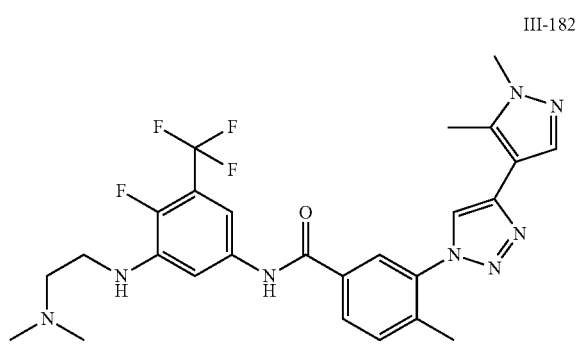 [SMILES: Cc1ccc(C(=O)Nc2cc(N3CCN(C)CC3)c(C)c(C(F)(F)F)c2)cc1-n1cc(-c2cnn(C)c2C)nn1]
III-183
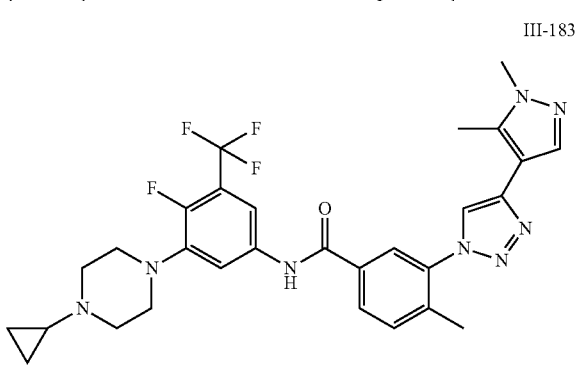

III-184
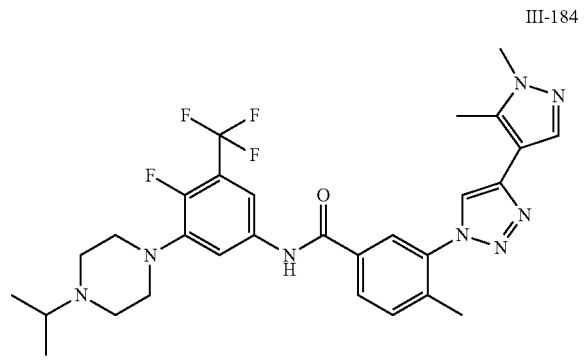
III-185
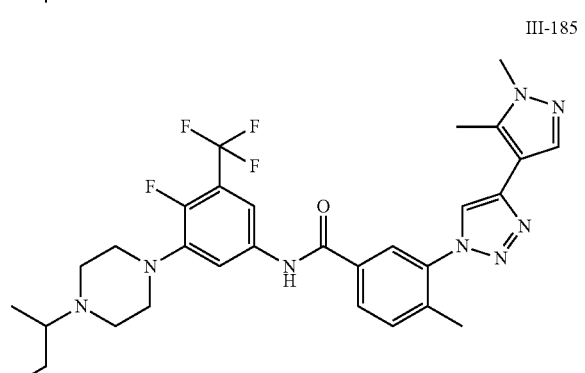
III-186
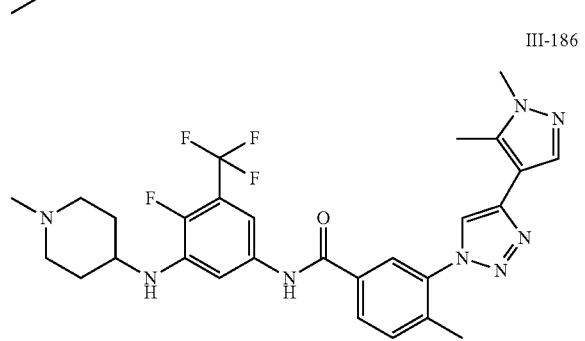
III-187
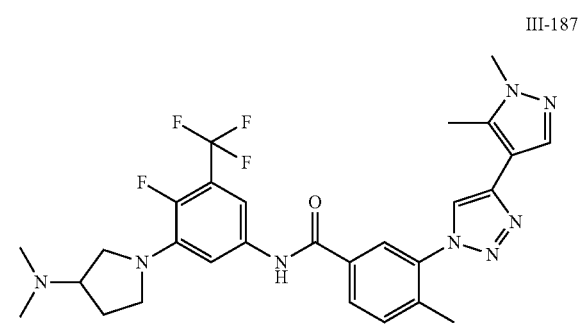
III-188
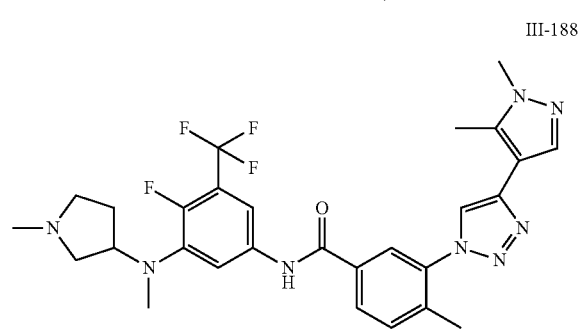
III-189
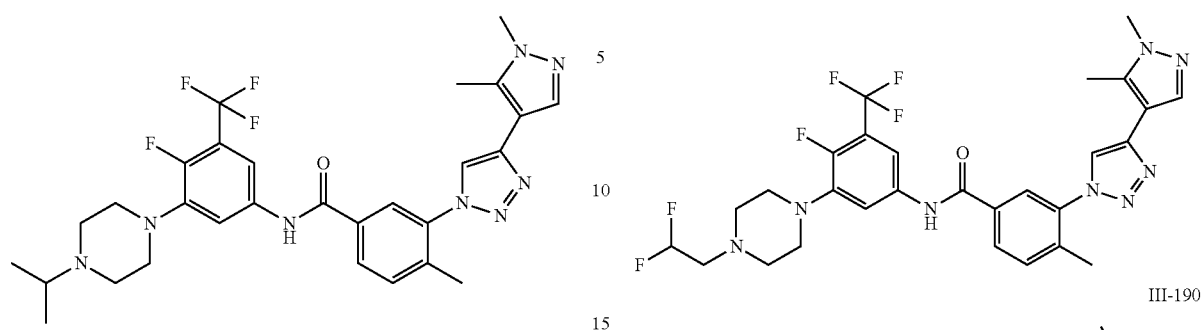
III-190
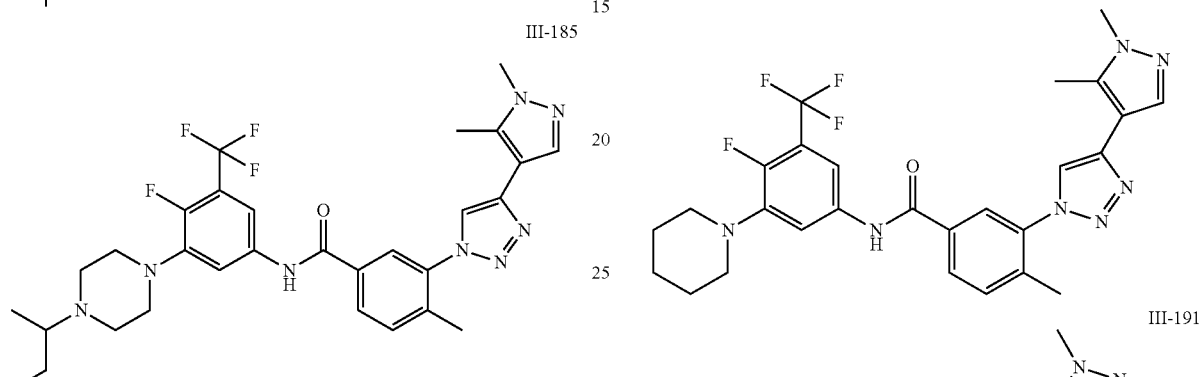
III-191
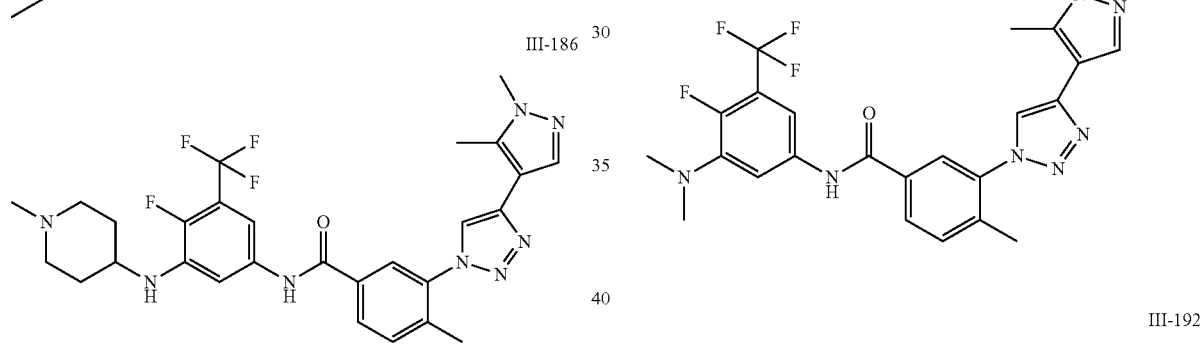
III-192
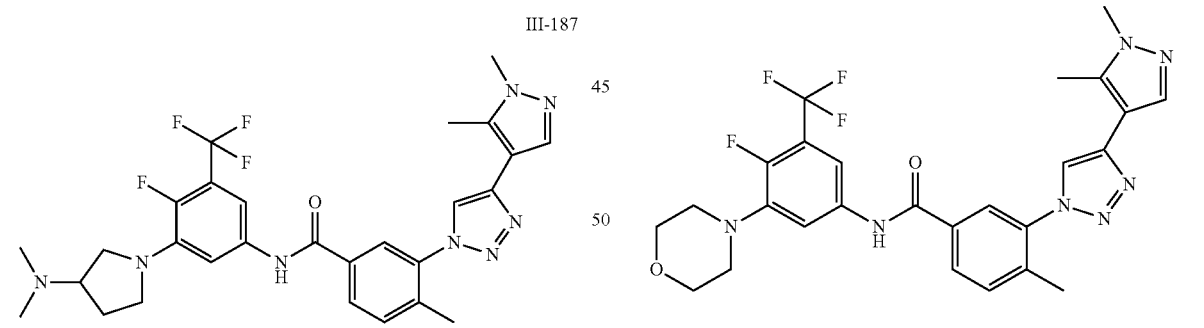
III-193
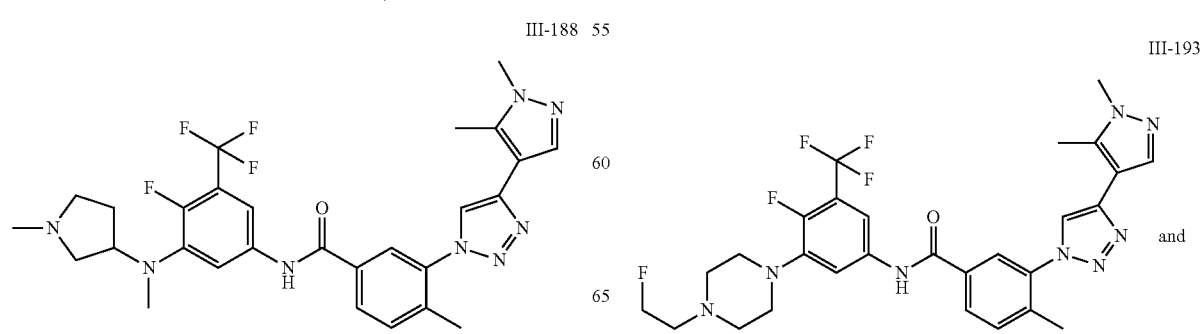
and III-194
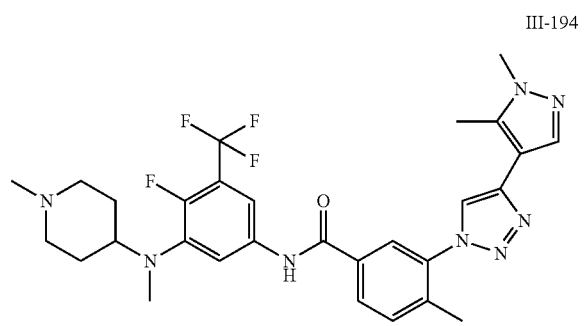
or pharmacologically acceptable salt thereof.
8. A compound selected from among:
VIII-1
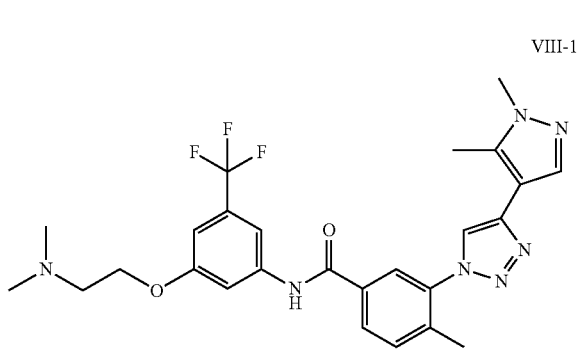
VIII-2
VIII-3
VIII-4
VIII-10
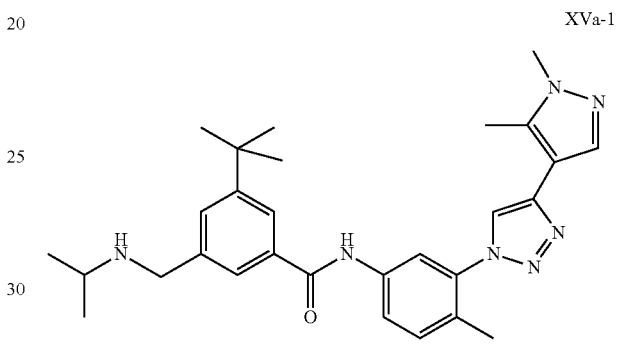
or pharmacologically acceptable salt thereof.
9. A compound selected from among:
XVa-1
XVa-2
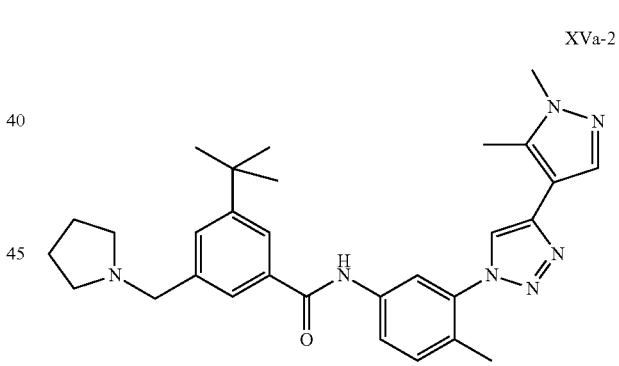
XVa-3
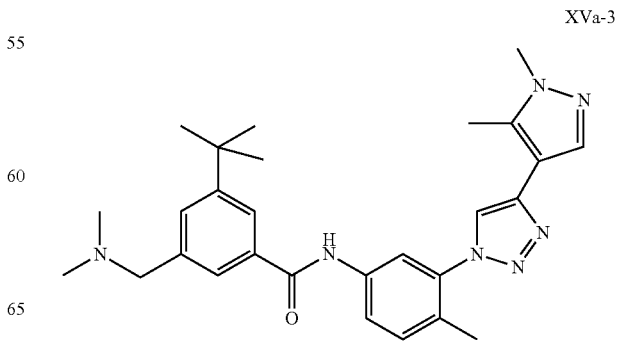
and XVa-30
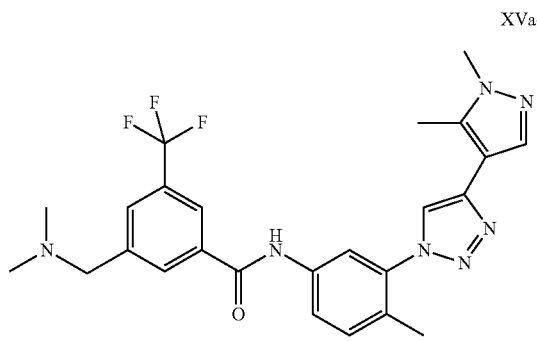
XVa-31
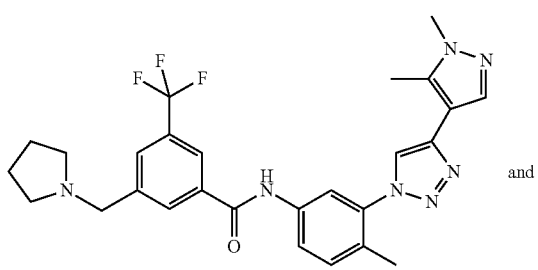
and
XVa-32
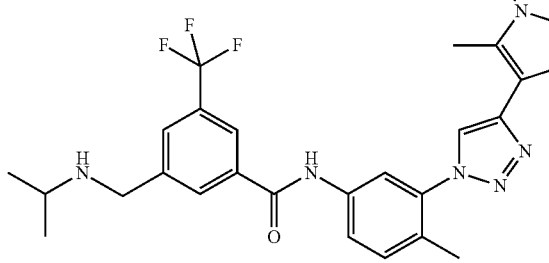
or pharmacologically acceptable salt thereof.
10. A compound selected from among:
XII-1
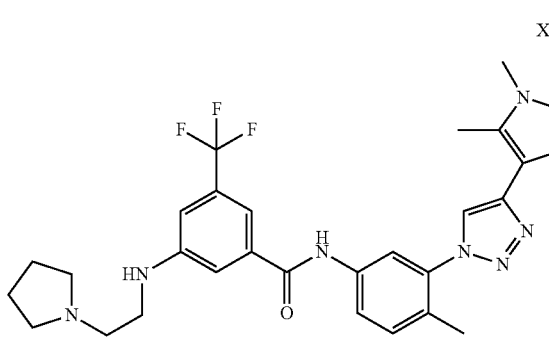
XII-2
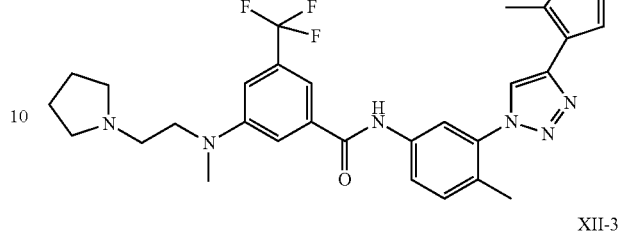
XII-3
XII-4
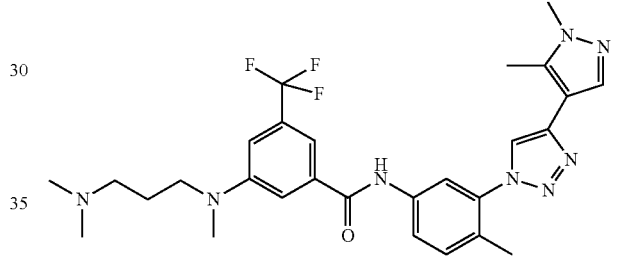
XII-5
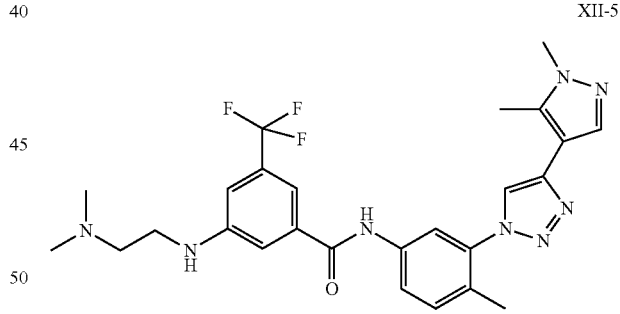
XII-6
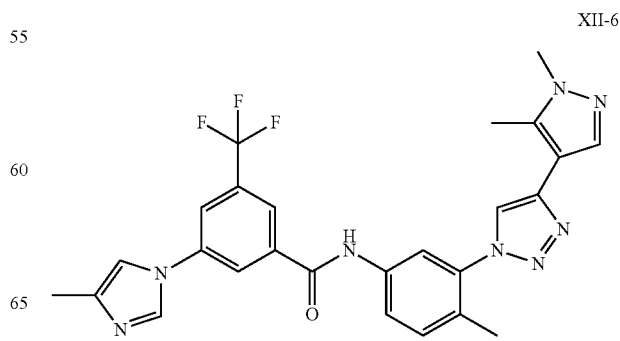

535
-continued
XII-11
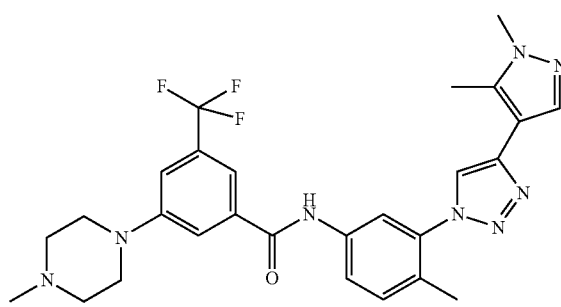
XII-12
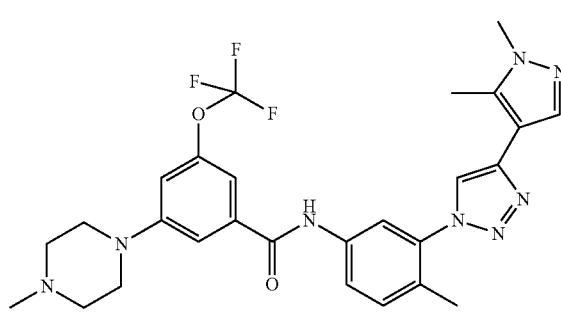
XII-28
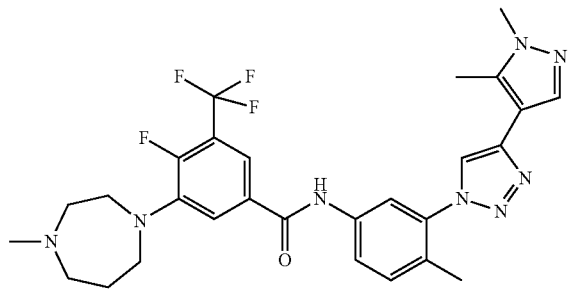
XII-29
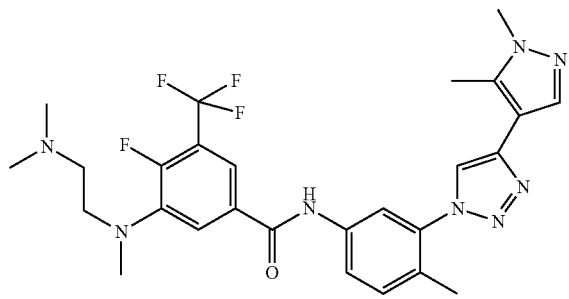
XII-30
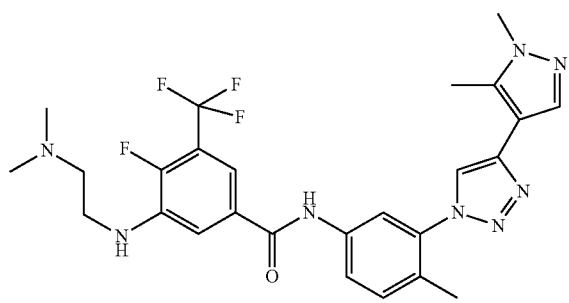
536
-continued
XII-34
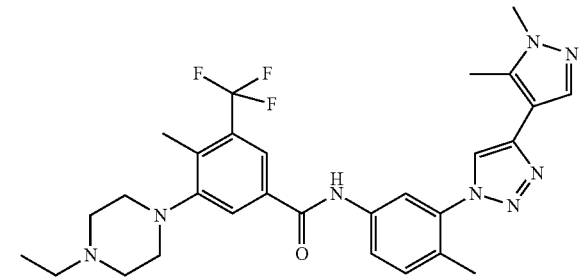
XII-35
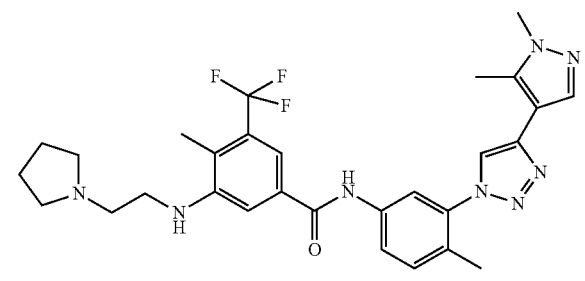
XII-36
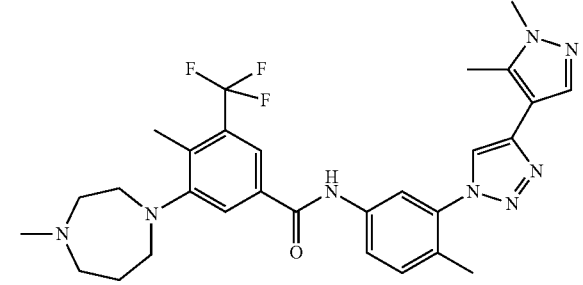
XII-37
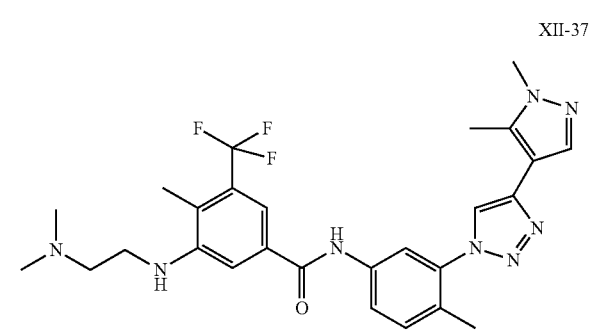
XII-38
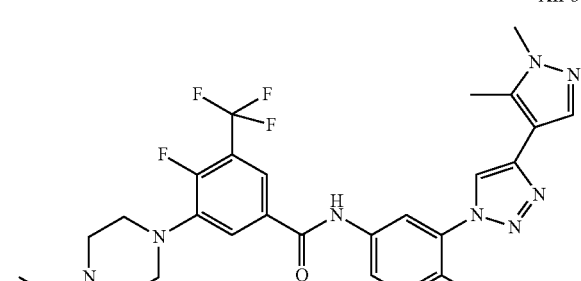

XII-39
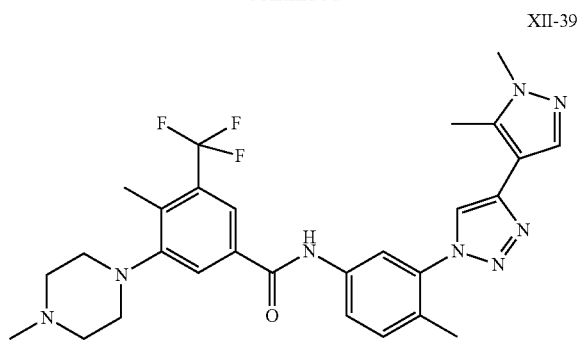
XII-40
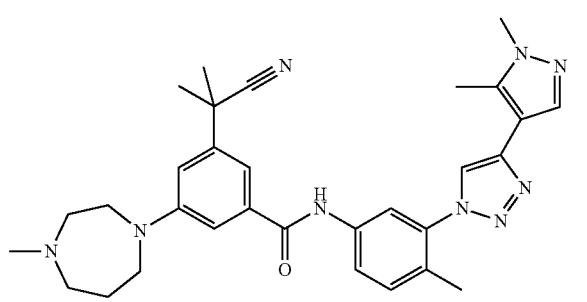
XII-41
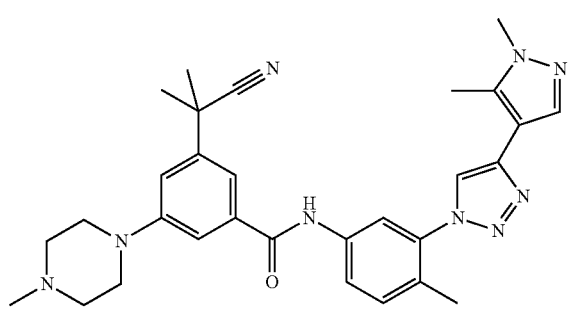
XII-42
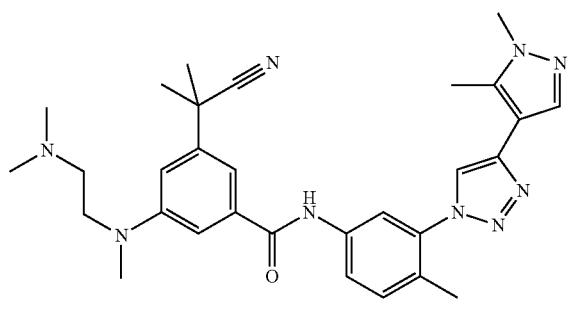
XII-43
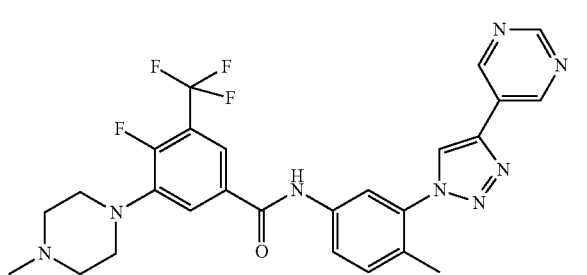
XII-51
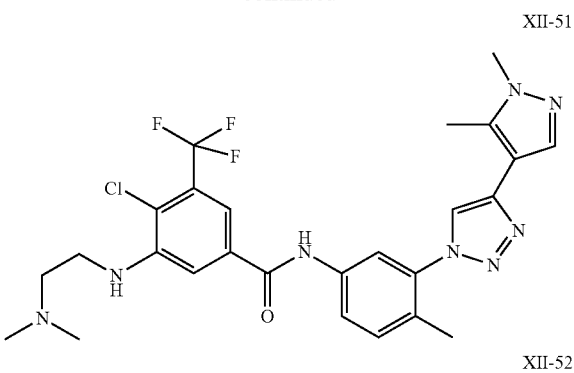
XII-52
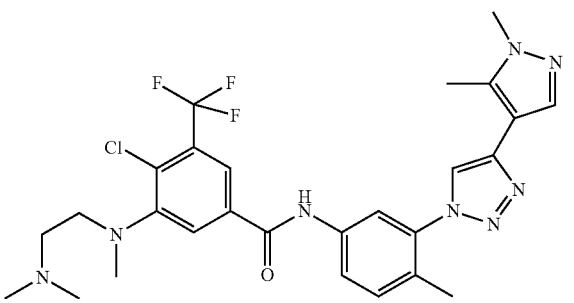
XII-53
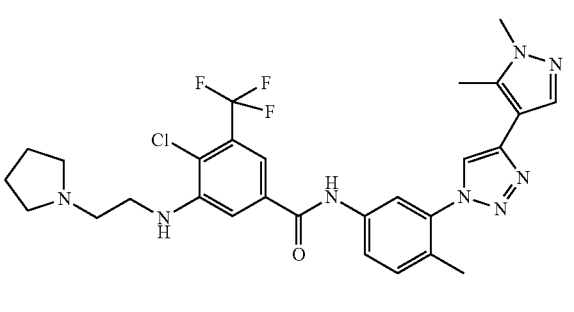
XII-54
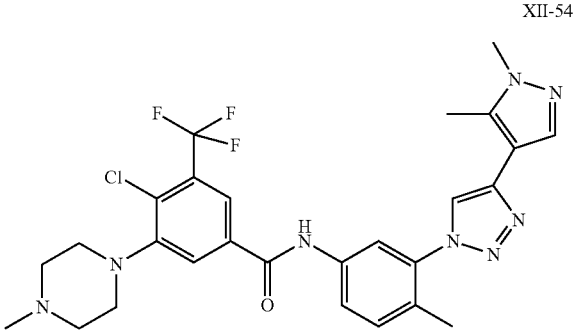
XII-55
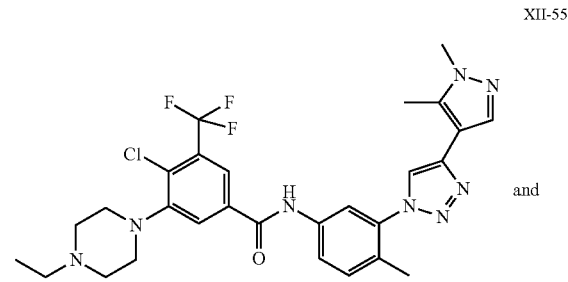
and

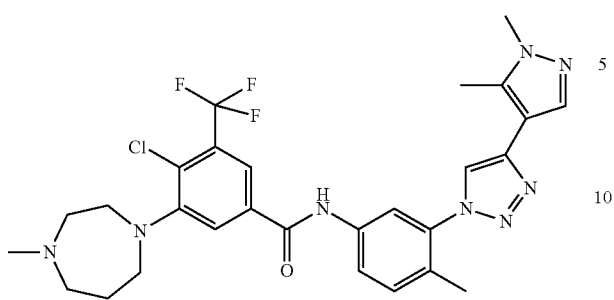

XII-56 or pharmacologically acceptable salt thereof.

11. A pharmaceutical composition comprising a therapeutically effective amount of a compound of the formula (1) according to claim 1 and one or more pharmaceutically acceptable excipients and/or carriers.

12. The pharmaceutical composition according to claim 10 further comprising at least one cytostatic or cytotoxic active substance different from the formula (1) in claim 1.

* * * * *